US010760062B2

(12) United States Patent
Naesby et al.

(10) Patent No.: US 10,760,062 B2
(45) Date of Patent: Sep. 1, 2020

(54) BIOSYNTHESIS OF PHENYLPROPANOIDS AND PHENYLPROPANOID DERIVATIVES

(71) Applicant: EVOLVA SA, Reinach (CH)

(72) Inventors: Michael Naesby, Huningue (FR); Ernesto Simón Vecilla, Glostrup (DK); Michael Eichenberger, Basel (CH); Beata Joanna Lehka, Valby Copenhagen (DK); Walden Emil Bjørn-Yoshimoto, Reinach (CH); Niels Bjerg Jensen, Kastrup (DK)

(73) Assignee: EVOLVA SA, Reinach (CH)

( * ) Notice: Subject to any disclaimer, the term of this patent is extended or adjusted under 35 U.S.C. 154(b) by 0 days.

(21) Appl. No.: 15/579,415

(22) PCT Filed: Jun. 6, 2016

(86) PCT No.: PCT/EP2016/062818
§ 371 (c)(1),
(2) Date: Dec. 4, 2017

(87) PCT Pub. No.: WO2016/193504
PCT Pub. Date: Dec. 8, 2016

(65) Prior Publication Data
US 2018/0142216 A1    May 24, 2018

Related U.S. Application Data

(60) Provisional application No. 62/171,742, filed on Jun. 5, 2015, provisional application No. 62/331,023, filed on May 3, 2016, provisional application No. 62/337,576, filed on May 17, 2016.

(51) Int. Cl.
| | |
|---|---|
| *C12N 9/02* | (2006.01) |
| *C12P 7/26* | (2006.01) |
| *C12P 19/44* | (2006.01) |
| *C12P 7/22* | (2006.01) |
| *C12N 9/10* | (2006.01) |
| *C12N 15/81* | (2006.01) |
| *C12N 9/06* | (2006.01) |

(52) U.S. Cl.
CPC ............ *C12N 9/001* (2013.01); *C12N 9/002* (2013.01); *C12N 9/1029* (2013.01); *C12N 9/1037* (2013.01); *C12N 15/81* (2013.01); *C12P 7/22* (2013.01); *C12P 7/26* (2013.01); *C12P 19/44* (2013.01); *C12Y 103/01038* (2013.01); *C12Y 103/01094* (2015.07); *C12Y 203/01095* (2013.01)

(58) Field of Classification Search
None
See application file for complete search history.

(56) References Cited

U.S. PATENT DOCUMENTS

| | | |
|---|---|---|
| 8,343,739 B2 | 1/2013 | Katz et al. |
| 2014/0045233 A1 | 2/2014 | Hilmer et al. |

OTHER PUBLICATIONS

Dare et al. Plant Physiology and Biochemistry, vol. 72, Nov. 2013, pp. 54-61 (Year: 2013).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Accession Q99190. Nov. 1, 1996. (Year: 1996).*
Accession P40526. Feb. 1, 1995 (Year: 1995).*
Accession Q9M2U2. Oct. 1, 2000. (Year: 2000).*
Accession Q96562. Feb. 1, 1997 (Year: 1997).*
Accession Q9ZWR1. SEp. 11, 2007 (Year: 2007).*
Ageitos et al., "Oily yeasts as oleaginous cell factories," Appl Microbiol Biotechnol. 90(4):1219-27 (May 2011).
Austin et al., "The chalcone synthase superfamily of type III polyketide synthases," Nat Prod Rep. 20(1):79-110 (2003).
Bankar et al., "Environmental and industrial applications of Yarrowia lipolytica," Appl Microbiol Biotechnol. 84(5):847-65 (Oct. 2009).
Bateman, et al., "Pfam 3.1: 1313 multiple alignments and profile HMMs match the majority of proteins," Nucleic Acids Res. 27(1):260-2 (Jan. 1999).
Beopoulos et al., "Yarrowia lipolytica: A model and a tool to understand the mechanisms implicated in lipid accumulation," Biochimie 91(6):692-6 (Jun. 2009).
Chenna et al., "Multiple sequence alignment with the Clustal series of programs," Nucleic Acids Res. 31 (13):3497-500 (Jul. 2003).
Dare et al., "The role of enoyl reductase genes in phloridzin biosynthesis in apple," Plant Physiol Biochem. 72:54-61 (2013).
Fairhead et al., "New vectors for combinatorial deletions in yeast chromosomes and for gap-repair cloning using split-marker recombination," Yeast. 12(14):1439-57 (1996).
GenBank Accession No. CAA70435, dated Apr. 18, 2005 (pg. 1-2).
Gietz & Schiestl, "High-efficiency yeast transformation using the LiAc/SS carrier DNA/PEG method," Nat Protoc. 2 (1):31-4 (2007).
Gosch et al., "Biosynthesis of phloridzin in apple (Malus domestica Borkh.)" Plant Science 176 223-231 (2009).
Ibdah et al., "Identification and cloning of an NADPH-dependent hydroxycinnamoyl-CoA double bond reductase involved in dihydrochalcone formation in Malus×domestica Bork," Phytochemistry. 107:24-31 (2014).
Koopman et al., "De novo production of the flavonoid naringenin in engineered Saccharomyces cerevisiae," Microb Cell Fact. 11:155 (2012).

(Continued)

*Primary Examiner* — Christian L Fronda
(74) *Attorney, Agent, or Firm* — McDonnell Boehnen Hulbert & Berghoff LLP

(57) ABSTRACT

Provided herein are methods and compositions for producing phenylpropanoid derivatives, such as chalcones and stilbenes, and dihydrophenylpropanoid derivatives, such as dihydrochalcones and dihydrostilbenes, in microorganisms. In particular, the disclosure provides recombinant microorganisms and methods of use thereof for producing phenylpropanoid derivative compounds and dihydrophenylpropanoid derivative compounds.

20 Claims, 24 Drawing Sheets

Specification includes a Sequence Listing.

(56) References Cited

OTHER PUBLICATIONS

Li et al. "High-density cultivation of oleaginous yeast Rhodosporidium toruloides Y4 in fed-batch culture," Enzyme and Microbial Technology 41(3):312-7 (Aug. 2007).

Nicaud, "Yarrowia lipolytica," Yeast 29(10):409-18 (Oct. 2012).

Osmani et al., "Substrate specificity of plant UDP-dependent glycosyltransferases predicted from crystal structures and homology modeling," Phytochemistry 70(3):325-47 (2009).

Saenge et al., "Potential use of oleaginous red yeast Rhodotorula glutinis for the bioconversion of crude glycerol from biodiesel plant to lipids and carotenoids," Process Biochemistry 46(1):210-8 (Jan. 2011).

Sauer, "Amorfrutins: A promising class of natural products that are beneficial to health,"Chembiochem 15(9):1231-8 (2014).

Shao et al., "DNA assembler, an in vivo genetic method for rapid construction of biochemical pathways," Nucleic Acids Res. 37(2):e16 (2009).

Sonnhammer et al., "Pfam: a comprehensive database of protein domain families based on seed alignments," Proteins 28(3):405-20 (Jul. 1997).

Sonnhammer et al., "Pfam: multiple sequence alignments and HMM-profiles of protein domains," Nucleic Acid Res. 26(1):320-2 (Jan. 1998).

Welch et al., "Designing genes for successful protein expression," Methods Enzymol. 498:43-66 (2011).

Werner et al., "Synthesis of non-natural flavanones and dihydrochalcones in metabolically engineered yeast," Journal of Molecular Catalysis B Enzymatic 66(3-4):257-263 (2010).

Zhu et al., "A multi-omic map of the lipid-producing yeast Rhodosporidium toruloides," Nature Commun. 3:1112 (Oct. 2012).

International Search Report and Written Opinion corresponding to Application No. PCT/EP2016/062818; dated Jul. 27, 2016. pp. 1-11.

International Preliminary Report on Patentability corresponding to Application No. PCT/EP2016/062818; dated Dec. 5, 2017, pp. 1-8.

Christensen et al. "A chalcone synthase with an unusual substrate preference is expressed in barley leaves in response to UV light and pathogen attack," Plant Mol Biol. 37(5):849-57 (1998).

Ferrer et al., "Structure of chalcone synthase and the molecular basis of plant polyketide biosynthesis," Nat Struct Biol. 6(8):775-84 (1999).

Heckman et al., "Gene splicing and mutagenesis by PCR-driven overlap extension," Nat Protoc. 2(4):924-32 (2007).

* cited by examiner

BIOSYNTHESIS OF PHENYLPROPANOIDS AND PHENYLPROPANOID DERIVATIVES

CROSS-REFERENCE TO RELATED APPLICATIONS

This application claims the benefit of U.S. Provisional Application No. 62/171,742, filed Jun. 5, 2015, U.S. Provisional Application No. 62/331,023, filed May 3, 2016, and U.S. Provisional Application No. 62/337,576, filed May 17, 2016, the disclosures of each of which are hereby incorporated by reference in their entireties.

REFERENCE TO AN ELECTRONIC SEQUENCE LISTING

The contents of the electronic sequence listing ("sequencelisting.txt"; size: 353,721 bytes; created: Jan. 17, 2018) is herein incorporated by reference in its entirety.

BACKGROUND

Field of the Invention

Provided herein are methods and compositions for biosynthetic production of compounds in host organisms. In particular, the disclosure relates to biosynthetic production of phenylpropanoid derivative compounds, such as chalcones and stilbenes, and of dihydrophenylpropanoid derivative compounds, such as dihydrochalcones and dihydrostilbenes.

Description of Related Art

Phenylpropanoids are a diverse family of phenolic compounds produced biosynthetically in plants from phenolic amino acid precursors. Phenylpropanoids and their derivatives have desirable applications, for example in the food and healthcare industries.

An exemplary phenylpropanoid derivative is naringenin, a compound that is also an intermediate in the production of downstream phenylpropanoid derivatives. Naringenin has the chemical structure:

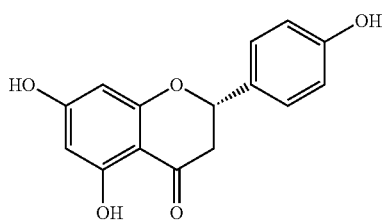 [SMILES: O=C1C[C@@H](c2ccc(O)cc2)Oc2cc(O)cc(O)c21]

Naringenin is produced naturally in plants, and also biosynthetically in cells genetically engineered with components of a flavonoid biosynthesis pathway (see e.g., Koopman et al., (2012) *Microbial Cell Factories* 2012, 11:155). For example, cells engineered to produce coumaroyl-CoA are further engineered with recombinant genes expressing proteins that convert coumaroyl-CoA to naringenin.

Another exemplary phenylpropanoid derivative is the stilbene resveratrol, which is also an intermediate in the production of other downstream phenylpropanoid derivatives. Resveratrol has the chemical structure:

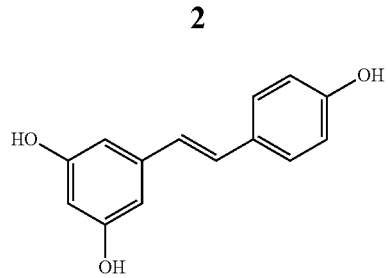

Resveratrol is also produced using a coumaroyl-CoA precursor molecule. Dihydrophenylpropanoids are phenylpropanoid derivatives wherein the double bond of the phenylpropanoid propene tail is reduced. Dihydrophenylpropanoids, such as dihydrocoumaroyl-CoA or dihydrocinnamoyl-CoA, provide important biosynthetic intermediates in the production of various desirable compounds, for example members of the dihydrochalcones and members of the dihydrostilbenoids.

Examples of dihydrostilbenoids are dihydroresveratrol and dihydropinosylvin, which are produced by stilbene synthase (STS)-catalyzed conversion of dihydrocoumaroyl-CoA or dihydrocinnamoyl-CoA respectively, and which are represented by the following chemical structures:

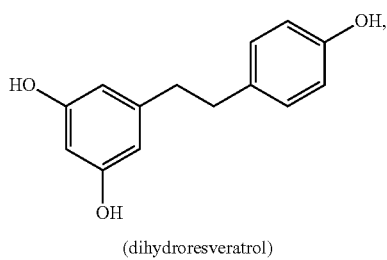
(dihydroresveratrol)

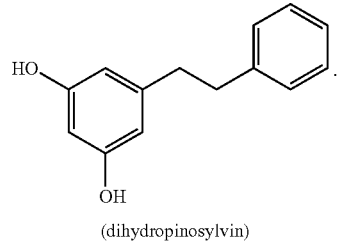
(dihydropinosylvin)

The amorfrutins are another class of dihydrophenylpropanoid-derived dihydrostilbenoid plant compounds with potential health benefits. See, e.g., Sauer, *Chembiochem* 2014, 15(9):1231-8. An example of an amorfrutin is amorfrutin 2, which is represented by the following chemical structure:

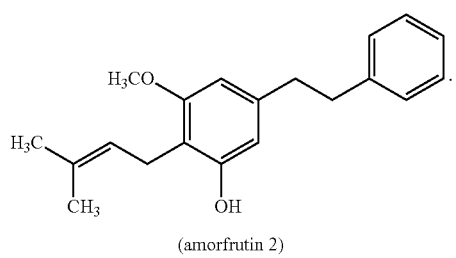 [SMILES: COc1cc(CCc2ccccc2)cc(O)c1CC=C(C)C]
(amorfrutin 2)

An example of a dihydrochalconoid compound is phlorizin. Phlorizin occurs in nature in some plants, including pear, apple, cherry, and other fruit trees. Phlorizin has been shown to inhibit Sodium/Glucose Cotransporter 1 (SGLT1) and Sodium/Glucose Cotransporter 2 (SGLT2), involved in glucose reabsorption from the intestine and liver. Accordingly, phlorizin has potential uses for controlling blood sugar levels, e.g., prevention of hyperglycemia in connection with Type 2 diabetes, as well as other potential uses to improve human health. Phlorizin is represented by the following chemical structure:

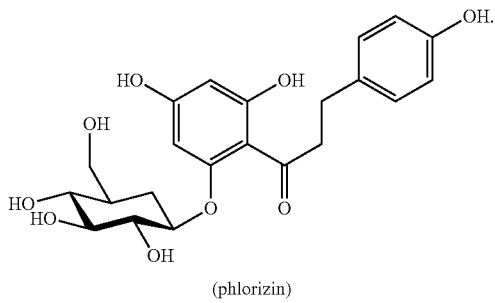

(phlorizin)

Another example of a dihydrophenylpropanoid derivative is the biosynthetic precursor for phlorizin, called phloretin (phlorizin is a 2'-glucoside of phloretin). Phloretin shares some of the same properties as phlorizin, including, for example, the ability to inhibit active transport of SGLT1 and SGLT2. Additionally, phloretin has been found to inhibit Glucose Transporter 2 (GLUT2). Phloretin is represented by the following chemical structure:

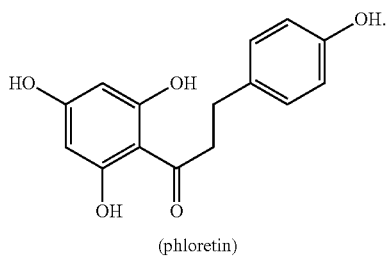 [SMILES: O=C(CCc1ccc(O)cc1)c1c(O)cc(O)cc1O]

(phloretin)

One step of the biosynthetic pathways for both dihydrochalcones (such as phloretin and phlorizin) and dihydrostilbenes is the conversion of a phenylpropanoid (e.g., p-coumaroyl-CoA) to a dihydrophenylpropanoid (e.g., p-dihydrocoumaroyl-CoA). Recombinant hosts engineered for p-coumaroyl-CoA biosynthesis are known in the art (See e.g. U.S. Pat. No. 8,343,739). However, there remains a need for the recombinant conversion of phenylpropanoids to dihydrophenylpropanoids.

In addition, current methods of producing naringenin, resveratrol, and other phenylpropanoid derivatives are limited by pathways that compete for phenylpropanoids such as coumaroyl-CoA as a substrate. For example, it is known that certain cells engineered to produce naringenin also produce phloretic acid by an unknown mechanism (see e.g., Koopman et al., (2012) *Microbial Cell Factories* 2012, 11:155). Phloretic acid is a dihydro-phenylpropanoid, and one step of the biosynthetic pathways for dihydrophenylpropanoid production is the conversion of a phenylpropanoid (e.g., p-coumaroyl-CoA) to a dihydrophenylpropanoid (e.g., p-dihydrocoumaroyl-CoA). However, the enzymes responsible for producing dihydrophenylpropanoids (and reducing, for example, naringenin production) are unknown. Accordingly, there is a need in the art for optimized production of phenylpropanoid derivatives such as naringenin in recombinant host cells.

SUMMARY

The methods and compositions disclosed herein are not limited to specific advantages or functionality.

In one aspect, the disclosure provides methods of modulating production of a phenylpropanoid derivative compound relative to a dihydrophenylpropanoid derivative compound in a recombinant host cell, the methods comprising: (a) increasing production of the phenylpropanoid derivative compound relative to the dihydrophenylpropanoid derivative compound by reducing or eliminating (i) double-bond reductase activity, or (ii) expression of a gene encoding a double-bond reductase polypeptide; or (b) decreasing production of the phenylpropanoid derivative compound relative to the dihydrophenylpropanoid derivative compound by increasing (i) double-bond reductase activity, or (ii) expression of a gene encoding a double-bond reductase polypeptide; wherein the phenylpropanoid derivative compound is a chalcone or stilbene, and wherein the dihydrophenylpropanoid derivative compound is a dihydrochalcone or dihydrostilbene. In some embodiments, the double-bond reductase polypeptide is: (a) an enoyl reductase polypeptide; or (b) a polyprenol reductase polypeptide. In some embodiments, the enoyl reductase polypeptide is *S. cerevisiae* trans-2-enoyl-CoA reductase TSC13. In some embodiments, the polyprenol reductase polypeptide is *S. cerevisiae* DFG10. In some embodiments, the phenylpropanoid derivative compound is naringenin, resveratrol, pinosylvin, pinocembrin chalcone, or pinocembrin. In some embodiments, the dihydrophenylpropanoid derivative compound is phloretin, phlorizin, dihydropinosylvin, 3-O-methyldihydropinosylvin, 2-isoprenyl-3-O-methyldihydropinosylvin, or dihydroresveratrol. In some embodiments, the gene encoding a reductase polypeptide comprises SEQ ID NO: 7 or SEQ ID NO: 43. In some embodiments, the gene encoding a reductase polypeptide comprises a nucleotide sequence with at least 70% identity to SEQ ID NO: 7 or at least 80% identity to SEQ ID NO: 43. In some embodiments, the gene encoding a reductase polypeptide encodes a polypeptide comprising (a) SEQ ID NO: 22; (b) SEQ ID NO: 26; (c) a polypeptide with at least 70% identity to SEQ ID NO: 22; or (d) a polypeptide with at least 75% identity to SEQ ID NO: 26.

In another aspect, the disclosure provides recombinant yeast cells comprising a gene encoding a double-bond reductase polypeptide, wherein expression of the gene or activity of the double-bond reductase polypeptide encoded thereby is reduced or eliminated. In some embodiments, the double-bond reductase polypeptide is: (i) an enoyl reductase polypeptide; or (ii) a polyprenol reductase polypeptide. In some embodiments, the enoyl reductase polypeptide is *S. cerevisiae* trans-2-enoyl-CoA reductase TSC13. In some embodiments, the polyprenol reductase polypeptide is *S. cerevisiae* DFG10. In some embodiments, the gene encoding a reductase polypeptide comprises SEQ ID NO: 7 or SEQ ID NO: 43. In some embodiments, the gene encoding a reductase polypeptide comprises a nucleotide sequence with at least 70% identity to SEQ ID NO: 7 or at least 80% identity to SEQ ID NO: 43. In some embodiments, the gene encoding a reductase polypeptide encodes a polypeptide comprising (a) SEQ ID NO: 22; (b) SEQ ID NO: 26; (c) a polypeptide with at least 70% identity to SEQ ID NO: 22; or (d) a polypeptide with at least 75% identity to SEQ ID NO: 26.

In some embodiments of the recombinant yeast cells disclosed herein, the recombinant yeast cells further comprise a recombinant gene encoding an enzyme that partially or completely complements the function of the double-bond reductase polypeptide. In some embodiments, the recombinant gene encoding an enzyme that partially or completely complements the function of the double-bond reductase polypeptide comprises: (a) any one of SEQ ID NOs: 94-96, or (b) a nucleotide sequence with at least 65% identity to any one of SEQ ID NOs: 94-96. In some embodiments, the recombinant gene encoding an enzyme that partially or completely complements the function of the double-bond reductase polypeptide encodes a polypeptide comprising: (a) any one of SEQ ID NOs: 65-67, or (b) a polypeptide with at least 65% identity to any one of SEQ ID NOs: 65-67.

In some embodiments of the recombinant yeast cells disclosed herein, the recombinant yeast cells further comprise a recombinant gene encoding a polyketide synthase Type III polypeptide. In some embodiments, the polyketide synthase Type III polypeptide is: (i) a chalcone synthase polypeptide; or (ii) a stilbene synthase polypeptide. In some embodiments, the gene encoding a chalcone synthase polypeptide comprises SEQ ID NO: 4. In some embodiments, the gene encoding a chalcone synthase polypeptide comprises a nucleotide sequence with at least 65% identity to SEQ ID NO: 4. In some embodiments, the gene encoding a chalcone synthase polypeptide encodes a polypeptide comprising (a) SEQ ID NO: 19; or (b) a polypeptide with at least 65% identity to SEQ ID NO: 19. In some embodiments, the gene encoding a stilbene synthase polypeptide comprises SEQ ID NO: 23. In some embodiments, the gene encoding a stilbene synthase polypeptide comprises a nucleotide sequence with at least 70% identity to SEQ ID NO: 23. In some embodiments, the gene encoding a stilbene synthase polypeptide encodes a polypeptide comprising (a) SEQ ID NO: 24; or (b) a polypeptide with at least 80% identity to SEQ ID NO: 24.

In some embodiments of the recombinant yeast cells disclosed herein, the recombinant yeast cells further comprise one or more of: (c) a recombinant gene encoding a phenylalanine ammonia lyase polypeptide; (d) a recombinant gene encoding a cinnamate 4-hydroxylase polypeptide; (e) a recombinant gene encoding a 4-coumarate-CoA ligase polypeptide; (f) a recombinant gene encoding a cytochrome p450 polypeptide; or (g) a recombinant gene encoding a chalcone isomerase polypeptide.

In some embodiments, the gene encoding a phenylalanine ammonia lyase polypeptide comprises SEQ ID NO: 1. In some embodiments, the gene encoding a phenylalanine ammonia lyase polypeptide comprises a nucleotide sequence with at least 70% identity to SEQ ID NO: 1. In some embodiments, the gene encoding a phenylalanine ammonia lyase polypeptide encodes a polypeptide comprising (a) SEQ ID NO: 16; or (b) a polypeptide with at least 70% identity to SEQ ID NO: 16.

In some embodiments, the gene encoding a cinnamate 4-hydroxylase polypeptide comprises SEQ ID NO: 2. In some embodiments, the gene encoding a cinnamate 4-hydroxylase polypeptide comprises a nucleotide sequence with at least 70% identity to SEQ ID NO: 2. In some embodiments, the gene encoding a cinnamate 4-hydroxylase polypeptide encodes a polypeptide comprising (a) SEQ ID NO: 17; or (b) a polypeptide with at least 70% identity to SEQ ID NO: 17.

In some embodiments, the gene encoding a 4-coumarate-CoA ligase polypeptide comprises SEQ ID NO: 3. In some embodiments, the gene encoding a 4-coumarate-CoA ligase polypeptide comprises a nucleotide sequence with at least 65% identity to SEQ ID NO: 3. In some embodiments, the gene encoding a 4-coumarate-CoA ligase polypeptide encodes a polypeptide comprising (a) SEQ ID NO: 18; or (b) a polypeptide with at least 65% identity to SEQ ID NO: 18.

In some embodiments, the gene encoding a cytochrome p450 polypeptide comprises SEQ ID NO: 6. In some embodiments, the gene encoding a cytochrome p450 polypeptide comprises a nucleotide sequence with at least 65% identity to SEQ ID NO: 6. In some embodiments, the gene encoding a cytochrome p450 polypeptide encodes a polypeptide comprising (a) SEQ ID NO: 21; or (b) a polypeptide with at least 65% identity to SEQ ID NO: 21.

In some embodiments, the gene encoding a chalcone isomerase polypeptide comprises any one of SEQ ID NOS: 80-86. In some embodiments, the gene encoding a chalcone isomerase polypeptide comprises a nucleotide sequence with at least 60% identity to any one of SEQ ID NOS: 80-86. In some embodiments, the gene encoding a chalcone isomerase polypeptide encodes a polypeptide comprising (a) any one of SEQ ID NOS: 87-93; or (b) a polypeptide with at least 65% identity to any one of SEQ ID NOS: 87-93.

In some embodiments of the recombinant yeast cells disclosed herein, the recombinant yeast cells are capable of producing a phenylpropanoid or a phenylpropanoid derivative compound. In some embodiments, the phenylpropanoid is cinnamic acid or coumaric acid. In some embodiments, the phenylpropanoid derivative compound is a chalcone compound or a stilbenoid compound.

In some embodiments, the recombinant yeast cells are *Saccharomyces cerevisiae* cells, *Schizosaccharomyces pombe* cells, *Yarrowia lipolytica* cells, *Candida glabrata* cells, *Ashbya gossypii* cells, *Cyberlindnera jadinii* cells, *Pichia pastoris* cells, *Kluyveromyces lactis* cells, *Hansenula polymorpha* cells, *Candida boidinii* cells, *Arxula adeninivorans* cells, *Xanthophyllomyces dendrorhous* cells, or *Candida albicans* cells. In some embodiments, the recombinant yeast cells are *Saccharomycetes*. In some embodiments, the recombinant yeast cells are cells from the *Saccharomyces cerevisiae* species.

In another aspect, the disclosure provides methods of producing phenylpropanoid or phenylpropanoid derivative compounds, the methods comprising growing recombinant yeast cells as disclosed herein in a culture medium under conditions in which recombinant genes are expressed, and wherein phenylpropanoids or phenylpropanoid derivative compounds are synthesized by the recombinant yeast cells. In some embodiments, the phenylpropanoid compounds are cinnamic acid or coumaric acid. In some embodiments the phenylpropanoid derivative compounds are chalcone compounds or stilbene compounds. In some embodiments, the chalcone compounds comprise resveratrol.

In another aspect, the disclosure provides methods of producing a compound of formula (III):

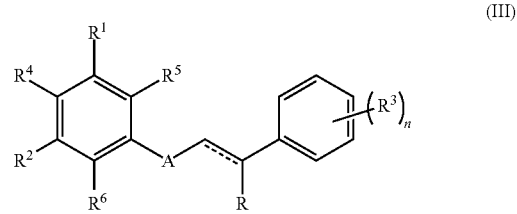

or a pharmaceutically acceptable salt thereof, wherein
A is a bond or C=O;
n is an integer 0, 1, 2, 3, or 4;
R is hydrogen when ≡ is a double bond, or R and $R^5$ together with the atoms to which they are attached form a 6-member heterocyclyl when A is C=O and ≡ is a single bond;
$R^1$ is hydrogen or —$OR^{11}$;
wherein each $R^{11}$ is independently hydrogen, $C_1$-$C_6$ alkyl, or glycosyl;
$R^2$ is hydrogen, —$OR^{11}$, $C_1$-$C_{12}$ alkyl, or $C_2$-$C_{12}$ alkenyl, wherein alkyl and alkenyl are optionally substituted with one or more $R^7$;
or $R^2$ and $R^6$ together with the atoms to which they are attached form a 5- to 7-member heterocyclyl optionally substituted with one or more $R^7$ groups;
or $R^2$ and $R^4$ together with the atoms to which they are attached form a 5- to 7-member heterocyclyl optionally substituted with one or more $R^7$ groups;
$R^3$ is independently selected from nitro, $C_1$-$C_6$ alkyl, $C_2$-$C_6$ alkenyl, $C_1$-$C_6$ haloalkyl, $C_1$-$C_6$ hydroxyalkyl, —$OR^{12}$, —$N(R^{12})_2$, —$C(O)R^{12}$, —$C(O)OR^{12}$, —$C(O)N(R^{12})_2$, and —$S(O)_2R^{12}$, wherein each $R^{12}$ is independently hydrogen or $C_1$-$C_6$ alkyl;
$R^4$ is hydrogen, —$OR^{11}$, $C_1$-$C_{12}$ alkyl, or $C_2$-$C_{12}$ alkenyl, wherein alkyl and alkenyl are optionally substituted with one or more $R^7$;
or $R^4$ and $R^2$ together with the atoms to which they are attached form a 5- to 7-member heterocyclyl optionally substituted with one or more $R^7$ groups;
$R^5$ is hydrogen, —$OR^{11}$, —$C(O)OR^{10}$, or —$C(O)N(R^{10})_2$, wherein each $R^{10}$ is independently hydrogen or $C_1$-$C_6$ alkyl; and
$R^6$ is hydrogen, $C_1$-$C_6$ alkyl, $C_2$-$C_6$ alkenyl, —$OR^{11}$, —$N(R^{10})_2$, —$C(O)R^{10}$, —$C(O)OR^{10}$, or —$C(O)N(R^{10})_2$, wherein alkyl and alkenyl are optionally substituted with one or more $R^8$; or $R^6$ and $R^2$ together with the atoms to which they are attached form a 5- to 7-member heterocyclyl optionally substituted with one or more $R^8$ groups;
each $R^7$ and $R^8$ is independently halogen, cyano, nitro, $C_1$-$C_6$ alkyl, $C_2$-$C_6$ alkenyl, $C_1$-$C_6$ haloalkyl, $C_1$-$C_6$ hydroxyalkyl, —$OR^{13}$, —$SR^{13}$, —$N(R^{13})_2$, —$C(O)R^{13}$, —$C(O)OR^{13}$, —$C(O)N(R^{13})_2$, or —$S(O)_2R^{13}$, wherein each $R^{13}$ is independently hydrogen or $C_1$-$C_6$ alkyl,
comprising growing a recombinant yeast cell of the disclosure in a culture medium under conditions in which the recombinant genes are expressed, and wherein the compound of formula I is synthesized by the recombinant yeast cell. In some embodiments, the methods further comprise harvesting the compounds. In some embodiments, the methods further comprise isolating the compounds.

In another aspect, the disclosure provides recombinant host cells comprising: (a) a recombinant gene encoding an enoyl reductase polypeptide; and (b) a recombinant gene encoding a polyketide synthase Type III polypeptide. In some embodiments, the enoyl reductase polypeptide is overexpressed. In some embodiments, the enoyl reductase polypeptide is a trans-2-enoyl-CoA reductase. In some embodiments, the trans-2-enoyl-CoA reductase is S. cerevisiae TSC13. In some embodiments, the gene encoding the enoyl reductase polypeptide comprises SEQ ID NO: 7. In some embodiments, the gene encoding an enoyl reductase polypeptide has at least 70% identity to SEQ ID NO: 7. In some embodiments, the gene encoding an enoyl reductase polypeptide encodes a polypeptide comprising (a) SEQ ID NO: 22; or (b) a polypeptide with at least 70% identity to SEQ ID NO: 22

In some embodiments, the recombinant gene encoding a polyketide synthase Type III polypeptide comprises: (i) a recombinant gene encoding a chalcone synthase polypeptide; or (ii) a recombinant gene encoding a stilbene synthase polypeptide. In some embodiments, the gene encoding a chalcone synthase polypeptide comprises one of SEQ ID NOs: 4, 27, or 68-70. In some embodiments, the gene encoding a chalcone synthase polypeptide comprises a nucleotide sequence with at least 65% identity to one of SEQ ID NOs: 4, 27, or 68-70. In some embodiments, the gene encoding a chalcone synthase polypeptide encodes a polypeptide comprising (a) one of SEQ ID NOs: 19, 49, or 71-73; (b) a polypeptide with at least 65% identity to one of SEQ ID NOs: 19, 49, or 71-73; or (c) a polypeptide with at least 90% sequence identity to one of SEQ ID NOs: 19 or 71-73 in the combined regions spanning amino acids 95-105, 132-142, 191-201, and 266-276 of the one of SEQ ID NOs: 19 or 71-73. In some embodiments, the gene encoding a stilbene synthase polypeptide comprises SEQ ID NO: 23. In some embodiments, the gene encoding a stilbene synthase polypeptide comprises a nucleotide sequence with at least 70% identity to SEQ ID NO: 23. In some embodiments, the gene encoding a stilbene synthase polypeptide encodes a polypeptide comprising (a) SEQ ID NO: 24; or (b) a polypeptide with at least 80% identity to SEQ ID NO: 24.

In some embodiments, the recombinant host cells further comprise one or more of: (c) a recombinant gene encoding a phenylalanine ammonia lyase polypeptide; (d) a recombinant gene encoding a cinnamate 4-hydroxylase polypeptide; (e) a recombinant gene encoding a 4-coumarate-CoA ligase polypeptide; (f) a recombinant gene encoding a cytochrome p450 polypeptide; or (g) a recombinant gene encoding a UDP glycosyl transferase (UGT) polypeptide. In some embodiments, the gene encoding a phenylalanine ammonia lyase polypeptide comprises SEQ ID NO: 1. In some embodiments, the gene encoding a phenylalanine ammonia lyase polypeptide comprises a nucleotide sequence with at least 70% identity to SEQ ID NO: 1. In some embodiments, the gene encoding a phenylalanine ammonia lyase polypeptide encodes a polypeptide comprising (a) SEQ ID NO: 16; or (b) a polypeptide with at least 70% identity to SEQ ID NO: 16. In some embodiments, the gene encoding a cinnamate 4-hydroxylase polypeptide comprises SEQ ID NO: 2. In some embodiments, the gene encoding a cinnamate 4-hydroxylase polypeptide comprises a nucleotide sequence with at least 70% identity to SEQ ID NO: 2. In some embodiments, the gene encoding a cinnamate 4-hydroxylase polypeptide encodes a polypeptide comprising (a) SEQ ID NO: 17; or (b) a polypeptide with at least 70% identity to SEQ ID NO: 17. In some embodiments, the gene encoding a 4-coumarate-CoA ligase polypeptide comprises SEQ ID NO: 3. In some embodiments, the gene encoding a 4-coumarate-CoA ligase polypeptide comprises a nucleotide sequence with at least 65% identity to SEQ ID NO: 3. In some embodiments, the gene encoding a 4-coumarate-CoA ligase polypeptide encodes a polypeptide comprising (a) SEQ ID NO: 18; or (b) a polypeptide with at least 65% identity to SEQ ID NO: 18. In some embodiments, the gene encoding a UDP glycosyl transferase (UGT) polypeptide comprises SEQ ID NO: 5. In some embodiments, the gene encoding a UDP glycosyl transferase (UGT) polypeptide comprises a nucleotide sequence with at least 65% identity to SEQ ID NO: 5. In some embodiments, the gene encoding a UDP glycosyl transferase (UGT) polypeptide encodes a polypeptide comprising (a) SEQ ID NO: 20; or (b) a polypeptide with at least 70% identity to SEQ ID NO: 20.

In some embodiments, the recombinant host cell is a yeast cell, a plant cell, a mammalian cell, an insect cell, a fungal cell, or a bacterial cell. In some embodiments, the bacterial cell comprises an *Escherichia* cell, a *Lactobacillus* cell, a *Lactococcus* cell, a *Cornebacterium* cell, an *Acetobacter* cell, an *Acinetobacter* cell, or a *Pseudomonas* cell. In some embodiments, the yeast cell comprises a *Saccharomyces cerevisiae* cell, a *Schizosaccharomyces pombe* cell, a *Yarrowia lipolytica* cell, a *Candida glabrata* cell, a *Ashbya gossypii* cell, a *Cyberlindnera jadinii* cell, a *Pichia pastoris* cell, a *Kluyveromyces lactis* cell, a *Hansenula polymorpha* cell, a *Candida boidinii* cell, an *Arxula adeninivorans* cell, a *Xanthophyllomyces dendrorhous* cell, or a *Candida albicans* cell. In some embodiments, the yeast cell is a Saccharomycete. In some embodiments, the yeast cell is a cell from the *Saccharomyces cerevisiae* species.

In another aspect, the disclosure provides methods of producing dihydrophenylpropanoid derivative compounds, such as dihydrochalcone compounds or dihydrostilbene compounds, comprising growing a recombinant host cell as disclosed herein in a culture medium under conditions in which the recombinant genes are expressed, and wherein said compound is synthesized by the recombinant host cell. In some embodiments, the methods are methods of producing a dihydrochalcone compound. In some embodiments, the dihydrochalcone compound is phloretin or a phloretin derivative. In some embodiments, the phloretin derivative is phlorizin. In some embodiments, the methods are methods of producing a dihydrostilbenoid compound.

In another aspect, the disclosure provides methods of producing compounds of formula (III):

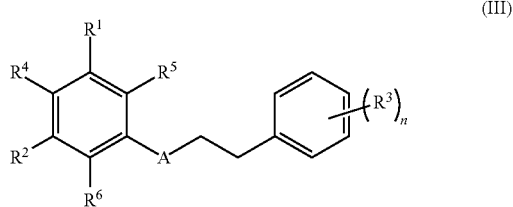

(III)

or a pharmaceutically acceptable salt thereof, wherein
A is a bond or C=O;
n is an integer 0, 1, 2, 3, or 4;
$R^1$ is hydrogen or $-OR^{11}$;
wherein each $R^{11}$ is independently hydrogen, $C_1$-$C_6$ alkyl, or glycosyl;
$R^2$ is hydrogen, $-OR^{11}$, $C_1$-$C_{12}$ alkyl, or $C_2$-$C_{12}$ alkenyl, wherein alkyl and alkenyl are optionally substituted with one or more $R^7$;
or $R^2$ and $R^6$ together with the atoms to which they are attached form a 5- to 7-member heterocyclyl optionally substituted with one or more $R^7$ groups;
or $R^2$ and $R^4$ together with the atoms to which they are attached form a 5- to 7-member heterocyclyl optionally substituted with one or more $R^7$ groups;
$R^3$ is independently selected from nitro, $C_1$-$C_6$ alkyl, $C_2$-$C_6$ alkenyl, $C_1$-$C_6$ haloalkyl, $C_1$-$C_6$ hydroxyalkyl, $-OR^{12}$, $-N(R^{12})_2$, $-C(O)R^{12}$, $-C(O)OR^{12}$, $-C(O)N(R^{12})_2$, and $-S(O)_2R^{12}$, wherein each $R^{12}$ is independently hydrogen or $C_1$-$C_6$ alkyl;

$R^4$ is hydrogen, $-OR^{11}$, $C_1$-$C_{12}$ alkyl, or $C_2$-$C_{12}$ alkenyl, wherein alkyl and alkenyl are optionally substituted with one or more $R^7$;
or $R^4$ and $R^2$ together with the atoms to which they are attached form a 5- to 7-member heterocyclyl optionally substituted with one or more $R^7$ groups;
$R^5$ is hydrogen or $-OR^{11}$; and
$R^6$ is hydrogen, $C_1$-$C_6$ alkyl, $C_2$-$C_6$ alkenyl, $-OR^{11}$, or $-N(R^{10})_2$, wherein each $R^{10}$ is independently hydrogen or $C_1$-$C_6$ alkyl, and wherein alkyl and alkenyl are optionally substituted with one or more $R^8$; or $R^6$ and $R^2$ together with the atoms to which they are attached form a 5- to 7-member heterocyclyl optionally substituted with one or more $R^8$ groups;
each $R^7$ and $R^8$ is independently halogen, cyano, nitro, $C_1$-$C_6$ alkyl, $C_2$-$C_6$ alkenyl, $C_1$-$C_6$ haloalkyl, $C_1$-$C_6$ hydroxyalkyl, $-OR^{13}$, $-SR^{13}$, $-N(R^{13})_2$, $-C(O)R^{13}$, $-C(O)OR^{13}$, $-C(O)N(R^{13})_2$, or $-S(O)_2R^{13}$, wherein each $R^{13}$ is independently hydrogen or $C_1$-$C_6$ alkyl, comprising growing a recombinant host cell as disclosed herein in a culture medium under conditions in which the recombinant genes are expressed, and wherein the compound of formula III is synthesized by the recombinant host cell. In some embodiments, the methods further comprise harvesting the compounds from the culture media. In some embodiments, the methods further comprise isolating the compounds from the culture media.

These and other features and advantages will be more fully understood from the following detailed description taken together with the accompanying claims.

BRIEF DESCRIPTION OF THE DRAWINGS

The following detailed description can be best understood when read in conjunction with the following drawings in which.

DETAILED DESCRIPTION

Figure 1:
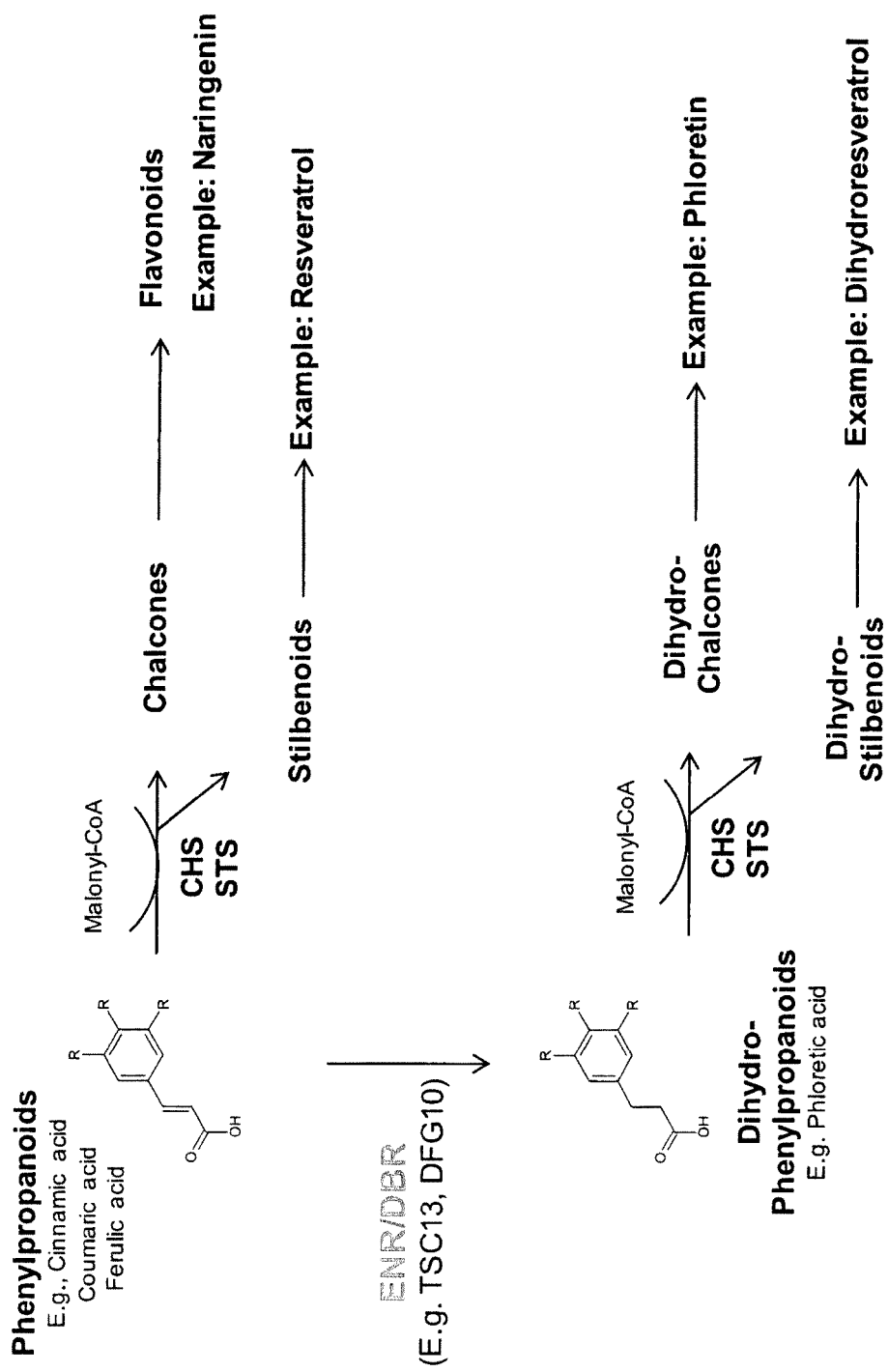
FIG. 1 contrasts the biosynthesis of phenylpropanoid-derived chalcones and stilbenes with biosynthesis of dihydrophenylpropanoid-derived dihydrochalcones and dihydrostilbenes. The action of a double bond reductase (DBR) separates these biosynthetic branches.
Figure 2:
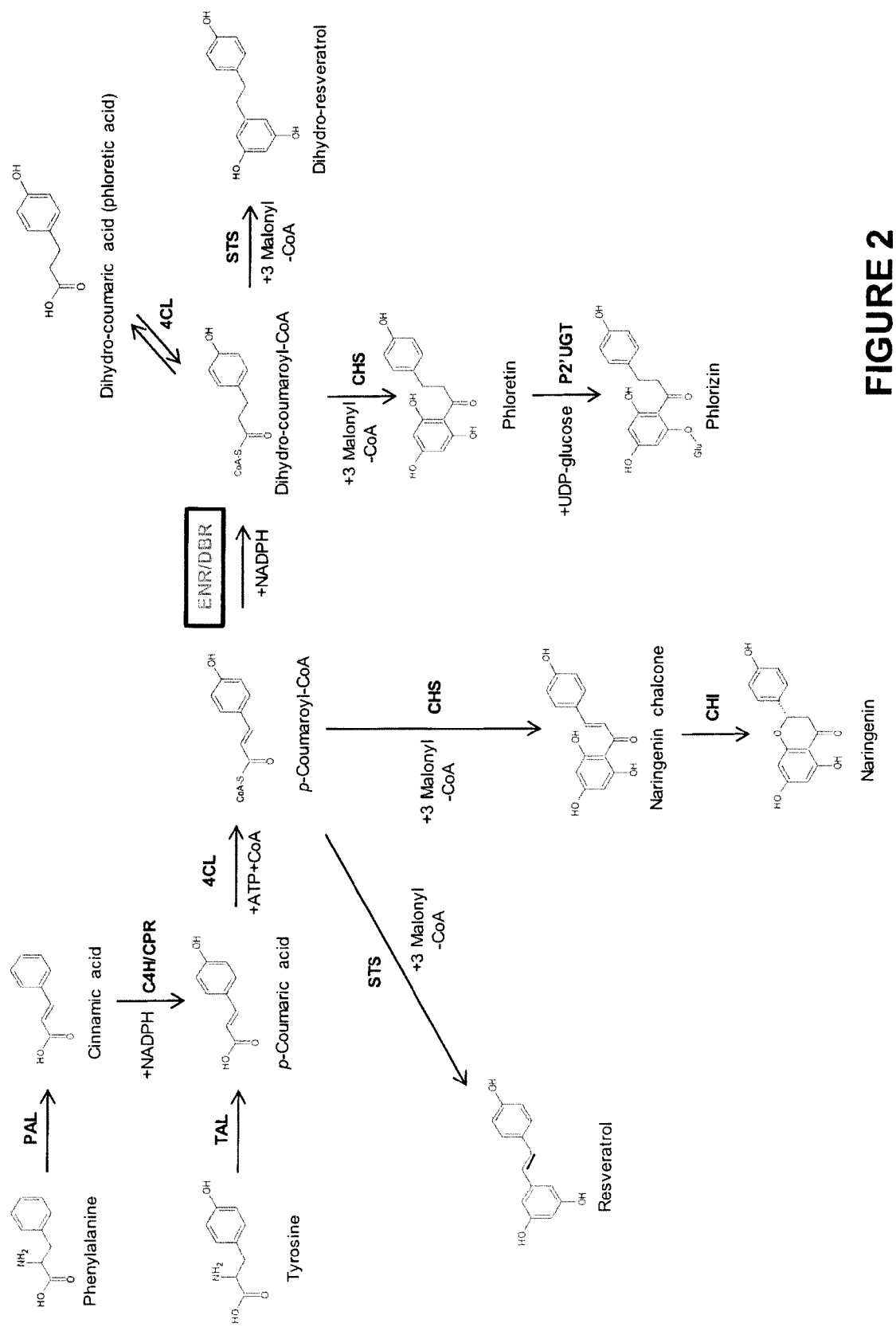
FIG. 2 shows the phenylpropanoid pathway branching from p-coumaric acid to a variety of phenylpropanoid derivatives and dihydrophenylpropanoid derivatives, separated by the action of a DBR enzyme. (The corresponding pathway from cinnamic acid (instead of p-coumaric acid) is shown in FIG. 3.) The actions of two PKS type III enzymes are shown on each side: chalcone synthase (CHS) and stilbene synthase (STS). Other enzyme abbreviations are: phenylalanine lyase (PAL or TAL); cinnamate-4-hydroxylase (C4H) which requires the activity of a reductase (CPR); 4-Coumaroyl-CoA ligase (4CL); chalcone isomerase (CHI); and the phlorizin glucosyl transferase (P2'UGT).
Figure 3:
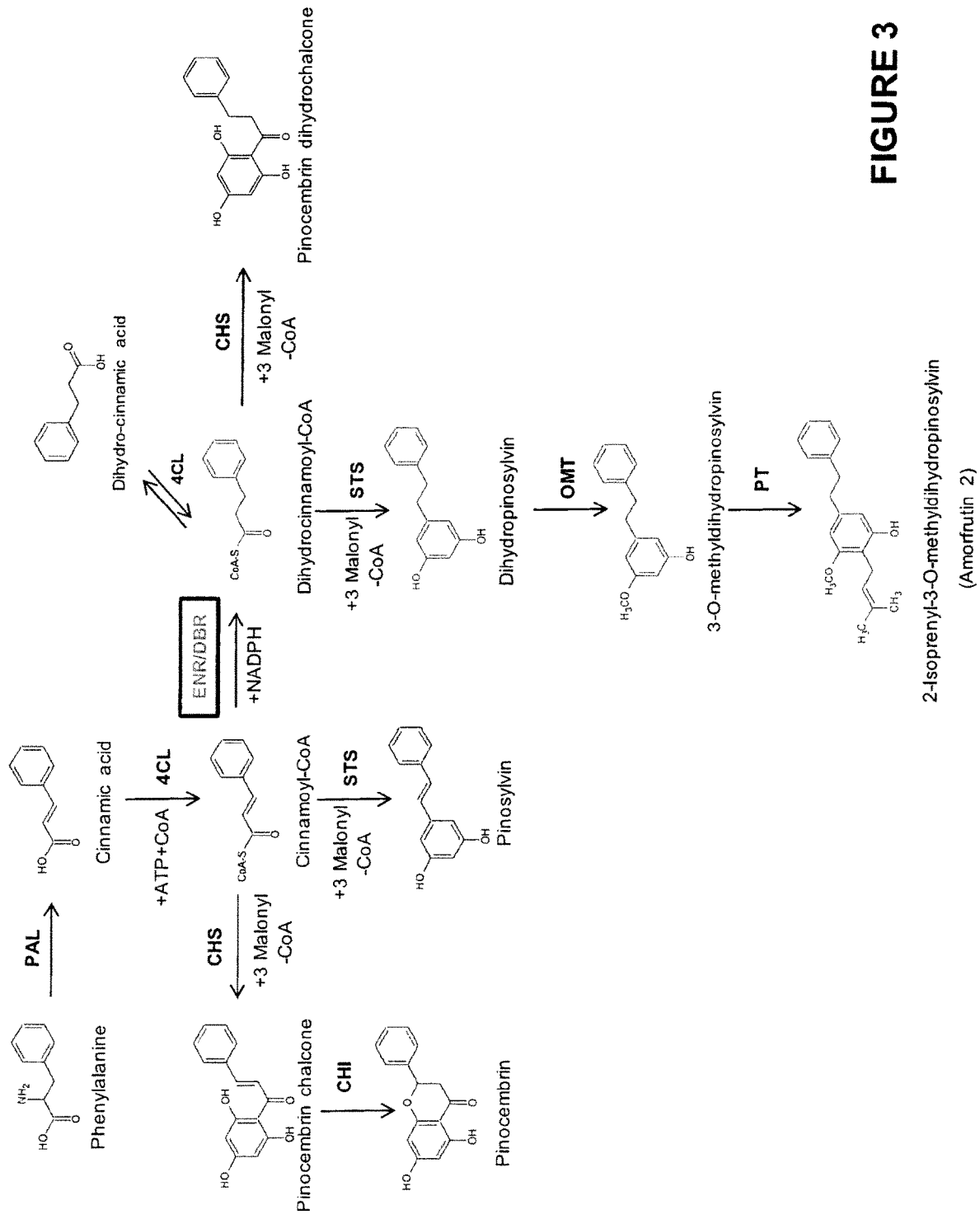
FIG. 3 shows phenylpropanoid/dihydrophenylpropanoid pathways branching from cinnamic acid (rather than p-coumaric acid, as shown in FIG. 2). As in FIG. 2, two branches are shown on each side, represented by CHS and STS. Other enzyme abbreviations are: O-methyl transferase (OMT) and prenyltransferase (PT).

All publications, patents and patent applications cited herein are hereby expressly incorporated by reference for all purposes.

Because many phenylpropanoid derivatives and dihydrophenylpropanoid derivatives are useful as, inter alia, pharmaceutical compounds, there is a need for efficient methods of their production. For example, the dihydrochalcones phlorizin and phloretin are useful for controlling blood sugar levels, as well as other potential uses to improve human health. The chalcone naringenin, and the stilbene resveratrol, are useful for controlling blood sugar levels, as well as other potential uses to improve human health.

Accordingly, provided herein are materials and methods useful for biosynthesis of phenylpropanoid derivatives, including chalcones and stilbenes, and dihydrophenylpropanoid derivatives, including dihydrochalcones and dihydrostilbenes. In some embodiments, the disclosure provides recombinant hosts and methods for biosynthesis of naringenin and other chalcones. In some embodiments, the disclosure provides recombinant hosts and methods for biosynthesis of resveratrol and other stilbenes. In some embodiments, the disclosure provides recombinant hosts and methods for biosynthesis of phlorizin and phlorizin precursors.

Before describing the disclosed methods and compositions in detail, a number of terms will be defined. As used herein, the singular forms "a", "an", and "the" include plural referents unless the context clearly dictates otherwise. For example, reference to a "nucleic acid" means one or more nucleic acids.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of this invention.

For the purposes of describing and defining this invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Methods well known to those skilled in the art can be used to construct the genetic expression constructs and recombinant cells disclosed herein. These methods include in vitro recombinant DNA techniques, synthetic techniques, in vivo recombination techniques, and polymerase chain reaction (PCR) techniques. See, for example, techniques as described in Maniatis et al., 1989, MOLECULAR CLONING: A LABORATORY MANUAL, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, Calif.).

As used herein, the terms "polynucleotide", "nucleotide", "oligonucleotide", and "nucleic acid" can be used interchangeably to refer to nucleic acid comprising DNA, RNA, derivatives thereof, or combinations thereof.

As used herein, the terms "microorganism," "microorganism host," "microorganism host cell," "recombinant host," "host cell," and "recombinant host cell" can be used interchangeably. As used herein, the term "recombinant host" is intended to refer to a host, the genome of which has been augmented by at least one DNA sequence. Such DNA sequences include but are not limited to genes or DNA sequences that are not naturally present, that are not normally transcribed into RNA, nor translated into protein ("expressed") natively in the cell, and other genes or DNA sequences one desires to introduce into a host. It will be appreciated that typically the genome of a recombinant host described herein is augmented through stable introduction of one or more recombinant genes. Generally, introduced DNA is not originally resident in the host that is the recipient of the DNA, but it is within the scope of this disclosure to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms.

As used herein, the term "gene" refers to a polynucleotide unit comprised of at least one of the DNA sequences disclosed herein, or any DNA sequences encoding the amino acid sequences disclosed herein, or any DNA sequence that hybridizes to the complement of the coding sequence disclosed herein. Preferably, the term includes coding and non-coding regions, and preferably all sequences necessary for normal gene expression including promoters, enhancers, and other regulatory sequences.

As used herein, the term "recombinant gene" refers to a gene or DNA sequence that is introduced into a recipient host, regardless of whether the same or a similar gene or DNA sequence may already be present in such a host. "Introduced," or "augmented" in this context, is known in the art to mean introduced or augmented by the hand of man. Thus, a recombinant gene can be a DNA sequence from another species, or can be a DNA sequence that originated from or is present in the same species, but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA. The recombinant genes are particularly encoded by cDNA.

A recombinant gene encoding a polypeptide described herein comprises the coding sequence for that polypeptide, operably linked in sense orientation to one or more regulatory regions suitable for expressing the polypeptide. Because many microorganisms can be capable of expressing multiple gene products from a polycistronic mRNA, multiple polypeptides are optionally expressed under the control of a single regulatory region for those microorganisms, if desired. A coding sequence and a regulatory region are operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene. In many cases, the coding sequence for a polypeptide described herein is identified in a species other than the recombinant microorganism, i.e., is a heterologous nucleic acid. Thus, the coding sequence can be from other prokaryotic or eukaryotic microorganisms, from plants or from animals. In some cases, however, the coding sequence is a sequence that is native to the microorganism and is being reintroduced into that organism.

As used herein, the term "engineered biosynthetic pathway" refers to a biosynthetic pathway that occurs in a recombinant host, as described herein, and does not naturally occur in the host. In some embodiments, the engineered biosynthetic pathway comprises enzymes naturally produced by the host, wherein in certain embodiments the extent and amount of expression of the genes encoding these enzymes are altered in the recombinant host; in some embodiments these enzymes are overexpressed in the recombinant host.

As used herein, the term "endogenous" gene refers to a gene that originates from and is produced or synthesized within a particular organism, tissue, or cell.

As used herein, the terms "heterologous sequence" and "heterologous coding sequence" are used to describe a sequence derived from a species other than the recombinant host. In some embodiments, the recombinant host is an *S. cerevisiae* cell, and a heterologous sequence is derived from an organism other than *S. cerevisiae*. A heterologous coding sequence, for example, can be from a prokaryotic microorganism, a eukaryotic microorganism, a plant, an animal, an insect, or a fungus different than the recombinant host expressing the heterologous sequence. In some embodiments, a coding sequence is a sequence that is native to the host.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned at further distance, for example as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region may be present, e.g., introns, enhancers, upstream activation regions, transcription terminators, and inducible elements. One or more genes can be combined in a recombinant nucleic acid construct in "modules" useful for a discrete aspect of compound production. Combining a plurality of genes in a module, particularly a polycistronic module, facilitates the use of the module in a variety of species. In addition to genes useful for compound production, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular microorganism is obtained, using appropriate codon bias tables for that microorganism. Nucleic acids may also be optimized to a GC-content preferable to a particular microorganism, and/or to reduce the number of repeat sequences. As isolated nucleic acids, these modified sequences can exist as purified molecules and can be incorporated into a vector or a virus for use in constructing modules for recombinant nucleic acid constructs. In addition, heterologous nucleic acids can be modified for increased or even optimal expression in the relevant microorganism. Thus, in some embodiments of the methods and compositions disclosed herein, heterologous nucleic acids have been codon optimized for expression in the relevant microorganism. Codon optimization may be performed by routine methods known in the art (See e.g., Welch, M., et al. (2011), Methods in Enzymology 498:43-66).

Phenylpropanoid Derivatives and Dihydrophenylpropanoid Derivatives

As used herein, the terms "chalcone" and "chalconoid" are interchangeable and refer to derivatives the compound of formula (I):

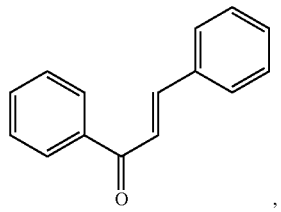

(I)

wherein formula (I) may be substituted at one or more suitable positions. Exemplary substituents include, but are not limited to, halogen, cyano, nitro, $C_1$-$C_6$ alkyl, $C_1$-$C_6$ haloalkyl, $C_1$-$C_6$ hydroxyalkyl, hydroxy, $C_1$-$C_6$ alkoxy, thiol, $C_1$-$C_6$ alkylthio, amino, $C_1$-$C_6$ alkyl amino, di-$C_1$-$C_6$ alkyl amino, carboxyl, $C_1$-$C_6$ alkoxycarbonyl, amido, and glycosyl.

As used herein, the terms "stilbene" and "stilbenoid" are interchangeable and refer to compounds based on the compound of formula (II):

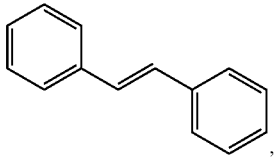

(II)

wherein formula (II) may be substituted at one or more suitable positions. Exemplary substituents include, but are not limited to, halogen, cyano, nitro, $C_1$-$C_6$ alkyl, $C_1$-$C_6$ haloalkyl, $C_1$-$C_6$ hydroxyalkyl, hydroxy, $C_1$-$C_6$ alkoxy, thiol, $C_1$-$C_6$ alkylthio, amino, $C_1$-$C_6$ alkyl amino, di-$C_1$-$C_6$ alkyl amino, carboxyl, $C_1$-$C_6$ alkoxycarbonyl, amido, and glycosyl.

As used herein, the terms "dihydrochalcone" and "dihydrochalconoid" are interchangeable and refer to derivatives the compound of formula (I):

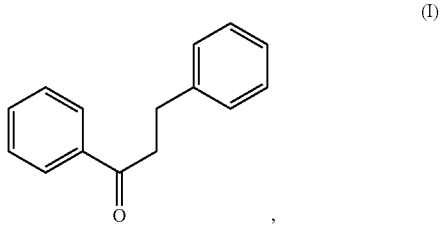 [SMILES: O=C(CCc1ccccc1)c1ccccc1]

(I)

wherein formula (I) may be substituted at one or more suitable positions. Exemplary substituents include, but are not limited to, halogen, cyano, nitro, $C_1$-$C_6$ alkyl, $C_1$-$C_6$ haloalkyl, $C_1$-$C_6$ hydroxyalkyl, hydroxy, $C_1$-$C_6$ alkoxy, thiol, $C_1$-$C_6$ alkylthio, amino, $C_1$-$C_6$ alkyl amino, di-$C_1$-$C_6$ alkyl amino, carboxyl, $C_1$-$C_6$ alkoxycarbonyl, amido, and glycosyl.

As used herein, the terms "dihydrostilbene" and "dihydrostilbenoid" are interchangeable and refer to compounds based on the compound of formula (II):

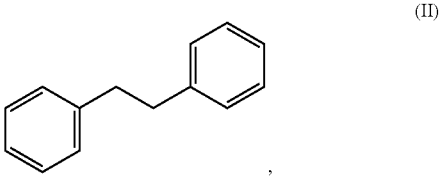 [SMILES: c1ccc(CCc2ccccc2)cc1]

(II)

wherein formula (II) may be substituted at one or more suitable positions. Exemplary substituents include, but are not limited to, halogen, cyano, nitro, $C_1$-$C_6$ alkyl, $C_1$-$C_6$ haloalkyl, $C_1$-$C_6$ hydroxyalkyl, hydroxy, $C_1$-$C_6$ alkoxy, thiol, $C_1$-$C_6$ alkylthio, amino, $C_1$-$C_6$ alkyl amino, di-$C_1$-$C_6$ alkyl amino, carboxyl, $C_1$-$C_6$ alkoxycarbonyl, amido, and glycosyl.

As used herein, the term "phenylpropanoid" refers to compounds based on a 3-phenylprop-2-enoate backbone. Examples of such compounds include, but are not limited to, cinnamic acid, coumaric acid, caffeic acid, ferulic acid, 5-hydroxyferulic acid, sinapinic acid, cinnamoyl-CoA, p-coumaroyl-CoA, and the like.

As used herein, the terms "phenylpropanoid derivative" and "phenylpropanoid derivative compound" are interchangeable and refer to any compound derived from, synthesized from, or biosynthesized from a phenylpropanoid; i.e. a phenylpropanoid derivative includes any compound for which a phenylpropanoid compound is a precursor or intermediate. Examples of phenylpropanoid derivatives include, but are not limited to, stilbene compounds and chalcone compounds. Specific examples of phenylpropanoid derivatives include, but are not limited to, naringenin, resveratrol, pinosylvin, pinocembrin chalcone, and pinocembrin.

As used herein, the term "dihydrophenylpropanoid" refers to compounds based on a phenylpropanoate backbone. Examples of such compounds include, but are not limited to, dihydrocinnamic acid, phloretic acid, 3,4-dihydroxyhydrocinnamic acid, hydroferulic acid, dihydrocoumaroyl-CoA, dihydrocinnamoyl-CoA, and the like.

As used herein, the terms "dihydrophenylpropanoid derivative" and "dihydrophenylpropanoid derivative compound" are interchangeable and refer to any compound derived from, synthesized from, or biosynthesized from a dihydrophenylpropanoid; i.e. a dihydrophenylpropanoid derivative includes any compound for which a dihydrophenylpropanoid compound is a precursor or intermediate. Examples of dihydrophenylpropanoid derivatives include, but are not limited to, dihydrostilbenoid compounds and dihydrochalcone compounds. Specific examples of dihydrophenylpropanoid derivatives include, but are not limited to, phloretin, phlorizin, dihydropinosylvin, 3-O-methyldihydropinosylvin, 2-isoprenyl-3-O-methyldihydropinosylvin (amorfrutin 2; IUPAC: 3-methoxy-2-(3-methylbut-2-en-1-yl)-5-phenethylphenol), and dihydroresveratrol.

As used herein, the terms "phenylpropanoid pathway," "phenylpropanoid derivative pathway," "phenylpropanoid derivative synthesis pathway," and "phenylpropanoid derivative biosynthesis pathway" are interchangeable and refer to any biosynthesis pathway in which a phenylpropanoid is a precursor or intermediate and in which a phenylpropanoid derivative compound is a product. Phenylpropanoid derivatives, such as chalcones and stilbenes, are biosynthesized according to phenylpropanoid derivative biosynthesis pathways.

As used herein, the terms "dihydrophenylpropanoid pathway," "dihydrophenylpropanoid derivative pathway," "dihydrophenylpropanoid derivative synthesis pathway," and "dihydrophenylpropanoid derivative biosynthesis pathway" are interchangeable and refer to any biosynthesis pathway in which a phenylpropanoid or dihydrophenylpropanoid is a precursor or intermediate and in which a dihydrophenylpropanoid derivative compound is a product. Dihydrophenylpropanoid derivatives, such as dihydrochalcones and dihydrostilbenes, are biosynthesized according to dihydrophenylpropanoid derivative biosynthesis pathways.

As used herein, the term "alkyl" means a straight or branched chain hydrocarbon containing from 1 to 20 carbon atoms unless otherwise specified. The term "$C_m$-$C_n$ alkyl" means an alkyl group having from m to n carbon atoms. For example, "$C_1$-$C_6$ alkyl" is an alkyl group having from one to six carbon atoms. Representative examples of alkyl include, but are not limited to, methyl, ethyl, n-propyl, isopropyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means a straight or branched chain hydrocarbon containing from 2 to 20 carbons, unless otherwise specified, and containing at least one carbon-carbon double bond. The term "$C_m$-$C_n$ alkenyl" means an alkenyl group having from m to n carbon atoms. For example, "$C_2$-$C_6$ alkenyl" is an alkenyl group having from one to six carbon atoms. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl, and 2-propyl-2-heptenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The terms "cyano" and "nitrile" as used herein, mean a —CN group.

The term "halogen" as used herein, means —Cl, —Br, —I or —F.

The term "haloalkyl" refers to an alkyl group, which is substituted with one or more halogen atoms.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle may be attached through either cyclic moiety (e.g., either through heterocycle or through phenyl.) Representative examples of heterocycle include, but are not limited to, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, trithianyl, 2,3-dihydrobenzofuran-2-yl, and indolinyl.

The term "hydroxyalkyl" refers to an alkyl group, which is substituted with one or more —OH groups.

As used herein, the term "glycosyl" means is a univalent radical obtained by removing the hemiacetal hydroxyl group from the cyclic form of a monosaccharide or disaccharide. The monosaccharide or monosaccharides units can be selected from any 5-9 carbon atom containing sugars consisting of aldoses (e.g. D-glucose, D-galactose, D-mannose, D-ribose, D-arabinose, L-arabinose, D-xylose, etc.), ketoses (e.g. D-fructose, D-sorbose, D-tagatose, etc.), deoxysugars (e.g. L-rhamnose, L-fucose, etc.), deoxy-aminosugars (e.g. N-acetylglycosamine, N-acetylmannosamine, N-acetylgalactosamine, etc.), uronic acids, ketoaldonic acids (e.g. sialic acid) and like.

The term "nitro" as used herein, means a —$NO_2$ group.

The phrase "one or more" substituents, as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term, unless stated otherwise.

The term "substituted," as used herein, means that a hydrogen radical of the designated moiety is replaced with the radical of a specified substituent, provided that the substitution results in a stable or chemically feasible compound.

Biosynthesis of Phenylpropanoid Derivative Compounds

In one aspect, the disclosure provides recombinant host cells engineered to reduce or eliminate expression of genes or activity of polypeptides in a phenylpropanoid derivative biosynthetic pathway. In some embodiments, the recombinant hosts have reduced or eliminated capacity to carry out reduction of an enoyl double bond of a phenylpropanoid to a dihydrophenylpropanoid, thereby reducing or eliminating production of dihydrophenylpropanoids and dihydrophenylpropanoid derivatives in favor of phenylpropanoids and phenylpropanoid derivatives. For example, in some embodiments the recombinant hosts have reduced or eliminated capacity to carry out reduction of the double bond of p-coumaroyl-CoA to dihydrocoumaroyl-CoA, or to carry out reduction of the double bond of cinnamoyl-CoA to dihydrocinnamoyl-CoA. In some embodiments, reduction of an enoyl double bond is carried out by an enoyl reductase. In some embodiments, reduction of an enoyl double bond is carried out by a polyprenol reductase. These reductases are also referred to collectively as double bond reductases (DBRs). Thus DBRs are a class of reductases that includes, inter alia, enoyl reductases and polyprenol reductases.

In some embodiments, the enoyl reductase comprises *Saccharomyces cerevisiae* trans-2-enoyl-CoA reductase (TSC13), or a functional homolog thereof. In some embodiments, the enoyl reductase is encoded by a gene comprising the sequence disclosed herein as SEQ ID NO: 7. In some embodiments, the enoyl reductase is encoded by a gene with at least 70% identity to SEQ ID NO: 7. In some embodiments, the enoyl reductase is a polypeptide with at least 70% identity to SEQ ID NO: 22.

In some embodiments, the polyprenol reductase comprises the *Saccharomyces cerevisiae* polyprenol reductase DFG10, or a functional homolog thereof. In some embodiments, the polyprenol reductase is encoded by a gene comprising the sequence disclosed herein as SEQ ID NO: 43. In some embodiments, the polyprenol reductase is encoded by a gene with at least 80% identity to SEQ ID NO: 43. In some embodiments, the polyprenol reductase is a polypeptide with at least 75% identity to SEQ ID NO: 26.

As used herein, "reduced expression" refers to expression of a gene or protein at a level lower than the native expression of the gene or protein. For example, in some embodiments the activity of a reductase is reduced by decreasing the amount of protein product, or expression, of a gene encoding the reductase.

Reduction or elimination (i.e., disruption) of expression of a gene can be accomplished by any known method, including insertions, missense mutations, frame shift mutations, deletion, substitutions, or replacement of a DNA sequence, or any combinations thereof. Insertions include the insertion of the entire genes, which may be of any origin. Reduction or elimination of gene expression can, for example, comprise altering or replacing a promoter, an enhancer, or splice site of a gene, leading to inhibition of production of the normal gene product partially or completely. In some embodiments, reduction or elimination of gene expression comprises altering the total level of the protein product expressed in the cell or organism. In other embodiments, disruption of a gene comprises reducing or eliminating the activity of the protein product of the gene in a cell or organism. In some embodiments of the disclosure, the disruption is a null disruption, wherein there is no significant expression of the gene. In some embodiments the disruption of a gene in a host cell or organism occurs on both chromosomes, in which case it is a homozygous disruption. In other embodiments the disruption of a gene in a host cell or organism occurs on only one chromosome, leaving the other chromosomal copy intact, in which case it is a heterozygous gene disruption. In still other embodiments each copy of a gene in a host cell or organism is disrupted differently.

Reduction or elimination of gene expression may also comprise gene knock-out or knock-down. A "gene knock-out" refers to a cell or organism in which the expression of one or more genes is eliminated. A "gene knock-down" refers to a cell or organism in which the level of one or more genes is reduced, but not completely eliminated.

In some embodiments, expression of a gene is reduced or eliminated by techniques such as RNA interference (RNAi), a process by which RNA molecules are used to inhibit gene expression, typically by causing destruction of specific mRNA molecules. RNAi is also known as co-suppression, post-transcriptional gene silencing (PTGS), and quelling.

As used herein, "reduced activity" refers to activity of a polypeptide, such as, for example, an enzyme, at a level lower than the native activity level of the polypeptide. Any means of reducing activity of a polypeptide can be used in the disclosed embodiments. For example, the sequence or the structure of the double-bond reductase may be altered, resulting in lower activity towards the original substrates of the enzyme. In another example, the activity of a double-bond reductase polypeptide may be reduced by growing a host cell in the presence of an inhibitor of the double-bond reductase polypeptide, or by co-expressing or co-producing an inhibitor of the double-bond reductase polypeptide.

In some embodiments, recombinant yeast cells disclosed herein further comprise a recombinant gene encoding an enzyme that partially or completely complements the function of the double-bond reductase polypeptide. As used herein, the phrase "complements the function of" refers to an enzyme that carries out some or all of the native functions of the enzyme it "complements." For example, reduction or elimination of expression or activity of a DBR polypeptide may, in some embodiments, result in lethality or poor growth of host cells. To ameliorate the resulting lethality or poor growth, a complementary enzyme may be introduced (e.g., recombinantly) that carries out the activity of the reduced/eliminated DBR necessary for growth, but which does not catalyze the conversion of phenylpropanoids into dihydrophenylpropanoids (e.g., which does not take coumaric acid or cinnamic acid as a substrate). Examples of enzymes that partially or completely complement the function of a DBR include, without limitation, other enoyl reductases and polyprenol reductases.

In some embodiments, the recombinant gene encoding an enzyme that partially or completely complements the function of the double-bond reductase polypeptide comprises: (a) any one of SEQ ID NOs: 94-96, or (b) a nucleotide sequence with at least 65% identity to any one of SEQ ID NOs: 94-96. In some embodiments, the recombinant gene encoding an enzyme that partially or completely complements the function of the double-bond reductase polypeptide encodes a polypeptide comprising: (a) any one of SEQ ID NOs: 65-67, or (b) a polypeptide with at least 65% identity to any one of SEQ ID NOs: 65-67.

In some embodiments of the recombinant yeast cells disclosed herein, the recombinant yeast cells further comprise a recombinant gene encoding a polyketide synthase Type III polypeptide. In some embodiments In some embodiments, recombinant yeast cells of the disclosure are further engineered to overexpress a recombinant polyketide synthase Type III polypeptide. In some embodiments, the recombinant polyketide synthase Type III polypeptide comprises: (i) a recombinant chalcone synthase polypeptide; or (ii) a recombinant stilbene synthase polypeptide.

In some embodiments, the recombinant host cells further comprise one or more polypeptides of a phenylpropanoid derivative biosynthesis pathway. In some embodiments, recombinant genes are provided that catalyze formation of intermediates in the biosynthesis of chalcones, stilbenes, or other phenylpropanoid derivatives. Intermediates comprise, inter alia, cinnamic acid, cinnamoyl-CoA, p-coumaric acid, p-coumaroyl CoA, naringenin, and resveratrol.

In some embodiments, recombinant cells further comprise an endogenous or recombinant gene encoding a phenylalanine ammonia lyase polypeptide, which catalyzes the formation of cinnamic acid. In some embodiments, the recombinant host cells express a polypeptide with homology to the *Arabidopsis thaliana* PAL2 gene. In some embodiments, the recombinant host cells express a recombinant gene comprising the sequence disclosed herein as SEQ ID NO: 1. In other embodiments, the recombinant host cells express a recombinant gene with at least 70% identity to SEQ ID NO: 1. In still other embodiments, the recombinant host cells express a recombinant polypeptide with at least 70% identity to SEQ ID NO: 16.

In certain embodiments, the recombinant host cells are engineered to express one or more recombinant polypeptides that catalyze the formation of p-coumaric acid. Thus, in some embodiments, recombinant cells further comprise a recombinant gene encoding a cinnamate 4-hydroxylase polypeptide. In some embodiments, the recombinant host cells express a cinnamate 4-hydroxylase gene comprising SEQ ID NO: 2. In further embodiments, the cinnamate 4-hydroxylase gene has at least 70% identity to SEQ ID NO: 2. Also provided are recombinant host cells comprising a recombinant gene encoding a cinnamate 4-hydroxylase polypeptide with at least 70% identity to SEQ ID NO: 17.

In some embodiments, the host cell is engineered to express recombinant polypeptides that catalyze the formation of p-coumaroyl-CoA or cinnamoyl-CoA. Accordingly, in some embodiments, recombinant cells further comprise a gene encoding a 4-coumarate-CoA ligase polypeptide. In particular embodiments, the 4-coumarate-CoA ligase gene comprises SEQ ID NO: 3. In particular embodiments, the 4-coumarate-CoA ligase gene has at least 65% identity to SEQ ID NO: 3. In still other embodiments, the recombinant gene encodes a 4-coumarate-CoA ligase polypeptide with at least 65% identity to SEQ ID NO: 18.

In some embodiments, the disclosure provides recombinant host cells engineered to express recombinant polypeptides that catalyze the formation of phenylpropanoids, such as cinnamic acid and coumaric acid, and/or that catalyze the formation of phenylpropanoid derivatives, such as chalcones and stilbenoids.

In certain embodiments, the recombinant host cells are engineered to express recombinant polypeptides that catalyze the formation of chalcones, such as naringenin precursor compounds, from coumaroyl-CoA or cinnamoyl-CoA. Thus, in some embodiments, recombinant cells further comprise one or more chalcone synthase genes. In certain embodiments, the recombinant host cells express a heterologous gene with homology to *Hordeum vulgare* chalcone synthase 2. In other embodiments, the recombinant host cells express a recombinant gene comprising the sequence of SEQ ID NO: 4. In still other embodiments, the recombinant host cells express a recombinant gene with at least 65% identity to SEQ ID NO: 4. In still other embodiments, the recombinant host cells express a recombinant polypeptide with at least 65% identity to SEQ ID NO: 19.

In some embodiments, the disclosure provides recombinant host cells engineered to express recombinant polypeptides that catalyze the formation of stilbenoids from p-coumaroyl-CoA or cinnamoyl-CoA. Thus, in some embodiments, recombinant host cells further comprise one or more stilbene synthase genes.

In some embodiments, the recombinant host cells express a heterologous gene with homology to a *Pinus densiflora* stilbene synthase gene. In other embodiments, the recombinant host cells express a recombinant gene comprising the sequence of SEQ ID NO: 23. In still other embodiments, the recombinant host cells express a recombinant gene with least 70% identity to SEQ ID NO: 23. In still other embodiments, the recombinant host cells express a recombinant polypeptide with at least 80% identity to SEQ ID NO: 24.

In some embodiments, recombinant host cells further comprise a recombinant gene encoding a recombinant cytochrome p450 polypeptide, wherein the recombinant cytochrome p450 gene is encoded by SEQ ID NO: 6. In embodiments, the recombinant cytochrome p450 gene has at least 65% identity to SEQ ID NO: 6. In still other embodiments, the recombinant gene encodes a cytochrome p450 polypeptide with at least 65% identity to SEQ ID NO: 21.

In some embodiments, recombinant host cells further comprise a gene encoding a recombinant chalcone isomerase polypeptide, wherein the recombinant chalcone isomerase is encoded by the nucleotide sequence of any one of SEQ ID NOS: 80-86. In some embodiments, the recombinant chalcone isomerase gene has at least 60% identity to any one of SEQ ID NOS: 80-86. In other embodiments, the chalcone isomerase polypeptide has at least 65% identity to any one of SEQ ID NOS: 87-93.

In another aspect, the disclosure provides methods of producing phenylpropanoids, such as cinnamic acid and coumaric acid, and/or of producing phenylpropanoid derivatives, such as chalcones or stilbenes, comprising growing a recombinant yeast cell as disclosed herein in a culture medium under conditions in which the recombinant genes are expressed, and wherein said compound is synthesized by the recombinant yeast cell.

In some embodiments, the methods of the disclosure are used to produce a chalcone compound. In some embodiments, the chalcone compound is naringenin or a naringenin derivative. In addition to naringenin, some embodiments disclosed herein are useful for producing other chalcones, e.g., Isoliquiritigenin (liquiritigenin chalcone), Butein (Butin chalcone), Pinocembrin chalcone, Eriodictyol chalcone and Homoeriodictyol chalcone.

In some embodiments, the methods of the disclosure are used to produce a stilbenoid compound. In some embodiments the stilbene compound is resveratrol. In addition to resveratrol, some embodiments of the present disclosure are useful for producing other stilbenoids, e.g. Piceatannol, Dihydroresveratrol, Resveratrol 3-O-glucoside (Piceid, polydatin), epsilon-Viniferin, delta-Viniferin and Pallidol.

In some embodiments, the methods of producing a chalcone or a stilbene compound further comprise harvesting the said compound. As used herein, the term "harvesting" refers to any means of collecting a compound, which may or may not comprise isolating the compound. In some embodiments, the methods of producing a chalcone or a stilbene compound further comprise isolating said compound.

In another aspect, the disclosure provides methods of producing a compound of formula (III):

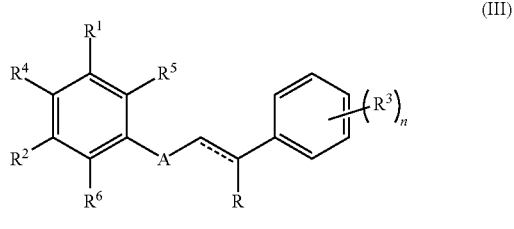

(III)

or a pharmaceutically acceptable salt thereof, wherein
A is a bond or C=O;
n is an integer 0, 1, 2, 3, or 4;
R is hydrogen when ⸗ is a double bond, or R and $R^5$ together with the atoms to which they are attached form a 6-member heterocyclyl when A is C=O and ⸗ is a single bond;
$R^1$ is hydrogen or —$OR^{11}$;
  wherein each $R^{11}$ is independently hydrogen, $C_1$-$C_6$ alkyl, or glycosyl;
$R^2$ is hydrogen, —$OR^{11}$, $C_1$-$C_{12}$ alkyl, or $C_2$-$C_{12}$ alkenyl, wherein alkyl and alkenyl are optionally substituted with one or more $R^7$;
  or $R^2$ and $R^6$ together with the atoms to which they are attached form a 5- to 7-member heterocyclyl optionally substituted with one or more $R^7$ groups;
  or $R^2$ and $R^4$ together with the atoms to which they are attached form a 5- to 7-member heterocyclyl optionally substituted with one or more $R^7$ groups;
$R^3$ is independently selected from nitro, $C_1$-$C_6$ alkyl, $C_2$-$C_6$ alkenyl, $C_1$-$C_6$ haloalkyl, $C_1$-$C_6$ hydroxyalkyl, —$OR^{12}$, —$N(R^{12})_2$, —$C(O)R^{12}$, —$C(O)OR^{12}$, —$C(O)N(R^{12})_2$, and —$S(O)_2R^{12}$, wherein each $R^{12}$ is independently hydrogen or $C_1$-$C_6$ alkyl;
$R^4$ is hydrogen, —$OR^{11}$, $C_1$-$C_{12}$ alkyl, or $C_2$-$C_{12}$ alkenyl, wherein alkyl and alkenyl are optionally substituted with one or more $R^7$;
  or $R^4$ and $R^2$ together with the atoms to which they are attached form a 5- to 7-member heterocyclyl optionally substituted with one or more $R^7$ groups;
$R^5$ is hydrogen, —$OR^{11}$, —$C(O)OR^{10}$, or —$C(O)N(R^{10})_2$, wherein each $R^{10}$ is independently hydrogen or $C_1$-$C_6$ alkyl; and
$R^6$ is hydrogen, $C_1$-$C_6$ alkyl, $C_2$-$C_6$ alkenyl, —$OR^{11}$, —$N(R^{10})_2$, —$C(O)R^{10}$, —$C(O)OR^{10}$, or —$C(O)N(R^{10})_2$, wherein alkyl and alkenyl are optionally substituted with one or more $R^8$; or $R^6$ and $R^2$ together with the atoms to which they are attached form a 5- to 7-member heterocyclyl optionally substituted with one or more $R^8$ groups;
  each $R^7$ and $R^8$ is independently halogen, cyano, nitro, $C_1$-$C_6$ alkyl, $C_2$-$C_6$ alkenyl, $C_1$-$C_6$ haloalkyl, $C_1$-$C_6$ hydroxyalkyl, —$OR^{13}$, —$SR^{13}$, —$N(R^{13})_2$, —$C(O)R^{13}$, —$C(O)OR^{13}$, —$C(O)N(R^{13})_2$, or —$S(O)_2R^{13}$, wherein each $R^{13}$ is independently hydrogen or $C_1$-$C_6$ alkyl,
comprising growing a recombinant host cell as disclosed herein in a culture medium under conditions in which the recombinant genes are expressed, and wherein the compound of formula (III) is synthesized by the recombinant host cell.

In some embodiments, the compound of formula (III) is not a compound wherein $R^1$, $R^2$, and $R^4$ are independently hydrogen.

In some embodiments, the compound of formula (III) is of formula (IV):

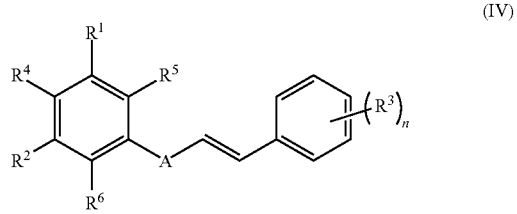

(IV)

or a pharmaceutically acceptable salt thereof, wherein
A is a bond or C=O;
n is an integer 0, 1, 2, 3, or 4;
$R^1$ is hydrogen or —$OR^{11}$;
  wherein each $R^{11}$ is independently hydrogen, $C_1$-$C_6$ alkyl, or glycosyl;
$R^2$ is hydrogen, —$OR^{11}$, $C_1$-$C_{12}$ alkyl, or $C_2$-$C_{12}$ alkenyl, wherein alkyl and alkenyl are optionally substituted with one or more $R^7$;
  or $R^2$ and $R^6$ together with the atoms to which they are attached form a 5- to 7-member heterocyclyl optionally substituted with one or more $R^7$ groups;
  or $R^2$ and $R^4$ together with the atoms to which they are attached form a 5- to 7-member heterocyclyl optionally substituted with one or more $R^7$ groups;
$R^3$ is independently selected from nitro, $C_1$-$C_6$ alkyl, $C_2$-$C_6$ alkenyl, $C_1$-$C_6$ haloalkyl, $C_1$-$C_6$ hydroxyalkyl, —$OR^{12}$, —$N(R^{12})_2$, —$C(O)R^{12}$, —$C(O)OR^{12}$, —$C(O)N(R^{12})_2$, and —$S(O)_2R^{12}$, wherein each $R^{12}$ is independently hydrogen or $C_1$-$C_6$ alkyl;
$R^4$ is hydrogen, —$OR^{11}$, $C_1$-$C_{12}$ alkyl, or $C_2$-$C_{12}$ alkenyl, wherein alkyl and alkenyl are optionally substituted with one or more $R^7$;
  or $R^4$ and $R^2$ together with the atoms to which they are attached form a 5- to 7-member heterocyclyl optionally substituted with one or more $R^7$ groups;
$R^5$ is hydrogen, —$OR^{11}$, —$C(O)OR^{10}$, or —$C(O)N(R^{10})_2$, wherein each $R^{10}$ is independently hydrogen or $C_1$-$C_6$ alkyl; and
$R^6$ is hydrogen, $C_1$-$C_6$ alkyl, $C_2$-$C_6$ alkenyl, —$OR^{11}$, —$N(R^{10})_2$, —$C(O)R^{10}$, —$C(O)OR^{10}$, or —$C(O)N(R^{10})_2$, wherein alkyl and alkenyl are optionally substituted with one or more $R^8$; or $R^6$ and $R^2$ together with the atoms to which they are attached form a 5- to 7-member heterocyclyl optionally substituted with one or more $R^8$ groups;
  each $R^7$ and $R^8$ is independently halogen, cyano, nitro, $C_1$-$C_6$ alkyl, $C_2$-$C_6$ alkenyl, $C_1$-$C_6$ haloalkyl, $C_1$-$C_6$ hydroxyalkyl, —$OR^{13}$, —$SR^{13}$, —$N(R^{13})_2$, —$C(O)R^{13}$, —$C(O)OR^{13}$, —$C(O)N(R^{13})_2$, or —$S(O)_2R^{13}$, wherein each $R^{13}$ is independently hydrogen or $C_1$-$C_6$ alkyl.

In some embodiments, the compound of formula (IV) is not a compound wherein $R^1$, $R^2$, and $R^4$ are independently hydrogen.

In some embodiments, the compound of formula (IV) is a stilbenoid compound, where A is a bond. For example, the stilbenoids produced by the methods of the invention include those of formula (IV-A):

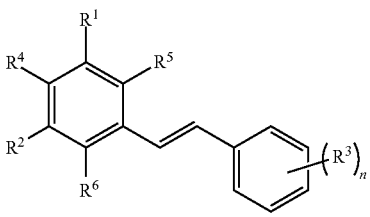

(IV-A)

or a pharmaceutically acceptable salt thereof, wherein
n is an integer 0, 1, 2, 3, or 4;
$R^1$ is hydrogen or —$OR^{11}$;
  wherein each $R^{11}$ is independently hydrogen, $C_1$-$C_6$ alkyl, or glycosyl;
$R^2$ is hydrogen, —$OR^{11}$, $C_1$-$C_{12}$ alkyl, or $C_2$-$C_{12}$ alkenyl, wherein alkyl and alkenyl are optionally substituted with one or more $R^7$;
  or $R^2$ and $R^6$ together with the atoms to which they are attached form a 5- to 7-member heterocyclyl optionally substituted with one or more $R^7$ groups;
  or $R^2$ and $R^4$ together with the atoms to which they are attached form a 5- to 7-member heterocyclyl optionally substituted with one or more $R^7$ groups;
$R^3$ is independently selected from nitro, $C_1$-$C_6$ alkyl, $C_2$-$C_6$ alkenyl, $C_1$-$C_6$ haloalkyl, $C_1$-$C_6$ hydroxyalkyl, —$OR^{12}$, —$N(R^{12})_2$, —$C(O)R^{12}$, —$C(O)OR^{12}$, —$C(O)N(R^{12})_2$, and —$S(O)_2R^{12}$, wherein each $R^{12}$ is independently hydrogen or $C_1$-$C_6$ alkyl;
$R^4$ is hydrogen, —$OR^{11}$, $C_1$-$C_{12}$ alkyl, or $C_2$-$C_{12}$ alkenyl, wherein alkyl and alkenyl are optionally substituted with one or more $R^7$;
  or $R^4$ and $R^2$ together with the atoms to which they are attached form a 5- to 7-member heterocyclyl optionally substituted with one or more $R^7$ groups;
$R^5$ is hydrogen, —$OR^{11}$, —$C(O)OR^{10}$, or —$C(O)N(R^{10})_2$, wherein each $R^{10}$ is independently hydrogen, or $C_1$-$C_6$ alkyl; and
$R^6$ is hydrogen, $C_1$-$C_6$ alkyl, $C_2$-$C_6$ alkenyl, —$OR^{11}$, —$N(R^{10})_2$, —$C(O)R^{10}$, —$C(O)OR^{10}$, or —$C(O)N(R^{10})_2$, wherein alkyl and alkenyl are optionally substituted with one or more $R^8$; or $R^6$ and $R^2$ together with the atoms to which they are attached form a 5- to 7-member heterocyclyl optionally substituted with one or more $R^8$ groups;
each $R^7$ and $R^8$ is independently halogen, cyano, nitro, $C_1$-$C_6$ alkyl, $C_2$-$C_6$ alkenyl, $C_1$-$C_6$ haloalkyl, $C_1$-$C_6$ hydroxyalkyl, —$OR^{13}$, —$SR^{13}$, —$N(R^{13})_2$, —$C(O)R^{13}$, —$C(O)OR^{13}$, —$C(O)N(R^{13})_2$, or —$S(O)_2R^{13}$, wherein each $R^{13}$ is independently hydrogen or $C_1$-$C_6$ alkyl.

In some embodiments, compounds of formula (IV-A) are those wherein:
n is an integer 0, 1, 2, 3, or 4;
$R^1$ is hydrogen or —$OR^{11}$;
$R^2$ is hydrogen, —$OR^{11}$, $C_1$-$C_{12}$ alkyl, or $C_2$-$C_{12}$ alkenyl, wherein alkyl and alkenyl are optionally substituted with one or more $R^7$;
  or $R^2$ and $R^6$ together with the atoms to which they are attached form a 5- to 7-member heterocyclyl optionally substituted with one or more $R^7$ groups;
  or $R^2$ and $R^4$ together with the atoms to which they are attached form a 5- to 7-member heterocyclyl optionally substituted with one or more $R^7$ groups;
$R^3$ is independently selected from nitro, $C_1$-$C_6$ alkyl, $C_2$-$C_6$ alkenyl, $C_1$-$C_6$ haloalkyl, $C_1$-$C_6$ hydroxyalkyl, —$OR^{12}$, —$N(R^{12})_2$, —$C(O)R^{12}$, —$C(O)OR^{12}$, —$C(O)N(R^{12})_2$, and —$S(O)_2R^{12}$, wherein each $R^{12}$ is independently hydrogen or $C_1$-$C_6$ alkyl;
$R^4$ is —$OR^{11}$, $C_1$-$C_{12}$ alkyl or $C_2$-$C_{12}$ alkenyl, wherein alkyl and alkenyl are optionally substituted with one or more $R^7$;
  or $R^4$ and $R^2$ together with the atoms to which they are attached form a 5- to 7-member heterocyclyl optionally substituted with one or more $R^7$ groups;
$R^5$ is hydrogen, —$OR^{11}$, —$C(O)OR^{10}$, or —$C(O)N(R^{10})_2$, wherein each $R^{10}$ is independently hydrogen or $C_1$-$C_6$ alkyl; and
$R^6$ is hydrogen, $C_1$-$C_6$ alkyl, $C_2$-$C_6$ alkenyl, —$OR^{11}$, —$N(R^{10})_2$, —$C(O)R^{10}$, —$C(O)OR^{10}$, or —$C(O)N(R^{10})_2$, wherein alkyl and alkenyl are optionally substituted with one or more $R^8$; or $R^6$ and $R^2$ together with the atoms to which they are attached form a 5- to 7-member heterocyclyl optionally substituted with one or more $R^8$ groups;
each $R^7$ and $R^8$ is independently halogen, cyano, nitro, $C_1$-$C_6$ alkyl, $C_2$-$C_6$ alkenyl, $C_1$-$C_6$ haloalkyl, $C_1$-$C_6$ hydroxyalkyl, —$OR^{13}$, —$SR^{13}$, —$N(R^{13})_2$, —$C(O)R^{13}$, —$C(O)OR^{13}$, —$C(O)N(R^{13})_2$, or —$S(O)_2R^{13}$, wherein each $R^{13}$ is independently hydrogen or $C_1$-$C_6$ alkyl.

In some embodiments, compounds of formula (IV-A) are those wherein:
n is an integer 0, 1, 2, 3, or 4;
$R^1$ is —$OR^{11}$;
$R^2$ is —$OR^{11}$, $C_1$-$C_{12}$ alkyl, or $C_2$-$C_{12}$ alkenyl, wherein alkyl and alkenyl are optionally substituted with one or more $R^7$; wherein $R^{11}$ is independently hydrogen or $C_1$-$C_6$ alkyl;
  or $R^2$ and $R^6$ together with the atoms to which they are attached form a 5- to 7-member heterocyclyl optionally substituted with one or more $R^7$ groups;
  or $R^2$ and $R^4$ together with the atoms to which they are attached form a 5- to 7-member heterocyclyl optionally substituted with one or more $R^7$ groups;
$R^3$ is independently selected from $C_1$-$C_6$ hydroxyalkyl, —$OR^{12}$, —$N(R^{12})_2$, —$C(O)OR^{12}$, and —$C(O)N(R^{12})_2$, wherein each $R^{12}$ is independently hydrogen or $C_1$-$C_6$ alkyl;
$R^4$ is —$OR^{11}$ or $C_2$-$C_{12}$ alkenyl, wherein alkenyl is optionally substituted with one or more $R^7$;
  or $R^4$ and $R^2$ together with the atoms to which they are attached form a 5- to 7-member heterocyclyl optionally substituted with one or more $R^7$ groups;
$R^5$ is hydrogen or —$C(O)OR^{10}$, wherein $R^{10}$ is independently hydrogen or $C_1$-$C_6$ alkyl; and
$R^6$ is hydrogen, $C_2$-$C_6$ alkenyl, or —$C(O)OR^{10}$, wherein alkenyl is optionally substituted with one or more $R^8$; or $R^6$ and $R^2$ together with the atoms to which they are attached form a 5- to 7-member heterocyclyl optionally substituted with one or more $R^8$ groups;
each $R^7$ and $R^8$ is independently halogen, cyano, nitro, $C_1$-$C_6$ alkyl, $C_2$-$C_6$ alkenyl, $C_1$-$C_6$ haloalkyl, $C_1$-$C_6$ hydroxyalkyl, —$OR^{13}$, —$SR^{13}$, —$N(R^{13})_2$, —$C(O)R^{13}$, —$C(O)OR^{13}$, —$C(O)N(R^{13})_2$, or —$S(O)_2R^{13}$, wherein each $R^{13}$ is independently hydrogen or $C_1$-$C_6$ alkyl.

In some embodiments, compounds of formula (IV-A) are those wherein n is 0. In other embodiments, compounds of formula (IV-A) are those where $R^1$—$OR^{11}$, and $R^{11}$ is hydrogen or methyl. Some embodiments provide compounds of formula (IV-A) where $R^1$ is hydrogen.

Some embodiments provide compounds of formula (IV-A) where $R^2$ is —$OR^{11}$, and $R^{11}$ is independently hydrogen or $C_1$-$C_6$ alkyl. In some embodiments, $R^{11}$ is hydrogen or methyl. Other embodiments provide compounds of formula (IV-A) where $R^2$ is hydrogen.

Some embodiments provide compounds of formula (IV-A) where $R^4$ is —$OR^{11}$, and $R^{11}$ is independently hydrogen or $C_1$-$C_6$ alkyl. In some embodiments, $R^{11}$ is hydrogen or methyl. Other embodiments provide compounds of formula (IV-A) where $R^4$ is $C_2$-$C_{12}$ alkenyl optionally substituted with one or more $R^7$. In some embodiments, $R^4$ is $C_2$-$C_{12}$ alkenyl optionally substituted with hydroxy. In some embodiments, $R^4$ is 3-methylbut-2-en-1-yl optionally substituted with hydroxy. In some embodiments, $R^4$ is 3-methylbut-2-en-1-yl.

Some embodiments provide compounds of formula (IV-A) where $R^5$ is hydrogen.

Some embodiments provide compounds of formula (IV-A) where $R^6$ is hydrogen or —$C(O)OR^{10}$. In one embodiment, $R^6$ is hydrogen or —$C(O)OH$.

Representative examples of compounds of formula (IV-A) include, but are not limited to the following: resveratrol, astringin, pterostilbene, pinosylvin, piceatannol, piceid,

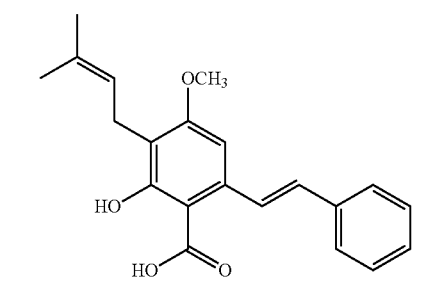

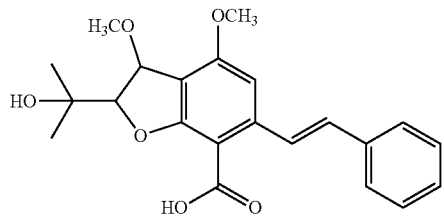

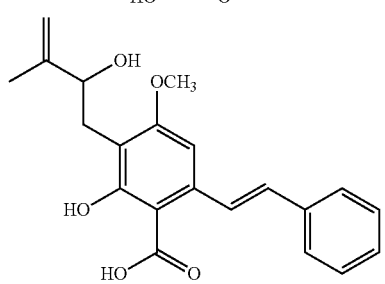

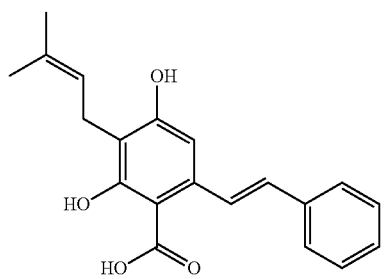

-continued

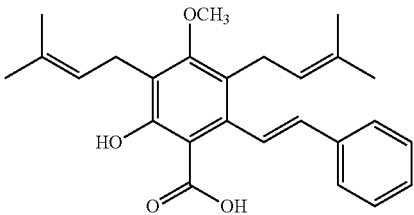

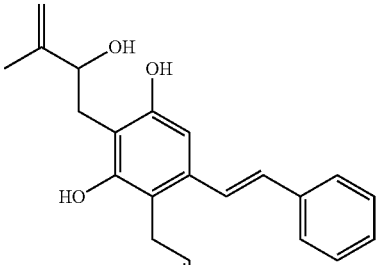

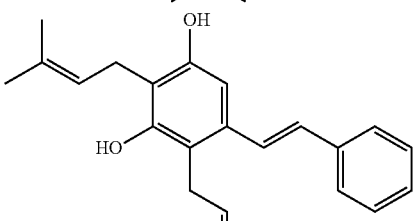

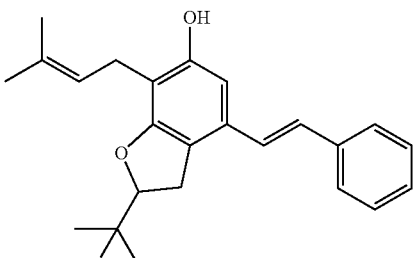

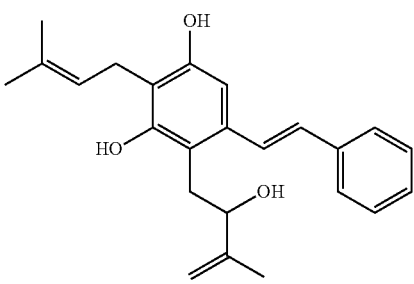

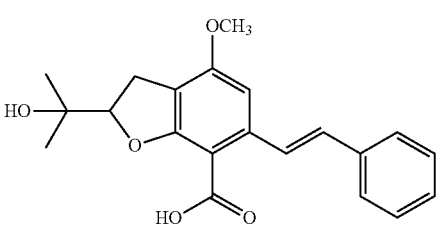

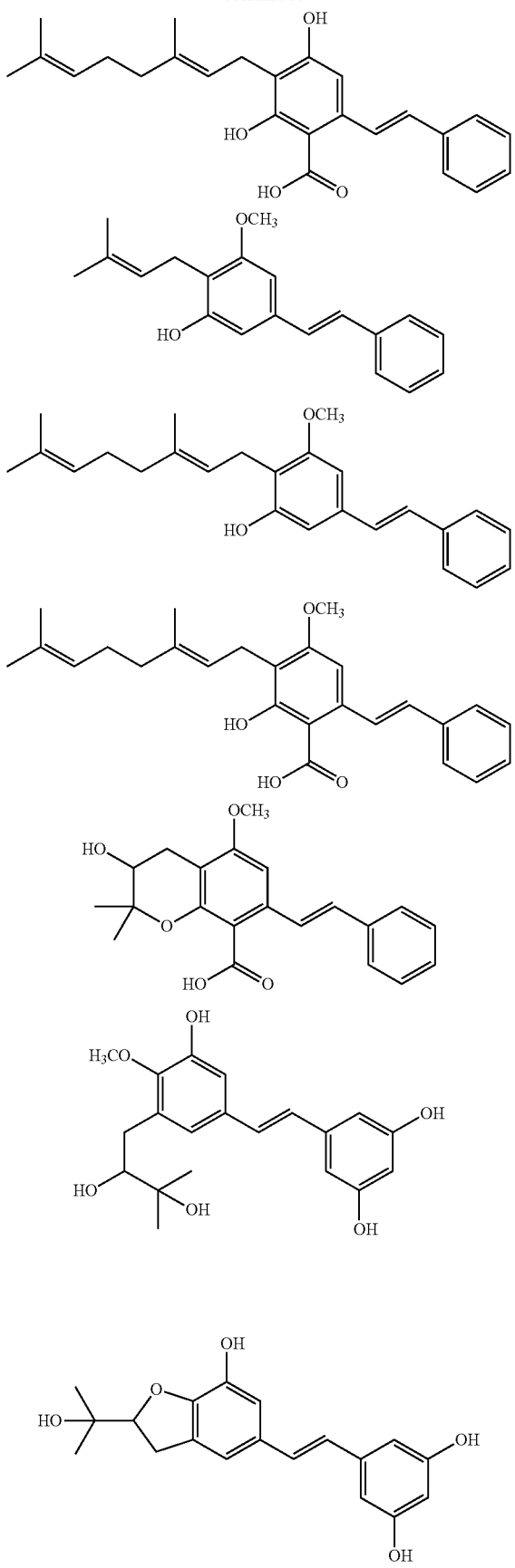

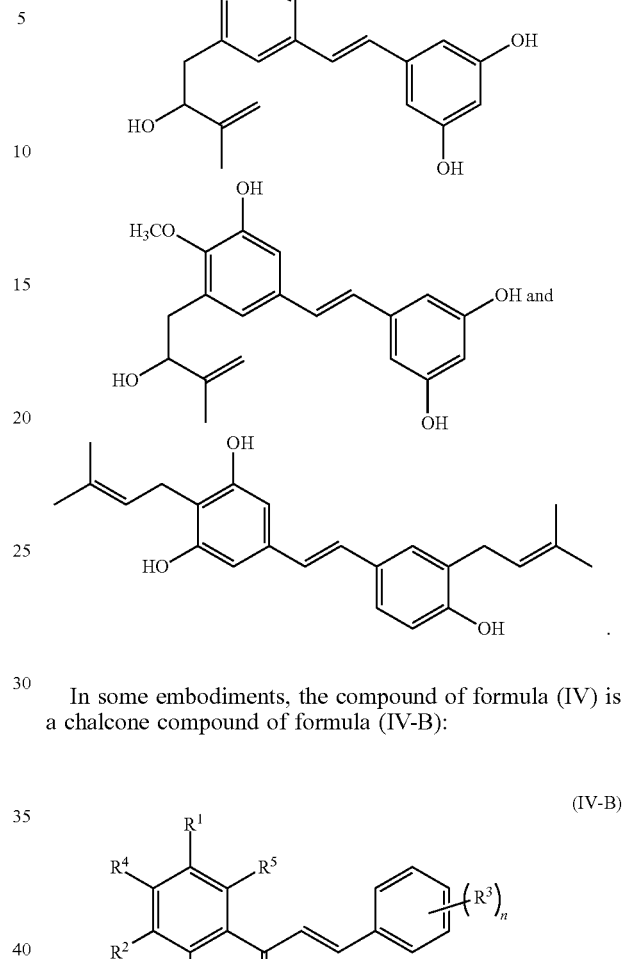

In some embodiments, the compound of formula (IV) is a chalcone compound of formula (IV-B):

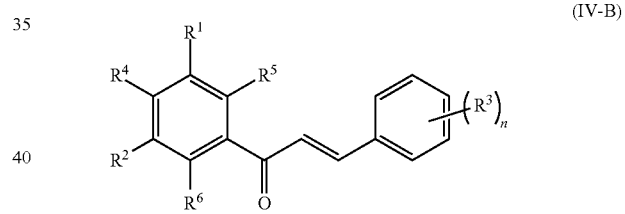

(IV-B)

or a pharmaceutically acceptable salt thereof, wherein
n is an integer 0, 1, 2, 3, or 4;
$R^1$ is hydrogen or —$OR^{11}$;
  wherein each $R^{11}$ is independently hydrogen, $C_1$-$C_6$ alkyl, or glycosyl;
$R^2$ is hydrogen, —$OR^{11}$, $C_1$-$C_{12}$ alkyl, or $C_2$-$C_{12}$ alkenyl, wherein alkyl and alkenyl are optionally substituted with one or more $R^7$;
  or $R^2$ and $R^6$ together with the atoms to which they are attached form a 5- to 7-member heterocyclyl optionally substituted with one or more $R^7$ groups;
  or $R^2$ and $R^4$ together with the atoms to which they are attached form a 5- to 7-member heterocyclyl optionally substituted with one or more $R^7$ groups;
$R^3$ is independently selected from nitro, $C_1$-$C_6$ alkyl, $C_2$-$C_6$ alkenyl, $C_1$-$C_6$ haloalkyl, $C_1$-$C_6$ hydroxyalkyl, —$OR^{12}$, —$N(R^{12})_2$, —$C(O)R^{12}$, —$C(O)OR^{12}$, —$C(O)N(R^{12})_2$, and —$S(O)_2R^{12}$, wherein each $R^{12}$ is independently hydrogen or $C_1$-$C_6$ alkyl;
$R^4$ is hydrogen, —$OR^{11}$, $C_1$-$C_{12}$ alkyl, or $C_2$-$C_{12}$ alkenyl, wherein alkyl and alkenyl are optionally substituted with one or more $R^7$;
  or $R^4$ and $R^2$ together with the atoms to which they are attached form a 5- to 7-member heterocyclyl optionally substituted with one or more $R^7$ groups;

$R^5$ is hydrogen, —$OR^{11}$, —$C(O)OR^{10}$, or —$C(O)N(R^{10})_2$, wherein each $R^{10}$ is independently hydrogen or $C_1$-$C_6$ alkyl; and $R^6$ is hydrogen, $C_1$-$C_6$ alkyl, $C_2$-$C_6$ alkenyl, —$OR^{11}$, —$N(R^{10})_2$, —$C(O)R^{10}$, —$C(O)OR^{10}$, or —$C(O)N(R^{10})_2$, wherein alkyl and alkenyl are optionally substituted with one or more $R^8$; or $R^6$ and $R^2$ together with the atoms to which they are attached form a 5- to 7-member heterocyclyl optionally substituted with one or more $R^8$ groups;

each $R^7$ and $R^8$ is independently halogen, cyano, nitro, $C_1$-$C_6$ alkyl, $C_2$-$C_6$ alkenyl, $C_1$-$C_6$ haloalkyl, $C_1$-$C_6$ hydroxyalkyl, —$OR^{13}$, —$SR^{13}$, —$N(R^{13})_2$, —$C(O)R^{13}$, —$C(O)OR^{13}$, —$C(O)N(R^{13})_2$, or —$S(O)_2R^{13}$, wherein each $R^{13}$ is independently hydrogen or $C_1$-$C_6$ alkyl.

In some embodiments, compounds of formula (IV-B) are those wherein:

n is an integer 0, 1, 2, 3, or 4;

$R^1$ is hydrogen or —$OR^{11}$;

$R^2$ is hydrogen, —$OR^{11}$, $C_1$-$C_{12}$ alkyl, or $C_2$-$C_{12}$ alkenyl, wherein alkyl and alkenyl are optionally substituted with one or more $R^7$;

or $R^2$ and $R^6$ together with the atoms to which they are attached form a 5- to 7-member heterocyclyl optionally substituted with one or more $R^7$ groups;

or $R^2$ and $R^4$ together with the atoms to which they are attached form a 5- to 7-member heterocyclyl optionally substituted with one or more $R^7$ groups;

$R^3$ is independently selected from nitro, $C_1$-$C_6$ alkyl, $C_2$-$C_6$ alkenyl, $C_1$-$C_6$ haloalkyl, $C_1$-$C_6$ hydroxyalkyl, —$OR^{12}$, —$N(R^{12})_2$, —$C(O)R^{12}$, —$C(O)OR^{12}$, —$C(O)N(R^{12})_2$, and —$S(O)_2R^{12}$, wherein each $R^{12}$ is independently hydrogen or $C_1$-$C_6$ alkyl;

$R^4$ is —$OR^{11}$, $C_1$-$C_{12}$ alkyl or $C_2$-$C_{12}$ alkenyl, wherein alkyl and alkenyl are optionally substituted with one or more $R^7$;

or $R^4$ and $R^2$ together with the atoms to which they are attached form a 5- to 7-member heterocyclyl optionally substituted with one or more $R^7$ groups;

$R^5$ is hydrogen, —$OR^{11}$, —$C(O)OR^{10}$, or —$C(O)N(R^{10})_2$, wherein each $R^{10}$ is independently hydrogen or $C_1$-$C_6$ alkyl; and $R^6$ is hydrogen, $C_1$-$C_6$ alkyl, $C_2$-$C_6$ alkenyl, —$OR^{11}$, —$N(R^{10})_2$, —$C(O)R^{10}$, —$C(O)OR^{10}$, or —$C(O)N(R^{10})_2$, wherein alkyl and alkenyl are optionally substituted with one or more $R^8$; or $R^6$ and $R^2$ together with the atoms to which they are attached form a 5- to 7-member heterocyclyl optionally substituted with one or more $R^8$ groups;

each $R^7$ and $R^8$ is independently halogen, cyano, nitro, $C_1$-$C_6$ alkyl, $C_2$-$C_6$ alkenyl, $C_1$-$C_6$ haloalkyl, $C_1$-$C_6$ hydroxyalkyl, —$OR^{13}$, —$SR^{13}$, —$N(R^{13})_2$, —$C(O)R^{13}$, —$C(O)OR^{13}$, —$C(O)N(R^{13})_2$, or —$S(O)_2R^{13}$, wherein each $R^{13}$ is independently hydrogen or $C_1$-$C_6$ alkyl.

In some embodiments, compounds of formula (IV-B) are those wherein:

n is an integer 0, 1, 2, 3, or 4;

$R^1$ is hydrogen or —$OR^{11}$;

$R^2$ is hydrogen, —$OR^{11}$, $C_1$-$C_{12}$ alkyl, or $C_2$-$C_{12}$ alkenyl, wherein alkyl and alkenyl are optionally substituted with one or more $R^7$; wherein $R^{11}$ is independently hydrogen or $C_1$-$C_6$ alkyl;

or $R^2$ and $R^6$ together with the atoms to which they are attached form a 5- to 7-member heterocyclyl optionally substituted with one or more $R^7$ groups;

or $R^2$ and $R^4$ together with the atoms to which they are attached form a 5- to 7-member heterocyclyl optionally substituted with one or more $R^7$ groups;

$R^3$ is independently selected from $C_1$-$C_6$ hydroxyalkyl, —$OR^{12}$, —$N(R^{12})_2$, —$C(O)OR^{12}$, and —$C(O)N(R^{12})_2$, wherein each $R^{12}$ is independently hydrogen or $C_1$-$C_6$ alkyl;

$R^4$ is —$OR^{11}$ or $C_2$-$C_{12}$ alkenyl, wherein alkenyl is optionally substituted with one or more $R^7$;

or $R^4$ and $R^2$ together with the atoms to which they are attached form a 5- to 7-member heterocyclyl optionally substituted with one or more $R^7$ groups;

$R^5$ is hydrogen or —$C(O)OR^{10}$, wherein $R^{10}$ is independently hydrogen or $C_1$-$C_6$ alkyl; and $R^6$ is hydrogen, $C_2$-$C_6$ alkenyl, or —$C(O)OR^{10}$, wherein alkenyl is optionally substituted with one or more $R^8$; or $R^6$ and $R^2$ together with the atoms to which they are attached form a 5- to 7-member heterocyclyl optionally substituted with one or more $R^8$ groups;

each $R^7$ and $R^8$ is independently halogen, cyano, nitro, $C_1$-$C_6$ alkyl, $C_2$-$C_6$ alkenyl, $C_1$-$C_6$ haloalkyl, $C_1$-$C_6$ hydroxyalkyl, —$OR^{13}$, —$SR^{13}$, —$N(R^{13})_2$, —$C(O)R^{13}$, —$C(O)OR^{13}$, —$C(O)N(R^{13})_2$, or —$S(O)_2R^{13}$, wherein each $R^{13}$ is independently hydrogen or $C_1$-$C_6$ alkyl.

In some embodiments, compounds of formula (IV-B) are those wherein n is 0. In other embodiments, compounds of formula (IV-B) are those where $R^1$ is —$OR^{11}$, and $R^{11}$ is hydrogen or methyl. Some embodiments provide compounds of formula (IV-B) where $R^1$ is hydrogen.

Some embodiments provide compounds of formula (IV-B) where $R^2$ is —$OR^{11}$, and $R^{11}$ is independently hydrogen or $C_1$-$C_6$ alkyl. In some embodiments, $R^{11}$ is hydrogen or methyl. Other embodiments provide compounds of formula (IV-B) where $R^2$ is hydrogen.

Some embodiments provide compounds of formula (IV-B) where $R^4$ is —$OR^{11}$, and $R^{11}$ is independently hydrogen or $C_1$-$C_6$ alkyl. In some embodiments, $R^{11}$ is hydrogen or methyl. Other embodiments provide compounds of formula (IV-B) where $R^4$ is $C_2$-$C_{12}$ alkenyl optionally substituted with one or more $R^7$. In some embodiments, $R^4$ is $C_2$-$C_{12}$ alkenyl optionally substituted with hydroxy. In some embodiments, $R^4$ is 3-methylbut-2-en-1-yl optionally substituted with hydroxy. In some embodiments, $R^4$ is 3-methylbut-2-en-1-yl.

Some embodiments provide compounds of formula (IV-B) where $R^5$ is hydrogen.

Some embodiments provide compounds of formula (IV-B) where $R^6$ is hydrogen or —$C(O)OR^{10}$. In one embodiment, $R^6$ is hydrogen or —$C(O)OH$.

Representative examples of compounds of formula (IV-B) include, but are not limited to pinocembrin chalcone and naringenin chalcone.

In some embodiments, the compound of formula (III) is a compound of formula (V):

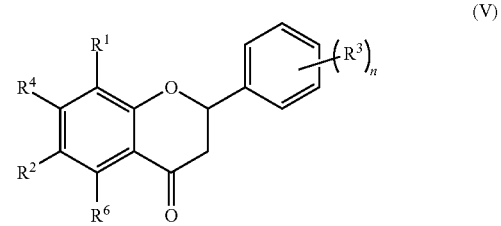

or a pharmaceutically acceptable salt thereof, wherein
n is an integer 0, 1, 2, 3, or 4;
$R^1$ is hydrogen or —$OR^{11}$;
  wherein each $R^{11}$ is independently hydrogen, $C_1$-$C_6$ alkyl, or glycosyl;
$R^2$ is hydrogen, —$OR^{11}$, $C_1$-$C_{12}$ alkyl, or $C_2$-$C_{12}$ alkenyl, wherein alkyl and alkenyl are optionally substituted with one or more $R^7$;
  or $R^2$ and $R^6$ together with the atoms to which they are attached form a 5- to 7-member heterocyclyl optionally substituted with one or more $R^7$ groups;
  or $R^2$ and $R^4$ together with the atoms to which they are attached form a 5- to 7-member heterocyclyl optionally substituted with one or more $R^7$ groups;
$R^3$ is independently selected from nitro, $C_1$-$C_6$ alkyl, $C_2$-$C_6$ alkenyl, $C_1$-$C_6$ haloalkyl, $C_1$-$C_6$ hydroxyalkyl, —$OR^{12}$, —$N(R^{12})_2$, —$C(O)R^{12}$, —$C(O)OR^{12}$, —$C(O)N(R^{12})_2$, and —$S(O)_2R^{12}$, wherein each $R^{12}$ is independently hydrogen or $C_1$-$C_6$ alkyl;
$R^4$ is hydrogen, —$OR^{11}$, $C_1$-$C_{12}$ alkyl, or $C_2$-$C_{12}$ alkenyl, wherein alkyl and alkenyl are optionally substituted with one or more $R^7$;
  or $R^4$ and $R^2$ together with the atoms to which they are attached form a 5- to 7-member heterocyclyl optionally substituted with one or more $R^7$ groups; and
$R^6$ is hydrogen, $C_1$-$C_6$ alkyl, $C_2$-$C_6$ alkenyl, —$OR^{11}$, —$N(R^{10})_2$, —$C(O)R^{10}$, —$C(O)OR^{10}$, or —$C(O)N(R^{10})_2$, wherein alkyl and alkenyl are optionally substituted with one or more $R^8$; or $R^6$ and $R^2$ together with the atoms to which they are attached form a 5- to 7-member heterocyclyl optionally substituted with one or more $R^8$ groups;
  each $R^7$ and $R^8$ is independently halogen, cyano, nitro, $C_1$-$C_6$ alkyl, $C_2$-$C_6$ alkenyl, $C_1$-$C_6$ haloalkyl, $C_1$-$C_6$ hydroxyalkyl, —$OR^{13}$, —$SR^{13}$, —$N(R^{13})_2$, —$C(O)R^{13}$, —$C(O)OR^{13}$, —$C(O)N(R^{13})_2$, or —$S(O)_2R^{13}$, wherein each $R^{13}$ is independently hydrogen or $C_1$-$C_6$ alkyl.

In some embodiments, compounds of formula (V) are those wherein:
n is an integer 0, 1, 2, 3, or 4;
$R^1$ is hydrogen or —$OR^{11}$;
$R^2$ is hydrogen, —$OR^{11}$, $C_1$-$C_{12}$ alkyl, or $C_2$-$C_{12}$ alkenyl, wherein alkyl and alkenyl are optionally substituted with one or more $R^7$;
  or $R^2$ and $R^6$ together with the atoms to which they are attached form a 5- to 7-member heterocyclyl optionally substituted with one or more $R^7$ groups;
  or $R^2$ and $R^4$ together with the atoms to which they are attached form a 5- to 7-member heterocyclyl optionally substituted with one or more $R^7$ groups;
$R^3$ is independently selected from nitro, $C_1$-$C_6$ alkyl, $C_2$-$C_6$ alkenyl, $C_1$-$C_6$ haloalkyl, $C_1$-$C_6$ hydroxyalkyl, —$OR^{12}$, —$N(R^{12})_2$, —$C(O)R^{12}$, —$C(O)OR^{12}$, —$C(O)N(R^{12})_2$, and —$S(O)_2R^{12}$, wherein each $R^{12}$ is independently hydrogen or $C_1$-$C_6$ alkyl;
$R^4$ is —$OR^{11}$, $C_1$-$C_{12}$ alkyl or $C_2$-$C_{12}$ alkenyl, wherein alkyl and alkenyl are optionally substituted with one or more $R^7$;
  or $R^4$ and $R^2$ together with the atoms to which they are attached form a 5- to 7-member heterocyclyl optionally substituted with one or more $R^7$ groups; and
$R^6$ is hydrogen, $C_1$-$C_6$ alkyl, $C_2$-$C_6$ alkenyl, —$OR^{11}$, —$N(R^{10})_2$, —$C(O)R^{10}$, —$C(O)OR^{10}$, or —$C(O)N(R^{10})_2$, wherein alkyl and alkenyl are optionally substituted with one or more $R^8$; or $R^6$ and $R^2$ together with the atoms to which they are attached form a 5- to 7-member heterocyclyl optionally substituted with one or more $R^8$ groups;
  each $R^7$ and $R^8$ is independently halogen, cyano, nitro, $C_1$-$C_6$ alkyl, $C_2$-$C_6$ alkenyl, $C_1$-$C_6$ haloalkyl, $C_1$-$C_6$ hydroxyalkyl, —$OR^{13}$, —$SR^{13}$, —$N(R^{13})_2$, —$C(O)R^{13}$, —$C(O)OR^{13}$, —$C(O)N(R^{13})_2$, or —$S(O)_2R^{13}$, wherein each $R^{13}$ is independently hydrogen or $C_1$-$C_6$ alkyl.

In some embodiments, compounds of formula (V) are those wherein:
n is an integer 0, 1, 2, 3, or 4;
$R^1$ is hydrogen or —$OR^{11}$;
$R^2$ is hydrogen, —$OR^{11}$, $C_1$-$C_{12}$ alkyl, or $C_2$-$C_{12}$ alkenyl, wherein alkyl and alkenyl are optionally substituted with one or more $R^7$; wherein $R^{11}$ is independently hydrogen or $C_1$-$C_6$ alkyl;
  or $R^2$ and $R^6$ together with the atoms to which they are attached form a 5- to 7-member heterocyclyl optionally substituted with one or more $R^7$ groups;
  or $R^2$ and $R^4$ together with the atoms to which they are attached form a 5- to 7-member heterocyclyl optionally substituted with one or more $R^7$ groups;
$R^3$ is independently selected from $C_1$-$C_6$ hydroxyalkyl, —$OR^{12}$, —$N(R^{12})_2$, —$C(O)OR^{12}$, and —$C(O)N(R^{12})_2$, wherein each $R^{12}$ is independently hydrogen or $C_1$-$C_6$ alkyl;
$R^4$ is —$OR^{11}$ or $C_2$-$C_{12}$ alkenyl, wherein alkenyl is optionally substituted with one or more $R^7$;
  or $R^4$ and $R^2$ together with the atoms to which they are attached form a 5- to 7-member heterocyclyl optionally substituted with one or more $R^7$ groups; and
$R^6$ is hydrogen, $C_2$-$C_6$ alkenyl, or —$C(O)OR^{10}$, wherein alkenyl is optionally substituted with one or more $R^8$; or $R^6$ and $R^2$ together with the atoms to which they are attached form a 5- to 7-member heterocyclyl optionally substituted with one or more $R^8$ groups;
  each $R^7$ and $R^8$ is independently halogen, cyano, nitro, $C_1$-$C_6$ alkyl, $C_2$-$C_6$ alkenyl, $C_1$-$C_6$ haloalkyl, $C_1$-$C_6$ hydroxyalkyl, —$OR^{13}$, —$SR^{13}$, —$N(R^{13})_2$, —$C(O)R^{13}$, —$C(O)OR^{13}$, —$C(O)N(R^{13})_2$, or —$S(O)_2R^{13}$, wherein each $R^{13}$ is independently hydrogen or $C_1$-$C_6$ alkyl.

In some embodiments, compounds of formula (V) are those wherein n is 0. In other embodiments, compounds of formula (V) are those where $R^1$ is —$OR^{11}$, and $R^{11}$ is hydrogen or methyl. Some embodiments provide compounds of formula (V) where $R^1$ is hydrogen.

Some embodiments provide compounds of formula (V) where $R^2$ is —$OR^{11}$, and $R^{11}$ is independently hydrogen or $C_1$-$C_6$ alkyl. In some embodiments, $R^{11}$ is hydrogen or methyl. Other embodiments provide compounds of formula (V) where $R^2$ is hydrogen.

Some embodiments provide compounds of formula (V) where $R^4$ is —$OR^{11}$, and $R^{11}$ is independently hydrogen or $C_1$-$C_6$ alkyl. In some embodiments, $R^{11}$ is hydrogen or methyl. Other embodiments provide compounds of formula (V) where $R^4$ is $C_2$-$C_{12}$ alkenyl optionally substituted with one or more $R^7$. In some embodiments, $R^4$ is $C_2$-$C_{12}$ alkenyl optionally substituted with hydroxy. In some embodiments, $R^4$ is 3-methylbut-2-en-1-yl optionally substituted with hydroxy. In some embodiments, $R^4$ is 3-methylbut-2-en-1-yl.

Some embodiments provide compounds of formula (V) where $R^6$ is hydrogen or —$C(O)OR^{10}$. In one embodiment, $R^6$ is hydrogen or —$C(O)OH$.

Representative examples of compounds of formula (V) include, but are not limited to pinocembrin, hesperetin, eriodictyol, homoeriodictyol, and naringenin.

In some embodiments, the methods of producing a compound of any one of formulae (III), (IV), (IV-A), (IV-B), or (V) further comprise harvesting the said compound. In some embodiments, the methods of producing a compound of any one of formulae (III), (IV), (IV-A), (IV-B), or (V) further comprise isolating said compound.

Biosynthesis of Dihydrophenylpropanoid Derivative Compounds

In another aspect, the disclosure provides recombinant host cells engineered with one or more heterologous recombinant genes in a phenylpropanoid derivative biosynthetic pathway. In some embodiments, the recombinant hosts are capable of carrying out the reduction of an enoyl double bond of a phenylpropanoid to produce a dihydrophenylpropanoid by recombinant expression of a double-bond reductase (DBR), such as an enoyl reductase (ENR). For example, in some embodiments the recombinant hosts are capable of reducing the double bond of p-coumaroyl-CoA to dihydrocoumaroyl-CoA, or of reducing the double bond of cinnamoyl-CoA to dihydrocinnamoyl-CoA.

In some embodiments the enoyl reductase is overexpressed. As used herein, the term "overexpression" refers to expression of a gene or protein at a level higher than the native expression of the gene or protein.

In some embodiments, the enoyl reductase comprises the *Saccharomyces cerevisiae* trans-2-enoyl-CoA reductase (TSC13), or a functional homolog thereof. In some embodiments, the recombinant enoyl reductase is encoded by a gene comprising the sequence disclosed herein as SEQ ID NO: 7. In some embodiments, the recombinant enoyl reductase is encoded by a gene with at least 70% identity to SEQ ID NO: 7. In some embodiments, the recombinant enoyl reductase (a) comprises a polypeptide of SEQ ID NO: 22, or (b) comprises a polypeptide with at least 70% identity to SEQ ID NO: 22.

In some embodiments, recombinant host cells co-express, along with the recombinant enoyl reductase, a recombinant polyketide synthase Type III polypeptide. In some embodiments, the recombinant polyketide synthase Type III polypeptide comprises: (i) a recombinant chalcone synthase polypeptide; or (ii) a recombinant stilbene synthase polypeptide.

In some embodiments, the recombinant host cells further comprise one or more polypeptides of a dihydrophenylpropanoid derivative biosynthesis pathway. In some embodiments, recombinant genes are provided that catalyze formation of intermediates in dihydrochalcone or dihydrostilbene biosynthesis. Intermediates comprise, inter alia, cinnamic acid, cinnamoyl-CoA, dihydrocinnamoyl-CoA, p-coumaric acid, p-coumaroyl CoA, p-dihydrocoumaroyl CoA, and phloretin.

In some embodiments, the recombinant cells further comprise an endogenous or recombinant gene encoding a phenylalanine ammonia lyase polypeptide, which catalyzes the formation of cinnamic acid. In some embodiments, the recombinant host cells express a polypeptide with homology to the *Arabidopsis thaliana* PAL2 gene. In some embodiments, the recombinant host cells express a recombinant gene comprising the sequence disclosed herein as SEQ ID NO: 1. In other embodiments, the recombinant host cells express a recombinant gene with at least 70% identity to SEQ ID NO: 1. In still other embodiments, the recombinant host cells express (a) a recombinant polypeptide comprising SEQ ID NO: 16, or (b) a recombinant polypeptide with at least 70% identity to SEQ ID NO: 16.

In certain embodiments, the recombinant host cells are engineered to express one or more recombinant polypeptides that catalyze the formation of p-coumaric acid. Thus, some embodiments comprise a host cell expressing a recombinant gene encoding a cinnamate 4-hydroxylase polypeptide. In some embodiments, the recombinant host cells express a cinnamate 4-hydroxylase gene comprising SEQ ID NO: 2. In further embodiments, the cinnamate 4-hydroxylase gene has at least 70% identity to SEQ ID NO: 2. Also provided are recombinant host cells comprising a recombinant gene encoding (a) a cinnamate 4-hydroxylase polypeptide comprising SEQ ID NO: 17; or (b) a cinnamate 4-hydroxylase polypeptide with at least 70% identity to SEQ ID NO: 17.

In some embodiments, the host cell is engineered to express recombinant polypeptides that catalyze the formation of p-coumaroyl-CoA or cinnamoyl-CoA. Accordingly, in certain embodiments, the host cells express a recombinant gene encoding a 4-coumarate-CoA ligase polypeptide. In particular embodiments, the 4-coumarate-CoA ligase gene comprises SEQ ID NO: 3. In particular embodiments, the 4-coumarate-CoA ligase gene has at least 65% identity to SEQ ID NO: 3. In other embodiments, the recombinant gene encodes (a) a 4-coumarate-CoA ligase polypeptide comprising SEQ ID NO: 18, or (b) a 4-coumarate-CoA ligase polypeptide with at least 65% identity to SEQ ID NO: 18.

In some embodiments, the disclosure provides recombinant host cells engineered to express recombinant polypeptides that catalyze the formation of dihydrophenylpropanoid derivatives, such as dihydrochalcones and dihydrostilbenoids. In some embodiments, the host cells are engineered to express recombinant polypeptides that catalyze the formation of phlorizin compound, and/or phlorizin precursor compounds from, e.g., dihydrocoumaroyl-CoA or dihydrocinnamoyl-CoA. In certain embodiments, the recombinant host cells are engineered to express recombinant polypeptides that catalyze the formation of phlorizin precursor compounds, including phloretin, from p-dihydrocoumaroyl-CoA or dihydrocinnamoyl-CoA.

In some embodiments, the recombinant host cells comprise one or more chalcone synthase genes. In certain embodiments, the recombinant host cells express a heterologous gene encoding *Hordeum vulgare* chalcone synthase 2 (HvCHS2) or a homolog or functional analog thereof. In some embodiments, the recombinant host cells express a recombinant gene comprising one of SEQ ID NOs: 4 or 68-70. In some embodiments, the recombinant host cells express a recombinant gene with at least 65% identity to one of SEQ ID NOs: 4 or 68-70. In some embodiments, the recombinant host cells express (a) a recombinant polypeptide comprising (a) one of SEQ ID NOs: 19 or 71-73; (b) a polypeptide with at least 65% identity to one of SEQ ID NOs: 19 or 71-73; or (c) a polypeptide with at least 90% sequence identity to one of SEQ ID NOs: 19 or 71-73 in the combined regions spanning amino acids 95-105, 132-142, 191-201, and 266-276 of the one of SEQ ID NOs: 19 or 71-73.

In some embodiments, the recombinant host cells of the disclosure comprise a nucleic acid sequence encoding chalcone synthase 2 (CHS2) of *Hordeum vulgare*, wherein the nucleic acid sequence comprises one or more nucleic acid substitutions selected from the group consisting of G595A, A799T, and A801T. In some embodiments, the recombinant host cells of the disclosure comprise a nucleic acid sequence encoding chalcone synthase 2 (CHS2) of *Hordeum vulgare* comprising one or more amino acid substitutions selected from the group consisting of A199T and I267F.

In certain embodiments, the recombinant host cells express a heterologous gene encoding *Hypericum androsaemum* chalcone synthase (HaCHS) or a homolog or functional analog thereof. In some embodiments, the recombinant host cells express a recombinant gene comprising SEQ ID NO: 27 or a recombinant gene with at least 65% sequence identity to SEQ ID NO: 27. In some embodiments, the recombinant host cells express a recombinant polypeptide comprising SEQ ID NO: 49 or a recombinant polypeptide with at least 65% sequence identity to SEQ ID NO: 49.

In some embodiments, the disclosure provides recombinant host cells engineered to express recombinant polypeptides that catalyze the formation of phlorizin from phloretin. In certain embodiments, the recombinant hosts are engineered with a heterologous UDP glycosyl transferase (UGT) with homology to the *Malus domestica* P2'UGT gene. In other embodiments, the recombinant hosts disclosed herein comprise a heterologous gene comprising SEQ ID NO: 5. In yet other embodiments, the recombinant hosts comprise a heterologous gene with at least 65% identity to SEQ ID NO: 5. In still other embodiments, the recombinant hosts express (a) a UGT polypeptide comprising SEQ ID NO: 20, or (b) a UGT polypeptide with at least 70% identity to SEQ ID NO: 20.

In some embodiments, the disclosure provides recombinant host cells engineered to express recombinant polypeptides that catalyze the formation of dihydrostilbenoids from p-dihydrocoumaroyl-CoA or dihydrocinnamoyl-CoA. Thus, in some embodiments, the recombinant host cells comprise one or more stilbene synthase genes.

In some embodiments, the recombinant host cells express a heterologous gene with homology to a *Pinus densiflora* stilbene synthase gene. In other embodiments, the recombinant host cells express a recombinant gene comprising the sequence of SEQ ID NO: 23. In still other embodiments, the recombinant host cells express a recombinant gene with at least 70% identity to SEQ ID NO: 23. In still other embodiments, the recombinant host cells express (a) a recombinant polypeptide comprising SEQ ID NO: 24, or (b) a recombinant polypeptide with at least 80% identity to SEQ ID NO: 24.

In some embodiments, the disclosure provides recombinant host cells that express a recombinant gene encoding a recombinant cytochrome p450 polypeptide, wherein the recombinant cytochrome p450 gene is encoded by SEQ ID NO: 6. In embodiments, the recombinant cytochrome p450 gene has at least 65% identity to SEQ ID NO: 6. In still other embodiments, the recombinant gene encodes (a) a cytochrome p450 polypeptide comprising SEQ ID NO: 21, or (b) a cytochrome p450 polypeptide with at least 65% identity to SEQ ID NO: 21.

In another aspect, the disclosure provides methods of producing a dihydrochalcone or a dihydrostilbene compound, comprising growing a recombinant host cell as disclosed herein in a culture medium under conditions in which the recombinant genes are expressed, and wherein said compound is synthesized by the recombinant host cell.

In some embodiments, the methods of the disclosure are used to produce a dihydrochalcone compound. In some embodiments, the dihydrochalcone compound is phloretin or a phloretin derivative. In some embodiments, the phloretin derivative is phlorizin.

In addition to phlorizin, some embodiments disclosed herein are useful for producing other dihydrochalcones, e.g., neohesperidin dihydrochalcone (NHDC).

In some embodiments, the methods of the disclosure are used to produce a dihydrostilbenoid compound.

In some embodiments, the methods of producing a dihydrochalcone or a dihydrostilbene compound further comprise harvesting the said compound. As used herein, the term "harvesting" refers to any means of collecting a compound, which may or may not comprise isolating the compound. In some embodiments, the methods of producing a dihydrochalcone or a dihydrostilbene compound further comprise isolating said compound.

In another aspect, the disclosure provides methods of producing a compound of formula (III):

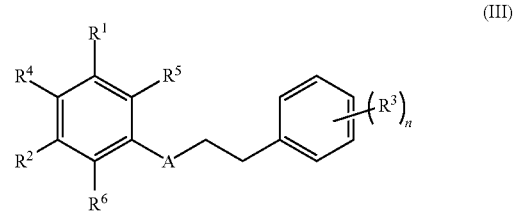

(III)

or a pharmaceutically acceptable salt thereof, wherein
A is a bond or C=O;
n is an integer 0, 1, 2, 3, or 4;
$R^1$ is hydrogen or —$OR^{11}$;
    wherein each $R^{11}$ is independently hydrogen, $C_1$-$C_6$ alkyl, or glycosyl;
$R^2$ is hydrogen, —$OR^{11}$, $C_1$-$C_{12}$ alkyl, or $C_2$-$C_{12}$ alkenyl, wherein alkyl and alkenyl are optionally substituted with one or more $R^7$;
    or $R^2$ and $R^6$ together with the atoms to which they are attached form a 5- to 7-member heterocyclyl optionally substituted with one or more $R^7$ groups;
    or $R^2$ and $R^4$ together with the atoms to which they are attached form a 5- to 7-member heterocyclyl optionally substituted with one or more $R^7$ groups;
$R^3$ is independently selected from nitro, $C_1$-$C_6$ alkyl, $C_2$-$C_6$ alkenyl, $C_1$-$C_6$ haloalkyl, $C_1$-$C_6$ hydroxyalkyl, —$OR^{12}$, —$N(R^{12})_2$, —$C(O)R^{12}$, —$C(O)OR^{12}$, —$C(O)N(R^{12})_2$, and —$S(O)_2R^{12}$, wherein each $R^{12}$ is independently hydrogen or $C_1$-$C_6$ alkyl;
$R^4$ is hydrogen, —$OR^{11}$, $C_1$-$C_{12}$ alkyl, or $C_2$-$C_{12}$ alkenyl, wherein alkyl and alkenyl are optionally substituted with one or more $R^7$;
    or $R^4$ and $R^2$ together with the atoms to which they are attached form a 5- to 7-member heterocyclyl optionally substituted with one or more $R^7$ groups;
$R^5$ is hydrogen or —$OR^{11}$; and
$R^6$ is hydrogen, $C_1$-$C_6$ alkyl, $C_2$-$C_6$ alkenyl, —$OR^{11}$, or —$N(R^{10})_2$, wherein each $R^{10}$ is independently hydrogen or $C_1$-$C_6$ alkyl, and wherein alkyl and alkenyl are optionally substituted with one or more $R^8$; or $R^6$ and $R^2$ together with the atoms to which they are attached form a 5- to 7-member heterocyclyl optionally substituted with one or more $R^8$ groups;
each $R^7$ and $R^8$ is independently halogen, cyano, nitro, $C_1$-$C_6$ alkyl, $C_2$-$C_6$ alkenyl, $C_1$-$C_6$ haloalkyl, $C_1$-$C_6$ hydroxyalkyl, —$OR^{13}$, —$SR^{13}$, —$N(R^{13})_2$, —$C(O)R^{13}$, —$C(O)OR^{13}$, —$C(O)N(R^{13})_2$, or —$S(O)_2R^{13}$, wherein each $R^{13}$ is independently hydrogen or $C_1$-$C_6$ alkyl, comprising growing a recombinant host cell as disclosed herein in a culture medium under conditions in which the recombinant genes are expressed, and wherein the compound of formula (III) is synthesized by the recombinant host cell.

In some embodiments, the compound of formula (III) is not a compound wherein $R^1$, $R^2$, and $R^4$ are independently hydrogen.

In some embodiments, the compound of formula (III) is a dihydrostilbenoid compound, where A is a bond. For example, the dihydrostilbenoids produced by the methods of the invention include those of formula (III-A):

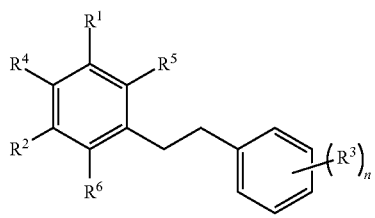

(III-A)

or a pharmaceutically acceptable salt thereof, wherein
n is an integer 0, 1, 2, 3, or 4;
$R^1$ is hydrogen or —$OR^{11}$;
  wherein each $R^{11}$ is independently hydrogen, $C_1$-$C_6$ alkyl, or glycosyl;
$R^2$ is hydrogen, —$OR^{11}$, $C_1$-$C_{12}$ alkyl, or $C_2$-$C_{12}$ alkenyl, wherein alkyl and alkenyl are optionally substituted with one or more $R^7$;
  or $R^2$ and $R^6$ together with the atoms to which they are attached form a 5- to 7-member heterocyclyl optionally substituted with one or more $R^7$ groups;
  or $R^2$ and $R^4$ together with the atoms to which they are attached form a 5- to 7-member heterocyclyl optionally substituted with one or more $R^7$ groups;
$R^3$ is independently selected from nitro, $C_1$-$C_6$ alkyl, $C_2$-$C_6$ alkenyl, $C_1$-$C_6$ haloalkyl, $C_1$-$C_6$ hydroxyalkyl, —$OR^{12}$, —$N(R^{12})_2$, —$C(O)R^{12}$, —$C(O)OR^{12}$, —$C(O)N(R^{12})_2$, and —$S(O)_2R^{12}$, wherein each $R^{12}$ is independently hydrogen or $C_1$-$C_6$ alkyl;
$R^4$ is hydrogen, —$OR^{11}$, $C_1$-$C_{12}$ alkyl, or $C_2$-$C_{12}$ alkenyl, wherein alkyl and alkenyl are optionally substituted with one or more $R^7$;
  or $R^4$ and $R^2$ together with the atoms to which they are attached form a 5- to 7-member heterocyclyl optionally substituted with one or more $R^7$ groups;
$R^5$ is hydrogen or —$OR^{11}$; and
$R^6$ is hydrogen, $C_1$-$C_6$ alkyl, $C_2$-$C_6$ alkenyl, —$OR^{11}$, or —$N(R^{10})_2$, wherein each $R^{10}$ is independently hydrogen, or $C_1$-$C_6$ alkyl, and wherein alkyl and alkenyl are optionally substituted with one or more $R^8$; or $R^6$ and $R^2$ together with the atoms to which they are attached form a 5- to 7-member heterocyclyl optionally substituted with one or more $R^8$ groups;
  each $R^7$ and $R^8$ is independently halogen, cyano, nitro, $C_1$-$C_6$ alkyl, $C_2$-$C_6$ alkenyl, $C_1$-$C_6$ haloalkyl, $C_1$-$C_6$ hydroxyalkyl, —$OR^{13}$, —$SR^{13}$, —$N(R^{13})_2$, —$C(O)R^{13}$, —$C(O)OR^{13}$, —$C(O)N(R^{13})_2$, or —$S(O)_2R^{13}$, wherein each $R^{13}$ is independently hydrogen or $C_1$-$C_6$ alkyl.

In some embodiments, compounds of formula (III-A) are those wherein:
n is an integer 0, 1, 2, 3, or 4;
$R^1$ is hydrogen or —$OR^{11}$;
$R^2$ is hydrogen, —$OR^{11}$, $C_1$-$C_{12}$ alkyl, or $C_2$-$C_{12}$ alkenyl, wherein alkyl and alkenyl are optionally substituted with one or more $R^7$;
  or $R^2$ and $R^6$ together with the atoms to which they are attached form a 5- to 7-member heterocyclyl optionally substituted with one or more $R^7$ groups;
  or $R^2$ and $R^4$ together with the atoms to which they are attached form a 5- to 7-member heterocyclyl optionally substituted with one or more $R^7$ groups;
$R^3$ is independently selected from nitro, $C_1$-$C_6$ alkyl, $C_2$-$C_6$ alkenyl, $C_1$-$C_6$ haloalkyl, $C_1$-$C_6$ hydroxyalkyl, —$OR^{12}$, —$N(R^{12})_2$, —$C(O)R^{12}$, —$C(O)OR^{12}$, —$C(O)N(R^{12})_2$, and —$S(O)_2R^{12}$, wherein each $R^{12}$ is independently hydrogen or $C_1$-$C_6$ alkyl;
$R^4$ is —$OR^{11}$, $C_1$-$C_{12}$ alkyl or $C_2$-$C_{12}$ alkenyl, wherein alkyl and alkenyl are optionally substituted with one or more $R^7$;
  or $R^4$ and $R^2$ together with the atoms to which they are attached form a 5- to 7-member heterocyclyl optionally substituted with one or more $R^7$ groups;
$R^5$ is hydrogen or —$OR^{11}$; and
$R^6$ is hydrogen, $C_1$-$C_6$ alkyl, $C_2$-$C_6$ alkenyl, —$OR^{11}$, or —$N(R^{10})_2$, wherein each $R^{10}$ is independently hydrogen or $C_1$-$C_6$ alkyl, and wherein alkyl and alkenyl are optionally substituted with one or more $R^8$; or $R^6$ and $R^2$ together with the atoms to which they are attached form a 5- to 7-member heterocyclyl optionally substituted with one or more $R^8$ groups;
  each $R^7$ and $R^8$ is independently halogen, cyano, nitro, $C_1$-$C_6$ alkyl, $C_2$-$C_6$ alkenyl, $C_1$-$C_6$ haloalkyl, $C_1$-$C_6$ hydroxyalkyl, —$OR^{13}$, —$SR^{13}$, —$N(R^{13})_2$, —$C(O)R^{13}$, —$C(O)OR^{13}$, —$C(O)N(R^{13})_2$, or —$S(O)_2R^{13}$, wherein each $R^{13}$ is independently hydrogen or $C_1$-$C_6$ alkyl.

In some embodiments, compounds of formula (III-A) are those wherein:
n is an integer 0, 1, 2, 3, or 4;
$R^1$ is —$OR^{11}$;
$R^2$ is —$OR^{11}$, $C_1$-$C_{12}$ alkyl, or $C_2$-$C_{12}$ alkenyl, wherein alkyl and alkenyl are optionally substituted with one or more $R^7$; wherein $R^{11}$ is independently hydrogen or $C_1$-$C_6$ alkyl;
  or $R^2$ and $R^6$ together with the atoms to which they are attached form a 5- to 7-member heterocyclyl optionally substituted with one or more $R^7$ groups;
  or $R^2$ and $R^4$ together with the atoms to which they are attached form a 5- to 7-member heterocyclyl optionally substituted with one or more $R^7$ groups;
$R^3$ is independently selected from $C_1$-$C_6$ hydroxyalkyl, —$OR^{12}$, —$N(R^{12})_2$, —$C(O)OR^{12}$, and —$C(O)N(R^{12})_2$, wherein each $R^{12}$ is independently hydrogen or $C_1$-$C_6$ alkyl;
$R^4$ is —$OR^{11}$ or $C_2$-$C_{12}$ alkenyl, wherein alkenyl is optionally substituted with one or more $R^7$;
  or $R^4$ and $R^2$ together with the atoms to which they are attached form a 5- to 7-member heterocyclyl optionally substituted with one or more $R^7$ groups;
$R^5$ is hydrogen; and
$R^6$ is hydrogen or $C_2$-$C_6$ alkenyl, wherein alkenyl is optionally substituted with one or more $R^8$; or $R^6$ and $R^2$ together with the atoms to which they are attached form a 5- to 7-member heterocyclyl optionally substituted with one or more $R^8$ groups;
  each $R^7$ and $R^8$ is independently halogen, cyano, nitro, $C_1$-$C_6$ alkyl, $C_2$-$C_6$ alkenyl, $C_1$-$C_6$ haloalkyl, $C_1$-$C_6$ hydroxyalkyl, —$OR^{13}$, —$SR^{13}$, —$N(R^{13})_2$, —$C(O)R^{13}$, —$C(O)OR^{13}$, —$C(O)N(R^{13})_2$, or —$S(O)_2R^{13}$, wherein each $R^{13}$ is independently hydrogen or $C_1$-$C_6$ alkyl.

In some embodiments, compounds of formula (III-A) are those wherein n is 0. In other embodiments, compounds of formula (III-A) are those where $R^1$—$OR^{11}$, and $R^{11}$ is hydrogen or methyl. Some embodiments provide compounds of formula (III-A) where $R^1$ is hydrogen.

Some embodiments provide compounds of formula (III-A) where $R^2$ is —$OR^{11}$, and $R^{11}$ is independently hydrogen or $C_1$-$C_6$ alkyl. In some embodiments, $R^{11}$ is hydrogen or methyl. Other embodiments provide compounds of formula (III-A) where $R^2$ is hydrogen.

Some embodiments provide compounds of formula (III-A) where $R^4$ is —$OR^{11}$, and $R^{11}$ is independently hydrogen or $C_1$-$C_6$ alkyl. In some embodiments, $R^{11}$ is hydrogen or methyl. Other embodiments provide compounds of formula (III-A) where $R^4$ is $C_2$-$C_{12}$ alkenyl optionally substituted with one or more $R^7$. In some embodiments, $R^4$ is $C_2$-$C_{12}$ alkenyl optionally substituted with hydroxy. In some embodiments, $R^4$ is 3-methylbut-2-en-1-yl optionally substituted with hydroxy. In some embodiments, $R^4$ is 3-methylbut-2-en-1-yl.

Some embodiments provide compounds of formula (III-A) where $R^5$ is hydrogen.

Some embodiments provide compounds of formula (III-A) where $R^6$ is hydrogen.

Representative examples of compounds of formula (III-A) include, but are not limited to the following: dihydroresveratrol, dihydropinosylvin, amorfrutin 2,

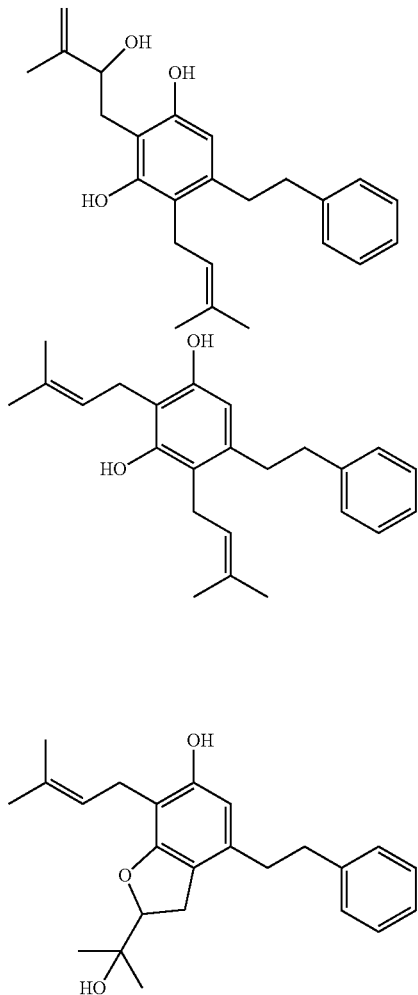

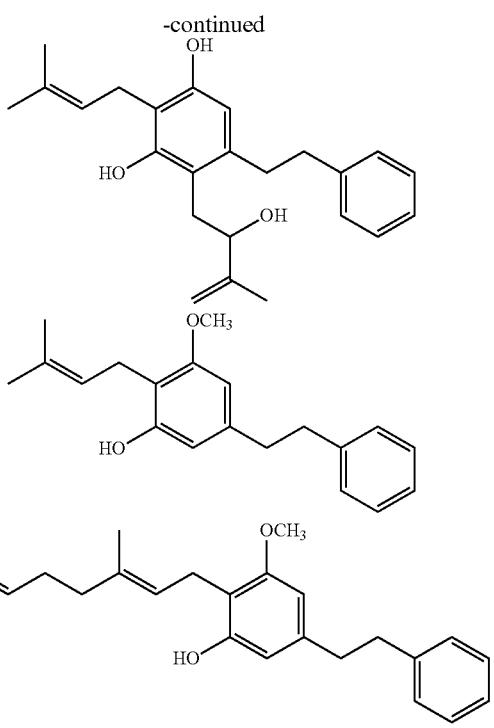

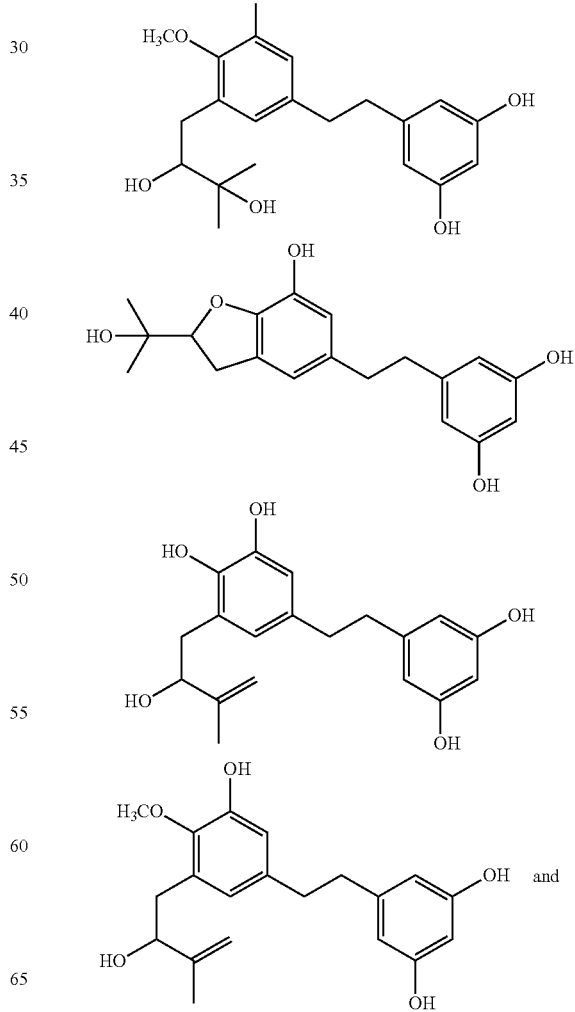

-continued

In some embodiments, the compound of formula (III) is a dihydrochalcone compound of formula (III-B):

(III-B)

or a pharmaceutically acceptable salt thereof, wherein
n is an integer 0, 1, 2, 3, or 4;
$R^1$ is hydrogen or $-OR^{11}$;
  wherein each $R^{11}$ is independently hydrogen, $C_1$-$C_6$ alkyl, or glycosyl;
$R^2$ is hydrogen, $-OR^{11}$, $C_1$-$C_{12}$ alkyl, or $C_2$-$C_{12}$ alkenyl, wherein alkyl and alkenyl are optionally substituted with one or more $R^7$;
  or $R^2$ and $R^6$ together with the atoms to which they are attached form a 5- to 7-member heterocyclyl optionally substituted with one or more $R^7$ groups;
  or $R^2$ and $R^4$ together with the atoms to which they are attached form a 5- to 7-member heterocyclyl optionally substituted with one or more $R^7$ groups;
$R^3$ is independently selected from nitro, $C_1$-$C_6$ alkyl, $C_2$-$C_6$ alkenyl, $C_1$-$C_6$ haloalkyl, $C_1$-$C_6$ hydroxyalkyl, $-OR^{12}$, $-N(R^{12})_2$, $-C(O)R^{12}$, $-C(O)OR^{12}$, $-C(O)N(R^{12})_2$, and $-S(O)_2R^{12}$, wherein each $R^{12}$ is independently hydrogen or $C_1$-$C_6$ alkyl;
$R^4$ is hydrogen, $-OR^{11}$, $C_1$-$C_{12}$ alkyl, or $C_2$-$C_{12}$ alkenyl, wherein alkyl and alkenyl are optionally substituted with one or more $R^7$;
  or $R^4$ and $R^2$ together with the atoms to which they are attached form a 5- to 7-member heterocyclyl optionally substituted with one or more $R^7$ groups;
$R^5$ is hydrogen or $-OR^{11}$; and
$R^6$ is hydrogen, $C_1$-$C_6$ alkyl, $C_2$-$C_6$ alkenyl, $-OR^{11}$, or $-N(R^{10})_2$, wherein each $R^{10}$ is independently hydrogen or $C_1$-$C_6$ alkyl, and wherein alkyl and alkenyl are optionally substituted with one or more $R^8$; or $R^6$ and $R^2$ together with the atoms to which they are attached form a 5- to 7-member heterocyclyl optionally substituted with one or more $R^8$ groups;
each $R^7$ and $R^8$ is independently halogen, cyano, nitro, $C_1$-$C_6$ alkyl, $C_2$-$C_6$ alkenyl, $C_1$-$C_6$ haloalkyl, $C_1$-$C_6$ hydroxyalkyl, $-OR^{13}$, $-SR^{13}$, $-N(R^{13})_2$, $-C(O)R^{13}$, $-C(O)OR^{13}$, $-C(O)N(R^{13})_2$, or $-S(O)_2R^{13}$, wherein each $R^{13}$ is independently hydrogen or $C_1$-$C_6$ alkyl.

In some embodiments, compounds of formula (III-B) are those wherein:
n is an integer 0, 1, 2, 3, or 4;
$R^1$ is hydrogen or $-OR^{11}$;
$R^2$ is hydrogen, $-OR^{11}$, $C_1$-$C_{12}$ alkyl, or $C_2$-$C_{12}$ alkenyl, wherein alkyl and alkenyl are optionally substituted with one or more $R^7$;
  or $R^2$ and $R^6$ together with the atoms to which they are attached form a 5- to 7-member heterocyclyl optionally substituted with one or more $R^7$ groups;
  or $R^2$ and $R^4$ together with the atoms to which they are attached form a 5- to 7-member heterocyclyl optionally substituted with one or more $R^7$ groups;
$R^3$ is independently selected from nitro, $C_1$-$C_6$ alkyl, $C_2$-$C_6$ alkenyl, $C_1$-$C_6$ haloalkyl, $C_1$-$C_6$ hydroxyalkyl, $-OR^{12}$, $-N(R^{12})_2$, $-C(O)R^{12}$, $-C(O)OR^{12}$, $-C(O)N(R^{12})_2$, and $-S(O)_2R^{12}$, wherein each $R^{12}$ is independently hydrogen or $C_1$-$C_6$ alkyl;
$R^4$ is $-OR^{11}$, $C_1$-$C_{12}$ alkyl or $C_2$-$C_{12}$ alkenyl, wherein alkyl and alkenyl are optionally substituted with one or more $R^7$;
  or $R^4$ and $R^2$ together with the atoms to which they are attached form a 5- to 7-member heterocyclyl optionally substituted with one or more $R^7$ groups;
$R^5$ is hydrogen or $-OR^{11}$; and
$R^6$ is hydrogen, $C_1$-$C_6$ alkyl, $C_2$-$C_6$ alkenyl, $-OR^{11}$, or $-N(R^{10})_2$, wherein each $R^{10}$ is independently hydrogen or $C_1$-$C_6$ alkyl, and wherein alkyl and alkenyl are optionally substituted with one or more $R^8$; or $R^6$ and $R^2$ together with the atoms to which they are attached form a 5- to 7-member heterocyclyl optionally substituted with one or more $R^8$ groups;
each $R^7$ and $R^8$ is independently halogen, cyano, nitro, $C_1$-$C_6$ alkyl, $C_2$-$C_6$ alkenyl, $C_1$-$C_6$ haloalkyl, $C_1$-$C_6$ hydroxyalkyl, $-OR^{13}$, $-SR^{13}$, $-N(R^{13})_2$, $-C(O)R^{13}$, $-C(O)OR^{13}$, $-C(O)N(R^{13})_2$, or $-S(O)_2R^{13}$, wherein each $R^{13}$ is independently hydrogen or $C_1$-$C_6$ alkyl.

In some embodiments, compounds of formula (III-B) are those wherein:
n is an integer 0, 1, 2, 3, or 4;
$R^1$ is hydrogen or $-OR^{11}$;
$R^2$ is hydrogen, $-OR^{11}$, $C_1$-$C_{12}$ alkyl, or $C_2$-$C_{12}$ alkenyl, wherein alkyl and alkenyl are optionally substituted with one or more $R^7$; wherein $R^{11}$ is independently hydrogen or $C_1$-$C_6$ alkyl;
  or $R^2$ and $R^6$ together with the atoms to which they are attached form a 5- to 7-member heterocyclyl optionally substituted with one or more $R^7$ groups;
  or $R^2$ and $R^4$ together with the atoms to which they are attached form a 5- to 7-member heterocyclyl optionally substituted with one or more $R^7$ groups;
$R^3$ is independently selected from $C_1$-$C_6$ hydroxyalkyl, $-OR^{12}$, $-N(R^{12})_2$, $-C(O)OR^{12}$, and $-C(O)N(R^{12})_2$, wherein each $R^{12}$ is independently hydrogen or $C_1$-$C_6$ alkyl;
$R^4$ is $-OR^{11}$ or $C_2$-$C_{12}$ alkenyl, wherein alkenyl is optionally substituted with one or more $R^7$;
  or $R^4$ and $R^2$ together with the atoms to which they are attached form a 5- to 7-member heterocyclyl optionally substituted with one or more $R^7$ groups;
$R^5$ is hydrogen; and
$R^6$ is hydrogen or $C_2$-$C_6$ alkenyl, wherein alkenyl is optionally substituted with one or more $R^8$; or $R^6$ and $R^2$ together with the atoms to which they are attached form a 5- to 7-member heterocyclyl optionally substituted with one or more $R^8$ groups;
each $R^7$ and $R^8$ is independently halogen, cyano, nitro, $C_1$-$C_6$ alkyl, $C_2$-$C_6$ alkenyl, $C_1$-$C_6$ haloalkyl, $C_1$-$C_6$ hydroxyalkyl, $-OR^{13}$, $-SR^{13}$, $-N(R^{13})_2$, $-C(O)$ $R^{13}$, —C(O)OR$^{13}$, —C(O)N(R$^{13}$)$_2$, or —S(O)$_2$R$^{13}$, wherein each R$^{13}$ is independently hydrogen or C$_1$-C$_6$ alkyl.

In some embodiments, compounds of formula (III-B) are those wherein n is 0. In other embodiments, compounds of formula (III-B) are those where R$^1$ is —OR$^{11}$, and R$^{11}$ is hydrogen or methyl. Some embodiments provide compounds of formula (III-B) where R$^1$ is hydrogen.

Some embodiments provide compounds of formula (III-B) where R$^2$ is —OR$^{11}$, and R$^{11}$ is independently hydrogen or C$_1$-C$_6$ alkyl. In some embodiments, R$^{11}$ is hydrogen or methyl. Other embodiments provide compounds of formula (III-B) where R$^2$ is hydrogen.

Some embodiments provide compounds of formula (III-B) where R$^4$ is —OR$^{11}$, and R$^{11}$ is independently hydrogen or C$_1$-C$_6$ alkyl. In some embodiments, R$^{11}$ is hydrogen or methyl. Other embodiments provide compounds of formula (III-B) where R$^4$ is C$_2$-C$_{12}$ alkenyl optionally substituted with one or more R$^7$. In some embodiments, R$^4$ is C$_2$-C$_{12}$ alkenyl optionally substituted with hydroxy. In some embodiments, R$^4$ is 3-methylbut-2-en-1-yl optionally substituted with hydroxy. In some embodiments, R$^4$ is 3-methylbut-2-en-1-yl.

Some embodiments provide compounds of formula (III-B) where R$^5$ is hydrogen.

Some embodiments provide compounds of formula (III-B) where R$^6$ is hydrogen.

Representative examples of compounds of formula (III-B) include, but are not limited to phloretin, phlorizin, and pinocembrin dihydrochalcone.

In some embodiments, the methods of producing a compound of any one of formulae (III), (III-A), or (III-B) further comprise harvesting the said compound. In some embodiments, the methods of producing a compound of any one of formulae (III), (III-A), or (III-B) further comprise isolating said compound.

Functional Homologs

Functional homologs of the polypeptides described above are also suitable for use in producing dihydrophenylpropanoid derivatives in a recombinant host as provided herein. A functional homolog is a polypeptide that has sequence similarity to a reference polypeptide, and that carries out one or more of the biochemical or physiological function(s) of the reference polypeptide. A functional homolog and the reference polypeptide can be a natural occurring polypeptide, and the sequence similarity can be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, can themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide-polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of phenylpropanoid or dihydrophenylpropanoid derivative biosynthesis pathway polypeptides. Sequence analysis can involve BLAST, Reciprocal BLAST, or PSI-BLAST analysis of non-redundant databases using a TSC13, CHS2, or P2'UGT amino acid sequence as the reference sequence. Amino acid sequence is, in some instances, deduced from the nucleotide sequence. Those polypeptides in the database that have greater than 40% sequence identity are candidates for further evaluation for suitability as a phenylpropanoid or dihydrophenylpropanoid derivative biosynthesis pathway polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in phenylpropanoid or dihydrophenylpropanoid derivative biosynthesis pathway polypeptides, e.g., conserved functional domains.

Conserved regions can be identified by locating a region within the primary amino acid sequence of a phenylpropanoid or dihydrophenylpropanoid derivative biosynthesis pathway polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. The information included at the Pfam database is described in Sonnhammer et al., Nucl. Acids Res., 26:320-322 (1998); Sonnhammer et al., Proteins, 28:405-420 (1997); and Bateman et al., Nucl. Acids Res., 27:260-262 (1999). Conserved regions also can be determined by aligning sequences of the same or related polypeptides from closely related species. Closely related species preferably are from the same family. In some embodiments, alignment of sequences from two different species is adequate to identify such homologs.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

For example, polypeptides suitable for producing phlorizin in a recombinant host include functional homologs of TSC13, CHS2, and P2'UGT. In another example, homologs suitable for producing naringenin in a recombinant host include recombinant homologs of chalcone synthase and/or chalcone isomerase genes.

Methods to modify the substrate specificity of, for example, a chalcone synthase, a chalcone isomerase, a stilbene synthase, TSC13, CHS2, or P2'UGT, are known to those skilled in the art, and include without limitation site-directed/rational mutagenesis approaches, random directed evolution approaches and combinations in which random mutagenesis/saturation techniques are performed near the active site of the enzyme. For example see Osmani et al., 2009, Phytochemistry 70: 325-347.

A candidate sequence typically has a length that is from 80% to 200% of the length of the reference sequence, e.g., 82, 85, 87, 89, 90, 93, 95, 97, 99, 100, 105, 110, 115, 120, 130, 140, 150, 160, 170, 180, 190, or 200% of the length of the reference sequence. A functional homolog polypeptide typically has a length that is from 95% to 105% of the length of the reference sequence, e.g., 90, 93, 95, 97, 99, 100, 105, 110, 115, or 120% of the length of the reference sequence, or any range between. A % identity for any candidate nucleic acid or polypeptide relative to a reference nucleic acid or polypeptide can be determined as follows. A reference sequence (e.g., a nucleic acid sequence or an amino acid sequence described herein) is aligned to one or more candidate sequences using the computer program ClustalW (version 1.83, default parameters), which allows alignments of nucleic acid or polypeptide sequences to be carried out across their entire length (global alignment). Chenna et al., 2003, *Nucleic Acids Res.* 31(13):3497-500.

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: % age; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: % age; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

It will be appreciated that functional homologs, e.g. of enzymes involved in phenylpropanoid derivative or dihydrophenylpropanoid biosynthesis, such as TSC13, CHS2, and P2'UGT, can include additional amino acids that are not involved in the enzymatic activities carried out by the enzymes.

Recombinant Nucleic Acids

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. "Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also can include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region can be present, e.g., introns, enhancers, upstream activation regions, transcription terminators, and inducible elements.

Recombinant Hosts

Recombinant hosts can be used to express polypeptides for phenylpropanoid derivative or dihydrophenylpropanoid derivative production, including mammalian, insect, plant, and algal cells. A number of prokaryotes and eukaryotes are also suitable for use in constructing the recombinant microorganisms described herein, e.g., gram-negative bacteria, yeast, and fungi. A species and strain selected for use as a phenylpropanoid derivative or dihydrophenylpropanoid derivative production strain is first analyzed to determine which production genes are endogenous to the strain and which genes are not present. Genes for which an endogenous counterpart is not present in the strain are advantageously assembled in one or more recombinant constructs, which are then transformed into the strain in order to supply the missing function(s).

The constructed and genetically engineered microorganisms provided herein can be cultivated using conventional fermentation processes, including, inter alia, chemostat, batch, fed-batch cultivations, continuous perfusion fermentation, and continuous perfusion cell culture.

Carbon sources of use in the instant method include any molecule that can be metabolized by the recombinant host cell to facilitate growth and/or production of the phenylpropanoid derivative or dihydrophenylpropanoid derivative. Examples of suitable carbon sources include, but are not limited to, sucrose (e.g., as found in molasses), fructose, xylose, ethanol, glycerol, glucose, cellulose, starch, cellobiose or other glucose comprising polymer. In embodiments employing yeast as a host, for example, carbons sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g., protein, and then provided with a source of carbon only during the fed-batch phase.

Exemplary prokaryotic and eukaryotic species are described in more detail below. However, it will be appreciated that other species can be suitable. For example, suitable species can be in a genus such as *Agaricus, Aspergillus, Bacillus, Candida, Corynebacterium, Eremothecium, Escherichia, Fusarium/Gibberella, Kluyveromyces, Laetiporus, Lentinus, Phaffia, Phanerochaete, Pichia, Physcomitrella, Rhodoturula, Saccharomyces, Schizosaccharomyces, Sphaceloma, Xanthophyllomyces* or *Yarrowia*. Exemplary species from such genera include *Lentinus tigrinus, Laetiporus sulphureus, Phanerochaete chrysosporium, Pichia pastoris, Cyberlindnera jadinii, Physcomitrella patens, Rhodoturula glutinis 32, Rhodoturula mucilaginosa, Phaffia rhodozyma UBV-AX, Xanthophyllomyces dendrorhous, Fusarium fujikuroi/Gibberella fujikuroi, Candida utilis, Candida glabrata, Candida albicans*, and *Yarrowia lipolytica.*

In some embodiments, a microorganism can be a prokaryote such as *Escherichia coli, Rhodobacter sphaeroides, Rhodobacter capsulatus*, or *Rhodotorula toruloides*.

In some embodiments, a microorganism can be an Ascomycete such as *Gibberella fujikuroi, Kluyveromyces lactis, Schizosaccharomyces pombe, Aspergillus niger, Yarrowia lipolytica, Ashbya gossypii*, or *Saccharomyces cerevisiae.*

In some embodiments, a microorganism can be an algal cell such as *Blakeslea trispora, Dunaliella sauna, Haematococcus piuvialis, Chlorella* sp., *Undaria pinnatifida, Sargassum, Laminaria japonica, Scenedesmus almeriensis* species.

In some embodiments, a microorganism can be a cyanobacterial cell such as *Blakeslea trispora, Dunaliella sauna, Haematococcus pluvialis, Chlorella* sp., *Undaria pinnatifida, Sargassum, Laminaria japonica, Scenedesmus aimeriensis.*

*Saccharomyces* Spp.

*Saccharomyces* is a widely used chassis organism in synthetic biology, and can be used as the recombinant microorganism platform. For example, there are libraries of mutants, plasmids, detailed computer models of metabolism and other information available for *S. cerevisiae*, allowing for rational design of various modules to enhance product yield. Methods are known for making recombinant microorganisms.

*Aspergillus* Spp.

*Aspergillus* species such as *A. oryzae, A. niger* and *A. sojae* are widely used microorganisms in food production and can also be used as the recombinant microorganism platform. Nucleotide sequences are available for genomes of *A. nidulans, A. fumigatus, A. oryzae, A. ciavatus, A. flavus, A. niger*, and *A. terreus*, allowing rational design and modification of endogenous pathways to enhance flux and increase product yield. Metabolic models have been developed for *Aspergillus*. Generally, *A. niger* is cultured for the industrial production of a number of food ingredients such as citric acid and gluconic acid, and thus species such as *A. niger* are generally suitable for producing phenylpropanoid derivatives or dihydrophenylpropanoid derivatives.

*Escherichia Coli*

*Escherichia coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Agaricus, Gibberella*, and *Phanerochaete* Spp.

*Agaricus, Gibberella*, and *Phanerochaete* spp. can be useful because they are known to produce large amounts of isoprenoids in culture. Thus, precursors for producing large amounts of phenylpropanoid derivatives or dihydrophenylpropanoid derivatives are already produced by endogenous genes.

*Arxula Adeninivorans (Blastobotrys Adeninivorans)*

*Arxula adeninivorans* is a dimorphic yeast (it grows as a budding yeast like the baker's yeast up to a temperature of 42° C., above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

*Yarrowia Lipolytica.*

*Yarrowia lipolytica* is a dimorphic yeast (see *Arxula adeninivorans*) and belongs to the family Hemiascomycetes. The entire genome of *Yarrowia lipolytica* is known. *Yarrowia* species is aerobic and considered to be non-pathogenic. *Yarrowia* is efficient in using hydrophobic substrates (e.g. alkanes, fatty acids, oils) and can grow on sugars. It has a high potential for industrial applications and is an oleaginous microorganism. *Yarrowia lipolyptica* can accumulate lipid content to approximately 40% of its dry cell weight and is a model organism for lipid accumulation and remobilization. See e.g. Nicaud, 2012, *Yeast* 29(10):409-18; Beopoulos et al., 2009, *Biohimie* 91(6):692-6; Bankar et al., 2009, *Appl Microbiol Biotechnol.* 84(5):847-65.

*Rhodotorula* Sp.

*Rhodotorula* is a unicellular, pigmented yeast. The oleaginous red yeast, *Rhodotorula glutinis*, has been shown to produce lipids and carotenois from crude glycerol (Saenge et al., 2011, *Process Biochemistry* 46(1):210-8). *Rhodotorula toruloides* strains have been shown to be an efficient fed-batch fermentation system for improved biomass and lipid productivity (Li et al., 2007, *Enzyme and Microbial Technology* 41:312-7).

Rhodosporidium Toruloides

*Rhodosporidium toruloides* is an oleaginous yeast and useful for engineering lipid-production pathways (See e.g. Zhu et al., 2013, *Nature Commun.* 3:1112; Ageitos et al., 2011, *Applied Microbiology and Biotechnology* 90(4):1219-27).

Candida Boidinii

*Candida boidinii* is a methylotrophic yeast (it can grow on methanol). Like other methylotrophic species such as *Hansenula polymorpha* and *Pichia pastoris*, it provides an excellent platform for producing heterologous proteins. Yields in a multigram range of a secreted foreign protein have been reported. A computational method, IPRO, recently predicted mutations that experimentally switched the cofactor specificity of *Candida boidinii* xylose reductase from NADPH to NADH.

Hansenula Polymorpha (Pichia Angusta)

*Hansenula polymorpha* is another methylotrophic yeast (see *Candida boidinii*). It can furthermore grow on a wide range of other substrates; it is thermo-tolerant and can assimilate nitrate (see also *Kluyveromyces lactis*). It has been applied to producing hepatitis B vaccines, insulin and interferon alpha-2a for the treatment of hepatitis C, furthermore to a range of technical enzymes.

Kluyveromyces Lactis

*Kluyveromyces lactis* is yeast regularly applied to producing kefir. It can grow on several sugars, most importantly on lactose which is present in milk and whey. It has successfully been applied among others for producing chymosin (an enzyme that is usually present in the stomach of calves) for producing cheese. Production takes place in fermenters on a 40,000 L scale.

Pichia Pastoris

*Pichia pastoris* is a methylotrophic yeast (see *Candida boidinii* and *Hansenula polymorpha*). It provides an efficient platform for producing foreign proteins. Platform elements are available as a kit and it is worldwide used in academia for producing proteins. Strains have been engineered that can produce complex human N-glycan (yeast glycans are similar but not identical to those found in humans).

Physcomitrella Spp.

*Physcomitrella mosses*, when grown in suspension culture, have characteristics similar to yeast or other fungal cultures. This genera is becoming an important type of cell for producing plant secondary metabolites, which can be difficult to produce in other types of cells.

Methods of Producing Phenylpropanoid Derivatives and Dihydrophenylpropanoid Derivatives Recombinant hosts described herein can be used in methods to produce phenylpropanoid derivatives or dihydrophenylpropanoid derivatives.

For example, the method can include growing the recombinant host in a culture medium under conditions in which phenylpropanoid derivative or dihydrophenylpropanoid derivative biosynthesis genes are expressed. The recombinant host can be grown in a fed batch or continuous process. Typically, the recombinant host is grown in a fermentor at a defined temperature(s) for a desired period of time. Depending on the particular host used in the method, other recombinant genes can also be present and expressed. Levels of substrates and intermediates can be determined by extracting samples from culture media for analysis according to published methods.

After the recombinant host has been grown in culture for the desired period of time, phenylpropanoid derivatives (such as naringenin, resveratrol, pinosylvin, pinocembrin chalcone, and pinocembrin) or dihydrophenylpropanoid derivatives (such as phlorizin or phlorizin precursors) can then be recovered from the culture using various techniques known in the art. In some embodiments, a permeabilizing agent can be added to aid the feedstock entering into the host, and to aid in product release from the host. For example, a crude lysate of the cultured microorganism can be centrifuged to obtain a supernatant. The resulting supernatant can then be applied to a chromatography column, e.g., a C-18 column, and washed with water to remove hydrophilic compounds, followed by elution of the compound(s) of interest with a solvent such as methanol. The compound(s) can then be further purified by preparative HPLC according to methods known in the art.

It will be appreciated that the various genes discussed herein can be present in two or more recombinant hosts rather than a single host. When a plurality of recombinant host is used, they can be grown in a mixed culture to produce phenylpropanoid derivatives or dihydrophenylpropanoid derivatives.

Alternatively, the two or more hosts each can be grown in a separate culture medium and the product of the first culture medium, e.g., a naringenin, resveratrol, or phlorizin precursor, can be introduced into second culture medium to be converted into a subsequent intermediate, or into an end product such as, for example, naringenin, resveratrol, or phlorizin, respectively. The product produced by the second, or final host is then recovered. It will also be appreciated that in some embodiments, a recombinant host is grown using nutrient sources other than a culture medium and utilizing a system other than a fermentor.

In some embodiments, phenylpropanoid derivatives or dihydrophenylpropanoid derivatives are produced in vivo through expression of one or more enzymes involved in a phenylpropanoid derivative biosynthesis pathway or dihydrophenylpropanoid derivative biosynthetic pathway in a recombinant host. For example, a naringenin-producing or resveratrol-producing recombinant host wherein one or more genes encoding a *Saccharomyces cerevisiae* trans-2-enoyl-CoA reductase polypeptide are underexpressed or unexpressed, and expressing recombinant genes encoding, one or more of an *Arabidopsis thaliana* phenylalanine ammonia lyase (PAL2) polypeptide, a gene encoding a *Ammi majus* cinnamate 4-hydroxylase (CH4) polypeptide, a gene encoding a *Arabidopsis thaliana* 4-coumarate-CoA ligase (4CL2) polypeptide, a gene encoding a *Hordeum vulgare* chalcone synthase 2 (CHS2) polypeptide, and/or a gene encoding a cytochrome P450 reductase (CPR1) polypeptide can be used to produce a chalcone compound, e.g. naringenin, in vivo.

As another example, a phlorizin-producing recombinant host expressing one or more of a gene encoding a *Saccharomyces cerevisiae* trans-2-enoyl-CoA reductase (TSC13) polypeptide, a gene encoding an *Arabidopsis thaliana* phenylalanine ammonia lyase (PAL2) polypeptide, a gene encoding a *Ammi majus* cinnamate 4-hydroxylase (C4H) polypeptide, a gene encoding a *Arabidopsis thaliana* 4-coumarate-CoA ligase (4CL2) polypeptide, a gene encoding a *Hordeum vulgare* chalcone synthase 2 (CHS2) polypeptide, a gene encoding a cytochrome P450 reductase (CPR1) polypeptide, and/or a gene encoding a *Malus domestica* P2′UGT polypeptide can be used to produce phlorizin in vivo.

As another example, a stilbenoid (such as resveratrol)-producing recombinant host wherein one or more genes encoding a *Saccharomyces cerevisiae* trans-2-enoyl-CoA reductase polypeptide are underexpressed or unexpressed, and expressing recombinant genes encoding one or more of an *Arabidopsis thaliana* phenylalanine ammonia lyase (PAL2) polypeptide, a gene encoding a *Ammi majus* cinnamate 4-hydroxylase (CH4) polypeptide, a gene encoding a *Arabidopsis thaliana* 4-coumarate-CoA ligase (4CL2) polypeptide, and/or a gene encoding a stilbene synthase (STS) polypeptide, can be used to produce a stilbenoid compound, e.g. resveratrol, in vivo.

As another example, a dihydrostilbenoid (such as dihydroresveratrol)-producing recombinant host expressing one or more of a gene encoding a *Saccharomyces cerevisiae* trans-2-enoyl-CoA reductase (TSC13) polypeptide, a gene encoding an *Arabidopsis thaliana* phenylalanine ammonia lyase (PAL2) polypeptide, a gene encoding a *Ammi majus* cinnamate 4-hydroxylase (C4H) polypeptide, a gene encoding a *Arabidopsis thaliana* 4-coumarate-CoA ligase (4CL2) polypeptide, and/or a gene encoding a stilbene synthase (STS) polypeptide, can be used to produce a dihydrostilbenoid compound in vivo.

In some embodiments, phenylpropanoid derivatives or dihydrophenylpropanoid derivatives are produced through contact of a precursor of the desired compound with one or more enzymes involved in the phenylpropanoid derivative or dihydrophenylpropanoid derivative biosynthesis pathway in vitro. For example, contacting p-coumaroyl-CoA with a chalcone synthase polypeptide can result in production of a naringenin or naringenin derivative compound in vitro. In some embodiments, a naringenin precursor is produced through contact of an upstream naringenin precursor with one or more enzymes involved in the naringenin pathway in vitro. As another example, contacting p-coumaroyl-CoA with a chalcone synthase enzyme, in the absence of a trans-2-enoyl-CoA reductase enzyme, can result in production of naringenin in vitro. As another example, contacting phloretin with a P2'UGT polypeptide can result in production of a phlorizin compound in vitro. In some embodiments, a phlorizin precursor is produced through contact of an upstream phlorizin precursor with one or more enzymes involved in the phlorizin pathway in vitro. As another example, contacting p-coumaroylCoA with a trans-2-enoyl-CoA reductase enzyme can result in production of p-dihydrocoumaroyl CoA in vitro.

In some embodiments, a phenylpropanoid derivative or dihydrophenylpropanoid derivative is produced by bioconversion. For bioconversion to occur, a host cell expressing one or more enzymes involved in the phenylpropanoid derivative or dihydrophenylpropanoid derivative biosynthesis pathway takes up and modifies a phenylpropanoid derivative precursor or dihydrophenylpropanoid derivative precursor in the cell; following modification in vivo, the phenylpropanoid derivative or dihydrophenylpropanoid derivative remains in the cell and/or is excreted into the culture medium. For example, a host cell expressing a gene encoding a chalcone synthase polypeptide can take up coumaroyl CoA and convert it to naringenin in the cell; following conversion in vivo, a naringenin compound is excreted into the culture medium. As another example, a host cell expressing a gene encoding a UGT polypeptide can take up phloretin and glycosylate phloretin in the cell; following glycosylation in vivo, a phlorizin compound is excreted into the culture medium.

In some embodiments, phenylpropanoid derivatives or dihydrophenylpropanoid derivatives as disclosed herein are isolated and purified to homogeneity (e.g., at least 90%, 92%, 94%, 96%, or 98% pure). In other embodiments, phenylpropanoid derivatives or dihydrophenylpropanoid derivatives are isolated as an extract from a recombinant host or in vitro production method. In this respect, phenylpropanoid derivatives or dihydrophenylpropanoid derivatives may be isolated, but not necessarily purified to homogeneity. Desirably, the amount of phenylpropanoid derivatives or dihydrophenylpropanoid derivatives produced can be from about 1 mg/L to about 20,000 mg/L or higher. For example about 1 to about 100 mg/L, about 30 to about 100 mg/L, about 50 to about 200 mg/L, about 100 to about 500 mg/L, about 100 to about 1,000 mg/L, about 250 to about 5,000 mg/L, about 1,000 to about 15,000 mg/L, or about 2,000 to about 10,000 mg/L of phenylpropanoid derivatives or dihydrophenylpropanoid derivatives can be produced. In general, longer culture times will lead to greater amounts of product. Thus, the recombinant microorganism can be cultured for from 1 day to 7 days, from 1 day to 5 days, from 3 days to 5 days, about 3 days, about 4 days, or about 5 days.

EXAMPLES

The Examples that follow are illustrative of specific embodiments disclosed herein and various uses thereof. They are set forth for explanatory purposes only and are not to be taken as limiting.

Example 1: Production of Phloretin in Yeast

Materials and Methods:

The *S. cerevisiae* strains used in Examples 1 and 2 are listed in Table 1:

TABLE 1

Strains used in Examples 1 and 2. Three different plasmids (pPHLO, pPHLON, pPHLOZ) were assembled by in vivo homologous recombination in the background strain Sc1.0 to make strains Sc1.1, Sc1.2 and Sc1.3.

| Strain | Description |
|---|---|
| Sc1.0 | *S. cerevisiae* background strain |
| Sc1.1 | Sc1.0 + pPHLO |
| Sc1.2 | Sc1.0 + pPHLON |
| Sc1.3 | Sc1.0 + pPHLOZ |

The genes used in Examples 1 and 2 are listed in Table 2:

TABLE 2

Genes used in Examples 1 and 2.

| Gene name | SEQ ID NO: | Source of sequence |
|---|---|---|
| PAL2 At | 1 | *Arabidopsis thaliana* |
| C4H Am | 2 | *Ammi majus* |
| 4CL2 At | 3 | *Arabidopsis thaliana* |
| CHS2 Hv | 4 | *Hordeum vulgare* |
| P2'UGT Md | 5 | *Malus domestica* |
| CPR1 Sc | 6 | *Saccharomyces cerevisiae* |
| TSC13 Sc | 7 | *Saccharomyces cerevisiae* |

Chemical reference compounds were purchased from Sigma-Aldrich, Switzerland (naringenin, phlorizin) or Extrasynthese, France (phloretin).

Gene Cloning:

Synthetic genes, codon optimized for expression in yeast, were manufactured by DNA2.0 Inc., Menlo Park, Calif., USA or GeneArt AG, Regensburg, Germany (SEQ ID NOs: 1, 2, 4, and 5). During synthesis all genes except PAL2 At were provided, at the 5'-end, with the DNA sequence AAGCTTAAA comprising a HindIII restriction recognition site and a Kozak sequence, and at the 3'-end the DNA sequence CCGCGG comprising a SacII recognition site. By PCR, PAL2 At was provided, at the 5'-end, with the DNA sequence AAGCTTAAA comprising a HindIII restriction recognition site and a Kozak sequence, and at the 3'-end the DNA sequence CCGCGG comprising a SacII recognition site. The *A. thaliana* gene 4CL2 (SEQ ID NO: 3) was amplified by PCR from first strand cDNA. The 4CL2 sequence has one internal HindIII, and one internal SacII site, and was therefore cloned, using the In-Fusion HD Cloning Plus kit (Clontech Inc.), into HindIII and SacII, according to manufacturers' instruction. *S. cerevisiae* genes were amplified from genomic DNA of background strain Sc1.0 by PCR (SEQ ID NOs: 6 and 7). During PCR, the two genes were provided, at the 5'-end, with the DNA sequence AAGCTTAAA comprising a HindIII restriction recognition site and a Kozak sequence, and at the 3'-end the DNA sequence CCGCGG comprising a SacII recognition site. An internal SacII site of SEQ ID NO: 6 was removed with a silent point mutation (C519T) by site directed mutagenesis. All genes were cloned into HindIII and SacII of pUC18 based vectors containing yeast expression cassettes derived from native yeast promoters and terminators. Promoters and terminators, described by Shao et al. (Nucl. Acids Res. 2009, 37(2):e16), had been prepared by PCR from yeast genomic DNA. Each expression cassette was flanked by 60 bp homologous recombination tag (HRT) sequences, on both sides, and the cassette including these HRTs were in turn flanked by AscI recognition site. The HRTs were designed such that the 3'-end tag of the first expression cassette fragment was identical to the 5'-end tag of the second expression cassette fragment, and so forth. Three helper fragments (SEQ ID NOs:11-14) were used to assemble multi-expression plasmids in yeast by homologous recombination. One helper fragment comprised a yeast auxotrophic marker (URA3) and the bacterial pSC101 origin of replication (SEQ ID NO: 11). The second helper fragment comprised the ARS4/CEN6 sequence for replication in yeast and the bacterial chloramphenicol resistance marker (SEQ ID NO: 12). Both fragments had flanking HRTs. The third fragment was designed only with HRTs separated by a short 600 bp spacer sequence. This helper fragment contained different HRTs depending on the number of gene expression cassettes the resulting multi-expression plasmid contains (SEQ ID NO: 13 for 6 genes (e.g., pPHLO and pPHLON); and SEQ ID NO: 14 for 7 genes (e.g., pPHLOZ)). All helper fragments had been cloned in a pUC18 based backbone for amplification in *E. coli*. All fragments were cloned in AscI sites from where they could be excised.

To prepare the three plasmids, pPHLO, pPHLON and pPHLOZ (SEQ ID NOs:8-10), plasmid DNA from the three helper plasmids was mixed with plasmid DNA from each of the plasmids containing the expression cassettes. Three different mixes, comprising different sets of genes as listed in Table 3, were prepared. The mixes of plasmid DNA were digested with AscI. This releases all fragments from the plasmid backbone and creates fragments with HRTs at the ends, these being sequentially overlapping with the HRT of the next fragment. Yeast strain Sc1.0 was transformed with each of the digested mixes, and the plasmids pPHLO, pPHLON and pPHLOZ were assembled in vivo by homologous recombination as described by Shao et al. 2009.

TABLE 3

Multi-expression plasmids used in Examples 1 and 2.

| Name | SEQ ID NO: | Genes in HRT vectors |
|---|---|---|
| pPHLO | 8 | CHS2 Hv, TSC13 Sc, 4CL2 At, PAL2 At, C4H Am, CPR1 Sc |
| pPHLON | 9 | CHS2 Hv, 663 bp stuffer, 4CL2 At, PAL2 At, C4H Am, CPR1 Sc |
| pPHLOZ | 10 | CHS2 Hv, TSC13 Sc, 4CL2 At, PAL2 At, C4H Am, CPR1 Sc, P2'UGT Md | pPHLO contained the whole biosynthetic pathway to convert phenylalanine to phloretin, comprising PAL2 At, C4H Am, CPR1 Sc, 4CL2 At, TSC13 Sc and CHS2 Hv. pPHLON is equivalent to pPHLO, except that TSC13 Sc is replaced by a non-expressed stuffer sequence (SEQ ID NO: 15), and pPHLOZ is equivalent to pPHLO except that it contains an additional expression cassette with P2'UGT Md.

Growth Conditions:

The engineered yeast strains were grown in 2.5 mL standard SC-all broth (Sc1.0) or SC-Ura, i.e., without uracil (Sc1.1, Sc1.2 and Sc1.3), and with 2% glucose (ForMedium, Hunstanton, U.K.) in 24 deep well plates (Kuhner AG, Switzerland). Cultures were grown with constant shaking at 300 RPM with 5 cm amplitude at 30° C. for 72 hours. They were inoculated from a preculture grown at the same conditions in 0.4 mL medium for 24 hours to an OD of 0.1.

Analytical Procedures:

Sample preparation: Yeast cultures were diluted with an equal volume of 100% methanol. After vigorous mixing by vortexing at 1500 RPM for 30 seconds, cells were spun down for 5 minutes at 4000×g. The pellet and the supernatant were separated. Without further purification, 5 μL of supernatant were injected in a UPLC instrument (Waters Acquity™ Ultra Performance Liquid chromatography, Waters, Milford, Mass., USA), coupled to a Single Quadrupole Detector (SQD) mass spectrometer (Waters, Milford, Mass., USA).

Stationary Phase: the column used was a Waters Acquity UPLC® Bridged Ethyl Hybrid (BEH) C18 1.7□m 2.1×100 mm. Liquid Chromatography method: Mobile Phase A: H2O+0.1% Formic Acid. Mobile Phase B: Acetonitrile+ 0.1% Formic Acid.

Running Conditions:

| Time (min) | Flow (mL/min) | % mobile phase A | % mobile phase B |
|---|---|---|---|
| T = 0 | 0.400 | 80 | 20 |
| 8.0 | 0.400 | 65 | 35 |
| 8.1 | 0.400 | 0 | 100 |
| 10.0 | 0.400 | 0 | 100 |
| 10.1 | 0.400 | 80 | 20 |
| 12.0 | 0.400 | 80 | 20 |

PDA parameters: λ range: 210 nm to 400 nm.
Resolution: 1.2 nm.
Sampling rate: 20 points/sec.
SQD parameters: Source: Electrospray ionization in the positive mode (ESI+).
Capillary: 3.5 kV. Cone: 30 V. Extractor: 3V.
Source temperature: 150° C.

Desolvation temperature: 350° C. Gas flow was set at 50 L/hr for the cone and at 450 L/hr for desolation.

MS mode: SIR (selected ion recording) mode. Ion masses to be recorded were chosen so as to detect the compounds of interest (see results).

The column was kept at a constant temperature of 35° C.

Results:

The supernatants, after ethanol dilution, of Sc1.0, Sc1.1, and Sc1.2 cultures were analyzed by UPLC-MS and the ion chromatograms of the expected mass of phloretin (m/z=274.3 Da) and the expected mass of naringenin (m/z=272.3 Da) were recorded. The areas under the peaks were integrated and production of phloretin and naringenin was calculated based on standard curves. The amounts of phloretin and naringenin produced by Sc1.1 and Sc1.2 were compared (FIG. 4) showing that the overexpression of TSC13 in combination with the core flavonoid pathway in Sc1.1 increased the phloretin production by a factor of 1.9, whereas the naringenin production is decreased by a factor of 11.8. The background strain Sc1.0 without overexpression of any of the genes did not produce any phloretin or naringenin.

The art describes plant enzymes proposed to convert phenylpropanoids to dihydrophenylpropanoids. Dare et al. (Plant Physiol Biochem. 2013, 72:54-61) proposed two proteins, ENRL3 and ENRL5, to be involved in the conversion. Analysis of the protein sequences places these enzymes in the group of enoyl reductases normally involved in VLCFA synthesis. Ibdah et al. (*Phytochemistry.* 2014, 107:24-31) described another enzyme MdHCDBR to be involved in the conversion. The MdHCDBR protein sequence indicates that it belongs to the group of double bond reductases which normally reduces small aldehydes.

Figure 4:
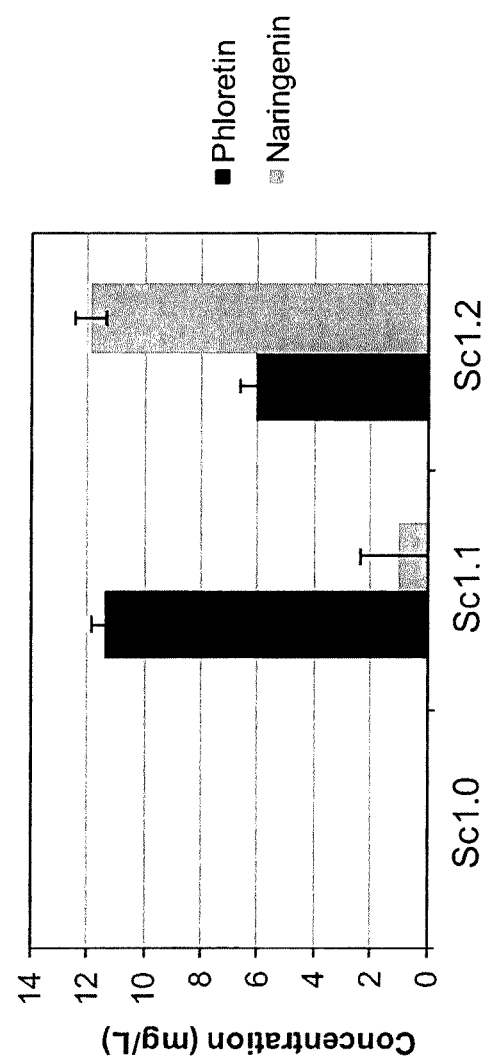
FIG. 4 shows production of the dihydro-coumaroyl-CoA derivative phloretin (m/z=274.3 Da) and the p-coumaroyl-CoA derivative naringenin (m/z 272.3) in strains Sc1.0, Sc1.1, and Sc1.2 based on UPLC-MS peak integration. Production of the phenylpropanoid naringenin is increased when Tsc13 activity or expression is low.

Synthetic, yeast codon-optimized gene versions of the three reductases ENRL3, ENRL5, and MdHCDBR were expressed in yeast together with enzymes of the remaining pathway to phloretin. After chemical analysis of the cultures, no increase in phloretin production was observed (data not shown). However, surprisingly and unexpectedly, small amounts of phloretin were observed to be produced in a strain that expressed no heterologous reductase. This prompted testing of native reductases of yeast, to see if any of these were involved. Out of several native reductases, TSC13 was identified as having reductase activity. As shown in FIG. 4, overexpression of TSC13 confirmed that the activity of this enzyme, together with the remaining heterologous pathway, was crucial for efficient production of phloretin.

Because *Saccharomyces cerevisiae* TSC13 has previously been known only to be involved in enoyl-reduction during fatty acid synthesis producing the 26-carbon very long chain fatty acids (VLCFA) from palmitate, p-coumaroyl-CoA is a highly unexpected substrate for TSC13. The use of overexpression of TSC13 to produce precursors of dihydrochalcones, such as phlorizin and phloretin, and dihydrostilbenoids was thus surprising and unexpected.

Example 2: Production of Phlorizin in Yeast

Materials and Methods:

The materials and methods of Example 2 are the same as those described for Example 1.

Figure 5:
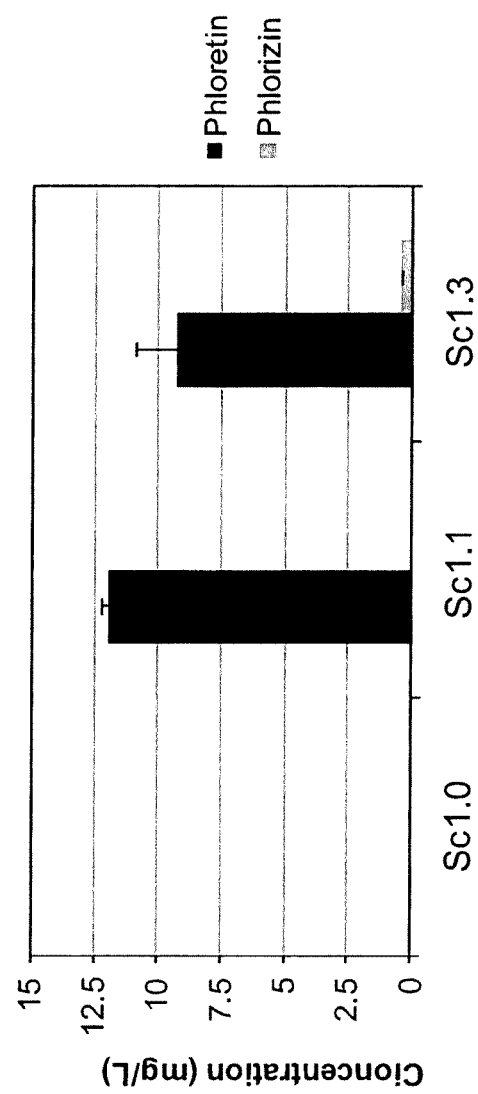
FIG. 5 shows production of phloretin (m/z=274.3 Da) and phlorizin (m/z=436.4 Da) in strains Sc1.0, Sc1.1, and Sc1.3 based on LC-MS peak integration.

Results:

The supernatants, after ethanol dilution, of Sc1.0, Sc1.1 and Sc1.3 cultures were analyzed by LC-MS and the ion chromatograms of the expected mass of phloretin (m/z=274.3 Da) and the expected mass of phlorizin (m/z=436.4) were extracted. The areas under the peaks were integrated and production of phloretin and phlorizin was calculated based on a standard curves. The additional overexpression of P2'UGT Md in Sc1.3 resulted in a production of 0.4 mg/L of phlorizin (FIG. 5). The background strain Sc1.0 without overexpression of any of the genes did not produce any phloretin or phlorizin.

Example 3: Production of Phloretin in Yeast with Various Chalcone Synthases

Materials and Methods:

The materials and methods of Example 3 are the same as those described for Example 1, except that a different parental strain and different CHS sequences were used.

The *S. cerevisiae* strains used in Example 3 are listed in Table 4:

TABLE 4

Strains used in Example 3. Twelve different plasmids (pPHCHS1-12) were assembled by in vivo homologous recombination in the background strain Sc3.0 to make strains Sc3.1-Sc3.12.

| Strain | Description |
| --- | --- |
| Sc3.0 | *S. cerevisiae* background strain |
| Sc3.1 | Sc3.0 + pPHCHS1 |
| Sc3.2 | Sc3.0 + pPHCHS2 |
| Sc3.3 | Sc3.0 + pPHCHS3 |
| Sc3.4 | Sc3.0 + pPHCHS4 |
| Sc3.5 | Sc3.0 + pPHCHS5 |
| Sc3.6 | Sc3.0 + pPHCHS6 |
| Sc3.7 | Sc3.0 + pPHCHS7 |
| Sc3.8 | Sc3.0 + pPHCHS8 |
| Sc3.9 | Sc3.0 + pPHCHS9 |
| Sc3.10 | Sc3.0 + pPHCHS10 |
| Sc3.11 | Sc3.0 + pPHCHS11 |
| Sc3.12 | Sc3.0 + pPHCHS12 |

The additional genes used in Example 3 are listed in Table 5:

TABLE 5

Additional genes used in Example 3.

| Gene name | SEQ ID NO: | Source of sequence |
| --- | --- | --- |
| CHS Ha | 27 | *Hypericum androsaemum* |
| CHS Pc | 28 | *Petroselinum crispum* |
| CHS Ph | 29 | *Petunia hybrid* |
| CHS1 Hv | 30 | *Hordeum vulgare* |
| CHS2 Hv | 4 | *Hordeum vulgare* |
| CHS Sb | 31 | *Scutellaria baicalensis* |
| CHS Md c co | 32 | *Malus domestica* |
| CHS Md a | 33 | *Malus domestica* |
| CHS Md b | 34 | *Malus domestica* |
| CHS Md c | 35 | *Malus domestica* |
| CHS Md d | 36 | *Malus domestica* |

Gene Cloning:

Synthetic genes, codon optimized for expression in yeast, were manufactured by DNA2.0 Inc., Menlo Park, Calif., USA or GeneArt AG, Regensburg, Germany (SEQ ID NOs: 4 and 27-32). During synthesis all genes were provided, at the 5'-end, with the DNA sequence AAGCTTAAA comprising a HindIII restriction recognition site and a Kozak sequence, and at the 3'-end the DNA sequence CCGCGG comprising a SacII recognition site. The *M. domestica* genes CHSa,b,c,d (SEQ ID NOs: 33-36) were amplified by PCR from first strand cDNA. They were cloned using the In- Fusion HD Cloning Plus kit (Clontech Inc.), into HindIII and SacII, according to manufacturers' instructions. All genes were cloned into HindIII and SacII of pUC18 based HRT vectors.

To prepare the twelve plasmids, pPHCHS1-12, plasmid DNA from the three helper plasmids were mixed with plasmid DNA from each of the plasmids containing the expression cassettes. Twelve different mixes, comprising different sets of genes as listed in Table 6, were prepared. The mixes of plasmid DNA were digested with AscI. This released all fragments from the plasmid backbone and created fragments with HRTs at the ends, these being sequentially overlapping with the HRT of the next fragment. Background yeast strain Sc3.0 was transformed with each of the digested mixes, and the plasmids pPHCHS1-12 were assembled in vivo by homologous recombination as described by Shao et al. 2009.

TABLE 6

Multi-expression plasmids used in Example 3.

| Name | Genes in HRT vectors |
| --- | --- |
| pPHCHS1 | CHS Ha, TSC13 Sc, 4CL2 At, PAL2 At, C4H Am, CPR1 Sc |
| pPHCHS2 | CHS Pc, TSC13 Sc, 4CL2 At, PAL2 At, C4H Am, CPR1 Sc |
| pPHCHS3 | CHS Ph, TSC13 Sc, 4CL2 At, PAL2 At, C4H Am, CPR1 Sc |
| pPHCHS4 | CHS1 Hv, TSC13 Sc, 4CL2 At, PAL2 At, C4H Am, CPR1 Sc |
| pPHCHS5 | CHS2 Hv, TSC13 Sc, 4CL2 At, PAL2 At, C4H Am, CPR1 Sc |
| pPHCHS6 | CHS Sb, TSC13 Sc, 4CL2 At, PAL2 At, C4H Am, CPR1 Sc |
| pPHCHS7 | CHS Md c co, TSC13 Sc, 4CL2 At, PAL2 At, C4H Am, CPR1 Sc |
| pPHCHS8 | CHS Md a, TSC13 Sc, 4CL2 At, PAL2 At, C4H Am, CPR1 Sc |
| pPHCHS9 | CHS Md b, TSC13 Sc, 4CL2 At, PAL2 At, C4H Am, CPR1 Sc |
| pPHCHS10 | CHS Md c, TSC13 Sc, 4CL2 At, PAL2 At, C4H Am, CPR1 Sc |
| pPHCHS11 | CHS Md d, TSC13 Sc, 4CL2 At, PAL2 At, C4H Am, CPR1 Sc |
| pPHCHS12 | 663 bp stuffer, TSC13 Sc, 4CL2 At, C4H Am, CPR1 Sc |

Figure 6:
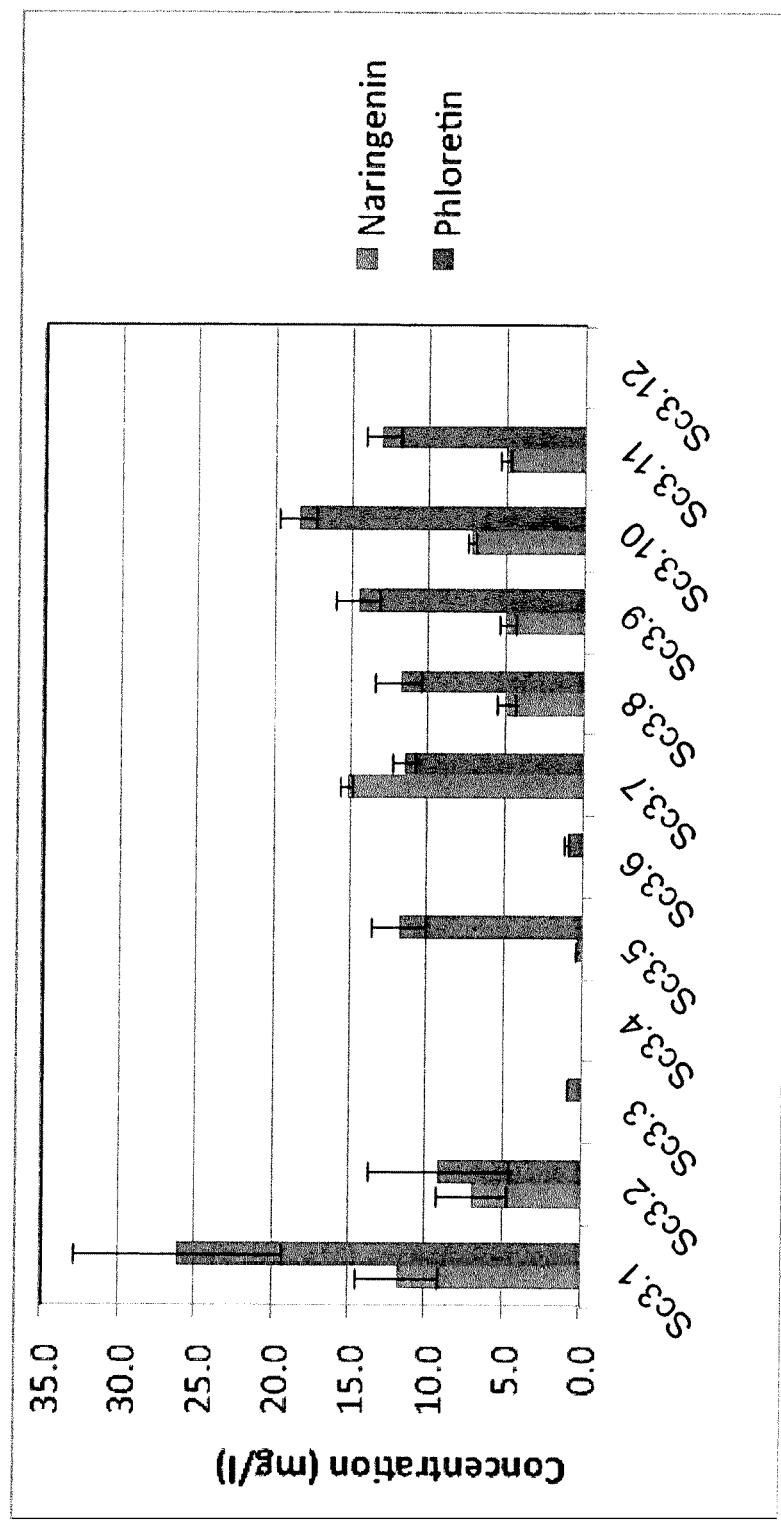
FIG. 6 shows production of phloretin (m/z=274.3 Da) and phlorizin (m/z=436.4 Da) (based on LC-MS peak integration) in yeast strains with eleven different chalcone synthases.

Results:

The supernatants, after ethanol dilution, of Sc3.1-Sc3.12 cultures were analyzed by LC-MS and the ion chromatograms of the expected mass of phloretin (m/z=274.3 Da) and the expected mass of naringenin (m/z=272.3 Da) were recorded. The areas under the peaks were integrated and production of phloretin and naringenin was calculated based on standard curves (FIG. 6). Of the eleven CHSs tested, production of phloretin was observed for ten of them. The highest phloretin titer of 26.2 mg/l was observed with CHS Ha (strain Sc3.1).

Example 4: Production of Dihydroresveratrol in Yeast

Materials and Methods:

The materials and methods of Example 4 were the same as those described for Example 1, except that a different parental strain and two additional type 3 polyketide synthase sequences were used.

The S. cerevisiae strains used in Example 4 are listed in Table 7:

TABLE 7

Strains used in Example 4. Four different plasmids (pDHR1, pDHR2, pDHRN1 and pDHRN2) were assembled by in vivo homologous recombination in the background strain Sc4.0 to make strains Sc4.1-Sc4.4.

| Strain | Description |
| --- | --- |
| Sc4.0 | S. cerevisiae background strain |
| Sc4.1 | Sc4.0 + pDHR1 |
| Sc4.2 | Sc4.0 + pDHR2 |
| Sc4.3 | Sc4.0 + pDHRN1 |
| Sc4.4 | Sc4.0 + pDHRN2 |

The additional genes used in Example 4 are listed in Table 8:

TABLE 8

Additional genes used in Example 4.

| Gene name | SEQ ID NO: | Source of sequence |
| --- | --- | --- |
| STS Vp | 37 | Vitis pseudoreticulata |
| VST1 Vv | 38 | Vitis vinifera |

Gene Cloning:

The synthetic genes were codon optimized for expression in yeast (SEQ ID NOs: 37-38). During synthesis, the genes were provided, at the 5'-end, with the DNA sequence AAA comprising a Kozak sequence. The genes contained one and two internal HindIII sites, and were therefore cloned using the In-Fusion HD Cloning Plus kit (Clontech Inc.), into HindIII and SacII, according to manufacturers' instructions.

To prepare the four plasmids, pDHR1, pDHR2, pDHRN1, and pDHRN2, plasmid DNA from the three helper plasmids was mixed with plasmid DNA from each of the plasmids containing the expression cassettes. Four different mixes, comprising different sets of genes as listed in Table 9, were prepared. The mixes of plasmid DNA were digested with AscI. This released all fragments from the plasmid backbone and created fragments with HRTs at the ends, these being sequentially overlapping with the HRT of the next fragment. Background yeast strain Sc4.0 was transformed with each of the digested mixes, and the plasmids pDHR1, pDHR2, pDHRN1 and pDHRN2 were assembled in vivo by homologous recombination as described by Shao et al. 2009.

TABLE 9

Multi-expression plasmids used in Example 4.

| Name | Genes in HRT vectors |
| --- | --- |
| pDHR1 | STS Vp, TSC13 Sc, 4CL2 At, PAL2 At, C4H Am, CPR1 Sc |
| pDHR2 | VST1 Vv, TSC13 Sc, 4CL2 At, PAL2 At, C4H Am, CPR1 Sc |
| pDHRN1 | STS Vp, 663 bp stuffer, 4CL2 At, PAL2 At, C4H Am, CPR1 Sc |
| pDHRN2 | VST1 Vv, 663 bp stuffer, 4CL2 At, PAL2 At, C4H Am, CPR1 Sc |

Figure 8:
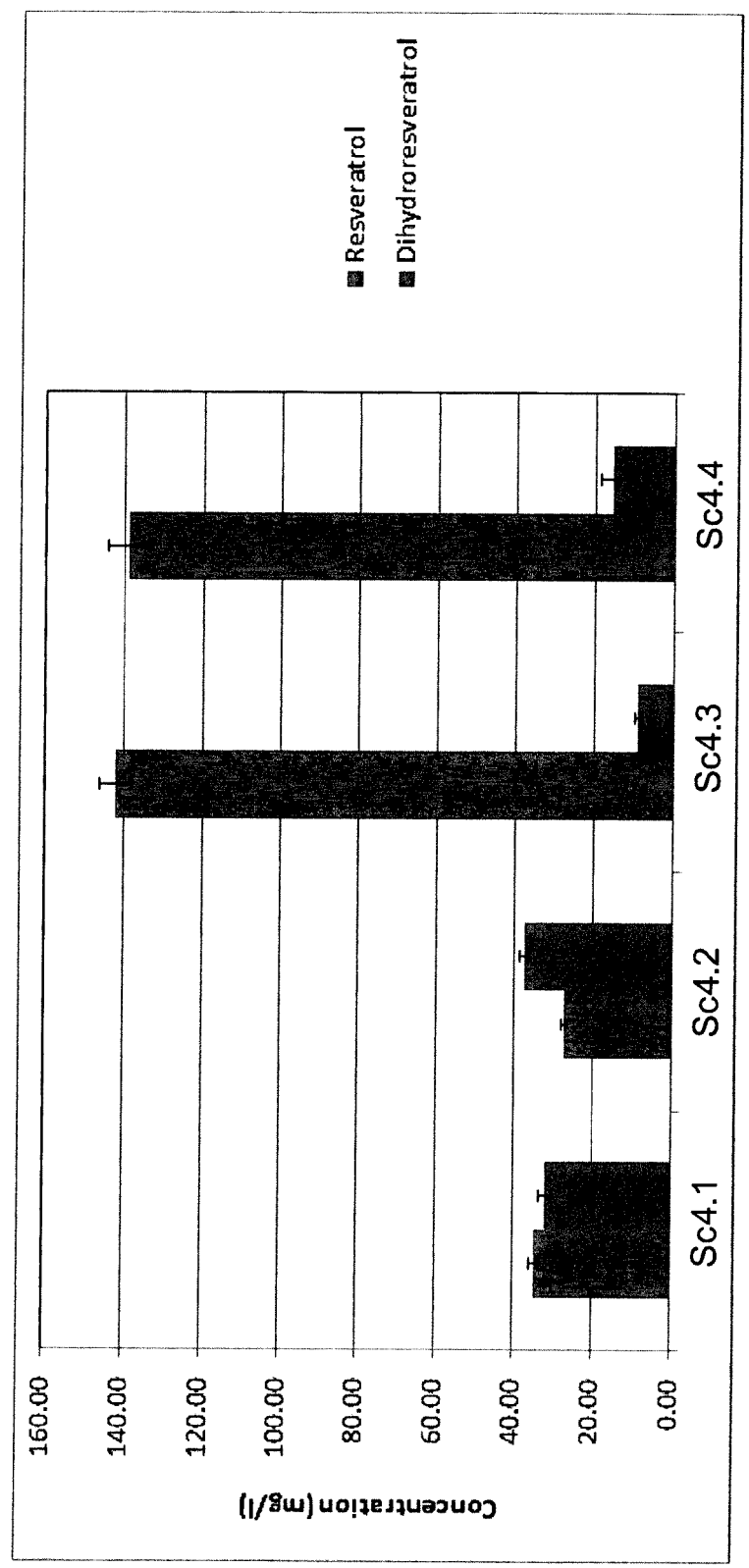
FIG. 8 shows the production of resveratrol (m/z=228.2 Da) and dihydroresveratrol (m/z=230.2 Da) (based on LC-MS peak integration) in yeast strains overexpressing TSC13 in combination with the core stilbene pathway.

Results:

The supernatants, after ethanol dilution, of Sc4.1-Sc4.4 cultures were analyzed by LC-MS and the ion chromatograms of the expected mass of dihydroresveratrol (m/z=230.2 Da) and resveratrol (m/z=228.2 Da) were recorded. The areas under the peaks were integrated. As shown in FIG. 8, the amounts of dihydroresveratrol and resveratrol produced by strains Sc4.1-Sc4.4 were compared, showing that the overexpression of TSC13 in combination with the core stilbene pathway (Sc4.1 and Sc4.2 in comparison with Sc4.3 and Sc4.4) resulted in increased dihydroresveratrol production, whereas the resveratrol production decreased.

Example 5: Comparison of Double Bond Reductases for Production of Phloretin

Materials and Methods:

The materials and methods of Example 5 are the same as those described for Example 1, except that a different parental strain and various double bond reductase sequences were used.

The *S. cerevisiae* strains for Example 5 are listed in Table 10:

TABLE 10

Strains for Example 5. Twelve different plasmids (pPHDR1-12) were assembled by in vivo homologous recombination in the background strain Sc5.0 to make strains Sc5.1 through Sc5.12.

| Strain | Description |
| --- | --- |
| Sc5.0 | *S. cerevisiae* background strain |
| Sc5.1 | Sc5.0 + pPHDR1 |
| Sc5.2 | Sc5.0 + pPHDR2 |
| Sc5.3 | Sc5.0 + pPHDR3 |
| Sc5.4 | Sc5.0 + pPHDR4 |
| Sc5.5 | Sc5.0 + pPHDR5 |
| Sc5.6 | Sc5.0 + pPHDR6 |
| Sc5.7 | Sc5.0 + pPHDR7 |
| Sc5.8 | Sc5.0 + pPHDR8 |
| Sc5.9 | Sc5.0 + pPHDR9 |
| Sc5.10 | Sc5.0 + pPHDR10 |
| Sc5.11 | Sc5.0 + pPHDR11 |
| Sc5.12 | Sc5.0 + pPHDR12 |

The additional genes for Example 5 are listed in Table 11:

TABLE 11

Additional genes for Example 5.

| Gene name | SEQ ID NO: | Source of sequence |
| --- | --- | --- |
| ENR3 | 39 | *Malus domestica* |
| ENR5 | 40 | *Malus domestica* |
| ZS1 Ri | 41 | *Rubus idaeus* |
| ENR | 42 | *Eubacterium ramulus* |
| DFG10 | 43 | *Saccharomyces cerevisiae* |
| HCDBR | 44 | *Malus domestica* |
| ENR | 45 | *Arabidopsis thaliana* |
| ENR | 46 | *Gossypium hirsutum* |
| ENR | 47 | *Malus domestica* |
| TSC13 | 48 | *Kluyveromyces lactis* |

Gene Cloning:

The synthetic genes, codon optimized for expression in yeast, were manufactured by GeneArt AG, Regensburg, Germany (SEQ ID NOs: 39-48). During synthesis, the genes were provided, at the 5'-end, with the DNA sequence AAGCTTAAA comprising a HindIII restriction recognition site and a Kozak sequence, and at the 3'-end the DNA sequence CCGCGG comprising a SacII recognition site. The genes were cloned into HindIII and SacII of pUC18 based HRT vectors.

To prepare the twelve plasmids, pPHDR1-12, plasmid DNA from the three helper plasmids was mixed with plasmid DNA from each of the plasmids containing the expression cassettes. Twelve different mixes, comprising different sets of genes as listed in Table 12, were prepared. The mixes of plasmid DNA were digested with AscI. This released all fragments from the plasmid backbone and created fragments with HRTs at the ends, these being sequentially overlapping with the HRT of the next fragment. Background yeast strain Sc5.0 was transformed with each of the digested mixes, and the plasmids pPHDR1-12 were assembled in vivo by homologous recombination as described by Shao et al. 2009.

TABLE 12

Multi-expression plasmids used in Example 5.

| Name | Genes in HRT vectors |
| --- | --- |
| pPHDR1 | CHS Ha, ENR3 Md, 4CL2 At, PAL2 At, C4H Am, CPR1 Sc |
| pPHDR2 | CHS Ha, ENR5 Md, 4CL2 At, PAL2 At, C4H Am, CPR1 Sc |
| pPHDR3 | CHS Ha, ZS1 Ri, 4CL2 At, PAL2 At, C4H Am, CPR1 Sc |
| pPHDR4 | CHS Ha, ENR Er, 4CL2 At, PAL2 At, C4H Am, CPR1 Sc |
| pPHDR5 | CHS Ha, DFG10 Sc, 4CL2 At, PAL2 At, C4H Am, CPR1 Sc |
| pPHDR6 | CHS Ha, TSC13 Sc, 4CL2 At, PAL2 At, C4H Am, CPR1 Sc |
| pPHDR7 | CHS Ha, HCDBR Md, 4CL2 At, PAL2 At, C4H Am, CPR1 Sc |
| pPHDR8 | CHS Ha, ENR At, 4CL2 At, PAL2 At, C4H Am, CPR1 Sc |
| pPHDR9 | CHS Ha, ENR Gh, 4CL2 At, PAL2 At, C4H Am, CPR1 Sc |
| pPHDR10 | CHS Ha, ENR Md, 4CL2 At, PAL2 At, C4H Am, CPR1 Sc |
| pPHDR11 | CHS Ha, TSC13 Kl, 4CL2 At, PAL2 At, C4H Am, CPR1 Sc |
| pPHDR12 | CHS Ha, 663 bp stuffer, 4CL2 At, PAL2 At, C4H Am, CPR1 Sc |

Figure 7:
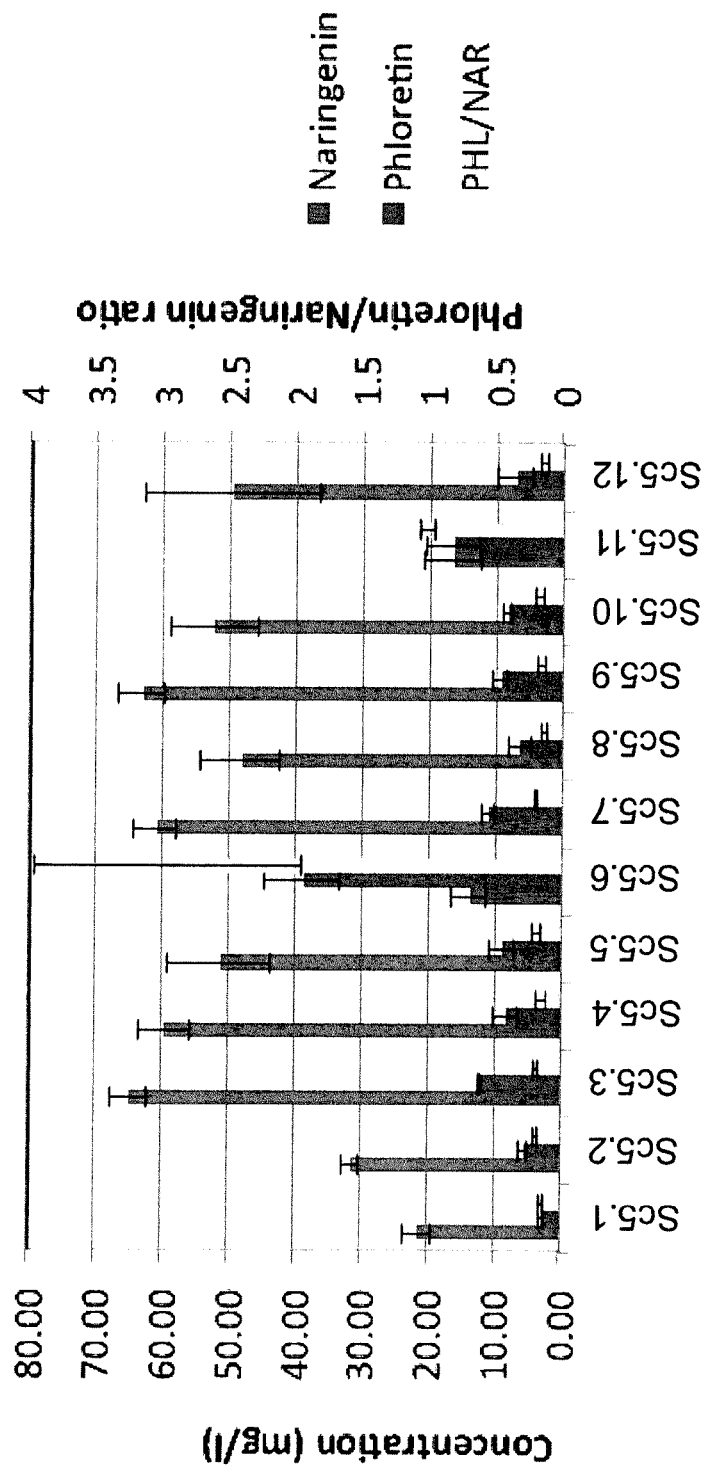
FIG. 7 shows the production of phloretin (m/z=274.3 Da) and naringenin (m/z=272.3 Da) (based on LC-MS peak integration) in yeast strains overexpressing a variety of different enoyl reductases, along with the ratio of phloretin to naringenin production for each strain.

Results:

The supernatants, after ethanol dilution, of Sc5.1-Sc5.12 cultures were analyzed by LC-MS and the ion chromatograms of the expected mass of phloretin (m/z=274.3 Da) and the expected mass of naringenin (m/z=272.3 Da) were recorded. The areas under the peaks were integrated and production of phloretin and naringenin was calculated based on standard curves (FIG. 7). Of the eleven ENRs which were overexpressed, an increase of the ratio of phloretin to naringenin compared with the control strain (Sc5.12) was only observed for TSC13 Sc (strain Sc5.6) and TSC13 Kl (strain Sc5.11), the latter of which is a TSC13 homologue from the fungus *K. lactis*, which is closely related to *S. cerevisiae*. The highest phloretin titer of 38.6 mg/l was observed with TSC13 Sc (strain Sc5.6).

Example 6: Mutants of CHS-2 Hv with Increased Specificity and Activity

In order to achieve the highest yield of dihydrochalcones, the enzymatic reactions of each step of the biosynthetic pathway should have both high activity and high specificity for the substrate of the preferred reaction. For example, in the extension of dihydro-phenylpropanoid-CoA with 3 units of malonyl-CoA, the yield of the target product is improved if the condensing enzyme, the chalcone synthase (CHS), has high activity and specificity for the dihydro-phenylpropanoid-CoA over phenylpropanoid-CoA. Higher activity can be achieved to some extent by increasing the copy number of the relevant gene in the recombinant host. However, higher specificity is more difficult to engineer, and poor specificity leads to loss of precursor, and therefore carbon source, going into undesired products, and to side product formation that might complicate purification and down stream processes of the desired product. As described in Example 3, a number of CHS enzymes were tested for activity on a dihydro-phenylpropanoid-CoA substrate, and the HaCHS showed the highest activity. However, this enzyme also showed activity toward the non-reduced phenylpropanoid-CoA, leading to formation of naringenin (see strain Sc3.1 in FIG. 6, which has the HaCHS). Surprisingly, the HvCHS2 (see strain Sc3.5 in FIG. 6) has a much higher preference for the reduced substrate, and produces very little naringenin.

The normal substrate of CHS enzymes are the CoA-activated non- or mono-hydroxylated phenyl-propanoids cinnamic and p-coumaric acids. However, a few enzymes, including the HvCHS2 from *Hordeum vulgare* (SEQ ID NO: 19; see also GenBank Accession No. CAA70435; Christensen et al., 1998, *Plant Mol Biol.* 37(5):849-57), have been shown to prefer substrates which have been further hydroxylated and/or methylated, such as the CoA activated caffeic and ferulic acids. This enzyme is induced by UV light or by pathogen attack. The protein sequence of this enzyme has less than 80% amino acid identity with other CHS enzymes, although the catalytic site is conserved (Austin & Noel, 2003, *Nat. Prod. Rep.* 20(1):79-110). Inspection of the protein sequence and alignment to the MsCHS from *Medicago sativa*, for which the structure has been elucidated (Ferrer et al., 1999, *Nat. Struct. Biol.* 6:775-784), shows HvCHS2 comprises regions of highly conserved sequence, but also regions where there are clear differences. Some of the latter regions overlap with regions that have been predicted as important for functional diversity, e.g. the regions comprising amino acids 95-105, 132-142, 191-201, and 266-276.

This Example demonstrates that by selectively exchanging amino acids in these regions the substrate specificity and activity can be altered. Surprisingly, this is also the case for the non-natural substrate dihydro-coumaroyl-CoA, for which improved activity, as well as increased selectivity over p-coumaroyl-CoA, is demonstrated. Bearing in mind that the natural substrates of this enzyme are caffeoyl-CoA and feruloyl-CoA, this is highly unexpected. The unexpectedness of these results is further emphasized by the fact that the enzyme HvCHS2 is derived from a plant, *Hordeum vulgare*, in which dihydrochalcones have not been reported.

Materials and Methods:

The materials and methods of Example 6 are the same as those described for Example 1, except that a different parental strain and different CHS sequences were used.

The *S. cerevisiae* strains for Example 6 are listed in Table 13:

TABLE 13

Strains used in Example 6. Four different plasmids (pCHSM1-4) were assembled by in vivo homologous recombination in the background strain Sc6.0 to make strains Sc6.1-Sc6.4.

| Strain | Description |
| --- | --- |
| Sc6.0 | *S. cerevisiae* background strain |
| Sc6.1 | Sc6.0 + pCHSM1 |
| Sc6.2 | Sc6.0 + pCHSM2 |
| Sc6.3 | Sc6.0 + pCHSM3 |
| Sc6.4 | Sc6.0 + pCHSM4 |

The additional genes for Example 6 are listed in Table 14:

TABLE 14

Additional genes for Example 6.

| Gene name | SEQ ID NO | Derived from: | SEQ ID NO of corresponding protein sequence |
| --- | --- | --- | --- |
| CHS2 Hv (A199T) | 68 | SEQ ID NO: 4 | 71 |
| CHS2 Hv (I267F) | 69 | SEQ ID NO: 4 | 72 |
| CHS2 Hv (A199T/I267F) | 70 | SEQ ID NO: 4 | 73 |

Gene Cloning:

Three variants of CHS2 Hv (SEQ ID NOs: 68-70), containing mutations in the substrate binding pocket (A199T) and the cyclization pocket (I267F) of the enzyme (as described by Ferrer et al. 2009), were prepared by overlap extension PCR as described by Heckman et al., 2007, *Nat. Protoc.* 2:924-932, using primers EVPR13492-13497 (Table 15).

To prepare the four plasmids, pCHSM1-4, plasmid DNA from the three helper plasmids were mixed with plasmid DNA from each of the plasmids containing the expression cassettes. Four different mixes, comprising different sets of genes as listed in Table 16, were prepared. The mixes of plasmid DNA were digested with AscI. This released all fragments from the plasmid backbone and created fragments with HRTs at the ends, these being sequentially overlapping with the HRT of the next fragment. Background yeast strain Sc6.0 was transformed with each of the digested mixes, and the plasmids pCHSM1-4 were assembled in vivo by homologous recombination as described by Shao et al. 2009.

TABLE 15

Primers used in Example 6.

| Name | Sequence | Description |
| --- | --- | --- |
| EVPR13492 | ACAAAAAGCTTAAAATGGCTGCAGTAAG (SEQ ID NO: 74) | Forward primer for restriction enzyme-based cloning of mutants of CHS2 Hv |
| EVPR13493 | ACGTGCCGCGGTCATG (SEQ ID NO: 75) | Reverse primer for restriction enzyme-based cloning of mutants of CHS2 Hv |
| EVPR13494 | ATGGACCTCTGAAGGTCATAGCAGTTATCTC (SEQ ID NO: 76) | Reverse primer for A199T mutation on CHS2 Hv by overlap extension PCR |
| EVPR13495 | GAGATAACTGCTATGACCTTCAGAGGTCCAT (SEQ ID NO: 77) | Forward primer for A199T mutation on CHS2 Hv by overlap extension PCR |
| EVPR13496 | ACATCTTTTAATAAATGAAAAGTTAAACCAGCTTCTGT (SEQ ID NO: 78) | Reverse primer for I267F mutation on CHS2 Hv by overlap extension PCR |
| EVPR13497 | ACAGAAGCTGGTTTAACTTTTCATTTATTAAAAGATGT (SEQ ID NO: 79) | Forward primer for I267F mutation on CHS2 Hv by overlap extension PCR |

TABLE 16

Multi-expression plasmids used in Example 6.

| Name | Genes in HRT vectors |
|---|---|
| pCHSM1 | CHS2 Hv, TSC13 Sc, 4CL2 At, PAL2 At, C4H Am, CPR1 Sc |
| pCHSM2 | CHS2 Hv (A199T), TSC13 Sc, 4CL2 At, PAL2 At, C4H Am, CPR1 Sc |
| pCHSM3 | CHS2 Hv (I267F), TSC13 Sc, 4CL2 At, PAL2 At, C4H Am, CPR1 Sc |
| pCHSM4 | CHS2 Hv (A199T/I267F), TSC13 Sc, 4CL2 At, PAL2 At, C4H Am, CPR1 Sc |

Figure 9:
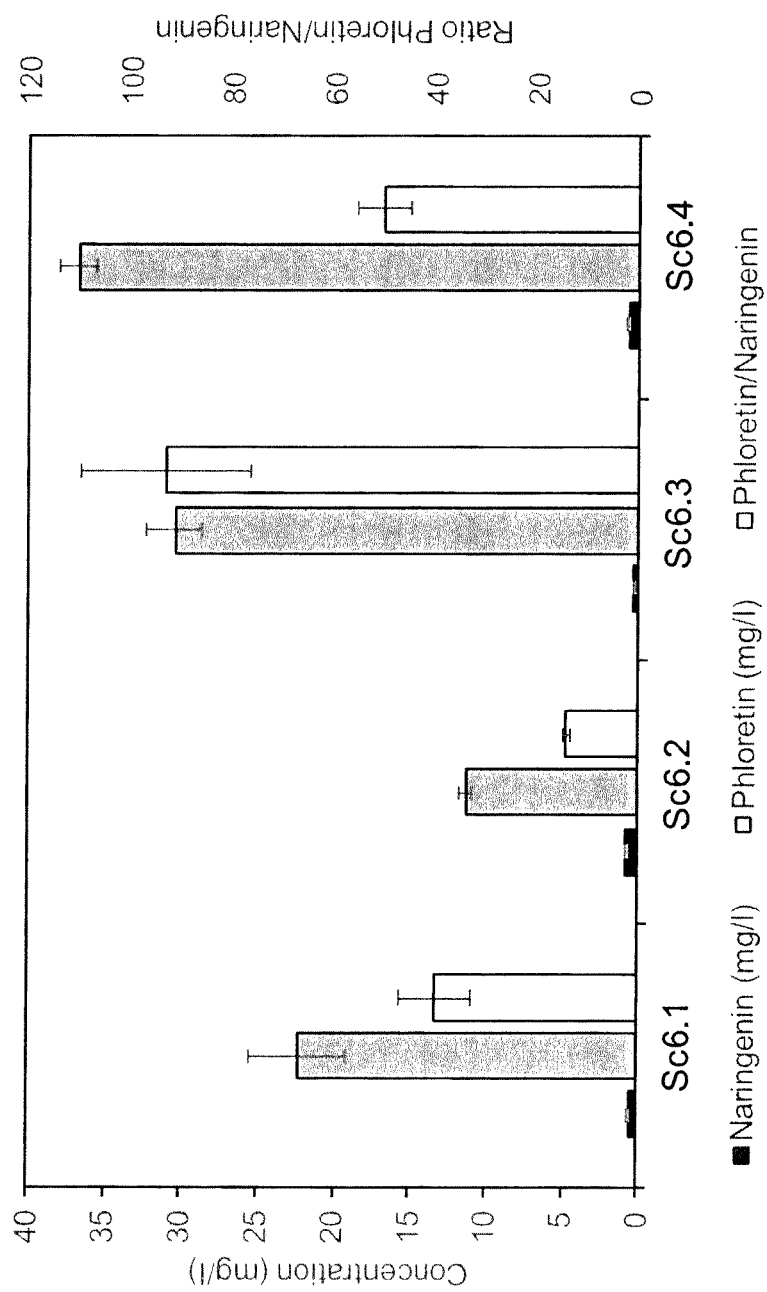
FIG. 9 shows the production of phloretin (m/z=274.3 Da) and naringenin (m/z=272.3 Da) (based on LC-MS peak integration) in yeast strains overexpressing the native enzyme and three mutants of CHS2 Hv, along with the ratio of phloretin to naringenin production for each strain.

Results:

The supernatants, after methanol dilution, of Sc6.1-Sc6.4 cultures were analyzed by LC-MS and the ion chromatograms of the expected mass of phloretin (m/z=274.3 Da) and the expected mass of naringenin (m/z=272.3 Da) were recorded. The areas under the peaks were integrated and production of phloretin and naringenin was calculated based on standard curves (FIG. 9). Of the four CHSs tested, production of phloretin was observed for all of them. The highest phloretin titer was observed with CHS2 Hv (A199T/I267F) (SEQ ID NO: 73) (strain Sc6.4), which also exhibited increased specificity over the parent enzyme CHS2 Hv. Even higher specificity, calculated as the ratio of phloretin to naringenin was exhibited by CHS2 Hv (I267F) (strain Sc6.3) (SEQ ID NO: 72).

Example 7: Production of Pinocembrin Dihydrochalcone

There are no previous reports of dihydro-cinnamoyl-CoA being used as substrate by a chalcone synthase (CHS) to produce pinocembrin dihydrochalcone. This Example presents results demonstrating that the CHS from *Hypericum androsaemum* (HaCHS) (and, putatively, by extension, many other CHS enzymes) is capable of using dihydro-cinnamoyl-CoA as a substrate. By overexpressing TSC13 in yeast, dihydro-cinnamoyl-CoA is produced, which can then be used by the CHS.

Materials and Methods:

The materials and methods of Example 7 are the same as those described for Example 1, except that that a different parental strain and different CHS sequences were used. Also, C4H Am and CPR1 Sc were not used in this example, in order to make the nonhydroxylated precursor cinnamoyl-CoA instead of p-coumaroyl-CoA.

The *S. cerevisiae* strains used in Example 7 are listed in Table 17:

TABLE 17

Strains used in Example 7. Two different plasmids (pPIN1-2) were assembled by in vivo homologous recombination in the background strain Sc7.0 to make strains PIN and PINDHC.

| Strain | Description |
|---|---|
| Sc7.0 | *S. cerevisiae* background strain |
| PIN | Sc7.0 + pPIN1 |
| PINDHC | Sc7.0 + pPIN2 |

Gene Cloning:

To prepare the two plasmids, pPIN1 and pPIN2, plasmid DNA from the three helper plasmids were mixed with plasmid DNA from each of the plasmids containing the expression cassettes. Two different mixes, comprising different sets of genes as listed in Table 18, were prepared. The mixes of plasmid DNA were digested with AscI. This released all fragments from the plasmid backbone and created fragments with HRTs at the ends, these being sequentially overlapping with the HRT of the next fragment. Background yeast strain Sc7.0 was transformed with each of the digested mixes, and the plasmids pPIN1 and pPIN2 were assembled by in vivo homologous recombination as described by Shao et al. 2009.

TABLE 18

Multi-expression plasmids used in Example 7.

| Name | Genes in HRT vectors |
|---|---|
| pPIN1 | CHS Ha, 663 bp stuffer, 4CL2 At, PAL2 At |
| pPIN2 | CHS Ha, TSC13 Sc, 4CL2 At, PAL2 At |

Figure 10:
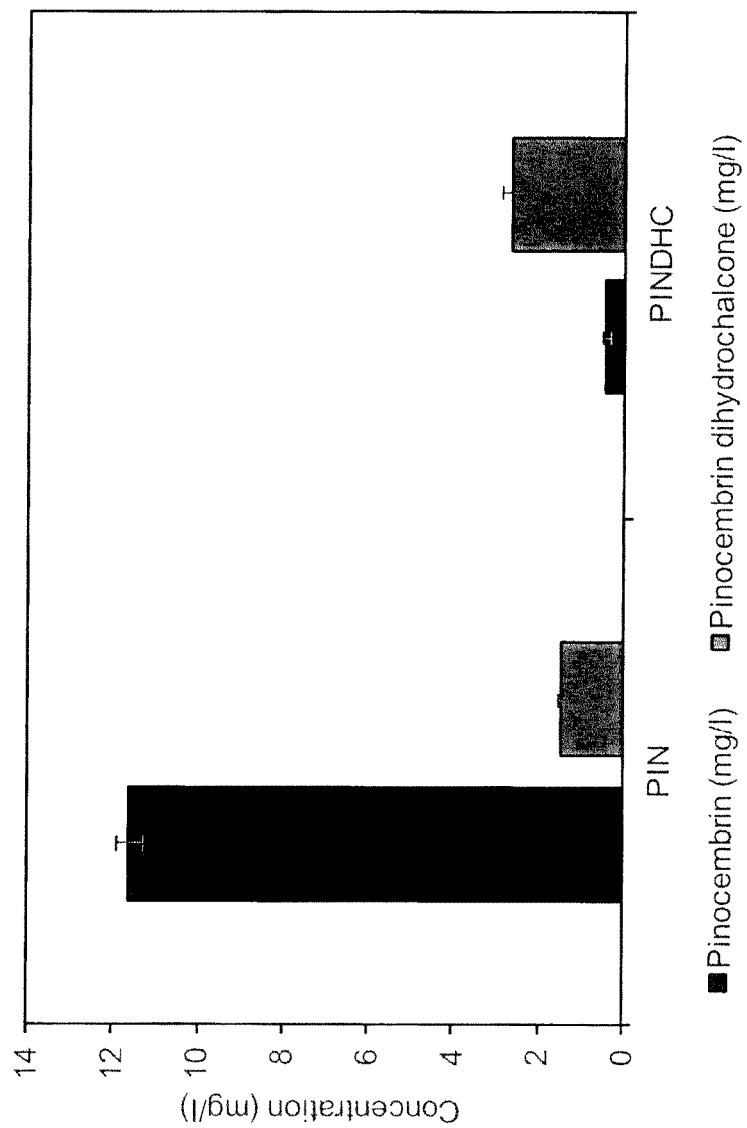
FIG. 10 shows the production of pinocembrin dihydrochalcone (m/z=258.3 Da) and pinocembrin (m/z=256.3 Da) (based on LC-MS peak integration) in PIN and PINDHC strains of S. cerevisiae.

Results:

The supernatants, after methanol dilution, of PIN and PINDHC cultures were analyzed by LC-MS and the ion chromatograms of the expected mass of pinocembrin dihydrochalcone (m/z=258.3 Da) and the expected mass of pinocembrin (m/z=256.3 Da) were recorded. The areas under the peaks were integrated and production of pinocembrin dihydrochalcone and pinocembrin was calculated based on standard curves (FIG. 10). The overexpression of TSC13 Sc clearly increased dihydrochalcone over flavanone production, showing that the enzyme also accepts dihydro-cinnamoyl-CoA as substrate.

Example 8: Identification of Deletion Strains with Increased Phenylpropanoid Derivative Production Relative to Dihydro-Phenylpropanoid Derivative Production Yeast reductase knockout strains (i.e. yeast strains where one or both copies of a reductase gene have been removed) were analyzed for their activity in making resveratrol and phloretic acid. Knockout strains were obtained from the Yeast Knockout Library (Stanford University, California). Knockouts used in a first round of experiments are shown in Table 19. Knockouts used in a second round of experiments are shown in Table 20.

TABLE 19

Round-1 reductase knockout strains.

oye2/oye2
osm1/osm1
TSC13/tsc13
gre2/gre2
frd1/frd1
aad4/aad4
shh3/shh3
ymr226c/ymr226c
ypl088w/ypl088w
yml131w/yml131w
ari1/ari1
aad3/aad3
aad6/aad6
ydr541c/ydr541c
adh7/adh7
oye3/oye3
dfg10/dfg10
sps19/sps19
irc24/irc24
ylr460c/ylr460c TABLE 19-continued Round-1 reductase knockout strains.

zta1/zta1
adh6/adh6
SDH3/sdh3

TABLE 20

Round 2 knockout strains.

lot6/lot6
zta1/zta1
ypl088w/ypl088w
yml131w/yml131w
ydl124w/ydl124w
yjr096w/yjr096w
osm1/osm1
sps19/sps19
ERG27/erg27
ydr541c/ydr541c
ayr1/ayr1
TSC13/tsc13
dfg10/dfg10

In both rounds of experiments, the deletion mutants and corresponding wild-type strains were transformed with a Rho0011 plasmid (pESC-HIS with TEF-At4CL2+TDH3-VvVST1) according to methods known in the art (see, e.g., Gietz & Schiestl, Nat. Protoc. 2007, 2(1):31-34). The reductase knock out strains were tested as homozygous diploids when possible (e.g. dfg10/dfg10). However, in cases of homozygous lethality, the reductases were analyzed in a heterozygous background. For example, homozygous deletion of TSC13 results in lethality, so the tsc13 mutant was tested as a heterozygous diploid (i.e. TSC13/tsc13).

For each strain, four transformants were each inoculated in 1 mL synthetic media lacking histidine (SC-His) and incubated overnight at 30° C., 400 rpm. The next day, 50 µL of each culture was transferred into 0.5 mL of fresh medium and 50 µL of 100 mg/mL p-Coumaric acid dissolved in 96% ethanol was added. The cultures were incubated for another 72 hours and their OD600 was measured in order to correct the production values by the number of cells present. 100 µL of each culture was added to 100 µL of 96% ethanol (to facilitate polyphenol solubility), mixed, and centrifuged, and supernatant was used for measuring compounds by high-pressure liquid chromatography (HPLC).

Figure 11:
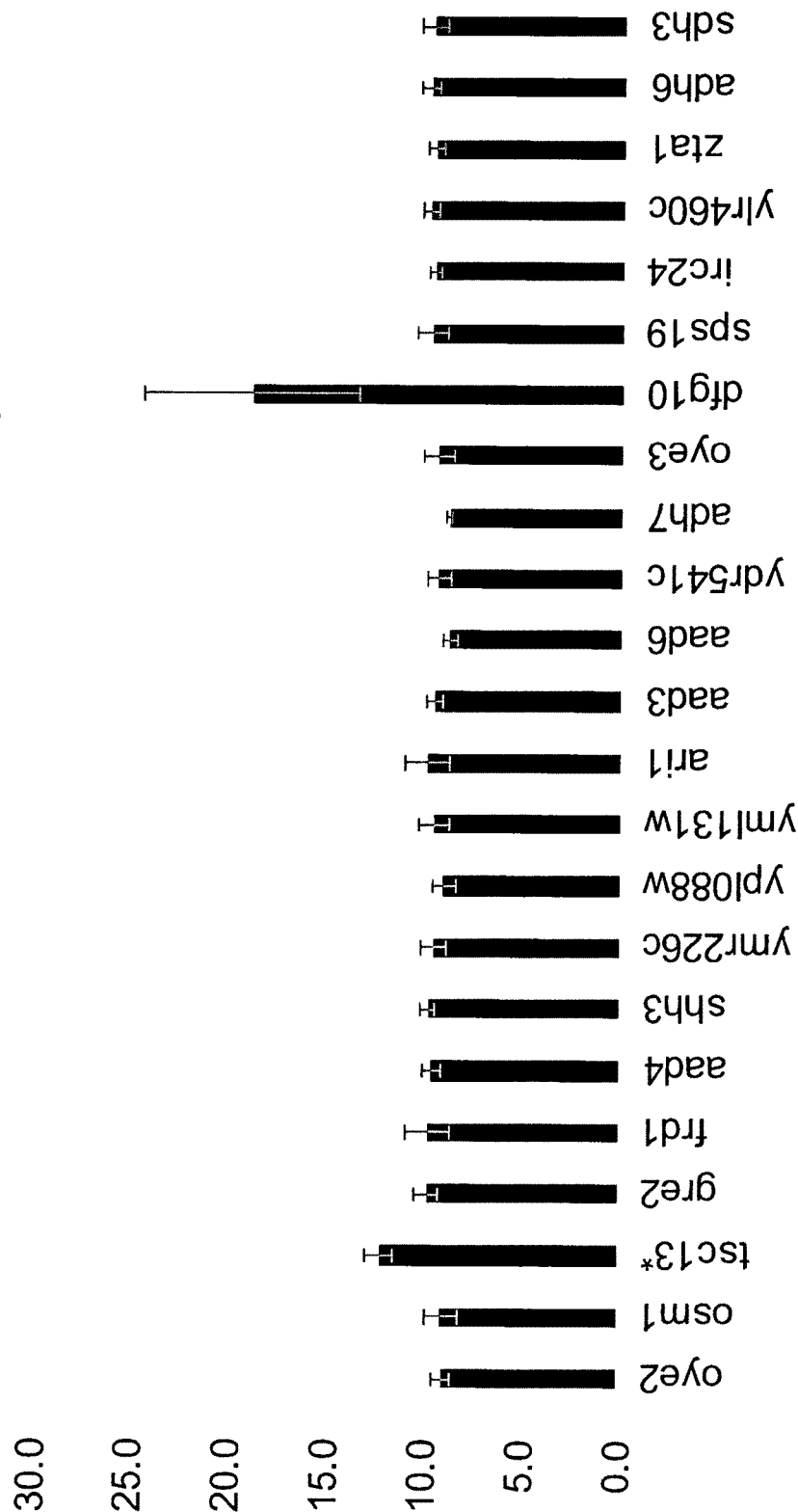
FIG. 11 shows the ratio of resveratrol to phloretic acid produced by a variety of yeast reductase knockout strains.
Figure 12:
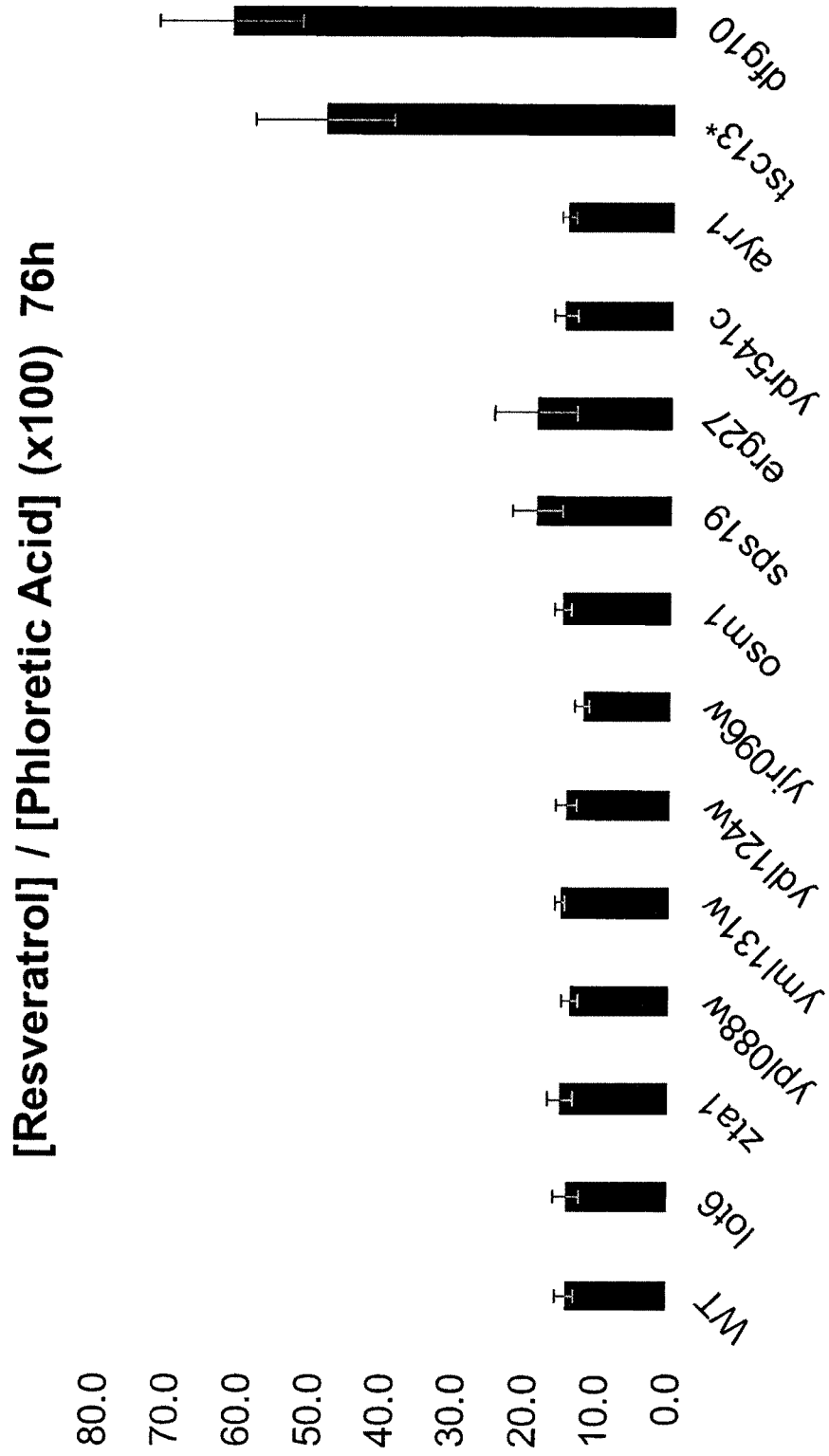
FIG. 12 shows the ratio of resveratrol to phloretic acid produced by additional yeast reductase knockout strains.

The levels of resveratrol and phloretic acid were determined by HPLC for the wild-type control strain and for the deletion strains. Data were analyzed as the ratio between resveratrol and phloretic acid produced in those strains. These data are presented in FIG. 11 (Round 1) and FIG. 12 (Round 2).

The two cases shown in FIGS. 5 and 6 (TSC13/tsc13 and dfg10/dfg10 knockouts) where the resveratrol/phloretic acid ratio was significantly higher indicate strains in which coumaric acid was accumulated rather than being converted to dihydrocoumarate. The resulting increase in resveratrol production and concomitant reduction in phloretic acid levels demonstrate that TSC13 and DFG10 are capable of reduction of the double bond of p-coumaroyl-CoA, and that reducing or eliminating the activity of TSC13 and/or DFG10 results in an increased ratio of stilbene, chalcone, or flavonoid versus their dihydro counterparts.

Example 9: Further Identification of Deletion Strains with Increased Phenylpropanoid Derivative Production Relative to Dihydro-Phenylpropanoid Derivative Production The experiments described in Example 8 were continued with a third round in which chalcone synthase (CHS) and chalcone isomerase (CHI) were used in place of resveratrol synthase. Knockouts used in the third round of experiments are shown in Table 21.

TABLE 21

Round 3 knockout strains.

oye2/oye2
ylr460c/ylr460c
adh7/adh7
ydr541c/ydr541c
gre2/gre2
adh6/adh6
yml131w/yml131w
ymr226c/ymr226c
oye3/oye3
ypl088w/ypl088w
aad4/aad4
aad6/aad6
dfg10/dfg10
zta1/zta1
ari1/ari1
aad3/aad3
frd1/frd1
shh3/shh3
osm1/osm1
lot6/lot6
ayr1/ayr1
yjr096w/yjr096w
ydl124w/ydl124w
TSC13/tsc13
SDH3/sdh3
ERG27/erg27

For the identification of endogenous reductase, a plasmid coding for the partial naringenin-producing pathway (At4Cl, MsCHI and HaCHS) was assembled in vivo in the Round 3 knockout strains by the transformation-associated homologous recombination method described by Shao et al. 2008. The fragments for this plasmid were obtained from the AscI-digested plasmid mixture indicated in Table 22.

TABLE 22

AscI-digested plasmid mixture used to create plasmid coding for the partial naringenin-producing pathway. The right-hand column shows the concentration of each plasmid (equimolar ratio) used for transformation of each knockout strain.

| Plasmid pEVE | Content | Conc. ng/µl |
| --- | --- | --- |
| 4730 | URA3, Ampr | 330.5 |
| 1968 | Sc ORI: ARS/CEN, Ampr | 245.5 |
| 3852 | pGPD1- HaCHS-tCYC1, Ampr | 273.5 |
| 3996 | pPGK1- MsCHI-tADH2, Ampr | 223.8 |
| 4957 | pTEF1- At4CL- tENO2, Ampr | 211.8 |
| 1916 | 600 bp, Ampr | 227.6 |

Transformed strains (6 replicates of each) were inoculated in synthetic media lacking uracil (SC-Ura) and incubated for 24 h at 30° C., 400 rpm in 96-deep well plates. The next day, 50 µL was transferred into 0.5 ml fresh SC medium (with uracil) containing 5 µL of 100 mg/mL p-coumaric acid in 96% ethanol. The transformants were then incubated for 96 h at 30° C., 400 rpm in 96-deep-well plates. 100 µL of each culture was added to 100 µL of 96% ethanol (to facilitate polyphenol solubility), mixed, and centrifuged, and the supernatant was used for measuring compounds by high-pressure liquid chromatography (HPLC).

Figure 13:
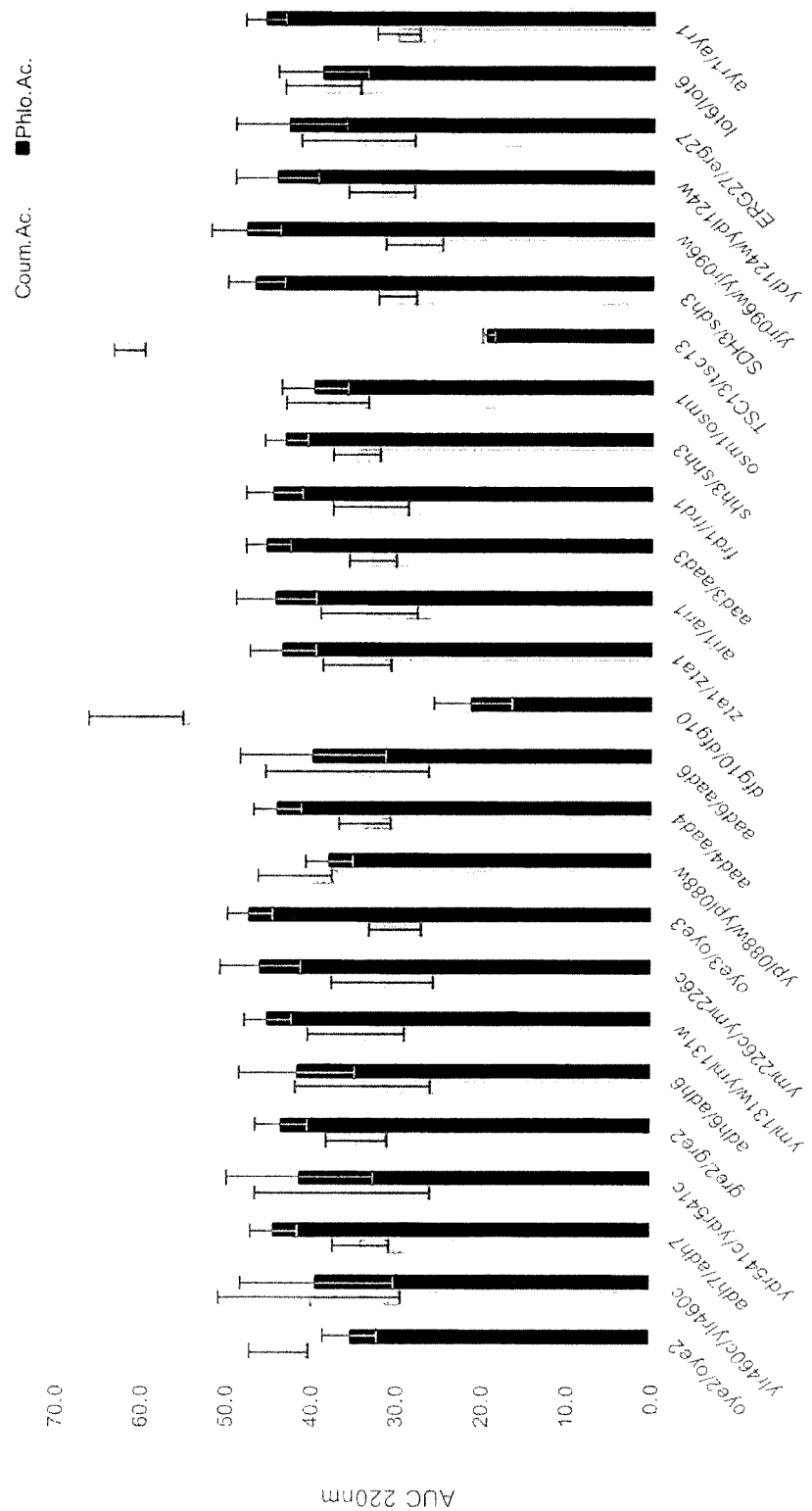
FIG. 13 shows the level of coumaric acid consumed and phloretic acid produced by different knockout strains after 4 days of growth in SC media.

Out of 26 CoA-dependent double bound reductase knockouts, two of them, TSC13/Tsc13 and dfg10/dfg10, consumed less coumaric acid and consequently produced less phloretic acid (FIG. 13) as compared to the other strains tested.

Example 10: Overexpression of TSC13 and DFG10

Studies were conducted in which TSC13 and DFG10 were overexpressed. The yeast strains used for this Example are shown in Table 23.

TABLE 23

S. cerevisiae strains used for Example 10.

| Strain | Genotype |
|---|---|
| Sc10.0 | S. cerevisiae background strain. |
| Sc10.1 | Strain Sc10.0 + X.2::DR/pTDH3-AtPAL2-tPGI1/TEF2-C4H L5 ATR2-tCYC1/pPGK1-HaCHS-tENO2/pTEF1-PhCHI-tFBA1/pPDC1-At4CI-tADH2 |
| Sc10.2 | Strain Sc10.0 + X.2::DR/pTDH3-AtPAL2-tPGI1/TEF2-C4H L5 ATR2-tCYC1/pPGK1-HaCHS-tENO2/pTEF1-PhCHI-tFBA1/pPDC1-At4CI-tTDH2, XI.2::DR pTDH3-AtPAL2-tPGI1/pPGK1-HaCHS-tENO2, XVI-20::DR pTDH3-AtPAL2-tPGI1/TEF2-C4H L5 ATR2-tCYC1/pPGK1-HaCHS-tENO2, X-4::DR pTEF1-HaCHS-tCYC1, X.3::DR/pTDH3-AtPAL2-tPGI1/pTEF2-AtPAL1-tCYC1/pPGK1-HaCHS-tENO2/pTEF1-AnPAL1-tFBA1/pTPI1 AtPAL2 CO2-tADH1/pPDC1-RtPAL-tTDH2, XI-5::DR/pTEF2-Ha CHS CO4-tCYC1/pPGK1-Ha CHS-tENO2/pTEF1-HaCHS CO1-tFBA1/pPDC1-HaCHS CO6-tTDH2, XII.5::DR pTEF1-Aro4 K229L-tCYC1 |

The reductases TSC13 and DFG10 were overexpressed on centromeric plasmid p416gpd (PSB 33) (plasmid pROP 492 with TSC13 and pROP 493 with DFG10) in strain Sc10.1 and multicopy plasmid p426gpd (PSB34) (plasmid pROP 494 with TSC13 and pROP 495 with DFG10) in strain Sc10.2 (strain accumulating coumaric acid). These additional strains are shown in Table 24.

TABLE 24

Additional S. cerevisiae strains produced for Example 10.

| Strain | Genotype |
|---|---|
| Sc10.3 | Strain Sc10.1 + PSB33 (control) |
| Sc10.4 | Strain Sc10.1 + pROP 492 (with TSC13) |
| Sc10.5 | Strain Sc10.1 + pROP 493 (with DFG10) |
| Sc10.6 | Strain Sc10.2 + PSB34 (control) |
| Sc10.7 | Strain Sc10.2 + pROP 494 (with TSC13) |
| Sc10.8 | Strain Sc10.2 + pROP 495 (with DFG10) |

For each tested strain, six colonies were inoculated in 0.5 mL synthetic media lacking uracil (SC-Ura) and incubated overnight at 30° C., 400 rpm in 96-deep-well plates. The next day, 50 µL of each culture was transferred into 0.5 mL of fresh SC medium (without uracil). The transformants were then incubated for 72 h at 30° C., 400 rpm in 96-deep-well plates. Samplings were performed after 72 h growth, starting with OD600 measurements (made on an EnVision 2104 Plate Reader). 100 µL of each culture was combined with 100 µL of 96% ethanol, whirl-mixed for 30 sec. at 1500 rpm and centrifuged for 10 min. at 4000×g. The supernatant was then analyzed by high-pressure liquid chromatography (HPLC).

Figure 14:
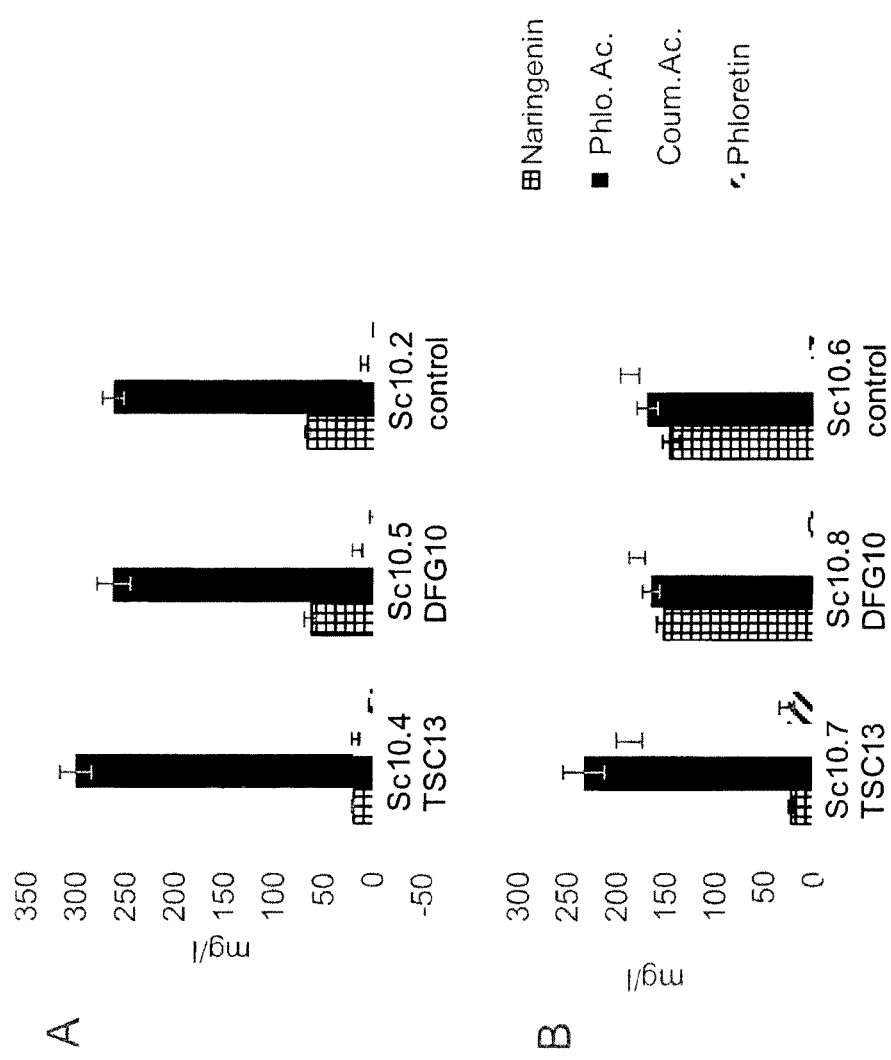
FIG. 14 shows the phenylpropanoid pathway profile in: base strain Sc10.1 overexpressing TSC13 (pROP492) (in strain Sc10.4) and DFG10 (pROP493) (in strain Sc10.5) on the centromeric plasmid PSB33 (control strain Sc10.3) (FIG. 14A), and in base strain Sc10.2 overexpressing TSC13 (pROP494) (in strain Sc10.7) and DFG10 (pROP495) (in strain Sc10.8) on PSB34 (control strain Sc10.6) (FIG. 14B).

Overexpression of TSC13 in strain Sc10.4 on the centromeric plasmid pROP492, and in strain Sc10.7 on the multicopy plasmid pROP494 resulted in a significant decrease in the level of naringenin, as well as a slight increase in the level of phloretic acid and its derivative phloretin when compared to control strains Sc10.3 and Sc10.6 (FIG. 14).

Strain Sc10.2, which accumulates coumaric acid, was used as a base strain for strains Sc10.6-Sc10.8 in order to increase the level of the reductase's substrate, thus increasing the likelihood of observing an effect due to overexpression of DFG10. Nevertheless, neither of the strains in which DFG10 was overexpressed (on centromeric pROP493 plasmid in strain Sc10.5, and on multicopy plasmid pROP495 in strain Sc10.8) exhibited an alteration in the phenylpropanoid pathway when compared to control strains Sc 4.3 and Sc10.6 (FIG. 14).

Based on the increased levels of phloretic acid in response to TSC13 overexpression, but not DFG10 overexpression, these results suggest that Tsc13 is the primary enzyme responsible for reducing coumaric acid to phloretic acid in yeast, whereas the role of Dfg10 is secondary.

Example 11: Identification of the Phenylpropanoid Substrate of the Endogenous Reductase in S. Cerevisiae In order to determine which substrates are accepted by the endogenous S. cerevisiae reductase, strains were generated expressing various combinations of A. thaliana phenylalanine ammonia lyase (AtPAL2), cinnamate-4-hydroxylase (AtC4H), and 4-coumaroyl-CoA ligase (At4CL). Strains are shown in Table 25.

TABLE 25

Strains produced for Example 11.

| Strain | Genotype |
|---|---|
| Sc11.0 | S. cerevisiae background strain |
| Sc11.1 | Strain Sc11.0 + XI.2::DR pTDH3-AtPAL2-tPGI1 |
| Sc11.2 | Strain Sc11.0 + XI.2::DR pTDH3-AtPAL2-tPGI1/TEF2-C4H L5 ATR2-tCYC1 |
| Sc11.3 | Strain Sc11.0 + XI.2::DR pTDH3-AtPAL2-tPGI1/TEF2-C4H L5 ATR2-tCYC1/pPDC1-At4CI-tTDH2 |
| Sc11.4 | Strain Sc11.0 + XI.2::DR pTDH3-AtPAL2-tPGI1/pPDC1-At4CI-tTDH2 |

For each strain, six colonies were inoculated in 0.5 mL synthetic media lacking uracil (SC-Ura) and incubated overnight at 30° C., 400 rpm in 96-deep-well plates. The next day, 50 µL of each culture was transferred into 0.5 mL of fresh SC medium (without uracil). The transformants were then incubated for 72 h at 30° C., 400 rpm in 96-deep-well plates. Samplings were performed after 72 h growth, starting with OD600 measurements (made on an EnVision 2104

Plate Reader). 100 μL of each culture was combined with 100 μL of 96% ethanol, whirl-mixed for 30 sec. at 1500 rpm and centrifuged for 10 min. at 4000×g. The supernatant was then analyzed by high-pressure liquid chromatography (HPLC).

Figure 15A:
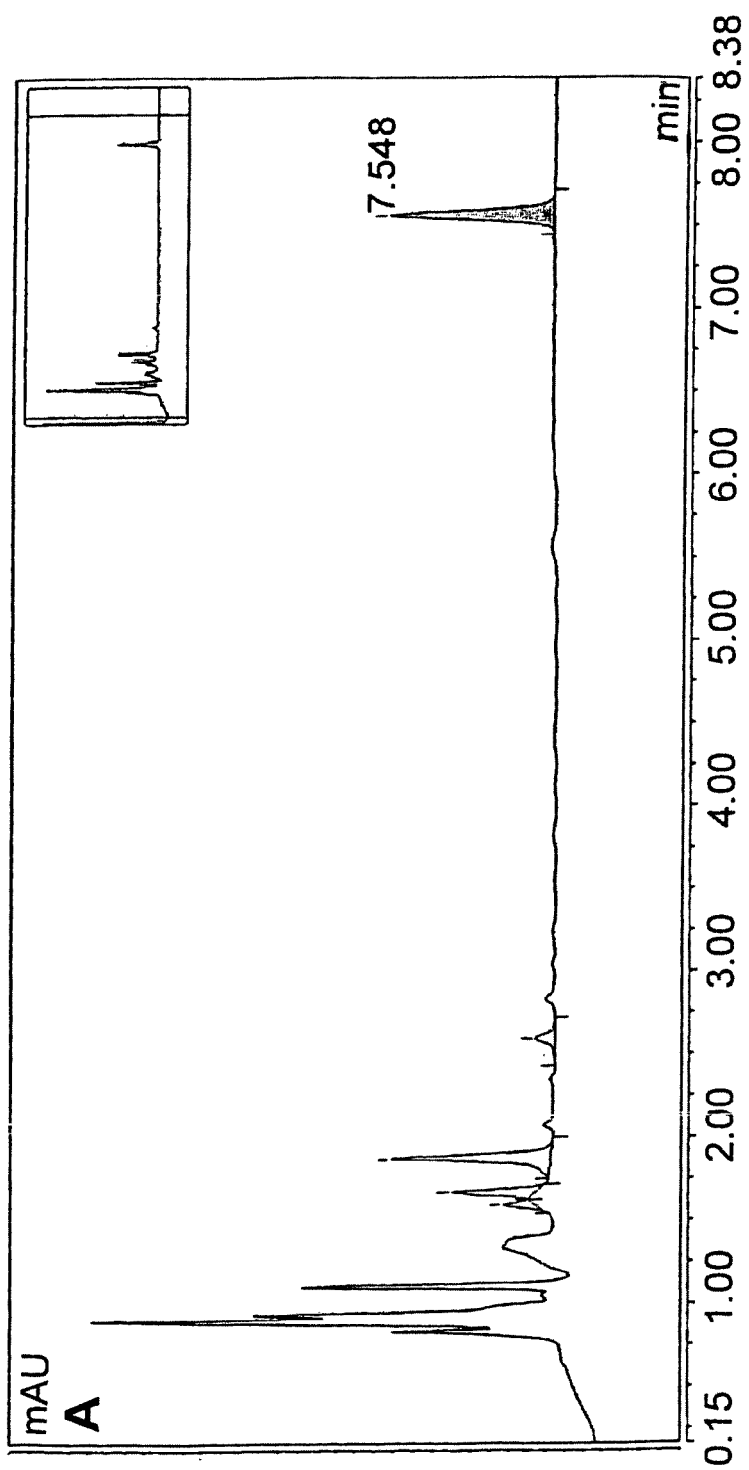
FIG. 15 shows chromatograms of S. cerevisiae strains with: (A) PAL alone, which results in production of cinnamic acid, (B) PAL with C4HL5ATR2, which results in production coumaric acid, (C) PAL with C4HL5ATR2 and 4Cl, which results in production of phloretic acid (dihydrocoumaric acid), and (D) PAL with 4Cl, which results in production of dihydrocinnamic acid.
Figure 15A:
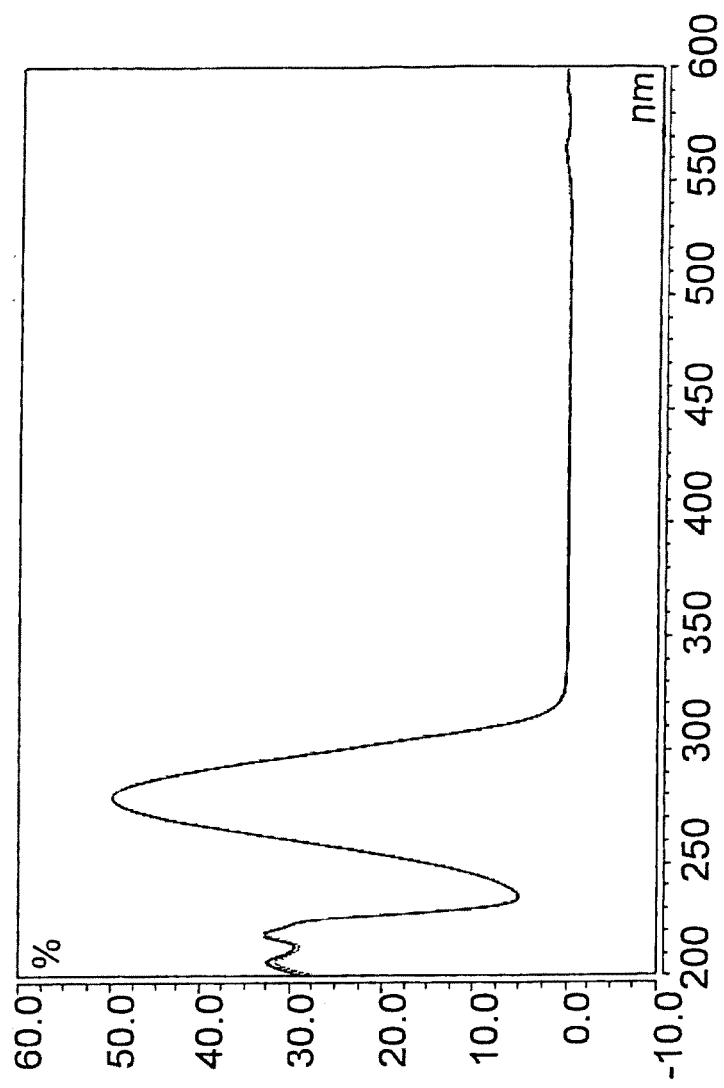
Figure 15B:
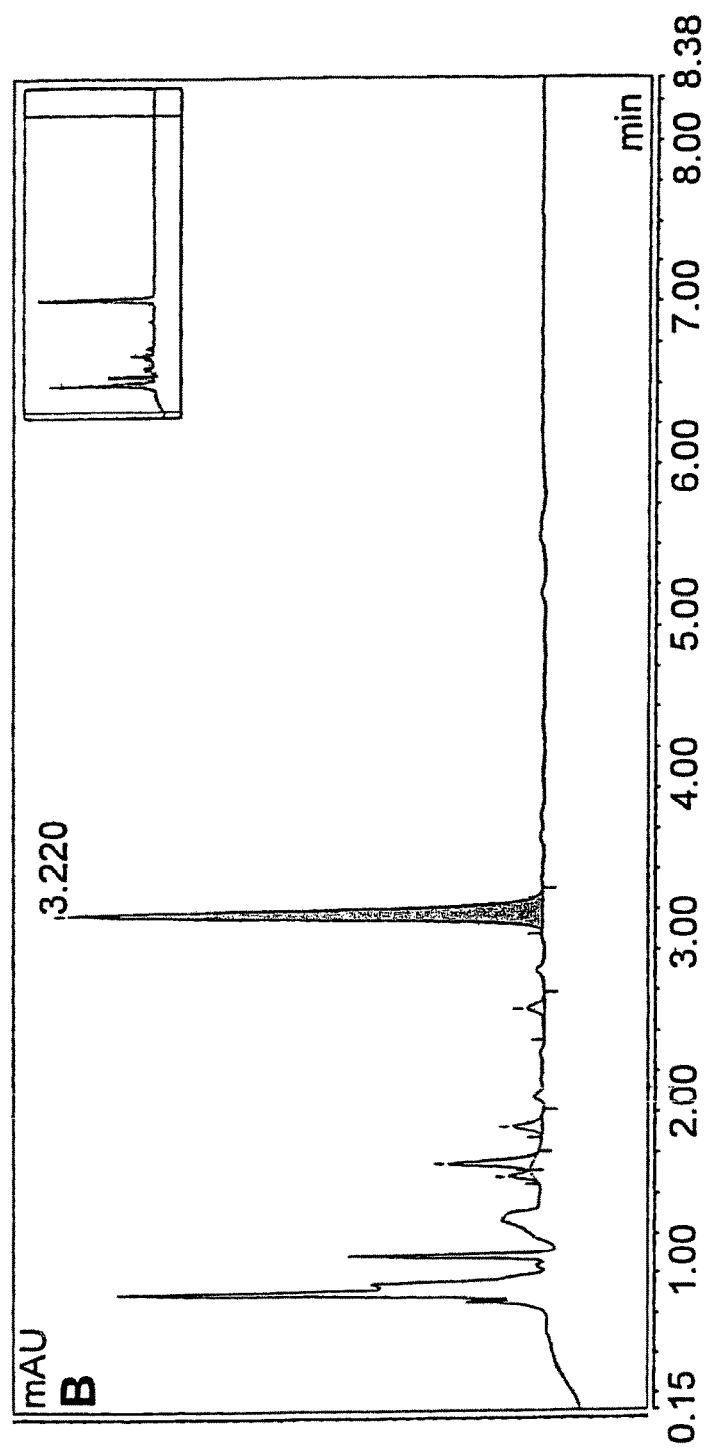
Figure 15B:
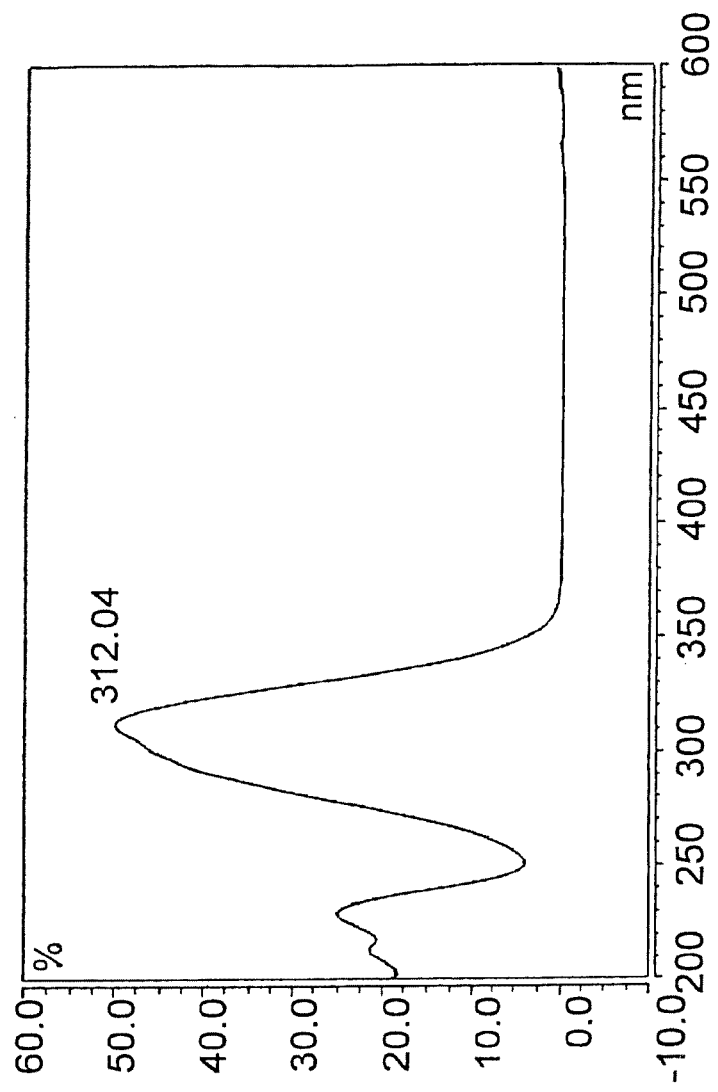
Figure 15C:
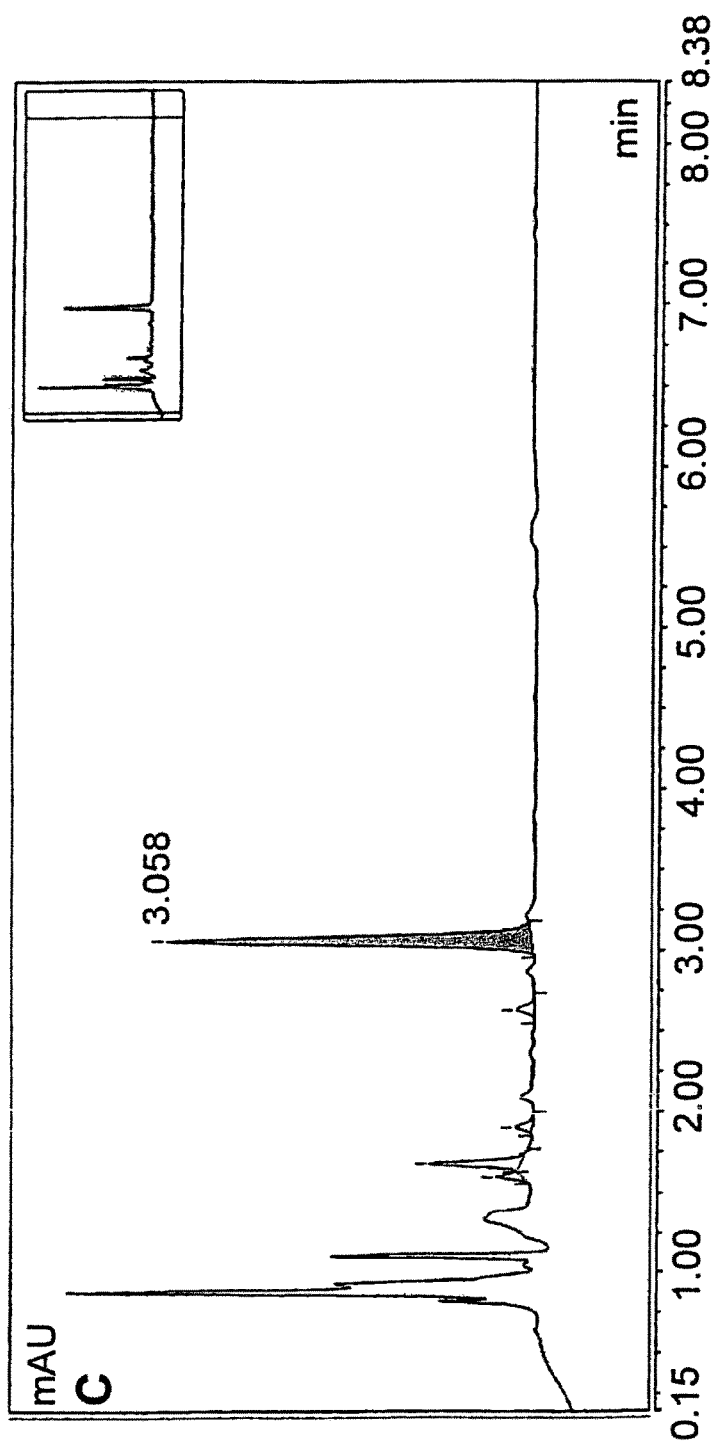
Figure 15C:
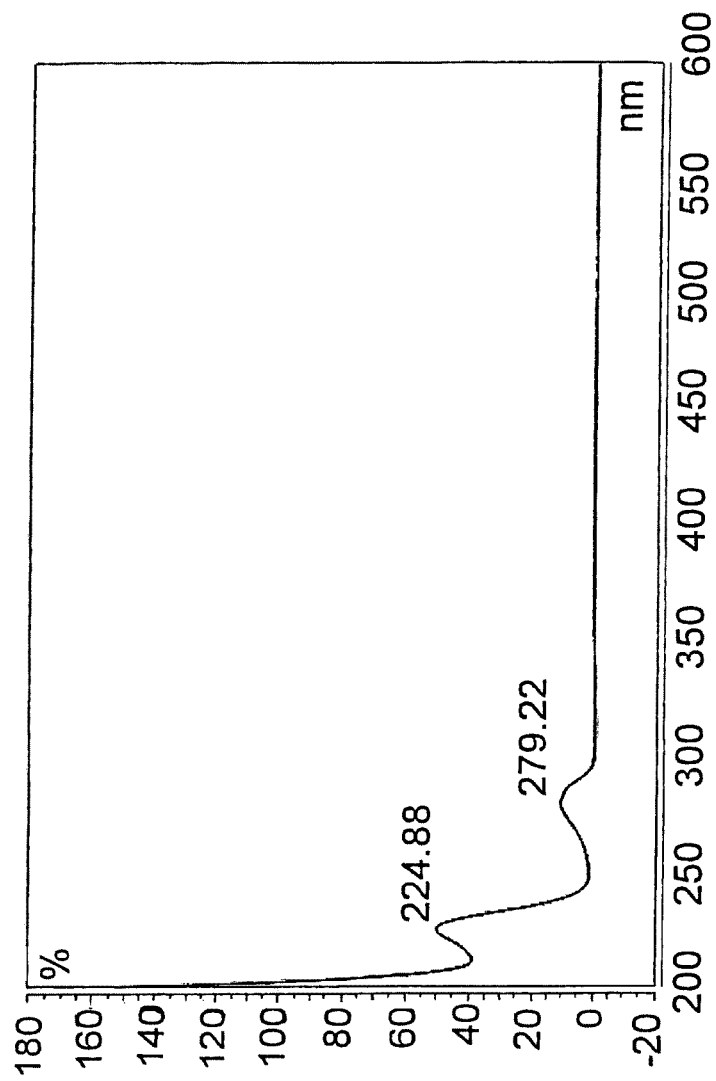
Figure 15D:
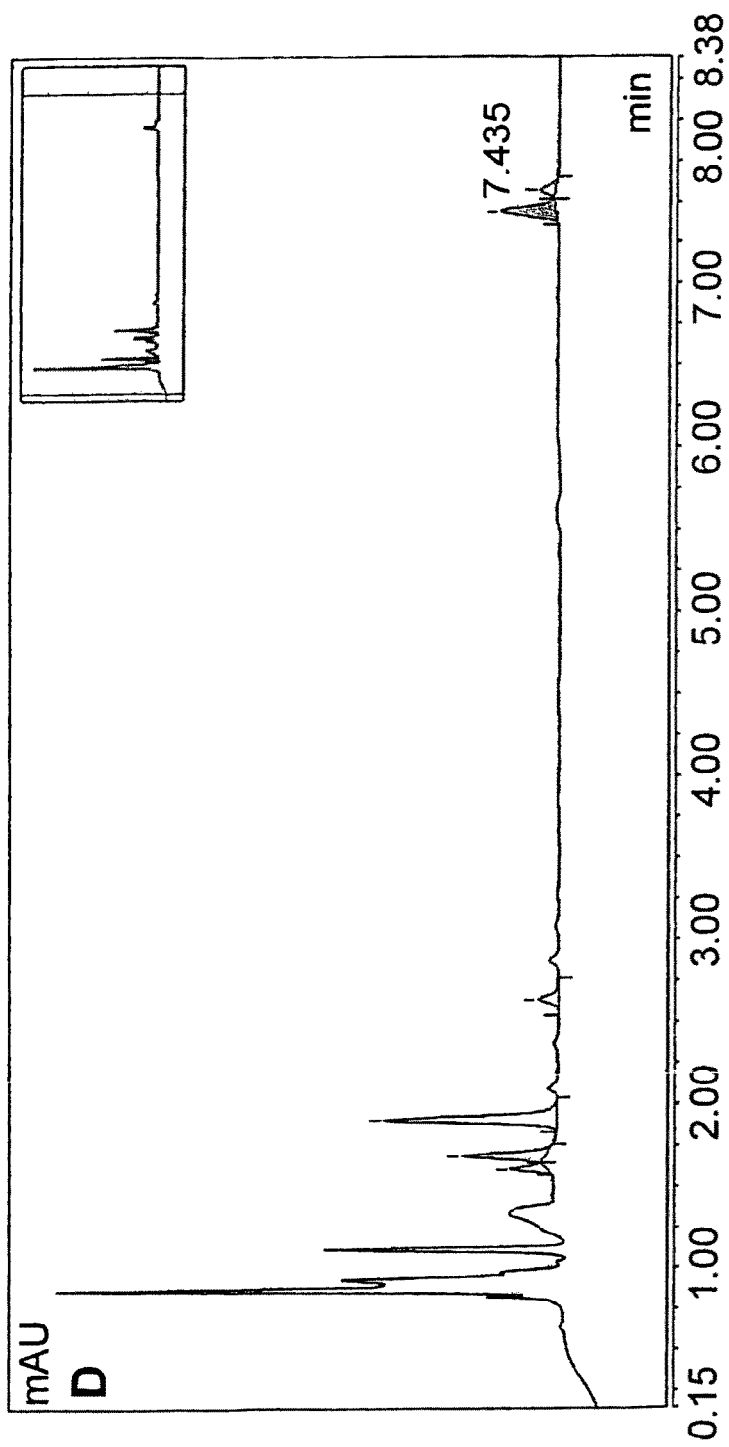
Figure 15D:
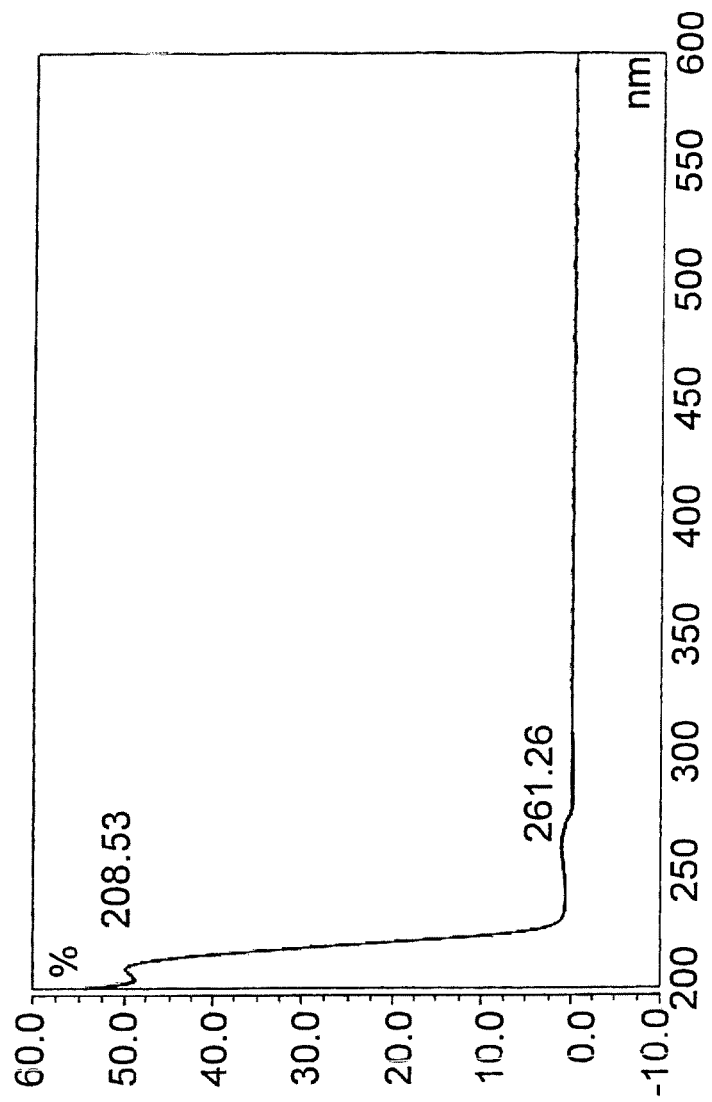

Of the strains tested, phloretic acid was only formed in strain Sc11.3 expressing AtPAL, AtC4H, and At4Cl (FIG. 15C), which demonstrates that coumaroyl-CoA acts as a substrate for the yeast's endogenous reductase. In the strain co-expressing PAL and 4Cl (Sc11.4), dihydroxycinnamic acid was formed together with cinnamic acid (FIG. 15D), in contrast to the strain with PAL only (Sc11.1) (FIG. 15A), in which cinnamic acid accumulated. These results indicate that cinnamoyl-CoA also acts as a substrate for the endogenous reductase.

Example 12: Substituting TSC13 with Alternative Genes

The native ORF of TSC13 was replaced in strain Sc10.1 with by following TSC13 orthologues: *Arabidospis thaliana* (AtECR) (SEQ ID NO: 95), *Gossypium hirsutum* (GhECR2) (SEQ ID NO: 95), and *Malus domestica* (MdECR) (SEQ ID NO: 96), according to the method described by Fairhead et al. using a split URA3 cassette (Fairhead et al., 1996, *Yeast* 12:1439-1457). ORF replacement was obtained by co-transformation of yeast with a pair of recombinant DNA fragments each carrying a part of the URA3 marker that is regenerated upon recombination and used for selection. The marker was removed afterwards resulting in a clean, full replacement of the ORF. The introduced homologs were placed under the native TSC13 promoter. The correct insert was verified by PCR and confirmed by sequencing the PCR fragment. Two of each PCR-confirmed transformants was subjected to further experimentation, with the exception of the GhECR2 transformant, for which only one colony was obtained.

To test the production of phenylpropanoid derivatives in the strains with TSC13 homologs, the cells were cultivated in Synthetic fed-batch (SC) media (m2p-labs) for 72 h. The growth of strains was measured by reading OD 600 after cultivating the strains in SC media for 72 h.

The substitution of the ORF of wild-type TSC13 with orthologs from *Arabidospis thaliana* (AtECR), *Gossypium hirsutum* (GhECR2), and *Malus domestica* (MdECR) resulted in the survival of the strains; because the knockout of TSC13 is typically lethal, the survival of these strains demonstrates that these orthologs are able to compensate for the loss of Tsc13.

None of the plant orthologs, when expressed in the naringenin producing strain (Sc10.1), gave rise to any phloretic acid production. This suggests that the activity of ScTsc13 on CoA-activated phenylpropanoids is a specific feature of this enzyme, which is not conserved in the orthologs tested.

Figure 16:
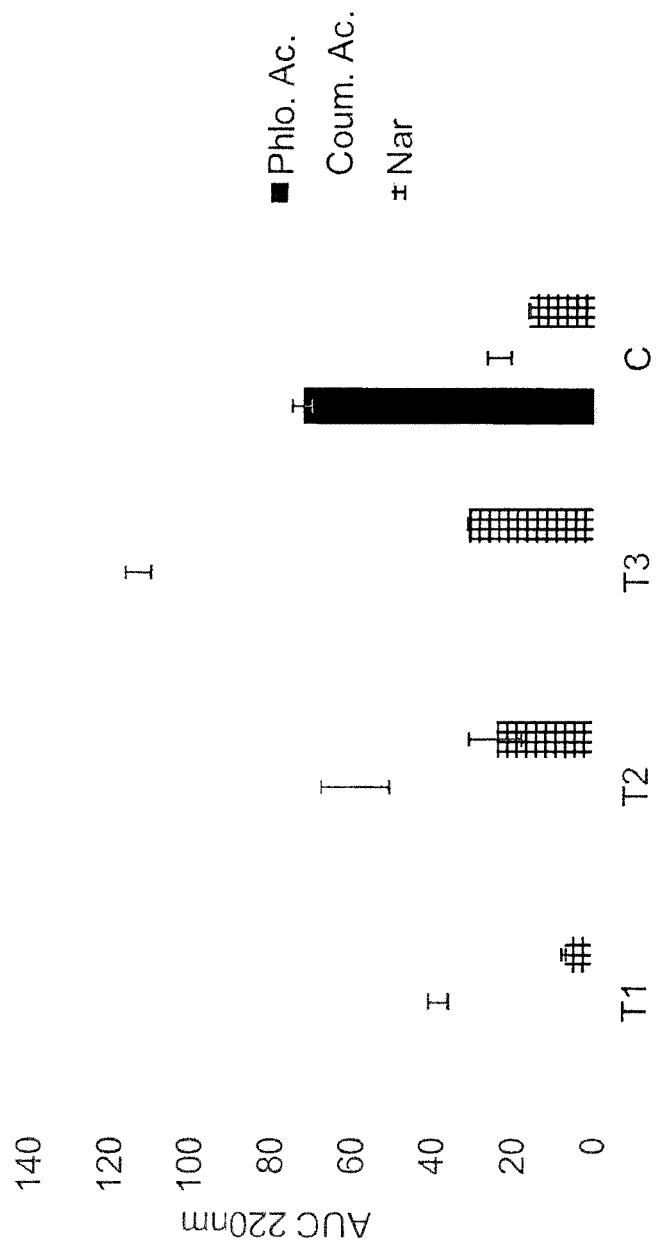
FIG. 16 shows production of phenylpropanoid pathway intermediates in S. cerevisiae strains with different Tsc13 orthologues. The production test was done in synthetic fed-batch media. T1—strain expressing AtECR, T2—strain expressing Gh2ECR, T3—strain expressing MdECR, C—background strain control.
Figure 17:
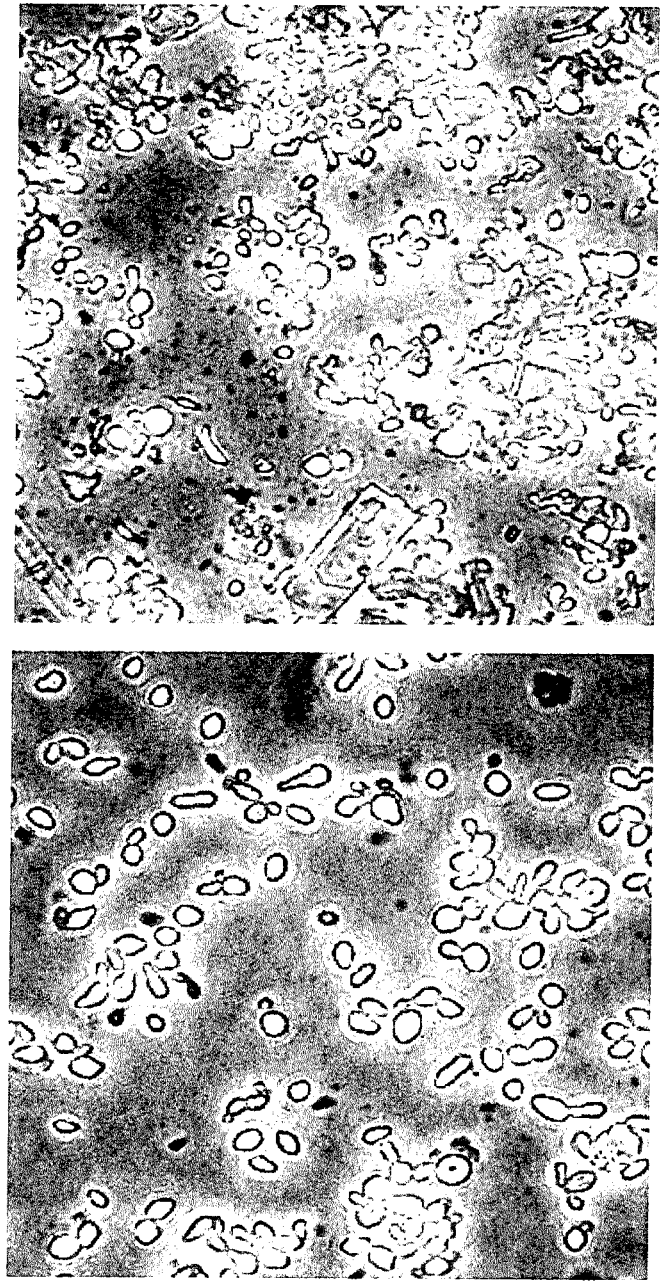
FIG. 17 shows morphology of yeast cells grown for 72 h. Background control strain is shown on the left, strain expressing MdECR is shown on the right. Magnification 400×.

Of all of the strains tested, the strain with the MdECR ortholog produced the most coumaric acid and naringenin (FIG. 16). The strain with AtECR ortholog grew poorly (62% reduction after 72 h of growth) (FIG. 17). The growth of the strains expressing GhECR2 and MdECR was also reduced, but to a lower extent (approximately 50 and 30% respectively) than the AtECR-expressing strain.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

Sequences

SEQ ID NO: 1
Nucleic acid sequence encoding phenylalanine ammonia lyase (PAL2) of *Arabidopsis thaliana* codon optimized for expression in *S. cerevisiae*

SEQ ID NO: 2
Codon-optimized nucleic acid sequence encoding cinnamate 4-hydroxylase (C4H) of *Ammi majus*, codon optimized for expression in *S. cerevisiae*

SEQ ID NO: 3
Nucleic acid sequence encoding 4-coumarate - CoA ligase 2 (4CL2) of *Arabidopsis thaliana*

SEQ ID NO: 4
Nucleic acid sequence encoding chalcone synthase (CHS2) of *Hordeum vulgare*, codon optimized for expression in *S. cerevisiae*

SEQ ID NO: 5
Nucleic acid sequence encoding glycosyltransferase P2'UGT of *Malus domestica*, codon optimized for expression in *S. cerevisiae*

SEQ ID NO: 6
Nucleic acid sequence encoding cytochrome p450 CPR1 (Ncp1) of *Saccharomyces cerevisiae*

SEQ ID NO: 7
Nucleic acid sequence encoding trans-2-enoyl-CoA reductase (NADPH) (TSC13) of *Saccharomyces cerevisiae*

SEQ ID NO: 8
Nucleic acid sequence for pPHLO Multi-Expression Plasmid

SEQ ID NO: 9
Nucleic acid sequence for pPHLON Multi-Expression Plasmid

SEQ ID NO: 10
Nucleic acid sequence for pPHLOZ Multi-Expression Plasmid

SEQ ID NO: 11
Nucleic acid sequence for helper fragment comprising URA3 and pSC101 origin of replication SEQ ID NO: 12
Nucleic acid sequence for helper fragment comprising ARS4/CEN6 and bacterial chloramphenicol resistance marker SEQ ID NO: 13
Nucleic acid sequence for helper fragment (closing linker) for multi-expression plasmid containing 6 genes SEQ ID NO: 14
Nucleic acid sequence for helper fragment (closing linker) for multi-expression plasmid containing 7 genes SEQ ID NO: 15
Nucleic acid sequence for non-expressed stuffer sequence SEQ ID NO: 16
Protein sequence of PAL2 of *Arabidopsis thaliana*

SEQ ID NO: 17
Protein sequence of C4H of *Ammi majus*

SEQ ID NO: 18
Protein sequence of 4CL2 of *Arabidopsis thaliana*

SEQ ID NO: 19
Protein sequence of CHS2 of *Hordeum vulgare* (see also GenBank Accession No. CAA70435)

SEQ ID NO: 20
Protein sequence of P2'UGT of *Malus domestica*

SEQ ID NO: 21
Protein sequence of CPR1 of *Saccharomyces cerevisiae*

SEQ ID NO: 22
Protein sequence of TSC13 of *Saccharomyces cerevisiae*

SEQ ID NO: 23
Nucleic acid sequence encoding stilbene synthase STS-2 of *Pinus densiflora*, codon optimized for expression in *S. cerevisiae*

SEQ ID NO: 24
Protein sequence of STS-2 of *Pinus densiflora*

SEQ ID NO: 25
Protein sequence of TSC13 of *Kluyveromyces lactis*

SEQ ID NO: 26
Protein sequence of DFG10 of *Saccharomyces cerevisiae*

SEQ ID NO: 27
Nucleic acid sequence encoding chalcone synthase (CHS) of *Hypericum androsaemum*, codon optimized for expression in *S. cerevisiae*

SEQ ID NO: 28
Nucleic acid sequence encoding chalcone synthase (CHS) of *Petroselinum crispum*, codon optimized for expression in *S. cerevisiae*

SEQ ID NO: 29
Nucleic acid sequence encoding chalcone synthase (CHS) of *Petunia hybrida*, codon optimized for expression in *S. cerevisiae*

SEQ ID NO: 30
Nucleic acid sequence encoding chalcone synthase (CHS1) of *Hordeum vulgare*, codon optimized for expression in *S. cerevisiae*

SEQ ID NO: 31
Nucleic acid sequence encoding chalcone synthase (CHS) of *Scutellaria baicalensis*, codon optimized for expression in *S. cerevisiae*

SEQ ID NO: 32
Nucleic acid sequence encoding chalcone synthase (CHSc) of *Malus domestica*, codon optimized for expression in *S. cerevisiae*

SEQ ID NO: 33
Nucleic acid sequence encoding chalcone synthase (CHSa) of *Malus domestica*.

SEQ ID NO: 34
Nucleic acid sequence encoding chalcone synthase (CHSb) of *Malus domestica*.

SEQ ID NO: 35
Nucleic acid sequence encoding chalcone synthase (CHSc) of *Malus domestica*.

SEQ ID NO: 36
Nucleic acid sequence encoding chalcone synthase (CHSd) of *Malus domestica*.

SEQ ID NO: 37
Nucleic acid sequence encoding stilbene synthase (STS) of *Vitis pseudoreticulata*, codon optimized for expression in *S. cerevisiae*

SEQ ID NO: 38
Nucleic acid sequence encoding stilbene synthase (VST1) of *Vitis vinifera*, codon optimized for expression in *S. cerevisiae*

SEQ ID NO: 39
Nucleic acid sequence encoding Enoyl-ACP reductase 3 (ENR3) of *Malus domestica*, codon optimized for expression in *S. cerevisiae*

SEQ ID NO: 40
Nucleic acid sequence encoding Enoyl-ACP reductase 5 (ENR5) of *Malus domestica*, codon optimized for expression in *S. cerevisiae*

SEQ ID NO: 41
Nucleic acid sequence encoding ketone/zingerone synthase (ZS1) of *Rubus idaeus*, codon optimized for expression in *S. cerevisiae*

SEQ ID NO: 42
Nucleic acid sequence encoding enoate reductase (ENR) of *Eubacterium ramulus*, codon optimized for expression in *S. cerevisiae*

SEQ ID NO: 43
Nucleic acid sequence encoding polyprenol reductase (DFG10) of *Saccharomyces cerevisiae*

SEQ ID NO: 44
Nucleic acid sequence encoding NADPH-dependent hydroxycinnamoyl-DoA double bond reductase (HCDBR) of *Malus domestica*, codon optimized for expression in *S. cerevisiae*

SEQ ID NO: 45
Nucleic acid sequence encoding very-long-chain enoyl-CoA reductase (ENR) of *Arabidopsis thaliana*, codon optimized for expression in *S. cerevisiae*

SEQ ID NO: 46
Nucleic acid sequence encoding trans-2-enoyl-CoA reductase (ENR) of *Gossypium hirsutum*, codon optimized for expression in *S. cerevisiae*

SEQ ID NO: 47
Nucleic acid sequence encoding predicted very-long-chain enoyl-CoA reductase (ENR) of *Malus domestica*, codon optimized for expression in *S. cerevisiae*

SEQ ID NO: 48
Nucleic acid sequence encoding very-long-chain enoyl-CoA reductase (TSC13) of *Kluyveromyces lactis*, codon optimized for expression in *S. cerevisiae*

SEQ ID NO: 49
Protein sequence of CHS of *Hypericum androsaemum*

SEQ ID NO: 50
Protein sequence of CHS of *Petroselinum crispum*

SEQ ID NO: 51
Protein sequence of CHS of *Petunia hybrida*

SEQ ID NO: 52
Protein sequence of CHS1 of *Hordeum vulgare*

SEQ ID NO: 53
Protein sequence of CHS of *Scutellaria baicalensis*

SEQ ID NO: 54
Protein sequence of CHSa of *Malus domestica*

SEQ ID NO: 55
Protein sequence of CHSb of *Malus domestica*

SEQ ID NO: 56
Protein sequence of CHSc of *Malus domestica*

SEQ ID NO: 57
Protein sequence of CHSd of *Malus domestica*

SEQ ID NO: 58
Protein sequence of STS of *Vitis pseudoreticulata*

SEQ ID NO: 59
Protein sequence of VST1 of *Vitis vinifera*

SEQ ID NO: 60
Protein sequence of ENR3 of *Malus domestica*

SEQ ID NO: 61
Protein sequence of ENR5 of *Malus domestica*

SEQ ID NO: 62
Protein sequence of ZS1 of *Rubus idaeus*

SEQ ID NO: 63
Protein sequence of ENR of *Eubacterium ramulus*

SEQ ID NO: 64
Protein sequence of HCDBR of *Malus domestica*

SEQ ID NO: 65
Protein sequence of Enoyl-acyl carrier protein reductase (ENR) of *Arabidopsis thaliana*, Genbank Accession No. NP_191096

SEQ ID NO: 66
Protein sequence of Enoyl-acyl carrier protein reductase (ENR) of *Gossypium hirsutum*, Genbank Accession No. ABV60089

SEQ ID NO: 67
Protein sequence of predicted Enoyl-acyl carrier protein reductase (ENR) of *Malus domestica*, Genbank Accession No. XP_008382818

SEQ ID NO: 68
Nucleic acid sequence encoding chalcone synthase (CHS2) of *Hordeum vulgare*, with G595A mutation, codon optimized for expression in *S. cerevisiae*

SEQ ID NO: 69
Nucleic acid sequence encoding chalcone synthase (CHS2) of *Hordeum vulgare*, with A799T and A801T mutation, codon optimized for expression in *S. cerevisiae*

SEQ ID NO: 70
Nucleic acid sequence encoding chalcone synthase (CHS2) of *Hordeum vulgare*, with G595A, A799T and A801T mutation, codon optimized for expression in *S. cerevisiae*

SEQ ID NO: 71
Protein sequence of CHS2 (A199T) of *Hordeum vulgare*

SEQ ID NO: 72
Protein sequence of CHS2 (I267F) of *Hordeum vulgare*

SEQ ID NO: 73
Protein sequence of CHS2 (A199T, I267F) of *Hordeum vulgare*

SEQ ID NOs: 74-79
Primers used in Example 6 (see Table 15)

SEQ ID NO: 80
DNA sequence encoding chalcone isomerase (CHI) of *Citrus sinensis*

SEQ ID NO: 81
DNA sequence encoding chalcone isomerase A (CHI-A) of *Petunia hybrida*

SEQ ID NO: 82
DNA sequence encoding chalcone isomerase B (CHI-B) of *Petunia hybrida*

SEQ ID NO: 83
DNA sequence encoding chalcone isomerase (CHI) of *Pisum sativum*

SEQ ID NO: 84
DNA sequence encoding chalcone isomerase (CHI) of *Pueraria Montana* var. *lobata*

SEQ ID NO: 85
DNA sequence encoding chalcone isomerase (CHI) of *Oryza sativa* subsp. *japonica*

SEQ ID NO: 86
DNA sequence encoding chalcone isomerase 1 (CHI1) of *Medicago sativa*

SEQ ID NO: 87
Protein sequence of chalcone isomerase (CHI) of *Citrus sinensis*

SEQ ID NO: 88
Protein sequence of chalcone isomerase A (CHI1) of *Petunia hybrida*

SEQ ID NO: 89
Protein sequence of chalcone isomerase B (CHI2) of *Petunia hybrida*

SEQ ID NO: 90
Protein sequence of chalcone isomerase (CHI) of *Pisum sativum*

-continued

SEQ ID NO: 91
Protein sequence of chalcone isomerase
(CHI) of Pueraria montana

SEQ ID NO: 92
Protein sequence of chalcone isomerase
(CHI) of Oryza sativa subsp. japonica SEQ ID NO: 93
Protein sequence of chalcone isomerase 1
(CHI1) of Medicago sativa SEQ ID NO: 94
DNA sequence encoding Enoyl-acyl carrier
protein reductase (ENR) of Arabidopsis
thaliana SEQ ID NO: 95
DNA sequence encoding Enoyl-acyl carrier
protein reductase (ENR) of Gossypium
hirsutum SEQ ID NO: 96
DNA sequence predicted encoding Enoyl-
acyl carrier protein reductase (ENR) of
Malus domestica SEQ ID NO: 97
DNA sequence encoding C4H L5 ATR2
fusion protein (C4H and ATR2) from
Arabidopsis thaliana codon optimized for
expression in S. cerevisiae SEQ ID NO: 98
DNA sequence encoding phenylalanine
ammonia lyase (AtPAL1) of Arabidopsis
thaliana codon optimized for expression in
S. cerevisiae SEQ ID NO: 99
DNA sequence encoding phenylalanine
ammonia lyase (AtPAL2 CO2) of
Arabidopsis thaliana codon optimized for
expression in S. cerevisiae (second version;
c.f. SEQ ID NO: 1)

SEQ ID NO: 100
DNA sequence encoding phenylalanine
ammonia lyase (AnPAL1) of Aspergillus
niger codon optimized for expression
in S. cerevisiae SEQ ID NO: 101
DNA sequence encoding
phenylalanine/tyrosine ammonia lyase of
Rhodosporidium toruloides (RtPAL) codon
optimized for expression in S. cerevisiae SEQ ID NO: 102
DNA sequence encoding chalcone synthase
from Hypericum androsaemum (HaCHS
CO1) codon optimized for expression
in S. cerevisiae
(codon optimized version 1)

SEQ ID NO: 103
DNA sequence encoding chalcone synthase
from Hypericum androsaemum (HaCHS
CO4) codon optimized for expression
in S. cerevisiae
(codon optimized version 4)

SEQ ID NO: 104
DNA sequence encoding chalcone synthase
from Hypericum androsaemum (HaCHS
CO6) codon optimized for expression in
S. cerevisiae
(codon optimized version 6)

SEQ ID NO: 105
Protein sequence of C4H-L5-ATR2 fusion
protein (C4H and ATR2) from Arabidopsis
thaliana SEQ ID NO: 106
Protein sequence of phenylalanine ammonia
lyase (AtPAL1) of Arabidopsis thaliana SEQ ID NO: 107
Protein sequence of phenylalanine ammonia
lyase (AnPAL1) of Aspergillus niger,
Genbank accession no. XP_001401803.

SEQ ID NO: 108
Protein sequence of phenylalanine ammonia
lyase from Rhodosporidium toruloides
(RtPAL), Genbank Accession No. P11544

SEQ ID NO: 109
Protein sequence of chalcone synthase from
Hypericum androsaemum (HaCHS),
Genbank Accession No. Q9FUB7

SEQ ID NO: 1
ATGGACCAAATTGAAGCAATGCTATGCGGTGGTGGTGAAAAGAC

CAAGGTGGCCGTAACGACAAAAACTCTTGCAGATCCTTTGAATTG

GGGTCTGGCAGCTGACCAGATGAAAGGTAGCCATCTGGATGAAG

TTAAGAAGATGGTTGAGGAATACAGAAGACCAGTCGTAAATCTAG

GCGGCGAGACATTGACGATAGGACAGGTAGCTGCTATTTCGACC

GTTGGCGGTTCAGTGAAGGTAGAACTTGCAGAAACAAGTAGAGC

CGGAGTTAAGGCTTCATCAGATTGGGTCATGGAAAGTATGAACA

AGGGCACAGATTCCTATGGCGTTACCACAGGCTTTGGTGCTACC

TCTCATAGAAGAACTAAAAATGGCACTGCTTTGCAAACAGAACTG

ATCAGATTCCTTAACGCCGGTATTTTCGGTAATACAAAGGAAACT

TGCCATACATTACCCCAATCGGCAACAAGAGCTGCTATGCTTGTT

AGGGTGAACACTTTGTTGCAAGGTTACTCTGGAATAAGGTTTGAA

ATTCTTGAGGCCATCACTTCACTATTGAACCACAACATTTCTCCTT

CGTTGCCCTTAAGAGGAACAATAACTGCCAGCGGTGATTGGTT

CCCCTTTCATATATCGCAGGCTTATTAACGGGAAGACCTAATTCA

AAGGCCACTGGTCCAGACGGAGAATCCTTAACCGCTAAGGAAGC

ATTTGAGAAAGCTGGTATTTCAACTGGTTTCTTTGATTTgCAACCC

AAGGAAGGTTTAGCCCTGGTGAATGGCACCGCTGTCGGCAGCG

GTATGGCATCCATGGTGTTGTTTGAAGCTAACGTACAAGCAGTTT

TGGCCGAAGTTTTGTCCGCAATTTTTGCCGAAGTCATGAGTGGAA

AACCTGAGTTTACTGATCACTTGACCCACAGGTTAAAACATCACC

CAGGACAAATTGAAGCAGCAGCTATCATGGAGCACATTTTGGAC

GGCTCTAGCTACATGAAGTTAGCCCAGAAGGTTCATGAAATGGA

CCCTTTGCAAAAACCCAAACAAGATAGATATGCTTTAAGGACATC

CCCACAATGGCTTGGCCCTCAAATTGAAGTAATTAGACAAGCTAC

AAAGTCTATAGAAAGAGAGATCAACTCTGTTAACGATAATCCACT

TATTGATGTGTCGAGGAATAAGGCAATACATGGAGGCAATTTCCA

GGGTACACCCATAGGAGTCAGTATGGATAATACCAGGCTTGCCA

```
TAGCCGCAATTGGCAAATTAATGTTTGCCCAATTTTCTGAATTGG
TCAATGACTTCTACAATAACGGTTTGCCTTCGAATCTGACCGCAT
CTTCTAACCCTAGTCTTGATTATGGTTTCAAAGGTGCTGAGATAG
CAATGGCAAGCTATTGTTCAGAGCTGCAATATCTAGCCAACCCAG
TAACCTCTCATGTACAATCAGCCGAACAACACAATCAGGATGTTA
ATTCTTTGGGCCTGATTTCATCAAGAAAAACAAGCGAGGCCGTTG
ATATCCTTAAATTAATGTCCACAACATTTTTAGTGGGTATATGCCA
GGCCGTAGATTTgAGACACTTGGAAGAGAATTTGAGACAGACAG
TGAAAAATACCGTATCACAGGTTGCAAAAAGGTTCTAACTACAG
GTATCAATGGTGAATTGCACCCATCAAGATTCTGTGAAAAAGATT
TATTAAAAGTTGTAGATAGAGAACAAGTATTTACTTACGTTGACGA
TCCATGTAGCGCTACTTATCCATTGATGCAGAGATTGAGACAAGT
TATTGTAGATCACGCTTTATCCAATGGTGAAACTGAGAAAAATGC
CGTTACTTCAATATTCCAAAAGATAGGTGCCTTTGAAGAAGAACT
GAAGGCAGTTTTACCAAAGGAAGTCGAAGCTGCTAGAGCCGCAT
ACGGAAATGGTACTGCCCCTATACCAAATAGAATCAAAGAGTGTA
GGTCGTACCCTTTGTACAGATTCGTTAGAGAAGAGTTGGGAACC
AAATTACTAACTGGTGAAAAAGTCGTTAGCCCAGGTGAAGAATTT
GACAAGGTATTCACAGCTATGTGCGAGGGAAAGTTGATAGATCC
ACTTATGGATTGCTTGAAAGAGTGGAATGGTGCACCTATTCCAAT
CTGCTAA
                                      SEQ ID NO: 2
ATGATGGATTTTGTTTTGTTAGAAAAAGCTCTTCTTGGTTTGTTCA
TTGCAACTATAGTAGCCATCACAATCTCTAAGCTAAGGGGAAAGA
AACTTAAGTTGCCTCCAGGCCCAATCCCTGTCCCAGTGTTTGGTA
ATTGGTTACAAGTTGGCGACGACTTAAACCAGAGGAATTTGGTAG
AGTATGCTAAAAAGTTCGGCGACTTATTTCTACTTAGGATGGGTC
AAAGAAACTTGGTCGTGGTTTCATCCCCTGACTTAGCAAAAGACG
TACTACATACCCAGGGTGTCGAGTTCGGAAGTAGAACTAGAAAT
GTTGTGTTTGATATTTTCACAGGCAAAGGTCAAGATATGGTTTTTA
CCGTATACAGCGAGCACTGGAGGAAAATGAGAAGAATAATGACT
GTCCCATTCTTTACAAACAAAGTGGTTCAACAGTATAGGTTCGGA
TGGGAGGACGAAGCCGCTAGAGTAGTCGAGGATGTTAAGGCAA
ATCCTGAAGCCGCTACCAACGGTATTGTGTTGAGGAATAGATTAC
AACTTTTGATGTACAACAATATGTATAGAATAATGTTTGACAGGAG
ATTTGAATCTGTTGATGATCCATTATTCCTAAAACTTAAGGCATTG
AATGGCGAGAGATCAAGGTTAGCTCAATCCTTTGAATACAACTTC
GGTGACTTCATTCCTATATTGAGGCCATTCTTGAGAGGATATCTT
AAGTTGTGTCAGGAAATCAAGGACAAAAGGTTAAAGCTATTCAAG
GACTACTTCGTCGACGAGAGAAAAAAGTTGGAGAGTATCAAGAG
CGTAGGTAATAACTCCTTAAAGTGCGCCATAGATCATATTATCGA
GGCACAAGAAAAAGGCGAGATAAACGAGGATAACGTGTTATACA
TCGTCGAGAATATCAACGTGGCTGCCATTGAAACTACACTTTGGT
CTATTGAATGGGGTATAGCAGAACTAGTGAATAACCCTGAAATCC
AGAAAAAATTGAGACACGAATTAGACACCGTACTTGGAGCTGGT
GTTCAAATTTGTGAACCAGATGTTCAAAAATTGCCTTATCTACAG
GCCGTGATAAAAGAGACTTTAAGGTACAGGATGGCAATTCCATTG
TTAGTCCCACATATGAATCTTCACGAAGCCAAATTGGCCGGCTAT
GATATCCCTGCAGAGAGCAAAATTTTGGTAAACGCTTGGTGGTTA
GCCAATAATCCAGCACATTGGAACAAACCTGATGAGTTTAGACCA
GAAAGATTTTTGGAGGAAGAATCCAAGGTCGAGGCTAATGGAAA
CGACTTTAAGTACATCCCTTTCGGTGTTGGCAGAAGATCTTGCCC
AGGTATAATTCTTGCTTTACCAATCCTTGGAATAGTAATTGGTAG
GTTGGTTCAAAACTTCGAGTTACTTCCACCTCCAGGCCAAAGCAA
AATAGATACAGCCGAAAAAGGTGGACAGTTTTCATTGCAAATCCT
AAAGCATTCCACTATTGTGTGTAAACCTAGAAGTTCTTAA
                                      SEQ ID NO: 3
ATGACGACACAAGATGTGATAGTCAATGATCAGAATGATCAGAAA
CAGTGTAGTAATGACGTCATTTTCCGATCGAGATTGCCTGATATA
TACATCCCTAACCACCTCCCACTCCACGACTACATCTTCGAAAAT
ATCTCAGAGTTCGCCGCTAAGCCATGCTTGATCAACGGTCCCAC
CGGCGAAGTATACACCTACGCCGATGTCCACGTAACATCTCGGA
AACTCGCCGCCGGTCTTCATAACCTCGGCGTGAAGCAACACGAC
GTTGTAATGATCCTCCTCCCGAACTCTCCTGAAGTAGTCCTCACT
TTCCTTGCCGCCTCCTTCATCGGCGCAATCACCACCTCCGCGAA
CCCGTTCTTCACTCCGGCGGAGATTTCTAAACAAGCCAAAGCCT
CCGCGGCGAAACTCATCGTCACTCAATCCCGTTACGTCGATAAA
ATCAAGAACCTCCAAAACGACGGCGTTTTGATCGTCACCACCGA
CTCCGACGCCATCCCCGAAAACTGCCTCCGTTTCTCCGAGTTAA
CTCAGTCCGAAGAACCACGAGTGGACTCAATACCGGAGAAGATT
TCGCCAGAAGACGTCGTGGCGCTTCCTTTCTCATCCGGCACGAC
GGGTCTCCCCAAAGGAGTGATGCTAACACACAAAGGTCTAGTCA
CGAGCGTGGCGCAGCAAGTCGACGGCGAGAATCCGAATCTTTA
CTTCAACAGAGACGACGTGATCCTCTGTGTCTTGCCTATGTTCCA
TATATACGCTCTCAACTCCATCATGCTCTGTAGTCTCAGAGTTGG
TGCCACGATCTTGATAATGCCTAAGTTCGAAATCACTCTCTTGTT
AGAGCAGATACAAAGGTGTAAAGTCACGGTGGCTATGGTCGTGC
CACCGATCGTTTTAGCTATCGCGAAGTCGCCGGAGACGGAGAAG
TATGATCTGAGCTCGGTTAGGATGGTAAGTCTGGGAGCAGCTCC
TCTTGGTAAGGAGCTTGAAGATGCTATTAGTGCTAAGTTTCCTAA
CGCCAAGCTTGGTCAGGGCTATGGGATGACAGAAGCAGGTCCG
GTGCTAGCAATGTCGTTAGGGTTTGCTAAAGAGCCGTTTCCAGT
```

-continued

GAAGTCAGGAGCATGTGGTACGGTGGTGAGGAACGCCGAGATG

AAGATACTTGATCCAGACACAGGAGATTCTTTGCCTAGGAACAAA

CCCGGCGAAATATGCATCCGTGGCAACCAAATCATGAAAGGCTA

TCTCAATGACCCCTTGGCCACGGCATCGACGATCGATAAAGATG

GTTGGCTTCACACTGGAGACGTCGGATTTATCGATGATGACGAC

GAGCTTTTCATTGTGGATAGATTGAAAGAACTCATCAAGTACAAA

GGATTTCAAGTGGCTCCAGCTGAGCTAGAGTCTCTCCTCATAGG

TCATCCAGAAATCAATGATGTTGCTGTCGTCGCCATGAAGGAAGA

AGATGCTGGTGAGGTTCCTGTTGCGTTTGTGGTGAGATCGAAAG

ATTCAAATATATCCGAAGATGAAATCAAGCAATTCGTGTCAAAAC

AGGTTGTGTTTTATAAGAGAATCAACAAAGTGTTCTTCACTGACT

CTATTCCTAAAGCTCCATCAGGGAAGATATTGAGGAAGGATCTAA

GAGCAAGACTAGCAAATGGATTAATGAACTAG

SEQ ID NO: 4
ATGGCTGCAGTAAGATTGAAAGAAGTTAGAATGGCACAGAGGGC

TGAAGGTTTAGCTACAGTTTTAGCAATCGGTACTGCCGTTCCAGC

TAATTGTGTTTATCAAGCTACCTATCCAGATTATTATTTAGGGTT

ACTAAAAGTGAGCACTTGGCAGATTTAAAGGAGAAGTTTCAAAGA

ATGTGTGACAAATCAATGATTAGAAAGAGACACATGCACTTGACC

GAGGAAATATTGATCAAGAACCCAAAGATCTGTGCACACATGGA

GACCTCATTGGATGCTAGACACGCCATCGCATTAGTTGAAGTTCC

CAAATTGGGCCAAGGTGCAGCTGAGAAGGCCATTAAGGAGTGG

GGCCAACCCTTGTCTAAGATTACTCATTTGGTATTTTGCACAACA

TCCGGCGTTGACATGCCCGGTGCTGATTACCAATTAACAAAGTT

GTTAGGTTTGTCCCCTACAGTCAAAAGGTTAATGATGTACCAACA

AGGTTGCTTTGGTGGTGCAACTGTTTTGAGATTGGCAAAAGATAT

CGCTGAAAATAATAGAGGTGCCAGAGTGTTAGTCGTTTGTTCCGA

GATAACTGCTATGGCCTTCAGAGGTCCATGCAAGAGTCATTTAGA

TTCCTTGGTAGGTCATGCCTTGTTCGGTGATGGTGCCGCTGCTG

CAATTATAGGCGCTGACCCAGACCAATTAGACGAACAACCAGTTT

TCCAGTTGGTATCAGCTTCTCAGACTATATTACCAGAATCAGAAG

GTGCCATAGATGGCCATTTAACAGAAGCTGGTTTAACTATACATT

TATTAAAAGATGTTCCTGGTTTAATTTCAGAGAACATTGAACAGG

CTTTGGAGGATGCCTTTGAACCTTAGGTATTCATAACTGGAATT

CAATTTTCTGGATTGCACATCCTGGTGGCCCTGCCATTTTAGCA

GAGTTGAAGATAGAGTAGGATTGGATAAGAAGAGAATGAGGGCT

TCTAGGGAAGTGTTATCTGAATACGGAAATATGTCTAGTGCCTCT

GTGTTGTTTGTGTTAGATGTCATGAGGAAAAGTTCTGCTAAAGAC

GGATTGGCAACCACAGGAGAAGGAAAAGATTGGGGAGTGTTGTT

TGGATTCGGACCAGGCTTGACTGTAGAAACCTTAGTGTTGCATA

GTGTCCCAGTCCCTGTCCCTACTGCAGCTTCTGCATGA

SEQ ID NO: 5
ATGGGTGATGTCATTGTCTTGTATGCTTCTCCAGGTATGGGTCAT

ATAGTTTCCATGGTTGAATTGGGTAAATTCATCGTTCATAGATAC

GGTCCACACAAGTTCTCTATTACTATCTTGTACACCTGTGGTTCC

ATCGTTGATACTGCTTCTATTCCAGTTTACATCAGAAGAATCTCCC

ATTCCCATCCATTCATCTCATTCAGACAATTCCCAAGAGTTACCAA

CAACATCACCAGAAACATTTCCGTTCCAGCTATTACCTTCGACTT

CATCAGACAAAATGATCCACATGTTAGATCCGCCTTGCAAGAAAT

TTCAAAGTCTGCTACTGTTAGAGCCTTCATCATTGATTTGTTCTGT

ACTTCCGCTTTGCCAATCGGTAAAGAATTCAACATTCCAACCTAC

TACTTCAGAACTTCTGGTGCTGCTATTTTGGCTGCTTTCTTGTACT

TGCCAAAGATCGATGAACAAACTAAGACCACCGAATCTTTCAAGG

ATTTGAGAGATACCGTTTTCGAATTTCCAGGTTGGAAATCTCCAT

TGAAGGCTACTCATATGGTTCAATTGGTTTTGGATAGAAACGATC

CAGCCTACTCTGATATGATCTACTTCTGTTCTCATTTGCCAAAGTC

CAACGGTATTATCGTTAACACCTTCGAAGAATTGGAACCACCATC

TGTTTTACAAGCTATTGCTGGTGGTTTGTGTGTTCCAGATGGTCC

AACTCCACCAGTTTATTATGTTGGTCCATTGATCGAAGAAGAAAA

AGAATTGTCCAAGGATGCTGATGCTGCCGAAAAGAAGATTGCTT

GTCTTGGTTGGATAAGCAACCATCTAGATCCGTTTTGTTCTTGTG

TTTTGGTTCCATGGGTTCTTTTCCAGCTGCTCAATTGAAAGAAATT

GCCAATGGTTTGGAAGCCTCTGGTCAAAGATTTTTGTGGGTTGTT

AAGAAGCCACCAGTCGAAGAAAAATCCAAACAAGTTCATGGTGTT

GACGACTTCGATTTGAAAGGTGTTTTGCCAGAAGGTTTCTTGGAA

AGAACTGCTGATAGAGGTATGGTTGTAAAATCTTGGGCTCCACAA

GTTGTCGTCTTGAAGAAAGAATCTGTTGGTGGTTTCGTTACTCAT

TGTGGTTGGAATTCTGTTTTGGAAGCTGTTGTTGCTGGTGTTCCA

ATGATTGCTTGGCCATTATATGCTGAACAACACATGAATAGAAAC

GTCTTGGTTACCGATATGGAAATCGCTATTGGTGTCGAACAAAGA

GATGAAGAAGGTGGTTTTGTTTCCGGTGAAGAAGTTGAAAGAAG

AGTTAGAGAATTGATGGAATCCGAAGGTGGTAGAGTTTTGAGAG

AAAGATGTAAAAGTTGGGTGAAATGGCTTCTGCTGCTTTAGGTG

AAACTGGTTCTTCTACTAGAAACTTGGTCAACTTCGTTTCCTCCAT

TACCTGA

SEQ ID NO: 6
ATGCCGTTTGGAATAGACAACACCGACTTCACTGTCCTGGCGGG

GCTAGTGCTTGCCGTGCTACTGTACGTAAAGAGAAACTCCATCAA

GGAACTGCTGATGTCCGATGACGGAGATATCACAGCTGTCAGCT

CGGGCAACAGAGACATTGCTCAGGTGGTGACCGAAAACAACAAG

AACTACTTGGTGTTGTATGCGTCGCAGACTGGGACTGCCGAGGA

TTACGCCAAAAAGTTTTCCAAGGAGCTGGTGGCCAAGTTCAACCT

-continued

```
AAACGTGATGTGCGCAGATGTTGAGAACTACGACTTTGAGTCGC

TAAACGATGTGCCCGTCATAGTCTCGATTTTTATCTCTACATATG

GTGAAGGAGACTTCCCCGACGGGGCGGTCAACTTTGAAGACTTT

ATTTGTAATGCGGAAGCGGGTGCACTATCGAACCTGAGGTATAA

TATGTTTGGTCTGGGAAATTCTACTTATGAATTCTTTAATGGTGCC

GCCAAGAAGGCCGAGAAGCATCTCTCCGCTGCGGGCGCTATCA

GACTAGGCAAGCTCGGTGAAGCTGATGATGGTGCAGGAACTACA

GACGAAGATTACATGGCCTGGAAGGACTCCATCCTGGAGGTTTT

GAAAGACGAACTGCATTTGGACGAACAGGAAGCCAAGTTCACCT

CTCAATTCCAGTACACTGTGTTGAACGAAATCACTGACTCCATGT

CGCTTGGTGAACCCTCTGCTCACTATTTGCCCTCGCATCAGTTGA

ACCGCAACGCAGACGGCATCCAATTGGGTCCCTTCGATTTGTCT

CAACCGTATATTGCACCCATCGTGAAATCTCGCGAACTGTTCTCT

TCCAATGACCGTAATTGCATCCACTCTGAATTTGACTTGTCCGGC

TCTAACATCAAGTACTCCACTGGTGACCATCTTGCTGTTTGGCCT

TCCAACCCATTGGAAAAGGTCGAACAGTTCTTATCCATATTCAAC

CTGGACCCTGAAACCATTTTTGACTTGAAGCCCCTGGATCCCAC

CGTCAAAGTGCCCTTCCCAACGCCAACTACTATTGGCGCTGCTA

TTAAACACTATTTGGAAATTACAGGACCTGTCTCCAGACAATTGTT

TTCATCTTTGATTCAGTTCGCCCCCAACGCTGACGTCAAGGAAAA

ATTGACTCTGCTTTCGAAAGACAAGGACCAATTCGCCGTCGAGAT

AACCTCCAAATATTTCAACATCGCAGATGCTCTGAAATATTTGTCT

GATGGCGCCAAATGGGACACCGTACCCATGCAATTCTTGGTCGA

ATCAGTTCCCCAAATGACTCCTCGTTACTACTCTATCTCTTCCTCT

TCTCTGTCTGAAAAGCAAACCGTCCATGTCACCTCCATTGTGGAA

AACTTTCCTAACCCAGAATTGCCTGATGCTCCTCCAGTTGTTGGT

GTTACGACTAACTTGTTAAGAAACATTCAATTGGCTCAAAACAAT

GTTAACATTGCCGAAACTAACCTACCTGTTCACTACGATTTAAAT

GGCCCACGTAAACTTTTCGCCAATTACAAATTGCCCGTCCACGTT

CGTCGTTCTAACTTCAGATTGCCTTCCAACCCTTCCACCCCAGTT

ATCATGATCGGTCCAGGTACCGGTGTTGCCCCATTCCGTGGGTT

TATCAGAGAGCGTGTCGCGTTCCTCGAATCACAAAAGAAGGGCG

GTAACAACGTTTCGCTAGGTAAGCATATACTGTTTTATGGATCCC

GTAACACTGATGATTTCTTGTACCAGGACGAATGGCCAGAATACG

CCAAAAAATTGGATGGTTCGTTCGAAATGGTCGTGGCCCATTCCA

GGTTGCCAAACACCAAAAAAGTTTATGTTCAAGATAAATTAAAGG

ATTACGAAGACCAAGTATTTGAAATGATTAACAACGGTGCATTTAT

CTACGTCTGTGGTGATGCAAAGGGTATGGCCAAGGGTGTGTCAA

CCGCATTGGTTGGCATCTTATCCCGTGGTAAATCCATTACCACTG

ATGAAGCAACAGAGCTAATCAAGATGCTCAAGACTTCAGGTAGAT

ACCAAGAAGATGTCTGGTAA
```

SEQ ID NO: 7
```
ATGCCTATCACCATAAAAAGCCGCTCTAAAGGGTTAAGGGACAC

TGAAATTGACTTATCCAAAAAGCCTACTTTAGATGATGTTTTGAAA

AAAATCTCTGCTAATAACCACAATATCAGCAAGTACAGGATAAGA

TTAACCTACAAAAAGGAATCTAAACAAGTTCCGGTTATTTCAGAAT

CGTTTTTTCAAGAAGAGGCTGATGACTCAATGGAATTCTTCATCA

AAGATTTGGGTCCCCAAATTTCATGGAGATTAGTCTTCTTTTGTG

AGTATTTGGGTCCAGTCTTGGTTCACTCCCTTTTTTATTATCTATC

TACCATTCCCACAGTTGTTGATAGATGGCACAGTGCTAGCTCCGA

CTATAATCCATTTTTAAACAGGGTTGCATATTTTTTAATTTTAGGA

CATTATGGAAAGAGATTATTTGAAACCTTATTTGTTCACCAATTCT

CTTTAGCTACTATGCCAATTTTCAACCTGTTCAAAAATTGTTTCCA

TTACTGGGTTCTAAGCGGTCTCATTTCATTCGGTTACTTTGGCTA

CGGCTTCCCCTTTGGGAATGCTAAGTTATTCAAATACTATTCATAT

TTGAAATTGGATGACTTGAGTACATTAATTGGTCTTTTCGTGCTTT

CAGAACTATGGAACTTTTATTGCCACATTAAATTGCGCCTATGGG

GTGACTATCAAAGAAGCATGGTAACGCTAAGATCCGTGTCCCAT

TGAATCAAGGTATTTTCAATCTTTTTGTTGCTCCCAACTATACTTT

TGAAGTTTGGTCTTGGATTTGGTTTACTTTTGTGTTCAAGTTCAAT

TTATTTGCCGTTTTATTTTTGACTGTTTCAACAGCTCAAATGTACG

CATGGGCTCAAAAGAAAAACAAAAAGTATCATACCAGAAGAGCAT

TCTTGATTCCATTTGTATTTTGA
```

SEQ ID NO: 8
```
ACGCGTCCAGTATCCCAGCAGATACGGGATATCGACATTTCTGC

ACCATTCCGGCGGGTATAGGTTTTATTGATGGCCTCATCCACAC

GCAGCAGCGTCTGTTCATCGTCGTGGCGGCCCATAATAATCTGC

CGGTCAATCAGCCAGCTTTCCTCACCCGGCCCCCATCCCCATAC

GCGCATTTCGTAGCGGTCCAGCTGGGAGTCGATACCGGCGGTC

AGGTAAGCCACACGGTCAGGAACGGGCGCTGAATAATGCTCTTT

CCGCTCTGCCATCACTTCAGCATCCGGACGTTCGCCAATTTTCG

CCTCCCACGTCTCACCGAGCGTGGTGTTTACGAAGGTTTTACGT

TTTCCCGTATCCCCTTTCGTTTTCATCCAGTCTTTGACAATCTGCA

CCCAGGTGGTGAACGGGCTGTACGCTGTCCAGATGTGAAAGGT

CACACTGTCAGGTGGCTCAATCTCTTCACCGGATGACGAAAACC

AGAGAATGCCATCACGGGTCCAGATCCCGGTCTTTTCGCAGATA

TAACGGGCATCAGTAAAGTCCAGCTCCTGCTGGCGGATGACGCA

GGCATTATGCTCGCAGAGATAAAACACGCTGGAGACGCGTTTTC

CCGTCTTTCAGTGCCTTGTTCAGTTCTTCCTGACGGGCGGTATAT

TTCTCCAGCTTGGCCTATGCGGCCCTGTCAGACCAAGTTTACGA

GCTCGCTTGGACTCCTGTTGATAGATCCAGTAATGACCTCAGAAC

TCCATCTGGATTTGTTCAGAACGCTCGGTTGCCGCCGGGCGTTT
```

-continued

TTTATTGGTGAGAATCCAAGCACTAGGGACAGTAAGACGGGTAA
GCCTGTTGATGATACCGCTGCCTTACTGGGTGCATTAGCCAGTC
TGAATGACCTGTCACGGGATAATCCGAAGTGGTCAGACTGGAAA
ATCAGAGGGCAGGAACTGCTGAACAGCAAAAAGTCAGATAGCAC
CACATAGCAGACCCGCCATAAAACGCCCTGAGAAGCCCGTGAC
GGGCTTTTCTTGTATTATGGGTAGTTTCCTTGCATGAATCCATAAA
AGGCGCCTGTAGTGCCATTTACCCCCATTCACTGCCAGAGCCGT
GAGCGCAGCGAACTGAATGTCACGAAAAAGACAGCGACTCAGGT
GCCTGATGGTCGGAGACAAAAGGAATATTCAGCGATTTGCCCGA
GCTTGCGAGGGTGCTACTTAAGCCTTTAGGGTTTTAAGGTCTGTT
TTGTAGAGGAGCAAACAGCGTTTGCGACATCCTTTTGTAATACTG
CGGAACTGACTAAAGTAGTGAGTTATACACAGGGCTGGGATCTA
TTCTTTTTATCTTTTTTTATTCTTTCTTTATTCTATAAATTATAACCA
CTTGAATATAAACAAAAAAAACACACAAAGGTCTAGCGGAATTTA
CAGAGGGTCTAGCAGAATTTACAAGTTTTCCAGCAAAGGTCTAGC
AGAATTTACAGATACCCACAACTCAAAGGAAAAGGACATGTAATT
ATCATTGACTAGCCCATCTCAATTGGTATAGTGATTAAAATCACCT
AGACCAATTGAGATGTATGTCTGAATTAGTTGTTTTCAAAGCAAAT
GAACTAGCGATTAGTCGCTATGACTTAACGGAGCATGAAACCAA
GCTAATTTTATGCTGTGTGGCACTACTCAACCCCACGATTGAAAA
CCCTACAAGGAAAGAACGGACGGTATCGTTCACTTATAACCAATA
CGCTCAGATGATGAACATCAGTAGGGAAAATGCTTATGGTGTATT
AGCTAAAGCAACCAGAGAGCTGATGACGAGAACTGTGGAAATCA
GGAATCCTTTGGTTAAAGGCTTTGAGATTTTCCAGTGGACAAACT
ATGCCAAGTTCTCAAGCGAAAAATTAGAATTAGTTTTTAGTGAAG
AGATATTGCCTTATCTTTTCCAGTTAAAAAAATTCATAAAATATAAT
CTGGAACATGTTAAGTCTTTTGAAAACAAATACTCTATGAGGATTT
ATGAGTGGTTATTAAAAGAACTAACACAAAAGAAAACTCACAAGG
CAAATATAGAGATTAGCCTTGATGAATTTAAGTTCATGTTAATGCT
TGAAAATAACTACCATGAGTTTAAAAGGCTTAACCAATGGGTTTT
GAAACCAATAAGTAAAGATTTAAACACTTACAGCAATATGAAATTG
GTGGTTGATAAGCGAGGCCGCCCGACTGATACGTTGATTTTCCA
AGTTGAACTAGATAGACAAATGGATCTCGTAACCGAACTTGAGAA
CAACCAGATAAAAATGAATGGTGACAAAATACCAACAACCATTAC
ATCAGATTCCTACCTACATAACGGACTAAGAAAAACACTACACGA
TGCTTTAACTGCAAAAATTCAGCTCACCAGTTTTGAGGCAAAATTT
TTGAGTGACATGCAAAGTAAGTATGATCTCAATGGTTCGTTCTCA
TGGCTCACGCAAAAACAACGAACCACACTAGAGAACATACTGGC
TAAATACGGAAGGATCTGAGGTTCTTATGGCTCTTGTATCTATCA
GTGAAGCATCAAGACTAACAAACAAAAGTAGAACAACTGTTCACC
GTTACATATCAAAGGGAAAACTGTCCATATGCACAGATGAAAACG

-continued

GTGTAAAAAAGATAGATACATCAGAGCTTTTACGAGTTTTTGGTG
CATTCAAAGCTGTTCACCATGAACAGATCGACAATGTAACGCGG
CCGCAGCCAATCAATTCTTGCGGAGAACTGTGAATGCGCAAACC
AACCCTTGGCAGAACATATCCATCGCGTCCGCCATCTCCAGCAG
CCGCACGCGGCGCATCGGGGGGGGGGGGGGGGGTTTCAATTC
ATCATTTTTTTTTATTCTTTTTTTTGATTTCGGTTTCCTTGAAATTT
TTTTGATTCGGTAATCTCCGAACAGAAGGAAGAACGAAGGAAGG
AGCACAGACTTAGATTGGTATATATACGCATATGTAGTGTTGAAG
AAACATGAAATTGCCCAGTATTCTTAACCCAACTGCACAGAACAA
AAACCTGCAGGAAACGAAGATAAATCATGTCGAAAGCTACATATA
AGGAACGTGCTGCTACTCATCCTAGTCCTGTTGCTGCCAAGCTAT
TTAATATCATGCACGAAAAGCAAACAAACTTGTGTGCTTCATTGG
ATGTTCGTACCACCAAGGAATTACTGGAGTTAGTTGAAGCATTAG
GTCCCAAAATTTGTTTACTAAAAACACATGTGGATATCTTGACTGA
TTTTTCCATGGAGGGCACAGTTAAGCCGCTAAAGGCATTATCCG
CCAAGTACAATTTTTTACTCTTCGAAGACAGAAAATTTGCTGACAT
TGGTAATACAGTCAAATTGCAGTACTCTGCGGGTGTATACAGAAT
AGCAGAATGGGCAGACATTACGAATGCACACGGTGTGGTGGGC
CCAGGTATTGTTAGCGGTTTGAAGCAGGCGGCAGAAGAAGTAAC
AAAGGAACCTAGAGGCCTTTTGATGTTAGCAGAATTGTCATGCAA
GGGCTCCCTATCTACTGGAGAATATACTAAGGGTACTGTTGACAT
TGCGAAGAGCGACAAAGATTTTGTTATCGGCTTTATTGCTCAAAG
AGACATGGGTGGAAGAGATGAAGGTTACGATTGGTTGATTATGA
CACCCGGTGTGGGTTTAGATGACAAGGGAGACGCATTGGGTCAA
CAGTATAGAACCGTGGATGATGTGGTCTCTACAGGATCTGACATT
ATTATTGTTGGAAGAGGACTATTTGCAAAGGGAAGGGATGCTAA
GGTAGAGGGTGAACGTTACAGAAAAGCAGGCTGGGAAGCATATT
TGAGAAGATGCGGCCAGCAAAACTAAAAAACTGTATTATAAGTAA
ATGCATGTATACTAAACTCACAAATTAGAGCTTCAATTTAATTATA
TCAGTTATTACCCGGCCGGGAATCTCGGTCGTAATGATTTTTATA
ATGACGAAAAAAAAAAATTGGAAAGAAAACCCCCCCCCCCCC
CCGCAGCGTTGGGTCCTGGCCACGGGTGCGCATGATCGTGCTC
CTGTCGTTGAGGACCCGGCTAGGCTGGCGGGGTTGCCTTACTG
GTTAGCAGAATGAATCACCGATACGCGAGCGAATGTGGCGGCC
GCACGCGTTCATCGTCCACCTCCGGAGAACAGGCCACCATCACG
CATCTGTGTCTGAATTTCATCACGACGCGCCTTAAGGGCACCAAT
AACTGCCTTAAAAAAATTACGCCCCGCCCTGCCACTCATCGCAGT
ACTGTTGTAATTCATTAAGCATTCTGCCGACATGGAAGCCATCAC
AGACGGCATGATGAACCTGAATCGCCAGCGGCATCAGCACCTTG
TCGCCTTGCGTATAATATTTGCCCATGGTGAAAACGGGGGCGAA

```
GAAGTTGTCCATATTGGCCACGTTTAAATCAAAACTGGTGAAACT
CACCCAGGGATTGGCTGAGACGAAAAACATATTCTCAATAAACC
CTTTAGGGAAATAGGCCAGGTTTTCACCGTAACACGCCACATCTT
GCGAATATATGTGTAGAAACTGCCGGAAATCGTCGTGGTATTCAC
TCCAGAGCGATGAAAACGTTTCAGTTTGCTCATGGAAAACGGTGT
AACAAGGGTGAACACTATCCCATATCACCAGCTCACCGTCTTTCA
TTGCCATACGGAATTCCGGATGAGCATTCATCAGGCGGGCAAGA
ATGTGAATAAAGGCCGGATAAAACTTGTGCTTATTTTTCTTTACG
GTCTTTAAAAAGGCCGTAATATCCAGCTGAACGGTCTGGTTATAG
GTACATTGAGCAACTGACTGAAATGCCTCAAAATGTTCTTTACGA
TGCCATTGGGATATATCAACGGTGGTATATCCAGTGATTTTTTCT
CCATTTTAGCTTCCTTAGCTCCTGAAAATCTCGATAACTCAAAAAA
TACGCCCGGTAGTGATCTTATTTCATTATGGTGAAAGTTGGAACC
TCTTACGTGCCGATCAACGTCTCATTTTCGCCAAAAGTTGGCCCA
GGGCTTCCCGGTATCAACAGGGACACCAGGATTTATTTATTCTGC
GAAGTGATCTTCCGTCACAGGTATTGGACCACCCTGTGGGTTTAT
AAGCGCGCTGCTGGCGTGTAAGGCGGTGACGGCGAAGGAAGG
GTCCTTTTCATCACGTGCTATAAAAATAATTATAATTTAAATTTTTT
AATATAAATATATAAATTAAAAATAGAAAGTAAAAAAAGAAATTAAA
GAAAAAATAGTTTTTGTTTTCCGAAGATGTAAAAGACTCTAGGGG
GATCGCCAACAAATACTACCTTTTATCTTGCTCTTCCTGCTCTCA
GGTATTAATGCCGAATTGTTTCATCTTGTCTGTGTAGAAGACCAC
ACACGAAAATCCTGTGATTTTACATTTTACTTATCGTTAATCGAAT
GTATATCTATTTAATCTGCTTTTCTTGTCTAATAAATATATATGTAA
AGTACGCTTTTTGTTGAAATTTTTTAAACCTTTGTTTATTTTTTTTT
CTTCATTCCGTAACTCTTCTACCTTCTTTATTTACTTTCTAAAATCC
AAATACAAAACATAAAAATAAATAAACACAGAGTAAATTCCCAAAT
TATTCCATCATTAAAAGATACGAGGCGCGTGTAAGTTACAGGCAA
GCGATCCGTCCTAAGAAACCATTATTATCATGACATTAACCTATAA
AAATAGGCGTATCACGAGGCCCTTTCGTCTCGCGCGTTTCGGTG
ATGACGGTGAAAACCTCTGACACATGCAGCTCCCGGAGACGGTC
ACAGCTTGTCTGTAAGCGGATGCCGGGAGCAGACAAGCCCGTC
AGGGCGCGTCAGCGGGTGTTGGCGGGTGTCGGGGCTGGCTTAA
CTATGCGGCATCAGAGCAGATTGTACTGAGAGTGCACCACGGCG
CGTGGCACCCTTGCGGGCCATGTCATACACCGCCTTCAGAGCAG
CCGGACCTATCTGCCCGTTACGCGCCAGCTTGCAAATTAAAGCC
TTCGAGCGTCCCAAAACCTTCTCAAGCAAGGTTTTCAGTATAATG
TTACATGCGTACACGCGTCTGTACAGAAAAAAAGAAAAATTTGA
AATATAAATAACGTTCTTAATACTAACATAACTATAAAAAAATAAAT
AGGGACCTAGACTTCAGGTTGTCTAACTCCTTCCTTTTCGGTTAG
AGCGGATGTGGGGGGAGGGCGTGAATGTAAGCGTGACATAACT
AATTACATGATATCGACAAAGGAAAAGGGGGACGGATCTCCGAG
GCCTCGGACCCGTCGGGCCGCCGTCGGACGTGCCGCGGTCAT
GCAGAAGCTGCAGTAGGGACAGGGACTGGGACACTATGCAACA
CTAAGGTTTCTACAGTCAAGCCTGGTCCGAATCCAAACAACACTC
CCCAATCTTTTCCTTCTCCTGTGGTTGCCAATCCGTCTTTAGCAG
AACTTTTCCTCATGACATCTAACACAAACAACACAGAGGCACTAG
ACATATTTCCGTATTCAGATAACACTTCCCTAGAAGCCCTCATTCT
CTTCTTATCCAATCCTACTCTATCTTCAACTCTGTCTAAAATGGCA
GGGCCACCAGGATGTGCAATCCAGAAAATTGAATTCCAGTTATG
AATACCTAAAGGTTCAAAGGCATCCTCCAAAGCCTGTTCAATGTT
CTCTGAAATTAAACCAGGAACATCTTTTAATAAATGTATAGTTAAA
CCAGCTTCTGTTAAATGGCCATCTATGGCACCTTCTGATTCTGGT
AATATAGTCTGAGAAGCTGATACCAACTGGAAAACTGGTTGTTCG
TCTAATTGGTCTGGGTCAGCGCCTATAATTGCAGCAGCGGCACC
ATCACCGAACAAGGCATGACCTACCAAGGAATCTAAATGACTCTT
GCATGGACCTCTGAAGGCCATAGCAGTTATCTCGGAACAAACGA
CTAACACTCTGGCACCTCTATTATTTTCAGCGATATCTTTTGCCAA
TCTCAAAACAGTTGCACCACCAAAGCAACCTTGTTGGTACATCAT
TAACCTTTTGACTGTAGGGACAAACCTAACAACTTTGTTAATTG
GTAATCAGCACCGGGCATGTCAACGCCGGATGTTGTGCAAAATA
CCAAATGAGTAATCTTAGACAAGGGTTGGCCCCACTCCTTAATGG
CCTTCTCAGCTGCACCTTGGCCCAATTTGGGAACTTCAACTAATG
CGATGGCGTGTCTAGCATCCAATGAGGTCTCCATGTGTGCACAG
ATCTTTGGGTTCTTGATCAATATTTCCTCGGTCAAGTGCATGTGT
CTCTTTCTAATCATTGATTTGTCACACATTCTTTGAAACTTCTCCTT
TAAATCTGCCAAGTGCTCACTTTTAGTAACCCTAAAATAATAATCT
GGATAGGTAGCTTGATAAACACAATTAGCTGGAACGGCAGTACC
GATTGCTAAAACTGTAGCTAAACCTTCAGCCCTCTGTGCCATTCT
AACTTCTTTCAATCTTACTGCAGCCATTTTAAGCTTTTTGTTTGTTT
ATGTGTGTTTATTCGAAACTAAGTTCTTGGTGTTTTAAAACTAAAA
AAAAGACTAACTATAAAAGTAGAATTTAAGAAGTTTAAGAAATAGA
TTTACAGAATTACAATCAATACCTACCGTCTTTATATACTTATTAGT
CAAGTAGGGGAATAATTTCAGGGAACTGGTTTCAACCTTTTTTTT
CAGCTTTTTCCAAATCAGAGAGAGCAGAAGGTAATAGAAGGTGT
AAGAAAATGAGATAGATACATGCGTGGGTCAATTGCCTTGTGTCA
TCATTTACTCCAGGCAGGTTGCATCACTCCATTGAGGTTGTGTCC
GTTTTTTGCCTGTTTGTGCCCCTGTTCTCTGTAGTTGCGCTAAGA
GAATGGACCTATGAACTGATGGTTGGTGAAGAAAACAATATTTTG
GTGCTGGGATTCTTTTTTTTTCTGGATGCCAGCTTAAAAAGCGGG
CTCCATTATATTTAGTGGATGCCAGGAATAAACTGTTCACCCAGA
```

-continued

```
CACCTACGATGTTATATATTCTGTGTAACCCGCCCCCTATTTTGG
GCATGTACGGGTTACAGCAGAATTAAAAGGCTAATTTTTTGACTA
AATAAAGTTAGGAAAATCACTACTATTAATTATTTACGTATTCTTTG
AAATGGCAGTATTGATAATGATAAACTCGAACTGGGCGCGTCGT
GCCGTCGTTGTTAATCACCACATGGTTATTCTGCTCAAACGTCCC
GGACGCCTGCGAACGCGCCGAAGGAAAATGAGAAATATCGAGG
GAGACGATTCAGAGGAGCAGGACAAACTATAACCGACTGTTTGT
TGGAGGATGCCGTACATAACGAACACTGCTGAAGCTACCATGTC
TACAGTTTAGAGGAATGGGTACAACTCACAGGCGAGGGATGGTG
TTCACTCGTGCTAGCAAACGCGGTGGGAGCAAAAAGTAGAATAT
TATCTTTTATTCGTGAAACTTCGAACACTGTCATCTAAAGATGCTA
TATACTAATATAGGCATACTTGATAATGAAAACTATAAATCGTAAA
GACATAAGAGATCCGCGGTCAAAATACAAATGGAATCAAGAATG
CTCTTCTGGTATGATACTTTTTGTTTTTCTTTTGAGCCCATGCGTA
CATTTGAGCTGTTGAAACAGTCAAAAATAAAACGGCAAATAAATT
GAACTTGAACACAAAAGTAAACCAAATCCAAGACCAAACTTCAAA
AGTATAGTTGGGAGCAACAAAAAGATTGAAAATACCTTGATTCAA
TGGGACACGGATCTTAGCGTTACCATGCTTCTTTTGATAGTCACC
CCATAGGCGCAATTTAATGTGGCAATAAAAGTTCCATAGTTCTGA
AAGCACGAAAAGACCAATTAATGTACTCAAGTCATCCAATTTCAA
ATATGAATAGTATTTGAATAACTTAGCATTCCCAAAGGGGAAGCC
GTAGCCAAAGTAACCGAATGAAATGAGACCGCTTAGAACCCAGT
AATGGAAACAATTTTTGAACAGGTTGAAAATTGGCATAGTAGCTA
AAGAGAATTGGTGAACAAATAAGGTTTCAAATAATCTCTTTCCATA
ATGTCCTAAAATTAAAAAATATGCAACCCTGTTTAAAAATGGATTA
TAGTCGGAGCTAGCACTGTGCCATCTATCAACAACTGTGGGAAT
GGTAGATAGATAATAAAAAGGGAGTGAACCAAGACTGGACCCA
AATACTCACAAAAGAAGACTAATCTCCATGAAATTTGGGGACCCA
AATCTTTGATGAAGAATTCCATTGAGTCATCAGCCTCTTCTTGAAA
AAACGATTCTGAAATAACCGGAACTTGTTTAGATTCCTTTTTGTAG
GTTAATCTTATCCTGTACTTGCTGATATTGTGGTTATTAGCAGAGA
TTTTTTTCAAAACATCATCTAAAGTAGGCTTTTTGGATAAGTCAAT
TTCAGTGTCCCTTAACCCTTTAGAGCGGCTTTTTATGGTGATAGG
CATTTTAAGCTTTGTTTTATATTTGTTGTAAAAAGTAGATAATTACT
TCCTTGATGATCTGTAAAAAAGAGAAAAAGAAAGCATCTAAGAAC
TTGAAAAACTACGAATTAGAAAAGACCAAATATGTATTTCTTGCAT
TGACCAATTTATGCAAGTTTATATATATGTAAATGTAAGTTTCACG
AGGTTCTACTAAACTAAACCACCCCCTTGGTTAGAAGAAAAGAGT
GTGTGAGAACAGGCTGTTGTTGTCACACGATTCGGACAATTCTGT
TTGAAAGAGAGAGTAACAGTACGATCGAACGAACTTTGCTCT
GGAGATCACAGTGGGCATCATAGCATGTGGTACTAAACCCTTTC
CCGCCATTCCAGAACCTTCGATTGCTTGTTACAAAACCTGTGAGC
CGTCGCTAGGACCTTGTTGTGTGACGAAATTGGAAGCTGCAATC
AATAGGAAGACAGGAAGTCGAGCGTGTCTGGGTTTTTTCAGTTTT
GTTCTTTTTGCAAACAAATCACGAGCGACGGTAATTTCTTTCTCG
ATAAGAGGCCACGTGCTTTATGAGGGTAACATCAATTCAAGAAG
GAGGGAAACACTTCCTTTTTCTGGCCCTGATAATAGTATGAGGGT
GAAGCCAAAATAAAGGATTCGCGCCCAAATCGGCATCTTTAAATG
CAGGTATGCGATAGTTCCTCACTCTTTCCTTACTCACGAGTAATT
CTTGCAAATGCCTATTATGCAGATGTTATAATATCTGTGCGTGGC
GCGTCCGGCTGTCTGCCATGCTGCCCGGTGTACCGACATAACC
GCCGGTGGCATAGCCGCGCATACGCGCCATTTCCTTCCATCTTG
TGATTCATGCTATCCATCTTTTTTGAGTATCCAATTAACGAAGACG
TTACCAGCTGATTGAAGGTTCTCAAAGTGACTGTACTCCATGTTT
TCTTATCATCCATGTAGTTATTTTTCAAACTGCAAATTCAAGAAAA
AGCCACGCGTGTGCACCTTTTTTTTCCCCTTCCAGTGCATTATGC
AATAGACAGCACGAGTCTTTGAAAAAGTAACTTATAAAACTGTAT
CAATTTTTAAACCTAAATAGATTCATAAACTATTCGTTAATATAAAG
TGTTCTAAACTATGATGAAAAATAAGCAGAAAAGACTAATAATTC
TTAGTTAAAAGCACTCCCTAGTTCATTAATCCATTTGCTAGTCTTG
CTCTTAGATCCTTCCTCAATATCTTCCCTGATGGAGCTTTAGGAA
TAGAGTCAGTGAAGAACACTTTGTTGATTCTCTTATAAAACACAAC
CTGTTTTGACACGAATTGCTTGATTTCATCTTCGGATATATTTGAA
TCTTTCGATCTCACCACAAACGCAACAGGAACCTCACCAGCATCT
TCTTCCTTCATGGCGACGACAGCAACATCATTGATTTCTGGATGA
CCTATGAGGAGAGACTCTAGCTCAGCTGGAGCCACTTGAAATCC
TTTGTACTTGATGAGTTCTTTCAATCTATCCACAATGAAAAGCTCG
TCGTCATCATCGATAAATCCGACGTCTCCAGTGTGAAGCCAACCA
TCTTTATCGATCGTCGATGCCGTGGCCAAGGGGTCATTGAGATA
GCCTTTCATGATTTGGTTGCCACGGATGCATATTTCGCCGGGTTT
GTTCCTAGGCAAAGAATCTCCTGTGTCTGGATCAAGTATCTTCAT
CTCGGCGTTCCTCACCACCGTACCACATGCTCCTGACTTCACTG
GAAACGGCTCTTTAGCAAACCCTAACGACATTGCTAGCACCGGA
CCTGCTTCTGTCATCCCATAGCCCTGACCAAGCTTGGCGTTAGG
AAACTTAGCACTAATAGCATCTTCAAGCTCCTTACCAAGAGGAGC
TGCTCCAGACTTAACCATCCTAACCGAGCTCAGATCATACTTCTC
CGTCTCCGGCGACTTCGCGATAGCTAAAACGATCGGTGGCACGA
CCATAGCCACCGTGACTTTACACCTTTGTATCTGCTCTAACAAGA
GAGTGATTTCGAACTTAGGCATTATCAAGATCGTGGCACCAACTC
TGAGACTACAGAGCATGATGGAGTTGAGAGCGTATATATGGAAC
ATAGGCAAGACACAGAGGATCACGTCGTCTCTGTTGAAGTAAAG
```

```
ATTCGGATTCTCGCCGTCGACTTGCTGCGCCACGCTCGTGACTA
GACCTTTGTGTGTTAGCATCACTCCTTTGGGGAGACCCGTCGTG
CCGGATGAGAAAGGAAGCGCCACGACGTCTTCTGGCGAAATCTT
CTCCGGTATTGAGTCCACTCGTGGTTCTTCGGACTGAGTTAACTC
GGAGAAACGGAGGCAGTTTTCGGGGATGGCGTCGGAGTCGGTG
GTGACGATCAAAACGCCGTCGTTTTGGAGGTTCTTGATTTTATCG
ACGTAACGGGATTGAGTGACGATGAGTTTCGCCGCGGAGGCTTT
GGCTTGTTTAGAAATCTCCGCCGGAGTGAAGAACGGGTTCGCGG
AGGTGGTGATTGCGCCGATGAAGGAGGCGGCAAGGAAAGTGAG
GACTACTTCAGGAGAGTTCGGGAGGAGGATCATTACAACGTCGT
GTTGCTTCACGCCGAGGTTATGAAGACCGGCGGCGAGTTTCCGA
GATGTTACGTGGACATCGGCGTAGGTGTATACTTCGCCGGTGGG
ACCGTTGATCAAGCATGGCTTAGCGGCGAACTCTGAGATATTTTC
GAAGATGTAGTCGTGGAGTGGGAGGTGGTTAGGGATGTATATAT
CAGGCAATCTCGATCGGAAAATGACGTCATTACTACACTGTTTCT
GATCATTCTGATCATTGACTATCACATCTTGTGTCGTCATtttAGCT
TTTTGTAATTAAAACTTAGATTAGATTGCTATGCTTTCTTTCTAATG
AGCAAGAAGTAAAAAAAGTTGTAATAGAACAAGAAAAATGAAACT
GAAACTTGAGAAATTGAAGACCGTTTATTAACTTAAATATCAATGG
GAGGTCATCGAAAGAGAAAAAAATCAAAAAAAAAAAATTTTCAAGA
AAAAGAAACGTGATAAAAATTTTTATTGCCTTTTTCGACGAAGAAA
AAGAAACGAGGCGGTCTCTTTTTTCTTTTCCAAACCTTTAGTACG
GGTAATTAACGACACCCTAGAGGAAGAAAGAGGGGAAATTTAGT
ATGCTGTGCTTGGGTGTTTTGAAGTGGTACGGCGATGCGCGGAG
TCCGAGAAAATCTGGAAGAGTAAAAAAGGAGTAGAAACATTTTGA
AGCTAGGCGCGTCAGCCGGTAAAGATTCCCCACGCCAATCGG
CTGGTTGCCTCCTTCGTGAAGACAAACTCACGCGCCTCCAAAAT
GAGCTATCAAAAACGATAGATCGATTAGGATGACTTTGAAATGAC
TCCGCAGTGGACTGGCCGTTAATTTCAAGCGTGAGTAAAATAGT
GCATGACAAAGATGAGCTAGGCTTTTGTAAAAATATCTTACGTT
GTAAAATTTTAGAAATCATTATTTCCTTCATATCATTTTGTCATTGA
CCTTCAGAAGAAAAGAGCCGACCAATAATATAAATAAATAAATAA
AAATAATATTCCATTATTTCTAAACAGATTCAATACTCATTAAAAAA
CTATATCAATTAATTTGAATTAACCGCGGTTAGCAGATTGGAATA
GGTGCACCATTCCACTCTTTCAAGCAATCCATAAGTGGATCTATC
AACTTTCCCTCGCACATAGCTGTGAATACCTTGTCAAATTCTTCA
CCTGGGCTAACGACTTTTTCACCAGTTAGTAATTTGGTTCCCAAC
TCTTCTCTAACGAATCTGTACAAAGGGTACGACCTACACTCTTTG
ATTCTATTTGGTATAGGGGCAGTACCATTTCCGTATGCGGCTCTA
GCAGCTTCGACTTCCTTTGGTAAAACTGCCTTCAGTTCTTCTTCA
AAGGCACCTATCTTTTGGAATATTGAAGTAACGGCATTTTTCTCA
GTTTCACCATTGGATAAAGCGTGATCTACAATAACTTGTCTCAAT
CTCTGCATCAATGGATAAGTAGCGCTACATGGATCGTCAACGTAA
GTAAATACTTGTTCTCTATCTACAACTTTTAATAAATCTTTTTCACA
GAATCTTGATGGGTGCAATTCACCATTGATACCTGTAGTTAGAAC
CTTTTTTGCAACCTGTGATACGGTATTTTTCACTGTCTGTCTCAAA
TTCTCTTCCAAGTGTCtcAAATCTACGGCCTGGCATATACCCACT
AAAAATGTTGTGGACATTAATTTAAGGATATCAACGGCCTCGCTT
GTTTTTCTTGATGAAATCAGGCCCAAAGAATTAACATCCTGATTGT
GTTGTTCGGCTGATTGTACATGAGAGGTTACTGGGTTGGCTAGA
TATTGCAGCTCTGAACAATAGCTTGCCATTGCTATCTCAGCACCT
TTGAAACCATAATCAAGACTAGGGTTAGAAGATGCGGTCAGATTC
GAAGGCAAACCGTTATTGTAGAAGTCATTGACCAATTCAGAAAAT
TGGGCAAACATTAATTTGCCAATTGCGGCTATGGCAAGCCTGGT
ATTATCCTACTGACTCCTATGGGTGTACCCTGGAAATTGCCTCC
ATGTATTGCCTTATTCCTCGACACATCAATAAGTGGATTATCGTTA
ACAGAGTTGATCTCTCTTTCTATAGACTTTGTAGCTGTCTAATTA
CTTCAATTTGAGGGCCAAGCCATTGTGGGGATGTCCTTAAAGCAT
ATCTATCTTGTTTGGGTTTTTGCAAAGGGTCCATTTCATGAACCTT
CTGGGCTAACTTCATGTAGCTAGAGCCGTCCAAAATGTGCTCCAT
GATAGCTGCTGCTTCAATTTGTCCTGGGTGATGTTTTAACCTGTG
GGTCAAGTGATCAGTAAACTCAGGTTTTCCACTCATGACTTCGGC
AAAAATTGCGGACAAAACTTCGGCCAAAACTGCTTGTACGTTAGC
TTCAAACAACACCATGGATGCCATACCGCTGCCGACAGCGGTGC
CATTCACCAGGGCTAAACCTTCCTTGGGTTGcAAATCAAAGAAAC
CAGTTGAAATACCAGCTTTCTCAAATGCTTCCTTAGCGGTTAAGG
ATTCTCCGTCTGGACCAGTGGCCTTTGAATTAGGTCTTCCCGTTA
ATAAGCCTGCGATATATGAAAGGGGAACCAAATCACCGCTGGCA
GTTATTGTTCCTCTTAAGGGCAACGAAGGAGAAATGTTGTGGTTC
AATAGTGAAGTGATGGCCTCAAGAATTTCAAACCTTATTCCAGAG
TAACCTTGCAACAAAGTGTTCACCCTAACAAGCATAGCAGCTCTT
GTTGCCGATTGGGGTAATGTATGGCAAGTTTCCTTTGTATTACCG
AAAATACCGGCGTTAAGGAATCTGATCAGTTCTGTTTGCAAAGCA
GTGCCATTTTAGTTCTTCTATGAGAGGTAGCACCAAAGCCTGTG
GTAACGCCATAGGAATCTGTGCCCTTGTTCATACTTTCCATGACC
CAATCTGATGAAGCCTTAACTCCGGCTCTACTTGTTTCTGCAAGT
TCTACCTTCACTGAACCGCCAACGGTCGAAATAGCAGCTACCTG
TCCTATCGTCAATGTCTCGCCGCCTAGATTTACGACTGGTCTTCT
GTATTCCTCAACCATCTTCTTAACTTCATCCAGATGGCTACCTTTC
ATCTGGTCAGCTGCCAGACCCCAATTCAAAGGATCTGCAAGAGT
TTTTGTCGTTACGGCCACCTTGGTCTTTTCACCACCACCGCATAG
```

-continued

```
CATTGCTTCAATTTGGTCCATTTTAAGCTTTTTGATAGATTTGACT
GTGTTATTTTGCGTGAGGTTATGAGTAGAAAATAATAATTGAGAA
AGGAATATGACAAGAAATATGAAAATAAAGGGAACAAACCCAAAT
CTGATTGCAAGGAGAGTGAAAGAGCCTTGTTTATATATTTTTTTTT
CCTATGTTCAACGAGGACAGCTAGGTTTATGCAAAAATGTGCCAT
CACCATAAGCTGATTCAAATGAGCTAAAAAAAAAATAGTTAGAAA
ATAAGGTGGTGTTGAACGATAGCAAGTAGATCAAGACACCGTCT
AACAGAAAAGGGGCAGCGGACAATATTATGCAATTATGAAGAA
AAGTACTCAAAGGGTCGGAAAAATATTCAAACGATATTTGCATAA
AATCCTCAATTGATTGATTATTCCATAGTAAAATACCGTAACAACA
CAAAATTGTTCTCAAATTCATAAATTATTCATTTTTTCCACGAGCC
TCATCACACGAAAAGTCAGAAGAGCATACATAATCTTTTAAATGC
ATAGGTTATGCATTTTGCAAATGCCACCAGGCAACAAAAATATGC
GTTTAGCGGGCGGAATCGGAAGGAAGCCGGAACCACCAAAAA
CTGGAAGCTACGTTTTTAAGGAAGGTATGGGTGCAGTGTGCTTAT
CTCAAGAAATATTAGTTATGATATAAGGTGTTGAAGTTTAGAGATA
GGTAAATAAACGCGGGGTGTGTTTATTACATGAAGAAGAAGTTAG
TTTCTGCCTTGCTTGTTTATCTTGCACATCACATCAGCGGAACAT
ATGCTCACCCAGTCGCATGGCGCGTACCACGGTGAACAATCCCC
GCTGGCTCATATTTGCCGCCGGTTCCCGTAAATCCTCCGGTACG
CGCCGGGCCGTATACTTACATATAGTAGATGTCAAGCGTAGGCG
CTTCCCCTGCCGGCTGTGAGGGCGCCATAACCAAGGTATCTATA
GACCGCCAATCAGCAAACTACCTCCGTACATTCATGTTGCACCCA
CACATTTATACACCCAGACCGCGACAAATTACCCATAAGGTTGTT
TGTGACGGCGTCGTACAAGAGAACGTGGGAACTTTTTAGGCTCA
CCAAAAAAGAAAGAAAAAATACGAGTTGCTGACAGAAGCCTCAA
GAAAAAAAAATTCTTCTTCGACTATGCTGGAGGCAGAGATGATC
GAGCCGGTAGTTAACTATATATAGCTAAATTGGTTCCATCACCTT
CTTTTCTGGTGTCGCTCCTTCAGTGCTATTTCTGGCTTTTCCTAT
TTTTTTTTTTCCATTTTCTTTCTCTCTTTCTAATATATAAATTCTCT
TGCATTTTCTATTTTTCTCTCATCTATTCTACTTGTTTATTCCCTT
CAAGGTTTTTTTTAAGGAGTACTTGTTTTTAGAATATACGGTCAA
CGAACTATAATTAACTAAACAAGCTTAAAATGATGGATTTTGTTTT
GTTAGAAAAGCTCTTCTTGGTTTGTTCATTGCAACTATAGTAGC
CATCACAATCTCTAAGCTAAGGGGAAAGAAACTTAAGTTGCCTCC
AGGCCCAATCCCTGTCCCAGTGTTTGGTAATTGGTTACAAGTTGG
CGACGACTTAAACCAGAGGAATTTGGTAGAGTATGCTAAAAAGTT
CGGCGACTTATTTCTACTTAGGATGGGTCAAAGAAACTTGGTCGT
GGTTTCATCCCCTGACTTAGCAAAAGACGTACTACATACCCAGG
GTGTCGAGTTCGGAAGTAGAACTAGAAATGTTGTGTTTGATATTT
TCACAGGCAAAGGTCAAGATATGGTTTTTACCGTATACAGCGAGC
```

```
ACTGGAGGAAAATGAGAAGAATAATGACTGTCCCATTCTTTACAA
ACAAAGTGGTTCAACAGTATAGGTTCGGATGGGAGGACGAAGCC
GCTAGAGTAGTCGAGGATGTTAAGGCAAATCCTGAAGCCGCTAC
CAACGGTATTGTGTTGAGGAATAGATTACAACTTTTGATGTACAA
CAATATGTATAGAATAATGTTTGACAGGAGATTTGAATCTGTTGAT
GATCCATTATTCCTAAAACTTAAGGCATTGAATGGCGAGAGATCA
AGGTTAGCTCAATCCTTTGAATACAACTTCGGTGACTTCATTCCT
ATATTGAGGCCATTCTTGAGAGGATATCTTAAGTTGTGTCAGGAA
ATCAAGGACAAAAGGTTAAAGCTATTCAAGGACTACTTCGTCGAC
GAGAGAAAAAGTTGGAGAGTATCAAGAGCGTAGGTAATAACTC
CTTAAAGTGCGCCATAGATCATATTATCGAGGCACAAGAAAAAGG
CGAGATAAACGAGGATAACGTGTTATACATCGTCGAGAATATCAA
CGTGGCTGCCATTGAAACTACACTTTGGTCTATTGAATGGGGTAT
AGCAGAACTAGTGAATAACCCTGAAATCCAGAAAAAATTGAGACA
CGAATTAGACACCGTACTTGGAGCTGGTGTTCAAATTTGTGAACC
AGATGTTCAAAAATTGCCTTATCTACAGGCCGTGATAAAAGAGAC
TTTAAGGTACAGGATGGCAATTCCATTGTTAGTCCCACATATGAA
TCTTCACGAAGCCAAATTGGCCGGCTATGATATCCCTGCAGAGA
GCAAAATTTTGGTAAACGCTTGGTGGTTAGCCAATAATCCAGCAC
ATTGGAACAAACCTGATGAGTTTAGACCAGAAAGATTTTTGGAGG
AAGAATCCAAGGTCGAGGCTAATGGAAACGACTTTAAGTACATC
CCTTTCGGTGTTGGCAGAAGATCTTGCCCAGGTATAATTCTTGCT
TTACCAATCCTTGGAATAGTAATTGGTAGGTTGGTTCAAAACTTC
GAGTTACTTCCACCTCCAGGCCAAAGCAAAATAGATACAGCCGA
AAAAGGTGGACAGTTTTCATTGCAAATCCTAAAGCATTCCACTAT
TGTGTGTAAACCTAGAAGTTCTTAACCGCGGACAAATCGCTCTTA
AATATATACCTAAAGAACATTAAAGCTATATTATAAGCAAAGATAC
GTAAATTTTGCTTATATTATTATACACATATCATATTTCTATATTTTT
AAGATTTGGTTATATAATGTACGTAATGCAAAGGAAATAAATTTTA
TACATTATTGAACAGCGTCCAAGTAACTACATTATGTGCACTAATA
GTTTAGCGTCGTGAAGACTTTATTGTGTCGCGAAAAGTAAAAATT
TTAAAAATTAGAGCACCTTGAACTTGCGAAAAAGGTTCTCATCAA
CTGTTTAAAAGGAGGATATCAGGTCCTATTTCTGACAAACAATAT
ACAAATTTAGTTTCAAAGGCGCGTTGCAAAATGGAATTTCGCCGC
AGCGGCCTGAATGGCTGTACCGCCTGACGCGGATGCGCCACGC
GCCGCATGCCGGTAGAGGTGTGGTCAATAAGAGCGACCTCATG
CTATACCTGAGAAAGCAACCTGACCTACAGGAAAGAGTTACTCAA
GAATAAGAATTTTCGTTTTAAAACCTAAGAGTCACTTTAAAATTTG
TATACACTTATTTTTTTTATAACTTATTTAATAATAAAAATCATAAAT
CATAAGAAATTCGCTTATTTAGAAGTGTCAACAACGTATCTACCAA
```

```
CGATTTGACCCTTTTCCATCTTTTCGTAAATTTCTGGCAAGGTAGA
CAAGCCGACAACCTTGATTGGAGACTTGACCAAACCTCTGGCGA
AGAAGTCCAAAGCTCTAGATCAATTTAGGCCTGCGGCCGCGGTT
ACCAGACATCTTCTTGGTATCTACCTGAAGTCTTGAGCATCTTGA
TTAGCTCTGTTGCTTCATCAGTGGTAATGGATTTACCACGGGATA
AGATGCCAACCAATGCGGTTGACACACCCTTGGCCATACCCTTT
GCATCACCACAGACGTAGATAAATGCACCGTTGTTAATCATTTCA
AATACTTGGTCTTCGTAATCCTTTAATTTATCTTGAACATAAACTTT
TTTGGTGTTTGGCAACCTGGAATGGGCCACGACCATTTCGAACG
AACCATCCAATTTTTTGGCGTATTCTGGCCATTCGTCCTGGTACA
AGAAATCATCAGTGTTACGGGATCCATAAAACAGTATATGCTTAC
CTAGCGAAACGTTGTTACCGCCCTTCTTTTGTGATTCGAGGAACG
CGACACGCTCTCTGATAAACCCACGGAATGGGGCAACACCGGTA
CCTGGACCGATCATGATAACTGGGGTGGAAGGGTTGGAAGGCA
ATCTGAAGTTAGAACGACGAACGTGGACGGGCAATTTGTAATTG
GCGAAAAGTTTACGTGGGCCATTTAAATCGTAGTGAACAGGTAG
GTTAGTTTCGGCAATGTTAACATTGTTTTGAGCCAATTGAATGTTT
CTTAACAAGTTAGTCGTAACACCAACAACTGGAGGAGCATCAGG
CAATTCTGGGTTAGGAAAGTTTTCCACAATGGAGGTGACATGGA
CGGTTTGCTTTTCAGACAGAGAAGAGGAAGAGATAGAGTAGTAA
CGAGGAGTCATTTGGGGAACTGATTCGACCAAGAATTGCATGGG
TACGGTGTCCCATTTGGCGCCATCAGACAAATATTTCAGAGCATC
TGCGATGTTGAAATATTTGGAGGTTATCTCGACGGCGAATTGGTC
CTTGTCTTTCGAAAGCAGAGTCAATTTTTCCTTGACGTCAGCGTT
GGGGGCGAACTGAATCAAAGATGAAAACAATTGTCTGGAGACAG
GTCCTGTAATTTCCAAATAGTGTTTAATAGCAGCGCCAATAGTAG
TTGGCGTTGGGAAGGGCACTTTGACGGTGGGATCCAGGGGCTT
CAAGTCAAAAATGGTTTCAGGGTCCAGGTTGAATATGGATAAGAA
CTGTTCGACCTTTTCCAATGGGTTGGAAGGCCAAACAGCAAGAT
GGTCACCAGTGGAGTACTTGATGTTAGAGCCGGACAAGTCAAAT
TCAGAGTGGATGCAATTACGGTCATTGGAAGAGAACAGTTCGCG
AGATTTCACGATGGGTGCAATATACGGTTGAGACAAATCGAAGG
GACCCAATTGGATGCCGTCTGCGTTGCGGTTCAACTGATGCGAG
GGCAAATAGTGAGCAGAGGGTTCACCAAGCGACATGGAGTCAGT
GATTTCGTTCAACACAGTGTACTGGAATTGAGAGGTGAACTTGGC
TTCCTGTTCGTCCAAATGCAGTTCGTCTTTCAAAACCTCCAGGAT
GGAGTCCTTCCAGGCCATGTAATCTTCGTCTGTAGTTCCTGCACC
ATCATCAGCTTCACCGAGCTTGCCTAGTCTGATAGCGCCCGCAG
CGGAGAGATGCTTCTCGGCCTTCTTGGCGGCACCATTAAAGAAT
TCATAAGTAGAATTTCCCAGACCAAACATATTATACCTCAGGTTC
GATAGTGCACCCGCTTCCGCATTACAAATAAAGTCTTCAAAGTTG
ACCGCCCCGTCGGGGAAGTCTCCTTCACCATATGTAGAGATAAA
AATCGAGACTATGACGGGCACATCGTTTAGCGACTCAAAGTCGT
AGTTCTCAACATCTGCGCACATCACGTTTAGGTTGAACTTGGCCA
CCAGCTCCTTGGAAAACTTTTTGGCGTAATCCTCGGCAGTCCCA
GTCTGCGACGCATACAACACCAAGTAGTTCTTGTTGTTTTCGGTC
ACCACCTGAGCAATGTCTCTGTTGCCCGAGCTGACAGCTGTGAT
ATCTCCGTCATCGGACATCAGCAGTTCCTTGATGGAGTTTCTCTT
TACGTACAGTAGCACGGCAAGCACTAGCCCCGCCAGGACAGTG
AAGTCGGTGTTGTCTATTCCAAACGGCATTTTACTAGTAAGCTTT
GTGATGATGTTTTATTTGTTTTGATTGGTGTCTTGTAAATAGAAAC
AAGAGAGAATAATAAACAAGTTAAGAATAAAAAACCAAAGGATGA
AAAAGAATGAATATGAAAAAGAGTAGAGAATAACTTTGAAAGGGG
ACCATGATATAACTGGAAAAAGAGGTTCTTGGAAATGAAAAGTT
ACCAAAGAGTATTTATAATTCAGAAAAAAAAGCCAACGAATATCG
TTTTGATGGCGAGCCTTTTTTTTTTTTAGGAAGACACTAAAGGTA
CCTAGCATCATATGGGAAGGAAAGGAAATCACTTGGAAGACATC
ACAAGCATTCATTTACCAAGAGAAAAAATATGCATTTTAGCTAAGA
TCCATTGAACAAAGCACTCACTCAACTCAACTGAATGAACGAAAG
AAGAAAGAACAGTAGAAAACACTTTGTGACGGTGCGGAACACAT
TTACGTAGCTATCATGCTGAATTCTACTATGAAAATCTCCCAATCT
GTCGATGGCAAAACGACCCACGTGGCAGAGTTGGGTCAAGTGC
CAGTTTCTGGATTAAGTAACAGATACAGACATCACACGCCATAGA
GGAATCCCGCCGTTGCGAGAGATGGAAAACAATAGAGCCGAAAT
TGTGGAAGCCCGATGTCTGGGTGTACATTTTTTTTTTTCTTTCTT
TCTCTTTCAATAATCTTTCCTTTTTCCATTTAGCTTGCCGGAAAAA
CTTTCGGGTAGCGAAAATCTTTCTGCCGGAAAAATTAGCTATTTT
TTTCTTCCTTATTATTTTTTAGTTCTGAAGTTTGACCAGGGCGCT
ACCCTGACCGTATCACAACCGACGATCCGGGGTCATGGCGGCTA
TTTTTTTTTTTTTTTTTTTTCCTTGTGATTGTTTATTTACATTTGGA
TCAATTCTAACAAAAAAAAAATAAGGGGGGAAAAATAATTCACCT
CTTTTTAATATTGTTTTGTACTGAGATTGATCTCCAAAATAGTAGC
ATTGGCGCGTGCCACCAACAGCCCCGCCAATGGCGCTGCCGAT
ACTCCCGACAATCCCCACCATTGCCTG
                                  SEQ ID NO: 9
ACGCGTCCAGTATCCCAGCAGATACGGGATATCGACATTTCTGC
ACCATTCCGGCGGGTATAGGTTTTATTGATGGCCTCATCCACAC
GCAGCAGCGTCTGTTCATCGTCGTGGCGGCCCATAATAATCTGC
CGGTCAATCAGCCAGCTTTCCTCACCCGGCCCCATCCCCATAC
GCGCATTTCGTAGCGGTCCAGCTGGGAGTCGATACCGGCGTC
AGGTAAGCCACACGGTCAGGAACGGGCGCTGAATAATGCTCTTT
CCGCTCTGCCATCACTTCAGCATCCGGACGTTCGCCAATTTTCG
```

-continued

```
CCTCCCACGTCTCACCGAGCGTGGTGTTTACGAAGGTTTTACGT
TTTCCCGTATCCCCTTTCGTTTTCATCCAGTCTTTGACAATCTGCA
CCCAGGTGGTGAACGGGCTGTACGCTGTCCAGATGTGAAAGGT
CACACTGTCAGGTGGCTCAATCTCTTCACCGGATGACGAAAACC
AGAGAATGCCATCACGGGTCCAGATCCCGGTCTTTTCGCAGATA
TAACGGGCATCAGTAAAGTCCAGCTCCTGCTGGCGGATGACGCA
GGCATTATGCTCGCAGAGATAAAACACGCTGGAGACGCGTTTTC
CCGTCTTTCAGTGCCTTGTTCAGTTCTTCCTGACGGGCGGTATAT
TTCTCCAGCTTGGCCTATGCGGCCCTGTCAGACCAAGTTTACGA
GCTCGCTTGGACTCCTGTTGATAGATCCAGTAATGACCTCAGAAC
TCCATCTGGATTTGTTCAGAACGCTCGGTTGCCGCCGGGCGTTT
TTTATTGGTGAGAATCCAAGCACTAGGGACAGTAAGACGGGTAA
GCCTGTTGATGATACCGCTGCCTTACTGGGTGCATTAGCCAGTC
TGAATGACCTGTCACGGGATAATCCGAAGTGGTCAGACTGGAAA
ATCAGAGGGCAGGAACTGCTGAACAGCAAAAAGTCAGATAGCAC
CACATAGCAGACCCGCCATAAAACGCCCTGAGAAGCCCGTGAC
GGGCTTTTCTTGTATTATGGGTAGTTTCCTTGCATGAATCCATAAA
AGGCGCCTGTAGTGCCATTTACCCCCATTCACTGCCAGAGCCGT
GAGCGCAGCGAACTGAATGTCACGAAAAAGACAGCGACTCAGGT
GCCTGATGGTCGGAGACAAAAGGAATATTCAGCGATTTGCCCGA
GCTTGCGAGGGTGCTACTTAAGCCTTTAGGGTTTTAAGGTCTGTT
TTGTAGAGGAGCAAACAGCGTTTGCGACATCCTTTTGTAATACTG
CGGAACTGACTAAAGTAGTGAGTTATACACAGGGCTGGGATCTA
TTCTTTTTATCTTTTTTTATTCTTTCTTTATTCTATAAATTATAACCA
CTTGAATATAAACAAAAAAAACACACAAAGGTCTAGCGGAATTTA
CAGAGGGTCTAGCAGAATTTACAAGTTTTCCAGCAAAGGTCTAGC
AGAATTTACAGATACCCACAACTCAAAGGAAAAGGACATGTAATT
ATCATTGACTAGCCCATCTCAATTGGTATAGTGATTAAAATCACCT
AGACCAATTGAGATGTATGTCTGAATTAGTTGTTTTCAAAGCAAAT
GAACTAGCGATTAGTCGCTATGACTTAACGGAGCATGAAACCAA
GCTAATTTTATGCTGTGTGGCACTACTCAACCCCACGATTGAAAA
CCCTACAAGGAAAGAACGGACGGTATCGTTCACTTATAACCAATA
CGCTCAGATGATGAACATCAGTAGGGAAAATGCTTATGGTGTATT
AGCTAAAGCAACCAGAGAGCTGATGACGAGAACTGTGGAAATCA
GGAATCCTTTGGTTAAAGGCTTTGAGATTTTCCAGTGGACAAACT
ATGCCAAGTTCTCAAGCGAAAAATTAGAATTAGTTTTTAGTGAAG
AGATATTGCCTTATCTTTTCCAGTTAAAAAAATTCATAAAATATAAT
CTGGAACATGTTAAGTCTTTTGAAAACAAATACTCTATGAGGATTT
ATGAGTGGTTATTAAAAGAACTAACACAAAAGAAAACTCACAAGG
CAAATATAGAGATTAGCCTTGATGAATTTAAGTTCATGTTAATGCT
```

-continued

```
TGAAAATAACTACCATGAGTTTAAAAGGCTTAACCAATGGGTTTT
GAAACCAATAAGTAAAGATTTAAACACTTACAGCAATATGAAATTG
GTGGTTGATAAGCGAGGCCGCCCGACTGATACGTTGATTTTCCA
AGTTGAACTAGATAGACAAATGGATCTCGTAACCGAACTTGAGAA
CAACCAGATAAAAATGAATGGTGACAAAATACCAACAACCATTAC
ATCAGATTCCTACCTACATAACGGACTAAGAAAAACACTACACGA
TGCTTTAACTGCAAAAATTCAGCTCACCAGTTTTGAGGCAAAATTT
TTGAGTGACATGCAAAGTAAGTATGATCTCAATGGTTCGTTCTCA
TGGCTCACGCAAAAACAACGAACCACACTAGAGAACATACTGGC
TAAATACGGAAGGATCTGAGGTTCTTATGGCTCTTGTATCTATCA
GTGAAGCATCAAGACTAACAAACAAAAGTAGAACAACTGTTCACC
GTTACATATCAAAGGGAAAACTGTCCATATGCACAGATGAAAACG
GTGTAAAAAAGATAGATACATCAGAGCTTTTACGAGTTTTTGGTG
CATTCAAAGCTGTTCACCATGAACAGATCGACAATGTAACGCGG
CCGCAGCCAATCAATTCTTGCGGAGAACTGTGAATGCGCAAACC
AACCCTTGGCAGAACATATCCATCGCGTCCGCCATCTCCAGCAG
CCGCACGCGGCGCATCGGGGGGGGGGGGGGGTTTCAATTC
ATCATTTTTTTTTATTCTTTTTTTGATTTCGGTTTCCTTGAAATTT
TTTTGATTCGGTAATCTCCGAACAGAAGGAAGAACGAAGGAAGG
AGCACAGACTTAGATTGGTATATATACGCATATGTAGTGTTGAAG
AAACATGAAATTGCCCAGTATTCTTAACCCAACTGCACAGAACAA
AAACCTGCAGGAAACGAAGATAAATCATGTCGAAAGCTACATATA
AGGAACGTGCTGCTACTCATCCTAGTCCTGTTGCTGCCAAGCTAT
TTAATATCATGCACGAAAAGCAAACAAACTTGTGTGCTTCATTGG
ATGTTCGTACCACCAAGGAATTACTGGAGTTAGTTGAAGCATTAG
GTCCCAAAATTTGTTTACTAAAAACACATGTGGATATCTTGACTGA
TTTTTCCATGGAGGGCACAGTTAAGCCGCTAAAGGCATTATCCG
CCAAGTACAATTTTTTACTCTTCGAAGACAGAAAATTTGCTGACAT
TGGTAATACAGTCAAATTGCAGTACTCTGCGGGTGTATACAGAAT
AGCAGAATGGGCAGACATTACGAATGCACACGGTGTGGTGGGC
CCAGGTATTGTTAGCGGTTTGAAGCAGGCGGCAGAAGAAGTAAC
AAAGGAACCTAGAGGCCTTTTGATGTTAGCAGAATTGTCATGCAA
GGGCTCCCTATCTACTGGAGAATATACTAAGGGTACTGTTGACAT
TGCGAAGAGCGACAAAGATTTTGTTATCGGCTTTATTGCTCAAAG
AGACATGGGTGGAAGAGATGAAGGTTACGATTGGTTGATTATGA
CACCCGGTGTGGGTTTAGATGACAAGGGAGACGCATTGGGTCAA
CAGTATAGAACCGTGGATGATGTGGTCTCTACAGGATCTGACATT
ATTATTGTTGGAAGAGGACTATTTGCAAAGGGAAGGGATGCTAA
GGTAGAGGGTGAACGTTACAGAAAAGCAGGCTGGGAAGCATATT
TGAGAAGATGCGGCCAGCAAAACTAAAAAACTGTATTATAAGTAA
ATGCATGTATACTAAACTCACAAATTAGAGCTTCAATTTAATTATA
```

-continued

TCAGTTATTACCCGGCCGGGAATCTCGGTCGTAATGATTTTTATA

ATGACGAAAAAAAAAAAATTGGAAAGAAAACCCCCCCCCCCCCC

CCGCAGCGTTGGGTCCTGGCCACGGGTGCGCATGATCGTGCTC

CTGTCGTTGAGGACCCGGCTAGGCTGGCGGGGTTGCCTTACTG

GTTAGCAGAATGAATCACCGATACGCGAGCGAATGTGGCGGCC

GCACGCGTTCATCGTCCACCTCCGGAGAACAGGCCACCATCACG

CATCTGTGTCTGAATTTCATCACGACGCGCCTTAAGGGCACCAAT

AACTGCCTTAAAAAAATTACGCCCCGCCCTGCCACTCATCGCAGT

ACTGTTGTAATTCATTAAGCATTCTGCCGACATGGAAGCCATCAC

AGACGGCATGATGAACCTGAATCGCCAGCGGCATCAGCACCTTG

TCGCCTTGCGTATAATATTTGCCCATGGTGAAAACGGGGCGAA

GAAGTTGTCCATATTGGCCACGTTTAAATCAAAACTGGTGAAACT

CACCCAGGGATTGGCTGAGACGAAAAACATATTCTCAATAAACC

CTTTAGGGAAATAGGCCAGGTTTTCACCGTAACACGCCACATCTT

GCGAATATATGTGTAGAAACTGCCGGAAATCGTCGTGGTATTCAC

TCCAGAGCGATGAAAACGTTTCAGTTTGCTCATGGAAAACGGTGT

AACAAGGGTGAACACTATCCCATATCACCAGCTCACCGTCTTTCA

TTGCCATACGGAATTCCGGATGAGCATTCATCAGGCGGGCAAGA

ATGTGAATAAAGGCCGGATAAAACTTGTGCTTATTTTTCTTTACG

GTCTTTAAAAAGGCCGTAATATCCAGCTGAACGGTCTGGTTATAG

GTACATTGAGCAACTGACTGAAATGCCTCAAAATGTTCTTTACGA

TGCCATTGGGATATATCAACGGTGGTATATCCAGTGATTTTTTCT

CCATTTTAGCTTCCTTAGCTCCTGAAAATCTCGATAACTCAAAAAA

TACGCCCGGTAGTGATCTTATTTCATTATGGTGAAAGTTGGAACC

TCTTACGTGCCGATCAACGTCTCATTTTCGCCAAAAGTTGGCCCA

GGGCTTCCCGGTATCAACAGGGACACCAGGATTTATTTATTCTGC

GAAGTGATCTTCCGTCACAGGTATTGGACCACCCTGTGGGTTTAT

AAGCGCGCTGCTGGCGTGTAAGGCGGTGACGGCGAAGGAAGG

GTCCTTTTCATCACGTGCTATAAAAATAATTATAATTTAAATTTTTT

AATATAAATATATAAATTAAAAATAGAAAGTAAAAAAAGAAATTAAA

GAAAAAATAGTTTTGTTTTCCGAAGATGTAAAAGACTCTAGGGG

GATCGCCAACAAATACTACCTTTTATCTTGCTCTTCCTGCTCTCA

GGTATTAATGCCGAATTGTTTCATCTTGTCTGTAGAAGACCAC

ACACGAAAATCCTGTGATTTTACATTTTACTTATCGTTAATCGAAT

GTATATCTATTTAATCTGCTTTTCTTGTCTAATAAATATATATGTAA

AGTACGCTTTTGTTGAAATTTTTAAACCTTTGTTTATTTTTTTT

CTTCATTCCGTAACTCTTCTACCTTCTTTATTTACTTTCTAAAATCC

AAATACAAAACATAAAAATAAATAAACACAGAGTAAATTCCCAAAT

TATTCCATCATTAAAAGATACGAGGCGCGTGTAAGTTACAGGCAA

GCGATCCGTCCTAAGAAACCATTATTATCATGACATTAACCTATAA

AAATAGGCGTATCACGAGGCCCTTTCGTCTCGCGCGTTTCGGTG

ATGACGGTGAAAACCTCTGACACATGCAGCTCCCGGAGACGGTC

ACAGCTTGTCTGTAAGCGGATGCCGGGAGCAGACAAGCCCGTC

AGGGCGCGTCAGCGGGTGTTGGCGGGTGTCGGGGCTGGCTTAA

CTATGCGGCATCAGAGCAGATTGTACTGAGAGTGCACCACGGCG

CGTGGCACCCTTGCGGGCCATGTCATACACCGCCTTCAGAGCAG

CCGGACCTATCTGCCCGTTACGCGCCAGCTTGCAAATTAAAGCC

TTCGAGCGTCCCAAAACCTTCTCAAGCAAGGTTTTCAGTATAATG

TTACATGCGTACACGCGTCTGTACAGAAAAAAAGAAAAATTTGA

AATATAAATAACGTTCTTAATACTAACATAACTATAAAAAAATAAAT

AGGGACCTAGACTTCAGGTTGTCTAACTCCTTCCTTTTCGGTTAG

AGCGGATGTGGGGGAGGGCGTGAATGTAAGCGTGACATAACT

AATTACATGATATCGACAAAGGAAAAGGGGGACGGATCTCCGAG

GCCTCGGACCCGTCGGGCCGCCGTCGGACGTGCCGCGGTCAT

GCAGAAGCTGCAGTAGGGACAGGGACTGGGACACTATGCAACA

CTAAGGTTTCTACAGTCAAGCCTGGTCCGAATCCAAACAACACTC

CCCAATCTTTTCCTTCTCCTGTGGTTGCCAATCCGTCTTTAGCAG

AACTTTTCCTCATGACATCTAACACAAACAACAGAGGCACTAG

ACATATTTCCGTATTCAGATAACACTTCCCTAGAAGCCCTCATTCT

CTTCTTATCCAATCCTACTCTATCTTCAACTCTGTCTAAAATGGCA

GGGCCACCAGGATGTGCAATCCAGAAAATTGAATTCCAGTTATG

AATACCTAAAGGTTCAAAGGCATCCTCCAAAGCCTGTTCAATGTT

CTCTGAAATTAAACCAGGAACATCTTTTAATAAATGTATAGTTAAA

CCAGCTTCTGTTAAATGGCCATCTATGGCACCTTCTGATTCTGGT

AATATAGTCTGAGAAGCTGATACCAACTGGAAAACTGGTTGTTCG

TCTAATTGGTCTGGGTCAGCGCCTATAATTGCAGCAGCGGCACC

ATCACCGAACAAGGCATGACCTACCAAGGAATCTAAATGACTCTT

GCATGGACCTCTGAAGGCCATAGCAGTTATCTCGGAACAAACGA

CTAACACTCTGGCACCTCTATTATTTTCAGCGATATCTTTTGCCAA

TCTCAAAACAGTTGCACCACCAAAGCAACCTTGTTGGTACATCAT

TAACCTTTGACTGTAGGGGACAAACCTAACAACTTTGTTAATTG

GTAATCAGCACCGGGCATGTCAACGCCGGATGTTGTGCAAAATA

CCAAATGAGTAATCTTAGACAAGGGTTGGCCCCACTCCTTAATGG

CCTTCTCAGCTGCACCTTGGCCCAATTTGGGAACTTCAACTAATG

CGATGGCGTGTCTAGCATCCAATGAGGTCTCCATGTGTGCACAG

ATCTTTGGGTTCTTGATCAATATTTCCTCGGTCAAGTGCATGTGT

CTCTTTCTAATCATTGATTTGTCACACATTCTTTGAAACTTCTCCTT

TAAATCTGCCAAGTGCTCACTTTTAGTAACCCTAAAATAATAATCT

GGATAGGTAGCTTGATAAACACAATTAGCTGGAACGGCAGTACC

GATTGCTAAAACTGTAGCTAAACCTTCAGCCCTCTGTGCCATTCT

AACTTCTTTCAATCTTACTGCAGCCATTTTAAGCTTTTTGTTTGTTT

-continued

```
ATGTGTGTTTATTCGAAACTAAGTTCTTGGTGTTTTAAAACTAAAA
AAAAGACTAACTATAAAAGTAGAATTTAAGAAGTTTAAGAAATAGA
TTTACAGAATTACAATCAATACCTACCGTCTTTATATACTTATTAGT
CAAGTAGGGGAATAATTTCAGGGAACTGGTTTCAACCTTTTTTTT
CAGCTTTTTCCAAATCAGAGAGAGCAGAAGGTAATAGAAGGTGT
AAGAAAATGAGATAGATACATGCGTGGGTCAATTGCCTTGTGTCA
TCATTTACTCCAGGCAGGTTGCATCACTCCATTGAGGTTGTGTCC
GTTTTTTGCCTGTTTGTGCCCCTGTTCTCTGTAGTTGCGCTAAGA
GAATGGACCTATGAACTGATGGTTGGTGAAGAAAACAATATTTTG
GTGCTGGGATTCTTTTTTTTCTGGATGCCAGCTTAAAAAGCGGG
CTCCATTATATTTAGTGGATGCCAGGAATAAACTGTTCACCCAGA
CACCTACGATGTTATATATTCTGTGTAACCCGCCCCCTATTTTGG
GCATGTACGGGTTACAGCAGAATTAAAAGGCTAATTTTTTGACTA
AATAAAGTTAGGAAAATCACTACTATTAATTATTTACGTATTCTTTG
AAATGGCAGTATTGATAATGATAAACTCGAACTGGGCGCGTCGT
GCCGTCGTTGTTAATCACCACATGGTTATTCTGCTCAAACGTCCC
GGACGCCTGCGAACGCGCCGAAGGAAAATGAGAAATATCGAGG
GAGACGATTCAGAGGAGCAGGACAAACTATAACCGACTGTTTGT
TGGAGGATGCCGTACATAACGAACACTGCTGAAGCTACCATGTC
TACAGTTTAGAGGAATGGGTACAACTCACAGGCGAGGGATGGTG
TTCACTCGTGCTAGCAAACGCGGTGGGAGCAAAAAGTAGAATAT
TATCTTTTATTCGTGAAACTTCGAACACTGTCATCTAAAGATGCTA
TATACTAATATAGGCATACTTGATAATGAAAACTATAAATCGTAAA
GACATAAGAGATCCGCGGATCCCCGGGTCGAGCCTGAACGGCC
TCGAGGCCTGAACGGCCTCGACGAATTCATTATTTGTAGAGCTC
ATCCATGCCATGTGTAATCCCAGCAGCAGTTACAAACTCAAGAAG
GACCATGTGGTCACGCTTTTCGTTGGGATCTTTCGAAAGGGCAG
ATTGTGTCGACAGGTAATGGTTGTCTGGTAAAAGGACAGGGCCA
TCGCCAATTGGAGTATTTTGTTGATAATGGTCTGCTAGTTGAACG
GATCCATCTTCAATGTTGTGGCGAATTTTGAAGTTAGCTTTGATTC
CATTCTTTTGTTGTCTGCCGTGATGTATACATTGTGTGAGTTATA
GTTGTACTCGAGTTTGTGTCCGAGAATGTTTCCATCTTCTTTAAAA
TCAATACCTTTTAACTCGATACGATTAACAAGGGTATCACCTTCAA
ACTTGACTTCAGCACGCGTCTTGTAGTTCCCGTCATCTTTGAAAG
ATATAGTGCGTTCCTGTACATAACCTTCGGGCATGGCACTCTTGA
AAAAGTCATGCCGTTTCATATGATCCGGATAACGGGAAAAGCATT
GAACACCATAAGAGAAAGTAGTGACAAGTGTTGGCCATGGAACA
GGTAGTTTTCCAGTAGTGCAAATAAATTTAAGGGTAAGCTGGCCC
TGCAGGCCAAGCTTTGTTTTATATTTGTTGTAAAAAGTAGATAATT
ACTTCCTTGATGATCTGTAAAAAAGAGAAAAAGAAAGCATCTAAG
```

-continued

```
AACTTGAAAAACTACGAATTAGAAAAGACCAAATATGTATTTCTTG
CATTGACCAATTTATGCAAGTTTATATATATGTAAATGTAAGTTTC
ACGAGGTTCTACTAAACTAAACCACCCCCTTGGTTAGAAGAAAAG
AGTGTGTGAGAACAGGCTGTTGTTGTCACACGATTCGGACAATT
CTGTTTGAAAGAGAGAGAGTAACAGTACGATCGAACGAACTTTG
CTCTGGAGATCACAGTGGGCATCATAGCATGTGGTACTAAACCC
TTTCCCGCCATTCCAGAACCTTCGATTGCTTGTTACAAAACCTGT
GAGCCGTCGCTAGGACCTTGTTGTGTGACGAAATTGGAAGCTGC
AATCAATAGGAAGACAGGAAGTCGAGCGTGTCTGGGTTTTTCA
GTTTTGTTCTTTTTGCAAACAAATCACGAGCGACGGTAATTTCTTT
CTCGATAAGAGGCCACGTGCTTTATGAGGGTAACATCAATTCAAG
AAGGAGGGAAACACTTCCTTTTTCTGGCCCTGATAATAGTATGAG
GGTGAAGCCAAAATAAAGGATTCGCGCCCAAATCGGCATCTTTA
AATGCAGGTATGCGATAGTTCCTCACTCTTTCCTTACTCACGAGT
AATTCTTGCAAATGCCTATTATGCAGATGTTATAATATCTGTGCGT
GGCGCGTCCGGCTGTCTGCCATGCTGCCCGGTGTACCGACATA
ACCGCCGGTGGCATAGCCGCGCATACGCGCCATTTCCTTCCATC
TTGTGATTCATGCTATCCATCTTTTTTGAGTATCCAATTAACGAAG
ACGTTACCAGCTGATTGAAGGTTCTCAAAGTGACTGTACTCCATG
TTTTCTTATCATCCATGTAGTTATTTTTCAAACTGCAAATTCAAGAA
AAAGCCACGCGTGTGCACCTTTTTTTTCCCCTTCCAGTGCATTAT
GCAATAGACAGCACGAGTCTTTGAAAAAGTAACTTATAAAACTGT
ATCAATTTTTAAACCTAAATAGATTCATAAACTATTCGTTAATATAA
AGTGTTCTAAACTATGATGAAAAAATAAGCAGAAAAGACTAATAAT
TCTTAGTTAAAAGCACTCCCTAGTTCATTAATCCATTTGCTAGTCT
TGCTCTTAGATCCTTCCTCAATATCTTCCCTGATGGAGCTTTAGG
AATAGAGTCAGTGAAGAACACTTTGTTGATTCTCTTATAAAACACA
ACCTGTTTTGACACGAATTGCTTGATTTCATCTTCGGATATATTTG
AATCTTTCGATCTCACCACAAACGCAACAGGAACCTCACCAGCAT
CTTCTTCCTTCATGGCGACGACAGCAACATCATTGATTTCTGGAT
GACCTATGAGGAGAGACTCTAGCTCAGCTGGAGCCACTTGAAAT
CCTTTGTACTTGATGAGTTCTTTCAATCTATCCACAATGAAAAGCT
CGTCGTCATCATCGATAAATCCGACGTCTCCAGTGTGAAGCCAA
CCATCTTTATCGATCGTCGATGCCGTGGCCAAGGGGTCATTGAG
ATAGCCTTTCATGATTTGGTTGCCACGGATGCATATTTCGCCGGG
TTTGTTCCTAGGCAAAGAATCTCCTGTGTCTGGATCAAGTATCTT
CATCTCGGCGTTCCTCACCACCGTACCACATGCTCCTGACTTCA
CTGGAAACGGCTCTTTAGCAAACCCTAACGACATTGCTAGCACC
GGACCTGCTTCTGTCATCCCATAGCCCTGACCAAGCTTGGCGTT
AGGAAACTTAGCACTAATAGCATCTTCAAGCTCCTTACCAAGAGG
AGCTGCTCCAGACTTAACCATCCTAACCGAGCTCAGATCATACTT
```

-continued

CTCCGTCTCCGGCGACTTCGCGATAGCTAAAACGATCGGTGGCA

CGACCATAGCCACCGTGACTTTACACCTTTGTATCTGCTCTAACA

AGAGAGTGATTTCGAACTTAGGCATTATCAAGATCGTGGCACCAA

CTCTGAGACTACAGAGCATGATGGAGTTGAGAGCGTATATATGG

AACATAGGCAAGACACAGAGGATCACGTCGTCTCTGTTGAAGTA

AAGATTCGGATTCTCGCCGTCGACTTGCTGCGCCACGCTCGTGA

CTAGACCTTTGTGTGTTAGCATCACTCCTTTGGGGAGACCCGTC

GTGCCGGATGAGAAAGGAAGCGCCACGACGTCTTCTGGCGAAA

TCTTCTCCGGTATTGAGTCCACTCGTGGTTCTTCGGACTGAGTTA

ACTCGGAGAAACGGAGGCAGTTTTCGGGGATGGCGTCGGAGTC

GGTGGTGACGATCAAAACGCCGTCGTTTTGGAGGTTCTTGATTTT

ATCGACGTAACGGGATTGAGTGACGATGAGTTTCGCCGCGGAG

GCTTTGGCTTGTTTAGAAATCTCCGCCGGAGTGAAGAACGGGTT

CGCGGAGGTGGTGATTGCGCCGATGAAGGAGGCGGCAAGGAAA

GTGAGGACTACTTCAGGAGAGTTCGGGAGGAGGATCATTACAAC

GTCGTGTTGCTTCACGCCGAGGTTATGAAGACCGGCGGCGAGTT

TCCGAGATGTTACGTGGACATCGGCGTAGGTGTATACTTCGCCG

GTGGGACCGTTGATCAAGCATGGCTTAGCGGCGAACTCTGAGAT

ATTTTCGAAGATGTAGTCGTGGAGTGGGAGGTGGTTAGGGATGT

ATATATCAGGCAATCTCGATCGGAAAATGACGTCATTACTACACT

GTTTCTGATCATTCTGATCATTGACTATCACATCTTGTGTCGTCAT tttAGCTTTTTGTAATTAAAACTTAGATTAGATTGCTATGCTTTCTTT

CTAATGAGCAAGAAGTAAAAAAAGTTGTAATAGAACAAGAAAAAT

GAAACTGAAACTTGAGAAATTGAAGACCGTTTATTAACTTAAATAT

CAATGGGAGGTCATCGAAAGAGAAAAAAATCAAAAAAAAAATTT

TCAAGAAAAGAAACGTGATAAAAATTTTTATTGCCTTTTTCGACG

AAGAAAAAGAAACGAGGCGGTCTCTTTTTTCTTTTCCAAACCTTTA

GTACGGGTAATTAACGACACCCTAGAGGAAGAAAGAGGGGAAAT

TTAGTATGCTGTGCTTGGGTGTTTTGAAGTGGTACGGCGATGCG

CGGAGTCCGAGAAAATCTGGAAGAGTAAAAAAGGAGTAGAAACA

TTTTGAAGCTAGGCGCGTCAGCCGGTAAAGATTCCCCACGCCAA

TCCGGCTGGTTGCCTCCTTCGTGAAGACAAACTCACGCGCCTCC

AAAATGAGCTATCAAAAACGATAGATCGATTAGGATGACTTTGAA

ATGACTCCGCAGTGGACTGGCCGTTAATTTCAAGCGTGAGTAAA

ATAGTGCATGACAAAAGATGAGCTAGGCTTTTGTAAAAATATCTT

ACGTTGTAAAATTTTAGAAATCATTATTTCCTTCATATCATTTTGTC

ATTGACCTTCAGAAGAAAAGAGCCGACCAATAATATAAATAAATA

AATAAAAATAATATTCCATTATTTCTAAACAGATTCAATACTCATTA

AAAAACTATATCAATTAATTTGAATTAACCGCGGTTAGCAGATTGG

AATAGGTGCACCATTCCACTCTTTCAAGCAATCCATAAGTGGATC

-continued

TATCAACTTTCCCTCGCACATAGCTGTGAATACCTTGTCAAATTCT

TCACCTGGGCTAACGACTTTTTCACCAGTTAGTAATTTGGTTCCC

AACTCTTCTCTAACGAATCTGTACAAAGGGTACGACCTACACTCT

TTGATTCTATTTGGTATAGGGGCAGTACCATTTCCGTATGCGGCT

CTAGCAGCTTCGACTTCCTTTGGTAAAACTGCCTTCAGTTCTTCT

TCAAAGGCACCTATCTTTTGGAATATTGAAGTAACGGCATTTTTCT

CAGTTTCACCATTGGATAAAGCGTGATCTACAATAACTTGTCTCA

ATCTCTGCATCAATGGATAAGTAGCGCTACATGGATCGTCAACGT

AAGTAAATACTTGTTCTCTATCTACAACTTTTAATAAATCTTTTTCA

CAGAATCTTGATGGGTGCAATTCACCATTGATACCTGTAGTTAGA

ACCTTTTTTGCAACCTGTGATACGGTATTTTTCACTGTCTGTCTCA

AATTCTCTTCCAAGTGTCTcAAATCTACGGCCTGGCATATACCCA

CTAAAAATGTTGTGGACATTAATTTAAGGATATCAACGGCCTCGC

TTGTTTTTCTTGATGAAATCAGGCCCAAAGAATTAACATCCTGATT

GTGTTGTTCGGCTGATTGTACATGAGAGGTTACTGGGTTGGCTA

GATATTGCAGCTCTGAACAATAGCTTGCCATTGCTATCTCAGCAC

CTTTGAAACCATAATCAAGACTAGGGTTAGAAGATGCGGTCAGAT

TCGAAGGCAAACCGTTATTGTAGAAGTCATTGACCAATTCAGAAA

ATTGGGCAAACATTAATTTGCCAATTGCGGCTATGGCAAGCCTG

GTATTATCCATACTGACTCCTATGGGTGTACCCTGGAAATTGCCT

CCATGTATTGCCTTATTCCTGACACATCAATAAGTGGATTATCG

TTAACAGAGTTGATCTCTCTTTCTATAGACTTTGTAGCTTGTCTAA

TTACTTCAATTTGAGGGCAAGCCATTGTGGGGATGTCCTTAAAG

CATATCTATCTTGTTTGGGTTTTTGCAAAGGGTCCATTTCATGAAC

CTTCTGGGCTAACTTCATGTAGCTAGAGCCGTCCAAAATGTGCTC

CATGATAGCTGCTGCTTCAATTTGTCCTGGGTGATGTTTTAACCT

GTGGGTCAAGTGATCAGTAAACTCAGGTTTTCCACTCATGACTTC

GGCAAAAATTGCGGACAAAACTTCGGCCAAAACTGCTTGTACGTT

AGCTTCAAACAACACCATGGATGCCATACCGCTGCCGACAGCGG

TGCCATTCACCAGGGCTAAACCTTCCTTGGGTTGcAAATCAAAGA

AACCAGTTGAAATACCAGCTTTCTCAAATGCTTCCTTAGCGGTTA

AGGATTCTCCGTCTGGACCAGTGGCCTTTGAATTAGGTCTTCCC

GTTAATAAGCCTGCGATATATGAAAGGGGAACCAAATCACCGCT

GGCAGTTATTGTTCCTCTTAAGGGCAACGAAGGAGAAATGTTGT

GGTTCAATAGTGAAGTGATGGCCTCAAGAATTTCAAACCTTATTC

CAGAGTAACCTTGCAACAAAGTGTTCACCCTAACAAGCATAGCA

GCTCTTGTTGCCGATTGGGGTAATGTATGGCAAGTTCCTTTGTA

TTACCGAAAATACCGGCGTTAAGGAATCTGATCAGTTCTGTTTGC

AAAGCAGTGCCATTTTTAGTTCTTCTATGAGAGGTAGCACCAAAG

CCTGTGGTAACGCCATAGGAATCTGTGCCCTTGTTCATACTTTCC

ATGACCCAATCTGATGAAGCCTTAACTCCGGCTCTACTTGTTTCT

-continued

GCAAGTTCTACCTTCACTGAACCGCCAACGGTCGAAATAGCAGC
TACCTGTCCTATCGTCAATGTCTCGCCGCCTAGATTTACGACTGG
TCTTCTGTATTCCTCAACCATCTTCTTAACTTCATCCAGATGGCTA
CCTTTCATCTGGTCAGCTGCCAGACCCCAATTCAAAGGATCTGCA
AGAGTTTTTGTCGTTACGGCCACCTTGGTCTTTTCACCACCACCG
CATAGCATTGCTTCAATTTGGTCCATTTTAAGCTTTTTGATAGATT
TGACTGTGTTATTTTGCGTGAGGTTATGAGTAGAAAATAATAATTG
AGAAAGGAATATGACAAGAAATATGAAAATAAAGGGAACAAACCC
AAATCTGATTGCAAGGAGAGTGAAAGAGCCTTGTTTATATATTTTT
TTTTCCTATGTTCAACGAGGACAGCTAGGTTTATGCAAAAATGTG
CCATCACCATAAGCTGATTCAAATGAGCTAAAAAAAAAATAGTTA
GAAAATAAGGTGGTGTTGAACGATAGCAAGTAGATCAAGACACC
GTCTAACAGAAAAGGGGCAGCGGACAATATTATGCAATTATGAA
GAAAAGTACTCAAAGGGTCGGAAAAATATTCAAACGATATTTGCA
TAAAATCCTCAATTGATTGATTATTCCATAGTAAAATACCGTAACA
ACACAAAATTGTTCTCAAATTCATAAATTATTCATTTTTTCCACGA
GCCTCATCACACGAAAAGTCAGAAGAGCATACATAATCTTTTAAA
TGCATAGGTTATGCATTTTGCAAATGCCACCAGGCAACAAAAATA
TGCGTTTAGCGGGCGGAATCGGGAAGGAAGCCGGAACCACCAA
AAACTGGAAGCTACGTTTTTAAGGAAGGTATGGGTGCAGTGTGC
TTATCTCAAGAAATATTAGTTATGATATAAGGTGTTGAAGTTTAGA
GATAGGTAAATAAACGCGGGGTGTGTTTATTACATGAAGAAGAA
GTTAGTTTCTGCCTTGCTTGTTTATCTTGCACATCACATCAGCGG
AACATATGCTCACCCAGTCGCATGGCGCGTACCACGGTGAACAA
TCCCCGCTGGCTCATATTTGCCGCCGGTTCCCGTAAATCCTCCG
GTACGCGCCGGGCCGTATACTTACATATAGTAGATGTCAAGCGT
AGGCGCTTCCCCTGCCGGCTGTGAGGGCGCCATAACCAAGGTA
TCTATAGACCGCCAATCAGCAAACTACCTCCGTACATTCATGTTG
CACCCACACATTTATACACCCAGACCGCGACAAATTACCCATAAG
GTTGTTTGTGACGGCGTCGTACAAGAGAACGTGGGAACTTTTTA
GGCTCACCAAAAAGAAAGAAAAAATACGAGTTGCTGACAGAAG
CCTCAAGAAAAAAAATTCTTCTTCGACTATGCTGGAGGCAGAG
ATGATCGAGCCGGTAGTTAACTATATATAGCTAAATTGGTTCCAT
CACCTTCTTTTCTGGTGTCGCTCCTTCTAGTGCTATTTCTGGCTTT
TCCTATTTTTTTTTTCCATTTTTCTTTCTCTTTCTAATATATAAA
TTCTCTTGCATTTTCTATTTTTCTCTATCTATTCTACTTGTTTATT
CCCTTCAAGGTTTTTTTTAAGGAGTACTTGTTTTTAGAATATACG
GTCAACGAACTATAATTAACTAAACAAGCTTAAAATGATGGATTTT
GTTTTGTTAGAAAAAGCTCTTCTTGGTTTGTTCATTGCAACTATAG
TAGCCATCACAATCTCTAAGCTAAGGGGAAAGAAACTTAAGTTGC

-continued

CTCCAGGCCCAATCCCTGTCCCAGTGTTTGGTAATTGGTTACAAG
TTGGCGACGACTTAAACCAGAGGAATTTGGTAGAGTATGCTAAAA
AGTTCGGCGACTTATTTCTACTTAGGATGGGTCAAAGAAACTTGG
TCGTGGTTTCATCCCCTGACTTAGCAAAAGACGTACTACATACCC
AGGGTGTCGAGTTCGGAAGTAGAACTAGAAATGTTGTGTTTGATA
TTTTCACAGGCAAAGGTCAAGATATGGTTTTTACCGTATACAGCG
AGCACTGGAGGAAAATGAGAAGAATAATGACTGTCCCATTCTTTA
CAAACAAAGTGGTTCAACAGTATAGGTTCGGATGGGAGGACGAA
GCCGCTAGAGTAGTCGAGGATGTTAAGGCAAATCCTGAAGCCGC
TACCAACGGTATTGTGTTGAGGAATAGATTACAACTTTTGATGTA
CAACAATATGTATAGAATAATGTTTGACAGGAGATTTGAATCTGTT
GATGATCCATTATTCCTAAAACTTAAGGCATTGAATGGCGAGAGA
TCAAGGTTAGCTCAATCCTTTGAATACAACTTCGGTGACTTCATT
CCTATATTGAGGCCATTCTTGAGAGGATATCTTAAGTTGTGTCAG
GAAATCAAGGACAAAAGGTTAAAGCTATTCAAGGACTACTTCGTC
GACGAGAGAAAAAGTTGGAGAGTATCAAGAGCGTAGGTAATAA
CTCCTTAAAGTGCGCCATAGATCATATTATCGAGGCACAAGAAAA
AGGCGAGATAAACGAGGATAACGTGTTATACATCGTCGAGAATA
TCAACGTGGCTGCCATTGAAACTACACTTTGGTCTATTGAATGGG
GTATAGCAGAACTAGTGAATAACCCTGAAATCCAGAAAAATTGA
GACACGAATTAGACACCGTACTTGGAGCTGGTGTTCAAATTTGTG
AACCAGATGTTCAAAAATTGCCTTATCTACAGGCCGTGATAAAAG
AGACTTTAAGGTACAGGATGGCAATTCCATTGTTAGTCCCACATA
TGAATCTTCACGAAGCCAAATTGGCCGGCTATGATATCCCTGCA
GAGAGCAAAATTTTGGTAAACGCTTGGTGGTTAGCCAATAATCCA
GCACATTGGAACAAACCTGATGAGTTTAGACCAGAAAGATTTTTG
GAGGAAGAATCCAAGGTCGAGGCTAATGGAAACGACTTTAAGTA
CATCCCTTTCGGTGTTGGCAGAAGATCTTGCCCAGGTATAATTCT
TGCTTTACCAATCCTTGGAATAGTAATTGGTAGGTTGGTTCAAAA
CTTCGAGTTACTTCCACCTCCAGGCCAAAGCAAAATAGATACAGC
CGAAAAGGTGGACAGTTTTCATTGCAAATCCTAAAGCATTCCAC
TATTGTGTGTAAACCTAGAAGTTCTTAACCGCGGACAAATCGCTC
TTAAATATATACCTAAAGAACATTAAAGCTATATTATAAGCAAAGA
TACGTAAATTTTGCTTATATTATTATACACATATCATATTTCTATAT
TTTTAAGATTTGGTTATATAATGTACGTAATGCAAAGGAAATAAAT
TTTATACATTATTGAACAGCGTCCAAGTAACTACATTATGTGCACT
AATAGTTTAGCGTCGTGAAGACTTTATTGTGTCGCGAAAAGTAAA
AATTTTAAAAATTAGAGCACCTTGAACTTGCGAAAAAGGTTCTCAT
CAACTGTTTAAAAGGAGGATATCAGGTCCTATTTCTGACAAACAA
TATACAAATTTAGTTTCAAAGGCGCGTTGCAAAATGGAATTTCGC
CGCAGCGGCCTGAATGGCTGTACCGCCTGACGCGGATGCGCCA

```
CGCGCCGCATGCCGGTAGAGGTGTGGTCAATAAGAGCGACCTC
ATGCTATACCTGAGAAAGCAACCTGACCTACAGGAAAGAGTTACT
CAAGAATAAGAATTTTCGTTTTAAAACCTAAGAGTCACTTTAAAAT
TTGTATACACTTATTTTTTTTATAACTTATTTAATAATAAAAATCATA
AATCATAAGAAATTCGCTTATTTAGAAGTGTCAACAACGTATCTAC
CAACGATTTGACCCTTTTCCATCTTTTCGTAAATTTCTGGCAAGGT
AGACAAGCCGACAACCTTGATTGGAGACTTGACCAAACCTCTGG
CGAAGAAGTCCAAAGCTCTAGATCAATTTAGGCCTGCGGCCGCG
GTTACCAGACATCTTCTTGGTATCTACCTGAAGTCTTGAGCATCT
TGATTAGCTCTGTTGCTTCATCAGTGGTAATGGATTTACCACGGG
ATAAGATGCCAACCAATGCGGTTGACACACCCTTGGCCATACCC
TTTGCATCACCACAGACGTAGATAAATGCACCGTTGTTAATCATT
TCAAATACTTGGTCTTCGTAATCCTTTAATTTATCTTGAACATAAA
CTTTTTTGGTGTTTGGCAACCTGGAATGGGCCACGACCATTTCGA
ACGAACCATCCAATTTTTTGGCGTATTCTGGCCATTCGTCCTGGT
ACAAGAAATCATCAGTGTTACGGGATCCATAAAACAGTATATGCT
TACCTAGCGAAACGTTGTTACCGCCCTTCTTTTGTGATTCGAGGA
ACGCGACACGCTCTCTGATAAACCCACGGAATGGGGCAACACC
GGTACCTGGACCGATCATGATAACTGGGGTGGAAGGGTTGGAA
GGCAATCTGAAGTTAGAACGACGAACGTGGACGGGCAATTTGTA
ATTGGCGAAAAGTTTACGTGGGCCATTTAAATCGTAGTGAACAGG
TAGGTTAGTTTCGGCAATGTTAACATTGTTTTGAGCCAATTGAAT
GTTTCTTAACAAGTTAGTCGTAACACCAACAACTGGAGGAGCATC
AGGCAATTCTGGGTTAGGAAAGTTTTCCACAATGGAGGTGACAT
GGACGGTTTGCTTTTCAGACAGAGAAGAGGAAGAGATAGAGTAG
TAACGAGGAGTCATTTGGGGAACTGATTCGACCAAGAATTGCAT
GGGTACGGTGTCCCATTTGGCGCCATCAGACAAATATTTCAGAG
CATCTGCGATGTTGAAATATTTGGAGGTTATCTCGACGGCGAATT
GGTCCTTGTCTTTCGAAAGCAGAGTCAATTTTTCCTTGACGTCAG
CGTTGGGGGCGAACTGAATCAAAGATGAAAACAATTGTCTGGAG
ACAGGTCCTGTAATTTCCAAATAGTGTTTAATAGCAGCGCCAATA
GTAGTTGGCGTTGGGAAGGGCACTTTGACGGTGGGATCCAGGG
GCTTCAAGTCAAAAATGGTTTCAGGGTCCAGGTTGAATATGGATA
AGAACTGTTCGACCTTTTCCAATGGGTTGGAAGGCCAAACAGCA
AGATGGTCACCAGTGGAGTACTTGATGTTAGAGCCGGACAAGTC
AAATTCAGAGTGGATGCAATTACGGTCATTGGAAGAGAACAGTTC
GCGAGATTTCACGATGGGTGCAATATACGGTTGAGACAAATCGA
AGGGACCCAATTGGATGCCGTCTGCGTTGCGGTTCAACTGATGC
GAGGGCAAATAGTGAGCAGAGGGTTCACCAAGCGACATGGAGT
CAGTGATTTCGTTCAACACAGTGTACTGGAATTGAGAGGTGAACT
TGGCTTCCTGTTCGTCCAAATGCAGTTCGTCTTTCAAAACCTCCA
GGATGGAGTCCTTCCAGGCCATGTAATCTTCGTCTGTAGTTCCTG
CACCATCATCAGCTTCACCGAGCTTGCCTAGTCTGATAGCGCCC
GCAGCGGAGAGATGCTTCTCGGCCTTCTTGGCGGCACCATTAAA
GAATTCATAAGTAGAATTTCCCAGACCAAACATATTATACCTCAG
GTTCGATAGTGCACCCGCTTCCGCATTACAAATAAAGTCTTCAAA
GTTGACCGCCCCGTCGGGGAAGTCTCCTTCACCATATGTAGAGA
TAAAAATCGAGACTATGACGGGCACATCGTTTAGCGACTCAAAGT
CGTAGTTCTCAACATCTGCGCACATCACGTTTAGGTTGAACTTGG
CCACCAGCTCCTTGGAAAACTTTTTGGCGTAATCCTCGGCAGTC
CCAGTCTGCGACGCATACAACACCAAGTAGTTCTTGTTGTTTTCG
GTCACCACCTGAGCAATGTCTCTGTTGCCCGAGCTGACAGCTGT
GATATCTCCGTCATCGGACATCAGCAGTTCCTTGATGGAGTTTCT
CTTTACGTACAGTAGCACGGCAAGCACTAGCCCCGCCAGGACAG
TGAAGTCGGTGTTGTCTATTCCAAACGGCATTTTACTAGTAAGCT
TTGTGATGATGTTTTATTTGTTTTGATTGGTGTCTTGTAAATAGAA
ACAAGAGAATAATAAACAAGTTAAGAATAAAAAACCAAAGGAT
GAAAAGAATGAATATGAAAAGAGTAGAGAATAACTTTGAAAGG
GGACCATGATATAACTGGAAAAAGAGGTTCTTGGAAATGAAAAG
TTACCAAAGAGTATTTATAATTCAGAAAAAAAGCCAACGAATATC
GTTTTGATGGCGAGCCTTTTTTTTTTTAGGAAGACACTAAAGGT
ACCTAGCATCATATGGGAAGGAAAGGAAATCACTTGGAAGACAT
CACAAGCATTCATTTACCAAGAGAAAAAATATGCATTTTAGCTAA
GATCCATTGAACAAAGCACTCACTCAACTCAACTGAATGAACGAA
AGAAGAAAGAACAGTAGAAAACACTTTGTGACGGTGCGGAACAC
ATTTACGTAGCTATCATGCTGAATTCTACTATGAAAATCTCCCAAT
CTGTCGATGGCAAAACGACCCACGTGGCAGAGTTGGGTCAAGTG
CCAGTTTCTGGATTAAGTAACAGATACAGACATCACACGCCATAG
AGGAATCCCGCCGTTGCGAGAGATGGAAAACAATAGAGCCGAAA
TTGTGGAAGCCCGATGTCTGGGTGTACATTTTTTTTTTTCTTTCT
TTCTCTTTCAATAATCTTTCCTTTTTCCATTTAGCTTGCCGGAAAA
ACTTTCGGGTAGCGAAAATCTTTCTGCCGGAAAAATTAGCTATTT
TTTTCTTCCTTATTATTTTTTAGTTCTGAAGTTTGACCAGGGCGC
TACCCTGACCGTATCACAACCGACGATCCGGGGTCATGGCGGCT
ATTTTTTTTTTTTTTTTTTCCTTGTGATTGTTTATTTACATTTGG
ATCAATTCTAACAAAAAAAAAATAAGGGGGGAAAAATAATTCACC
TCTTTTTAATATTGTTTTGTACTGAGATTGATCTCCAAAATAGTAG
CATTGGCGCGTGCCACCAACAGCCCCGCCAATGGCGCTGCCGA
TACTCCCGACAATCCCCACCATTGCCCTG
```

SEQ ID NO: 10

ACGCGCCTCCAACTGGCACCGCTGGCTTGAACAACAATACCAGC
CTTCCAACTTCTGTAAATAACGGCGGTACGCCAGTGCCACCAGT
ACCGTTACCTTTCGGTATACCTCCTTTCCCCATGTTTCCAATGCC
CTTCATGCCTCCAACGGCTACTATCACAAATCCTCATCAAGCTGA
CGCAAGCCCTAAGAAATGAATAACAATACTGACAGTACTAAATAA
TTGCCTACTTGGCTTCACATACGTTGCATACGTCGATATAGATAA
TAATGATAATGACAGCAGGATTATCGTAATACGTAATAGTTGAAA
ATCTCAAAAATGTGTGGGTCATTACGTAAATAATGATAGGAATGG
GATTCTTCTATTTTTCCTTTTTCCATTCTAGCAGCCGTCGGGAAAA
CGTGGCATCCTCTCTTTCGGGCTCAATTGGAGTCACGCTGCCGT
GAGCATCCTCTCTTTCCATATCTAACAACTGAGCACGTAACCAAT
GGAAAAGCATGAGCTTAGCGTTGCTCCAAAAAAGTATTGGATGG
TTAATACCATTTGTCTGTTCTCTTCTGACTTTGACTCCTCAAAAAA
AAAAAATCTACAATCAACAGATCGCTTCAATTACGCCCTCACAAA
AACTTTTTTCCTTCTTCTTCGCCCACGTTAAATTTTATCCCTCATG
TTGTCTAACGGATTTCTGCACTTGATTTATTATAAAAAAGACAAAG
ACATAATACTTCTCTATCAATTTCAGTTATTGTTCTTCCTTGCGTTA
TTCTTCTGTTCTTCTTTTTCTTTTGTCATATATAACCATAACCAAGT
AATACATATTCAAAAAGCTTAAAATGGGTGATGTCATTGTCTTGTA
TGCTTCTCCAGGTATGGGTCATATAGTTTCCATGGTTGAATTGGG
TAAATTCATCGTTCATAGATACGGTCCACACAAGTTCTCTATTACT
ATCTTGTACACCTGTGGTTCCATCGTTGATACTGCTTCTATTCCA
GTTTACATCAGAAGAATCTCCCATTCCCATCCATTCATCTCATTCA
GACAATTCCCAAGAGTTACCAACAACATCACCAGAAACATTTCCG
TTCCAGCTATTACCTTCGACTTCATCAGACAAAATGATCCACATG
TTAGATCCGCCTTGCAAGAAATTTCAAAGTCTGCTACTGTTAGAG
CCTTCATCATTGATTTGTTCTGTACTTCCGCTTTGCCAATCGGTAA
AGAATTCAACATTCCAACCTACTACTTCAGAACTTCTGGTGCTGC
TATTTTGGCTGCTTTCTTGTACTTGCCAAAGATCGATGAACAAACT
AAGACCACCGAATCTTTCAAGGATTTGAGAGATACCGTTTTCGAA
TTTCCAGGTTGGAAATCTCCATTGAAGGCTACTCATATGGTTCAA
TTGGTTTTGGATAGAAACGATCCAGCCTACTCTGATATGATCTAC
TTCTGTTCTCATTTGCCAAAGTCCAACGGTATTATCGTTAACACCT
TCGAAGAATTGGAACCACCATCTGTTTTACAAGCTATTGCTGGTG
GTTTGTGTGTTCCAGATGGTCCAACTCCACCAGTTTATTATGTTG
GTCCATTGATCGAAGAAGAAAAAGAATTGTCCAAGGATGCTGAT
GCTGCCGAAAAAGAAGATTGCTTGTCTTGGTTGGATAAGCAACC
ATCTAGATCCGTTTTGTTCTTGTGTTTTGGTTCCATGGGTTCTTTT
CCAGCTGCTCAATTGAAAGAAATTGCCAATGGTTTGGAAGCCTCT
GGTCAAAGATTTTTGTGGGTTGTTAAGAAGCCACCAGTCGAAGAA

AAATCCAAACAAGTTCATGGTGTTGACGACTTCGATTTGAAAGGT
GTTTTGCCAGAAGGTTTCTTGGAAAGAACTGCTGATAGAGGTATG
GTTGTAAAATCTTGGGCTCCACAAGTTGTCGTCTTGAAGAAAGAA
TCTGTTGGTGGTTTCGTTACTCATTGTGGTTGGAATTCTGTTTTG
GAAGCTGTTGTTGCTGGTGTTCCAATGATTGCTTGGCCATTATAT
GCTGAACAACACATGAATAGAAACGTCTTGGTTACCGATATGGAA
ATCGCTATTGGTGTCGAACAAAGAGATGAAGAAGGTGGTTTTGTT
TCCGGTGAAGAAGTTGAAAGAAGAGTTAGAGAATTGATGGAATC
CGAAGGTGGTAGAGTTTTGAGAGAAAGATGTAAAAAGTTGGGTG
AAATGGCTTCTGCTGCTTTAGGTGAAACTGGTTCTTCTACTAGAA
ACTTGGTCAACTTCGTTTCCTCCATTACCTGACCGCGGATTTAAC
TCCTTAAGTTACTTTAATGATTTAGTTTTTATTATTAATAATTCATG
CTCATGACATCTCATATACACGTTTATAAAACTTAAATAGATTGAA
AATGTATTAAAGATTCCTCAGGGATTCGATTTTTTTGGAAGTTTTT
GTTTTTTTTTTCCTTGAGATGCTGTAGTATTTGGGAACAATTATACA
ATCGAAAGATATATGCTTACATTCGACCGTTTTAGCCGTGATCAT
TATCCTATAGTAACATAACCTGAAGCATAACTGACACTACTATCAT
CAATACTTGTCACATGAGGCGCGTCTTAAGCAGAATTTCTGTCAT
CATGGACAGCACGGAACGGGTGAAGCTGCGCCAGTTCTGACGC
GTCCAGTATCCCAGCAGATACGGGATATCGACATTTCTGCACCAT
TCCGGCGGGTATAGGTTTTATTGATGGCCTCATCCACACGCAGC
AGCGTCTGTTCATCGTCGTGGCGCCCCATAATAATCTGCCGGTC
AATCAGCCAGCTTTCCTCACCCGGCCCCCATCCCCATACGCGCA
TTTCGTAGCGGTCCAGCTGGGAGTCGATACCGGCGGTCAGGTAA
GCCACACGGTCAGGAACGGGCGCTGAATAATGCTCTTTCCGCTC
TGCCATCACTTCAGCATCCGGACGTTCGCCAATTTTCGCCTCCCA
CGTCTCACCGAGCGTGGTGTTTACGAAGGTTTTACGTTTTCCCGT
ATCCCCTTTCGTTTTCATCCAGTCTTTGACAATCTGCACCCAGGT
GGTGAACGGGCTGTACGCTGTCCAGATGTGAAAGGTCACACTGT
CAGGTGGCTCAATCTCTTCACCGGATGACGAAAACCAGAGAATG
CCATCACGGGTCCAGATCCCGGTCTTTTCGCAGATATAACGGGC
ATCAGTAAAGTCCAGCTCCTGCTGGCGGATGACGCAGGCATTAT
GCTCGCAGAGATAAAACACGCTGGAGACGCGTTTTCCCGTCTTT
CAGTGCCTTGTTCAGTTCTTCCTGACGGGCGGTATATTTCTCCAG
CTTGGCCTATGCGCCCTGTCAGACCAAGTTTACGAGCTCGCTT
GGACTCCTGTTGATAGATCCAGTAATGACCTCAGAACTCCATCTG
GATTTGTTCAGAACGCTCGGTTGCCGCCGGGCGTTTTTATTGGT
GAGAATCCAAGCACTAGGGACAGTAAGACGGGTAAGCCTGTTGA
TGATACCGCTGCCTTACTGGGTGCATTAGCCAGTCTGAATGACC
TGTCACGGGATAATCCGAAGTGGTCAGACTGGAAAATCAGAGGG

-continued

```
CAGGAACTGCTGAACAGCAAAAAGTCAGATAGCACCACATAGCA
GACCCGCCATAAAACGCCCTGAGAAGCCCGTGACGGGCTTTTCT
TGTATTATGGGTAGTTTCCTTGCATGAATCCATAAAAGGCGCCTG
TAGTGCCATTTACCCCCATTCACTGCCAGAGCCGTGAGCGCAGC
GAACTGAATGTCACGAAAAAGACAGCGACTCAGGTGCCTGATGG
TCGGAGACAAAAGGAATATTCAGCGATTTGCCCGAGCTTGCGAG
GGTGCTACTTAAGCCTTTAGGGTTTTAAGGTCTGTTTTGTAGAGG
AGCAAACAGCGTTTGCGACATCCTTTTGTAATACTGCGGAACTGA
CTAAAGTAGTGAGTTATACACAGGGCTGGGATCTATTCTTTTTAT
CTTTTTTATTCTTTCTTTATTCTATAAATTATAACCACTTGAATATA
AACAAAAAAAACACACAAAGGTCTAGCGGAATTTACAGAGGGTCT
AGCAGAATTTACAAGTTTTCCAGCAAAGGTCTAGCAGAATTTACA
GATACCCACAACTCAAAGGAAAAGGACATGTAATTATCATTGACT
AGCCCATCTCAATTGGTATAGTGATTAAAATCACCTAGACCAATT
GAGATGTATGTCTGAATTAGTTGTTTTCAAAGCAAATGAACTAGC
GATTAGTCGCTATGACTTAACGGAGCATGAAACCAAGCTAATTTT
ATGCTGTGTGGCACTACTCAACCCCACGATTGAAAACCCTACAA
GGAAAGAACGGACGGTATCGTTCACTTATAACCAATACGCTCAG
ATGATGAACATCAGTAGGGAAAATGCTTATGGTGTATTAGCTAAA
GCAACCAGAGAGCTGATGACGAGAACTGTGGAAATCAGGAATCC
TTTGGTTAAAGGCTTTGAGATTTTCCAGTGGACAAACTATGCCAA
GTTCTCAAGCGAAAAATTAGAATTAGTTTTTAGTGAAGAGATATTG
CCTTATCTTTTCCAGTTAAAAAAATTCATAAAATATAATCTGGAAC
ATGTTAAGTCTTTTGAAAACAAATACTCTATGAGGATTTATGAGTG
GTTATTAAAAGAACTAACACAAAAGAAAACTCACAAGGCAAATAT
AGAGATTAGCCTTGATGAATTTAAGTTCATGTTAATGCTTGAAAAT
AACTACCATGAGTTTAAAAGGCTTAACCAATGGGTTTTGAAACCA
ATAAGTAAAGATTTAAACACTTACAGCAATATGAAATTGGTGGTT
GATAAGCGAGGCCGCCCGACTGATACGTTGATTTTCCAAGTTGA
ACTAGATAGACAAATGGATCTCGTAACCGAACTTGAGAACAACCA
GATAAAAATGAATGGTGACAAAATACCAACAACCATTACATCAGA
TTCCTACCTACATAACGGACTAAGAAAAACACTACACGATGCTTT
AACTGCAAAATTCAGCTCACCAGTTTTGAGGCAAAATTTTTGAG
TGACATGCAAAGTAAGTATGATCTCAATGGTTCGTTCTCATGGCT
CACGCAAAAACAACGAACCACACTAGAGAACATACTGGCTAAATA
CGGAAGGATCTGAGGTTCTTATGGCTCTTGTATCTATCAGTGAAG
CATCAAGACTAACAAACAAAAGTAGAACAACTGTTCACCGTTACA
TATCAAAGGGAAAACTGTCCATATGCACAGATGAAAACGGTGTAA
AAAAGATAGATACATCAGAGCTTTTACGAGTTTTTGGTGCATTCA
AAGCTGTTCACCATGAACAGATCGACAATGTAACGCGGCCGCAG
CCAATCAATTCTTGCGGAGAACTGTGAATGCGCAAACCAACCCTT
```

-continued

```
GGCAGAACATATCCATCGCGTCCGCCATCTCCAGCAGCCGCACG
CGGCGCATCGGGGGGGGGGGGGGGGGTTTCAATTCATCATTTT
TTTTTTATTCTTTTTTTTGATTTCGGTTTCCTTGAAATTTTTTTGATT
CGGTAATCTCCGAACAGAAGGAAGAACGAAGGAAGGAGCACAG
ACTTAGATTGGTATATATACGCATATGTAGTGTTGAAGAAACATG
AAATTGCCCAGTATTCTTAACCCAACTGCACAGAACAAAACCTG
CAGGAAACGAAGATAAATCATGTCGAAAGCTACATATAAGGAAC
GTGCTGCTACTCATCCTAGTCCTGTTGCTGCCAAGCTATTTAATA
TCATGCACGAAAAGCAAACAAACTTGTGTGCTTCATTGGATGTTC
GTACCACCAAGGAATTACTGGAGTTAGTTGAAGCATTAGGTCCCA
AAATTTGTTTACTAAAAACACATGTGGATATCTTGACTGATTTTTC
CATGGAGGGCACAGTTAAGCCGCTAAAGGCATTATCCGCCAAGT
ACAATTTTTTACTCTTCGAAGACAGAAAATTTGCTGACATTGGTAA
TACAGTCAAATTGCAGTACTCTGCGGGTGTATACAGAATAGCAGA
ATGGGCAGACATTACGAATGCACACGGTGTGGTGGGCCCAGGT
ATTGTTAGCGGTTTGAAGCAGGCGGCAGAAGAAGTAACAAAGGA
ACCTAGAGGCCTTTTGATGTTAGCAGAATTGTCATGCAAGGGCTC
CCTATCTACTGGAGAATATACTAAGGGTACTGTTGACATTGCGAA
GAGCGACAAAGATTTTGTTATCGGCTTTATTGCTCAAAGAGACAT
GGGTGGAAGAGATGAAGGTTACGATTGGTTGATTATGACACCCG
GTGTGGGTTTAGATGACAAGGGAGACGCATTGGGTCAACAGTAT
AGAACCGTGGATGATGTGGTCTCTACAGGATCTGACATTATTATT
GTTGGAAGAGGACTATTTGCAAAGGGAAGGGATGCTAAGGTAGA
GGGTGAACGTTACAGAAAAGCAGGCTGGGAAGCATATTTGAGAA
GATGCGGCCAGCAAAACTAAAAAACTGTATTATAAGTAAATGCAT
GTATACTAAACTCACAAATTAGAGCTTCAATTTAATTATATCAGTT
ATTACCCGGCCGGGAATCTCGGTCGTAATGATTTTTATAATGACG
AAAAAAAAAAATTGGAAAGAAAACCCCCCCCCCCCCCCCGCAG
CGTTGGGTCCTGGCCACGGGTGCGCATGATCGTGCTCCTGTCG
TTGAGGACCCGGCTAGGCTGGCGGGGTTGCCTTACTGGTTAGC
AGAATGAATCACCGATACGCGAGCGAATGTGGCGGCCGCACGC
GTTCATCGTCCACCTCCGGAGAACAGGCCACCATCACGCATCTG
TGTCTGAATTTCATCACGACGCGCCTTAAGGGCACCAATAACTGC
CTTAAAAAAATTACGCCCCGCCCTGCCACTCATCGCAGTACTGTT
GTAATTCATTAAGCATTCTGCCGACATGGAAGCCATCACAGACG
GCATGATGAACCTGAATCGCCAGCGGCATCAGCACCTTGTCGCC
TTGCGTATAATATTTGCCCATGGTGAAAACGGGGCGAAGAAGT
TGTCCATATTGGCCACGTTTAAATCAAAACTGGTGAAACTCACCC
AGGGATTGGCTGAGACGAAAAACATATTCTCAATAAACCCTTTAG
GGAAATAGGCCAGGTTTTCACCGTAACACGCCACATCTTGCGAA
```

-continued

```
TATATGTGTAGAAACTGCCGGAAATCGTCGTGGTATTCACTCCAG
AGCGATGAAAACGTTTCAGTTTGCTCATGGAAAACGGTGTAACAA
GGGTGAACACTATCCCATATCACCAGCTCACCGTCTTTCATTGCC
ATACGGAATTCCGGATGAGCATTCATCAGGCGGGCAAGAATGTG
AATAAAGGCCGGATAAAACTTGTGCTTATTTTTCTTTACGGTCTTT
AAAAAGGCCGTAATATCCAGCTGAACGGTCTGGTTATAGGTACAT
TGAGCAACTGACTGAAATGCCTCAAAATGTTCTTTACGATGCCAT
TGGGATATATCAACGGTGGTATATCCAGTGATTTTTTCTCCATTT
TAGCTTCCTTAGCTCCTGAAAATCTCGATAACTCAAAAATACGC
CCGGTAGTGATCTTATTTCATTATGGTGAAAGTTGGAACCTCTTA
CGTGCCGATCAACGTCTCATTTTCGCCAAAAGTTGGCCCAGGGC
TTCCCGGTATCAACAGGGACACCAGGATTTATTTATTCTGCGAAG
TGATCTTCCGTCACAGGTATTGGACCACCCTGTGGGTTTATAAGC
GCGCTGCTGGCGTGTAAGGCGGTGACGGCGAAGGAAGGGTCCT
TTTCATCACGTGCTATAAAAATAATTATAATTTAAATTTTTTAATAT
AAATATATAAATTAAAAATAGAAAGTAAAAAAAGAAATTAAAGAAA
AAATAGTTTTTGTTTTCCGAAGATGTAAAAGACTCTAGGGGATC
GCCAACAAATACTACCTTTTATCTTGCTCTTCCTGCTCTCAGGTAT
TAATGCCGAATTGTTTCATCTTGTCTGTGTAGAAGACCACACACG
AAAATCCTGTGATTTTACATTTTACTTATCGTTAATCGAATGTATAT
CTATTTAATCTGCTTTTCTTGTCTAATAAATATATATGTAAAGTACG
CTTTTTGTTGAAATTTTTTAAACCTTTGTTTATTTTTTTTCTTCATT
CCGTAACTCTTCTACCTTCTTTATTTACTTTCTAAAATCCAAATACA
AAACATAAAAATAAATAAACACAGAGTAAATTCCCAAATTATTCCA
TCATTAAAAGATACGAGGCGCGTGTAAGTTACAGGCAAGCGATC
CGTCCTAAGAAACCATTATTATCATGACATTAACCTATAAAAATAG
GCGTATCACGAGGCCCTTTCGTCTCGCGCGTTTCGGTGATGACG
GTGAAAACCTCTGACACATGCAGCTCCCGGAGACGGTCACAGCT
TGTCTGTAAGCGGATGCCGGGAGCAGACAAGCCCGTCAGGGCG
CGTCAGCGGGTGTTGGCGGGTGTCGGGGCTGGCTTAACTATGC
GGCATCAGAGCAGATTGTACTGAGAGTGCACCACGGCGCGTGG
CACCCTTGCGGGCCATGTCATACACCGCCTTCAGAGCAGCCGGA
CCTATCTGCCCGTTACGCGCCAGCTTGCAAATTAAAGCCTTCGA
GCGTCCCAAAACCTTCTCAAGCAAGGTTTTCAGTATAATGTTACA
TGCGTACACGCGTCTGTACAGAAAAAAAGAAAAATTTGAAATAT
AAATAACGTTCTTAATACTAACATAACTATAAAAAAATAAATAGGG
ACCTAGACTTCAGGTTGTCTAACTCCTTCCTTTTCGGTTAGAGCG
GATGTGGGGGAGGGCGTGAATGTAAGCGTGACATAACTAATTA
CATGATATCGACAAAGGAAAAGGGGACGGATCTCCGAGGCCT
CGGACCCGTCGGGCCGCCGTCGGACGTGCCGCGGTCATGCAG
AAGCTGCAGTAGGGACAGGGACTGGGACACTATGCAACACTAAG
```

-continued

```
GTTTCTACAGTCAAGCCTGGTCCGAATCCAAACAACACTCCCCAA
TCTTTTCCTTCTCCTGTGGTTGCCAATCCGTCTTTAGCAGAACTTT
TCCTCATGACATCTAACACAAACAACACAGAGGCACTAGACATAT
TTCCGTATTCAGATAACACTTCCCTAGAAGCCCTCATTCTCTTCTT
ATCCAATCCTACTCTATCTTCAACTCTGTCTAAAATGGCAGGGCC
ACCAGGATGTGCAATCCAGAAAATTGAATTCCAGTTATGAATACC
TAAAGGTTCAAAGGCATCCTCCAAAGCCTGTTCAATGTTCTCTGA
AATTAAACCAGGAACATCTTTTAATAAATGTATAGTTAAACCAGCT
TCTGTTAAATGGCCATCTATGGCACCTTCTGATTCTGGTAATATA
GTCTGAGAAGCTGATACCAACTGGAAAACTGGTTGTTCGTCTAAT
TGGTCTGGGTCAGCGCCTATAATTGCAGCAGCGGCACCATCACC
GAACAAGGCATGACCTACCAAGGAATCTAAATGACTCTTGCATG
GACCTCTGAAGGCCATAGCAGTTATCTCGGAACAAACGACTAAC
ACTCTGGCACCTCTATTATTTTCAGCGATATCTTTTGCCAATCTCA
AAACAGTTGCACCACCAAAGCAACCTTGTTGGTACATCATTAACC
TTTTGACTGTAGGGGACAAACCTAACAACTTTGTTAATTGGTAAT
CAGCACCGGGCATGTCAACGCCGGATGTTGTGCAAAATACCAAA
TGAGTAATCTTAGACAAGGGTTGGCCCCACTCCTTAATGGCCTTC
TCAGCTGCACCTTGGCCCAATTTGGGAACTTCAACTAATGCGATG
GCGTGTCTAGCATCCAATGAGGTCTCCATGTGTGCACAGATCTTT
GGGTTCTTGATCAATATTTCCTCGGTCAAGTGCATGTGTCTCTTT
CTAATCATTGATTTGTCACACATTCTTTGAAACTTCTCCTTTAAAT
CTGCCAAGTGCTCACTTTTAGTAACCCTAAAATAATAATCTGGATA
GGTAGCTTGATAAACACAATTAGCTGGAACGGCAGTACCGATTG
CTAAAACTGTAGCTAAACCTTCAGCCCTCTGTGCCATTCTAACTT
CTTTCAATCTTACTGCAGCCATTTTAAGCTTTTGTTTGTTTATGT
GTGTTTATTCGAAACTAAGTTCTTGGTGTTTAAAACTAAAAAAAA
GACTAACTATAAAAGTAGAATTTAAGAAGTTTAAGAAATAGATTTA
CAGAATTACAATCAATACCTACCGTCTTTATATACTTATTAGTCAA
GTAGGGGAATAATTTCAGGGAACTGGTTTCAACCTTTTTTTTCAG
CTTTTTTCCAAATCAGAGAGCAGAAGGTAATAGAAGGTGTAAGA
AAATGAGATAGATACATGCGTGGGTCAATTGCCTTGTGTCATCAT
TTACTCCAGGCAGGTTGCATCACTCCATTGAGGTTGTGTCCGTTT
TTTGCCTGTTTGTGCCCCTGTTCTCTGTAGTTGCGCTAAGAGAAT
GGACCTATGAACTGATGGTTGGTGAAGAAAACAATATTTTGGTGC
TGGGATTCTTTTTTTTTCTGGATGCCAGCTTAAAAAGCGGGCTCC
ATTATATTTAGTGGATGCCAGGAATAAACTGTTCACCCAGACACC
TACGATGTTATATATTCTGTGTAACCCGCCCCCTATTTTGGGCAT
GTACGGGTTACAGCAGAATTAAAAGGCTAATTTTTTGACTAAATA
AAGTTAGGAAAATCACTACTATTAATTATTTACGTATTCTTTGAAAT
```

-continued

```
GGCAGTATTGATAATGATAAACTCGAACTGGGCGCGTCGTGCCG
TCGTTGTTAATCACCACATGGTTATTCTGCTCAAACGTCCCGGAC
GCCTGCGAACGCGCCGAAGGAAAATGAGAAATATCGAGGGAGA
CGATTCAGAGGAGCAGGACAAACTATAACCGACTGTTTGTTGGA
GGATGCCGTACATAACGAACACTGCTGAAGCTACCATGTCTACA
GTTTAGAGGAATGGGTACAACTCACAGGCGAGGGATGGTGTTCA
CTCGTGCTAGCAAACGCGGTGGGAGCAAAAGTAGAATATTATC
TTTTATTCGTGAAACTTCGAACACTGTCATCTAAAGATGCTATATA
CTAATATAGGCATACTTGATAATGAAAACTATAAATCGTAAAGACA
TAAGAGATCCGCGGTCAAAATACAAATGGAATCAAGAATGCTCTT
CTGGTATGATACTTTTTGTTTTTCTTTTGAGCCCATGCGTACATTT
GAGCTGTTGAAACAGTCAAAAATAAAACGGCAAATAAATTGAACT
TGAACACAAAAGTAAACCAAATCCAAGACCAAACTTCAAAAGTAT
AGTTGGGAGCAACAAAAAGATTGAAAATACCTTGATTCAATGGGA
CACGGATCTTAGCGTTACCATGCTTCTTTTGATAGTCACCCCATA
GGCGCAATTTAATGTGGCAATAAAAGTTCCATAGTTCTGAAAGCA
CGAAAAGACCAATTAATGTACTCAAGTCATCCAATTTCAAATATGA
ATAGTATTTGAATAACTTAGCATTCCCAAAGGGGAAGCCGTAGCC
AAAGTAACCGAATGAAATGAGACCGCTTAGAACCCAGTAATGGA
AACAATTTTTGAACAGGTTGAAAATTGGCATAGTAGCTAAAGAGA
ATTGGTGAACAAATAAGGTTTCAAATAATCTCTTTCCATAATGTCC
TAAAATTAAAAAATATGCAACCCTGTTTAAAAATGGATTATAGTCG
GAGCTAGCACTGTGCCATCTATCAACAACTGTGGGAATGGTAGA
TAGATAATAAAAAGGGAGTGAACCAAGACTGGACCCAAATACTC
ACAAAAGAAGACTAATCTCCATGAAATTTGGGGACCCAAATCTTT
GATGAAGAATTCCATTGAGTCATCAGCCTCTTCTTGAAAAAACGA
TTCTGAAATAACCGGAACTTGTTTAGATTCCTTTTTGTAGGTTAAT
CTTATCCTGTACTTGCTGATATTGTGGTTATTAGCAGAGATTTTTT
TCAAAACATCATCTAAAGTAGGCTTTTTGGATAAGTCAATTTCAGT
GTCCCTTAACCCTTTAGAGCGGCTTTTTATGGTGATAGGCATTTT
AAGCTTTGTTTTATATTTGTTGTAAAAAGTAGATAATTACTTCCTTG
ATGATCTGTAAAAAGAGAAAAAGAAAGCATCTAAGAACTTGAAA
AACTACGAATTAGAAAAGACCAAATATGTATTTCTTGCATTGACCA
ATTTATGCAAGTTTATATATATGTAAATGTAAGTTTCACGAGGTTC
TACTAAACTAAACCACCCCCTTGGTTAGAAGAAAAGAGTGTGTGA
GAACAGGCTGTTGTTGTCACACGATTCGGACAATTCTGTTTGAAA
GAGAGAGAGTAACAGTACGATCGAACGAACTTTGCTCTGGAGAT
CACAGTGGGCATCATAGCATGTGGTACTAAACCCTTTCCCGCCA
TTCCAGAACCTTCGATTGCTTGTTACAAAACCTGTGAGCCGTCGC
TAGGACCTTGTTGTGTGACGAAATTGGAAGCTGCAATCAATAGGA
AGACAGGAAGTCGAGCGTGTCTGGGTTTTTTCAGTTTTGTTCTTT
```

-continued

```
TTGCAAACAAATCACGAGCGACGGTAATTTCTTTCTCGATAAGAG
GCCACGTGCTTTATGAGGGTAACATCAATTCAAGAAGGAGGGAA
ACACTTCCTTTTTCTGGCCCTGATAATAGTATGAGGGTGAAGCCA
AAATAAAGGATTCGCGCCCAAATCGGCATCTTTAAATGCAGGTAT
GCGATAGTTCCTCACTCTTTCCTTACTCACGAGTAATTCTTGCAA
ATGCCTATTATGCAGATGTTATAATATCTGTGCGTGGCGCGTCCG
GCTGTCTGCCATGCTGCCCGGTGTACCGACATAACCGCCGGTG
GCATAGCCGCGCATACGCGCCATTTCCTTCCATCTTGTGATTCAT
GCTATCCATCTTTTTTGAGTATCCAATTAACGAAGACGTTACCAG
CTGATTGAAGGTTCTCAAAGTGACTGTACTCCATGTTTTCTTATCA
TCCATGTAGTTATTTTTCAAACTGCAAATTCAAGAAAAAGCCACG
CGTGTGCACCTTTTTTTTCCCCTTCCAGTGCATTATGCAATAGAC
AGCACGAGTCTTTGAAAAAGTAACTTATAAAACTGTATCAATTTTT
AAACCTAAATAGATTCATAAACTATTCGTTAATATAAAGTGTTCTA
AACTATGATGAAAAAATAAGCAGAAAAGACTAATAATTCTTAGTTA
AAAGCACTCCCTAGTTCATTAATCCATTTGCTAGTCTTGCTCTTAG
ATCCTTCCTCAATATCTTCCCTGATGGAGCTTTAGGAATAGAGTC
AGTGAAGAACACTTTGTTGATTCTCTTATAAAACACAACCTGTTTT
GACACGAATTGCTTGATTTCATCTTCGGATATATTTGAATCTTTCG
ATCTCACCACAAACGCAACAGGAACCTCACCAGCATCTTCTTCCT
TCATGGCGACGACAGCAACATCATTGATTTCTGGATGACCTATGA
GGAGAGACTCTAGCTCAGCTGGAGCCACTTGAAATCCTTTGTAC
TTGATGAGTTCTTTCAATCTATCCACAATGAAAAGCTCGTCGTCAT
CATCGATAAATCCGACGTCTCCAGTGTGAAGCCAACCATCTTTAT
CGATCGTCGATGCCGTGGCCAAGGGGTCATTGAGATAGCCTTTC
ATGATTTGGTTGCCACGGATGCATATTTCGCCGGGTTTGTTCCTA
GGCAAAGAATCTCCTGTGTCTGGATCAAGTATCTTCATCTCGGCG
TTCCTCACCACCGTACCACATGCTCCTGACTTCACTGGAAACGG
CTCTTTAGCAAACCCTAACGACATTGCTAGCACCGGACCTGCTTC
TGTCATCCCATAGCCCTGACCAAGCTTGGCGTTAGGAAACTTAG
CACTAATAGCATCTTCAAGCTCCTTACCAAGAGGAGCTGCTCCAG
ACTTAACCATCCTAACCGAGCTCAGATCATACTTCTCCGTCTCCG
GCGACTTCGCGATAGCTAAAACGATCGGTGGCACGACCATAGCC
ACCGTGACTTTACACCTTTGTATCTGCTCTAACAAGAGAGTGATT
TCGAACTTAGGCATTATCAAGATCGTGGCACCAACTCTGAGACTA
CAGAGCATGATGGAGTTGAGAGCGTATATATGGAACATAGGCAA
GACACAGAGGATCACGTCGTCTCTGTTGAAGTAAAGATTCGGATT
CTCGCCGTCGACTTGCTGCGCCACGCTCGTGACTAGACCTTTGT
GTGTTAGCATCACTCCTTTGGGGAGACCCGTCGTGCCGGATGAG
AAAGGAAGCGCCACGACGTCTTCTGGCGAAATCTTCTCCGGTAT
```

```
TGAGTCCACTCGTGGTTCTTCGGACTGAGTTAACTCGGAGAAAC
GGAGGCAGTTTTCGGGGATGGCGTCGGAGTCGGTGGTGACGAT
CAAAACGCCGTCGTTTTGGAGGTTCTTGATTTTATCGACGTAACG
GGATTGAGTGACGATGAGTTTCGCCGCGGAGGCTTTGGCTTGTT
TAGAAATCTCCGCCGGAGTGAAGAACGGGTTCGCGGAGGTGGT
GATTGCGCCGATGAAGGAGGCGGCAAGGAAAGTGAGGACTACT
TCAGGAGAGTTCGGGAGGAGGATCATTACAACGTCGTGTTGCTT
CACGCCGAGGTTATGAAGACCGGCGGCGAGTTTCCGAGATGTTA
CGTGGACATCGGCGTAGGTGTATACTTCGCCGGTGGGACCGTT
GATCAAGCATGGCTTAGCGGCGAACTCTGAGATATTTTCGAAGAT
GTAGTCGTGGAGTGGGAGGTGGTTAGGGATGTATATATCAGGCA
ATCTCGATCGGAAAATGACGTCATTACTACACTGTTTCTGATCATT
CTGATCATTGACTATCACATCTTGTGTCGTCATtttAGCTTTTTGTAA
TTAAAACTTAGATTAGATTGCTATGCTTTCTTTCTAATGAGCAAGA
AGTAAAAAAAGTTGTAATAGAACAAGAAAAATGAAACTGAAACTT
GAGAAATTGAAGACCGTTTATTAACTTAAATATCAATGGGAGGTC
ATCGAAAGAGAAAAAATCAAAAAAAAAAATTTTCAAGAAAAAGAA
ACGTGATAAAAATTTTTATTGCCTTTTTCGACGAAGAAAAAGAAAC
GAGGCGGTCTCTTTTTTCTTTTCCAAACCTTTAGTACGGGTAATTA
ACGACACCCTAGAGGAAGAAAGAGGGGAAATTTAGTATGCTGTG
CTTGGGTGTTTTGAAGTGGTACGGCGATGCGCGGAGTCCGAGAA
AATCTGGAAGAGTAAAAAGGAGTAGAAACATTTTGAAGCTAGGC
GCGTCAGCCGGTAAAGATTCCCCACGCCAATCCGGCTGGTTGCC
TCCTTCGTGAAGACAAACTCACGCGCCTCCAAAATGAGCTATCAA
AAACGATAGATCGATTAGGATGACTTTGAAATGACTCCGCAGTGG
ACTGGCCGTTAATTTCAAGCGTGAGTAAAATAGTGCATGACAAAA
GATGAGCTAGGCTTTTGTAAAAATATCTTACGTTGTAAAATTTTAG
AAATCATTATTTCCTTCATATCATTTTGTCATTGACCTTCAGAAGA
AAAGAGCCGACCAATAATATAAATAAATAAATAAAAATAATATTCC
ATTATTTCTAAACAGATTCAATACTCATTAAAAAACTATATCAATTA
ATTTGAATTAACCGCGGTTAGCAGATTGGAATAGGTGCACCATTC
CACTCTTTCAAGCAATCCATAAGTGGATCTATCAACTTTCCCTCG
CACATAGCTGTGAATACCTTGTCAAATTCTTCACCTGGGCTAACG
ACTTTTTCACCAGTTAGTAATTTGGTTCCCAACTCTTCTCTAACGA
ATCTGTACAAAGGGTACGACCTACACTCTTTGATTCTATTTGGTAT
AGGGGCAGTACCATTTCCGTATGCGGCTCTAGCAGCTTCGACTT
CCTTTGGTAAAACTGCCTTCAGTTCTTCTTCAAAGGCACCTATCTT
TTGGAATATTGAAGTAACGGCATTTTTTCTCAGTTTCACCATTGGAT
AAAGCGTGATCTACAATAACTTGTCTCAATCTCTGCATCAATGGA
TAAGTAGCGCTACATGGATCGTCAACGTAAGTAAATACTTGTTCT
CTATCTACAACTTTTAATAAATCTTTTTCACAGAATCTTGATGGGT GCAATTCACCATTGATACCTGTAGTTAGAACCTTTTTTGCAACCT
GTGATACGGTATTTTTCACTGTCTGTCTCAAATTCTCTTCCAAGTG
TCTcAAATCTACGGCCTGGCATATACCCACTAAAAATGTTGTGGA
CATTAATTTAAGGATATCAACGGCCTCGCTTGTTTTTCTTGATGAA
ATCAGGCCCAAAGAATTAACATCCTGATTGTGTTGTTCGGCTGAT
TGTACATGAGAGGTTACTGGGTTGGCTAGATATTGCAGCTCTGAA
CAATAGCTTGCCATTGCTATCTCAGCACCTTTGAAACCATAATCA
AGACTAGGGTTAGAAGATGCGGTCAGATTCGAAGGCAAACCGTT
ATTGTAGAAGTCATTGACCAATTCAGAAAATTGGGCAAACATTAA
TTTGCCAATTGCGGCTATGGCAAGCCTGGTATTATCCATACTGAC
TCCTATGGGTGTACCCTGGAAATTGCCTCCATGTATTGCCTTATT
CCTCGACACATCAATAAGTGGATTATCGTTAACAGAGTTGATCTC
TCTTTCTATAGACTTTGTAGCTTGTCTAATTACTTCAATTTGAGGG
CCAAGCCATTGTGGGGATGTCCTTAAAGCATATCTATCTTGTTTG
GGTTTTTGCAAAGGGTCCATTTCATGAACCTTCTGGGCTAACTTC
ATGTAGCTAGAGCCGTCCAAAATGTGCTCCATGATAGCTGCTGC
TTCAATTTGTCCTGGGTGATGTTTTAACCTGTGGGTCAAGTGATC
AGTAAACTCAGGTTTTCCACTCATGACTTCGGCAAAAATTGCGGA
CAAAACTTCGGCCAAAACTGCTTGTACGTTAGCTTCAAACAACAC
CATGGATGCCATACCGCTGCCGACAGCGGTGCCATTCACCAGG
GCTAAACCTTCCTTGGGTTGcAAATCAAAGAAACCAGTTGAAATA
CCAGCTTTCTCAAATGCTTCCTTAGCGGTTAAGGATTCTCCGTCT
GGACCAGTGGCCTTTGAATTAGGTCTTCCCGTTAATAAGCCTGC
GATATATGAAAGGGGAACCAAATCACCGCTGGCAGTTATTGTTCC
TCTTAAGGGCAACGAAGGAGAAATGTTGTGGTTCAATAGTGAAGT
GATGGCCTCAAGAATTTCAAACCTTATTCCAGAGTAACCTTGCAA
CAAAGTGTTCACCCTAACAAGCATAGCAGCTCTTGTTGCCGATTG
GGGTAATGTATGGCAAGTTTCCTTTGTATTACCGAAAATACCGGC
GTTAAGGAATCTGATCAGTTCTGTTTGCAAAGCAGTGCCATTTTT
AGTTCTTCTATGAGAGGTAGCACCAAAGCCTGTGGTAACGCCAT
AGGAATCTGTGCCCTTGTTCATACTTTCCATGACCCAATCTGATG
AAGCCTTAACTCCGGCTCTACTTGTTTCTGCAAGTTCTACCTTCA
CTGAACCGCCAACGGTCGAAATAGCAGCTACCTGTCCTATCGTC
AATGTCTCGCCGCCTAGATTTACGACTGGTCTTCTGTATTCCTCA
ACCATCTTCTTAACTTCATCCAGATGGCTACCTTTCATCTGGTCA
GCTGCCAGACCCCAATTCAAAGGATCTGCAAGAGTTTTTGTCGTT
ACGGCCACCTTGGTCTTTTCACCACCACCGCATAGCATTGCTTCA
ATTTGGTCCATTTTAAGCTTTTTGATAGATTTGACTGTGTTATTTT
GCGTGAGGTTATGAGTAGAAAATAATAATTGAGAAAGGAATATGA
CAAGAAATATGAAAATAAAGGGAACAAACCCAAATCTGATTGCAA
```

-continued

```
GGAGAGTGAAAGAGCCTTGTTTATATATTTTTTTTCCTATGTTCA
ACGAGGACAGCTAGGTTTATGCAAAAATGTGCCATCACCATAAG
CTGATTCAAATGAGCTAAAAAAAAAATAGTTAGAAAATAAGGTGG
TGTTGAACGATAGCAAGTAGATCAAGACACCGTCTAACAGAAAAA
GGGGCAGCGGACAATATTATGCAATTATGAAGAAAAGTACTCAAA
GGGTCGGAAAAATATTCAAACGATATTTGCATAAAATCCTCAATT
GATTGATTATTCCATAGTAAAATACCGTAACAACACAAAATTGTTC
TCAAATTCATAAATTATTCATTTTTTCCACGAGCCTCATCACACGA
AAAGTCAGAAGAGCATACATAATCTTTTAAATGCATAGGTTATGC
ATTTTGCAAATGCCACCAGGCAACAAAAATATGCGTTTAGCGGGC
GGAATCGGGAAGGAAGCCGGAACCACCAAAAACTGGAAGCTAC
GTTTTTAAGGAAGGTATGGGTGCAGTGTGCTTATCTCAAGAAATA
TTAGTTATGATATAAGGTGTTGAAGTTTAGAGATAGGTAAATAAAC
GCGGGGTGTGTTTATTACATGAAGAAGAAGTTAGTTTCTGCCTTG
CTTGTTTATCTTGCACATCACATCAGCGGAACATATGCTCACCCA
GTCGCATGGCGCGTACCACGGTGAACAATCCCCGCTGGCTCATA
TTTGCCGCCGGTTCCCGTAAATCCTCCGGTACGCGCCGGGCCG
TATACTTACATATAGTAGATGTCAAGCGTAGGCGCTTCCCCTGCC
GGCTGTGAGGGCGCCATAACCAAGGTATCTATAGACCGCCAATC
AGCAAACTACCTCCGTACATTCATGTTGCACCCACACATTTATAC
ACCCAGACCGCGACAAATTACCCATAAGGTTGTTTGTGACGGCG
TCGTACAAGAGAACGTGGGAACTTTTTAGGCTCACCAAAAAGAA
AGAAAAAATACGAGTTGCTGACAGAAGCCTCAAGAAAAAAAAAT
TCTTCTTCGACTATGCTGGAGGCAGAGATGATCGAGCCGGTAGT
TAACTATATATAGCTAAATTGGTTCCATCACCTTCTTTTCTGGTGT
CGCTCCTTCTAGTGCTATTTCTGGCTTTTCCTATTTTTTTTTTCCA
TTTTTCTTTCTCTCTTTCTAATATATAAATTCTCTTGCATTTTCTATT
TTTCTCTCTATCTATTCTACTTGTTTATTCCCTTCAAGGTTTTTTTT
TAAGGAGTACTTGTTTTTAGAATATACGGTCAACGAACTATAATTA
ACTAAACAAGCTTAAAATGATGGATTTTGTTTGTTAGAAAAGCT
CTTCTTGGTTTGTTCATTGCAACTATAGTAGCCATCACAATCTCTA
AGCTAAGGGGAAAGAAACTTAAGTTGCCTCCAGGCCCAATCCCT
GTCCCAGTGTTTGGTAATTGGTTACAAGTTGGCGACGACTTAAAC
CAGAGGAATTTGGTAGAGTATGCTAAAAAGTTCGGCGACTTATTT
CTACTTAGGATGGGTCAAAGAAACTTGGTCGTGGTTTCATCCCCT
GACTTAGCAAAAGACGTACTACATACCCAGGGTGTCGAGTTCGG
AAGTAGAACTAGAAATGTTGTGTTTGATATTTTCACAGGCAAAGG
TCAAGATATGGTTTTTACCGTATACAGCGAGCACTGGAGGAAAT
GAGAAGAATAATGACTGTCCCATTCTTTACAAACAAAGTGGTTCA
ACAGTATAGGTTCGGATGGGAGGACGAAGCCGCTAGAGTAGTC
GAGGATGTTAAGGCAAATCCTGAAGCCGCTACCAACGGTATTGT
```

-continued

```
GTTGAGGAATAGATTACAACTTTTGATGTACAACAATATGTATAGA
ATAATGTTTGACAGGAGATTTGAATCTGTTGATGATCCATTATTCC
TAAAACTTAAGGCATTGAATGGCGAGAGATCAAGGTTAGCTCAAT
CCTTTGAATACAACTTCGGTGACTTCATTCCTATATTGAGGCCATT
CTTGAGAGGATATCTTAAGTTGTGTCAGGAAATCAAGGACAAAAG
GTTAAAGCTATTCAAGGACTACTTCGTCGACGAGAGAAAAAGTT
GGAGAGTATCAAGAGCGTAGGTAATAACTCCTTAAAGTGCGCCA
TAGATCATATTATCGAGGCACAAGAAAAAGGCGAGATAAACGAG
GATAACGTGTTATACATCGTCGAGAATATCAACGTGGCTGCCATT
GAAACTACACTTTGGTCTATTGAATGGGGTATAGCAGAACTAGTG
AATAACCCTGAAATCCAGAAAAAATTGAGACACGAATTAGACACC
GTACTTGGAGCTGGTGTTCAAATTTGTGAACCAGATGTTCAAAAA
TTGCCTTATCTACAGGCCGTGATAAAAGAGACTTTAAGGTACAGG
ATGGCAATTCCATTGTTAGTCCCACATATGAATCTTCACGAAGCC
AAATTGGCCGGCTATGATATCCCTGCAGAGAGCAAAATTTTGGTA
AACGCTTGGTGGTTAGCCAATAATCCAGCACATTGGAACAAACCT
GATGAGTTTAGACCAGAAAGATTTTTGGAGGAAGAATCCAAGGT
CGAGGCTAATGGAAACGACTTTAAGTACATCCCTTTCGGTGTTGG
CAGAAGATCTTGCCCAGGTATAATTCTTGCTTTACCAATCCTTGG
AATAGTAATTGGTAGGTTGGTTCAAAACTTCGAGTTACTTCCACC
TCCAGGCCAAAGCAAAATAGATACAGCCGAAAAAGGTGGACAGT
TTTCATTGCAAATCCTAAAGCATTCCACTATTGTGTGTAAACCTAG
AAGTTCTTAACCGCGGACAAATCGCTCTTAAATATATACCTAAAG
AACATTAAAGCTATATTATAAGCAAAGATACGTAAATTTTGCTTAT
ATTATTATACACATATCATATTTCTATATTTTTAAGATTTGGTTATA
TAATGTACGTAATGCAAAGGAAATAAATTTTATACATTATTGAACA
GCGTCCAAGTAACTACATTATGTGCACTAATAGTTTAGCGTCGTG
AAGACTTTATTGTGTCGCGAAAAGTAAAAATTTTAAAAATTAGAGC
ACCTTGAACTTGCGAAAAAGGTTCTCATCAACTGTTTAAAGGAG
GATATCAGGTCCTATTTCTGACAAACAATATACAAATTTAGTTTCA
AAGGCGCGTTGCAAATGGAATTTCGCCGCAGCGGCCTGAATGG
CTGTACCGCCTGACGCGGATGCGCCACGCGCCGCATGCCGGTA
GAGGTGTGGTCAATAAGAGCGACCTCATGCTATACCTGAGAAAG
CAACCTGACCTACAGGAAAGAGTTACTCAAGAATAAGAATTTTCG
TTTTTAAACCTAAGAGTCACTTTAAAATTTGTATACACTTATTTTTT
TTATAACTTATTTAATAATAAAAATCATAAATCATAAGAAATTCGCT
TATTTAGAAGTGTCAACAACGTATCTACCAACGATTTGACCCTTTT
CCATCTTTTCGTAAATTTCTGGCAAGGTAGACAAGCCGACAACCT
TGATTGGAGACTTGACCAAACCTCTGGCGAAGAAGTCCAAAGCT
CTAGATCAATTTAGGCCTGCGGCCGCGGTTACCAGACATCTTCTT
```

```
GGTATCTACCTGAAGTCTTGAGCATCTTGATTAGCTCTGTTGCTT
CATCAGTGGTAATGGATTTACCACGGGATAAGATGCCAACCAAT
GCGGTTGACACACCCTTGGCCATACCCTTTGCATCACCACAGAC
GTAGATAAATGCACCGTTGTTAATCATTTCAAATACTTGGTCTTCG
TAATCCTTTAATTTATCTTGAACATAAACTTTTTTGGTGTTTGGCAA
CCTGGAATGGGCCACGACCATTTCGAACGAACCATCCAATTTTTT
GGCGTATTCTGGCCATTCGTCCTGGTACAAGAAATCATCAGTGTT
ACGGGATCCATAAAACAGTATATGCTTACCTAGCGAAACGTTGTT
ACCGCCCTTCTTTTGTGATTCGAGGAACGCGACACGCTCTCTGA
TAAACCCACGGAATGGGGCAACACCGGTACCTGGACCGATCATG
ATAACTGGGGTGGAAGGGTTGGAAGGCAATCTGAAGTTAGAACG
ACGAACGTGGACGGGCAATTTGTAATTGGCGAAAAGTTTACGTG
GGCCATTTAAATCGTAGTGAACAGGTAGGTTAGTTTCGGCAATGT
TAACATTGTTTTGAGCCAATTGAATGTTTCTTAACAAGTTAGTCGT
AACACCAACAACTGGAGGAGCATCAGGCAATTCTGGGTTAGGAA
AGTTTTCCACAATGGAGGTGACATGGACGGTTTGCTTTTCAGACA
GAGAAGAGGAAGAGATAGAGTAGTAACGAGGAGTCATTTGGGA
ACTGATTCGACCAAGAATTGCATGGGTACGGTGTCCCATTTGGC
GCCATCAGACAAATATTTCAGAGCATCTGCGATGTTGAAATATTT
GGAGGTTATCTCGACGGCGAATTGGTCCTTGTCTTTCGAAAGCA
GAGTCAATTTTTCCTTGACGTCAGCGTTGGGGGCGAACTGAATC
AAAGATGAAAACAATTGTCTGGAGACAGGTCCTGTAATTTCCAAA
TAGTGTTTAATAGCAGCGCCAATAGTAGTTGGCGTTGGGAAGGG
CACTTTGACGGTGGGATCCAGGGGCTTCAAGTCAAAAATGGTTT
CAGGGTCCAGGTTGAATATGGATAAGAACTGTTCGACCTTTTCCA
ATGGGTTGGAAGGCCAAACAGCAAGATGGTCACCAGTGGAGTAC
TTGATGTTAGAGCCGGACAAGTCAAATTCAGAGTGGATGCAATTA
CGGTCATTGGAAGAGAACAGTTCGCGAGATTTCACGATGGGTGC
AATATACGGTTGAGACAAATCGAAGGGACCCAATTGGATGCCGT
CTGCGTTGCGGTTCAACTGATGCGAGGGCAAATAGTGAGCAGAG
GGTTCACCAAGCGACATGGAGTCAGTGATTTCGTTCAACACAGT
GTACTGGAATTGAGAGGTGAACTTGGCTTCCTGTTCGTCCAAATG
CAGTTCGTCTTTCAAAACCTCCAGGATGGAGTCCTTCCAGGCCAT
GTAATCTTCGTCTGTAGTTCCTGCACCATCATCAGCTTCACCGAG
CTTGCCAGTCTGATAGCGCCCGCAGCGGAGAGATGCTTCTCGG
CCTTCTTGGCGGCACCATTAAAGAATTCATAAGTAGAATTTCCCA
GACCAAACATATTATACCTCAGGTTCGATAGTGCACCCGCTTCCG
CATTACAAATAAAGTCTTCAAAGTTGACCGCCCCGTCGGGGAAG
TCTCCTTCACCATATGTAGAGATAAAAATCGAGACTATGACGGGC
ACATCGTTTAGCGACTCAAAGTCGTAGTTCTCAACATCTGCGCAC
ATCACGTTTAGGTTGAACTTGGCCACCAGCTCCTTGGAAAACTTT
```
```
TTGGCGTAATCCTCGGCAGTCCCAGTCTGCGACGCATACAACAC
CAAGTAGTTCTTGTTGTTTTCGGTCACCACCTGAGCAATGTCTCT
GTTGCCCGAGCTGACAGCTGTGATATCTCCGTCATCGGACATCA
GCAGTTCCTTGATGGAGTTTCTCTTTACGTACAGTAGCACGGCAA
GCACTAGCCCCGCCAGGACAGTGAAGTCGGTGTTGTCTATTCCA
AACGGCATTTTACTAGTAAGCTTTGTGATGATGTTTTATTTGTTTT
GATTGGTGTCTTGTAAATAGAAACAAGAGAGAATAATAAACAAGT
TAAGAATAAAAACCAAAGGATGAAAAAGAATGAATATGAAAAG
AGTAGAGAATAACTTTGAAAGGGGACCATGATATAACTGGAAAAA
AGAGGTTCTTGGAAATGAAAAGTTACCAAAGAGTATTTATAATTC
AGAAAAAAAGCCAACGAATATCGTTTTGATGGCGAGCCTTTTTT
TTTTTTTAGGAAGACACTAAAGGTACCTAGCATCATATGGGAAGG
AAAGGAAATCACTTGGAAGACATCACAAGCATTCATTTACCAAGA
GAAAAAATATGCATTTTAGCTAAGATCCATTGAACAAAGCACTCA
CTCAACTCAACTGAATGAACGAAAGAAGAAAGAACAGTAGAAAAC
ACTTTGTGACGGTGCGGAACACATTTACGTAGCTATCATGCTGAA
TTCTACTATGAAAATCTCCCAATCTGTCGATGGCAAAACGACCCA
CGTGGCAGAGTTGGGTCAAGTGCCAGTTTCTGGATTAAGTAACA
GATACAGACATCACACGCCATAGAGGAATCCCGCCGTTGCGAGA
GATGGAAAACAATAGAGCCGAAATTGTGGAAGCCCGATGTCTGG
GTGTACATTTTTTTTTTTCTTTCTTTCTCTTTCAATAATCTTTCCTT
TTTCCATTTAGCTTGCCGGAAAAACTTTCGGGTAGCGAAAATCTT
TCTGCCGGAAAAATTAGCTATTTTTTTCTTCCTTATTATTTTTTTAG
TTCTGAAGTTTGACCAGGGCGCTACCCTGACCGTATCACAACCG
ACGATCCGGGGTCATGGCGGCTATTTTTTTTTTTTTTTTTTTCC
TTGTGATTGTTTATTTACATTTGGATCAATTCTAACAAAAAAAAAAT
AAGGGGGGAAAAATAATTCACCTCTTTTTAATATTGTTTTGTACTG
AGATTGATCTCCAAAATAGTAGCATTGGCGCGTGCCACCAACAG
CCCCGCCAATGGCGCTGCCGATACTCCCGACAATCCCCACCATT
GCCTG
                                    SEQ ID NO: 11
TTTCCCGTCTTTCAGTGCCTTGTTCAGTTCTTCCTGACGGGCGGT
ATATTTCTCCAGCTTGGCCTATGCGGCCCTGTCAGACCAAGTTTA
CGAGCTCGCTTGGACTCCTGTTGATAGATCCAGTAATGACCTCA
GAACTCCATCTGGATTTGTTCAGAACGCTCGGTTGCCGCCGGGC
GTTTTTTATTGGTGAGAATCCAAGCACTAGGGACAGTAAGACGG
GTAAGCCTGTTGATGATACCGCTGCCTTACTGGGTGCATTAGCC
AGTCTGAATGACCTGTCACGGGATAATCCGAAGTGGTCAGACTG
GAAAATCAGAGGGCAGGAACTGCTGAACAGCAAAAGTCAGATA
GCACCACATAGCAGACCCGCCATAAAACGCCCTGAGAAGCCCGT
GACGGGCTTTTCTTGTATTATGGGTAGTTTCCTTGCATGAATCCA
```

-continued

TAAAAGGCGCCTGTAGTGCCATTTACCCCCATTCACTGCCAGAG
CCGTGAGCGCAGCGAACTGAATGTCACGAAAAAGACAGCGACTC
AGGTGCCTGATGGTCGGAGACAAAAGGAATATTCAGCGATTTGC
CCGAGCTTGCGAGGGTGCTACTTAAGCCTTTAGGGTTTTAAGGT
CTGTTTTGTAGAGGAGCAAACAGCGTTTGCGACATCCTTTTGTAA
TACTGCGGAACTGACTAAAGTAGTGAGTTATACACAGGGCTGGG
ATCTATTCTTTTTATCTTTTTTTATTCTTTCTTTATTCTATAAATTAT
AACCACTTGAATATAAACAAAAAAAACACACAAAGGTCTAGCGGA
ATTTACAGAGGGTCTAGCAGAATTTACAAGTTTTCCAGCAAAGGT
CTAGCAGAATTTACAGATACCCACAACTCAAAGGAAAAGGACATG
TAATTATCATTGACTAGCCCATCTCAATTGGTATAGTGATTAAAAT
CACCTAGACCAATTGAGATGTATGTCTGAATTAGTTGTTTTCAAA
GCAAATGAACTAGCGATTAGTCGCTATGACTTAACGGAGCATGA
AACCAAGCTAATTTTATGCTGTGTGGCACTACTCAACCCCACGAT
TGAAAACCCTACAAGGAAAGAACGGACGGTATCGTTCACTTATAA
CCAATACGCTCAGATGATGAACATCAGTAGGGAAAATGCTTATG
GTGTATTAGCTAAAGCAACCAGAGAGCTGATGACGAGAACTGTG
GAAATCAGGAATCCTTTGGTTAAAGGCTTTGAGATTTTCCAGTGG
ACAAACTATGCCAAGTTCTCAAGCGAAAAATTAGAATTAGTTTTA
GTGAAGAGATATTGCCTTATCTTTTCCAGTTAAAAAAATTCATAAA
ATATAATCTGGAACATGTTAAGTCTTTTGAAAACAAATACTCTATG
AGGATTTATGAGTGGTTATTAAAAGAACTAACACAAAAGAAAACT
CACAAGGCAAATATAGAGATTAGCCTTGATGAATTTAAGTTCATG
TTAATGCTTGAAAATAACTACCATGAGTTTAAAAGGCTTAACCAAT
GGGTTTTGAAACCAATAAGTAAAGATTTAAACACTTACAGCAATAT
GAAATTGGTGGTTGATAAGCGAGGCCGCCCGACTGATACGTTGA
TTTTCCAAGTTGAACTAGATAGACAAATGGATCTCGTAACCGAAC
TTGAGAACAACCAGATAAAAATGAATGGTGACAAAATACCAACAA
CCATTACATCAGATTCCTACCTACATAACGGACTAAGAAAAACAC
TACACGATGCTTTAACTGCAAAAATTCAGCTCACCAGTTTTGAGG
CAAAATTTTGAGTGACATGCAAAGTAAGTATGATCTCAATGGTT
CGTTCTCATGGCTCACGCAAAAACAACGAACCACACTAGAGAAC
ATACTGGCTAAATACGAAGGATCTGAGGTTCTTATGGCTCTTGT
ATCTATCAGTGAAGCATCAAGACTAACAAACAAAAGTAGAACAAC
TGTTCACCGTTACATATCAAAGGGAAAACTGTCCATATGCACAGA
TGAAAACGGTGTAAAAAAGATAGACATCAGAGCTTTTACGAGT
TTTTGGTGCATTCAAAGCTGTTCACCATGAACAGATCGACAATGT
AACGCGGCCGCAGCCAATCAATTCTTGCGGAGAACTGTGAATGC
GCAAACCAACCCTTGGCAGAACATATCCATCGCGTCCGCCATCT
CCAGCAGCCGCACGCGGCGCATCGGGGGGGGGGGGGGGTT

-continued

TCAATTCATCATTTTTTTTTTATTCTTTTTTTTGATTTCGGTTTCCTT
GAAATTTTTTGATTCGGTAATCTCCGAACAGAAGGAAGAACGAA
GGAAGGAGCACAGACTTAGATTGGTATATATACGCATATGTAGTG
TTGAAGAAACATGAAATTGCCCAGTATTCTTAACCCAACTGCACA
GAACAAAAACCTGCAGGAAACGAAGATAAATCATGTCGAAAGCT
ACATATAAGGAACGTGCTGCTACTCATCCTAGTCCTGTTGCTGCC
AAGCTATTTAATATCATGCACGAAAAGCAAACAAACTTGTGTGCT
TCATTGGATGTTCGTACCACCAAGGAATTACTGGAGTTAGTTGAA
GCATTAGGTCCCAAAATTTGTTTACTAAAAACACATGTGGATATCT
TGACTGATTTTTCCATGGAGGGCACAGTTAAGCCGCTAAAGGCA
TTATCCGCCAAGTACAATTTTTTACTCTTCGAAGACAGAAAATTTG
CTGACATTGGTAATACAGTCAAATTGCAGTACTCTGCGGGTGTAT
ACAGAATAGCAGAATGGGCAGACATTACGAATGCACACGGTGTG
GTGGGCCCAGGTATTGTTAGCGGTTTGAAGCAGGCGGCAGAAG
AAGTAACAAAGGAACCTAGAGGCCTTTTGATGTTAGCAGAATTGT
CATGCAAGGGCTCCCTATCTACTGGAGAATATACTAAGGGTACT
GTTGACATTGCGAAGAGCGACAAAGATTTTGTTATCGGCTTTATT
GCTCAAAGAGACATGGGTGGAAGAGATGAAGGTTACGATTGGTT
GATTATGACACCCGGTGTGGGTTTAGATGACAAGGGAGACGCAT
TGGGTCAACAGTATAGAACCGTGGATGATGTGGTCTCTACAGGA
TCTGACATTATTATTGTTGGAAGAGGACTATTTGCAAAGGGAAGG
GATGCTAAGGTAGAGGGTGAACGTTACAGAAAAGCAGGCTGGG
AAGCATATTTGAGAAGATGCGGCCAGCAAAACTAAAAAACTGTAT
TATAAGTAAATGCATGTATACTAAACTCACAAATTAGAGCTTCAAT
TTAATTATATCAGTTATTACCCGGCCGGGAATCTCGGTCGTAATG
ATTTTTATAATGACGAAAAAAAAAAAATTGGAAAGAAAACCCCCC
CCCCCCCCCGCAGCGTTGGGTCCTGGCCACGGGTGCGCATGA
TCGTGCTCCTGTCGTTGAGGACCCGGCTAGGCTGGCGGGGTTG
CCTTACTGGTTAGCAGAATGAATCACCGATACGCGAGCGAATGT
GGCGGCCGCACGCGTTCATCGTCCACCTCCGGAGAACAGGCCA
CCATCACGCATCTGTGTCTGAATTTCATCACG

SEQ ID NO: 12
TCATCGTCCACCTCCGGAGAACAGGCCACCATCACGCATCTGTG
TCTGAATTTCATCACGACGCGCCTTAAGGGCACCAATAACTGCCT
TAAAAAAATTACGCCCCGCCCTGCCACTCATCGCAGTACTGTTGT
AATTCATTAAGCATTCTGCCGACATGGAAGCCATACAGACGGC
ATGATGAACCTGAATCGCCAGCGGCATCAGCACCTTGTCGCCTT
GCGTATAATATTTGCCCATGGTGAAAACGGGGGCGAAGAAGTTG
TCCATATTGGCCACGTTTAAATCAAAACTGGTGAAACTCACCCAG
GGATTGGCTGAGACGAAAACATATTCTCAATAAACCCTTTAGGG
AAATAGGCCAGGTTTTCACCGTAACACGCCACATCTTGCGAATAT

ATGTGTAGAAACTGCCGGAAATCGTCGTGGTATTCACTCCAGAG
CGATGAAAACGTTTCAGTTTGCTCATGGAAAACGGTGTAACAAGG
GTGAACACTATCCCATATCACCAGCTCACCGTCTTTCATTGCCAT
ACGGAATTCCGGATGAGCATTCATCAGGCGGGCAAGAATGTGAA
TAAAGGCCGGATAAAACTTGTGCTTATTTTTCTTTACGGTCTTTAA
AAAGGCCGTAATATCCAGCTGAACGGTCTGGTTATAGGTACATTG
AGCAACTGACTGAAATGCCTCAAAATGTTCTTTACGATGCCATTG
GGATATATCAACGGTGGTATATCCAGTGATTTTTTTCTCCATTTTA
GCTTCCTTAGCTCCTGAAAATCTCGATAACTCAAAAAATACGCCC
GGTAGTGATCTTATTTCATTATGGTGAAAGTTGGAACCTCTTACG
TGCCGATCAACGTCTCATTTTCGCCAAAAGTTGGCCCAGGGCTT
CCCGGTATCAACAGGGACACCAGGATTTATTTATTCTGCGAAGTG
ATCTTCCGTCACAGGTATTGGACCACCCTGTGGGTTTATAAGCG
CGCTGCTGGCGTGTAAGGCGGTGACGGCGAAGGAAGGGTCCTT
TTCATCACGTGCTATAAAAATAATTATAATTTAAATTTTTTAATATA
AATATATAAATTAAAAATAGAAAGTAAAAAAAGAAATTAAAGAAAA
AATAGTTTTTGTTTTCCGAAGATGTAAAAGACTCTAGGGGGATCG
CCAACAAATACTACCTTTTATCTTGCTCTTCCTGCTCTCAGGTATT
AATGCCGAATTGTTTCATCTTGTCTGTGTAGAAGACCACACACGA
AAATCCTGTGATTTTACATTTTACTTATCGTTAATCGAATGTATATC
TATTTAATCTGCTTTTCTTGTCTAATAAATATATATGTAAAGTACGC
TTTTTGTTGAAATTTTTTAAACCTTTGTTTATTTTTTTTTCTTCATTC
CGTAACTCTTCTACCTTCTTTATTTACTTTCTAAAATCCAAATACAA
AACATAAAAATAAATAAACACAGAGTAAATTCCCAAATTATTCCAT
CATTAAAAGATACGAGGCGCGTGTAAGTTACAGGCAAGCGATCC
GTCCTAAGAAACCATTATTATCATGACATTAACCTATAAAAATAGG
CGTATCACGAGGCCCTTTCGTCTCGCGCGTTTCGGTGATGACGG
TGAAAACCTCTGACACATGCAGCTCCCGGAGACGGTCACAGCTT
GTCTGTAAGCGGATGCCGGGAGCAGACAAGCCCGTCAGGGCGC
GTCAGCGGGTGTTGGCGGGTGTCGGGGCTGGCTTAACTATGCG
GCATCAGAGCAGATTGTACTGAGAGTGCACCACGGCGCGTGGC
ACCCTTGCGGGCCATGTCATACACCGCCTTCAGAGCAGCCGGAC
CTATCTGCCCGTT

SEQ ID NO: 13
GCCACCAACAGCCCCGCCAATGGCGCTGCCGATACTCCCGACA
ATCCCCACCATTGCCTGACGCGTCCAGTATCCCAGCAGATACGG
GATATCGACATTTCTGCACCATTCCGGCGGGTATAGGTTTTATTG
ATGGCCTCATCCACACGCAGCAGCGTCTGTTCATCGTCGTGGCG
GCCCATAATAATCTGCCGGTCAATCAGCCAGCTTTCCTCACCCG
GCCCCCATCCCCATACGCGCATTTCGTAGCGGTCCAGCTGGGA
GTCGATACCGGCGGTCAGGTAAGCCACACGGTCAGGAACGGGC
GCTGAATAATGCTCTTTCCGCTCTGCCATCACTTCAGCATCCGGA
CGTTCGCCAATTTTCGCCTCCCACGTCTCACCGAGCGTGGTGTT
TACGAAGGTTTTACGTTTTCCCGTATCCCCTTTCGTTTTCATCCAG
TCTTTGACAATCTGCACCCAGGTGGTGAACGGGCTGTACGCTGT
CCAGATGTGAAAGGTCACACTGTCAGGTGGCTCAATCTCTTCAC
CGGATGACGAAAACCAGAGAATGCCATCACGGGTCCAGATCCC
GGTCTTTTCGCAGATATAACGGGCATCAGTAAAGTCCAGCTCCT
GCTGGCGGATGACGCAGGCATTATGCTCGCAGAGATAAAACACG
CTGGAGACGCGTTTTCCCGTCTTTCAGTGCCTTGTTCAGTTCTTC
CTGACGGGCGGTATATTTCTCCAGCTT

SEQ ID NO: 14
CTTAAGCAGAATTTCTGTCATCATGGACAGCACGGAACGGGTGA
AGCTGCGCCAGTTCTGACGCGTCTCCAGCGTGTTTTATCTCTGC
GAGCATAATGCCTGCGTCATCCGCCAGCAGGAGCTGGACTTTAC
TGATGCCCGTTATATCTGCGAAAAGACCGGGATCTGGACCCGTG
ATGGCATTCTCTGGTTTTCGTCATCCGGTGAAGAGATTGAGCCAC
CTGACAGTGTGACCTTTCACATCTGGACAGCGTACAGCCCGTTC
ACCACCTGGGTGCAGATTGTCAAAGACTGGATGAAAACGAAAGG
GGATACGGGAAAACGTAAAACCTTCGTAAACACCACGCTCGGTG
AGACGTGGGAGGCGAAAATTGGCGAACGTCCGGATGCTGAAGT
GATGGCAGAGCGGAAAGAGCATTATTCAGCGCCCGTTCCTGACC
GTGTGGCTTACCTGACCGCCGGTATCGACTCCCAGCTGGACCG
CTACGAAATGCGCGTATGGGGATGGGGGCCGGGTGAGGAAAGC
TGGCTGATTGACCGGCAGATTATTATGGGCCGCCACGACGATGA
ACAGAGCTGCTGCGTGTGGATGAGGCCATCAATAAAACCTATA
CCCGCCGGAATGGTGCAGAAATGTCGATATCCCGTATCGCTGG
GATACTGGACGCGTTTTCCCGTCTTTCAGTGCCTTGTTCAGTTCT
TCCTGACGGGCGGTATATTTCTCCAGCTT

SEQ ID NO: 15
GGCCTGCAGGGCCAGCTTACCCTTAAATTTATTTGCACTACTGGA
AAACTACCTGTTCCATGGCCAACACTTGTCACTACTTTCTCTTATG
GTGTTCAATGCTTTTCCCGTTATCCGGATCATATGAAACGGCATG
ACTTTTTCAAGAGTGCCATGCCCGAAGGTTATGTACAGGAACGC
ACTATATCTTTCAAAGATGACGGGAACTACAAGACGCGTGCTGAA
GTCAAGTTTGAAGGTGATACCCTTGTTAATCGTATCGAGTTAAAA
GGTATTGATTTTAAAGAAGATGGAAACATTCTCGGACACAAACTC
GAGTACAACTATAACTCACACAATGTATACATCACGGCAGACAAA
CAAAAGAATGGAATCAAAGCTAACTTCAAAATTCGCCACAACATT
GAAGATGGATCCGTTCAACTAGCAGACCATTATCAACAAAATACT
CCAATTGGCGATGGCCCTGTCCTTTTACCAGACAACCATTACCTG
TCGACACAATCTGCCCTTTCGAAAGATCCCAACGAAAAGCGTGA
CCACATGGTCCTTCTTGAGTTTGTAACTGCTGCTGGGATTACACA

TGGCATGGATGAGCTCTACAAATAATGAATTCGTCGAGGCCGTT

CAGGCCTCGAGGCCGTTCAGGCTCGACCCGGGGAT

SEQ ID NO: 16
MDQIEAMLCGGGEKTKVAVTTKTLADPLNWGLAADQMKGSHLDEV

KKMVEEYRRPVVNLGGETLTIGQVAAISTVGGSVKVELAETSRAGV

KASSDWVMESMNKGTDSYGVTTGFGATSHRRTKNGTALQTELIRF

LNAGIFGNTKETCHTLPQSATRAAMLVRVNTLLQGYSGIRFEILEAIT

SLLNHNISPSLPLRGTITASGDLVPLSYIAGLLTGRPNSKATGPDGES

LTAKEAFEKAGISTGFFDLQPKEGLALVNGTAVGSGMASMVLFEAN

VQAVLAEVLSAIFAEVMSGKPEFTDHLTHRLKHHPGQIEAAAIMEHIL

DGSSYMKLAQKVHEMDPLQKPKQDRYALRTSPQWLGPQIEVIRQA

TKSIEREINSVNDNPLIDVSRNKAIHGGNFQGTPIGVSMDNTRLAIAAI

GKLMFAQFSELVNDFYNNGLPSNLTASSNPSLDYGFKGAEIAMASY

CSELQYLANPVTSHVQSAEQHNQDVNSLGLISSRKTSEAVDILKLMS

TTFLVGICQAVDLRHLEENLRQTVKNTVSQVAKKVLTTGINGELHPS

RFCEKDLLKVVDREQVFTYVDDPCSATYPLMQRLRQVIVDHALSNG

ETEKNAVTSIFQKIGAFEEELKAVLPKEVEAARAAYGNGTAPIPNRIK

ECRSYPLYRFVREELGTKLLTGEKVVSPGEEFDKVFTAMCEGKLIDP

LMDCLKEWNGAPIPIC

SEQ ID NO: 17
MMDFVLLEKALLGLFIATIVAITISKLRGKKLKLPPGPIPVPVFGNWLQ

VGDDLNQRNLVEYAKKFGDLFLLRMGQRNLVVVSSPDLAKDVLHT

QGVEFGSRTRNVVFDIFTGKGQDMVFTVYSEHWRKMRRIMTVPFF

TNKVVQQYRFGWEDEAARVVEDVKANPEAATNGIVLRNRLQLLMY

NNMYRIMFDRRFESVDDPLFLKLKALNGERSRLAQSFEYNFGDFIPI

LRPFLRGYLKLCQEIKDKRLKLFKDYFVDERKKLESIKSVGNNSLKC

AIDHIIEAQEKGEINEDNVLYIVENINVAAIETTLWSIEWGIAELVNNP

EIQKKLRHELDTVLGAGVQICEPDVQKLPYLQAVIKETLRYRMAIPLLVP

HMNLHEAKLAGYDIPAESKILVNAWWLANNPAHWNKPDEFRPERFL

EEESKVEANGNDFKYIPFGVGRRSCPGIILALPILGIVIGRLVQNFELL

PPPGQSKIDTAEKGGQFSLQILKHSTIVCKPRSS

SEQ ID NO: 18
MTTQDVIVNDQNDQKQCSNDVIFRSRLPDIYIPNHLPLHDYIFENISE

FAAKPCLINGPTGEVYTYADVHVTSRKLAAGLHNLGVKQHDVVMILL

PNSPEVVLTFLAASFIGAITTSANPFFTPAEISKQAKASAAKLIVTQSR

YVDKIKNLQNDGVLIVTTDSDAIPENCLRFSELTQSEEPRVDSIPEKIS

PEDVVALPFSSGTTGLPKGVMLTHKGLVTSVAQQVDGENPNLYFN

RDDVILCVLPMFHIYALNSIMLCSLRVGATILIMPKFEITLLLEQIQRCK

VTVAMVVPPIVLAIAKSPETEKYDLSSVRMVKSGAAPLGKELEDAISA

KFPNAKLGQGYGMTEAGPVLAMSLGFAKEPFPVKSGACGTVVRNA

EMKILDPDTGDSLPRNKPGEICIRGNQIMKGYLNDPLATASTIDKDG

WLHTGDVGFIDDDDELFIVDRLKELIKYKGFQVAPAELESLLIGHPEI

NDVAVVAMKEEDAGEVPVAFVVRSKDSNISEDEIKQFVSKQVVFYK

RINKVFFTDSIPKAPSGKILRKDLRARLANGLMN

SEQ ID NO: 19
MAAVRLKEVRMAQRAEGLATVLAIGTAVPANCVYQATYPDYYFRVT

KSEHLADLKEKFQRMCDKSMIRKRHMHLTEEILIKNPKICAHMETSL

DARHAIALVEVPKLGQGAAEKAIKEWGQPLSKITHLVFCTTSGVDMP

GADYQLTKLLGLSPTVKRLMMYQQGCFGGATVLRLAKDIAENNRGA

RVLVVCSEITAMAFRGPCKSHLDSLVGHALFGDGAAAAIIGADPDQL

DEQPVFQLVSASQTILPESEGAIDGHLTEAGLTIHLLKDVPGLISENIE

QALEDAFEPLGIHNWNSIFWIAHPGGPAILDRVEDRVGLDKKRMRA

SREVLSEYGNMSSASVLFVLDVMRKSSAKDGLATTGEGKDWGVLF

GFGPGLTVETLVLHSVPVPVPTAASA

SEQ ID NO: 20
MGDVIVLYASPGMGHIVSMVELGKFIVHRYGPHKFSITILYTCGSIVD

TASIPVYIRRISHSHPFISFRQFPRVTNNITRNISVPAITFDFIRQNDPH

VRSALQEISKSATVRAFIIDLFCTSALPIGKEFNIPTYYFRTSGAAILAA

FLYLPKIDEQTKTTESFKDLRDTVFEFPGWKSPLKATHMVQLVLDRN

DPAYSDMIYFCSHLPKSNGIIVNTFEELEPPSVLQAIAGGLCVPDGPT

PPVYYVGPLIEEEKELSKDADAAEKDCLSWLDKQPSRSVLFLCFG

SMGSFPAAQLKEIANGLEASGQRFLWVVKKPPVEEKSKQVHGVDD

FDLKGVLPEGFLERTADRGMVVKSWAPQVVVLKKESVGGFVTHCG

WNSVLEAVVAGVPMIAWPLYAEQHMNRNVLVTDMEIAIGVEQRDEE

GGFVSGEEVERRVRELMESEGGRVLRERCKKLGEMASAALGETGS

STRNLVNFVSSIT

SEQ ID NO: 21
MPFGIDNTDFTVLAGLVLAVLLYVKRNSIKELLMSDDGDITAVSSGN

RDIAQVVTENNKNYLVLYASQTGTAEDYAKKFSKELVAKFNLNVMC

ADVENYDFESLNDVPVIVSIFISTYGEGDFPDGAVNFEDFICNAEAGA

LSNLRYNMFGLGNSTYEFFNGAAKKAEKHLSAAGAIRLGKLGEADD

GAGTTDEDYMAWKDSILEVLKDELHLDEQEAKFTSQFQYTVLNEITD

SMSLGEPSAHYLPSHQLNRNADGIQLGPFDLSQPYIAPIVKSRELFS

SNDRNCIHSEFDLSGSNIKYSTGDHLAVWPSNPLEKVEQFLSIFNLD

PETIFDLKPLDPTVKVPFPTPTTIGAAIKHYLEITGPVSRQLFSSLIQFA

PNADVKEKLTLLSKDKDQFAVEITSKYFNIADALKYLSDGAKWDTVP

MQFLVESVPQMTPRYYSISSSSLSEKQTVHVTSIVENFPNPELPDAP

PVVGVTTNLLRNIQLAQNNVNIAETNLPVHYDLNGPRKLFANYKLPV

HVRRSNFRLPSNPSTPVIMIGPGTGVAPFRGFIRERVAFLESQKKGG

NNVSLGKHILFYGSRNTDDFLYQDEWPEYAKKLDGSFEMVVAHSRL

PNTKKVYVQDKLKDYEDQVFEMINNGAFIYVCGDAKGMAKGVSTAL

VGILSRGKSITTDEATELIKMLKTSGRYQEDVW

SEQ ID NO: 22
MPITIKSRSKGLRDTEIDLSKKPTLDDVLKKISANNHNISKYRIRLTYK
KESKQVPVISESFFQEEADDSMEFFIKDLGPQISWRLVFFCEYLGPV
LVHSLFYYLSTIPTVVDRWHSASSDYNPFLNRVAYFLILGHYGKRLF
ETLFVHQFSLATMPIFNLFKNCFHYWVLSGLISFGYFGYGFPFGNAK
LFKYYSYLKLDDLSTLIGLFVLSELWNFYCHIKLRLWGDYQKKHGNA
KIRVPLNQGIFNLFVAPNYTFEVWSWIWFTFVFKFNLFAVLFLTVSTA
QMYAWAQKKNKKYHTRRAFLIPFVF

SEQ ID NO: 23
ATGGGTGGTGTTGATTTTGAAGGTTTCAGAAAGTTGCAAAGAGCT
GACGGTTTTGCTTCCATTTTGGCTATTGGTACTGCTAATCCACCA
AACGCTGTTGATCAATCTACTTACCCAGATTACTACTTCAGAATCA
CCGGTAACGAACATAACACTGAATTGAAGGACAAGTTCAAGAGA
ATCTGCGAAAGATCCGCTATCAAGCAAAGATATATGTACTTGACC
GAAGAAATCTTGAAAAAGAACCCAGATGTTTGCGCCTTTGTTGAA
GTTCCATCTTTGGATGCTAGACAAGCTATGTTGGCTATGGAAGTT
CCAAGATTGGCTAAAGAAGCTGCTGAAAAGGCTATCCATGAATG
GGGTCAATCAAGTCTGGTATTACCCATTTGATTTTCTGTTCTACT
ACCACCCCAGATTTGCCAGGTGCTGATTTCGAAGTTGCTAAGTTG
TTGGGTTTACACCCATCTGTTAAGAGAGTTGGTGTTTTCCAACAT
GGTTGTTTTGCTGGTGGTACTGTTTTGAGATTAGCTAAGGATTTG
GCCGAAAACAATAGAGGTGCTAGAGTTTTGGTTATCTGCTCTGAA
ACTACTGCTGTTACTTTTAGAGGTCCATCTGAAACCCATTTGGAT
TCTTTGGTTGGTCAAGCTTTGTTTGGTGATGGTGCTTCTGCTTTG
ATAGTTGGTGCTGATCCAATTCCACAAGTTGAAAAAGCTTGCTTC
GAAATTGTCAGAACCTCTCAAACTGTTGTTCCAAATTCAGATGGT
GCTATTGGTGGTAAGGTTAGAGAAGTTGGTTTGACCTTCCAATTG
AAGGGTGCTGTTCCAGATTTGATTTCCGCTAACATTGAAAACTGC
TTGGTTGAAGCTTTCTCCCAATTCAAAATTTGCGACTGGAACAAG
TTGTTCTGGGTTGTTCATCCAGGTGGTAGAGCTATTTTGGATAGA
GTTGAAGCTAAGTTGAACTTGGACCCAACTAAGTTGATTCCAACC
AGACATGTTATGTCCGAATACGGTAATATGTCCTCTGCTTGCGTT
CATTTCATTTTGGACGAAACTAGAAAGGCCTCTTTGAGAAATGGT
TGTTCTACAACTGGTGAAGGTTTGGAAATGGGTGTTTTGTTCGGT
TTTGGTCCAGGTTTGACTATTGAAACCGTTGTTTTGAAGTCCGTC
CCATTACAATGA

SEQ ID NO: 24
MGGVDFEGFRKLQRADGFASILAIGTANPPNAVDQSTYPDYYFRIT
GNEHNTELKDKFKRICERSAIKQRYMYLTEEILKKNPDVCAFVEVPS
LDARQAMLAMEVPRLAKEAAEKAIHEWGQSKSGITHLIFCSTTTPDL
PGADFEVAKLLGLHPSVKRVGVFQHGCFAGGTVLRLAKDLAENNR
GARVLVICSETTAVTFRGPSETHLDSLVGQALFGDGASALIVGADPI

PQVEKACFEIVRTSQTVVPNSDGAIGGKVREVGLTFQLKGAVPDLIS
ANIENCLVEAFSQFKICDWNKLFWVVHPGGRAILDRVEAKLNLDPTK
LIPTRHVMSEYGNMSSACVHFILDETRKASLRNGCSTTGEGLEMGV
LFGFGPGLTIETVVLKSVPLQ

SEQ ID NO: 25
MSASSSIFIKSRSKSLKDVKLEVPTENTLTYQSVLQQISKSNHNISVN
RLRLSYLKEGKQVAIGPSELNDVGKKNTFDSVNEWYVKDLGPQISW
RLVFFIEYLGPILIHSLVYLLSLNATVRDKFHSKNVPYNDFFNKFIYRLI
MVHYLKREFETLFIHSFSLETMPLFNLFKNSFHYWILNGLISLGYFGY
GFPFANKTLYRVYSALKISDFRVLTALFGLSEMFNFYIHVALRRWGD
EQKRNGVTKRVPLNSGLFKLLVAPNYTFESWAWMFFTLLFKLNLFS
VLFLVVSVVQMYLWAQKKNKKYGTKRAFLIPFLF

SEQ ID NO: 26
MYFDEEQLLKYTIYAYRLSFFVGICSLFIAKSCLPEFLQYGKTYRPKE
NSKYSSILERIKKFTVPKAYFSHFYYLATFLSLVTLYFYPKFPIVWIIFG
HSLRRLYETLYVLHYTSNSRMNWSHYLVGIWFYSVLLLILNISLYKNS
IPNTLNMNAFIIFCIASWDQYKNHVILANLVKYSLPTGRLFRLVCCPH
YLDEIIIYSTLLPYEQEFYLTLVWVITSLTISALETKNYYRHKFKDNHVA
PYAIIPFII

SEQ ID NO: 27
ATGGTTACTGTTGAAGAAGTTAGAAAAGCTCAAAGGGCAGAAGG
TCCAGCCACAGTGATGGCTATTGGAACCGCAGTTCCTCCAAATT
GTGTAGATCAGGCCACTTATCCTGACTACTACTTTAGAATAACAA
ACTCTGAGCATAAGGCTGAATTGAAAGAAAAGTTCCAAAGGATGT
GCGACAAATCACAGATCAAGAAAAGATACATGTACCTTAATGAGG
AAGTCCTAAAGGAAAACCCAAATATGTGTGCATACATGGCCCCTT
CCCTTGACGCTAGACAAGATATTGTGGTTGTAGAGGTCCCAAAAT
TGGGCAAGGAAGCAGCTGTTAAAGCCATAAAGGAATGGGGTCAA
CCTAAGAGCAAAATCACCCACCTTGTGTTTTGCACTACAAGCGGA
GTTGACATGCCAGGCGCAGATTATCAGCTAACCAAACTTTTGGGT
TTAAGGCCTTCTGTAAAAAGATTGATGATGTACCAACAAGGTTGT
TTCGCTGGAGGCACTGTCTTAAGACTAGCCAAGGATCTTGCAGA
GAACAACAAAGGTGCTAGGGTGTTGGTTGTATGCTCAGAAATTAC
AGCCGTCACCTTTAGAGGACCAACTGACACTCACTTAGATTCCCT
AGTTGGTCAGGCATTGTTTGGCGACGGTGCTGCCGCAATAATCA
TTGGAAGTGATCCTATTCCAGAGGTGGAAAAGCCTCTTTTTGAAC
TTGTTAGCGCTGCCCAAACTATATTGCCAGATTCTGAGGGTGCAA
TCGACGGCCACTTAAGGGAAGTAGGTCTAACCTTCCATCTTTTGA
AGATGTCCCTGGTTTAATTTCAAAGAACGTGGAAAAATCCCTAA
CAGAGGCTTTTAAACCATTGGGTATAAGTGACTGGAATAGCTTAT
TCTGGATCGCTCACCCAGGCGGCCCTGCCATACTTGACCAGGTT
GAAGCAAAATTGAGCTTAAAGCCAGAAAAACTAAGAGCTACTAGA

CATGTATTGTCAGAGTATGGTAACATGTCCAGTGCCTGTGTCCTT
TTCATTTTGGATGAAATGAGGAGAAAAAGCAAGGAGGACGGCCT
AAAAACCACAGGTGAGGGAATCGAATGGGGTGTTCTATTCGGCT
TTGGTCCAGGCCTTACTGTGGAGACAGTTGTACTTCATTCAGTCG
CAATTAATTAG

SEQ ID NO: 28
ATGGCTAATCATCATAATGCTGAAATTGAGGAAATAAGAAACAGA
CAAAGAGCCCAGGGTCCAGCTAATATCTTGGCAATTGGAACTGC
CACACCTTCTAATTGTGTTTATCAAGCTGATTACCCAGACTATTAC
TTCAGAATCACCAACTCAGAGCACATGACAGACTTAAAGTTGAAA
TTCAAGAGAATGTGCGAAAAGAGTATGATAAGAAAGAGATACATG
CACATCACCGAGGAGTATTTGAAGGAGAACCCTAACGTGTGCGC
CTACGAGGCCCCAAGTTTAGACGCTAGACAGGACTTGGTAGTCG
TTGAAGTGCCAAGATTAGGAAAAGAAGCCGCTAGTAAGGCCATT
AAAGAATGGGGACAACCAAAATCTAAGATCACTCACTTAATATTC
TGTACAACCTCCGGTGTCGACATGCCAGGTGCAGACTACCAATT
GACAAAGTTATTGGGATTAAGACCAAGTGTGAAAAGATTCATGAT
GTATCAGCAAGGATGCTTCGCAGGAGGTACTGTTTTGAGATTGG
CAAAGGACTTAGCCGAAAATAACGCTGGTGCCAGAGTATTAGTG
GTGTGTTCTGAAATTACAGCCGTGACTTTCAGAGGACCATCCGA
CTCCCACTTGGATAGTTTAGTTGGTCAGGCTTTGTTTGGTGACGG
AGCCGCAGCCGTGATATTAGGAAGTGACCCTGATTTGTCAGTCG
AAAGACCATTATTCCAGTTGATTTCTGCCGCACAAACTATCTTAC
CAGACAGTGATGGAGCTATAGACGGTCATTTGAGAGAAGTGGGT
TTAACATTTCATTTGTTAAAAGATGTTCCTGGTTTAATAAGTAAGA
ATATTGAAAAGTCATTGAAGGAGGCTTTCGGTCCAATAGGAATTA
GTGATTGGAACTCCTTATTTTGGATAGCACACCCAGGAGGTCCT
GCTATATTGGACCAGGTAGAGTTGAAGTTAGGTTTAAAGGAAGA
GAAGATGAGAGCTACTAGACAAGTCTTAAGTGATTACGGTAACAT
GTCATCTGCCTGTGTTTTGTTCATATTAGACGAAATGAGAAAGAA
ATCAATTGAAGAGGGAAAAGCTACCACAGGAGAAGGATTAGACT
GGGGTGTTTTGTTCGGATTTGGTCCTGGATTGACTGTTGAAACC
GTAGTCTTACATAGTGTGCCTGCTACATTCACTCACTGA

SEQ ID NO: 29
ATGGTTACTGTTGAAGAATATAGAAAAGCTCAAAGGGCAGAGGG
TCCAGCCACAGTCATGGCTATTGGAACCGCAACTCCTACAAATTG
TGTGGATCAGTCTACCTACCCAGACTATTACTTTAGAATAACTAA
CTCAGAACATAAGACAGATTTGAAAGAAAAGTTCAAAAGGATGTG
CGAAAAGTCCATGATCAAAAAGAGATATATGCACTTAACCGAGGA
AATTCTAAAGGAGAACCCTAGTATGTGTGAGTACATGGCCCCAA
GCCTTGACGCTAGACAAGATATAGTTGTAGTCGAAGTGCCTAAG

CTAGGAAAAGAAGCAGCCCAGAAGGCTATCAAAGAATGGGGTCA
ACCAAAGAGCAAAATTACCCACCTTTTTTTCTGCACAACCTCAGG
AGTTGACATGCCTGGCTGTGATTATCAACTAACTAAACTTTTGGG
TTTAAGGCCATCCGTAAAGAGATTGATGATGTACCAGCAAGGTTG
CTTTGCAGGAGGCACAGTCTTAAGACTAGCTAAAGATCTTGCCG
AAAATAATAAGGGTGCAAGGGTTTTGGTGGTTTGTAGTGAGATAA
CTGCTGTAACCTTCAGAGGACCTAACGACACTCACTTAGATAGCC
TAGTCGGTCAAGCCTTGTTTGGCGACGGTGCAGGAGCTATCATT
ATTGGTTCTGATCCAATACCTGGCGTGGAAAGGCCATTATTCGAA
CTTGTTTCAGCCGCACAGACTTTGTTACCTGATTCCCATGGTGCT
ATCGACGGACACCTAAGAGAGGTAGGTCTTACCTTTCATTTGTTA
AAAGATGTCCCTGGTTTAATTAGTAAGAATATAGAGAAGAGCTTG
GAAGAGGCCTTCAAGCCATTAGGAATCAGCGACTGGAACTCACT
TTTTTGGATTGCACATCCTGGCGGCCCAGCTATACTTGACCAAGT
TGAAATCAAATTGGGCCTAAAGCCTGAAAAATTGAAGGCCACAA
GAAATGTGTTATCCGATTATGGAAACATGAGTTCTGCATGTGTTC
TTTTTCATTTTGGATGAGATGAGGAAGGCTTCAGCTAAAGAAGGTC
TAGGCACTACAGGTGAGGGCTTGGAGTGGGGTGTACTATTCGGC
TTTGGACCAGGCCTTACCGTCGAAACTGTGGTTTTACACTCTGTA
GCCACATAA

SEQ ID NO: 30
ATGGCTGCTACAATGACCGTTGAAGAAGTGAGAAATGCTCAAAG
GGCCGAAGGTCCCGCAACAGTATTAGCCATTGGCACAGCTACTC
CAGCAAATTGTGTTTACCAGGCAGATTATCCAGACTATTATTTTAA
GATCACAAAATCAGATCACATGGCCGACTTGAAAGAAAAGTTTAA
AAGAATGTGTGATAAGAGTCAAATCAGAAAGAGGTATATGCATTT
GACCGAGGAAATTTTAGAGGAAAACCCAAATATGTGCGCTTACAT
GGCTCCTTCTTTGGATGCTAGGCAAGACATAGTAGTTGTGGAAG
TTCCCAAGTTGGGAAAGGCAGCTGCACAGAAGGCAATAAAAGAA
TGGGGTCAGCCAAGATCTAAGATAACTCATTTAGTCTTCTGTACT
ACTTCAGGTGTTGATATGCCCGGCGCTGACTATCAATTGACAAAG
ATGTTGGGTTTGAGACCATCAGTTAAAAGGTTGATGATGTACCAA
CAAGGATGTTTTGCCGGCGGAACCGTTTTGAGATTGGCTAAAGA
CTTGGCTGAGAACAATAGAGGAGCTAGAGTATTGGTTGTTTGCA
GTGAAATTACAGCTGTTACTTTTAGAGGCCCACACGAATCTCACT
TGGATTCTTTAGTAGGTCAAGCATTGTTTGGTGATGGAGCTGCCG
CAGTCATTATTGGTGCAGATCCAGATTTATCTGTCGAAAGACCAT
TGTTTCAATTAGTCTCTGCCTCTCAAACAATATTGCCAGACTCAG
AAGGTGCTATTGACGGTCACTTGAGGGAGGTGGGTTTAACTTTT
CATTTGTTAAAAGACGTACCTGGATTAATTAGTAAGAATATAGAAA
GAGCATTAGAAGAGGCTTTCAAACCTTTAGGCATTGATCATTGGA

-continued
ATTCAGTGTTCTGGATTGCACATCAGGGTGGTCCTGCTATCTTAG
ATATGGTTGAAGCCAAAGTTAACTTAAACAAAGAAAGAATGAGAG
CCACCAGGCATGTGTTAAGTGAATACGGCAACATGTCCTCCGCA
TGCGTATTATTCATCATGGATGAGATGAGAAAGAGATCAGCAGA
GGATGGTCATGCAACAACTGGTGAAGGAATGGATTGGGGTGTAT
TATTCGGCTTCGGACCTGGTTTAACTGTCGAGACCGTCGTCTTAC
ATTCCGTCCCTATCTCCGCCGGTGCCACTGCTTGA SEQ ID NO: 31
ATGGTTACTGTCGAAGAATTCCATAGGGCTACCAGGGCTGAAGG
TCCAGCTACCGTTTTAGCCATCGGTACTGCCAACCCTCCTAACTG
TGTCGAGCAATCCACCTACGCTGACTACTATTTCCGTATTTGTAA
GTCCGAACACCTAACCGACTTGAAAAAGAAGTTCGACCGTATGT
GTGAAAAGTCCTGTATCAAGAAGCGTTACATGCACTTGACCGAA
GAATTTTTAAAAGAGAATGATAACTTCACTGCTTATGAGGCTCCTT
CTTTGGACGCTCGTCAAGACATCGTCGTTGTCGAAATTCCTAAGT
TGGGTAAGGAAGCTGCCCAAAAAGCTATTAAGGAATGGGGTCAA
CCAAAGTCTAAAATTACTCACGTTATCTTCTGTACCACTTCTGGTG
TTGACATGCCAGGTGCCGACTACCAAATCACCAAGTTATTAGGTT
TACGTCCTTCCGTCAAGAGATTCATGATGTACCAACAAGGTTGCT
TCGCTGGTGGTACCGTCTTAAGAATGGCCAAGGATTTAGCCGAG
AATAATGCTGGTGCTAGAGTCCTAGTTGTCTGTTCCGAGATCACC
GCTATTACCTTCAGAGGCCCATCTGATACCCACTTAGATTCTTTA
GTTGGTCAAGCCTTATTCGGTGACGGTGCTGCTGCTGTTATTGTT
GGTTCCGATCCAATCGTCGGTGTTAAAGACCTTTGTTTCAATTG
GTTTCTGCTGCTCAGACTATTTTGCCAGACTCTGAAGGTGCTATT
GATGGTCACGTCAGAGAAGTTGGTTTGACTTTCCATTTGTTGAAG
GATGTTCCAGGTTTGATCTCTAAGGACATTGAAAAGTCTTTGAAA
GAGGCTTTCGCTCCATTGGGTATTTCCGATTGGAATTCCTTGTTT
TGGATTGTTCATCCAGGTGGTCCAGCTATCCTAGATCAAGTCGGT
GAAAAGCTAGGTTTGAAGCCTGAAATCATGGTCCCTACTAGACAC
GTTTTGTCTGAATACGGTAACATGTCTTCTGCTTGCGTCTTGTTC
GTCATGGATGAAATGCGTAAAGCCTCTGCTAAAGATGGTTGTACC
AGCACTGGTGAAGGTAAGGACTGGGGTGTCCTATTTGGCTTCGG
TCCAGGTTTGACTGTTGAAACCGTTGTTTTGCACAGCGTTCCTTT
AAACTAA SEQ ID NO: 32
ATGGTCACCGTCGAAGAAGTTAGAAAAGCTCAAAGAGCTGAAGG
TCCAGCTACTGTTTTGGCTATTGGTACTGCTACTCCACCAAATTG
TGTTGATCAAGCTACTTACCCAGACTACTACTTCAGAATTACCAA
CTCTGAACACAAGACCGAATTGAAAGAAAAGTTCCAAAGAATGTG
CGACAAGTCCATGATCAAGACCAGATATATGTACTTGACCGAAGA
AATCTTAAAAGAAAACCCAACCGTCTGCGAATATATGGCTCCATC -continued
TTTGGATGCTAGACAAGATATGGTTGTTGTTGAAGTTCCAAGATT
GGGTAAAGAAGCTGCTACTAAGGCTATCAAAGAATGGGGTCAAC
CTAAGTCTAAGATCACCCATTTGGTTTTCTGTACTACCTCTGGTG
TTGATATGCCAGGTGCTGATTATCAATTGACTAAGTTGTTGGGTT
TAAGACCATCCGTCAAGAGATTGATGATGTACCAACAAGGTTGTT
TTGCTGGTGGTACAGTTTTGAGATTGGCAAAAGATTTGGCCGAAA
ACAACAAAGGTGCTAGAGTTTTGGTTGTCTGCTCTGAAATTACTG
CTGTTACTTTTAGAGGTCCATCCGATACTCATTTGGATTCTTTGGT
TGGTCAAGCCTTGTTTGGTGATGGTGCTGCTGCTGTTATTATTGG
TTCTGATCCAGTTCCTGAAGTCGAAAAGCCATTATTCGAATTGGT
TTCTGCTGCCCAAACTATCTTGCCAGATTCAGATGGTGCTATTGA
TGGTCATTTGAGAGAAGTTGGTTTGACCTTCCATTTGTTGAAAGA
TGTCCCAGGTTTGATTTCCAAGAACATCGAAAAGTCTTTGAACGA
AGCCTTCAAGCCAATTGGTATTTCTGATTGGAATTCCTTGTTCTG
GATTGCTCATCCAGGTGGTCCAGCAATTTTGGATCAAGTTGAATC
TAAGTTGGCCTTGAAGCCAGAAAAATTGGAAGCTACTAGACAAGT
CTTGTCCGATTACGGTAATATGTCATCTGCTTGCGTTTTGTTCATC
TTGGATGAAGTCAGAAGAAAGTCTGCTGAAAAGGGTTTGAAAACT
ACTGGTGAAGGTTTGGAATGGGGTGTTTTGTTTGGTTTTGGTCCA
GGTTTAACTGTTGAAACCGTTGTCTTGCATTCTGTTGGTGCTTAA SEQ ID NO: 33
ATGGTTACAGTCGAGGAAGTTCGCAAGGCTCAACGGGCGGAGG
GTCCAGCCACAGTCATGGCCATCGGGACAGCAACTCCTTCCAAC
TGTGTGGATCAGGCTACCTACCCCGACTACTACTTTCGTATCACC
AACAGCGAGCACAAGGTTGAGCTCAAAGAAAAATTCCAGCGCAT
GTGCGACAAATCTATGATCAAGAAACGTTATATGTACTTGACTGA
AGAAATTTTAAAAGAGAACCCAAGTGTGTGCGAGTACATGGCTC
CTTCAATTGATGCAAGGCAGGACATGGTGGTTGTGGAAGTCCCA
AAACTTGGCAAAGAGGCTGCCACCAAAGCCATCAAGGAATGGGG
ACAGCCCAAGTCCAAAATCACCCACTTGGTCTTTTGCACCACCAG
CGGTGTCGACATGCCTGGCGCCGACTACCAACTCACCAAGCTCT
TGGGCCTCCGCCCCTCCGTCAAGCGCCTCATGATGTACCAGCAA
GGGTGCTTCGCCGGTGGGACGGTCCTCCGTTTGGCCAAGGACT
TGGCCGAAAACAACAAGGGTGCACGTGTTCTTGTTGTGTGCTCT
GAGATCACCGCGGTTACCTTCCGTGGGCCTAGTGACACCCACCT
TGATAGTCTTGTGGGCCAAGCTTTGTTTGGCGACGGTGCAGCGG
CCGTAATCATTGGTGCGGATCCAGTGCCCGAAGTCGAGAAGCCC
TTGTTTGAATTGGTGTCGGCGGCACAAACCATTCTCCCCGACAG
TGATGGGCTATCGACGGACATCTCCGTGAAGTAGGGCTTACAT
TTCACCTTCTCAAGGATGTTCCCGGGCTTATTTCGAAGAACATCG
AAAAGAGCCTTAATGAGGCTTTCAAGCCTATTGGGATTTCGGACT

GGAACTCACTCTTCTGGATTGCACACCCAGGTGGCCCTGCTATT

CTGGACCAAGTAGAGGCCAAGTTGGCATTGAAGCGGAGAAACT

AGAAGCAACAAGGCAAGTGTTGTCGGATTACGGTAACATGTCGA

GTGCTTGTGTGCTTTTTATTTTGGACGAGGTCAGGAGGAAGTCC

GCCGAGAAAGGACTCAAAACGACCGGGGAGGGACTGGAGTGGG

GTGTGCTTTTCGGATTTGGGCCCGGCCTCACGGTGGAGACCGTC

GTGCTTCACAGCGTGGGTTTAACGGCTTGA

SEQ ID NO: 34
ATGGTGACCGTCGAGGAAGTTCGCAAGGCTCAGAGGGCTGAGG

GTCCGGCCACAGTCTTAGCTATTGGGACTGCAACTCCTTCCAATT

GTGTAGACCAGGCCACATACCCTGACTACTACTTTCGTATCACCA

ACAGCGAGCACAAGACTGAGCTCAAAGAAAAATTTCAGCGCATG

TGTGACAAATCTATGATCAAGAAGCGTTACATGTACTTGACTGAA

GAAATTCTGAAAGAAAACCCGACTGTGTGCGAGTACATGGCTCC

CTCACTCGATGCTCGGCAGGACATGGTGGTTGTTGAAGTCCCAA

GGCTTGGCAAAGAAGCGGCCACCAAGGCAATTAAGGAATGGGG

ACAGCCCAAGTCTAAAATCACCCACTTGGTCTTTTGCACCACCAG

CGGTGTCGACATGCCCGGTGCCGACTACCAGCTCACCAAGCTAT

TGGGCCTCCGCCCATCCGTCAAGCGCCTCATGATGTACCAACAA

GGCTGTTTTGCTGGAGGCACGGTCCTCCGTTTGGCCAAGGACTT

GGCCGAAAACAACAAGGGTGCACGTGTTCTTGTTGTGTGCTCTG

AGATCACCGCGGTCACCTTCCGAGGGCCTAGTGACACCCACCTT

GATAGTCTTGTGGGCCAAGCTTTGTTTGGCGACGGTGCAGCGGC

CGTCATCATTGGTGCAGATCCATTGCCCGAAGTCGAGAAACCCT

TATTTGAGCTAGTGTCTGCTGCCCAAACCATCCTCCCCGACAGT

GATGGGCTATTGACGGACATCTTCGTGAAGTTGGGCTTACATTT

CACCTTCTCAAGGATGTTCCCGGGCTTATTTCGAAGAACATCGAA

AAGAGCCTTAATGAGGCCTTCAAGCCTATAGGCATCTCGGACTG

GAACTCGCTTTTCTGGATTGCACACCCTGGTGGCCCTGCTATTCT

AGACCAAGTAGAGTCCAAGTTGGCACTTAAGCGGAGAAACTAG

AAGCAACAAGGCAAGTGCTGTCTAATTACGGCAACATGTCAAGT

GCGTGTGTCTTGTTTATTTTGGACGAGGTGAGGAGGAAATCCGC

TGAGAAAGGACTCAAAACAACTGGAGAAGGACTGGAGTGGGGC

GTGCTCTTCGGATTTGGGCCTGGCCTCACTGTCGAGACCGTTGT

GCTTCACAGTGTGGCTGCTTGA

SEQ ID NO: 35
ATGGTGACCGTCGAAGAAGTTCGCAAGGCTCAACGGGCTGAGG

GTCCGGCCACTGTTTTGGCCATTGGGACAGCAACTCCTCCCAAC

TGTGTGGATCAAGCCACATACCCCGACTATTACTTTCGTATCACC

AACAGTGAGCACAAGACTGAGCTCAAAGAAAAATTCCAGCGCAT

GTGTGACAAATCTATGATCAAGAAGCGTTACATGTACTTGACTGA

AGAAATTCTGAAAGAGAACCCAACTGTGTGCGAGTACATGGCTC

CCTCACTCGATGCTCGGCAGGACATGGTGGTTGTTGAAGTCCCA

AGGCTTGGCAAAGAGGCTGCCACCAAGGCCATTAAGGAATGGG

GACAGCCCAAGTCCAAAATCACCCACTTGGTCTTTTGCACCACCA

GCGGTGTCGACATGCCCGGCGCCGACTACCAACTCACCAAGCT

CTTGGGCCTCCGCCCCTCCGTCAAGCGCCTCATGATGTACCAAC

AAGGTTGCTTCGCCGGCGGGACGGTCCTCCGTTTGGCCAAGGA

CTTGGCCGAGAACAACAAGGGTGCACGTGTTCTTGTTGTGTGCT

CTGAGATCACCGCAGTCACCTTCCGCGGGCCTAGTGACACCCAC

CTTGACAGTCTTGTGGGTCAAGCCTTGTTTGGTGACGGCGCAGC

GGCCGTCATCATTGGTTCGGATCCAGTGCCCGAAGTCGAGAAGC

CCTTGTTTGAATTGGTGTCAGCAGCACAAACCATTCTTCCCGACA

GTGATGGGGCTATTGACGGCCATCTCCGTGAAGTAGGGCTTACA

TTTCACCTTCTCAAGGACGTTCCTGGGCTTATTTCCAAGAATATC

GAAAAGAGCCTTAACGAGGCCTTCAAGCCTATAGGCATTTCAGA

CTGGAACTCGCTCTTCTGGATTGCACACCCAGGTGGCCCTGCTA

TTCTGGACCAAGTAGAGTCCAAGTTGGCCCTTAAGCGGAGAAA

CTAGAAGCTACAAGGCAAGTGCTGTCTGATTACGGCAACATGTC

GAGTGCGTGTGTCTTGTTTATTTTGGACGAAGTGAGGAGGAAGT

CTGCTGAGAAAGGACTCAAAACAACTGGAGAAGGACTGGAGTGG

GGCGTACTCTTCGGATTTGGGCCTGGCCTCACTGTTGAGACCGT

TGTGCTTCACAGTGTGGGTGCTTGA

SEQ ID NO: 36
ATGGTGACTGTCCAGGAAGTTCGCAAGGCTCAACGGGCTGAGG

GTCCGGCCACAGTATTCGCCATTGGGACAGCAACTCCTCCCAAT

TGTGTGGACCAAGCCACATACCCCGACTATTACTTTCGTATCACC

AACAGTGAGCACAAGCTGAGCTCAAAGAAAAATTCCAGCGCAT

GTGTGACAAATCTATGATCAAGAAGCGTTACATGTACTTGACTGA

GGAAATTCTAAAGGAGAATCCAAGTGTGTGCGAGTACATGGCAC

CATCACTTGATGCTCGGCAGGACATGGTGGTTGTTGAAGTCCCA

AGGCTTGGCAAAGAGGCTGCCACCAAGGCCATCAAGGAATGGG

GACAGCCCAAGTCCAAAATCACCCACTTGGTCTTTTGCACCACCA

GCGGTGTCGACATGCCCGGCGCTGACTACCAGCTCACCAAGCT

ATTGGGCCTCCGCCCCTCTGTTAAGCGCCTCATGATGTACCAAC

AAGGTTGTTTCGCTGGAGGCACGGTTCTCCGTTTGGCCAAGGAC

TTGGCCGAAAACAACAAGGGTGCACGTGTTCTTGTTGTGTGCTC

TGAGATCACCGCGGTCACCTTCCGTGGGCCTAGTGACACCCACC

TTGACAGTCTTGTGGGTCAAGCCTTGTTTGGCGACGGTGCAGCG

GCCGTCATCATTGGTGCCGACCCAGTGCCCGAAGTCGAGAAGC

CCTTGTTTGAATTGGTCTCGGCGGCACAAACCATTCTCGCTGACA

GTGATGGGGCTATCGACGGACATCTCCGTGAAGTAGGGCTTACG

-continued

TTTCACCTTTTGAAGGACGTTCCCGGGCTTATTTCAAAGAACATC
GAAAAGAGCCTTAACGAGGCCTTCAAGCCTATAGGCATTTCGGA
CTGGAACTCACTCTTCTGGATTGCACACCCAGGTGGCCCTGCTA
TTCTGGACCAAGTAGAGGCCAAGTTGGCGTTGAAGCGGAGAAA
TTAGAAGCGACAAGGCAAGTGTTGTCAGATTACGGCAACATGTC
GAGTGCGTGTGTCTTGTTTATTTTGGACGAGGTGAGGAGGAAGT
CAGCTGAGAAAGGACTGGAGACAACTGGAGAAGGACTGGAATG
GGGTGTGCTATTTGGATTTGGGCCTGGCCTCACGGTGGAGACC
GTCGTGCTTCACAGCGTGGCTGCTTGA

SEQ ID NO: 37
ATGGCCTCCGTTGAAGAAATTAGAAATGCTCAAAGAGCTAAGGG
TCCAGCTACTATTTTGGCTATTGGTACTGCTACTCCAGATCATTG
TGTTTACCAATCTGATTACGCCGACTACTACTTCAGAGTTACTAA
GTCTGAACACATGACCGAATTGAAGAAAAAGTTCAACAGAATCTG
CGACAAGTCCATGATCAAGAAGAGATATATCCACTTGACCGAAG
AAATGTTGGAAGAACATCCAAACATTGGTGCTTATATGGCTCCAT
CCTTGAACATCAGACAAGAAATTATCACTGCCGAAGTTCCAAAGT
TGGGTAAAGAAGCTGCTTTGAAGGCTTTGAAAGAATGGGGTCAA
CCTAAGTCTAAGATCACCCATTTGGTTTTCTGTACTACCTCTGGT
GTTGAAATGCCAGGTGCTGATTACAAATTGGCTAACTTGTTGGGT
TTGGAAACCTCTGTTAGAAGAGTTATGTTGTACCATCAAGGTTGT
TATGCTGGTGGTACTGTTTTGAGAACTGCTAAAGATTTGGCTGAA
AACAATGCTGGTGCTAGAGTTTTGGTTGTTTGCTCTGAAATTACC
GTTGTTACTTTCAGAGGTCCATCTGAAGATGCTTTGGATTCTTTG
GTTGGTCAAGCTTTGTTTGGTGATGGTTCTGCTGTTATAGTT
GGTTCTGATCCAGATATCTCCATCGAAAGACCTTTGTTCCAATTG
GTTTCAGCTGCTCAAACTTTCATTCCAAATTCTGCTGGTGCAATT
GCTGGTAACTTGAGAGAAGTTGGTTTGACTTTTCATTTGTGGCCA
AACGTTCCAACTTTGATCTCCGAAAACATTGAAAACTGTTTGACC
AAGGCCTTTGATCCAATCGGTATTTCTGATTGGAATTCCTTGTTCT
GGATTGCTCATCCAGGTGGTCCAGCAATTTTGGATGCTGTTGAA
GCTAAGGTTGGTTTGGATAAGCAAAAGTTGAAGGCCACCAGACA
CATTTTGTCTGAATACGGTAATATGTCCTCTGCCTGCGTTTTGTTT
ATTTTGGACGAAATGAGAAAGAAGTCCTTGAAAGAAGGTAAGACT
ACTACAGGTGAAGGTTTGGATTGGGGTGTTTTGTTCGGTTTTGGT
CCAGGTTTGACTATTGAAACTGTTGTCTTGCATTCCGTTGGTACT
GATTCTAACTGA

SEQ ID NO: 38
ATGGCCTCTGTTGAAGAATTCAGAAATGCTCAAAGAGCTAAAGGT
CCAGCTACCATTTTGGCTATTGGTACTGCTACTCCAGATCATTGT
GTTTACCAATCTGATTACGCCGACTACTACTTCAGAGTTACTAAG
TCTGAACACATGACCGAATTGAAGAAAAAGTTCAACAGAATCTGC

-continued

GACAAGTCCATGATCAAGAAGAGATATATCCACTTGACCGAAGAA
ATGTTGGAAGAACATCCAAACATTGGTGCTTATATGGCTCCATCC
TTGAACATCAGACAAGAAATTATCACTGCCGAAGTTCCAAGATTG
GGTAGAGATGCTGCTTTGAAGGCTTTGAAAGAATGGGGTCAACC
TAAGTCTAAGATCACCCATTTGGTTTTCTGTACTACCTCTGGTGTT
GAAATGCCAGGTGCTGATTACAAATTGGCTAACTTGTTGGGTTTG
GAAACTTCCGTTAGAAGAGTTATGTTGTACCATCAAGGTTGTTAT
GCTGGTGGTACTGTTTTGAGAACTGCTAAAGATTTGGCTGAAAAC
AATGCTGGTGCTAGAGTTTTGGTTGTTTGCTCTGAAATTACCGTT
GTTACTTTCAGAGGTCCATCTGAAGATGCTTTGGATTCTTTGGTT
GGTCAAGCTTTGTTTGGTGATGGTTCTTCTGCTGTTATAGTTGGT
TCTGATCCAGATGTCTCTATCGAAAGACCTTTGTTCCAATTGGTTT
CTGCTGCTCAAACTTTCATTCCAAATTCTGCTGGTGCAATTGCTG
GTAACTTGAGAGAAGTTGGTTTGACTTTTCATTTGTGGCCAAACG
TTCCAACTTTGATCTCCGAAAACATTGAAAAGTGTTTGACCCAAG
CTTTCGATCCATTGGGTATTTCTGATTGGAATTCCTTGTTCTGGAT
TGCTCATCCAGGTGGTCCAGCAATTTTGGATGCTGTTGAAGCTAA
ATTGAACTTGGAAAAGAAGAAGTTGGAAGCCACCAGACATGTTTT
GTCTGAATACGGTAATATGTCCTCTGCTTGCGTTTTGTTCATTTTG
GACGAAATGAGAAAAAAGTCCTTGAAGGGTGAAAAGGCTACTAC
TGGTGAAGGTTTGGATTGGGGTGTTTTGTTCGGTTTTGGTCCAG
GTTTGACTATTGAAACTGTTGTCTTGCATTCTGTTCCAACCGTTAC
CAATTGA

SEQ ID NO: 39
ATGGCTACTACCGCTGCTTCTTCTTTACAAATGGCAACTGCTAGA
CCATGCATCTCTTCATCTAGAAGAGCTTTTGGTTCTTCTACCGCT
ATGTTGAATGGTAACTTTAAGGTTGCTTCCTGGACCAAATTATCTT
CCGCTTGTCATATCTCCTCTGTCCAATCTTTTCAAAGATGCTTCAC
CTCCTCATCTATGAAGTTGGATAAGTTCGTTACTAAGGCTATGGC
TGGTGCTTCTGAAAACAAACCAGTTTCTGGTTTGCCAATCAACTT
GAAAGGTAAGAGAGCTTTCATTGCTGGTGTTGCTGATGATAATGG
TTATGGTTGGGCTATTGCTAAATCTTTGGCTGCTGCTGGTGCTGA
AATTTTGGTTGGTACTTGGGTTCCAGCCTTGAATATTTTCGAATC
CTCTTTGAGAAGAGGTAAGTTCGACGAATCTAGAATTTTGCCAGA
TGGTTCCTTGATGGAAATCACTAAGGTTTATCCATTGGATGCCGT
TTTCGATAACCCAGAAGATGTTCCAGAAGAAATCAAGACCAACAA
AAGATACGCTGGTTCCTCTAATTGGACTGTTCAAGAAGCTGCTGA
ATGCGTTAAGAATGATTTCGGTTCCATCGATGTTTTGGTTCACTC
TTTGGCTAATGGTCCAGAAGTTGTTAAGCCTTTGTTGGAAACTTC
TAGAAAGGGTTACTTGGCTGCTATTTCTGCTTCATCTTACTCCTA
CGTCAGTTTGTTGAAACACTTCTTGCCAATTATCAACCCAGGTGG

TTCTTCCATTTCTTTGACTTACATTGCCTCCGAAAGAATCATTCCA
GGTTATGGTGGTGGTATGTCATCTGCTAAAGCTGCTTTGGAATCT
GATACAAGAGTTTTGGCTTTTGAAGCCGGTAGAAAGAAGGGTATT
AGAGTTAATACCATTTCCGCTGGTCCATTGAGATCAAGAGCTGCA
AAAGCTATTGGTTTCATCGATATGATGATCGACTACTCTTCTGCTA
ATGCCCCATTGGAAAAGAATTGTCTGCTGAAGAAGTTGGTAACA
CTGCTGCTTTTTTGGCTTCTCCATTGGCTTCAGCTATTACTGGTG
GTGTTATCTATGTTGACAATGGTTTGAATGCTATGGGTGTTGGTG
TTGACTCTCCAATCTTCGAAAATTTGAACATTCCAAAGGCCCAAC
ATTAA

SEQ ID NO: 40
ATGGCTACTACCGCTGCTTCTTCTTTACAAATGGCAACTGCTAGA
CCATGCATCTCTTCATCTAGAAGAGCTTTTGGTTCCTCCTCCAAA
ATGTTGAACGATAACTTTAAGGTTGCCTCCTGGTCTAAGTTATCTT
CTACTTGTCATACCTCCTCCGTCCAATCTTTTCAAAGATCCTTTAC
CTCCTCATCCATGAAGATGGATAAGTTCGTTACTAGAGCTATGGC
TGGTGCTTCTGAAAACAAACCAGTTTCTGGTTTGCCAATCGATTT
GAAAGGTAAGAGAGCTTTCATTGCTGGTGTTGCTGATGATAATGG
TTATGGTTGGGCTATTGCTAAATCTTTGGCTGCTGCTGGTGCTGA
AATTTTGGTTGGTACTTGGGTTCCAGCCTTGAATATTTTCGAATC
CTCTTTGAGAAGAGGTAAGTTCGATGAATCTAGAGTTTTGCCAGA
TGGTTCCTTGATGGAAATTACTAAGGTTTACCCATTGGATGCCGT
TTTCGATAATCCAGAAGATGTTCCAGAAGAAATCAAGACCAACAA
AAGATACGCTGGTTCTTCTAACTGGACTGTTCAAGAAGCTGCTGA
ATGTGTTAAGAACGATTTCGGTTCCATTGATATCTTGGTCCATTCT
TTGGCTAATGGTCCAGAAGTTGTTAAGCCTTTGTTGGAAACTTCT
AGAAAGGGTTACTTGGCTGCTATTTCTGCTTCATCTTACTCCTAC
GTCAGTTTGTTGAAACACTTCTTGCCAATTATCAACCCAGGTGGT
TCTTCCATTTCTTTGACTTACATTGCCTCCGAAAGAATCATTCCAG
GTTATGGTGGTGGTATGTCATCTGCTAAAGCTGCTTTGGAATCTG
ATACAAGAGTTTTGGCTTTTGAAGCCGGTAGAAGAAAGGGTATTA
GAGTTAACACAATTTCCGCTGGTCCATTGAGATCAAGAGCTGCAA
AAGCTATTGGTTTCATCGATATGATGATCGACTACTCTTCTGCTAA
TGCCCCATTGGAAAAGAATTGTCTGCTGATGAAGTTGGTAACAC
TGCTGCTTTTTTGGCTTCTCCATTGGCTTCAGCTATTACTGGTGG
TGTTATCTATGTTGACAATGGTTTGAATGCTATGGGTGTTGGTGT
TGACTCTCCAATCTTCGAAAATTTGAACATTCCAAAGGCCCAACA
TTAA

SEQ ID NO: 41
ATGGCTTCTGGTGGTGAAATGCAAGTCTCTAACAAGCAAGTTATC
TTCAGAGATTACGTTACCGGTTTCCCAAAAGAATCCGATATGGAA

TTGACCACCAGATCCATTACTTTGAAATTGCCACAAGGTTCTACC
GGTTTGTTGTTGAAAAACTTGTACTTGTCTTGCGACCCTTACATG
AGAGCTAGAATGACTAATCATCACAGATTGTCCTACGTCGATTCT
TTTAAACCAGGTTCCCCAATTATTGGTTACGGTGTTGCTAGAGTT
TTGGAATCTGGTAATCCAAAGTTTAACCCAGGTGATTTGGTTTGG
GGTTTTACTGGTTGGGAAGAATACTCTGTTATTACCGCTACTGAA
TCCTTGTTCAAGATCCATAATACCGATGTCCCATTGTCTTACTACA
CTGGTTTGTTGGGTATGCCAGGTATGACTGCTTATGCTGGTTTTT
ACGAAATTTGCTCTCCAAAAAAGGGTGAAACCGTTTATGTTTCTG
CTGCTTCAGGTGCTGTTGGTCAATTGGTCGGTCAATTTGCTAAGT
TGACTGGTTGTTATGTTGTTGGTTCTGCCGGTTCTAAAGAAAAGG
TTGATTTGTTGAAGAACAAGTTCGGTTTCGATGAAGCCTTCAACT
ACAAAGAAGAAGCTGATTTGGACGCTGCTTTGAGAAGATATTTTC
CAGATGGTATCGACATCTACTTCGAAAATGTTGGTGGTAAGATGT
TGGATGCTGTTTTGCCAAATATGAGACCAAAGGGTAGAATTGCTG
TTTGCGGTATGATTTCCCAATACAACTTGGAACAACCAGAAGGTG
TTAGAAACTTGATGGCTTTGATCGTTAAGCAAGTCAGAATGGAAG
GTTTCATGGTTTTCTCTTACTACCACTTGTACGGTAAATTCTTGGA
AACTGTCTTGCCTTACATCAAGCAAGGTAAGATTACCTACGTTGA
AGATGTTGTTGATGGTTTGGATAATGCTCCAGCTGCTTTAATTGG
TTTGTACTCTGGTAGAAACGTCGGTAAGCAAGTTGTTGTTGTTTC
CAGAGAATGA

SEQ ID NO: 42
ATGGCCGAAAAGAATCAATACTTCCCACACTTGTTTGAACCATTG
AAGGTTGGTTCTAAGACCATCAAGAACAGAATTGAAGCTGCTCCA
GCTTTGTTTGCTTTCGAACATTACATTGAATTGAACCCAGATCCAT
TCGGTTACACTACTCCAGTTCCAGAAAGAGCTTTTAGAATGTTGG
AAGCTAAAGCTAAAGGTGGTGCTGGTATAGTTTGTTTGGGTGAAT
TGTCTCCAAACCACGAATACGATAAGAGATTTCCATTCGAACCAT
ACTTGGACTTCACTTCCAGATCCGATAAGCAATTCGAAATCATGA
AAGAAACCGCCGAAATGATCAAATCTTACGGTGCTTTTCCAATGG
GTGAATTATTGTCTTGTGGTGAAATCAAGACCAACATCGGTGATG
GTATTAACCCAAAAGGTCCATCTGAAAAGGATTTGCCAGATGGTT
CTCATGTTGAAGCCTTTACCAAAGAAGAAATCTTGTCCTGCTACC
AAGATTACGTTACTGCTTGTAAATGGTTTCAAGCTGCTGGTTGGG
AAGGTATTATGATTCATTGTGGTCATGGTTGTTGCCAGCTCAAT
TTTTGTCTCCACAATACAACAAGAGAACCGATGAATACGGTGGTT
CTTTTGAAAACAGAGCTAGATTCACCGTCGACTTGTTGAAAACTG
TTAGAGAAGCTATGGGTCCAGATTTCGTCATTGAAATCAGAGTCT
CTTCCTCTGAACATTTGCCTGGTGGTTTAGAATTGGAAGATGCTG
TTAATTACTGCAAGTTGTGCGAACCTTACATCGATATGATCCATG

-continued
TTTCTTGCGGTCACTACTTGTCATCTTCTAGATCATGGGAATTCA
CTACTGCTTATGCTCCACATGGTCCAAATATTGAACCAGCTGCTG
TTATCAAGCAAAACGTTTCTATTCCAGTTGCTGCTGTTGGTGGTA
TCAATTCTCCAGAACAAGCTGAAGAAGCTATTGCCTCTGGTAAGA
TTGATATGGTTTCTATGGGTAGACAATTCTTCGCTGATCCAGCAT
TTCCTAACAAAGCAAAAGAAGGTCACGCTGACGAAATTAGAAGAT
GTTTGAGATGTGGTAGATGTTACCCAGGTCCATCAGGTGAACAC
GAAACTGAAATTTGGACTGTTAAGTTCCCACCATTGGATTCTTGT
ACCATTAACCCATATGATGTTTGGCCAGCTTCTCATCATAAGGTT
TTACCAGATAGAATGCCAAAACCAGAAGCCTCTAGAAAGGTTTTG
GTTGTAGGTGGTGGTTGCGGTGGTTTACAAACTGCTATTACTGCT
TCTGATAGAGGTCACCAAGTTATCTTGTGTGAAAAGTCTGGTGTT
TTGGGTGGTTTGATTAACTTCACTGATCATACCGATCACAAGGTC
GATATCAGAAACTTCAAGGATTTGTTGATCAGAGATGTTGAAAAA
AGACCAATCGAAGTCAGATTGAACTGTGAAGTTACCCCAGAATTG
ATTAGAGAAATTGCTCCAGAAGCTGTTGTTTTGGCTGTTGGTTCT
GATGATTTGATCTTGCCAATTGAAGGTATCGAAAACGCTGTTACT
GCTATGGATGTTTACTCTAATGATTTCGCCGGTTTGGGTAAATCC
ACTATAGTATTGGGTGGTGGTTTGGTTGGTTGTGAAGCTGCTGCT
GATTATATTGATCATGGTGTTGAAACCACCATCGTCGAAATGAAG
GGTGCTTTGATGCCAGAAACTACTGGTTTGTATAGAACCGCTGTT
CACGATTTCATTGATAAGAATGGTGGTAAGTACGAAGTTAACGCC
AAGGTTGTTAAGGTTGGTAAGGATTTTGTTGTTGCCGAACAAGAC
GGTAAAGAAATTACCATTAAGGCCGATTCTGTTGTCAATGCAATG
GGTAGAAGAGCACATGCTACTGAAGCCTTGGAAACAGCTATCAA
AGAAGCTGGTATTCCAGTCTGGAAAATTGGTGATTGTGTTAGAGC
TAGACAAATCGGTGACGCTGTAAGAGAAGGTTGGACTGCAGCTA
TGGAAATTATCTGA
                         SEQ ID NO: 43
ATGTACTTTGATGAAGAACAATTGCTAAAATATACTATATATGCCT
ATAGATTATCCTTTTTTGTAGGCATTTGCTCACTTTTCATAGCAAA
AAGTTGTCTACCAGAATTTCTTCAATATGGTAAAACCTACCGGCC
CAAAGAGAATTCAAAGTACTCAAGCATTTTAGAACGAATCAAGAA
GTTCACAGTTCCAAAGGCGTATTTTTCCCATTTTTACTATTTGGCT
ACCTTTCTATCCTTAGTCACCTTATATTTCTATCCTAAATTCCCCA
TCGTTTGGATCATATTTGGACACTCATTGCGCCGACTTTATGAAA
CGCTTTATGTACTACATTATACAAGCAATTCTAGGATGAATTGGTC
CCATTATCTAGTCGGTATATGGTTCTATTCCGTACTCTTGTTAATT
CTTAATATATCACTGTACAAGAACTCCATTCCAAATACGTTAAACA
TGAATGCTTTCATCATATTCTGCATAGCATCTTGGGATCAGTACA
AAAATCATGTTATTCTGGCCAATCTGGTTAAATATTCGCTGCCAA -continued
CAGGAAGGCTTTTCAGGTTGGTATGCTGTCCTCATTATCTCGATG
AAATAATCATTTATTCTACTCTGTTGCCCTATGAACAAGAATTTTA
CCTAACACTAGTTTGGGTAATCACAAGTTTGACTATATCCGCATT
GGAAACAAAAAATTATTACAGGCACAAATTTAAAGACAATCACGT
AGCCCCCTACGCCATAATACCTTTTATAATCTAG
                         SEQ ID NO: 44
ATGGCTGCTTCTACCGAAGGTGTTATCTCTAACAAGCAAGTTATC
TTGAAGGATTACGTTACCGGTTTCCCAAAAGAATCCGATATGCAA
TTGACTACTGCTACCACTAAGTTGAAATTGCCTGAAGGTTCTAAA
GGTGTCTTGGTCAAAAACTTGTACTTGTCTTGTGACCCTTACATG
AGATCCAGAATGACAAAAGAGAACCAGGTGCTTCTTACGTTGAT
TCATTTGATGCTGGTTCTCCAATCGTTGGTTATGGTGTTGCTAAA
GTTTTGGAATCGGTGACCCAAAGTTAAGAAGGGTGATTTGATT
TGGGGTATGACTGGTTGGGAAGAATACTCTGTTATTACCTCTACC
GAATCCTTGTTCAAGATCCAACATATCGATGTCCCATTGTCTTACT
ACACTGGTATTTTGGGTATGCCAGGTATGACAGCTTATGCTGGTT
TTTACGAAATCTGCAATCCAAAAAAGGGTGAAACCGTTTTTGTTT
CTGCTGCTTCTGGTGCTGTTGGTCAATTGGTCGGTCAATTTGCTA
AGTTGTTGGGTTGTTATGTTGTTGGTTCTGCCGGTTCCAAAGAAA
AGGTTGATTTGTTGAAGAACAAGTTCGGTTTCGATAACGCCTTCA
ACTACAAAGAAGAACCAGATTTGGACGCTGCTTTGAAGAGATATT
TTCCAGAAGGTATCGACATCTACTTCGAAAATGTTGGTGGTAAGA
TGTTGGATGCTGTTTTGCCAAATATGAGAGTTCATGGTAGAATTG
CTGTTTGCGGTTTGATCTCCCAATACAACATTGATGAACCAGAAG
GTTGCAGAAACTTGATGTACTTGATTATCAAGCAAGTCAGAATGC
AAGGTTTCTTGGTTTTCTCTTACTACCACTTGTACGAAAAGTTCTT
GGAAATGGTTTTGCCAGCCATCAAAGAAGGTAAATTGACCTACGT
TGAAGATGTCGTTGAAGGTTTAGAATCTGCTCCAGCTGCTTTAAT
TGGTTTGTATGCTGGTAGAAACGTTGGTAAGCAAGTTGTTGTTGT
CTCCAGAGAATGA
                         SEQ ID NO: 45
ATGAAGGTCACCGTCGTTTCTAGATCAGGTAGAGAAGTTTTGAAA
GCCCCATTGGATTTGCCAGATTCTGCTACTGTTGCTGACTTGCAA
GAAGCCTTTCATAAGAGAGCTAAGAAGTTCTACCCATCCAGACAA
AGATTGACTTTGCCAGTTACTCCAGGTTCTAAAGATAAGCCAGTT
GTCTTGAACTCCAAGAAGTCCTTGAAAGAATACTGTGACGGTAAC
AACAACTCCTTGACTGTTGTTTTAAGGATTTGGGTGCCCAAGTT
TCTTACAGAACTTTGTTCTTCTTCGAATACTGGGTCCTTTGTTGA
TCTACCCAGTTTTTACTACTTCCCAGTCTACAAGTTTTGGGTTA
CGGTGAAGATTGCGTTATCCATCCAGTTCAAACTTACGCTATGTA
CTACTGGTGTTTCCACTACTTCAAGAGAATCTTGGAAACCTTCTT
CGTCCACAGATTTTCTCATGCTACTTCTCCAATTGGTAACGTTTTC

```
AGAAACTGTGCCTATTACTGGTCTTTCGGTGCTTATATTGCTTACT
ACGTTAACCACCCATTATACACTCCAGTTTCAGACTTGCAAATGA
AGATTGGTTTTGGTTTCGGTTTGGTCTGTCAAGTTGCTAACTTCT
ACTGCCATATCTTGTTGAAGAACTTGAGAGATCCATCTGGTGCTG
GTGGTTATCAAATTCCAAGAGGTTTTTTGTTCAACATCGTTACCTG
TGCTAACTACACTACCGAAATCTATCAATGGTTGGGTTTCAACAT
TGCCACTCAAACTATTGCTGGTTACGTTTTTTTGGCTGTTGCCGC
TTTGATTATGACTAATTGGGCTTTGGGTAAGCACTCCAGATTGAG
AAAGATTTTCGATGGTAAAGACGGTAAGCCAAAGTATCCAAGAAG
ATGGGTTATTTTGCCACCATTCTTGTAA
                                       SEQ ID NO: 46
ATGAAGGTCACCTTGGTCAGTAGATCAGGTAGAGAATTCATTAAG
GGTGGTTTGGAATTGAACGATTCTGCTACTGTTGCTGACTTGCAA
GAAGCTATTCATAAGAGAACTAAGAAGTTCTACCCATCCAGACAA
AGATTGACTTTGCCAGTTCCATCTGGTTCTAGAGAAAGACCAGTT
ATCTTGAACTACAAGAAGTCCTTGAAGGATTACTGTGACGGTAAC
GAAAACACTTTGACCATCGTTTTTAAGGACTTGGGTCCACAAGTT
TCTTACAGAACTTTGTTCTTCTTCGAATATTTGGGTCCATTGATCT
TGTACCCAGTTTTCTATTACTTCCCAGTCTACAAGTACTTCGGTTA
CGAAGAAAGAGAGTTATCCACCCAGTTCAAACTTATGCCTTGTA
CTACTGGTGTTTCCACTACTTCAAGAGAATTATGGAAACCTTCTT
CATCCACAGATTCTCTCATGCTACTTCTCCATTGTCTAACGTTTTC
AGAAACTGTGCTTACTACTGGACTTTCGGTTCTTATATTGCCTACT
ACGTTAACCACCCATTATACACTCCAGTTTCAGACTTGCAAATGA
AGATTGGTTTTGGTTTCGGTATCGTTTGTCAATTGGCTAACTTCTA
CTGCCACATCATCTTGAAGAATTTGAGATCACCAGATGGTTCTGG
TGGTTACCAAATTCCAAGAGGTTTTTTGTTCAACATCGTTACCTGT
GCTAACTACACTACCGAAATCTATCAATGGTTGGGTTTCAACATT
GCTACTCAAACAGTTGCTGGTTACGTTTTCTTGGTTGTTGCTACC
TCTATTATGACTAATTGGGCCTTGGCTAAACACAGAAGATTGAAG
AAATTATTCGACGGTAAGGACGGTAGACCAAAGTATCCAAGAAG
ATGGGTTATTTTGCCACCATTCTTGTAA
                                       SEQ ID NO: 47
ATGAAGGTCACCGTCGTTTCTAGATCAGGTAGAGAAGTTGTTAAG
GGTGGTTTGGAATTGTCTGATTCTGCTACTGTTGCTGACTTGCAA
GATGCTATTCATAAGAGAACTAAGAAGTTCTACCCAGCCAGACAA
AGATTGACTTTGCCAGTTCAACCAGGTTCTAAAGAAAGACCAGTT
GTCTTGTCTTACAAGAAGTCATTGCAAGACTACATCTCCGGTAAC
TCTGATAACTTGACTGTTGTTTTCAAGGACTTGGGTCCACAAGTT
TCTTACAGAACTTTGTTCTTCTTCGAATATTTGGGTCCATTGATCT
TGTACCCAATCTTCTACTACTTCCCAGTTTACGATTACTTGGGTTT
```
```
CAAGGGTGATAGAGTTATCCATCCAGTTCAAACTTATGCCTTGTA
CTACTGGTGTTTCCACTACTTCAAGAGAATTATGGAAACCTTCTT
CGTCCACAGATTCTCTCATGCTACTTCTCCATTGTCTAACGTTTTC
AGAAACTGTGCCTACTATTGGTCTTTCGGTGCTTTTATTGCTTACT
ACTTGAACCACCCATTATACACTCCAGTTTCAGACTTGCAAATGA
AGATTGGTTTCGGTATTGGTATCATCTGCCAAATCTCTAACTTCTA
CTGCCACATCTTGTTGAGAAACTTGAGATCACCAGATGGTAATGG
TGGTTACCAAATTCCAAGAGGTTTCTTGTTCAACATCGTTACCTG
TGCTAACTACACTACCGAAATCTATCAATGGTTGGGTTTTAACATT
GCCACTCAAACAGTTGCCGGTTACATTTTTTTGATCGTTGCTGCT
TCTATCATGACCAATTGGGCTTTGGCTAAACACAGAAGATTGAAG
AAAATCTTCGATGGTAAGGACGGTAGACCAAAGTATCCAAGAAG
ATGGGTTATTTTGCCACCATTCTTGTAA
                                       SEQ ID NO: 48
ATGTCCGCCTCCTCCTCCATTTTCATCAAATCTAGATCCAAGTCC
TTGAAGGACGTTAAGTTAGAAGTTCCAACTGAAAACACCTTGACC
TACCAATCCGTTTTACAACAAATCTCCAAGTCCAACCACAACATC
TCCGTTAATAGATTGAGATTGTCCTACTTGAAAGAAGGTAAGCAA
GTTGCTATTGGTCCATCCGAATTGAATGATGTTGGTAAGAAGAAC
ACCTTCGACTCTGTTAATGAATGGTATGTCAAAGACTTGGGTCCA
CAAATTAGTTGGAGATTGGTTTTCTTCATCGAATATTTGGGTCCAA
TCTTGATCCACTCCTTGGTTTATTTGTTGTCTTTGAACGCTACCGT
CAGAGATAAGTTCCATTCAAGAATGTTCCATACAACGATTTCTTC
AACAAGTTCATCTACAGATTGATCATGGTCCACTACTTGAAGAGA
GAATTCGAAACCTTGTTCATCCATTCCTTCTCATTGGAAACTATGC
CTTTGTTCAACTTGTTCAAAAACTCCTTCCACTACTGGATCTTGAA
CGGTTTGATTTCTTTGGGTTACTTCGGTTACGGTTTTCCATTTGCT
AACAAGACCTTGTACAGAGTTTACTCCGCTTTGAAGATTTCCGAT
TTCAGAGTTTTGACTGCCTTGTTCGGTTTGTCTGAAATGTTTAACT
TCTACATCCACGTCGCTTTGAGAAGATGGGGTGATGAACAAAAA
AGAAACGGTGTTACTAAGAGAGTCCCATTGAATTCTGGTTTGTTT
AAGTTGTTGGTTGCCCCAAACTACACTTTTGAATCTTGGGCTTGG
ATGTTCTTCACCTTGTTGTTCAAGTTGAATTTGTTCTCCGTCTTGT
TCTTGGTTGTTTCCGTTGTTCAAATGTACTTGTGGGCCCAAAAGA
AAAACAAGAAGTACGGTACAAAGAGAGCCTTCTTGATTCCATTCT
TGTTCTAA
                                       SEQ ID NO: 49
MVTVEEVRKAQRAEGPATVMAIGTAVPPNCVDQATYPDYYFRITNS
EHKAELKEKFQRMCDKSQIKKRYMYLNEEVLKENPNMCAYMAPSL
DARQDIVVVEVPKLGKEAAVKAIKEWGQPKSKITHLVFCTTSGVDMP
GADYQLTKLLGLRPSVKRLMMYQQGCFAGGTVLRLAKDLAENNKG
ARVLVVCSEITAVTFRGPTDTHLDSLVGQALFGDGAAAIIIGSDPIPEV
```

EKPLFELVSAAQTILPDSEGAIDGHLREVGLTFHLLKDVPGLISKNVE
KSLTEAFKPLGISDWNSLFWIAHPGGPAILDQVEAKLSLKPEKLRAT
RHVLSEYGNMSSACVLFILDEMRRKSKEDGLKTTGEGIEWGVLFGF
GPGLTVETVVLHSVAIN

SEQ ID NO: 50
MANHHNAEIEEIRNRQRAQGPANILAIGTATPSNCVYQADYPDYYFR
ITNSEHMTDLKLKFKRMCEKSMIRKRYMHITEEYLKENPNVCAYEAP
SLDARQDLVVVEVPRLGKEAASKAIKEWGQPKSKITHLIFCTTSGVD
MPGADYQLTKLLGLRPSVKRFMMYQQGCFAGGTVLRLAKDLAENN
AGARVLVVCSEITAVTFRGPSDSHLDSLVGQALFGDGAAAVILGSDP
DLSVERPLFQLISAAQTILPDSDGAIDGHLREVGLTFHLLKDVPGLISK
NIEKSLKEAFGPIGISDWNSLFWIAHPGGPAILDQVELKLGLKEEKMR
ATRQVLSDYGNMSSACVLFILDEMRKKSIEEGKATTGEGLDWGVLF
GFGPGLTVETVVLHSVPATFTH

SEQ ID NO: 51
MVTVEEYRKAQRAEGPATVMAIGTATPTNCVDQSTYPDYYFRITNS
EHKTDLKEKFKRMCEKSMIKKRYMHLTEEILKENPSMCEYMAPSLD
ARQDIVVVEVPKLGKEAAQKAIKEWGQPKSKITHLFFCTTSGVDMP
GCDYQLTKLLGLRPSVKRLMMYQQGCFAGGTVLRLAKDLAENNKG
ARVLVVCSEITAVTFRGPNDTHLDSLVGQALFGDGAGAIIIGSDPIPG
VERPLFELVSAAQTLLPDSHGAIDGHLREVGLTFHLLKDVPGLISKNI
EKSLEEAFKPLGISDWNSLFWIAHPGGPAILDQVEIKLGLKPEKLKAT
RNVLSDYGNMSSACVLFILDEMRKASAKEGLGTTGEGLEWGVLFG
FGPGLTVETVVLHSVAT

SEQ ID NO: 52
MAATMTVEEVRNAQRAEGPATVLAIGTATPANCVYQADYPDYYFKI
TKSDHMADLKEKFKRMCDKSQIRKRYMHLTEEILEENPNMCAYMAP
SLDARQDIVVVEVPKLGKAAAQKAIKEWGQPRSKITHLVFCTTSGVD
MPGADYQLTKMLGLRPSVKRLMMYQQGCFAGGTVLRLAKDLAENN
RGARVLVVCSEITAVTFRGPHESHLDSLVGQALFGDGAAAVIIGADP
DLSVERPLFQLVSASQTILPDSEGAIDGHLREVGLTFHLLKDVPGLIS
KNIERALEEAFKPLGIDHWNSVFWIAHQGGPAILDMVEAKVNLNKER
MRATRHVLSEYGNMSSACVLFIMDEMRKRSAEDGHATTGEGMDW
GVLFGFGPGLTVETVVLHSVPISAGATA

SEQ ID NO: 53
MVTVEEFHRATRAEGPATVLAIGTANPPNCVEQSTYADYYFRICKSE
HLTDLKKKFDRMCEKSCIKKRYMHLTEEFLKENDNFTAYEAPSLDA
RQDIVVVEIPKLGKEAAQKAIKEWGQPKSKITHVIFCTTSGVDMPGA
DYQITKLLGLRPSVKRFMMYQQGCFAGGTVLRMAKDLAENNGAR
VLVVCSEITAITFRGPSDTHLDSLVGQALFGDGAAAVIVGSDPIVGVE
RPLFQLVSAAQTILPDSEGAIDGHVREVGLTFHLLKDVPGLISKDIEK
SLKEAFAPLGISDWNSLFWIVHPGGPAILDQVGEKLGLKPEIMVPTR

HVLSEYGNMSSACVLFVMDEMRKASAKDGCTSTGEGKDWGVLFG
FGPGLTVETVVLHSVPLN

SEQ ID NO: 54
MVTVEEVRKAQRAEGPATVMAIGTATPSNCVDQATYPDYYFRITNS
EHKVELKEKFQRMCDKSMIKKRYMYLTEEILKENPSVCEYMAPSIDA
RQDMVVVEVPKLGKEAATKAIKEWGQPKSKITHLVFCTTSGVDMPG
ADYQLTKLLGLRPSVKRLMMYQQGCFAGGTVLRLAKDLAENNKGA
RVLVVCSEITAVTFRGPSDTHLDSLVGQALFGDGAAAVIIGADPVPE
VEKPLFELVSAAQTILPDSDGAIDGHLREVGLTFHLLKDVPGLISKNIE
KSLNEAFKPIGISDWNSLFWIAHPGGPAILDQVEAKLALKPEKLEATR
QVLSDYGNMSSACVLFILDEVRRKSAEKGLKTTGEGLEWGVLFGFG
PGLTVETVVLHSVGLTA

SEQ ID NO: 55
MVTVEEVRKAQRAEGPATVLAIGTATPSNCVDQATYPDYYFRITNS
EHKTELKEKFQRMCDKSMIKKRYMYLTEEILKENPTVCEYMAPSLD
ARQDMVVVEVPRLGKEAATKAIKEWGQPKSKITHLVFCTTSGVDMP
GADYQLTKLLGLRPSVKRLMMYQQGCFAGGTVLRLAKDLAENNKG
ARVLVVCSEITAVTFRGPSDTHLDSLVGQALFGDGAAAVIIGADPLP
EVEKPLFELVSAAQTILPDSDGAIDGHLREVGLTFHLLKDVPGLISKNI
EKSLNEAFKPIGISDWNSLFWIAHPGGPAILDQVESKLALKPEKLEAT
RQVLSNYGNMSSACVLFILDEVRRKSAEKGLKTTGEGLEWGVLFGF
GPGLTVETVVLHSVAA

SEQ ID NO: 56
MVTVEEVRKAQRAEGPATVLAIGTATPPNCVDQATYPDYYFRITNS
EHKTELKEKFQRMCDKSMIKTRYMYLTEEILKENPTVCEYMAPSLDA
RQDMVVVEVPRLGKEAATKAIKEWGQPKSKITHLVFCTTSGVDMPG
ADYQLTKLLGLRPSVKRLMMYQQGCFAGGTVLRLAKDLAENNKGA
RVLVVCSEITAVTFRGPSDTHLDSLVGQALFGDGAAAVIIGSDPVPE
VEKPLFELVSAAQTILPDSDGAIDGHLREVGLTFHLLKDVPGLISKNIE
KSLNEAFKPIGISDWNSLFWIAHPGGPAILDQVESKLALKPEKLEATR
QVLSDYGNMSSACVLFILDEVRRKSAEKGLKTTGEGLEWGVLFGFG
PGLTVETVVLHSVGA

SEQ ID NO: 57
MVTVQEVRKAQRAEGPATVFAIGTATPPNCVDQATYPDYYFRITNS
EHKAELKEKFQRMCDKSMIKKRYMYLTEEILKENPSVCEYMAPSLD
ARQDMVVVEVPRLGKEAATKAIKEWGQPKSKITHLVFCTTSGVDMP
GADYQLTKLLGLRPSVKRLMMYQQGCFAGGTVLRLAKDLAENNKG
ARVLVVCSEITAVTFRGPSDTHLDSLVGQALFGDGAAAVIIGADPVP
EVEKPLFELVSAAQTILADSDGAIDGHLREVGLTFHLLKDVPGLISKNI
EKSLNEAFKPIGISDWNSLFWIAHPGGPAILDQVEAKLALKPEKLEAT
RQVLSDYGNMSSACVLFILDEVRRKSAEKGLETTGEGLEWGVLFGF
GPGLTVETVVLHSVAA

SEQ ID NO: 58
MASVEEIRNAQRAKGPATILAIGTATPDHCVYQSDYADYYFRVTKSE
HMTELKKKFNRICDKSMIKKRYIHLTEEMLEEHPNIGAYMAPSLNIRQ
EIITAEVPKLGKEAALKALKEWGQPKSKITHLVFCTTSGVEMPGADY
KLANLLGLETSVRRVMLYHQGCYAGGTVLRTAKDLAENNAGARVLV
VCSEITVVTFRGPSEDALDSLVGQALFGDGSAAVIVGSDPDISIERPL
FQLVSAAQTFIPNSAGAIAGNLREVGLTFHLWPNVPTLISENIENCLT
KAFDPIGISDWNSLFWIAHPGGPAILDAVEAKVGLDKQKLKATRHILS
EYGNMSSACVLFILDEMRKKSLKEGKTTTGEGLDWGVLFGFGPGLT
IETVVLHSVGTDSN

SEQ ID NO: 59
MASVEEFRNAQRAKGPATILAIGTATPDHCVYQSDYADYYFRVTKS
EHMTELKKKFNRICDKSMIKKRYIHLTEEMLEEHPNIGAYMAPSLNIR
QEIITAEVPRLGRDAALKALKEWGQPKSKITHLVFCTTSGVEMPGAD
YKLANLLGLETSVRRVMLYHQGCYAGGTVLRTAKDLAENNAGARVL
VVCSEITVVTFRGPSEDALDSLVGQALFGDGSSAVIVGSDPDVSIER
PLFQLVSAAQTFIPNSAGAIAGNLREVGLTFHLWPNVPTLISENIEKC
LTQAFDPLGISDWNSLFWIAHPGGPAILDAVEAKLNLEKKKLEATRH
VLSEYGNMSSACVLFILDEMRKKSLKGEKATTGEGLDWGVLFGFGP
GLTIETVVLHSVPTVTN

SEQ ID NO: 60
MATTAASSLQMATARPCISSSRRAFGSSTAMLNGNFKVASWTKLSS
ACHISSVQSFQRCFTSSSMKLDKFVTKAMAGASENKPVSGLPINLK
GKRAFIAGVADDNGYGWAIAKSLAAAGAEILVGTWVPALNIFESSLR
RGKFDESRILPDGSLMEITKVYPLDAVFDNPEDVPEEIKTNKRYAGS
SNWTVQEAAECVKNDFGSIDVLVHSLANGPEVVKPLLETSRKGYLA
AISASSYSYVSLLKHFLPIINPGGSSISLTYIASERIIPGYGGGMSSAKA
ALESDTRVLAFEAGRKKGIRVNTISAGPLRSRAAKAIGFIDMMIDYSS
ANAPLEKELSAEEVGNTAAFLASPLASAITGGVIYVDNGLNAMGVGV
DSPIFENLNIPKAQH

SEQ ID NO: 61
MATTAASSLQMATARPCISSSRRAFGSSSKMLNDNFKVASWSKLSS
TCHTSSVQSFQRSFTSSSMKMDKFVTRAMAGASENKPVSGLPIDLK
GKRAFIAGVADDNGYGWAIAKSLAAAGAEILVGTWVPALNIFESSLR
RGKFDESRVLPDGSLMEITKVYPLDAVFDNPEDVPEEIKTNKRYAGS
SNWTVQEAAECVKNDFGSIDILVHSLANGPEVVKPLLETSRKGYLAA
ISASSYSYVSLLKHFLPIINPGGSSISLTYIASERIIPGYGGGMSSAKAA
LESDTRVLAFEAGRRKGIRVNTISAGPLRSRAAKAIGFIDMMIDYSSA
NAPLEKELSADEVGNTAAFLASPLASAITGGVIYVDNGLNAMGVGVD
SPIFENLNIPKAQH

SEQ ID NO: 62
MASGGEMQVSNKQVIFRDYVTGFPKESDMELTTRSITLKLPQGSTG
LLLKNLYLSCDPYMRARMTNHHRLSYVDSFKPGSPIIGYGVARVLES

GNPKFNPGDLVWGFTGWEEYSVITATESLFKIHNTDVPLSYYTGLL
GMPGMTAYAGFYEICSPKKGETVYVSAASGAVGQLVGQFAKLTGC
YVVGSAGSKEKVDLLKNKFGFDEAFNYKEEADLDAALRRYFPDGIDI
YFENVGGKMLDAVLPNMRPKGRIAVCGMISQYNLEQPEGVRNLMA
LIVKQVRMEGFMVFSYYHLYGKFLETVLPYIKQGKITYVEDVVDGLD
NAPAALIGLYSGRNVGKQVVVVSRE

SEQ ID NO: 63
MAEKNQYFPHLFEPLKVGSKTIKNRIEAAPALFAFEHYIELNPDPFGY
TTPVPERAFRMLEAKAKGGAGIVCLGELSPNHEYDKRFPFEPYLDF
TSRSDKQFEIMKETAEMIKSYGAFPMGELLSCGEIKTNIGDGINPKG
PSEKDLPDGSHVEAFTKEEILSCYQDYVTACKWFQAAGWEGIMIHC
GHGWLPAQFLSPQYNKRTDEYGGSFENRARFTVDLLKTVREAMGP
DFVIEIRVSSSEHLPGGLELEDAVNYCKLCEPYIDMIHVSCGHYLSSS
RSWEFTTAYAPHGPNIEPAAVIKQNVSIPVAAVGGINSPEQAEEAIAS
GKIDMVSMGRQFFADPAFPNKAKEGHADEIRRCLRCGRCYPGPSG
EHETEIWTVKFPPLDSCTINPYDVWPASHHKVLPDRMPKPEASRKV
LVVGGGCGGLQTAITASDRGHQVILCEKSGVLGGLINFTDHTDHKV
DIRNFKDLLIRDVEKRPIEVRLNCEVTPELIREIAPEAVVLAVGSDDLIL
PIEGIENAVTAMDVYSNDFAGLGKSTIVLGGGLVGCEAAADYIDHGV
ETTIVEMKGALMPETTGLYRTAVHDFIDKNGGKYEVNAKVVKVGKD
FVVAEQDGKEITIKADSVVNAMGRRAHATEALETAIKEAGIPVWKIG
DCVRARQIGDAVREGWTAAMEII

SEQ ID NO: 64
MAASTEGVISNKQVILKDYVTGFPKESDMQLTTATTKLKLPEGSKGV
LVKNLYLSCDPYMRSRMTKREPGASYVDSFDAGSPIVGYGVAKVLE
SGDPKFKKGDLIWGMTGWEEYSVITSTESLFKIQHIDVPLSYYTGILG
MPGMTAYAGFYEICNPKKGETVFVSAASGAVGQLVGQFAKLLGCY
VVGSAGSKEKVDLLKNKFGFDNAFNYKEEPDLDAALKRYFPEGIDIY
FENVGGKMLDAVLPNMRVHGRIAVCGLISQYNIDEPEGCRNLMYLII
KQVRMQGFLVFSYYHLYEKFLEMVLPAIKEGKLTYVEDVVEGLESA
PAALIGLYAGRNVGKQVVVVSRE

SEQ ID NO: 65
MKVTVVSRSGREVLKAPLDLPDSATVADLQEAFHKRAKKFYPSRQR
LTLPVTPGSKDKPVVLNSKKSLKEYCDGNNNSLTVVFKDLGAQVSY
RTLFFFEYLGPLLIYPVFYYFPVYKFLGYGEDCVIHPVQTYAMYYWC
FHYFKRILETFFVHRFSHATSPIGNVFRNCAYYWSFGAYIAYYVNHP
LYTPVSDLQMKIGFGFGLVCQVANFYCHILLKNLRDPSGAGGYQIPR
GFLFNIVTCANYTTEIYQWLGFNIATQTIAGYVFLAVAALIMTNWALG
KHSRLRKIFDGKDGKPKYPRRWVILPPFL

SEQ ID NO: 66
MKVTLVSRSGREFIKGGLELNDSATVADLQEAIHKRTKKFYPSRQRL
TLPVPSGSRERPVILNYKKSLKDYCDGNENTLTIVFKDLGPQVSYRT

LFFFEYLGPLILYPVFYYFPVYKYFGYEEKRVIHPVQTYALYYWCFHY

FKRIMETFFIHRFSHATSPLSNVFRNCAYYWTFGSYIAYYVNHPLYT

PVSDLQMKIGFGFGIVCQLANFYCHIILKNLRSPDGSGGYQIPRGFLF

NIVTCANYTTEIYQWLGFNIATQTVAGYVFLVVATSIMTNWALAKHR

RLKKLFDGKDGRPKYPRRWVILPPFL

SEQ ID NO: 67
MKVTVVSRSGREVVKGGLELSDSATVADLQDAIHKRTKKFYPARQR

LTLPVQPGSKERPVVLSYKKSLQDYISGNSDNLTVVFKDLGPQVSY

RTLFFFEYLGPLILYPIFYYFPVYDYLGFKGDRVIHPVQTYALYYWCF

HYFKRIMETFFVHRFSHATSPLSNVFRNCAYYWSFGAFIAYYLNHPL

YTPVSDLQMKIGFGIGIICQISNFYCHILLRNLRSPDGNGGYQIPRGFL

FNIVTCANYTTEIYQWLGFNIATQTVAGYIFLIVAASIMTNWALAKHR

RLKKIFDGKDGRPKYPRRWVILPPFL

SEQ ID NO: 68
ATGGCTGCAGTAAGATTGAAAGAAGTTAGAATGGCACAGAGGGC

TGAAGGTTTAGCTACAGTTTTAGCAATCGGTACTGCCGTTCCAGC

TAATTGTGTTTATCAAGCTACCTATCCAGATTATTATTTTAGGGTT

ACTAAAAGTGAGCACTTGGCAGATTTAAAGGAGAAGTTTCAAAGA

ATGTGTGACAAATCAATGATTAGAAAGAGACACATGCACTTGACC

GAGGAAATATTGATCAAGAACCCAAAGATCTGTGCACACATGGA

GACCTCATTGGATGCTAGACACGCCATCGCATTAGTTGAAGTTCC

CAAATTGGGCCAAGGTGCAGCTGAGAAGGCCATTAAGGAGTGG

GGCCAACCCTTGTCTAAGATTACTCATTTGGTATTTTGCACAACA

TCCGGCGTTGACATGCCCGGTGCTGATTACCAATTAACAAAGTT

GTTAGGTTTGTCCCCTACAGTCAAAAGGTTAATGATGTACCAACA

AGGTTGCTTTGGTGGTGCAACTGTTTTGAGATTGGCAAAAGATAT

CGCTGAAAATAATAGAGGTGCCAGAGTGTTAGTCGTTTGTTCCGA

GATAACTGCTATGACCTTCAGAGGTCCATGCAAGAGTCATTTAGA

TTCCTTGGTAGGTCATGCCTTGTTCGGTGATGGTGCCGCTGCTG

CAATTATAGGCGCTGACCCAGACCAATTAGACGAACAACCAGTTT

TCCAGTTGGTATCAGCTTCTCAGACTATATTACCAGAATCAGAAG

GTGCCATAGATGGCCATTTAACAGAAGCTGGTTTAACTTATACATT

TATTAAAAGATGTTCCTGGTTTAATTTCAGAGAACATTGAACAGG

CTTTGGAGGATGCCTTTGAACCTTTAGGTATTCATAACTGGAATT

CAATTTTCTGGATTGCACATCCTGGTGGCCCTGCCATTTTAGACA

GAGTTGAAGATAGAGTAGGATTGGATAAGAAGAGAATGAGGGCT

TCTAGGGAAGTGTTATCTGAATACGGAAATATGTCTAGTGCCTCT

GTGTTGTTTGTGTTAGATGTCATGAGGAAAAGTTCTGCTAAAGAC

GGATTGGCAACCACAGGAGAAGGAAAAGATTGGGGAGTGTTGTT

TGGATTCGGACCAGGCTTGACTGTAGAAACCTTAGTGTTGCATA

GTGTCCCAGTCCCTGTCCCTACTGCAGCTTCTGCATGA

SEQ ID NO: 69
ATGGCTGCAGTAAGATTGAAAGAAGTTAGAATGGCACAGAGGGC

TGAAGGTTTAGCTACAGTTTTAGCAATCGGTACTGCCGTTCCAGC

TAATTGTGTTTATCAAGCTACCTATCCAGATTATTATTTTAGGGTT

ACTAAAAGTGAGCACTTGGCAGATTTAAAGGAGAAGTTTCAAAGA

ATGTGTGACAAATCAATGATTAGAAAGAGACACATGCACTTGACC

GAGGAAATATTGATCAAGAACCCAAAGATCTGTGCACACATGGA

GACCTCATTGGATGCTAGACACGCCATCGCATTAGTTGAAGTTCC

CAAATTGGGCCAAGGTGCAGCTGAGAAGGCCATTAAGGAGTGG

GGCCAACCCTTGTCTAAGATTACTCATTTGGTATTTTGCACAACA

TCCGGCGTTGACATGCCCGGTGCTGATTACCAATTAACAAAGTT

GTTAGGTTTGTCCCCTACAGTCAAAAGGTTAATGATGTACCAACA

AGGTTGCTTTGGTGGTGCAACTGTTTTGAGATTGGCAAAAGATAT

CGCTGAAAATAATAGAGGTGCCAGAGTGTTAGTCGTTTGTTCCGA

GATAACTGCTATGACCTTCAGAGGTCCATGCAAGAGTCATTTAGA

TTCCTTGGTAGGTCATGCCTTGTTCGGTGATGGTGCCGCTGCTG

CAATTATAGGCGCTGACCCAGACCAATTAGACGAACAACCAGTTT

TCCAGTTGGTATCAGCTTCTCAGACTATATTACCAGAATCAGAAG

GTGCCATAGATGGCCATTTAACAGAAGCTGGTTTAACTTTTCATT

TATTAAAAGATGTTCCTGGTTTAATTTCAGAGAACATTGAACAGG

CTTTGGAGGATGCCTTTGAACCTTTAGGTATTCATAACTGGAATT

CAATTTTCTGGATTGCACATCCTGGTGGCCCTGCCATTTTAGACA

GAGTTGAAGATAGAGTAGGATTGGATAAGAAGAGAATGAGGGCT

TCTAGGGAAGTGTTATCTGAATACGGAAATATGTCTAGTGCCTCT

GTGTTGTTTGTGTTAGATGTCATGAGGAAAAGTTCTGCTAAAGAC

GGATTGGCAACCACAGGAGAAGGAAAAGATTGGGGAGTGTTGTT

TGGATTCGGACCAGGCTTGACTGTAGAAACCTTAGTGTTGCATA

GTGTCCCAGTCCCTGTCCCTACTGCAGCTTCTGCATGA

SEQ ID NO: 70
ATGGCTGCAGTAAGATTGAAAGAAGTTAGAATGGCACAGAGGGC

TGAAGGTTTAGCTACAGTTTTAGCAATCGGTACTGCCGTTCCAGC

TAATTGTGTTTATCAAGCTACCTATCCAGATTATTATTTTAGGGTT

ACTAAAAGTGAGCACTTGGCAGATTTAAAGGAGAAGTTTCAAAGA

ATGTGTGACAAATCAATGATTAGAAAGAGACACATGCACTTGACC

GAGGAAATATTGATCAAGAACCCAAAGATCTGTGCACACATGGA

GACCTCATTGGATGCTAGACACGCCATCGCATTAGTTGAAGTTCC

CAAATTGGGCCAAGGTGCAGCTGAGAAGGCCATTAAGGAGTGG

GGCCAACCCTTGTCTAAGATTACTCATTTGGTATTTTGCACAACA

TCCGGCGTTGACATGCCCGGTGCTGATTACCAATTAACAAAGTT

GTTAGGTTTGTCCCCTACAGTCAAAAGGTTAATGATGTACCAACA

AGGTTGCTTTGGTGGTGCAACTGTTTTGAGATTGGCAAAAGATAT

```
CGCTGAAAATAATAGAGGTGCCAGAGTGTTAGTCGTTTGTTCCGA
GATAACTGCTATGGCCTTCAGAGGTCCATGCAAGAGTCATTTAGA
TTCCTTGGTAGGTCATGCCTTGTTCGGTGATGGTGCCGCTGCTG
CAATTATAGGCGCTGACCCAGACCAATTAGACGAACAACCAGTTT
TCCAGTTGGTATCAGCTTCTCAGACTATATTACCAGAATCAGAAG
GTGCCATAGATGGCCATTTAACAGAAGCTGGTTTAACTTTTCATT
TATTAAAAGATGTTCCTGGTTTAATTTCAGAGAACATTGAACAGG
CTTTGGAGGATGCCTTTGAACCTTTAGGTATTCATAACTGGAATT
CAATTTTCTGGATTGCACATCCTGGTGGCCCTGCCATTTTAGACA
GAGTTGAAGATAGAGTAGGATTGGATAAGAAGAGAATGAGGGCT
TCTAGGGAAGTGTTATCTGAATACGGAAATATGTCTAGTGCCTCT
GTGTTGTTTGTGTTAGATGTCATGAGGAAAAGTTCTGCTAAAGAC
GGATTGGCAACCACAGGAGAAGGAAAAGATTGGGGAGTGTTGTT
TGGATTCGGACCAGGCTTGACTGTAGAAACCTTAGTGTTGCATA
GTGTCCCAGTCCCTGTCCCTACTGCAGCTTCTGCATGA
```

SEQ ID NO: 71

```
MAAVRLKEVRMAQRAEGLATVLAIGTAVPANCVYQATYPDYYFRVT
KSEHLADLKEKFQRMCDKSMIRKRHMHLTEEILIKNPKICAHMETSL
DARHAIALVEVPKLGQGAAEKAIKEWGQPLSKITHLVFCTTSGVDMP
GADYQLTKLLGLSPTVKRLMMYQQGCFGGATVLRLAKDIAENNRGA
RVLVVCSEITAMTFRGPCKSHLDSLVGHALFGDGAAAAIIGADPDQL
DEQPVFQLVSASQTILPESEGAIDGHLTEAGLTIHLLKDVPGLISENIE
QALEDAFEPLGIHNWNSIFWIAHPGGPAILDRVEDRVGLDKKRMRA
SREVLSEYGNMSSASVLFVLDVMRKSSAKDGLATTGEGKDWGVLF
GFGPGLTVETLVLHSVPVPVPTAASA
```

SEQ ID NO: 72

```
MAAVRLKEVRMAQRAEGLATVLAIGTAVPANCVYQATYPDYYFRVT
KSEHLADLKEKFQRMCDKSMIRKRHMHLTEEILIKNPKICAHMETSL
DARHAIALVEVPKLGQGAAEKAIKEWGQPLSKITHLVFCTTSGVDMP
GADYQLTKLLGLSPTVKRLMMYQQGCFGGATVLRLAKDIAENNRGA
RVLVVCSEITAMAFRGPCKSHLDSLVGHALFGDGAAAAIIGADPDQL
DEQPVFQLVSASQTILPESEGAIDGHLTEAGLTFHLLKDVPGLISENI
EQALEDAFEPLGIHNWNSIFWIAHPGGPAILDRVEDRVGLDKKRMR
ASREVLSEYGNMSSASVLFVLDVMRKSSAKDGLATTGEGKDWGVL
FGFGPGLTVETLVLHSVPVPVPTAASA
```

SEQ ID NO: 73

```
MAAVRLKEVRMAQRAEGLATVLAIGTAVPANCVYQATYPDYYFRVT
KSEHLADLKEKFQRMCDKSMIRKRHMHLTEEILIKNPKICAHMETSL
DARHAIALVEVPKLGQGAAEKAIKEWGQPLSKITHLVFCTTSGVDMP
GADYQLTKLLGLSPTVKRLMMYQQGCFGGATVLRLAKDIAENNRGA
RVLVVCSEITAMTFRGPCKSHLDSLVGHALFGDGAAAAIIGADPDQL
DEQPVFQLVSASQTILPESEGAIDGHLTEAGLTFHLLKDVPGLISENI
EQALEDAFEPLGIHNWNSIFWIAHPGGPAILDRVEDRVGLDKKRMR
ASREVLSEYGNMSSASVLFVLDVMRKSSAKDGLATTGEGKDWGVL
FGFGPGLTVETLVLHSVPVPVPTAASA
```

SEQ ID NOs: 74-79
See Example 6, Table 15.

SEQ ID NO: 80

```
ATGAATCCATCTCCATCTGTTACTGAATTGCAAGTAGAGAACGTC
ACCTTTACCCCAAGTGTTCAGCCTCCAGGTAGTACTAAAAGCCAT
TTCTTAGGAGGCGCTGGTGAAAGAGGACTAGAGATTGAAGGCAA
GTTTGTGAAATTCACAGCAATAGGTGTATATCTTGAAGATGACGC
CGTCCCTTGTTAGCTGGTAAGTGGAAAGGAAAGACCGCAGAGG
AACTAACTGAATCTGTGGAGTTTTTCAGGGATGTTGTAACAGGCC
CATTTGAAAAATTCATGAAGGTCACCATGATCCTTCCTTTGACTG
GTGCCCAATACTCAGAAAAAGTTGCTGAGAATTGTATTGCAATAT
GGAAGTTTTTCGGAATCTATACAGACGCCGAAGCTAAAGCAATTG
AGAAGTTTACCGAAGTGTTCAAAGATGAAATATTTCCACCTGGTT
CCAGTATCCTTTTTACTCAGAGCCCAGGCTCTTTGACAATTTCATT
CTCCAAGGACGGTAGTATTCCTAAAGATGGAGTTGCTGTAATAGA
GTCTAACTTACTAAGCGAAGCCGTCCTTGAATCAATGATCGGTAA
AAATGGCGTGTCCCCAGCAGCTAAGAAAAGTTTGGCCGAGAGAT
TATCTGCACTATTGAACGTTACTTCAGATAAGATGAAATGA
```

SEQ ID NO: 81

```
ATGTCTCCACCAGTTTCTGTTACAAAAATGCAAGTCGAAAATTAT
GCTTTTGCACCAACAGTGAACCCTGCCGGTTCCACCAATACTTTG
TTCTTAGCTGGAGCAGGCCATAGAGGTCTAGAGATTGAAGGAAA
GTTTGTGAAATTCACAGCCATAGGCGTATACCTTGAGGAAAGTGC
TATCCCATTTTTGGCAGAAAAGTGGAAAGGTAAGACCCCTCAGG
AGTTAACTGATAGCGTCGAGTTCTTTAGGGACGTGGTTACAGGT
CCATTCGAAAAGTTTACCAGAGTAACTATGATTCTACCTCTTACA
GGAAAGCAATATTCTGAGAAAGTCGCCGAAAACTGTGTTGCTCA
CTGGAAGGGCATAGGTACCTACACTGATGACGAAGGAAGGGCA
ATCGAGAAATTCTTGGATGTGTTTAGATCAGAAACATTCCCACCT
GGTGCTTCCATTATGTTTACTCAGAGTCCATTAGGCTTGTTAACC
ATCAGCTTTGCCAAGGACGATTCAGTTACCGGTACTGCAAATGCT
GTAATCGAGAACAAACAACTATCAGAAGCCGTCCTTGAATCCATT
ATTGGAAAGCATGGTGTGAGTCCTGCAGCCAAATGCTCTGTTGC
CGAGAGAGTAGCAGAATTGTTAAAAAAGAGCTATGCTGAAGAGG
CCTCAGTGTTCGGCAAACCAGAAACCGAAAAGTCCACAATACCT
GTTATCGGTGTGTAG
```

SEQ ID NO: 82

```
ATGTCTCCATCTGTTTCTGTTACTAAAGTCCAAGTGGAAAATTATG
TCTTTCCTCCAACAGTGAAGCCTCCAGCTAGTACCAAAACTTTGT
TCTTAGGTGGAGCAGGCCATAGAGGTCTAGATGTTGAGGGAAAG
```

```
TTTGTGAAATTCACAGTTATTGGCGTATACCTTGAAGAGAGCGCC
GTCCAGTTTTTGGCTCCTAAGTGGAAAGGTAAGTCTGCAGAAGA
ATTAATACACTCAGTTGACTTCTTTAGGGATATCGTGACCGGTCC
ATTCGAGAAGTTTACTAGAGTTAGGTTCATTCTACCTCTTACAGG
AAAGCAATTTTCCGAAAAGTAGCCGAAAACTGTGTCGCTCATTG
GAAGGCAACCGGCACTTATAGTGACGCCGGTAGCAGAGCTATAG
AGAAATTCTTGAATGTGGTTAAGTCTGAAACATTTTTACCAGGAG
CATCAATCTTGTTTACCCAGTCCCCTTTAGGTAGTCTAACTATTTC
TTTCACAAAAGATGACAGCATATCCGAAGCTGGCAACGCCGTAA
TCGAGAACAAACAGTTTAGTGAGGCCGTCCTTGAGACTATTATTG
GTGAACACGGAGTTAGTCCAGCTGCCAAGTGCTCTATAGCAGCT
AGAATGTCAGAATTGTTCAAAAACAGCTTATTTTGA
                                          SEQ ID NO: 83
ATGTGTTGTTCTATTTTGCATCACAGAAATCCAAGGAGGGAACAT
GAGTTTCCTGCTGTTGTAACTTCACCAGTCACAGAAAACCACATA
TTCTTAGGTGGAGCAGGCGAGAGAGGTCTAACCATCAATGGAAC
TTTTATCAAATTCACATGTATAGGCGTGTATCTTGAAGATAAGGC
CGACAAATCCTTGGCTACCAAGTGGGAAGGCAAATTAGAGGAAC
TACTAGAAACATTGGATTTTTACAGAGACATCATTAGTGGCCCTTT
CGAGAAGTTAATAAGAAGGAGCAAAATCAAGGAATTGTCCGGTC
CAGAATATTCAAGAAAAGTCATGGAGAACTGCGTTGCACACTTAA
AGTCCGTAGGCACATACGGTGATGCCGAAGTGGAGGCTATTCAA
AATCTACAGAAACTTAGTAGAATGTTGATTTTTCACTTAGTTCTAT
TGAAGAAGAACAGGCAAAGCCCTGATGGAATATTAGGTCTTTCTT
CATCCAAAGATATCAGTATTCCAGAAAAGGAGGATGCAATAATCG
AGAATAAGGCCGCTTCTAGCGCAGTATTGGAGACTATGATTGGC
GAACATGCTGTCTCTCCAGACTTAAAAAGATGTCTAGCCGCAAG
GCTTCCAGCTTTGTTAAACGAAGGTACTTTCAAAATAGGAAATTGA
                                          SEQ ID NO: 84
ATGGCTGCTGCTGCTGTTGCTACTATTTCTGCCGTACAAGTC
GAATTTTTGGAGTTCCCAGCAGTGGTTACAAGCCCTGCCTCCGG
TAGAACCTATTTTTAGGAGGCGCTGGTGAAAGGGGACTAACTAT
AGAGGGCAAATTCATCAAGTTTACAGGTATTGGTGTATACCTTGA
AGATAAAGCAGTCAGTAGTTTGGCTGCCAAGTGGAAAGGAAAGC
CATCTGAAGAGTTAGTGGAAACCCTAGACTTCTATAGAGATATAA
TCTCAGGCCCTTTTGAAAAACTTATTAGGGGTTCCAAGATATTGC
CATTAAGTGGAGTTGAGTACAGCAAAAAGGTAATGGAAAATTGTG
TCGCACATATGAAATCTGTTGGTACTTATGGCGACGCTGAAGCC
GCAGCTATCGAGAAGTTCGCCGAAGCCTTTAAAAACGTGAATTTC
CAGCCTGGTGCTACAGTTTTTTACAGACAATCACCAGATGGAGTA
TTGGGTTTATCCTTCAGTGAGGACGTCACCATTCCTGATAACGAA
GCCGCAGTGATTGAAAATAAGGCTGTTTCTGCCGCAGTACTAGA
GACTATGATAGGCGAACACGCTGTCAGCCCAGATCTTAAAAGAT
CACTAGCATCCAGGCTTCCTGCCGTTCTAAGTCATGGTATCATTG
TGTGA
                                          SEQ ID NO: 85
ATGGCTGCTGTCTCTGAAGTTGAAGTTGACGGTGTCGTTTTCCCT
CCAGTTGCTAGACCACCAGGCTCTGGTCATGCTCACTTCTTGGC
TGGTGCTGGTGTCCGTGGTGTTGAAATCGCTGGTAATTTCATCAA
GTTCACCGCTATTGGCGTCTACCTAGAAGAAGGTGCCGCCGTTC
CAGCTTTGGCTAAGAAGTGGGCCGGTAAGTCTGCTGATGAGTTG
GCTGCTGATGCTGCCTTTTTCCGTGACGTTGTTACCGGTGACTTC
GAAAAATTCACCAGAGTCACCATGATCTTGCCACTAACCGGTGA
GCAGTATTCCGACAAGGTCACCGAAACTGTGTTGCTGCTTGGA
AGGCCGCTGGCGTTTATACTGACGCCGAAGGTGCTGCTGCTGAT
AAATTCAAGGAAGCCTTTAAACCACATTCCTTCCCACCAGGTGCT
TCTATCTTGTTCACTCATTCTCCACCAGGTGTCTTAACCGTTGCC
TTTAGCAAAGACTCCTCCGTCCCAGAAGGCGCTGTTGCTGCTGC
TGCTATCGAAAACAGGGCTTTGTGCGAAGCTGTCCTAGACTCCA
TTATCGGTGAGCATGGTGTTTCTCCAGCTGCCAAAAGATCCATCG
CTGCTCGTGTCTCTCAATTGTTGAAAGCTGAATCCACCGGCGAC
GTCGCTGCTGCTGAACCAGCTCCTGTCTCTGCTTAA
                                          SEQ ID NO: 86
ATGGCTGCTTCCATTACCGCTATTACCGTTGAAAATTTGGAATAC
CCAGCTGTTGTTACTTCTCCAGTTACTGGTAAGTCTTACTTTTTGG
GTGGTGCTGGTGAAAGAGGTTTGACTATTGAAGGTAACTTCATTA
AGTTCACCGCCATCGGTGTTTACTTGGAAGATATTGCTGTTGCTT
CTTTGGCTGCTAAATGGAAGGGTAAATCCTCCGAAGAATTATTGG
AAACCTTGGACTTCTACAGAGACATTATTTCTGGTCCATTCGAAA
AGTTGATCAGAGGTTCCAAGATCAGAGAATTGTCTGGTCCAGAAT
ACTCCAGAAAGGTTATGGAAAATTGCGTTGCCCATTTGAAGTCTG
TTGGTACTTATGGTGATGCTGAAGCTGAAGCTATGCAAAAATTTG
CTGAAGCCTTTAAGCCAGTTAATTTTCCACCAGGTGCTTCCGTTT
TTTACAGACAATCTCCAGATGGTATCTTGGGTTTGTCTTTTTCACC
AGATACCTCCATCCCAGAAAAGAAGCTGCTTTGATTGAAAACAA
GGCTGTTTCTTCTGCTGTCTTGGAAACTATGATTGGTGAACATGC
TGTTTCCCAGATTTGAAAAGATGTTTAGCTGCTAGATTGCCTGC
CTTGTTGAATGAAGGTGCTTTTAAGATTGGTAACTAA
                                          SEQ ID NO: 87
MNPSPSVTELQVENVTFTPSVQPPGSTKSHFLGGAGERGLEIEGKF
VKFTAIGVYLEDDAVPLLAGKWKGKTAEELTESVEFFRDVVTGPFEK
FMKVTMILPLTGAQYSEKVAENCIAIWKFFGIYTDAEAKAIEKFTEVF
```

KDEIFPPGSSILFTQSPGSLTISFSKDGSIPKDGVAVIESNLLSEAVLE
SMIGKNGVSPAAKKSLAERLSALLNVTSDKMK

SEQ ID NO: 88
MSPPVSVTKMQVENYAFAPTVNPAGSTNTLFLAGAGHRGLEIEGKF
VKFTAIGVYLEESAIPFLAEKWKGKTPQELTDSVEFFRDVVTGPFEK
FTRVTMILPLTGKQYSEKVAENCVAHWKGIGTYTDDEGRAIEKFLDV
FRSETFPPGASIMFTQSPLGLLTISFAKDDSVTGTANAVIENKQLSEA
VLESIIGKHGVSPAAKCSVAERVAELLKKSYAEEASVFGKPETEKSTI
PVIGV

SEQ ID NO: 89
MSPSVSVTKVQVENYVFPPTVKPPASTKTLFLGGAGHRGLDVEGKF
VKFTVIGVYLEESAVQFLAPKWKGKSAEELIHSVDFFRDIVTGPFEKF
TRVRFILPLTGKQFSEKVAENCVAHWKATGTYSDAGSRAIEKFLNVV
KSETFLPGASILFTQSPLGSLTISFTKDDSISEAGNAVIENKQFSEAVL
ETIIGEHGVSPAAKCSIAARMSELFKNSLF

SEQ ID NO: 90
MCCSILHHRNPRREHEFPAVVTSPVTENHIFLGGAGERGLTINGTFI
KFTCIGVYLEDKADKSLATKWEGKLEELLETLDFYRDIISGPFEKLIRR
SKIKELSGPEYSRKVMENCVAHLKSVGTYGDAEVEAIQNLQKLSRM
LIFHLVLLKKNRQSPDGILGLSSSKDISIPEKEDAIIENKAASSAVLETM
IGEHAVSPDLKRCLAARLPALLNEGTFKIGN

SEQ ID NO: 91
MAAAAAVATISAVQVEFLEFPAVVTSPASGRTYFLGGAGERGLTIEG
KFIKFTGIGVYLEDKAVSSLAAKWKGKPSEELVETLDFYRDIISGPFE
KLIRGSKILPLSGVEYSKKVMENCVAHMKSVGTYGDAEAAAIEKFAE
AFKNVNFQPGATVFYRQSPDGVLGLSFSEDVTIPDNEAAVIENKAVS
AAVLETMIGEHAVSPDLKRSLASRLPAVLSHGIIV

SEQ ID NO: 92
MAAVSEVEVDGVVFPPVARPPGSGHAHFLAGAGVRGVEIAGNFIKF
TAIGVYLEEGAAVPALAKKWAGKSADELAADAAFFRDVVTGDFEKF
TRVTMILPLTGEQYSDKVTENCVAAWKAAGVYTDAEGAAADKFKEA
FKPHSFPPGASILFTHSPPGVLTVAFSKDSSVPEGAVAAAAIENRAL
CEAVLDSIIGEHGVSPAAKRSIAARVSQLLKAESTGDVAAAEPAPVSA

SEQ ID NO: 93
MAASITAITVENLEYPAVVTSPVTGKSYFLGGAGERGLTIEGNFIKFT
AIGVYLEDIAVASLAAKWKGKSSEELLETLDFYRDIISGPFEKLIRGSK
IRELSGPEYSRKVMENCVAHLKSVGTYGDAEAEAMQKFAEAFKPVN
FPPPGASVFYRQSPDGILGLSFSPDTSIPEKEAALIENKAVSSAVLETM
IGEHAVSPDLKRCLAARLPALLNEGAFKIGN

SEQ ID NO: 94
AAGCTTAAAATGAAGGTCACCGTCGTTTCTAGATCAGGTAGAGAA
GTTTTGAAAGCCCCATTGGATTTGCCAGATTCTGCTACTGTTGCT
GACTTGCAAGAAGCCTTTCATAAGAGAGCTAAGAAGTTCTACCCA
TCCAGACAAAGATTGACTTTGCCAGTTACTCCAGGTTCTAAAGAT

AAGCCAGTTGTCTTGAACTCCAAGAAGTCCTTGAAAGAATACTGT
GACGGTAACAACAACTCCTTGACTGTTGTTTTTAAGGATTTGGGT
GCCCAAGTTTCTTACAGAACTTTGTTCTTCTTCGAATACTTGGGT
CCTTTTGTTGATCTACCCAGTTTTTTACTACTTCCCAGTCTACAAGT
TTTTGGGTTACGGTGAAGATTGCGTTATCCATCCAGTTCAAACTT
ACGCTATGTACTACTGGTGTTTCCACTACTTCAAGAGAATCTTGG
AAACCTTCTTCGTCCACAGATTTTCTCATGCTACTTCTCCAATTGG
TAACGTTTCAGAAACTGTGCCTATTACTGGTCTTTCGGTGCTTAT
ATTGCTTACTACGTTAACCACCCATTATACACTCCAGTTTCAGACT
TGCAAATGAAGATTGGTTTTGGTTTCGGTTTGGTCTGTCAAGTTG
CTAACTTCTACTGCCATATCTTGTTGAAGAACTTGAGAGATCCAT
CTGGTGCTGGTGGTTATCAAATTCCAAGAGGTTTTTTGTTCAACA
TCGTTACCTGTGCTAACTACACTACCGAAATCTATCAATGGTTGG
GTTTCAACATTGCCACTCAAACTATTGCTGGTTACGTTTTTTTGGC
TGTTGCCGCTTTGATTATGACTAATTGGGCTTTGGGTAAGCACTC
CAGATTGAGAAAGATTTTCGATGGTAAAGACGGTAAGCCAAAGTA
TCCAAGAAGATGGGTTATTTTGCCACCATTCTTGTAACCGCGG

SEQ ID NO: 95
AAGCTTAAAATGAAGGTCACCTTGGTCAGTAGATCAGGTAGAGA
ATTCATTAAGGGTGGTTTGGAATTGAACGATTCTGCTACTGTTGC
TGACTTGCAAGAAGCTATTCATAAGAGAACTAAGAAGTTCTACCC
ATCCAGACAAAGATTGACTTTGCCAGTTCCATCTGGTTCTAGAGA
AAGACCAGTTATCTTGAACTACAAGAAGTCCTTGAAGGATTACTG
TGACGGTAACGAAAACACTTTGACCATCGTTTTTAAGGACTTGGG
TCCACAAGTTTCTTACAGAACTTTGTTCTTCTTCGAATATTTGGGT
CCATTGATCTTGTACCCAGTTTTCTATTACTTCCCAGTCTACAAGT
ACTTCGGTTACGAAGAAAAGAGAGTTATCCACCCAGTTCAAACTT
ATGCCTTGTACTACTGGTGTTTCCACTACTTCAAGAGAATTATGG
AAACCTTCTTCATCCACAGATTCTCTCATGCTACTTCTCCATTGTC
TAACGTTTCAGAAACTGTGCTTACTACTGGACTTTCGGTTCTTAT
ATTGCTTACTACGTTAACCACCCATTATACACTCCAGTTTCAGAC
TTGCAAATGAAGATTGGTTTTGGTTTCGGTATCGTTTGTCAATTG
GCTAACTTCTACTGCCACATCATCTTGAAGAATTTGAGATCACCA
GATGGTTCTGGTGGTTACCAAATTCCAAGAGGTTTTTTGTTCAAC
ATCGTTACCTGTGCTAACTACACTACCGAAATCTATCAATGGTTG
GGTTTCAACATTGCTACTCAAACAGTTGCTGGTTACGTTTTCTTG
GTTGTTGCTACCTCTATTATGACTAATTGGGCCTTGGCTAAACAC
AGAAGATTGAGAAATTATTCGACGGTAAGGACGGTAGACCAAA
GTATCCAAGAAGATGGGTTATTTTGCCACCATTCTTGTAACCGCGG

SEQ ID NO: 96

ATGAAGGTCACCGTCGTTTCTAGATCAGGTAGAGAAGTTGTTAAG
GGTGGTTTGGAATTGTCTGATTCTGCTACTGTTGCTGACTTGCAA
GATGCTATTCATAAGAGAACTAAGAAGTTCTACCCAGCCAGACAA
AGATTGACTTTGCCAGTTCAACCAGGTTCTAAAGAAAGACCAGTT
GTCTTGTCTTACAAGAAGTCATTGCAAGACTACATCTCCGGTAAC
TCTGATAACTTGACTGTTGTTTTCAAGGACTTGGGTCCACAAGTT
TCTTACAGAACTTTGTTCTTCTTGAATATTTGGGTCCATTGATCT
TGTACCCAATCTTCTACTACTTCCCAGTTTACGATTACTTGGGTTT
CAAGGGTGATAGAGTTATCCATCCAGTTCAAACTTATGCCTTGTA
CTACTGGTGTTTCCACTACTTCAAGAGAATTATGGAAACCTTCTT
CGTCCACAGATTCTCTCATGCTACTTCTCCATTGTCTAACGTTTTC
AGAAACTGTGCCTACTATTGGTCTTTCGGTGCTTTTATTGCTTACT
ACTTGAACCACCCATTATACACTCCAGTTTCAGACTTGCAAATGA
AGATTGGTTTCGGTATTGGTATCATCTGCCAAATCTCTAACTTCTA
CTGCCACATCTTGTTGAGAAACTTGAGATCACCAGATGGTAATGG
TGGTTACCAAATTCCAAGAGGTTTCTTGTTCAACATCGTTACCTG
TGCTAACTACACTACCGAAATCTATCAATGGTTGGGTTTTAACATT
GCCACTCAAACAGTTGCCGGTTACATTTTTTTGATCGTTGCTGCT
TCTATCATGACCAATTGGGCTTTGGCTAAACACAGAAGATTGAAG
AAAATCTTCGATGGTAAGGACGGTAGACCAAAGTATCCAAGAAG
ATGGGTTATTTTGCCACCATTCTTGTAA

SEQ ID NO: 97

ATGGATTTGTTATTGCTGGAAAAGTCACTTATTGCTGTATTTGTGG
CAGTTATTCTAGCCACGGTtATTTCTAAATTAAGAGGTAAgAAACT
AAAACTACCTCCTGGTCCCATCCCCATACCAATTTTTGGTAATTG
GTTGCAAGTGGGCGATGATTTGAATCACAGAAATTTgGTAGACTA
TGCTAAGAAGTTCGGTGAcCTTTTCTTGCTTAGAATGGGTCAAAG
GAATTTGGTAGTGGTTAGCTCACCTGATTTGACTAAGGAGGTCTT
ATTAACGCAAGGCGTTGAGTTTGGCTCCAGAACTAGAAATGTTGT
GTTTGATATTTTCACTGGTAAaGGTCAAGATATGGTTTTTACAGTT
TACGGTGAGCACTGGAGAAAAATGAGAAGAATCATGACCGTACC
ATTCTTTACTAACAAGGTTGTTCAACAAAATAGAGAAGGTTGGGA
GTTTGAGGCAGCTTCCGTAGTGGAAGACGTAAAGAAAATCCAG
ATTCGGCCACAAAGGGTATAGTACTAAGAAAAAGACTACAATTGA
TGATGTACAACAATATGTTCAGAATTATGTTTGACAGAAGATTTGA
AAGTGAAGATGACCCTTTGTTCCTGAGACTTAAGGCTTTGAATGG
TGAAAGATCGAGATTGGCTCAAAGTTTCGAATATAATTACGGTGA
cTTTATTCCAATCTTAAGACCATTTTTGAGAGGCTATTTGAAAATTT
GCCAAGACGTCAAGGATAGGAGGATCGCTCTTTTCAAGAAGTAC
TTTGTGGACGAGAGAAAGCAAATAGCTTCTTCCAAGCCCACAGG

TTCGGAAGGTTTAAAATGTGCAATTGATCATATTTTAGAAGCTGAA
CAAAAAGGTGAAATtAACGAAGATAATGTTTTGTACATTGTAGAAA
ATATCAATGTGGCTGCAATAGAAACAACCTTATGGTCAATAGAAT
GGGGTATTGCTGAATTGGTGAATCACCCAGAAATACAATCTAAAC
TGAGAAACGAGCTAGATACCGTTTTAGGTCCAGGTGTCCAAGTTA
CAGAACCTGATTTgCATAAGTTACCCTACTTGCAAGCTGTGGTTA
AAGAAACCTTGAGATTGAGAATGGCTATTCCTCTTCTAGTTCCTC
ATATGAACCTACATGATGCTAAACTGGCCGGTTATGATATTCCAG
CAGAAAGTAAGATTTTAGTAAATGCATGGTGGTTGGCCAACAATC
CAAACAGTTGGAAAAAgCCTGAAGAATTcAGACCTGAAAGATTCT
TCGAAGAGGAATCTCATGTTGAAGCCAACGGAAATGACTTCAGA
TATGTACCTTTTGGCGTTGGCAGAAGATCGTGTCCAGGAATAATA
CTAGCCTTACCAATATTGGGTATCACAATTGGTAGGATGGTTCAA
AATTTTGAGTTGCTACCACCACCCGGACAATCGAAAGTCGATACT
TCAGAGAAAGGAGGACAATTCTCATTGCATATTTTGAATCATTCC
ATTATAGTCATGAAACCCAGAAATTGTagcgctgaagctgcagcaaaag
aagctgcagcUaaagaagctgcagcaaaagctTCCAGTAGCTCTTCCTCC
TCAACCTCGATGATCGAcTTAATGGCTGCTATTATAAAAGGAGAACCAG
TTATAGTTAGTGACCCTGCTAACGCAAGCGCTTACGAATCCGTTG
CAGCCGAGTTGTCAAGTATGCTTATAGAAAATAGACAGTTTGCTA
TGATTGTAACGACCAGCATCGCCGTTTTAATTGGTTGCATCGTGA
TGTTGGTGTGGAGGAGGAGCGGTTCGGGCAATTCAAAGAGGGT
TGAACCACTAAAGCCATTAGTTATCAAACCTAGAGAAGAGGAAAT
TGACGATGGAAGGAAGAAAGTCACTATATTCTTCGGCACCCAAA
CAGGTACAGCTGAAGGTTTTGCTAAGGCTCTAGGAGAAGAAGCA
AAAGCTAGATATGAAAAgACGAGATTcAAAATTGTCGATCTGGAT
GACTATGCCGCCGATGATGACGAATACGAAGAAAAATTGAAgAAA
GAAGATGTCGCATTTTTCTTCCTTGCCACCTACGGCGACGGTGA
ACCAACAGATAATGCCGCAAGGTTTTACAAGTGGTTTACTGAAGG
TAATGACAGAGGAGAATGGCTGAAGAATTTgAAATATGGTGTGTT
CGGCCTTGGTAACAGACAGTACGAGCATTTTAATAAGGTCGCTAA
GGTTGTAGATGATATACTTGTTGAACAAGGTGCTCAAAGGTTAGT
GCAGGTGGGCTTGGGTGACGATGATCAATGTATTGAAGATGACT
TTACTGCTTGGAGAGAAGCCTTGTGGCCTGAATTAGATACTATCC
TTAGAGAAGAAGGTGAcACTGCTGTTGCTACCCCCTACACTGCAG
CAGTCCTAGAATATAGAGTCTCAATCCATGATTCAGAAGACGCCA
AATTcAATGATATTAACATGGCCAACGGTAACGGTTACACCGTTTT
TGACGCACAACATCCATACAAAGCTAATGTTGCTGTTAAAAGGGA
ACTTCACACCCCAGAAAGTGACAGGTCATGTATACATTTGGAATT
TGATATCGCTGGTAGTGGTTTGACTTACGAAACAGGTGACCATGT
CGGAGTACTTTGCGATAATTTGTCAGAAACTGTTGATGAAGCTTT GAGGTTATTGGATATGTCACCAGATACTTACTTCTCATTGCATGC
AGAAAAAGAAGACGGAACTCCAATATCAAGCTCGCTTCCCCCTC
CATTCCCTCCCTGTAACTTAAGAACAGCCCTAACTAGATATGCTT
GTTTACTGTCTTCTCCAAAGAAAAGTGCTTTGGTTGCATTGGCAG
CCCACGCATCCGATCCTACCGAAGCTGAGAGATTAAAGCATTTG
GCTTCACCAGCCGGTAAAGATGAATACAGTAAGTGGGTAGTGGA
GAGCCAAAGATCGCTTTTAGAAGTGATGGCTGAGTTTCCAAGTG
CTAAACCTCCTCTGGGTGTATTTTTCGCTGGTGTGGCCCCAAGAT
TGCAGCCTAGATTTTATTCCATATCCTCATCTCCAAAAATTGCCGA
AACCAGAATTCACGTGACATGTGCTCTGGTCTACGAAAAgATGCC
AACAGGTAGGATTCACAAGGGTGTCTGTTCTACCTGGATGAAAAA
TGCTGTACCCTATGAAAAATCCGAAAATTGTTCTAGTGCACCAAT
TTTCGTAAGACAATCTAATTTCAAGTTACCAAGCGATTCTAAAGTA
CCCATTATTATGATCGGTCCAGGTACTGGTTTGGCCCCATTcAGA
GGCTTCTTGCAAGAAAGATTGGCTTTAGTGGAGAGTGGAGTTGA
ATTGGGTCCTTCAGTTTTATTCTTTGGTTGTAGAAACAGAAGAAT
GGACTTTATCTACGAAGAAGAATTGCAGAGATTTGTTGAAAGTGG
TGCATTGGCCGAATTGAGTGTTGCATTcAGCAGGGAAGGTCCAA
CCAAAGAATACGTTCAACACAAGATGATGGACAAGGCTTCTGATA
TCTGGAATATGATTTCCCAAGGTGCTTATTTgTATGTTTGTGGTGA
cGCTAAAGGAATGGCTAGAGATGTTCATAGATCACTGCATACAAT
CGCACAAGAACAAGGTAGCATGGATTCAACAAAAGCAGAGGGCT
TTGTAAAgAATCTTCAGACAAGCGGTAGATATCTGAGAGATGTAT
GGTAA SEQ ID NO: 98
ATGGAGATTAACGGGGCACACAAGAGCAACGGAGGAGGAGTGG
ACGCTATGTTATGCGGCGGAGACATCAAGACAAAGAACATGGTG
ATCAACGCGGAGGATCCTCTCAACTGGGGAGCTGCAGCGGAGC
AAATGAAAGGTAGCCATTTGGATGAAGTGAAGAGAATGGTTGCT
GAGTTTAGGAAGCCAGTTGTGAATCTTGGTGGTGAGACTCTGAC
CATTGGACAAGTGGCTGCGATCTCAACTATTGGTAACAGTGTGAA
GGTGGAGCTATCGGAGACAGCTAGAGCCGGTGTGAATGCTAGTA
GTGATTGGGTTATGGAGAGTATGAACAAAGGCACTGATAGTTATG
GTGTTACTACTGGTTTTGGTGCTACTTCTCATCGGAGAACCAAAA
ACGGTGTCGCACTTCAGAAGGAACTTATTAGATTCCTTAACGCCG
GAATATTCGGAAGCACGAAAGAAACAAGCCACACATTGCCACAC
TCCGCCACAAGAGCCGCCATGCTTGTACGAATCAACACTCTCCT
CCAAGGATTTTCCGGTATCCGATTTGAGATTCTCGAAGCAATTAC
CAGTTTCCTCAACAACAACATCACTCCATCTCTCCCCCTCCGTGG
TACAATCACCGCCTCCGGAGATCTCGTTCCTCTCTCCACATCGC
CGGACTTCTCACCGGTCGTCCCAATTCCAAAGCTACTGGTCCCA
ACGGTGAAGCTTTAACAGCAGAGGAAGCTTTCAAATTAGCAGGA
ATCAGCTCCGGATTCTTTGATCTCCAGCCTAAGGAAGGTCTCGC
GCTAGTCAATGGCACGGCGGTTGGATCTGGAATGGCGTCAATGG
TGTTATTCGAAACGAATGTTCTCTCTGTTTTGGCTGAGATTTTGTC
GGCGGTTTTCGCAGAGGTGATGAGTGGTAAGCCTGAGTTCACCG
ATCATCTCACTCACAGACTTAAACATCATCCCGGTCAAATCGAAG
CGGCGGCGATAATGGAGCATATCCTCGACGGAAGCTCGTACATG
AAATTAGCTCAGAAGCTTCACGAGATGGATCCGTTACAGAAACCT
AAACAAGATCGTTACGCTCTTCGTACTTCTCCTCAATGGTTAGGT
CCTCAAATCGAAGTGATCCGTTACGCAACGAAATCGATCGAGCG
TGAGATTAACTCCGTCAACGATAATCCGTTGATCGATGTTTCGAG
GAACAAGGCGATTCACGGTGGTAACTTCCAAGGAACACCAATCG
GAGTTTCAATGGATAACACGAGATTGGCGATAGCAGCGATTGGT
AAACTCATGTTTGCTCAATTCTCAGAGCTTGTGAATGATTTCTACA
ACAATGGTTTACCCTCGAATCTAACCGCTTCGAGGAATCCAAGTT
TGGATTATGGATTCAAGGGAGCTGAGATTGCAATGGCTTCTTATT
GTTCAGAGCTTCAATACTTAGCTAATCCTGTGACTAGCCATGTTC
AATCAGCAGAGCAACATAACCAAGATGTCAACTCTTTGGGACTAA
TCTCGTCTCGCAAAACTTCTGAAGCTGTTGATATTCTCAAGCTTAT
GTCAACAACGTTCCTCGTTGCGATTTGTCAAGCTGTGGATTTGAG
ACATTTGGAGGAGAATTTGAGACAGACTGTGAAGAACACTGTCTC
TCAAGTGGCGAAGAAAGTTCTTACTACTGGAGTCAATGGTGAGC
TTCATCCTTCTCGCTTCTGCGAAAAGGATTTACTCAAAGTTGTAG
ACCGTGAACAAGTCTACACATACGCGGATGATCCTTGTAGCGCA
ACGTACCCGTTGATTCAGAAGCTGAGACAAGTTATTGTTGACCAT
GCTTTGATCAATGGTGAGAGTGAGAAGAATGCAGTGACTTCAATC
TTCCATAAGATTGGAGCTTTCGAGGAGGAGCTTAAGGCAGTGCT
ACCGAAAGAAGTGGAAGCAGCAAGAGCAGCCTACGATAACGGA
ACATCGGCTATCCCGAACAGGATCAAGGAATGTAGGTCGTATCC
ATTGTATAGATTCGTGAGGGAAGAGCTTGGAACAGAGCTTTTGAC
CGGAGAGAAAGTGACGTCGCCTGGAGAAGAGTTCGACAAGGTTT
TCACGGCGATTTGTGAAGGTAAAATCATTGATCCGATGATGGAAT
GTCTCAACGAGTGGAACGGAGCTCCCATTCCAATATGTTAA SEQ ID NO: 99
ATGGATCAAATCGAAGCTATGTTGTGTGGTGGTGGTGAAAAAACA
AAAGTTGCTGTTACTACTAAGACCTTGGCTGATCCATTGAATTGG
GGTTTGGCTGCTGATCAAATGAAGGGTTCTCATTTGGATGAAGTC
AAGAAGATGGTCGAAGAATACAGAAGACCAGTTGTTAATTTGGGT
GGTGAAACTTTGACTATTGGTCAAGTTGCTGCTATTTCTACTGTT
GGTGGTTCTGTTAAGGTTGAATTGGCTGAAACTTCAAGAGCTGGT
GTTAAGGCTTCTTCTGATTGGGTTATGGAATCTATGAACAAGGGT

```
ACTGATTCTTACGGTGTTACTACAGGTTTTGGTGCTACTTCTCATA
GAAGAACTAAGAATGGTACTGCCTTGCAAACCGAATTGATCAGAT
TTTTGAACGCCGGTATTTTCGGTAACACCAAAGAAACTTGTCATA
CCTTGCCACAATCTGCTACTAGAGCTGCTATGTTGGTTAGAGTTA
ACACTTTGTTGCAAGGTTACTCCGGTATCAGATTCGAAATTTTGG
AAGCTATCACCTCCTTGTTGAACCATAACATTTCTCCATCTTTGCC
ATTGAGAGGTACTATTACTGCTTCTGGTGATTTGGTTCCATTGTC
TTATATTGCTGGTTTGTTGACTGGTAGACCAAACTCTAAAGCTAC
TGGTCCAGATGGTGAATCATTGACTGCTAAAGAAGCCTTTGAAAA
GGCTGGTATCTCTACTGGTTTTTTCGACTTGCAACCTAAAGAAGG
TTTGGCTTTGGTTAATGGTACAGCTGTTGGTTCTGGTATGGCTTC
TATGGTTTTGTTTGAAGCTAACGTTCAAGCTGTTTTGGCCGAAGT
TTTGTCTGCTATTTTTGCTGAAGTTATGTCCGGTAAGCCAGAATT
CACTGATCATTTGACCCATAGATTGAAACATCACCCAGGTCAAAT
TGAAGCTGCTGCAATTATGGAACATATCTTGGATGGTTCCTCTTA
CATGAAGTTGGCTCAAAAAGTTCACGAAATGGACCCATTGCAAAA
GCCAAAACAAGATAGATACGCTTTGAGAACTTCTCCACAATGGTT
GGGTCCACAAATAGAAGTTATTAGACAAGCCACCAAGTCCATCG
AAAGAGAAATCAATTCTGTTAACGACAACCCATTGATCGACGTCA
GTAGAAACAAAGCTATTCATGGTGGTAACTTCCAAGGTACTCCAA
TTGGTGTTTCTATGGACAACACTAGATTGGCTATTGCTGCCATTG
GTAAATTGATGTTCGCTCAATTCTCCGAATTGGTCAACGATTTTA
CAACAACGGTTTGCCTTCTAACTTGACCGCTTCTTCTAATCCATC
ATTGGATTACGGTTTTAAGGGTGCTGAAATTGCTATGGCTTCATA
CTGTTCTGAATTGCAATACTTGGCTAACCCAGTTACCTCTCATGT
TCAATCTGCTGAACAACACAATCAAGACGTTAACTCCTTGGGTTT
GATCTCTTCCAGAAAAACTTCTGAAGCCGTTGACATTTTGAAGTT
GATGTCTACTACCTTCTTGGTCGGTATTTGTCAAGCAGTTGATTT
GAGACACTTGGAAGAAACTTGAGACAAACCGTTAAGAACACCG
TTTCCCAAGTTGCTAAAAAGGTTTTGACTACCGGTATTAACGGTG
AATTGCATCCATCCAGATTCTGCGAAAAGATTTGTTGAAGGTCG
TTGACAGAGAACAAGTTTTCACCTATGTTGATGATCCATGTTCTG
CTACCTATCCATTGATGCAAAGATTGAGACAAGTCATCGTTGATC
ATGCTTTGTCTAATGGTGAAACCGAAAAGAACGCTGTTACCTCCA
TTTTCCAAAAGATTGGTGCTTTCGAAGAAGAATTGAAGGCCGTTT
TGCCAAAAGAAGTTGAAGCAGCTAGAGCAGCTTACGGTAACGGT
ACTGCTCCAATTCCAAATAGAATCAAAGAATGCAGATCCTACCCA
TTATACAGATTCGTTAGAGAAGAATTAGGTACTAAGTTGTTGACC
GGTGAAAAGGTTGTTTCTCCAGGTGAAGAATTCGATAAGGTTTTC
ACTGCTATGTGCGAAGGTAAATTGATCGATCCATTGATGGACTGC
TTGAAAGAATGGAATGGTGCTCCTATTCCTATCTGCTAA
```

SEQ ID NO: 100

```
ATGTTGGACAAGCACATCCCAGACGGTCACTTAGAAACCACTAG
CGCCCACTGGAGGGATTTAAACCAAGTTGTTCAAAACGGTGAATT
ATCTATTGACGGTTACTCCTTGTCCTTGGCCGATGTTGTTGCTGT
CGCTAAGTATGGTTGCCAACCAAGATTGACTGACAAGCCAGAGA
CTATTGATGCTATTAACGGTTCTGTCATCGCCTTGGCTGAATGTT
TAAGGGATGGTCATCACATTTACGGTGTTAACACTGGTTTTGGTG
GTTCTGCCGATTCCAGAACCAACCAGACCACTACTTTGCAAAGCT
CCTTGTTGCAATTGTTGCAATCCGGTATCTTAACTGCTTCTGACA
CTACCAATGAAGGTTTGCAGTTGAACTTGCAAGGTCAAAGCAGC
CATTCTATGCCATCTGAGTGGGTTAAAGCTACCATGTTGGTTCGT
TCTAACTCTGTCGCTAGAGGCCATTCTGCTGTCAGCTTGCCAGCT
ATTTCCGCCATTTTGAGATTGATCAGAGAAGATATCGTCCCAGTT
ATTCCATTGAGAGGTACTATCTCCGCTTCCGGTGACTTGATGCCA
TTGGCTTACGTTGTCGGTGCCATTGAAGGTTCTCCAGGTATTTAC
GTTAGAGTCAAGGATGGTTCTGAACATCAAGTCGTTACCGCTCAA
AAGGCCCTACAAACTATCGGTGCTAAGGGTGTTACTTTGGGCCC
TAAAGAGGGTTTAGGTTTGGTCAATGGTACTGCTGCTTCTGGTGC
CTTAGCTGGTTTGGTTTTGTATGAGGCTCATCAATTGGCCGTCTT
GGCTCAAGCTGTCACCGCCTTAACTGTCGAAGCTATTCAAGGTT
CTACCGAATCCTTTCACCCTTTTATCGCTCAAGTCCGTCCACATG
AAGGTCAGATCGAGGCTGCTGAAAACATCCTATCTCTATTAAAAG
GTAGCTTGTTGGCCAGAGGTAGCTCTACTACCCAAACCAGAACC
GGTCTAGTCCAAGACAGATACTCCTTGAGAACTGCTTCTCAATGG
ATCGGTCCTCAATTGGAAGATTTATTGTTGGCCGACAGACAGGTC
CAAGTCGAACTAAATTCTACCAGCGACAACCCATTAATCGATACT
GGTTCTAAAACTTTCTACACTGGTGGTAACTTCCAAGCTACCAGC
ATTACCTCCGCTATGGAAAAGACTAGGTTGGCTTTGCAAATGTTC
GGTAAGATGTTATTCGTCCAATGTAATGAAATGATCGACCCAAAC
TTGAACAACGGTCTACCTACCAACTTGGTTGCTGATGACCCATCC
TTGTCCTTCACCATGAAAGGCGTCGATATCAACATGGCTGCTTAT
ATGTCTGAATTGGCTTACTTGGCTAATCCAGTCTCCTCCCACGTT
CAAACTGCTGAAATGCAAAACCAAGCCTTGAACTCCTTGGCTTTC
GTTAGCGCTAGGTATACTATGAAAGCTGTTGATATCGTCTCTATG
ATGGGTGCTTGTGCTTTGTATGTCGCTTGTCAAGCCTTAGACTTG
AGGGTCTTGCAATTGCGTTTCTTCCAAAGAGTCCAAGGTGTCGCT
AAAGAAATCGCTCACGGTGCCTTTGGTAAGGCCTTGGAACCTTT
CGAAATCGACCAGGTTGCTGATCACTTGTCTGAAGCTATTCAAAA
CTCCTGGCCATCTACCTCTAGGTTGGACTTGAGAGACAGATGCA
```

AAAGGGTTGCTGAAATGTTTATCCCAGTCTTGTTCGGTGCTTTGT
TGCAAATTATCCCACAGAACAGACAAACCTCTGATTTATTCACCG
CCATCTCTGCTTGTAAGATGATTTCCGTTTTTAAGTTGGAAGGCG
TTTACAGAGAAGTTTTCGCTGAATTTTGCACTTCCCAACCTACCG
CTGACTTTTTGGGTACCGGTACTAAGGAAATCTACACCTTCATCA
GACACGACTTGAGAGTCCCATTCCACCAGGGTTTCGTCGAACAT
CCATCCGCCTCTCAAACCGACTTACCAGAAACTATCAACGGTAGA
GTTAAAAAGACCGTCGGTGGTTGGATTTCTGTCGTTTACGAAGCC
TTGAGAAATGGTACCTTAAGCGGTACTATTTTGAACTCCTTCCAA
CAATAA

SEQ ID NO: 101

ATGGCTCCATCATTGGATTCTATTTCTCATTCTTTTGCAAACGGTG
TTGCATCTGCAAAACAAGCTGTTAATGGTGCATCTACTAATTTGG
CAGTTGCTGGTTCTCATTTACCAACTACCCAAGTTACACAAGTTG
ATATTGTTGAAAAGATGTTAGCAGCACCTACTGATTCTACCTTGG
AATTGGATGGTTACTCTTTAAATTTAGGTGATGTTGTTTCTGCAGC
TAGAAAGGGTAGACCAGTTAGAGTTAAAGATTCTGATGAAATTAG
ATCTAAAATTGATAAATCTGTTGAATTTTTGAGATCTCAATTATCAA
TGTCAGTTTATGGTGTTACAACTGGTTTCGGTGGTTCAGCTGATA
CTAGAACTGAAGATGCAATTTCTTTACAAAAGGCATTGTTGGAAC
ATCAATTATGTGGTGTTTTGCCTTCATCATTCGATTCTTTTAGATT
AGGTAGAGGTTTAGAAAACTCTTTGCCATTAGAAGTTGTTAGAGG
TGCAATGACAATTAGAGTTAATTCTTTAACAAGAGGTCATTCTGCT
GTTAGATTGGTTGTTTTAGAAGCTTTGACTAACTTTTTGAACCATG
GTATTACTCCAATTGTTCCATTAAGAGGTACAATTTCTGCATCTGG
TGATTTGTCTCCTTTGTCTTATATTGCAGCTGCTATTTCAGGTCAT
CCAGATTCAAAGGTTCATGTTGTTCATGAAGGTAAGGAAAAGATT
TTATATGCAAGAGAAGCTATGGCTTTATTTAATTTAGAACCAGTTG
TTTTAGGTCCTAAGGAAGGTTTAGGTTTAGTTAACGGTACAGCTG
TTTCAGCATCTATGGCTACCTTAGCTTTGCATGATGCTCATATGTT
ATCTTTGTTATCTCAATCATTAACAGCTATGACTGTTGAAGCTATG
GTTGGTCATGCTGGTTCTTTTCATCCATTCTTGCATGATGTTACCA
GACCTCATCCAACACAAATTGAAGTTGCTGGTAATATTAGAAAGT
TGTTAGAAGGTTCTAGATTCGCAGTTCATCATGAAGAAGAAGTTA
AAGTTAAGGATGATGAAGGTATTTTGAGACAAGATAGATACCCAT
TGAGAACTTCACCACAATGGTTGGGTCCATTGGTTTCTGATTTGA
TTCATGCTCATGCAGTTTTGACCATTGAAGCAGGTCAATCTACAA
CAGATAATCCATTGATTGATGTTGAAAACAAAACATCACATCATG
GTGGTAATTTTCAAGCAGCTGCTGTTGCTAATACAATGGAAAAGA
CAAGATTAGGTTTGGCACAAATTGGTAAGTTAAATTTCACACAATT
AACTGAAATGTTGAATGCAGGTATGAATAGAGGTTTGCCATCTTG

TTTGGCAGCTGAAGATCCTTCATTATCTTATCATTGTAAAGGTTTG
GATATTGCAGCAGCAGCTTATACTTCAGAATTAGGTCATTTAGCA
AATCCAGTTACTACACATGTTCAACCAGCTGAAATGGCTAATCAA
GCTGTTAATTCTTTAGCATTGATTTCAGCTAGAAGAACCACTGAAT
CAAACGATGTTTTGTCATTATTATTAGCTACTCATTTATATTGTGTT
TTACAAGCTATTGATTTGAGAGCAATTGAATTTGAATTTAAAAAGC
AATTTGGTCCAGCTATTGTTTCATTAATTGATCAACATTTTGGTTC
TGCAATGACTGGTTCAAATTTGAGAGATGAATTAGTTGAAAAGGT
TAACAAGACCTTGGCTAAAAGATTAGAACAAACTAACTCTTACGA
TTTGGTTCCAAGATGGCATGATGCTTTTTCTTTTGCTGCAGGTAC
AGTTGTTGAAGTTTTGTCATCTACCTCATTGTCTTTGGCAGCTGTT
AACGCTTGGAAAGTTGCTGCTGCTGAATCAGCTATTTCATTAACT
AGACAAGTTAGAGAAACTTTTTGGTCTGCTGCTTCAACTTCTTCA
CCTGCTTTGTCTTACTTGTCTCCAAGAACTCAAATTTTGTACGCTT
TCGTTAGAGAAGAATTGGGTGTTAAAGCTAGAAGAGGTGATGTTT
TCTTAGGTAAGCAAGAAGTTACTATTGGTTCTAATGTTTCTAAAAT
TTACGAAGCTATTAAATCAGGTAGAATTAATAACGTTTTGTTGAAG
ATGTTAGCATAA

SEQ ID NO: 102

ATGGTTACAGTCGAAGAAGTGAGAAAGGCTCAAAGAGCCGAGG
GACCAGCTACTGTCATGGCAATTGGTACCGCTGTACCTCCTAACT
GTGTCGATCAAGCTACATACCCTGACTATTACTTTAGAATTACAAA
TTCAGAACACAAAGCCGAACTGAAGGAAAAATTTCAAAGAATGTG
CGACAAATCTCAGATCAAAAAGAGATACATGTATTTAAACGAGGA
GGTTCTAAAAGAGAATCCAAATATGTGCGCGTACATGGCACCCT
CACTGGATGCAAGACAAGACATAGTCGTTGTTGAAGTACCAAAG
CTTGGTAAGGAGGCCGCCGTTAAGGCTATTAAGGAATGGGGCCA
ACCTAAATCTAAAATTACACATTTGGTCTTCTGTACAACCAGTGG
CGTGGATATGCCCGGTGCTGACTACCAACTAACCAAGTTGCTTG
GTTTAAGGCCCTCCGTTAAAAGATTAATGATGTATCAACAGGGTT
GTTTCGCTGGAGGAACAGTTCTAAGATTAGCTAAAGATTTAGCAG
AAAACAACAAAGGCGCTAGGGTACTTGTAGTATGTTCAGAAATCA
CTGCTGTAACTTTTCGTGGTCCAACCGACACTCATTTAGATTCCT
TAGTTGGACAGGCTCTATTTGGAGATGGGGCCGCCGCCATCATT
ATCGGTTCTGATCCGATCCCAGAGGTAGAGAAACCATTGTTCGA
ATTGGTTTCCGCTGCTCAAACAATTCTGCCTGACTCCGAAGGTGC
CATAGACGGTCACTTGAGAGAGGTCGGATTGACCTTTCATTTATT
AAAGGATGTGCCCGGTTTGATAAGTAAAAACGTCGAGAAATCCTT
AACTGAAGCATTCAAACCATTAGGGATATCCGATTGGAACAGTTT
ATTCTGGATCGCTCATCCAGGCGGTCCAGCCATCCTAGATCAAG
TAGAAGCTAAATTATCATTAAAACCTGAAAAGTTAAGAGCAACGA

```
GACATGTCTTGTCAGAATATGGTAATATGTCTAGCGCGTGTGTTC

TTTTCATCTTGGATGAAATGCGTAGAAAATCTAAAGAAGACGGTT

TGAAGACGACTGGTGAAGGTATTGAATGGGGTGTTTTGTTCGGC

TTTGGTCCGGGTCTAACCGTCGAAACTGTGGTATTGCACTCCGTT

GCCATAAATTAA
                                    SEQ ID NO: 103
GTTACCGTAGAAGAGGTACGTAAAGCTCAGAGAGCAGAGGGGC

CCGCTACCGTTATGGCCATTGGTACCGCCGTGCCGCCAAACTGC

GTTGATCAAGCTACTTATCCTGATTACTATTTCAGAATTACTAATT

CTGAACATAAGGCCGAATTGAAAGAGAAGTTTCAAAGGATGTGC

GACAAATCACAGATAAAGAAGCGTTATATGTACTTGAACGAAGAA

GTGTTGAAGGAAAATCCAAATATGTGTGCCTATATGGCTCCTTCA

TTAGATGCCAGACAAGATATTGTTGTGGTTGAAGTTCCCAAGTTG

GGCAAGGAAGCGGCAGTCAAAGCTATTAAGGAATGGGGACAAC

CAAAATCAAAAATTACGCATTTAGTGTTTTGTACCACTTCTGGCGT

AGATATGCCTGGTGCCGACTATCAATTAACGAAATTGCTTGGTTT

ACGTCCATCAGTAAAAAGATTGATGATGTATCAACAAGGTTGCTT

TGCCGGTGGTACAGTTCTTCGTCTTGCCAAGGACCTTGCAGAAA

ACAATAAGGGGCAAGGGTGTTGGTTGTATGTTCTGAAATAACG

GCCGTGACGTTTAGAGGTCCCACTGATACCCATTTGGATTCATTA

GTAGGCCAAGCTTTATTTGGTGACGGTGCAGCAGCAATCATAAT

CGGTTCCGATCCGATACCAGAAGTGGAAAAGCCTTTGTTTGAATT

GGTTAGCGCAGCCCAAACCATACTTCCAGACTCTGAAGGTGCAA

TTGATGGTCATTTGAGGGAGGTGGGTCTAACATTCCATCTTTTGA

AGGACGTGCCGGGACTTATTTCTAAGAATGTAGAAAAGTCTTTGA

CTGAAGCATTCAAACCACTGGGAATTTCTGACTGGAATTCTTTGT

TCTGGATCGCTCACCCAGGTGGCCCTGCGATTCTAGATCAGGTC

GAGGCAAAACTTTCACTAAAGCCTGAAAAATTGAGGGCGACGAG

ACATGTTTTGTCAGAATACGGCAATATGTCATCAGCTTGCGTATT

GTTCATATTGGATGAAATGAGAAGAAAATCTAAAGAGGATGGCCT

GAAAACGACTGGTGAAGGTATTGAATGGGGTGTCTTGTTTGGTTT

CGGTCCTGGCTTGACTGTCGAGACTGTTGTGTTGCATAGTGTTG

CTATTAATTGA
                                    SEQ ID NO: 104
ATGGTGACTGTTGAAGAAGTAAGAAAGGCTCAAAGAGCTGAAGG

TCCTGCTACTGTTATGGCCATAGGGACAGCGGTCCCACCAAACT

GTGTTGATCAGGCGACTTATCCTGATTATTATTTCAGAATCACGA

ATTCCGAGCACAAAGCCGAGCTAAAAGAGAAATTTCAAAGGATG

TGCGATAAAAGCCAGATAAAAAAGAGATATGTATCTAAATGAA

GAAGTCTTAAAAGAACCCGAACATGTGCGCTTACATGGCACC

ATCCCTAGATGCTAGACAAGATATCGTAGTGGTTGAAGTTCCAAA

GCTGGGTAAGGAGGCAGCGGTAAAAGCAATTAAGGAATGGGGC

CAACCAAAGTCAAAGATTACTCACTTAGTATTTTGCACTACTTCCG

GTGTAGATATGCCCGGTGCCGACTATCAACTTACCAAACTACTTG

GTTTGCGTCCAAGCGTTAAACGTCTAATGATGTACCAACAAGGAT

GCTTTGCTGGTGGCACCGTGTTAAGATTAGCAAAAGATCTGGCC

GAGAATAACAAGGCGCTAGAGTTTTAGTTGTATGTTCAGAAATT

ACGGCTGTGACTTTCAGAGGCCCTACAGACACTCATCTTGATTCA

TTAGTGGGCCAAGCTTTGTTCGGAGACGGAGCAGCAGCAATCAT

TATCGGTTCAGATCCAATTCCAGAAGTCGAAAAACCACTGTTCGA

ACTAGTTTCTGCAGCCCAAACAATTTTACCGGATTCTGAAGGCGC

TATTGACGGTCATTTAAGGGAAGTGGGTTTGACTTTCCATTTGTT

GAAAGACGTTCCAGGTCTGATATCCAAAAATGTGGAGAAATCATT

GACCGAAGCATTTAAACCATTGGGTATCTCTGATTGGAATTCACT

ATTTTGGATTGCTCACCCCGGTGGACCAGCAATACTGGATCAAG

TTGAAGCGAAATTGTCACTGAAGCCTGAAAAATTGAGGGCTACG

AGGCATGTGTTATCCGAATACGGGAATATGTCTAGCGCATGTGT

GTTGTTTATACTTGATGAAATGCGTAGGAAATCTAAGGAAGATGG

CTTGAAGACTACCGGTGAAGGTATTGAATGGGGTGTCTTATTTGG

ATTTGGCCCTGGTTTGACAGTGGAAACTGTTGTTCTTCACTCAGT

AGCTATTAATTAA
                                    SEQ ID NO: 105
MDLLLLEKSLIAVFVAVILATVISKLRGKKLKLPPGPIPIPIFGNWLQVG

DDLNHRNLVDYAKKFGDLFLLRMGQRNLVVVSSPDLTKEVLLTQGV

EFGSRTRNVVFDIFTGKGQDMVFTVYGEHWRKMRRIMTVPFFTNK

VVQQNREGWEFEAASVVEDVKKNPDSATKGIVLRKRLQLMMYNNM

FRIMFDRRFESEDDPLFLRLKALNGERSRLAQSFEYNYGDFIPILRPF

LRGYLKICQDVKDRRIALFKKYFVDERKQIASSKPTGSEGLKCAIDHI

LEAEQKGEINEDNVLYIVENINVAAIETTLWSIEWGIAELVNHPEIQSK

LRNELDTVLGPGVQVTEPDLHKLPYLQAVVKETLRLRMAIPLLVPHM

NLHDAKLAGYDIPAESKILVNAWWLANNPNSWKKPEEFRPERFFEE

ESHVEANGNDFRYVPFGVGRRSCPGIILALPILGITIGRMVQNFELLP

PPGQSKVDTSEKGGQFSLHILNHSIIVMKPRNCSAEAAAKEAAAKEA

AAKASSSSSSSTSMIDLMAAIIKGEPVIVSDPANASAYESVAAELSSM

LIENRQFAMIVTTSIAVLIGCIVMLVWRRSGSGNSKRVEPLKPLVIKP

REEEIDDGRKKVTIFFGTQTGTAEGFAKALGEEAKARYEKTRFKIVD

LDDYAADDDEYEEKLKKEDVAFFFLATYGDGEPTDNAARFYKWFTE

GNDRGEWLKNLKYGVFGLGNRQYEHFNKVAKVVDDILVEQGAQRL

VQVGLGDDDQCIEDDFTAWREALWPELDTILREEGDTAVATPYTAA

VLEYRVSIHDSEDAKFNDINMANGNGYTVFDAQHPYKANVAVKREL

HTPESDRSCIHLEFDIAGSGLTYETGDHVGVLCDNLSETVDEALRLL

DMSPDTYFSLHAEKEDGTPISSSLPPPFPPCNLRTALTRYACLLSSP
```

KKSALVALAAHASDPTEAERLKHLASPAGKDEYSKWVVESQRSLLE

VMAEFPSAKPPLGVFFAGVAPRLQPRFYSISSSPKIAETRIHVTCALV

YEKMPTGRIHKGVCSTWMKNAVPYEKSENCSSAPIFVRQSNFKLPS

DSKVPIIMIGPGTGLAPFRGFLQERLALVESGVELGPSVLFFGCRNR

RMDFIYEEELQRFVESGALAELSVAFSREGPTKEYVQHKMMDKASD

IWNMISQGAYLYVCGDAKGMARDVHRSLHTIAQEQGSMDSTKAEG

FVKNLQTSGRYLRDVW

SEQ ID NO: 106

MEINGAHKSNGGGVDAMLCGGDIKTKNMVINAEDPLNWGAAAEQM

KGSHLDEVKRMVAEFRKPVVNLGGETLTIGQVAAISTIGNSVKVELS

ETARAGVNASSDWVMESMNKGTDSYGVTTGFGATSHRRTKNGVA

LQKELIRFLNAGIFGSTKETSHTLPHSATRAAMLVRINTLLQGFSGIR

FEILEAITSFLNNNITPSLPLRGTITASGDLVPLSYIAGLLTGRPNSKAT

GPNGEALTAEEAFKLAGISSGFFDLQPKEGLALVNGTAVGSGMASM

VLFETNVLSVLAEILSAVFAEVMSGKPEFTDHLTHRLKHHPGQIEAA

AIMEHILDGSSYMKLAQKLHEMDPLQKPKQDRYALRTSPQWLGPQI

EVIRYATKSIEREINSVNDNPLIDVSRNKAIHGGNFQGTPIGVSMDNT

RLAIAAIGKLMFAQFSELVNDFYNNGLPSNLTASRNPSLDYGFKGAE

IAMASYCSELQYLANPVTSHVQSAEQHNQDVNSLGLISSRKTSEAV

DILKLMSTTFLVAICQAVDLRHLEENLRQTVKNTVSQVAKKVLTTGV

NGELHPSRFCEKDLLKVVDREQVYTYADDPCSATYPLIQKLRQVIVD

HALINGESEKNAVTSIFHKIGAFEEELKAVLPKEVEAARAAYDNGTSA

IPNRIKECRSYPLYRFVREELGTELLTGEKVTSPGEEFDKVFTAICEG

KIIDPMMECLNEWNGAPIPIC

SEQ ID NO: 107

MLDKHIPDGHLETTSAHWRDLNQVVQNGELSIDGYSLSLADVVAVA

KYGCQPRLTDKPETIDAINGSVIALAECLRDGHHIYGVNTGFGGSAD

SRTNQTTTLQSSLLQLLQSGILTASDTTNEGLQLNLQGQSSHSMPS

EWVKATMLVRSNSVARGHSAVSLPAISAILRLIREDIVPVIPLRGTISA

SGDLMPLAYVVGAIEGSPGIYVRVKDGSEHQVVTAQKALQTIGAKG

VTLGPKEGLGLVNGTAASGALAGLVLYEAHQLAVLAQAVTALTVEAI

QGSTESFHPFIAQVRPHEGQIEAAENILSLLKGSLLARGSSTTQTRT

GLVQDRYSLRTASQWIGPQLEDLLLADRQVQVELNSTSDNPLIDTG

SKTFYTGGNFQATSITSAMEKTRLALQMFGKMLFVQCNEMIDPNLN

NGLPTNLVADDPSLSFTMKGVDINMAAYMSELAYLANPVSSHVQTA

EMQNQALNSLAFVSARYTMKAVDIVSMMGACALYVACQALDLRVL

QLRFFQRVQGVAKEIAHGAFGKALEPFEIDQVADHLSEAIQNSWPS

TSRLDLRDRCKRVAEMFIPVLFGALLQIIPQNRQTSDLFTAISACKMI

SVFKLEGVYREVFAEFCTSQPTADFLGTGTKEIYTFIRHDLRVPFHQ

GFVEHPSASQTDLPETINGRVKKTVGGWISVVYEALRNGTLSGTILN

SFQQ

SEQ ID NO: 108

MAPSLDSISHSFANGVASAKQAVNGASTNLAVAGSHLPTTQVTQVD

IVEKMLAAPTDSTLELDGYSLNLGDVVSAARKGRPVRVKDSDEIRSK

IDKSVEFLRSQLSMSVYGVTTGFGGSADTRTEDAISLQKALLEHQLC

GVLPSSFDSFRLGRGLENSLPLEVVRGAMTIRVNSLTRGHSAVRLV

VLEALTNFLNHGITPIVPLRGTISASGDLSPLSYIAAAISGHPDSKVHV

VHEGKEKILYAREAMALFNLEPVVLGPKEGLGLVNGTAVSASMATL

ALHDAHMLSLLSQSLTAMTVEAMVGHAGSFHPFLHDVTRPHPTQIE

VAGNIRKLLEGSRFAVHHEEEVKVKDDEGILRQDRYPLRTSPQWLG

PLVSDLIHAHAVLTIEAGQSTTDNPLIDVENKTSHHGGNFQAAAVAN

TMEKTRLGLAQIGKLNFTQLTEMLNAGMNRGLPSCLAAEDPSLSYH

CKGLDIAAAAYTSELGHLANPVTTHVQPAEMANQAVNSLALISARRT

TESNDVLSLLLATHLYCVLQAIDLRAIEFEFKKQFGPAIVSLIDQHFGS

AMTGSNLRDELVEKVNKTLAKRLEQTNSYDLVPRWHDAFSFAAGT

VVEVLSSTSLSLAAVNAWKVAAAESAISLTRQVRETFWSAASTSSPA

LSYLSPRTQILYAFVREELGVKARRGDVFLGKQEVTIGSNVSKIYEAI

KSGRINNVLLKMLA

SEQ ID NO: 109

MVTVEEVRKAQRAEGPATVMAIGTAVPPNCVDQATYPDYYFRITNS

EHKAELKEKFQRMCDKSQIKKRYMYLNEEVLKENPNMCAYMAPSL

DARQDIVVVEVPKLGKEAAVKAIKEWGQPKSKITHLVFCTTSGVDMP

GADYQLTKLLGLRPSVKRLMMYQQGCFAGGTVLRLAKDLAENNKG

ARVLVVCSEITAVTFRGPTDTHLDSLVGQALFGDGAAAIIIGSDPIPEV

EKPLFELVSAAQTILPDSEGAIDGHLREVGLTFHLLKDVPGLISKNVE

KSLTEAFKPLGISDWNSLFWIAHPGGPAILDQVEAKLSLKPEKLRAT

RHVLSEYGNMSSACVLFILDEMRRKSKEDGLKTTGEGIEWGVLFGF

GPGLTVETVVLHSVAIN

---

What is claimed is:

1. A method of producing a chalcone compound or a stilbene compound, comprising growing a yeast cell capable of producing a phenylpropanoid or phenylpropanoid derivative compound in a culture medium,
wherein said chalcone compound or stilbene compound is synthesized by the yeast cell, and
wherein the yeast cell comprises a gene encoding a double-bond reductase polypeptide, wherein expression of the gene or activity of the double-bond reductase polypeptide encoded thereby is reduced or eliminated, and wherein the double-bond reductase polypeptide:
(i) comprises SEQ ID NO: 22;
(ii) comprises a polypeptide with at least 90% identity to SEQ ID NO: 22;
(iii) comprises SEQ ID NO: 26;
(iv) comprises a polypeptide with at least 90% identity to SEQ ID NO: 26;
(v) is encoded by a nucleic acid sequence comprising SEQ ID NO: 7;
(vi) is encoded by a nucleic acid sequence comprising a sequence with at least 90% identity to SEQ ID NO: 7;
(vii) is encoded by a nucleic acid sequence comprising SEQ ID NO: 43; or
(viii) is encoded by a nucleic acid sequence comprising a sequence with at least 90% identity to SEQ ID NO: 43.

2. The method of claim 1, wherein the double-bond reductase polypeptide is *S. cerevisiae* trans-2-enoyl-CoA reductase TSC13 or *S. cerevisiae* DFG10.

3. The method of claim 1, wherein the yeast cell is a recombinant yeast cell and comprises a recombinant gene encoding an enzyme that partially or completely complements the function of the double-bond reductase polypeptide, wherein the recombinant gene:

(a) is any one of SEQ ID NOs: 94-96;
(b) is a nucleotide sequence with at least 90% identity to any one of SEQ ID NOs: 94-96;
(c) encodes any one of SEQ ID NOs: 65-67; or
(d) encodes a polypeptide with at least 90% identity to any one of SEQ ID NOs: 65-67;
and wherein the method further comprises growing the recombinant yeast cell under conditions in which the recombinant gene encoding an anzyme that partially or completelty ocmplements the function of the double-bond reductase polypeptide is expressed.

4. The method of claim 1, wherein the yeast cell is a recombinant yeast cell and comprises a recombinant gene encoding a polyketide synthase Type III polypeptide, and wherein the method further comprises growing the recombinant yeast cell under conditions in which the recombinant gene encoding the polyketide synthase Type III polypeptide is expressed.

5. The method of claim 4, wherein the polyketide synthase Type III polypeptide is:
(a) a chalcone synthase polypeptide; or
(b) a stilbene synthase polypeptide.

6. The method of claim 5, wherein the polyketide synthase Type III polypeptide:
(i) is encoded by a nucleic acid sequence comprising SEQ ID NO: 4;
(ii) is encoded by a nucleic acid sequence comprising a sequence with at least 90% identity to SEQ ID NO: 4;
(iii) comprises SEQ ID NO: 19;
(iv) comprises a polypeptide sequence with at least 90% identity to SEQ ID NO: 19;
(v) is encoded by a nucleic acid sequence comprising SEQ ID NO: 23;

(vi) is encoded by a nucleic acid sequence comprising a sequence with at least 90% identity to SEQ ID NO: 23;
(vii) comprises SEQ ID NO: 24; or
(viii) comprises a polypeptide sequence with at least 90% identity to SEQ ID NO: 24.

7. The method of claim 4, wherein the recombinant yeast cell further comprises one or more of:
(a) a recombinant gene encoding a phenylalanine ammonia lyase polypeptide;
(b) a recombinant gene encoding a cinnamate 4-hydroxylase polypeptide;
(c) a recombinant gene encoding a 4-coumarate-CoA ligase polypeptide;
(d) a recombinant gene encoding a cytochrome p450 polypeptide; or
(e) a recombinant gene encoding a chalcone isomerase polypeptide.

8. The method of claim 7, wherein:
(a) the recombinant gene encoding the phenylalanine ammonia lyase polypeptide:
(i) comprises SEQ ID NO: 1;
(ii) comprises a nucleotide sequence with at least 90% identity to SEQ ID NO: 1;
(iii) encodes a polypeptide comprising SEQ ID NO: 16; or
(iv) encodes a polypeptide with at least 90% identity to SEQ ID NO: 16;
(b) the recombinant gene encoding the cinnamate 4-hydroxylase polypeptide:
(i) comprises SEQ ID NO: 2;
(ii) comprises a nucleotide sequence with at least 90% identity to SEQ ID NO: 2;
(iii) encodes a polypeptide comprising SEQ ID NO: 17; or
(iv) encodes a polypeptide with at least 90% identity to SEQ ID NO: 17;
(c) the recombinant gene encoding the 4-coumarate-CoA ligase polypeptide:
(i) comprises SEQ ID NO: 3;
(ii) comprises a nucleotide sequence with at least 90% identity to SEQ ID NO: 3;
(iii) encodes a polypeptide comprising SEQ ID NO: 18; or
(iv) encodes a polypeptide with at least 90% identity to SEQ ID NO: 18;
(d) the recombinant gene encoding the cytochrome p450 polypeptide:
(i) comprises SEQ ID NO: 6;
(ii) comprises a nucleotide sequence with at least 90% identity to SEQ ID NO: 6;
(iii) encodes a polypeptide comprising SEQ ID NO: 21; or
(iv) encodes a polypeptide with at least 90% identity to SEQ ID NO: 21; or
(e) the recombinant gene encoding the chalcone isomerase polypeptide:
(i) comprises any one of SEQ ID NOS: 80-86;
(ii) comprises a nucleotide sequence with at least 90% identity to any one of SEQ ID NOS: 80-86;
(iii) encodes a polypeptide comprising any one of SEQ ID NOS: 87-93; or
(iv) encodes a polypeptide a polypeptide with at least 90% identity to any one of SEQ ID NOS: 87-93.

9. The method of claim 1, wherein the phenylpropanoid compound is cinnamic acid or coumaric acid.

10. The method of claim 1, wherein the phenylpropanoid derivative compound is a chalcone compound or a stilbenoid compound.

11. The method of claim 10, wherein the stilbenoid compound is resveratrol.

12. The method of claim 1, wherein the yeast cell is a *Saccharomyces cerevisiae* cell, a *Schizosaccharomyces pombe* cell, a *Yarrowia lipolytica* cell, a *Candida glabrata* cell, a *Ashbya gossypii* cell, a *Cyberlindnera jadinii* cell, a *Pichia pastoris* cell, a *Kluyveromyces lactis* cell, a *Hansenula polymorpha* cell, a *Candida boidinii* cell, an *Arxula adeninivorans* cell, a *Xanthophyllomyces dendrorhous* cell, or a *Candida albicans* cell.

13. The method of claim 1, wherein the chalcone compound or stilbene compound is a compound of formula (III):

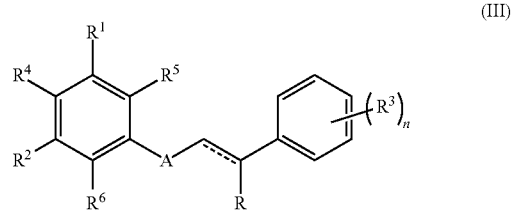

(III)

or a pharmaceutically acceptable salt thereof, wherein
A is a bond or C=O;
n is an integer 0, 1, 2, 3, or 4;
R is hydrogen when ═ is a double bond, or R and $R^5$ together with the atoms to which they are attached form a 6-member heterocyclyl when A is C=O and ═ is a single bond;
$R^1$ is hydrogen or —$OR^{11}$;
  wherein each $R^{11}$ is independently hydrogen, $C_1$-$C_6$ alkyl, or glycosyl;
$R^2$ is hydrogen, —$OR^{11}$, $C_1$-$C_{12}$ alkyl, or $C_2$-$C_{12}$ alkenyl, wherein alkyl and alkenyl are optionally substituted with one or more $R^7$;
or $R^2$ and $R^6$ together with the atoms to which they are attached form a 5- to 7-member heterocyclyl optionally substituted with one or more $R^7$ groups;
or $R^2$ and $R^4$ together with the atoms to which they are attached form a 5- to 7-member heterocyclyl optionally substituted with one or more $R^7$ groups;
$R^3$ is independently selected from nitro, $C_1$-$C_6$ alkyl, $C_2$-$C_6$ alkenyl, $C_1$-$C_6$ haloalkyl, $C_1$-$C_6$ hydroxyalkyl, —$OR^{12}$, —$N(R^{12})_2$, —$C(O)R^{12}$, —$C(O)OR^{12}$, —$C(O)N(R^{12})_2$, and —$S(O)_2R^{12}$, wherein each $R^{12}$ is independently hydrogen or $C_1$-$C_6$ alkyl;
$R^4$ is hydrogen, —$OR^{11}$, $C_1$-$C_{12}$ alkyl, or $C_2$-$C_{12}$ alkenyl, wherein alkyl and alkenyl are optionally substituted with one or more $R^7$;
or $R^4$ and $R^2$ together with the atoms to which they are attached form a 5- to 7-member heterocyclyl optionally substituted with one or more $R^7$ groups;
$R^5$ is hydrogen, —$OR^{11}$, —$C(O)OR^{10}$, or —$C(O)N(R^{10})_2$, wherein each $R^{10}$ is independently hydrogen or $C_1$-$C_6$ alkyl; and
$R^6$ is hydrogen, $C_1$-$C_6$ alkyl, $C_2$-$C_6$ alkenyl, —$OR^{11}$, —$N(R^{10})_2$, —$C(O)R^{10}$, —$C(O)OR^{10}$, or —$C(O)N(R^{10})_2$, wherein alkyl and alkenyl are optionally substituted with one or more $R^8$; or $R^6$ and $R^2$ together with the atoms to which they are attached form a 5- to 7-member heterocyclyl optionally substituted with one or more $R^8$ groups;

each $R^7$ and $R^8$ is independently halogen, cyano, nitro, $C_1$-$C_6$ alkyl, $C_2$-$C_6$ alkenyl, $C_1$-$C_6$ haloalkyl, $C_1$-$C_6$ hydroxyalkyl, —$OR^{13}$, —$SR^{13}$, —$N(R^{13})_2$, —$C(O)R^{13}$, —$C(O)OR^{13}$, —$C(O)N(R^{13})_2$, or —$S(O)_2R^{13}$, wherein each $R^{13}$ is independently hydrogen or $C_1$-$C_6$ alkyl.

14. The method of claim 1, further comprising harvesting said chalcone compound or stilbene compound.

15. The method of claim 1, further comprising isolating said chalcone compound or stilbene compound.

16. The method of claim 1, wherein the double-bond reductase polypeptide:
 (i) comprises SEQ ID NO: 22;
 (ii) comprises a polypeptide with at least 90% identity to SEQ ID NO: 22;
 (iii) is encoded by a nucleic acid sequence comprising SEQ ID NO: 7; or
 (iv) is encoded by a nucleic acid sequence comprising a sequence with at least 90% identity to SEQ ID NO: 7.

17. The method of claim 1, wherein said chalcone compound or stilbene compound is resveratrol.

18. The method of claim 17, further comprising isolating the resveratrol.

19. The method of claim 16, wherein said chalcone compound or stilbene compound is resveratrol.

20. The method of claim 19, further comprising isolating the resveratrol.

* * * * *

SEQUENCE LISTING

<160> NUMBER OF SEQ ID NOS: 109

<210> SEQ ID NO 1
<211> LENGTH: 2154
<212> TYPE: DNA
<213> ORGANISM: Arabidopsis thaliana

<400> SEQUENCE: 1

```
atggaccaaa ttgaagcaat gctatgcggt ggtggtgaaa agaccaaggt ggccgtaacg    60
acaaaaactc ttgcagatcc tttgaattgg ggtctggcag ctgaccagat gaaaggtagc   120
catctggatg aagttaagaa gatggttgag gaatacagaa gaccagtcgt aaatctaggc   180
ggcgagacat tgacgatagg acaggtagct gctatttcga ccgttggcgg ttcagtgaag   240
gtagaacttg cagaaacaag tagagccgga gttaaggctt catcagattg ggtcatggaa   300
agtatgaaca agggcacaga ttcctatggc gttaccacag gctttggtgc tacctctcat   360
agaagaacta aaaatggcac tgctttgcaa acagaactga tcagattcct taacgccggt   420
attttcggta atacaaagga aacttgccat acattacccc aatcggcaac aagagctgct   480
atgcttgtta gggtgaacac tttgttgcaa ggttactctg aataaggtt tgaaattctt   540
gaggccatca cttcactatt gaaccacaac atttctcctt cgttgccctt aagaggaaca   600
ataactgcca gcggtgattt ggttcccctt tcatatatcg caggcttatt aacgggaaga   660
cctaattcaa aggccactgg tccagacgga gaatccttaa ccgctaagga agcatttgag   720
aaagctggta tttcaactgg tttctttgat ttgcaaccca aggaaggttt agccctggtg   780
aatggcaccg ctgtcggcag cggtatggca tccatggtgt tgtttgaagc taacgtacaa   840
gcagttttgg ccgaagtttt gtccgcaatt tttgccgaag tcatgagtgg aaaacctgag   900
tttactgatc acttgaccca caggttaaaa catcacccag acaaattga agcagcagct   960
atcatggagc acattttgga cggctctagc tacatgaagt tagcccagaa ggttcatgaa  1020
atggacccct tgcaaaaacc caaacaagat agatatgctt taaggacatc cccacaatgg  1080
cttggccctc aaattgaagt aattagacaa gctacaaagt ctatagaaag agagatcaac  1140
tctgttaacg ataatccact tattgatgtg tcgaggaata aggcaataca tggaggcaat  1200
ttccagggta cacccatagg agtcagtatg gataatacca ggcttgccat agccgcaatt  1260
ggcaaattaa tgtttgccca atttctgaa ttggtcaatg acttctacaa taacggtttg  1320
ccttcgaatc tgaccgcatc ttctaaccct agtcttgatt atggtttcaa aggtgctgag  1380
atagcaatgg caagctattg ttcagagctg caatatctag ccaacccagt aacctctcat  1440
gtacaatcag ccgaacaaca caatcaggat gttaattctt tgggcctgat tcatcaaga   1500
aaaacaagcg aggccgttga tatccttaaa ttaatgtcca caacattttt agtgggtata  1560
tgccaggccg tagatttgag acacttggaa gagaatttga cagacagt gaaaatacc     1620
gtatcacagg ttgcaaaaaa ggttctaact acaggtatca atggtgaatt gcacccatca  1680
agattctgtg aaaagattt attaaaagtt gtagatagaa acaagtatt tacttacgtt    1740
gacgatccat gtagcgctac ttatccattg atgcagagat tgagacaagt tattgtagat  1800
cacgctttat ccaatggtga aactgagaaa atgccgtta cttcaatatt ccaaaagata   1860
ggtgcctttg aagaagaact gaaggcagtt ttaccaaagg aagtcgaagc tgctagagcc  1920
gcatacggaa atggtactgc ccctatacca aatagaatca aagagtgtag gtcgtaccct  1980
ttgtacagat tcgttagaga gagttggga accaaattac taactggtga aaaagtcgtt   2040
agcccaggtg aagaatttga caaggtattc acagctatgt gcgagggaaa gttgatagat  2100
ccacttatgg attgcttgaa agagtggaat ggtgcaccta ttccaatctg ctaa         2154
```

<210> SEQ ID NO 2
<211> LENGTH: 1521
<212> TYPE: DNA
<213> ORGANISM: Ammi majus

```
<400> SEQUENCE: 2
atgatggatt tgttttgtt agaaaaagct cttcttggtt tgttcattgc aactatagta      60
gccatcacaa tctctaagct aaggggaaag aaacttaagt tgcctccagg cccaatccct     120
gtcccagtgt ttggtaattg gttacaagtt ggcgacgact taaaccagag gaatttggta     180
gagtatgcta aaaagttcgg cgacttattt ctacttagga tgggtcaaag aaacttggtc     240
gtggtttcat cccctgactt agcaaaagac gtactacata cccagggtgt cgagttcgga     300
agtagaacta gaaatgttgt gtttgatatt ttcacaggca aaggtcaaga tatggttttt     360
accgtataca gcgagcactg gaggaaaatg agaagaataa tgactgtccc attctttaca     420
aacaaagtgg ttcaacagta taggttcgga tgggaggacg aagccgctag agtagtcgag     480
gatgttaagg caaatcctga agccgctacc aacggtattg tgttgaggaa tagattacaa     540
cttttgatgt acaacaatat gtatagaata atgtttgaca ggagatttga atctgttgat     600
gatccattat tcctaaaact taaggcattg aatggcgaga gatcaaggtt agctcaatcc     660
tttgaataca acttcggtga cttcattcct atattgaggc cattcttgag aggatatctt     720
aagttgtgtc aggaaatcaa ggacaaaagg ttaaagctat tcaaggacta cttcgtcgac     780
gagagaaaaa agttggagag tatcaagagc gtaggtaata actccttaaa gtgcgccata     840
gatcatatta tcgaggcaca agaaaaaggc gagataaacg aggataacgt gttatacatc     900
gtcgagaata tcaacgtggc tgccattgaa actacacttt ggtctattga atggggtata     960
gcagaactag tgaataaccc tgaaatccag aaaaaattga gacacgaatt agacaccgta    1020
cttggagctg tgtttcaaat ttgtgaacca gatgttcaaa aattgcctta tctacaggcc    1080
gtgataaaag agactttaag gtacaggatg gcaattccat tgttagtccc acatatgaat    1140
cttcacgaag ccaaattggc cggctatgat atccctgcag agagcaaaat tttggtaaac    1200
gcttggtggt tagccaataa tccagcacat tggaacaaac ctgatgagtt tagaccagaa    1260
agatttttgg aggaagaatc caaggtcgag gctaatggaa acgactttaa gtacatccct    1320
ttcggtgttg gcagaagatc ttgcccaggt ataattcttg cttaccaat ccttggaata    1380 gtaattggta ggttggttca aaacttcgag ttacttccac ctccaggcca aagcaaaata    1440
gatacagccg aaaaaggtgg acagttttca ttgcaaatcc taaagcattc cactattgtg    1500
tgtaaaccta gaagttctta a                                              1521

<210> SEQ ID NO 3
<211> LENGTH: 1671
<212> TYPE: DNA
<213> ORGANISM: Arabidopsis thaliana

<400> SEQUENCE: 3
atgacgacac aagatgtgat agtcaatgat cagaatgatc agaaacagtg tagtaatgac      60 gtcatttttcc gatcgagatt gcctgatata tacatcccta accacctccc actccacgac    120
tacatcttcg aaaatatctc agagttcgcc gctaagccat gcttgatcaa cggtcccacc    180
ggcgaagtat acacctacgc cgatgtccac gtaacatctc ggaaactcgc cgccggtctt    240 cataaccctcg gcgtgaagca acacgacgtt gtaatgatcc tcctcccgaa ctctcctgaa    300
gtagtcctca ctttccttgc cgcctccttc atcggcgcaa tcaccacctc cgcgaacccg    360
ttcttcactc cggcggagat ttctaaacaa gccaaagcct ccgcggcgaa actcatcgtc    420
actcaatccc gttacgtcga taaaatcaag aacctccaaa acgacggcgt tttgatcgtc    480
accaccgact ccgacgccat ccccgaaaac tgcctccgtt tctccgagtt aactcagtcc    540
```

```
gaagaaccac gagtggactc aataccggag aagatttcgc cagaagacgt cgtggcgctt    600 ccttctctcat ccggcacgac gggtctcccc aaaggagtga tgctaacaca caaaggtcta    660
gtcacgagcg tggcgcagca agtcgacggc gagaatccga atctttactt caacagagac    720
gacgtgatcc tctgtgtctt gcctatgttc catatatacg ctctcaactc catcatgctc    780
tgtagtctca gagttggtgc cacgatcttg ataatgccta agttcgaaat cactctcttg    840
ttagagcaga tacaaaggtg taaagtcacg gtggctatgg tcgtgccacc gatcgtttta    900
gctatcgcga agtcgccgga gacggagaag tatgatctga gctcggttag gatggttaag    960
tctggagcag ctcctcttgg taaggagctt gaagatgcta ttagtgctaa gtttcctaac   1020
gccaagcttg gtcagggcta tgggatgaca gaagcaggtc cggtgctagc aatgtcgtta   1080
gggtttgcta aagagccgtt tccagtgaag tcaggagcat gtggtacggt ggtgaggaac   1140
gccgagatga agatacttga tccagacaca ggagattctt tgcctaggaa caaacccggc   1200
gaaatatgca tccgtggcaa ccaaatcatg aaaggctatc tcaatgaccc cttggccacg   1260
gcatcgacga tcgataaaga tggttggctt cacactggag acgtcggatt tatcgatgat   1320
gacgacgagc ttttcattgt ggatagattg aaagaactca tcaagtacaa aggatttcaa   1380
gtggctccag ctgagctaga gtctctcctc ataggtcatc cagaaatcaa tgatgttgct   1440
gtcgtcgcca tgaaggaaga agatgctggt gaggttcctg ttgcgtttgt ggtgagatcg   1500
aaagattcaa atatatccga agatgaaatc aagcaattcg tgtcaaaaca ggttgtgttt   1560
tataagagaa tcaacaaagt gttcttcact gactctattc ctaaagctcc atcagggaag   1620
atattgagga aggatctaag agcaagacta gcaaatggat taatgaacta g            1671

<210> SEQ ID NO 4
<211> LENGTH: 1200
<212> TYPE: DNA
<213> ORGANISM: Hordeum vulgare

<400> SEQUENCE: 4
atggctgcag taagattgaa agaagttaga atggcacaga gggctgaagg tttagctaca     60
gttttagcaa tcggtactgc cgttccagct aattgtgttt atcaagctac ctatccagat    120
tattatttta gggttactaa aagtgagcac ttggcagatt taaggagaa gtttcaaaga    180 atgtgtgaca aatcaatgat tagaaagaga cacatgcact tgaccgagga atatattgatc   240 aagaacccaa agatctgtgc acacatggag acctcattgg atgctagaca cgccatcgca    300
ttagttgaag ttcccaaatt gggccaaggt gcagctgaga aggccattaa ggagtggggc    360 caaccctgt ctaagattac tcatttggta ttttgcacaa catccggcgt tgacatgccc    420
ggtgctgatt accaattaac aaagttgtta ggtttgtccc ctacagtcaa aaggttaatg    480
atgtaccaac aaggttgctt tggtggtgca actgttttga gattggcaaa agatatcgct    540
gaaaataata gaggtgccag agtgttagtc gtttgttccg agataactgc tatggccttc    600
agaggtccat gcaagagtca tttagattcc ttggtaggtc atgccttgtt cggtgatggt    660
gccgctgctg caattatagg cgctgaccca gaccaattag acgaacaacc agttttccag    720
ttggtatcag cttctcagac tatattacca gaatcagaag gtgccataga tggccattta    780
acagaagctg gtttaactat acatttatta aaagatgttc ctggtttaat ttcagagaac    840
attgaacagg ctttggagga tgcctttgaa ccttttaggta ttcataactg gaattcaatt    900
ttctggattg cacatcctgg tggccctgcc attttagaca gagttgaaga tagagtagga    960
```

| ttggataaga agagaatgag ggcttctagg gaagtgttat ctgaatacgg aaatatgtct | 1020 |
| agtgcctctg tgttgtttgt gttagatgtc atgaggaaaa gttctgctaa agacggattg | 1080 |
| gcaaccacag gagaaggaaa agattgggga gtgttgtttg gattcggacc aggcttgact | 1140 |
| gtagaaacct tagtgttgca tagtgtccca gtccctgtcc ctactgcagc ttctgcatga | 1200 |

<210> SEQ ID NO 5
<211> LENGTH: 1452
<212> TYPE: DNA
<213> ORGANISM: Malus domestica

<400> SEQUENCE: 5

| atgggtgatg tcattgtctt gtatgcttct ccaggtatgg gtcatatagt ttccatggtt | 60 |
| gaattgggta aattcatcgt tcatagatac ggtccacaca agttctctat tactatcttg | 120 |
| tacacctgtg gttccatcgt tgatactgct tctattccag tttacatcag aagaatctcc | 180 |
| cattcccatc cattcatctc attcagacaa ttcccaagag ttaccaacaa catcaccaga | 240 |
| aacatttccg ttccagctat taccttcgac ttcatcagac aaaatgatcc acatgttaga | 300 |
| tccgccttgc aagaaatttc aaagtctgct actgttagag ccttcatcat tgatttgttc | 360 |
| tgtacttccg ctttgccaat cggtaaagaa ttcaacattc aacctacta cttcagaact | 420 |
| tctggtgctg ctattttggc tgctttcttg tacttgccaa agatcgatga acaaactaag | 480 |
| accaccgaat ctttcaagga tttgagagat accgttttcg aatttccagg ttggaaatct | 540 |
| ccattgaagg ctactcatat ggttcaattg gttttggata gaaacgatcc agcctactct | 600 |
| gatatgatct acttctgttc tcatttgcca aagtccaacg gtattatcgt taacaccttc | 660 |
| gaagaattgg aaccaccatc tgttttacaa gctattgctg gtggtttgtg tgttccagat | 720 |
| ggtccaactc caccagttta ttatgttggt ccattgatcg aagaagaaaa agaattgtcc | 780 |
| aaggatgctg atgctgccga aaagaagat tgcttgtctt ggttggataa gcaaccatct | 840 |
| agatccgttt tgttccttgtg ttttggttcc atgggttctt ttccagctgc tcaattgaaa | 900 |
| gaaattgcca atggtttgga agcctctggt caaagatttt tgtgggttgt taagaagcca | 960 |
| ccagtcgaag aaaaatccaa acaagttcat ggtgttgacg acttcgattt gaaaggtgtt | 1020 |
| ttgccagaag gtttcttgga aagaactgct gatagaggta tggttgtaaa atctttgggct | 1080 |
| ccacaagttt tcgtcttgaa gaaagaatct gttggtggtt tcgttactca ttgtggttgg | 1140 |
| aattctgttt tggaagctgt tgttgctggt gttccaatga ttgcttggcc attatatgct | 1200 |
| gaacaacaca tgaatagaaa cgtcttggtt accgatatgg aaatcgctat tggtgtcgaa | 1260 |
| caaagagatg aagaaggtgg ttttgtttcc ggtgaagaag ttgaaagaag agttagagaa | 1320 |
| ttgatggaat ccgaaggtgg tagagtttg agagaaagat gtaaaaagtt gggtgaaatg | 1380 |
| gcttctgctg ctttaggtga aactggttct tctactagaa acttggtcaa cttcgtttcc | 1440 |
| tccattacct ga | 1452 |

<210> SEQ ID NO 6
<211> LENGTH: 2076
<212> TYPE: DNA
<213> ORGANISM: Saccharomyces cerevisiae

<400> SEQUENCE: 6

| atgccgtttg gaatagacaa caccgacttc actgtcctgg cggggctagt gcttgccgtg | 60 |
| ctactgtacg taaagagaaa ctccatcaag gaactgctga tgtccgatga cggagatatc | 120 |
| acagctgtca gctcgggcaa cagagacatt gctcaggtgg tgaccgaaaa caacaagaac | 180 |

```
tacttggtgt tgtatgcgtc gcagactggg actgccgagg attacgccaa aaagttttcc      240
aaggagctgg tggccaagtt caacctaaac gtgatgtgcg cagatgttga gaactacgac      300
tttgagtcgc taaacgatgt gcccgtcata gtctcgattt ttatctctac atatggtgaa      360
ggagacttcc ccgacggggc ggtcaacttt gaagacttta tttgtaatgc ggaagcgggt      420
gcactatcga acctgaggta taatatgttt ggtctgggaa attctactta tgaattcttt      480
aatggtgccg ccaagaaggc cgagaagcat ctctccgctg cgggcgctat cagactaggc      540
aagctcggtg aagctgatga tggtgcagga actacagacg aagattacat ggcctggaag      600
gactccatcc tggaggtttt gaaagacgaa ctgcatttgg acgaacagga agccaagttc      660
acctctcaat ccagtacac tgtgttgaac gaaatcactg actccatgtc gcttggtgaa       720
ccctctgctc actatttgcc ctcgcatcag ttgaaccgca acgcagacgg catccaattg      780
ggtcccttcg atttgtctca accgtatatt gcacccatcg tgaaatctcg cgaactgttc      840
tcttccaatg accgtaattg catccactct gaatttgact tgtccggctc taacatcaag      900
tactccactg gtgaccatct tgctgtttgg ccttccaacc cattggaaaa ggtcgaacag      960
ttcttatcca tattcaacct ggaccctgaa accattttg acttgaagcc cctggatccc      1020
accgtcaaag tgcccttccc aacgccaact actattggcg ctgctattaa acactatttg     1080
gaaattacag gacctgtctc cagacaattg ttttcatctt tgattcagtt cgcccccaac     1140
gctgacgtca aggaaaaatt gactctgctt tcgaaagaca aggaccaatt cgccgtcgag     1200
ataacctcca aatatttcaa catcgcagat gctctgaaat atttgtctga tggcgccaaa     1260
tgggacaccg tacccatgca attcttggtc gaatcagttc cccaaatgac tcctcgttac     1320
tactctatct cttcctcttc tctgtctgaa aagcaaaccg tccatgtcac ctccattgtg     1380
gaaaactttc ctaacccaga attgcctgat gctcctccag ttgttggtgt tacgactaac     1440
ttgttaagaa acattcaatt ggctcaaaac aatgttaaca ttgccgaaac taacctacct     1500
gttcactacg atttaaatgg cccacgtaaa cttttcgcca attacaaatt gcccgtccac     1560
gttcgtcgtt ctaacttcag attgccttcc aacccttcca ccccagttat catgatcggt     1620
ccaggtaccg gtgttgcccc attccgtggg tttatcagag agcgtgtcgc gttcctcgaa     1680
tcacaaaaga agggcggtaa caacgttttcg ctaggtaagc atatactgtt ttatggatcc    1740
cgtaacactg atgatttctt gtaccaggac gaatggccag aatacgccaa aaaattggat     1800
ggttcgttcg aaatggtcgt ggcccattcc aggttgccaa acaccaaaaa agtttatgtt     1860
caagataaat taaaggatta cgaagaccaa gtatttgaaa tgattaacaa cggtgcattt     1920
atctacgtct gtggtgatgc aaagggtatg gccaagggtg tgtcaaccgc attggttggc     1980
atcttatccc gtggtaaatc cattaccact gatgaagcaa cagagctaat caagatgctc     2040
aagacttcag gtagatacca agaagatgtc tggtaa                                2076
```

<210> SEQ ID NO 7
<211> LENGTH: 933
<212> TYPE: DNA
<213> ORGANISM: Saccharomyces cerevisiae

<400> SEQUENCE: 7

```
atgcctatca ccataaaaag ccgctctaaa gggttaaggg cactgaaat tgacttatcc        60 aaaaagccta ctttagatga tgttttgaaa aaaatctctg ctaataacca caatatcagc     120
aagtacagga taagattaac ctacaaaaag gaatctaaac aagttccggt tatttcagaa      180
```

| | |
|---|---|
| tcgttttttc aagaagaggc tgatgactca atggaattct tcatcaaaga tttgggtccc | 240 |
| caaatttcat ggagattagt cttcttttgt gagtatttgg gtccagtctt ggttcactcc | 300 |
| cttttttatt atctatctac cattcccaca gttgttgata gatggcacag tgctagctcc | 360 |
| gactataatc cattttaaa cagggttgca tattttaa ttttaggaca ttatggaaag | 420 |
| agattatttg aaaccttatt tgttcaccaa ttctctttag ctactatgcc aattttcaac | 480 |
| ctgttcaaaa attgtttcca ttactgggtt ctaagcggtc tcatttcatt cggttacttt | 540 |
| ggctacggct tcccctttgg gaatgctaag ttattcaaat actattcata tttgaaattg | 600 |
| gatgacttga gtacattaat tggtcttttc gtgctttcag aactatggaa cttttattgc | 660 |
| cacattaaat tgcgcctatg gggtgactat caaaagaagc atggtaacgc taagatccgt | 720 |
| gtcccattga atcaaggtat tttcaatctt tttgttgctc ccaactatac ttttgaagtt | 780 |
| tggtcttgga tttggtttac ttttgtgttc aagttcaatt tatttgccgt tttattttg | 840 |
| actgtttcaa cagctcaaat gtacgcatgg gctcaaaaga aaacaaaaa gtatcatacc | 900 |
| agaagagcat tcttgattcc atttgtattt tga | 933 |

<210> SEQ ID NO 8
<211> LENGTH: 22283
<212> TYPE: DNA
<213> ORGANISM: Artificial Sequence
<220> FEATURE:
<223> OTHER INFORMATION: pPHLO Multi-Expression Plasmid

<400> SEQUENCE: 8

| | |
|---|---|
| acgcgtccag tatcccagca gatacgggat atcgacattt ctgcaccatt ccggcgggta | 60 |
| taggttttat tgatggcctc atccacacgc agcagcgtct gttcatcgtc gtggcggccc | 120 |
| ataataatct gccggtcaat cagccagctt cctcacccg gcccccatcc ccatacgcgc | 180 |
| atttcgtagc ggtccagctg ggagtcgata ccggcggtca ggtaagccac acggtcagga | 240 |
| acgggcgctg aataatgctc tttccgctct gccatcactt cagcatccgg acgttcgcca | 300 |
| attttcgcct cccacgtctc accgagcgtg gtgtttacga aggttttacg ttttcccgta | 360 |
| tcccctttcg ttttcatcca gtcttttgaca atctgcaccc aggtggtgaa cgggctgtac | 420 |
| gctgtccaga tgtgaaaggt cacactgtca ggtggctcaa tctcttcacc ggatgacgaa | 480 |
| aaccagagaa tgccatcacg ggtccagatc ccggtctttt cgcagatata acgggcatca | 540 |
| gtaaagtcca gctcctgctg gcggatgacg caggcattat gctcgcagag ataaaacacg | 600 |
| ctggagacgc gttttcccgt cttcagtgc cttgttcagt tcttcctgac gggcggtata | 660 |
| tttctccagc ttggcctatg cggccctgtc agaccaagtt tacgagctcg cttggactcc | 720 |
| tgttgataga tccagtaatg acctcagaac tccatctgga tttgttcaga acgctcggtt | 780 |
| gccgccgggc gttttttatt ggtgagaatc caagcactag ggacagtaag acgggtaagc | 840 |
| ctgttgatga taccgctgcc ttactgggtg cattagccag tctgaatgac ctgtcacggg | 900 |
| ataatccgaa gtggtcagac tggaaaatca gagggcagga actgctgaac agcaaaaagt | 960 |
| cagatagcac cacatagcag acccgccata aaacgccctg agaagcccgt gacgggcttt | 1020 |
| tcttgtatta tgggtagttt ccttgcatga atccataaaa ggcgcctgta gtgccatta | 1080 |
| cccccattca ctgccagagc cgtgagcgca gcgaactgaa tgtcacgaaa agacagcga | 1140 |
| ctcaggtgcc tgatggtcgg agacaaaagg aatattcagc gatttgcccg agcttgcgag | 1200 |
| ggtgctactt aagcctttag ggtttaagg tctgttttgt agaggagcaa acagcgtttg | 1260 |
| cgacatcctt ttgtaatact gcggaactga ctaaagtagt gagttataca cagggctggg | 1320 |

```
atctattctt tttatctttt tttattcttt ctttattcta taaattataa ccacttgaat    1380
ataaacaaaa aaaacacaca aaggtctagc ggaatttaca gagggtctag cagaatttac    1440
aagttttcca gcaaaggtct agcagaattt acagataccc acaactcaaa ggaaaaggac    1500
atgtaattat cattgactag cccatctcaa ttggtatagt gattaaaatc acctagacca    1560
attgagatgt atgtctgaat tagttgtttt caaagcaaat gaactagcga ttagtcgcta    1620
tgacttaacg gagcatgaaa ccaagctaat tttatgctgt gtggcactac tcaaccccac    1680
gattgaaaac cctacaagga agaacggac ggtatcgttc acttataacc aatacgctca     1740
gatgatgaac atcagtaggg aaaatgctta tggtgtatta gctaaagcaa ccagagagct    1800
gatgacgaga actgtggaaa tcaggaatcc tttggttaaa ggctttgaga ttttccagtg    1860
gacaaactat gccaagttct caagcgaaaa attagaatta gttttagtg aagagatatt     1920 gccttatctt ttccagttaa aaaaattcat aaaatataat ctggaacatg ttaagtcttt    1980
tgaaaacaaa tactctatga ggatttatga gtggttatta aaagaactaa cacaaaagaa    2040
aactcacaag gcaaatatag agattagcct tgatgaattt aagttcatgt taatgcttga    2100
aaataactac catgagttta aaaggcttaa ccaatgggtt ttgaaaccaa taagtaaaga    2160
tttaaacact tacagcaata tgaaattggt ggttgataag cgaggccgcc cgactgatac    2220
gttgattttc caagttgaac tagatagaca aatggatctc gtaaccgaac ttgagaacaa    2280
ccagataaaa atgaatggtg acaaaatacc aacaaccatt acatcagatt cctacctaca    2340
taacggacta agaaaaacac tacacgatgc tttaactgca aaaattcagc tcaccagttt    2400
tgaggcaaaa tttttgagtg acatgcaaag taagtatgat ctcaatggtt cgttctcatg    2460
gctcacgcaa aaacaacgaa ccacactaga gaacatactg gctaaatacg gaaggatctg    2520
aggttcttat ggctcttgta tctatcagtg aagcatcaag actaacaaac aaaagtagaa    2580
caactgttca ccgttacata tcaaagggaa aactgtccat atgcacagat gaaaacggtg    2640
taaaaaagat agatacatca gagcttttac gagttttgg tgcattcaaa gctgttcacc     2700
atgaacagat cgacaatgta acgcggccgc agccaatcaa ttcttgcgga gaactgtgaa    2760
tgcgcaaacc aacccttggc agaacatatc catcgcgtcc gccatctcca gcagccgcac    2820
gcggcgcatc ggggggggg gggggggttt caattcatca ttttttttt attctttttt      2880 ttgatttcgg tttccttgaa attttttga ttcggtaatc tccgaacaga aggaagaacg     2940
aaggaaggag cacagactta gattggtata tatacgcata tgtagtgttg aagaaacatg    3000
aaattgccca gtattcttaa cccaactgca cagaacaaaa acctgcagga acgaagata     3060 aatcatgtcg aaagctacat ataaggaacg tgctgctact catcctagtc ctgttgctgc    3120
caagctattt aatatcatgc acgaaaagca aacaaacttg tgtgcttcat ggatgttcg     3180 taccaccaag gaattactgg agttagttga agcattaggt cccaaaattt gtttactaaa    3240
aacacatgtg gatatcttga ctgattttc catggagggc acagttaagc cgctaaaggc     3300
attatccgcc aagtacaatt ttttactctt cgaagacaga aaatttgctg acattggtaa    3360
tacagtcaaa ttgcagtact ctgcgggtgt atacagaata gcagaatggg cagacattac    3420
gaatgcacac ggtgtggtgg gcccaggtat tgttagcggt tgaagcagg cggcagaaga     3480 agtaacaaag gaacctagag gccttttgat gttagcagaa ttgtcatgca agggctccct    3540
atctactgga gaatatacta agggtactgt tgacattgcg aagagcgaca aagattttgt    3600
tatcggcttt attgctcaaa gagacatggg tggaagagat gaaggttacg attggttgat    3660
```

```
tatgacaccc ggtgtgggtt tagatgacaa gggagacgca ttgggtcaac agtatagaac    3720
cgtggatgat gtggtctcta caggatctga cattattatt gttggaagag gactatttgc    3780
aaagggaagg gatgctaagg tagagggtga acgttacaga aaagcaggct gggaagcata    3840
tttgagaaga tgcggccagc aaaactaaaa aactgtatta taagtaaatg catgtatact    3900
aaactcacaa attagagctt caatttaatt atatcagtta ttacccggcc gggaatctcg    3960
gtcgtaatga tttttataat gacgaaaaaa aaaaaattgg aaagaaaacc cccccccccc    4020
ccccgcagcg ttgggtcctg gccacggtgt cgcatgatcg tgctcctgtc gttgaggacc    4080
cggctaggct ggcggggttg ccttactggt tagcagaatg aatcaccgat acgcgagcga    4140
atgtggcggc cgcacgcgtt catcgtccac ctccggagaa caggccacca tcacgcatct    4200
gtgtctgaat tcatcacga cgcgccttaa gggcaccaat aactgcctta aaaaaattac    4260
gccccgccct gccactcatc gcagtactgt tgtaattcat taagcattct gccgacatgg    4320
aagccatcac agacggcatg atgaacctga atcgccagcg gcatcagcac cttgtcgcct    4380
tgcgtataat atttgcccat ggtgaaaacg ggggcgaaga agttgtccat attggccacg    4440
tttaaatcaa aactggtgaa actcacccag ggattggctg agacgaaaaa catattctca    4500
ataaacccctt tagggaaata ggccaggttt tcaccgtaac acgccacatc ttgcgaatat    4560
atgtgtagaa actgccggaa atcgtcgtgg tattcactcc agagcgatga aaacgtttca    4620
gtttgctcat ggaaaacggt gtaacaaggg tgaacactat cccatatcac cagctcaccg    4680
tctttcattg ccatacggaa ttccggatga gcattcatca ggcgggcaag aatgtgaata    4740
aaggccggat aaaacttgtg cttatttttc tttacggtct ttaaaaaggc cgtaatatcc    4800
agctgaacgg tctggttata ggtacattga gcaactgact gaaatgcctc aaaatgttct    4860
ttacgatgcc attgggatat atcaacggtg gtatatccag tgatttttt ctccatttta    4920
gcttccttag ctcctgaaaa tctcgataac tcaaaaaata cgcccggtag tgatcttatt    4980
tcattatggt gaaagttgga acctcttacg tgccgatcaa cgtctcattt tcgccaaaag    5040
ttggcccagg cttcccggt atcaacaggg acaccaggat ttatttattc tgcgaagtga    5100
tcttccgtca caggtattgg accaccctgt gggtttataa gcgcgctgct ggcgtgtaag    5160
gcggtgacgg cgaaggaagg gtccttttca tcacgtgcta taaaataat tataatttaa    5220
attttttaat ataatatat aaattaaaaa tagaaagtaa aaaagaaat taagaaaaa    5280
atagttttttg ttttccgaag atgtaaaaga ctctaggggg atcgccaaca aatactacct    5340
tttatcttgc tcttcctgct ctcaggtatt aatgccgaat tgtttcatct tgtctgtgta    5400
gaagaccaca cacgaaaatc ctgtgatttt acattttact tatcgttaat cgaatgtata    5460
tctatttaat ctgcttttct tgtctaataa atatatatgt aaagtacgct tttgttgaa    5520
atttttttaaa ccttttgttta tttttttttc ttcattccgt aactcttcta ccttcttat    5580
ttactttcta aaatcaaat acaaaacata aaataaata aacacagagt aaattcccaa    5640
attattccat cattaaaaga tacgaggcgc gtgtaagtta caggcaagcg atccgtccta    5700
agaaaccatt attatcatga cattaaccta taaaaatagg cgtatcacga ggccctttcg    5760
tctcgcgcgt ttcggtgatg acggtgaaaa cctctgacac atgcagctcc cggagacggt    5820
cacagcttgt ctgtaagcgg atgccgggag cagacaagcc cgtcagggcg cgtcagcggg    5880
tgttggcggg tgtcggggct ggcttaacta tgcggcatca gagcagattg tactgagagt    5940
gcaccacggc gcgtggcacc cttgcgggcc atgtcataca ccgccttcag agcagccgga    6000
cctatctgcc cgttacgcgc cagcttgcaa attaaagcct tcgagcgtcc caaaaccttc    6060
```

```
tcaagcaagg ttttcagtat aatgttacat gcgtacacgc gtctgtacag aaaaaaaaga    6120
aaaatttgaa atataaataa cgttcttaat actaacataa ctataaaaaa ataaataggg    6180
acctagactt caggttgtct aactccttcc ttttcggtta gagcggatgt ggggggaggg    6240
cgtgaatgta agcgtgacat aactaattac atgatatcga caaggaaaaa gggggacgga    6300
tctccgaggc ctcggacccg tcgggccgcc gtcggacgtg ccgcggtcat gcagaagctg    6360
cagtagggac agggactggg acactatgca acactaaggt ttctacagtc aagcctggtc    6420
cgaatccaaa caacactccc caatcttttc cttctcctgt ggttgccaat ccgtctttag    6480
cagaactttt cctcatgaca tctaacacaa acaacacaga ggcactagac atatttccgt    6540
attcagataa cacttcccta gaagccctca ttctcttctt atccaatcct actctatctt    6600
caactctgtc taaatggca gggccaccag gatgtgcaat ccagaaaatt gaattccagt     6660
tatgaatacc taaaggttca aaggcatcct ccaaagcctg ttcaatgttc tctgaaatta    6720
aaccaggaac atcttttaat aaatgtatag ttaaaccagc ttctgttaaa tggccatcta    6780
tggcaccttc tgattctggt aatatagtct gagaagctga taccaactgg aaaactggtt    6840
gttcgtctaa ttggtctggg tcagcgccta taattgcagc agcggcacca tcaccgaaca    6900
aggcatgacc taccaaggaa tctaaatgac tcttgcatgg acctctgaag gccatagcag    6960
ttatctcgga acaaacgact aacactctgg cacctctatt attttcagcg atatcttttg    7020
ccaatctcaa aacagttgca ccaccaaagc aaccttgttg gtacatcatt aaccttttga    7080
ctgtagggga caaacctaac aactttgtta attggtaatc agcaccgggc atgtcaacgc    7140
cggatgttgt gcaaaatacc aaatgagtaa tcttagacaa gggttggccc cactccttaa    7200
tggccttctc agctgcacct tggcccaatt tgggaacttc aactaatgcg atggcgtgtc    7260
tagcatccaa tgaggtctcc atgtgtgcac agatctttgg gttcttgatc aatatttcct    7320
cggtcaagtg catgtgtctc tttctaatca ttgatttgtc acacattctt tgaaacttct    7380
cctttaaatc tgccaagtgc tcactttag taaccctaaa ataataatct ggataggtag     7440
cttgataaac acaattagct ggaacggcag taccgattgc taaaactgta gctaaacctt    7500
cagccctctg tgccattcta acttctttca atcttactgc agccattta agcttttttgt    7560 ttgtttatgt gtgtttattc gaaactaagt tcttggtgtt ttaaaactaa aaaaaagact    7620
aactataaaa gtagaattta agaagtttaa gaaatagatt tacagaatta caatcaaatac   7680 ctaccgtctt tatatactta ttagtcaagt aggggaataa tttcagggaa ctggtttcaa    7740 ccttttttt cagcttttc caaatcagag agagcagaag gtaatagaag gtgtaagaaa      7800
atgagataga tacatgcgtg ggtcaattgc cttgtgtcat catttactcc aggcaggttg    7860
catcactcca ttgaggttgt gtccgttttt tgcctgtttg tgccctgtt ctctgtagtt     7920 gcgctaagag aatggaccta tgaactgatg gttggtgaag aaaacaatat tttggtgctg    7980
ggattctttt tttttctgga tgccagctta aaagcgggc tccattatat ttagtggatg     8040
ccaggaataa actgttcacc cagacaccta cgatgttata tattctgtgt aacccgcccc    8100 ctatttggg catgtacggg ttacagcaga attaaaaggc taattttttg actaaataaa     8160
gttaggaaaa tcactactat taattattta cgtattcttt gaaatggcag tattgataat    8220
gataaactcg aactgggcgc gtcgtgccgt cgttgttaat caccacatgg ttattctgct    8280
caaacgtccc ggacgcctgc gaacgcgccg aaggaaaatg agaaatatcg agggagacga    8340
ttcagaggag caggacaaac tataaccgac tgtttgttgg aggatgccgt acataacgaa    8400
```

```
cactgctgaa gctaccatgt ctacagttta gaggaatggg tacaactcac aggcgaggga      8460
tggtgttcac tcgtgctagc aaacgcggtg ggagcaaaaa gtagaatatt atcttttatt      8520
cgtgaaactt cgaacactgt catctaaaga tgctatatac taatataggc atacttgata      8580
atgaaaacta taaatcgtaa agacataaga gatccgcggt caaaatacaa atggaatcaa      8640
gaatgctctt ctggtatgat acttttttgtt tttcttttga gcccatgcgt acatttgagc     8700 tgttgaaaaca gtcaaaaata aaacggcaaa taaattgaac ttgaacacaa aagtaaacca     8760
aatccaagac caaacttcaa aagtatagtt gggagcaaca aaaagattga aaataccttg      8820
attcaatggg acacggatct tagcgttacc atgcttcttt tgatagtcac cccataggcg      8880
caatttaatg tggcaataaa agttccatag ttctgaaagc acgaaaagac caattaatgt      8940
actcaagtca tccaatttca aatatgaata gtatttgaat aacttagcat tcccaaaggg      9000
gaagccgtag ccaaagtaac cgaatgaaat gagaccgctt agaacccagt aatggaaaca     9060 attttttgaac aggttgaaaa ttggcatagt agctaaagag aattggtgaa caaataaggt    9120
ttcaaataat ctcttttccat aatgtcctaa aattaaaaaa tatgcaaccc tgtttaaaaa    9180
tggattatag tcggagctag cactgtgcca tctatcaaca actgtgggaa tggtagatag     9240
ataataaaaa agggagtgaa ccaagactgg acccaaatac tcacaaaaga agactaatct     9300
ccatgaaatt tggggaccca aatctttgat gaagaattcc attgagtcat cagcctcttc     9360 ttgaaaaaaac gattctgaaa taaccggaac ttgtttagat tccttttttgt aggttaatct   9420 tatcctgtac ttgctgatat tgtggttatt agcagagatt ttttcaaaa catcatctaa     9480 agtaggcttt ttgataagt caatttcagt gtcccttaac cctttagagc ggcttttat      9540 ggtgataggc atttttaagct ttgttttata tttgttgtaa aaagtagata attacttcct   9600
tgatgatctg taaaaagag aaaaagaaag catctaagaa cttgaaaaac tacgaattag     9660
aaaagaccaa atatgtattt cttgcattga ccaatttatg caagtttata tatatgtaaa    9720
tgtaagtttc acgaggttct actaaactaa accacccccct tggttagaag aaaagagtgt   9780
gtgagaacag gctgttgttg tcacacgatt cggacaattc tgtttgaaag agagagagta   9840
acagtacgat cgaacgaact ttgctctgga gatcacagtg ggcatcatag catgtggtac    9900 taaaccctttt cccgccattc cagaaccttc gattgcttgt tacaaaacct gtgagccgtc    9960
gctaggacct tgttgtgtga cgaaattgga agctgcaatc aataggaaga caggaagtcg    10020
agcgtgtctg ggttttttca gtttttgttct ttttgcaaac aaatcacgag cgacggtaat   10080
ttctttctcg ataagaggcc acgtgcttta tgagggtaac atcaattcaa gaaggaggga   10140
aacacttcct ttttctggcc ctgataatag tatgagggtg aagccaaaat aaaggattcg    10200
cgcccaaatc ggcatcttta aatgcaggta tgcgatagtt cctcactctt tccttactca    10260
cgagtaattc ttgcaaatgc ctattatgca gatgttataa tatctgtgcg tggcgcgtcc    10320
ggctgtctgc catgctgccc ggtgtaccga cataaccgcc ggtggcatag ccgcgcatac    10380
gcgccatttc cttccatctt gtgattcatg ctatccatct ttttttgagta ccaattaac    10440 gaagacgtta ccagctgatt gaaggttctc aaagtgactg tactccatgt tttcttatca    10500
tccatgtagt tattttttcaa actgcaaatt caagaaaaag ccacgcgtgt gcacctttt    10560 tttccccttc cagtgcatta tgcaatagac agcacgagtc tttgaaaaag taacttataa   10620
aactgtatca attttttaaac ctaaatagat tcataaacta ttcgttaata taagtgttc   10680 taaactgatga tgaaaaaata agcagaaaag actaataatt cttagttaaa agcactccct  10740
agttcattaa tccatttgct agtcttgctc ttagatcctt cctcaatatc ttccctgatg    10800
```

```
gagctttagg aatagagtca gtgaagaaca ctttgttgat tctcttataa aacacaacct   10860
gttttgacac gaattgcttg atttcatctt cggatatatt tgaatctttc gatctcacca   10920
caaacgcaac aggaacctca ccagcatctt cttccttcat ggcgacgaca gcaacatcat   10980
tgatttctgg atgacctatg aggagagact ctagctcagc tggagccact tgaaatcctt   11040
tgtacttgat gagttctttc aatctatcca caatgaaaag ctcgtcgtca tcatcgataa   11100
atccgacgtc tccagtgtga agccaaccat ctttatcgat cgtcgatgcc gtggccaagg   11160
ggtcattgag atagccttc atgatttggt tgccacggat gcatatttcg ccgggtttgt   11220
tcctaggcaa agaatctcct gtgtctggat caagtatctt catctcggcg ttcctcacca   11280
ccgtaccaca tgctcctgac ttcactggaa acggctcttt agcaaaccct aacgacattg   11340
ctagcaccgg acctgcttct gtcatcccat agccctgacc aagcttggcg ttaggaaact   11400
tagcactaat agcatcttca agctccttac caagaggagc tgctccagac ttaaccatcc   11460
taaccgagct cagatcatac ttctccgtct ccggcgactt cgcgatagct aaaacgatcg   11520
gtggcacgac catagccacc gtgactttac acctttgtat ctgctctaac aagagagtga   11580
tttcgaactt aggcattatc aagatcgtgg caccaactct gagactacag agcatgatgg   11640
agttgagagc gtatatatgg aacataggca agacacagag gatcacgtcg tctctgttga   11700
agtaaagatt cggattctcg ccgtcgactt gctgcgccac gctcgtgact agacctttgt   11760
gtgttagcat cactcctttg gggagacccg tcgtgccgga tgagaaagga agcgccacga   11820
cgtcttctgg cgaaatcttc tccggtattg agtccactcg tggttcttcg gactgagtta   11880
actcggagaa acggaggcag ttttcgggga tggcgtcgga gtcggtggtg acgatcaaaa   11940
cgccgtcgtt ttggaggttc ttgattttat cgacgtaacg ggattgagtg acgatgagtt   12000
tcgccgcgga ggctttggct tgtttagaaa tctccgccgg agtgaagaac gggttcgcgg   12060
aggtggtgat tgcgccgatg aaggaggcgg caaggaaagt gaggactact tcaggagagt   12120
tcgggaggag gatcattaca acgtcgtgtt gcttcacgcc gaggttatga agaccggcgg   12180
cgagtttccg agatgttacg tggacatcgg cgtaggtgta tacttcgccg gtgggaccgt   12240
tgatcaagca tggcttagcg gcgaactctg agatattttc gaagatgtag tcgtggagtg   12300
ggaggtggtt agggatgtat atatcaggca atctcgatcg gaaaatgacg tcattactac   12360
actgtttctg atcattctga tcattgacta tcacatcttg tgtcgtcatt ttagcttttt   12420
gtaattaaaa cttagattag attgctatgc tttctttcta atgagcaaga agtaaaaaaa   12480
gttgtaatag aacaagaaaa atgaaactga aacttgagaa attgaagacc gtttattaac   12540
ttaaatatca atgggaggtc atcgaaagag aaaaaaatca aaaaaaaaaa ttttcaagaa   12600
aaagaaacgt gataaaaatt tttattgcct ttttcgacga agaaaagaa acgaggcggt   12660
ctcttttttc ttttccaaac ctttagtacg ggtaattaac gacaccctag aggaagaaag   12720
aggggaaatt tagtatgctg tgcttgggtg ttttgaagtg gtacggcgat gcgcggagtc   12780
cgagaaaatc tggaagagta aaaaggagt agaaacattt tgaagctagg cgcgtcagcc   12840
ggtaaagatt ccccacgcca atccggctgg ttgcctcctt cgtgaagaca aactcacgcg   12900
cctccaaaat gagctatcaa aaacgataga tcgattagga tgactttgaa atgactccgc   12960
agtggactgg ccgttaattt caagcgtgag taaaatagtg catgacaaaa gatgagctag   13020
gcttttgtaa aaatatctta cgttgtaaaa ttttagaaat cattatttcc ttcatatcat   13080
tttgtcattg accttcagaa gaaaagagcc gaccaataat ataaataaat aaataaaaat   13140
```

```
aatattccat tatttctaaa cagattcaat actcattaaa aaactatatc aattaatttg   13200
aattaaccgc ggttagcaga ttggaatagg tgcaccattc cactctttca agcaatccat   13260
aagtggatct atcaactttc cctcgcacat agctgtgaat accttgtcaa attcttcacc   13320
tgggctaacg acttttttcac cagttagtaa tttggttccc aactcttctc taacgaatct   13380
gtacaaaggg tacgacctac actctttgat tctatttggt ataggggcag taccatttcc   13440
gtatgcggct ctagcagctt cgacttcctt tggtaaaact gccttcagtt cttcttcaaa   13500
ggcacctatc ttttggaata ttgaagtaac ggcatttttc tcagtttcac cattggataa   13560
agcgtgatct acaataactt gtctcaatct ctgcatcaat ggataagtag cgctacatgg   13620
atcgtcaacg taagtaaata cttgttctct atctacaact tttaataaat cttttcaca   13680 gaatcttgat gggtgcaatt caccattgat acctgtagtt agaaccttt ttgcaacctg   13740 tgatacggta ttttcactg tctgtctcaa attctcttcc aagtgtctca aatctacggc   13800
ctggcatata cccactaaaa atgttgtgga cattaattta aggatatcaa cggcctcgct   13860 tgttttctt gatgaaatca ggcccaaaga attaacatcc tgattgtgtt gttcggctga   13920
ttgtacatga gaggttactg ggttggctag atattgcagc tctgaacaat agcttgccat   13980
tgctatctca gcacctttga aaccataatc aagactaggg ttagaagatg cggtcagatt   14040
cgaaggcaaa ccgttattgt agaagtcatt gaccaattca gaaaattggg caaacattaa   14100
tttgccaatt gcggctatgg caagcctggt attatccata ctgactccta tgggtgtacc   14160
ctggaaattg cctccatgta ttgccttatt cctcgacaca tcaataagtg gattatcgtt   14220
aacagagttg atctctcttt ctatagactt tgtagcttgt ctaattactt caatttgagg   14280
gccaagccat tgtggggatg tccttaaagc atatctatct tgtttgggtt tttgcaaagg   14340
gtccatttca tgaaccttct gggctaactt catgtagcta gagccgtcca aaatgtgctc   14400
catgatagct gctgcttcaa tttgtcctgg gtgatgtttt aacctgtggg tcaagtgatc   14460
agtaaactca ggttttccac tcatgacttc ggcaaaaatt gcggacaaaa cttcggccaa   14520
aactgcttgt acgttagctt caaacaacac catggatgcc ataccgctgc cgacagcggt   14580
gccattcacc agggctaaac cttccttggg ttgcaaatca agaaaccag ttgaaatacc   14640 agctttctca aatgcttcct tagcggttaa ggattctccg tctggaccag tggcctttga   14700
attaggtctt cccgttaata agcctgcgat atatgaaagg ggaaccaaat caccgctggc   14760
agttattgtt cctcttaagg gcaacgaagg agaaatgttg tggttcaata gtgaagtgat   14820
ggcctcaaga atttcaaacc ttattccaga gtaaccttgc aacaaagtgt tcaccctaac   14880
aagcatagca gctcttgttg ccgattgggg taatgtatgg caagtttcct ttgtattacc   14940
gaaaataccg gcgttaagga atctgatcag ttctgtttgc aaagcagtgc cattttagt   15000 tcttctatga gaggtagcac caaagcctgt ggtaacgcca taggaatctg tgcccttgtt   15060
catactttcc atgacccaat ctgatgaagc cttaactccg gctctacttg tttctgcaag   15120
ttctaccttc actgaaccgc caacggtcga aatagcagct acctgtccta tcgtcaatgt   15180
ctcgccgcct agatttacga ctggtcttct gtattcctca accatcttct taacttcatc   15240
cagatggcta cctttcatct ggtcagctgc cagaccccaa ttcaaaggat ctgcaagagt   15300
ttttgtcgtt acggccacct ggtctttttc accaccaccg catagcattg cttcaatttg   15360
gtccatttta agctttttga tagatttgac tgtgttattt tgcgtgaggt tatgagtaga   15420
aaataataat tgagaaagga atatgacaag aaatatgaaa ataaagggaa caaacccaaa   15480
tctgattgca aggagagtga aagagccttg tttatatatt tttttttcct atgttcaacg   15540
```

```
aggacagcta ggtttatgca aaaatgtgcc atcaccataa gctgattcaa atgagctaaa    15600
aaaaaaatag ttagaaaata aggtggtgtt gaacgatagc aagtagatca agacaccgtc    15660
taacagaaaa aggggcagcg gacaatatta tgcaattatg aagaaaagta ctcaaagggt    15720
cggaaaaata ttcaaacgat atttgcataa aatcctcaat tgattgatta ttccatagta    15780
aaataccgta acaacacaaa attgttctca aattcataaa ttattcattt tttccacgag    15840
cctcatcaca cgaaaagtca gaagagcata cataatcttt taaatgcata ggttatgcat    15900
tttgcaaatg ccaccaggca acaaaaatat gcgtttagcg ggcggaatcg ggaaggaagc    15960
cggaaccacc aaaaactgga agctacgttt ttaaggaagg tatgggtgca gtgtgcttat    16020
ctcaagaaat attagttatg atataaggtg ttgaagttta gagataggta aataaacgcg    16080
gggtgtgttt attacatgaa gaagaagtta gtttctgcct tgcttgttta tcttgcacat    16140
cacatcagcg gaacatatgc tcacccagtc gcatggcgcg taccacggtg aacaatcccc    16200
gctggctcat atttgccgcc ggttcccgta aatcctccgg tacgcgccgg gccgtatact    16260
tacatatagt agatgtcaag cgtaggcgct tcccctgccg gctgtgaggg cgccataacc    16320
aaggtatcta tagaccgcca atcagcaaac tacctccgta cattcatgtt gcacccacac    16380
atttatacac ccagaccgcg acaaattacc cataaggttg tttgtgacgg cgtcgtacaa    16440
gagaacgtgg gaacttttta ggctcaccaa aaagaaaga aaaatacga gttgctgaca    16500 gaagcctcaa gaaaaaaaaa attcttcttc gactatgctg gaggcagaga tgatcgagcc    16560
ggtagttaac tatatatagc taaattggtt ccatcacctt cttttctggt gtcgctcctt    16620
ctagtgctat ttctggcttt tcctattttt ttttttccat ttttctttct ctctttctaa    16680
tatataaatt ctcttgcatt ttctattttt ctctctatct attctacttg tttattccct    16740
tcaaggtttt tttttaagga gtacttgttt ttagaatata cggtcaacga actataatta    16800
actaaacaag cttaaaatga tggattttgt tttgttagaa aaagctcttc ttggtttgtt    16860
cattgcaact atagtagcca tcacaatctc taagctaagg ggaaagaaac ttaagttgcc    16920
tccaggccca atccctgtcc cagtgtttgg taattggtta caagttggcg acgacttaaa    16980
ccagaggaat ttggtagagt atgctaaaaa gttcggcgac ttatttctac ttaggatggg    17040
tcaaagaaac ttggtcgtgg tttcatcccc tgacttagca aaagacgtac tacatacccca   17100 gggtgtcgag ttcggaagta gaactagaaa tgttgtgttt gatattttca caggcaaagg    17160
tcaagatatg gttttttaccg tatacagcga gcactggagg aaaatgagaa gaataatgac    17220
tgtcccattc tttacaaaca aagtggttca acagtatagg ttcggatggg aggacgaagc    17280
cgctagagta gtcgaggatg ttaaggcaaa tcctgaagcc gctaccaacg gtattgtgtt    17340
gaggaataga ttcaaacttt tgatgtacaa caatatgtat agaataatgt ttgacaggag    17400
atttgaatct gttgatgatc cattattcct aaaacttaag gcattgaatg gcgagagatc    17460
aaggttagct caatcctttg aatacaactt cggtgacttc attcctatat tgaggccatt    17520
cttgagagga tatcttaagt tgtgtcagga aatcaaggac aaaaggttaa agctattcaa    17580
ggactacttc gtcgacgaga gaaaaaagtt ggagagtatc aagagcgtag gtaataactc    17640
cttaaagtgc gccatagatc atattatcga ggcacaagaa aaaggcgaga taaacgagga    17700
taacgtgtta tacatcgtcg agaatatcaa cgtggctgcc attgaaacta cactttggtc    17760
tattgaatgg ggtatagcag aactagtgaa taacctgaa atccagaaaa aattgagaca    17820
cgaattagac accgtacttg gagctggtgt tcaaatttgt gaaccagatg ttcaaaaatt    17880
```

```
gccttatcta caggccgtga taaaagagac tttaaggtac aggatggcaa ttccattgtt    17940
agtcccacat atgaatcttc acgaagccaa attggccggc tatgatatcc ctgcagagag    18000
caaaattttg gtaaacgctt ggtggttagc caataatcca gcacattgga acaaacctga    18060
tgagtttaga ccagaaagat ttttggagga agaatccaag gtcgaggcta atggaaacga    18120
ctttaagtac atccctttcg gtgttggcag aagatcttgc ccaggtataa ttcttgcttt    18180
accaatcctt ggaatagtaa ttggtaggtt ggttcaaaac ttcgagttac ttccacctcc    18240
aggccaaagc aaaatagata cagccgaaaa aggtggacag ttttcattgc aaatcctaaa    18300
gcattccact attgtgtgta aacctagaag ttcttaaccg cggacaaatc gctcttaaat    18360
atatacctaa agaacattaa agctatatta taagcaaaga tacgtaaatt ttgcttatat    18420
tattatacac atatcatatt tctatatttt taagatttgg ttatataatg tacgtaatgc    18480
aaaggaaata aattttatac attattgaac agcgtccaag taactacatt atgtgcacta    18540
atagtttagc gtcgtgaaga ctttattgtg tcgcgaaaag taaaaatttt aaaaattaga    18600
gcaccttgaa cttgcgaaaa aggttctcat caactgttta aaaggaggat atcaggtcct    18660
atttctgaca aacaatatac aaatttagtt tcaaggcgc gttgcaaaat ggaatttcgc    18720
cgcagcggcc tgaatggctg taccgcctga cgcggatgcg ccacgcgccg catgccggta    18780
gaggtgtggt caataagagc gacctcatgc tatacctgag aaagcaacct gacctacagg    18840
aaagagttac tcaagaataa gaattttcgt tttaaaacct aagagtcact ttaaaatttg    18900
tatacactta ttttttttat aacttattta ataataaaaa tcataaatca taagaaaattc   18960 gcttatttag aagtgtcaac aacgtatcta ccaacgattt gaccctttc catcttttcg    19020 taaatttctg gcaaggtaga caagccgaca accttgattg gagacttgac caaacctctg    19080
gcgaagaagt ccaaagctct agatcaattt aggcctgcgg ccgcggttac cagacatctt    19140
cttggtatct acctgaagtc ttgagcatct tgattagctc tgttgcttca tcagtggtaa    19200
tggatttacc acgggataag atgccaacca atgcggttga cacacccttg gccatacccct   19260 ttgcatcacc acagacgtag ataaatgcac cgttgttaat catttcaaat acttggtctt    19320
cgtaatcctt taatttatct tgaacataaa cttttttggt gtttggcaac ctggaatggg    19380
ccacgaccat ttcgaacgaa ccatccaatt ttttggcgta ttctggccat tcgtcctggt    19440
acaagaaatc atcagtgtta cgggatccat aaaacagtat atgcttacct agcgaaacgt    19500
tgttaccgcc cttcttttgt gattcgagga acgcgacacg ctctctgata aacccacgga    19560
atggggcaac accggtacct ggaccgatca tgataactgg ggtggaaggg ttggaaggca    19620
atctgaagtt agaacgacga acgtggacgg gcaatttgta attggcgaaa agtttacgtg    19680
ggccatttaa atcgtagtga acaggtaggt tagtttcggc aatgttaaca ttgttttgag    19740
ccaattgaat gtttcttaac aagttagtcg taacaccaac aactggagga gcatcaggca    19800
attctgggtt aggaaagttt tccacaatgg aggtgacatg gacggtttgc ttttcagaca    19860
gagaagagga agagatagag tagtaacgag gagtcatttg gggaactgat tcgaccaaga    19920
attgcatggg tacggtgtcc catttggcgc catcagacaa atatttcaga gcatctgcga    19980
tgttgaaata tttggaggtt atctcgacgg cgaattggtc cttgtctttc gaaagcagag    20040
tcaatttttc cttgacgtca gcgttggggg cgaactgaat caaagatgaa aacaattgtc    20100
tggagacagg tcctgtaatt tccaaatagt gtttaatagc agcgccaata gtagttggcg    20160
ttgggaaggg cactttgacg gtgggatcca ggggcttcaa gtcaaaaatg gtttcagggt    20220
ccaggttgaa tatggataag aactgttcga ccttttccaa tgggttggaa ggccaaacag    20280
```

```
caagatggtc accagtggag tacttgatgt tagagccgga caagtcaaat tcagagtgga    20340
tgcaattacg gtcattggaa gagaacagtt cgcgagattt cacgatgggt gcaatatacg    20400
gttgagacaa atcgaaggga cccaattgga tgccgtctgc gttgcggttc aactgatgcg    20460
agggcaaata gtgagcagag ggttcaccaa gcgacatgga gtcagtgatt tcgttcaaca    20520
cagtgtactg gaattgagag gtgaacttgg cttcctgttc gtccaaatgc agttcgtctt    20580
tcaaaacctc caggatggag tccttccagg ccatgtaatc ttcgtctgta gttcctgcac    20640
catcatcagc ttcaccgagc ttgcctagtc tgatagcgcc cgcagcggag agatgcttct    20700
cggccttctt ggcggcacca ttaaagaatt cataagtaga atttcccaga ccaaacatat    20760
tatacctcag gttcgatagt gcacccgctt ccgcattaca aataaagtct tcaaagttga    20820
ccgcccccgtc ggggaagtct ccttcaccat atgtagagat aaaaatcgag actatgacgg    20880
gcacatcgtt tagcgactca aagtcgtagt tctcaacatc tgcgcacatc acgtttaggt    20940
tgaacttggc caccagctcc ttggaaaact ttttggcgta atcctcggca gtcccagtct    21000
gcgacgcata caacaccaag tagttcttgt tgttttcggt caccacctga gcaatgtctc    21060
tgttgcccga gctgacagct gtgatatctc cgtcatcgga catcagcagt tccttgatgg    21120
agtttctctt tacgtacagt agcacggcaa gcactagccc cgccaggaca gtgaagtcgg    21180
tgttgtctat tccaaacggc attttactag taagctttgt gatgatgttt tatttgtttt    21240
gattggtgtc ttgtaaatag aaacaagaga gaataataaa caagttaaga ataaaaaacc    21300
aaaggatgaa aaagaatgaa tatgaaaaag agtagagaat aactttgaaa ggggaccatg    21360
atataactgg aaaaagagg ttcttggaaa tgaaagtta ccaaagagta tttataattc    21420
agaaaaaaaa gccaacgaat atcgttttga tggcgagcct tttttttttt ttaggaagac    21480
actaaaggta cctagcatca tatgggaagg aaaggaaatc acttggaaga catcacaagc    21540
attcatttac caagagaaaa aatatgcatt ttagctaaga tccattgaac aaagcactca    21600
ctcaactcaa ctgaatgaac gaaagaagaa agaacagtag aaaacacttt gtgacggtgc    21660
ggaacacatt tacgtagcta tcatgctgaa ttctactatg aaaatctccc aatctgtcga    21720
tggcaaaacg acccacgtgg cagagttggg tcaagtgcca gtttctggat taagtaacag    21780
atacagacat cacacgccat agaggaatcc cgccgttgcg agagatggaa aacaatagag    21840
ccgaaattgt ggaagcccga tgtctgggtg tacattttt tttttctttt ctttctcttt    21900
caataatctt tccttttttcc atttagcttg ccggaaaaac tttcgggtag cgaaaatctt    21960
tctgccggaa aaattagcta ttttttttctt ccttattatt tttttagttc tgaagtttga    22020
ccagggcgct accctgaccg tatcacaacc gacgatccgg ggtcatggcg gctattttt    22080
ttttttttt tttttccttg tgattgttta tttacatttg gatcaattct aacaaaaaaa    22140
aaataaggg ggaaaaataa ttcacctctt tttaatattg ttttgtactg agattgatct    22200
ccaaaatagt agcattggcg cgtgccacca acagccccgc caatggcgct gccgatactc    22260
ccgacaatcc ccaccattgc ctg                                            22283
```

<210> SEQ ID NO 9
<211> LENGTH: 22010
<212> TYPE: DNA
<213> ORGANISM: Artificial Sequence
<220> FEATURE:
<223> OTHER INFORMATION: pPHLON Multi-Expression Plasmid

<400> SEQUENCE: 9

```
acgcgtccag tatcccagca gatacgggat atcgacattt ctgcaccatt ccggcgggta    60
taggttttat tgatggcctc atccacacgc agcagcgtct gttcatcgtc gtggcggccc   120
ataataatct gccggtcaat cagccagctt tcctcacccg gcccccatcc ccatacgcgc   180
atttcgtagc ggtccagctg ggagtcgata ccggcggtca ggtaagccac acggtcagga   240
acgggcgctg aataatgctc tttccgctct gccatcactt cagcatccgg acgttcgcca   300
attttcgcct cccacgtctc accgagcgtg gtgtttacga aggttttacg ttttcccgta   360
tcccctttcg ttttcatcca gtctttgaca atctgcaccc aggtggtgaa cgggctgtac   420
gctgtccaga tgtgaaaggt cacactgtca ggtggctcaa tctcttcacc ggatgacgaa   480
aaccagagaa tgccatcacg ggtccagatc ccggtctttt cgcagatata acgggcatca   540
gtaaagtcca gctcctgctg gcggatgacg caggcattat gctcgcagag ataaaacacg   600
ctggagacgc gttttcccgt ctttcagtgc cttgttcagt tcttcctgac gggcggtata   660
tttctccagc ttggcctatg cggccctgtc agaccaagtt tacgagctcg cttggactcc   720
tgttgataga tccagtaatg acctcagaac tccatctgga tttgttcaga acgctcggtt   780
gccgccgggc gttttttatt ggtgagaatc caagcactag gacagtaag acgggtaagc   840
ctgttgatga taccgctgcc ttactgggtg cattagccag tctgaatgac ctgtcacggg   900
ataatccgaa gtggtcagac tggaaaatca gagggcagga actgctgaac agcaaaaagt   960
cagatagcac cacatagcag acccgccata aaacgccctg agaagccgt gacgggcttt  1020
tcttgtatta tgggtagttt ccttgcatga atccataaaa ggcgcctgta gtgccattta  1080
cccccattca ctgccagagc cgtgagcgca gcgaactgaa tgtcacgaaa aagacagcga  1140
ctcaggtgcc tgatggtcgg agacaaaagg aatattcagc gatttgcccg agcttgcgag  1200
ggtgctactt aagcctttag ggttttaagg tctgttttgt agaggagcaa acagcgtttg  1260
cgacatcctt ttgtaatact gcggaactga ctaaagtagt gagttataca cagggctggg  1320
atctattctt tttatctttt tttattcttt ctttattcta taaattataa ccacttgaat  1380
ataaacaaaa aaaacacaca aaggtctagc ggaatttaca gagggtctag cagaatttac  1440
aagttttcca gcaaaggtct agcagaattt acagataccc acaactcaaa ggaaaaggac  1500
atgtaattat cattgactag cccatctcaa ttggtatagt gattaaaatc acctagacca  1560
attgagatgt atgtctgaat tagttgtttt caaagcaaat gaactagcga ttagtcgcta  1620
tgacttaacg gagcatgaaa ccaagctaat tttatgctgt gtggcactac tcaaccccac  1680
gattgaaaac cctacaagga aagaacggac ggtatcgttc acttataacc aatacgctca  1740
gatgatgaac atcagtaggg aaaatgctta tggtgtatta gctaaagcaa ccagagagct  1800
gatgacgaga actgtggaaa tcaggaatcc tttggttaaa ggctttgaga ttttccagtg  1860
gacaaactat gccaagttct caagcgaaaa attagaatta gttttagtg aagagatatt  1920
gccttatctt ttccagttaa aaaaattcat aaaatataat ctggaacatg ttaagtcttt  1980
tgaaaacaaa tactctatga ggatttatga gtggttatta aagaactaa cacaaaagaa  2040
aactcacaag gcaaatatag agattagcct tgatgaattt aagttcatgt taatgcttga  2100
aaataactac catgagttta aaggcttaa ccaatgggtt ttgaaaccaa taagtaaaga  2160
tttaaacact tacagcaata tgaaattggt ggttgataag cgaggccgcc cgactgatac  2220
gttgattttc caagttgaac tagatagaca aatggatctc gtaaccgaac ttgagaacaa  2280
ccagataaaa atgaatggtg acaaaatacc aacaaccatt acatcagatt cctacctaca  2340
taacggacta agaaaaacac tacacgatgc tttaactgca aaaattcagc tcaccagttt  2400
```

```
tgaggcaaaa ttttgagtg acatgcaaag taagtatgat ctcaatggtt cgttctcatg    2460
gctcacgcaa aaacaacgaa ccacactaga gaacatactg gctaaatacg gaaggatctg    2520
aggttcttat ggctcttgta tctatcagtg aagcatcaag actaacaaac aaaagtagaa    2580
caactgttca ccgttacata tcaaagggaa aactgtccat atgcacagat gaaaacggtg    2640
taaaaaagat agatacatca gagcttttac gagttttggg tgcattcaaa gctgttcacc    2700
atgaacagat cgacaatgta acgcggccgc agccaatcaa ttcttgcgga gaactgtgaa    2760
tgcgcaaacc aaccettggc agaacatatc catcgcgtcc gccatctcca gcagccgcac    2820
gcggcgcatc gggggggggg ggggggtttt caattcatca ttttttttt attcttttt      2880
ttgatttcgg tttccttgaa atttttttga ttcggtaatc tccgaacaga aggaagaacg    2940
aaggaaggag cacagactta gattggtata tatacgcata tgtagtgttg aagaaacatg    3000
aaattgccca gtattcttaa cccaactgca cagaacaaaa acctgcagga acgaagata     3060
aatcatgtcg aaagctacat ataaggaacg tgctgctact catcctagtc ctgttgctgc    3120
caagctattt aatatcatgc acgaaaagca aacaaacttg tgtgcttcat tggatgttcg    3180
taccaccaag gaattactgg agttagttga agcattaggt cccaaaattt gtttactaaa    3240
aacacatgtg gatatcttga ctgattttc catggagggc acagttaagc cgctaaaggc    3300
attatccgcc aagtacaatt ttttactctt cgaagacaga aaatttgctg acattggtaa    3360
tacagtcaaa ttgcagtact ctgcgggtgt atacagaata gcagaatggg cagacattac    3420
gaatgcacac ggtgtggtgg gcccaggtat tgttagcggt ttgaagcagg cggcagaaga    3480
agtaacaaag gaacctagag gccttttgat gttagcagaa ttgtcatgca agggctccct    3540
atctactgga gaatatacta agggtactgt tgacattgcg aagagcgaca agattttgt     3600
tatcggcttt attgctcaaa gagacatggg tggaagagat gaaggttacg attggttgat    3660
tatgacaccc ggtgtggggtt tagatgacaa gggagacgca ttgggtcaac agtatagaac    3720
cgtggatgat gtggtctcta caggatctga cattattatt gttggaagag gactatttgc    3780
aaagggaagg gatgctaagg tagagggtga acgttacaga aaagcaggct gggaagcata    3840
tttgagaaga tgcggccagc aaaactaaaa aactgtatta taagtaaatg catgtatact    3900
aaactcacaa attagagctt caatttaatt atatcagtta ttacccggcc gggaatctcg    3960
gtcgtaatga tttttataat gacgaaaaaa aaaaattgg aaagaaaacc cccccccccc     4020
ccccgcagcg ttgggtcctg gccacgggtg cgcatgatcg tgctcctgtc gttgaggacc    4080
cggctaggct ggcggggttg ccttactggt tagcagaatg aatcaccgat acgcgagcga    4140
atgtggcggc cgcacgcgtt catcgtccac ctccggagaa caggccacca tcacgcatct    4200
gtgtctgaat tcatcacga cgcgccttaa gggcaccaat aactgcctta aaaaattac     4260
gccccgccct gccactcatc gcagtactgt tgtaattcat taagcattct gccgacatgg    4320
aagccatcac agacggcatg atgaacctga atcgccagcg gcatcagcac cttgtcgcct    4380
tgcgtataat atttgcccat ggtgaaaacg ggggcgaaga agttgtccat attggccacg    4440
tttaaatcaa aactggtgaa actcacccag ggattggctg agacgaaaaa catattctca    4500
ataaccctt tagggaaata ggccaggttt tcaccgtaac acgccacatc ttgcgaatat    4560
atgtgtagaa actgccggaa atcgtcgtgg tattcactcc agagcgatga aaacgtttca    4620
gtttgctcat ggaaaacggt gtaacaaggg tgaacactat cccatatcac cagctcaccg    4680
tctttcattg ccatacggaa ttccggatga gcattcatca ggcgggcaag aatgtgaata    4740
```

```
aaggccggat aaaacttgtg cttattttc tttacggtct ttaaaaaggc cgtaatatcc    4800
agctgaacgg tctggttata ggtacattga gcaactgact gaaatgcctc aaaatgttct    4860
ttacgatgcc attgggatat atcaacggtg gtatatccag tgattttttt ctccatttta    4920
gcttccttag ctcctgaaaa tctcgataac tcaaaaaata cgcccggtag tgatcttatt    4980
tcattatggt gaaagttgga acctcttacg tgccgatcaa cgtctcattt tcgccaaaag    5040
ttggcccagg gcttcccggt atcaacaggg acaccaggat ttatttattc tgcgaagtga    5100
tcttccgtca caggtattgg accaccctgt gggtttataa gcgcgctgct ggcgtgtaag    5160
gcggtgacgg cgaaggaagg gtccttttca tcacgtgcta taaaaataat tataatttaa    5220
attttttaat ataaatatat aaattaaaaa tagaaagtaa aaaaagaaat taaagaaaaa    5280
atagtttttg ttttccgaag atgtaaaaga ctctagggggg atcgccaaca aatactacct    5340
tttatcttgc tcttcctgct ctcaggtatt aatgccgaat tgtttcatct tgtctgtgta    5400
gaagaccaca cacgaaaatc ctgtgatttt acatttact tatcgttaat cgaatgtata    5460
tctatttaat ctgcttttct tgtctaataa atatatatgt aaagtacgct ttttgttgaa    5520
attttttaaa cctttgttta tttttttttc ttcattccgt aactcttcta ccttctttat    5580
ttactttcta aaatccaaat acaaaacata aaaataaata aacacagagt aaattcccaa    5640
attattccat cattaaaaga tacgaggcgc gtgtaagtta caggcaagcg atccgtccta    5700
agaaaccatt attatcatga cattaaccta taaaaatagg cgtatcacga ggcccttcg    5760
tctcgcgcgt ttcggtgatg acggtgaaaa cctctgacac atgcagctcc cggagacggt    5820
cacagcttgt ctgtaagcgg atgccgggag cagacaagcc cgtcagggcg cgtcagcggg    5880
tgttggcggg tgtcggggct ggcttaacta tgcggcatca gagcagattg tactgagagt    5940
gcaccacggc gcgtggcacc cttgcgggcc atgtcataca ccgccttcag agcagccgga    6000
cctatctgcc cgttacgcgc cagcttgcaa attaaagcct tcgagcgtcc caaaaccttc    6060
tcaagcaagg ttttcagtat aatgttacat gcgtacacgc gtctgtacag aaaaaaaaga    6120
aaaatttgaa atataaataa cgttcttaat actaacataa ctataaaaaa ataaataggg    6180
acctagactt caggttgtct aactccttcc ttttcggtta gagcggatgt gggggaggg    6240
cgtgaatgta agcgtgacat aactaattac atgatatcga caaggaaaa gggggacgga    6300
tctccgagge ctcggacccg tcgggccgcc gtcggacgtg ccgcggtcat gcagaagctg    6360
cagtagggac agggactggg acactatgca acactaaggt ttctacagtc aagcctggtc    6420
cgaatccaaa caacactccc caatcttttc cttctcctgt ggttgccaat ccgtctttag    6480
cagaactttt cctcatgaca tctaacacaa acaacacaga ggcactagac atatttccgt    6540
attcagataa cacttcccta gaagccctca ttctcttctt atccaatcct actctatctt    6600
caactctgtc taaaatggca gggccaccag gatgtgcaat ccagaaaatt gaattccagt    6660
tatgaatacc taaaggttca aaggcatcct ccaaagcctg ttcaatgttc tctgaaatta    6720
aaccaggaac atctttaat aaatgtatag ttaaaccagc ttctgttaaa tggccatcta    6780
tggcaccttc tgattctggt aatatagtct gagaagctga taccaactgg aaaactggtt    6840
gttcgtctaa ttggtctggg tcagcgccta taattcagc agcggcacca tcaccgaaca    6900
aggcatgacc taccaaggaa tctaaatgac tcttgcatgg acctctgaag gccatagcag    6960
ttatctcgga acaaacgact aacactctgg cacctctatt attttcagcg atatctttg    7020
ccaatctcaa aacagttgca ccaccaaagc aaccttgttg gtacatcatt aacctttga    7080
ctgtagggga caaacctaac aactttgtta attggtaatc agcaccgggc atgtcaacgc    7140
```

```
cggatgttgt gcaaaatacc aaatgagtaa tcttagacaa gggttggccc cactccttaa    7200
tggccttctc agctgcacct tggcccaatt tgggaacttc aactaatgcg atggcgtgtc    7260
tagcatccaa tgaggtctcc atgtgtgcac agatctttgg gttcttgatc aatatttcct    7320
cggtcaagtg catgtgtctc tttctaatca ttgatttgtc acacattctt tgaaacttct    7380
cctttaaatc tgccaagtgc tcacttttag taaccctaaa ataataatct ggataggtag    7440
cttgataaac acaattagct ggaacggcag taccgattgc taaaactgta gctaaacctt    7500
cagccctctg tgccattcta acttctttca atcttactgc agccatttta agcttttgt     7560 ttgtttatgt gtgtttattc gaaactaagt tcttggtgtt ttaaaactaa aaaaaagact    7620
aactataaaa gtagaattta agaagtttaa gaaatagatt tacagaatta caatcaatac    7680
ctaccgtctt tatatactta ttagtcaagt aggggaataa tttcagggaa ctggtttcaa    7740
cctttttttt cagcttttc caaatcagag agagcagaag gtaatagaag gtgtaagaaa     7800
atgagataga tacatgcgtg ggtcaattgc cttgtgtcat catttactcc aggcaggttg    7860
catcactcca ttgaggttgt gtccgttttt tgcctgtttg tgccctgtt ctctgtagtt     7920 gcgctaagag aatggaccta tgaactgatg gttggtgaag aaaacaatat tttggtgctg    7980
ggattctttt tttttctgga tgccagctta aaaagcgggc tccattatat ttagtggatg    8040
ccaggaataa actgttcacc cagacaccta cgatgttata tattctgtgt aacccgcccc    8100
ctattttggg catgtacggg ttacagcaga attaaaaggc taatttttg actaaataaa     8160 gttaggaaaa tcactactat taattattta cgtattcttt gaaatggcag tattgataat    8220
gataaactcg aactgggcgc gtcgtgccgt cgttgttaat caccacatgg ttattctgct    8280
caaacgtccc ggacgcctgc gaacgcgccg aaggaaaatg agaaatatcg agggagacga    8340
ttcagaggag caggacaaac tataaccgac tgtttgttgg aggatgccgt acataacgaa    8400
cactgctgaa gctaccatgt ctacagttta gaggaatggg tacaactcac aggcgaggga    8460
tggtgttcac tcgtgctagc aaacgcggtg ggagcaaaaa gtagaatatt atcttttatt    8520
cgtgaaactt cgaacactgt catctaaaga tgctatatac taatataggc atacttgata    8580
atgaaaacta taaatcgtaa agacataaga gatccgcgga tccccgggtc gagcctgaac    8640
ggcctcgagg cctgaacggc tcgacgaat tcattatttg tagagctcat ccatgccatg     8700
tgtaatccca gcagcagtta caaactcaag aaggaccatg tggtcacgct tttcgttggg    8760
atctttcgaa agggcagatt gtgtcgacag gtaatggttg tctggtaaaa ggacagggcc    8820
atcgccaatt ggagtatttt gttgataatg gtctgctagt tgaacggatc catcttcaat    8880
gttgtggcga attttgaagt tagctttgat tccattcttt tgtttgtctg ccgtgatgta    8940
tacattgtgt gagttatagt tgtactcgag tttgtgtccg agaatgtttc catcttcttt    9000
aaaatcaata cctttttaact cgatacgatt aacaagggta tcaccttcaa acttgacttc    9060
agcacgcgtc ttgtagttcc cgtcatcttt gaaagatata gtgcgttcct gtacataacc    9120
ttcgggcatg gcactcttga aaaagtcatg ccgtttcata tgatccggat aacgggaaaa    9180
gcattgaaca ccataagaga aagtagtgac aagtgttggc catggaacag gtagttttcc    9240
agtagtgcaa ataaatttaa gggtaagctg gccctgcagg ccaagctttg ttttatattt    9300
gttgtaaaaa gtagataatt acttccttga tgatctgtaa aaagagaaa agaaagcat      9360 ctaagaactt gaaaaactac gaattagaaa agaccaaata tgtatttctt gcattgacca    9420
atttatgcaa gtttatatat atgtaaatgt aagtttcacg aggttctact aaactaaacc    9480
```

-continued

```
accccttgg ttagaagaaa agagtgtgtg agaacaggct gttgttgtca cacgattcgg      9540
acaattctgt ttgaaagaga gagagtaaca gtacgatcga acgaactttg ctctggagat      9600
cacagtgggc atcatagcat gtggtactaa acccttccc gccattccag aaccttcgat      9660
tgcttgttac aaaacctgtg agccgtcgct aggaccttgt tgtgtgacga aattggaagc      9720
tgcaatcaat aggaagacag gaagtcgagc gtgtctgggt ttttcagtt ttgttcttt       9780 tgcaaacaaa tcacgagcga cggtaatttc tttctcgata agaggccacg tgctttatga     9840
gggtaacatc aattcaagaa ggagggaaac acttcctttt tctgccctg ataatagtat      9900 gagggtgaag ccaaaataaa ggattcgcgc ccaaatcggc atctttaaat gcaggtatgc     9960
gatagttcct cactctttcc ttactcacga gtaattcttg caaatgccta ttatgcagat     10020
gttataatat ctgtgcgtgg cgcgtccggc tgtctgccat gctgcccggt gtaccgacat     10080
aaccgccggt ggcatagccg cgcatacgcg ccatttcctt ccatcttgtg attcatgcta     10140
tccatctttt ttgagtatcc aattaacgaa gacgttacca gctgattgaa ggttctcaaa     10200
gtgactgtac tccatgtttt cttatcatcc atgtagttat ttttcaaact gcaaattcaa    10260
gaaaaagcca cgcgtgtgca cctttttttt cccctcccag tgcattatgc aatagacagc    10320
acgagtcttt gaaaagtaa cttataaaac tgtatcaatt tttaaaccta aatagattca     10380
taaactattc gttaatataa agtgttctaa actatgatga aaaataagc agaaaagact     10440 aataattctt agtaaaagc actccctagt tcattaatcc atttgctagt cttgctctta    10500
gatccttcct caatatcttc cctgatggag ctttaggaat agagtcagtg aagaacactt    10560
tgttgattct cttataaaac acaacctgtt ttgacacgaa ttgcttgatt tcatcttcgg    10620
atatatttga atctttcgat ctcaccacaa acgcaacagg aacctcacca gcatcttctt    10680
ccttcatggc gacgacagca acatcattga tttctggatg acctatgagg agagactcta    10740
gctcagctgg agccacttga aatcctttgt acttgatgag ttctttcaat ctatccacaa    10800
tgaaaagctc gtcgtcatca tcgataaatc cgacgtctcc agtgtgaagc caaccatctt    10860
tatcgatcgt cgatgccgtg ccaagggg cattgagata gcctttcatg atttggttgc     10920
cacggatgca tatttcgccg ggtttgttcc taggcaaaga atctcctgtg tctggatcaa    10980
gtatcttcat ctcggcgttc ctcaccaccg taccacatgc tcctgacttc actggaaacg    11040
gctctttagc aaaccctaac gacattgcta gcaccggacc tgcttctgtc atcccatagc    11100
cctgaccaag cttggcgtta ggaaacttag cactaatagc atcttcaagc tccttaccaa    11160
gaggagctgc tccagactta accatcctaa ccgagctcag atcatacttc tccgtctccg    11220
gcgacttcgc gatagctaaa acgatcggtg gcacgaccat agccaccgtg actttacacc    11280
tttgtatctg ctctaacaag agagtgattt cgaacttagg cattatcaag atcgtggcac    11340
caactctgag actacagagc atgatggagt tgagagcgta tatatggaac ataggcaaga    11400
cacagaggat cacgtcgtct ctgttgaagt aaagattcgg attctcgccg tcgacttgct    11460
gcgccacgct cgtgactaga cctttgtgtg ttagcatcac tcctttgggg agaccgtcg     11520 tgccggatga gaaaggaagc gccacgacgt cttctggcga aatcttctcc ggtattgagt    11580
ccactcgtgg ttcttcggac tgagttaact cggagaaacg gaggcagttt tcggggatgg    11640
cgtcggagtc ggtggtgacg atcaaaacgc cgtcgttttg gaggttcttg attttatcga    11700
cgtaacggga ttgagtgacg atgagtttcg ccgcggaggc tttggcttgt ttagaaatct    11760
ccgccggagt gaagaacggg ttcgcggagg tggtgattgc gccgatgaag gaggcggcaa    11820
ggaaagtgag gactacttca ggagagttcg ggaggaggat cattacaacg tcgtgttgct    11880
```

```
tcacgccgag gttatgaaga ccggcggcga gtttccgaga tgttacgtgg acatcggcgt   11940
aggtgtatac ttcgccggtg ggaccgttga tcaagcatgg cttagcggcg aactctgaga   12000
tattttcgaa gatgtagtcg tggagtggga ggtggttagg gatgtatata tcaggcaatc   12060
tcgatcggaa aatgacgtca ttactacact gtttctgatc attctgatca ttgactatca   12120
catcttgtgt cgtcatttta gcttttgta attaaaactt agattagatt gctatgcttt    12180
ctttctaatg agcaagaagt aaaaaagtt gtaatagaac aagaaaatg aaactgaaac      12240 ttgagaaatt gaagaccgtt tattaactta aatatcaatg ggaggtcatc gaaagagaaa   12300
aaaatcaaaa aaaaaaattt tcaagaaaaa gaaacgtgat aaaaattttt attgcctttt   12360
tcgacgaaga aaaagaaacg aggcggtctc ttttttcttt tccaaacctt tagtacgggt   12420
aattaacgac accctagagg aagaaagagg ggaaatttag tatgctgtgc ttgggtgttt   12480
tgaagtggta cggcgatgcg cggagtccga aaaatctgg aagagtaaaa aaggagtaga    12540
aacattttga agctaggcgc gtcagccggt aaagattccc cacgccaatc cggctggttg   12600
cctccttcgt gaagacaaac tcacgcgcct ccaaaatgag ctatcaaaaa cgatagatcg   12660
attaggatga ctttgaaatg actccgcagt ggactggccg ttaatttcaa gcgtgagtaa   12720
aatagtgcat gacaaaagat gagctaggct tttgtaaaaa tatcttacgt tgtaaaattt   12780
tagaaatcat tatttccttc atatcatttt gtcattgacc ttcagaagaa aagagccgac   12840
caataatata aataaataaa taaaaataat attccattat ttctaaacag attcaatact   12900
cattaaaaaa ctatatcaat taatttgaat taaccgcggt tagcagattg gaataggtgc   12960
accattccac tctttcaagc aatccataag tggatctatc aactttccct cgcacatagc   13020
tgtgaatacc ttgtcaaatt cttcacctgg gctaacgact ttttcaccag ttagtaattt   13080
ggttcccaac tcttctctaa cgaatctgta caaagggtac gacctacact ctttgattct   13140
atttggtata ggggcagtac catttccgta tgcggctcta gcagcttcga cttcctttgg   13200
taaaactgcc ttcagttctt cttcaaaggc acctatcttt tggaatattg aagtaacggc   13260 attttttctca gtttcaccat tggataaagc gtgatctaca ataacttgtc tcaatctctg   13320
catcaatgga taagtagcgc tacatggatc gtcaacgtaa gtaaatactt gttctctatc   13380 tacaacttt aataaatctt tttcacagaa tcttgatggg tgcaattcac cattgatacc     13440
tgtagttaga acctttttg caacctgtga tacggtattt ttcactgtct gtctcaaatt     13500
ctcttccaag tgtctcaaat ctacggcctg gcatatacc actaaaaatg ttgtggacat     13560
taatttaagg atatcaacgg cctcgcttgt ttttcttgat gaaatcaggc ccaaagaatt   13620
aacatcctga ttgtgttgtt cggctgattg tacatgagag gttactgggt tggctagata   13680
ttgcagctct gaacaatagc ttgccattgc tatctcagca ccttttgaaac cataatcaag   13740 actagggtta aagatgcgg tcagattcga aggcaaaccg ttattgtaga agtcattgac     13800
caattcagaa aattgggcaa acattaattt gccaattgcg gctatggcaa gcctggtatt   13860
atccatactg actcctatgg gtgtaccctg aaattgcct ccatgtattg ccttattcct     13920
cgacacatca ataagtggat tatcgttaac agagttgatc tctctttcta tagactttgt   13980
agcttgtcta attacttcaa tttgagggcc aagccattgt ggggatgtcc ttaaagcata   14040
tctatcttgt ttgggttttt gcaaagggtc catttcatga accttctggg ctaacttcat   14100
gtagctagag ccgtccaaaa tgtgctccat gatagctgct gcttcaattt gtcctgggtg   14160
atgttttaac ctgtgggtca agtgatcagt aaactcaggt tttccactca tgacttcggc   14220
```

```
aaaaattgcg acaaaacttt cggccaaaac tgcttgtacg ttagcttcaa acaacaccat   14280
ggatgccata ccgctgccga cagcggtgcc attcaccagg gctaaacctt ccttgggttg   14340
caaatcaaag aaaccagttg aaataccagc tttctcaaat gcttccttag cggttaagga   14400
ttctccgtct ggaccagtgg cctttgaatt aggtcttccc gttaataagc ctgcgatata   14460
tgaaagggga accaaatcac cgctggcagt tattgttcct cttaagggca acgaaggaga   14520
aatgttgtgg ttcaatagtg aagtgatggc ctcaagaatt tcaaaccttc ttccagagta   14580
accttgcaac aaagtgttca ccctaacaag catagcagct cttgttgccg attggggtaa   14640
tgtatggcaa gtttcctttg tattaccgaa ataccggcg ttaaggaatc tgatcagttc    14700
tgtttgcaaa gcagtgccat ttttagttct tctatgagag gtagcaccaa agcctgtggt   14760
aacgccatag gaatctgtgc ccttgttcat actttccatg acccaatctg atgaagcctt   14820
aactccggct ctacttgttt ctgcaagttc taccttcact gaaccgccaa cggtcgaaat   14880
agcagctacc tgtcctatcg tcaatgtctc gccgcctaga tttacgactg gtcttctgta   14940
ttcctcaacc atcttcttaa cttcatccag atggctacct ttcatctggt cagctgccag   15000
accccaattc aaaggatctg caagagtttt tgtcgttacg gccaccttgg tcttttcacc   15060
accaccgcat agcattgctt caatttggtc cattttaagc tttttgatag atttgactgt   15120
gttattttgc gtgaggttat gagtagaaaa taataattga gaaaggaata tgacaagaaa   15180
tatgaaaata aagggaacaa acccaaatct gattgcaagg agagtgaaag agccttgttt   15240
atatattttt ttttcctatg ttcaacgagg acagctaggt ttatgcaaaa atgtgccatc   15300
accataagct gattcaaatg agctaaaaaa aaaatagtta gaaataaggt ggtgttgaa    15360 cgatagcaag tagatcaaga caccgtctaa cagaaaaagg ggcagcggac aatattatgc   15420
aattatgaag aaaagtactc aaagggtcgg aaaaatattc aaacgatatt tgcataaaat   15480
cctcaattga ttgattattc catagtaaaa taccgtaaca acacaaaatt gttctcaaat   15540
tcataaatta ttcattttt ccacgagcct catcacacga aaagtcagaa gagcatacat   15600
aatcttttaa atgcataggt tatgcatttt gcaaatgcca ccaggcaaca aaaatatgcg   15660
tttagcgggc ggaatcggga aggaagccgg aaccaccaaa aactggaagc tacgttttta   15720
aggaaggtat gggtgcagtg tgcttatctc aagaaatatt agttatgata taaggtgttg   15780
aagtttagag ataggtaaat aaacgcgggg tgtgttatt acatgaagaa gaagttagtt    15840
tctgccttgc ttgtttatct tgcacatcac atcagcggaa catatgctca cccagtcgca   15900
tggcgcgtac cacggtgaac aatccccgct ggctcatatt tgccgccggt tcccgtaaat   15960
cctccggtac gcgccgggcc gtatacttac atatagtaga tgtcaagcgt aggcgcttcc   16020
cctgccggct gtgagggcgc cataaccaag gtatctatag accgccaatc agcaaactac   16080
ctccgtacat tcatgttgca cccacacatt tatacaccca gaccgcgaca aattacccat   16140
aaggttgttt gtgacggcgt cgtacaagag aacgtgggaa cttttaggc tcaccaaaaa     16200 agaaagaaaa aatacgagtt gctgacagaa gcctcaagaa aaaaaaaatt cttcttcgac   16260
tatgctggag gcagagatga tcgagccggt agttaactat atatagctaa attggttcca   16320
tcaccttctt ttctggtgtc gctccttcta gtgctatttc tggcttttcc tattttttt    16380 tttccatttt tctttctctc tttctaatat ataaattctc ttgcattttc tatttttctc   16440
tctatctatt ctacttgttt attccctca aggtttttt ttaaggagta cttgttttta    16500
gaatatacgg tcaacgaact ataattaact aaacaagctt aaaatgatgg attttgtttt   16560
gttagaaaaa gctcttcttg gtttgttcat tgcaactata gtagccatca caatctctaa   16620
```

```
gctaagggga aagaaactta agttgcctcc aggcccaatc cctgtcccag tgtttggtaa    16680
ttggttacaa gttggcgacg acttaaacca gaggaatttg gtagagtatg ctaaaaagtt    16740
cggcgactta tttctactta ggatgggtca agaaacttg gtcgtggttt catcccctga     16800
cttagcaaaa gacgtactac atacccaggg tgtcgagttc ggaagtagaa ctagaaatgt    16860
tgtgtttgat attttcacag gcaaaggtca agatatggtt tttaccgtat acagcgagca    16920
ctggaggaaa atgagaagaa taatgactgt cccattcttt acaaacaaag tggttcaaca    16980
gtataggttc ggatgggagg acgaagccgc tagagtagtc gaggatgtta aggcaaatcc    17040
tgaagccgct accaacggta ttgtgttgag gaatagatta caacttttga tgtacaacaa    17100
tatgtataga ataatgtttg acaggagatt tgaatctgtt gatgatccat tattcctaaa    17160
acttaaggca ttgaatggcg agagatcaag gttagctcaa tcctttgaat acaacttcgg    17220
tgacttcatt cctatattga ggccattctt gagaggatat cttaagttgt gtcaggaaat    17280
caaggacaaa aggttaaagc tattcaagga ctacttcgtc gacgagagaa aaaagttgga    17340
gagtatcaag agcgtaggta ataactcctt aaagtgcgcc atagatcata ttatcgaggc    17400
acaagaaaaa ggcgagataa acgaggataa cgtgttatac atcgtcgaga atatcaacgt    17460
ggctgccatt gaaactacac tttggtctat tgaatggggt atagcagaac tagtgaataa    17520
ccctgaaatc cagaaaaaat tgagacacga attagacacc gtacttggag ctggtgttca    17580
aatttgtgaa ccagatgttc aaaaattgcc ttatctacag gccgtgataa aagagacttt    17640
aaggtacagg atgcaattc cattgttagt cccacatatg aatcttcacg aagccaaatt     17700
ggccggctat gatatccctg cagagagcaa aattttggta aacgcttggt ggttagccaa    17760
taatccagca cattggaaca aacctgatga gtttagacca gaaagatttt tggaggaaga    17820
atccaaggtc gaggctaatg gaaacgactt taagtacatc cctttcggtg ttggcagaag    17880
atcttgccca ggtataattc ttgctttacc aatccttgga atagtaattg gtaggttggt    17940
tcaaaacttc gagttacttc cacctccagg ccaaagcaaa atagatacag ccgaaaaagg    18000
tggacagttt tcattgcaaa tcctaaagca ttccactatt gtgtgtaaac ctagaagttc    18060
ttaaccgcgg acaaatcgct cttaaatata tacctaaaga acattaaagc tatattataa    18120
gcaaagatac gtaaattttg cttatattat tatacacata tcatatttct atattttaa     18180 gatttggtta tataatgtac gtaatgcaaa ggaaataaat tttatacatt attgaacagc    18240
gtccaagtaa ctacattatg tgcactaata gtttagcgtc gtgaagactt tattgtgtcg    18300
cgaaaagtaa aaatttaaa aattagagca ccttgaactt gcgaaaaagg ttctcatcaa     18360
ctgtttaaaa ggaggatatc aggtcctatt tctgacaaac aatatacaaa tttagtttca    18420
aaggcgcgtt gcaaatgga atttcgccgc agcggcctga atggctgtac cgcctgacgc     18480
ggatgcgcca cgcgccgcat gccggtagag gtgtggtcaa taagagcgac ctcatgctat    18540
acctgagaaa gcaacctgac ctacaggaaa gagttactca agaataagaa ttttcgtttt    18600
aaaacctaag agtcacttta aaatttgtat acacttattt tttttataac ttatttaata    18660
ataaaaatca taaatcataa gaaattcgct tatttagaag tgtcaacaac gtatctacca    18720
acgatttgac ccttttccat cttttcgtaa atttctggca aggtagacaa gccgacaacc    18780
ttgattggag acttgaccaa acctctggcg aagaagtcca aagctctaga tcaatttagg    18840
cctgcggccg cggttaccag acatcttctt ggtatctacc tgaagtcttg agcatcttga    18900
ttagctctgt tgcttcatca gtggtaatgg atttaccacg ggataagatg ccaaccaatg    18960
```

```
cggttgacac acccttggcc ataccctttg catcaccaca gacgtagata aatgcaccgt   19020
tgttaatcat ttcaaatact tggtcttcgt aatcctttaa tttatcttga acataaactt   19080
ttttggtgtt tggcaacctg aatgggcca cgaccatttc gaacgaacca tccaattttt   19140
tggcgtattc tggccattcg tcctggtaca agaaatcatc agtgttacgg gatccataaa   19200
acagtatatg cttacctagc gaaacgttgt taccgccctt cttttgtgat tcgaggaacg   19260
cgacacgctc tctgataaac ccacggaatg gggcaacacc ggtacctgga ccgatcatga   19320
taactggggt ggaagggttg gaaggcaatc tgaagttaga acgacgaacg tggacgggca   19380
atttgtaatt ggcgaaaagt ttacgtgggc catttaaatc gtagtgaaca ggtaggttag   19440
tttcggcaat gttaacattg ttttgagcca attgaatgtt tcttaacaag ttagtcgtaa   19500
caccaacaac tggaggagca tcaggcaatt ctgggttagg aaagttttcc acaatggagg   19560
tgacatggac ggtttgcttt tcagacagag aagaggaaga gatagagtag taacgaggag   19620
tcatttgggg aactgattcg accaagaatt gcatgggtac ggtgtcccat ttggcgccat   19680
cagacaaata tttcagagca tctgcgatgt tgaaatattt ggaggttatc tcgacggcga   19740
attggtcctt gtctttcgaa agcagagtca attttttcctt gacgtcagcg ttgggggcga   19800
actgaatcaa agatgaaaac aattgtctgg agacaggtcc tgtaatttcc aaatagtgtt   19860
taatagcagc gccaatagta gttggcgttg ggaagggcac tttgacggtg ggatccaggg   19920
gcttcaagtc aaaaatggtt tcagggtcca ggttgaatat ggataagaac tgttcgacct   19980
tttccaatgg gttggaaggc caaacagcaa gatggtcacc agtggagtac ttgatgttag   20040
agccggacaa gtcaaattca gagtggatgc aattacggtc attggaagag aacagttcgc   20100
gagatttcac gatgggtgca atatacggtt gagacaaatc gaagggaccc aattggatgc   20160
cgtctgcgtt gcggttcaac tgatgcgagg gcaaatagtg agcagagggt tcaccaagcg   20220
acatggagtc agtgatttcg ttcaacacag tgtactggaa ttgagaggtg aacttggctt   20280
cctgttcgtc caaatgcagt tcgtctttca aaacctccag gatggagtcc ttccaggcca   20340
tgtaatcttc gtctgtagtt cctgcaccat catcagcttc accgagcttg cctagtctga   20400
tagcgcccgc agcggagaga tgcttctcgg ccttcttggc ggcaccatta agaattcat   20460 aagtagaatt tcccagacca aacatattat acctcaggtt cgatagtgca cccgcttccg   20520
cattacaaat aaagtcttca aagttgaccg ccccgtcggg gaagtctcct tcaccatatg   20580
tagagataaa aatcgagact atgacgggca catcgtttag cgactcaaag tcgtagttct   20640
caacatctgc gcacatcacg tttaggttga acttggccac cagctccttg gaaaactttt   20700
tggcgtaatc ctcggcagtc ccagtctgcg acgcatacaa caccaagtag ttcttgttgt   20760
tttcggtcac cacctgagca atgtctctgt tgcccgagct gacagctgtg atatctccgt   20820
catcggacat cagcagttcc ttgatggagt ttctctttac gtacagtagc acggcaagca   20880
ctagccccgc caggacagtg aagtcggtgt tgtctattcc aaacggcatt ttactagtaa   20940
gctttgtgat gatgttttat ttgttttgat tggtgtcttg taaatagaaa caagagaaa   21000 taataaacaa gttaagaata aaaaccaaa ggatgaaaaa gaatgaatat gaaaagagt    21060 agagaataac tttgaaaggg gaccatgata taactgaaaa aaagaggttc ttggaaatga   21120
aaagttacca aagagtattt ataattcaga aaaaaagcc aacgaatatc gttttgatgg    21180
cgagcctttt ttttttttta ggaagacact aaaggtacct agcatcatat gggaaggaaa   21240
ggaaatcact tggaagacat cacaagcatt catttaccaa gagaaaaaat atgcatttta   21300
gctaagatcc attgaacaaa gcactcactc aactcaactg aatgaacgaa agaagaaaga   21360
```

```
acagtagaaa acactttgtg acggtgcgga acacatttac gtagctatca tgctgaattc    21420
tactatgaaa atctcccaat ctgtcgatgg caaaacgacc cacgtggcag agttgggtca    21480
agtgccagtt tctggattaa gtaacagata cagacatcac acgccataga ggaatcccgc    21540
cgttgcgaga gatggaaaac aatagagccg aaattgtgga agcccgatgt ctgggtgtac    21600 atttttttt tttctttctt tctctttcaa taatctttcc ttttccatt tagcttgccg    21660 gaaaaacttt cgggtagcga aaatctttct gccggaaaaa ttagctattt ttttcttcct    21720
tattattttt ttagttctga agtttgacca gggcgctacc ctgaccgtat cacaaccgac    21780 gatccgggt catggcggct attttttttt tttttttttt ttccttgtga ttgtttattt    21840
acatttggat caattctaac aaaaaaaaaa taaggggga aaataattc acctcttttt    21900 aatattgttt tgtactgaga ttgatctcca aaatagtagc attggcgcgt gccaccaaca    21960
gccccgccaa tggcgctgcc gatactcccg acaatcccca ccattgcctg                22010

<210> SEQ ID NO 10
<211> LENGTH: 24945
<212> TYPE: DNA
<213> ORGANISM: Artificial Sequence
<220> FEATURE:
<223> OTHER INFORMATION: pPHLOZ Multi-Expression Plasmid

<400> SEQUENCE: 10
acgcgcctcc aactggcacc gctggcttga acaacaatac cagccttcca acttctgtaa        60
ataacggcgg tacgccagtg ccaccagtac cgttaccttt cggtatacct cctttccca       120 tgtttccaat gcccttcatg cctccaacgg ctactatcac aaatcctcat caagctgacg       180
caagccctaa gaaatgaata acaatactga cagtactaaa taattgccta cttggcttca       240
catacgttgc atacgtcgat atagataata atgataatga cagcaggatt atcgtaatac       300
gtaatagttg aaaatctcaa aaatgtgtgg gtcattacgt aaataatgat aggaatggga       360
ttcttctatt tttccttttt ccattctagc agccgtcggg aaaacgtggc atcctctctt       420
tcgggctcaa ttggagtcac gctgccgtga gcatcctctc tttccatatc taacaactga       480
gcacgtaacc aatggaaaag catgagctta gcgttgctcc aaaaaagtat tggatggtta       540
ataccatttg tctgttctct ctgactttg actcctcaaa aaaaaaaat ctacaatcaa         600 cagatcgctt caattacgcc ctcacaaaaa ctttttttcct tcttcttcgc ccacgttaaa       660
ttttatccct catgttgtct aacggatttc tgcacttgat ttattataaa aaagacaaag       720
acataatact tctctatcaa tttcagttat tgttcttcct tgcgttattc ttctgttctt       780 cttttttcttt tgtcatatat aaccataacc aagtaataca tattcaaaaa gcttaaaatg       840
ggtgatgtca ttgtcttgta tgcttctcca ggtatgggtc atatagtttc catggttgaa       900
ttgggtaaat tcatcgttca tagatacggt ccacacaagt tctctattac tatcttgtac       960
acctgtggtt ccatcgttga tactgcttct attccagttt acatcagaag aatctcccat      1020
tcccatccat tcatctcatt cagacaattc ccaagagtta ccaacaacat caccagaaac      1080
atttccgttc cagctattac cttcgacttc atcagacaaa atgatccaca tgttagatcc      1140
gccttgcaag aaatttcaaa gtctgctact gttagagcct tcatcattga tttgttctgt      1200
acttccgctt tgccaatcgg taaagaattc aacattccaa cctactactt cagaacttct      1260
ggtgctgcta ttttggctgc tttccttgtac ttgccaaaga tcgatgaaca aactaagacc      1320
accgaatctt tcaaggattt gagagatacc gttttcgaat ttccaggttg gaaatctcca      1380
```

```
ttgaaggcta ctcatatggt tcaattggtt ttggatagaa acgatccagc ctactctgat   1440
atgatctact tctgttctca tttgccaaag tccaacggta ttatcgttaa caccttcgaa   1500
gaattggaac caccatctgt tttacaagct attgctggtg gtttgtgtgt tccagatggt   1560
ccaactccac cagtttatta tgttggtcca ttgatcgaag aagaaaaaga attgtccaag   1620
gatgctgatg ctgccgaaaa agaagattgc ttgtcttggt tggataagca accatctaga   1680
tccgttttgt tcttgtgttt tggttccatg ggttcttttc cagctgctca attgaaagaa   1740
attgccaatg gtttggaagc ctctggtcaa agattttttgt gggttgttaa gaagccacca   1800
gtcgaagaaa aatccaaaca agttcatggt gttgacgact tcgatttgaa aggtgttttg   1860
ccagaaggtt tcttggaaag aactgctgat agaggtatgg ttgtaaaatc ttgggctcca   1920
caagttgtcg tcttgaagaa agaatctgtt ggtggtttcg ttactcattg tggttggaat   1980
tctgttttgg aagctgttgt tgctggtgtt ccaatgattg cttggccatt atatgctgaa   2040
caacacatga atagaaacgt cttggttacc gatatggaaa tcgctattgg tgtcgaacaa   2100
agagatgaag aaggtggttt tgtttccggt gaagaagttg aaagaagagt tagagaattg   2160
atggaatccg aaggtggtag agttttgaga gaaagatgta aaaagttggg tgaaatggct   2220
tctgctgctt taggtgaaac tggttcttct actagaaact tggtcaactt cgtttcctcc   2280
attacctgac cgcggattta actccttaag ttactttaat gatttagttt ttattattaa   2340
taattcatgc tcatgacatc tcatatacac gtttataaaa cttaaataga ttgaaaatgt   2400
attaaagatt cctcagggat tcgattttttt tggaagtttt tgttttttttt tccttgagat   2460
gctgtagtat ttgggaacaa ttatacaatc gaaagatata tgcttacatt cgaccgtttt   2520
agccgtgatc attatcctat agtaacataa cctgaagcat aactgacact actatcatca   2580
atacttgtca catgaggcgc gtcttaagca gaatttctgt catcatggac agcacggaac   2640
gggtgaagct gcgccagttc tgacgcgtcc agtatcccag cagatacggg atatcgacat   2700
ttctgcacca ttccggcggg tataggtttt attgatggcc tcatccacac gcagcagcgt   2760
ctgttcatcg tcgtggcggc ccataataat ctgccggtca atcagccagc tttcctcacc   2820
cggcccccat cccatacgcg gcatttcgta gcggtccagc tgggagtcga taccggcggt   2880
caggtaagcc acacggtcag gaacgggcgc tgaataatgc tctttccgct ctgccatcac   2940
ttcagcatcc ggacgttcgc caattttcgc ctcccacgtc tcaccgagcg tggtgtttac   3000
gaaggtttta cgttttcccg tatccccttt cgttttcatc cagtctttga caatctgcac   3060
ccaggtggtg aacgggctgt acgctgtcca gatgtgaaag gtcacactgt caggtggctc   3120
aatctcttca ccggatgacg aaaaccagag aatgccatca cgggtccaga tcccggtctt   3180
ttcgcagata taacgggcat cagtaaagtc cagctcctgc tggcggatga cgcaggcatt   3240
atgctcgcag agataaaaca cgctggagac gcgttttccc gtctttcagt gccttgttca   3300
gttcttcctg acgggcggta tatttctcca gcttggccta gcggccctg tcagaccaag   3360
tttacgagct cgcttggact cctgttgata gatccagtaa tgacctcaga actccatctg   3420
gatttgttca gaacgctcgg ttgccgccgg gcgttttttta ttggtgagaa tccaagcact   3480
agggacagta gacgggtaa gcctgttgat gataccgctg ccttactggg tgcattagcc   3540
agtctgaatg acctgtcacg ggataatccg aagtggtcag actggaaaat cagagggcag   3600
gaactgctga acagcaaaaa gtcagatagc accacatagc agaccgcca taaaacgccc   3660
tgagaagccc gtgacgggct tttcttgtat tatgggtagt ttccttgcat gaatccataa   3720
aaggcgcctg tagtgccatt taccccccatt cactgccaga gccgtgagcg cagcgaactg   3780
```

```
aatgtcacga aaaagacagc gactcaggtg cctgatggtc ggagacaaaa ggaatattca    3840
gcgatttgcc cgagcttgcg agggtgctac ttaagccttt agggttttaa ggtctgtttt    3900
gtagaggagc aaacagcgtt tgcgacatcc ttttgtaata ctgcggaact gactaaagta    3960
gtgagttata cacagggctg ggatctattc tttttatctt tttttattct ttctttattc    4020
tataaattat aaccacttga atataaacaa aaaaaacaca caaaggtcta gcggaattta    4080
cagagggtct agcagaattt acaagttttc cagcaaaggt ctagcagaat ttacagatac    4140
ccacaactca aaggaaaagg acatgtaatt atcattgact agcccatctc aattggtata    4200
gtgattaaaa tcacctagac caattgagat gtatgtctga attagttgtt ttcaaagcaa    4260
atgaactagc gattagtcgc tatgacttaa cggagcatga aaccaagcta attttatgct    4320
gtgtggcact actcaacccc acgattgaaa accctacaag gaaagaacgg acggtatcgt    4380
tcacttataa ccaatacgct cagatgatga acatcagtag ggaaaatgct tatggtgtat    4440
tagctaaagc aaccagagag ctgatgacga gaactgtgga atcaggaat  cctttggtta    4500
aaggctttga gattttccag tggacaaact atgccaagtt ctcaagcgaa aaattagaat    4560
tagttttttag tgaagagata ttgccttatc ttttccagtt aaaaaaattc ataaaatata    4620
atctggaaca tgttaagtct tttgaaaaca atactctat  gaggatttat gagtggttat    4680
taaaagaact aacacaaaag aaaactcaca aggcaaatat agagattagc cttgatgaat    4740
ttaagttcat gttaatgctt gaaaataact accatgagtt taaaaggctt aaccaatggg    4800
ttttgaaacc aataagtaaa gatttaaaca cttacagcaa tatgaaattg gtggttgata    4860
agcgaggccg cccgactgat acgttgattt tccaagttga actagataga caaatggatc    4920
tcgtaaccga acttgagaac aaccagataa aaatgaatgg tgacaaaata ccaacaacca    4980
ttacatcaga ttcctaccta cataacggac taagaaaaac actacgat   gctttaactg    5040
caaaaattca gctcaccagt tttgaggcaa aattttttgag tgacatgcaa agtaagtatg    5100
atctcaatgg ttcgttctca tggctcacgc aaaaacaacg aaccacacta gagaacatac    5160
tggctaaata cggaaggatc tgaggttctt atggctcttg tatctatcag tgaagcatca    5220
agactaacaa acaaaagtag aacaactgtt caccgttaca tatcaaaggg aaaactgtcc    5280
atatgcacag atgaaaacgg tgtaaaaaag atagatacat cagagctttt acgagttttt    5340
ggtgcattca aagctgttca ccatgaacag atcgacaatg taacgcggcc gcagccaatc    5400
aattcttgcg gagaactgtg aatgcgcaaa ccaacccttg gcagaacata tccatcgcgt    5460
ccgccatctc cagcagccgc acgcggcgca tcggggggg  gggggggggt tcaattcat    5520
cattttttt  ttattctttt ttttgatttc ggtttccttg aattttttt  gattcggtaa    5580
tctccgaaca gaaggaagaa cgaaggaagg agcacagact tagattggta tatatacgca    5640
tatgtagtgt tgaagaaaca tgaaattgcc cagtattctt aacccaactg cacagaacaa    5700
aaacctgcag gaaacgaaga taatcatgt  cgaaagctac atataaggaa cgtgctgcta    5760
ctcatcctag tcctgttgct gccaagctat ttaatatcat gcacgaaaag caaacaaact    5820
tgtgtgcttc attggatgtt cgtaccacca aggaattact ggagttagtt gaagcattag    5880
gtcccaaaat ttgtttacta aaaacacatg tggatatctt gactgatttt tccatggagg    5940
gcacagttaa gccgctaaag gcattatccg ccaagtacaa tttttttactc ttcgaagaca    6000
gaaaatttgc tgacattggt aatacagtca aattgcagta ctctgcgggt gtatacagaa    6060
tagcagaatg ggcagacatt acgaatgcac acggtgtggt gggcccaggt attgttagcg    6120
```

```
gtttgaagca ggcggcagaa gaagtaacaa aggaacctag aggccttttg atgttagcag    6180
aattgtcatg caagggctcc ctatctactg gagaatatac taagggtact gttgacattg    6240
cgaagagcga caaagatttt gttatcggct ttattgctca agagacatg ggtggaagag     6300 atgaaggtta cgattggttg attatgacac ccggtgtggg tttagatgac aagggagacg    6360
cattgggtca acagtataga accgtggatg atgtggtctc tacaggatct gacattatta    6420
ttgttggaag aggactattt gcaaagggaa gggatgctaa ggtagagggt gaacgttaca    6480
gaaaagcagg ctgggaagca tatttgagaa gatgcggcca gcaaaactaa aaaactgtat    6540
tataagtaaa tgcatgtata ctaaactcac aaattagagc ttcaatttaa ttatatcagt    6600
tattacccgg ccgggaatct cggtcgtaat gatttttata atgacgaaaa aaaaaaaatt    6660
ggaaagaaaa ccccccccc cccccgcag cgttgggtcc tggccacggg tgcgcatgat      6720
cgtgctcctg tcgttgagga cccggctagg ctggcggggt tgccttactg gttagcagaa    6780
tgaatcaccg atacgcgagc gaatgtggcg gccgcacgcg ttcatcgtcc acctccggag    6840
aacaggccac catcacgcat ctgtgtctga atttcatcac gacgcgcctt aagggcacca    6900
ataactgcct taaaaaaatt acgccccgcc ctgccactca tcgcagtact gttgtaattc    6960
attaagcatt ctgccgacat ggaagccatc acagacggca tgatgaacct gaatcgccag    7020
cggcatcagc accttgtcgc cttgcgtata atatttgccc atggtgaaaa cggggcgaa    7080 gaagttgtcc atattggcca cgtttaaatc aaaactggtg aaactcaccc agggattggc    7140
tgagacgaaa aacatattct caataaaccc tttagggaaa taggccaggt tttcaccgta    7200
acacgccaca tcttgcgaat atatgtgtag aaactgccgg aaatcgtcgt ggtattcact    7260
ccagagcgat gaaaacgttt cagtttgctc atggaaaacg gtgtaacaag ggtgaacact    7320
atcccatatc accagctcac cgtctttcat tgccatacgg aattccggat gagcattcat    7380
caggcgggca agaatgtgaa taaaggccgg ataaaacttg tgcttatttt tctttacggt    7440 cttaaaaag gccgtaatat ccagctgaac ggtctggtta taggtacatt gagcaactga    7500
ctgaaatgcc tcaaaatgtt ctttacgatg ccattgggat atatcaacgg tggtatatcc    7560 agtgatttt ttctccattt tagcttcctt agctcctgaa aatctcgata actcaaaaaa     7620
tacgcccggt agtgatctta tttcattatg gtgaaagttg gaacctctta cgtgccgatc    7680
aacgtctcat tttcgccaaa agttggccca gggcttcccg gtatcaacag ggacaccagg    7740
atttatttat tctgcgaagt gatcttccgt cacaggtatt ggaccaccct gtgggtttat    7800
aagcgcgctg ctggcgtgta aggcggtgac ggcgaaggaa gggtccttt catcacgtgc     7860 tataaaaata attataattt aaattttta atataaatat ataaattaaa aatagaaagt     7920 aaaaaagaa attaagaaa aaatagtttt tgttttccga agatgtaaaa gactctaggg      7980
ggatcgccaa caaatactac cttttatctt gctcttcctg ctctcaggta ttaatgccga    8040
attgtttcat cttgtctgtg tagaagacca cacacgaaaa tcctgtgatt ttacatttta    8100
cttatcgtta atcgaatgta tatctatta atctgctttt cttgtctaat aaatatatat    8160
gtaaagtacg cttttgttg aaattttta aacctttgtt tatttttttt tcttcattcc     8220
gtaactcttc taccttcttt atttactttc taaaatccaa atacaaaaca taaaaataaa    8280
taaacacaga gtaaattccc aaattattcc atcattaaaa gatacgaggc gcgtgtaagt    8340
tacaggcaag cgatccgtcc taagaaacca ttattatcat gacattaacc tataaaaata    8400
ggcgtatcac gaggcccttt cgtctcgcgc gtttcggtga tgacggtgaa aacctctgac    8460
acatgcagct cccggagacg gtcacagctt gtctgtaagc ggatgccggg agcagacaag    8520
```

```
cccgtcaggg cgcgtcagcg ggtgttggcg ggtgtcgggg ctggcttaac tatgcggcat    8580
cagagcagat tgtactgaga gtgcaccacg gcgcgtggca cccttgcggg ccatgtcata    8640
caccgccttc agagcagccg gacctatctg cccgttacgc gccagcttgc aaattaaagc    8700
cttcgagcgt cccaaaacct tctcaagcaa ggttttcagt ataatgttac atgcgtacac    8760
gcgtctgtac agaaaaaaaa gaaaaatttg aaatataaat aacgttctta atactaacat    8820
aactataaaa aaataaatag ggacctagac ttcaggttgt ctaactcctt ccttttcggt    8880
tagagcggat gtggggggag ggcgtgaatg taagcgtgac ataactaatt acatgatatc    8940
gacaaaggaa aaggggacg gatctccgag gcctcggacc cgtcgggccg ccgtcggacg    9000
tgccgcggtc atgcagaagc tgcagtaggg acagggactg ggacactatg caacactaag    9060
gtttctacag tcaagcctgg tccgaatcca acaacactc cccaatcttt tccttctcct    9120
gtggttgcca atccgtcttt agcagaactt ttcctcatga catctaacac aaacaacaca    9180
gaggcactag acatatttcc gtattcagat aacacttccc tagaagccct cattctcttc    9240
ttatccaatc ctactctatc ttcaactctg tctaaaatgg cagggccacc aggatgtgca    9300
atccagaaaa ttgaattcca gttatgaata cctaaaggtt caaaggcatc ctccaaagcc    9360
tgttcaatgt tctctgaaat taaaccagga acatctttta ataaatgtat agttaaacca    9420
gcttctgtta aatggccatc tatggcacct tctgattctg gtaatatagt ctgagaagct    9480
gataccaact ggaaaactgg ttgttcgtct aattggtctg ggtcagcgcc tataattgca    9540
gcagcggcac catcaccgaa caaggcatga cctaccaagg aatctaaatg actcttgcat    9600
ggacctctga aggccatagc agttatctcg gaacaaacga ctaacactct ggcacctcta    9660
ttattttcag cgatatcttt tgccaatctc aaaacagttg caccaccaaa gcaaccttgt    9720
tggtacatca ttaaccttt gactgtaggg gacaaaccta acaactttgt taattggtaa    9780
tcagcaccgg gcatgtcaac gccggatgtt gtgcaaaata ccaatgagt aatcttagac    9840 aagggttggc cccactcctt aatggccttc tcagctgcac cttggcccaa tttgggaact    9900
tcaactaatg cgatggcgtg tctagcatcc aatgaggtct ccatgtgtgc acagatcttt    9960
gggttcttga tcaatatttc ctcggtcaag tgcatgtgtc tctttctaat cattgatttg   10020
tcacacattc tttgaaactt ctcctttaaa tctgccaagt gctcacttt agtaaccccta   10080 aaataataat ctggataggt agcttgataa acacaattag ctggaacggc agtaccgatt   10140
gctaaaactg tagctaaacc ttcagccctc tgtgccattc taacttcttt caatcttact   10200
gcagccattt taagcttttt gtttgtttat gtgtgtttat tcgaaactaa gttcttggtg   10260
ttttaaaact aaaaaaaga ctaactataa aagtagaatt taagaagttt aagaaataga   10320
tttacagaat tacaatcaat acctaccgtc tttatatact tattagtcaa gtaggggaat   10380
aatttcaggg aactggttc aaccttttttt ttcagctttt tccaaatcag agagagcaga   10440
aggtaataga aggtgtaaga aaatgagata gatacatgcg tgggtcaatt gccttgtgtc   10500
atcatttact ccaggcaggt tgcatcactc cattgaggtt gtgtccgttt tttgcctgtt   10560 tgtgccctg ttctctgtag ttgcgctaag agaatggacc tatgaactga tggttggtga   10620
agaaaacaat attttggtgc tgggattctt ttttttttctg gatgccagct taaaaagcgg   10680
gctccattat atttagtgga tgccaggaat aaactgttca cccagacacc tacgatgtta   10740
tatattctgt gtaacccgcc ccctatttg ggcatgtacg ggttacagca gaattaaaag   10800
gctaattttt tgactaaata aagttaggaa aatcactact attaattatt tacgtattct   10860
```

```
ttgaaatggc agtattgata atgataaact cgaactgggc gcgtcgtgcc gtcgttgtta   10920
atcaccacat ggttattctg ctcaaacgtc ccggacgcct gcgaacgcgc cgaaggaaaa   10980
tgagaaatat cgagggagac gattcagagg agcaggacaa actataaccg actgtttgtt   11040
ggaggatgcc gtacataacg aacactgctg aagctaccat gtctacagtt tagaggaatg   11100
ggtacaactc acaggcgagg gatggtgttc actcgtgcta gcaaacgcgg tgggagcaaa   11160
aagtagaata ttatctttta ttcgtgaaac ttcgaacact gtcatctaaa gatgctatat   11220
actaatatag gcatacttga taatgaaaac tataaatcgt aaagacataa gagatccgcg   11280
gtcaaaatac aaatggaatc aagaatgctc ttctggtatg atacttttg ttttctttt    11340
gagcccatgc gtacatttga gctgttgaaa cagtcaaaaa taaaacggca aataaattga   11400
acttgaacac aaaagtaaac caaatccaag accaaacttc aaaagtatag ttgggagcaa   11460
caaaaagatt gaaaatacct tgattcaatg ggacacggat cttagcgtta ccatgcttct   11520
tttgatagtc accccatagg cgcaatttaa tgtggcaata aaagttccat agttctgaaa   11580
gcacgaaaag accaattaat gtactcaagt catccaattt caaatatgaa tagtatttga   11640
ataacttagc attcccaaag gggaagccgt agccaaagta accgaatgaa atgagaccgc   11700
ttagaaccca gtaatggaaa caattttga acaggttgaa aattggcata gtagctaaag    11760
agaattggtg aacaaataag gtttcaaata atctctttcc ataatgtcct aaaattaaaa   11820
aatatgcaac cctgtttaaa aatggattat agtcggagct agcactgtgc catctatcaa   11880
caactgtggg aatggtagat agataataaa aaagggagtg aaccaagact ggacccaaat   11940
actcacaaaa gaagactaat ctccatgaaa tttggggacc caaatctttg atgaagaatt   12000
ccattgagtc atcagcctct tcttgaaaaa acgattctga ataaccgga acttgtttag    12060
attccttttt gtaggttaat cttatcctgt acttgctgat attgtggtta ttagcagaga   12120
ttttttttcaa aacatcatct aaagtaggct ttttggataa gtcaatttca gtgtccctta   12180
acccttttaga gcggcttttt atggtgatag gcattttaag cttttgtttta tatttgttgt   12240
aaaaagtaga taattacttc cttgatgatc tgtaaaaaag agaaaaagaa agcatctaag   12300
aacttgaaaa actacgaatt agaaaagacc aaatatgtat ttcttgcatt gaccaattta   12360
tgcaagttta tatatatgta aatgtaagtt tcacgaggtt ctactaaact aaaccacccc   12420
cttggttaga agaaaagagt gtgtgagaac aggctgttgt tgtcacacga ttcggacaat   12480
tctgtttgaa agagagagag taacagtacg atcgaacgaa cttgctctg gagatcacag    12540
tgggcatcat agcatgtggt actaaaccct ttcccgccat tccagaacct tcgattgctt   12600
gttacaaaac ctgtgagccg tcgctaggac cttgttgtgt gacgaaattg gaagctgcaa   12660
tcaataggaa gacaggaagt cgagcgtgtc tgggtttttt cagttttgtt cttttttgcaa   12720
acaaatcacg agcgacggta atttctttct cgataagagg ccacgtgctt tatgagggta   12780
acatcaattc aagaaggagg gaaacacttc ctttttctgg ccctgataat agtatgaggg   12840
tgaagccaaa ataaggatt cgcgcccaaa tcggcatctt taaatgcagg tatgcgatag    12900
ttcctcactc tttccttact cacgagtaat tcttgcaaat gcctattatg cagatgttat   12960
aatatctgtg cgtggcgcgt ccggctgtct gccatgctgc ccggtgtacc gacataaccg   13020
ccggtggcat agccgcgcat acgcgccatt tccttccatc ttgtgattca tgctatccat   13080
cttttttgag tatccaatta acgaagacgt taccagctga ttgaaggttc tcaaagtgac   13140
tgtactccat gttttcttat catccatgta gttattttc aaactgcaaa ttcaagaaaa    13200
agccacgcgt gtgcacccttt tttttcccct tccagtgcat tatgcaatag acagcacgag   13260
```

```
tctttgaaaa agtaacttat aaaactgtat caatttttaa acctaaaatag attcataaac   13320
tattcgttaa tataaagtgt tctaaactat gatgaaaaaa taagcagaaa agactaataa   13380
ttcttagtta aaagcactcc ctagttcatt aatccatttg ctagtcttgc tcttagatcc   13440
ttcctcaata tcttccctga tggagcttta ggaatagagt cagtgaagaa cactttgttg   13500
attctcttat aaaacacaac ctgttttgac acgaattgct tgatttcatc ttcggatata   13560
tttgaatctt tcgatctcac cacaaacgca acaggaacct caccagcatc ttcttccttc   13620
atggcgacga cagcaacatc attgatttct ggatgaccta tgaggagaga ctctagctca   13680
gctggagcca cttgaaatcc tttgtacttg atgagttctt tcaatctatc cacaatgaaa   13740
agctcgtcgt catcatcgat aaatccgacg tctccagtgt gaagccaacc atctttatcg   13800
atcgtcgatg ccgtggccaa ggggtcattg agatagcctt tcatgatttg gttgccacgg   13860
atgcatattt cgccgggttt gttcctaggc aaagaatctc ctgtgtctgg atcaagtatc   13920
ttcatctcgg cgttcctcac caccgtacca catgctcctg acttcactgg aaacggctct   13980
ttagcaaacc ctaacgacat tgctagcacc ggacctgctt ctgtcatccc atagccctga   14040
ccaagcttgg cgttaggaaa cttagcacta atagcatctt caagctcctt accaaggaga   14100
gctgctccag acttaaccat cctaaccgag ctcagatcat acttctccgt ctccggcgac   14160
ttcgcgatag ctaaaacgat cggtggcacg accatagcca ccgtgacttt acacctttgt   14220
atctgctcta acaagagagt gatttcgaac ttaggcatta tcaagatcgt ggcaccaact   14280
ctgagactac agagcatgat ggagttgaga gcgtatatat ggaacatagg caagacacag   14340
aggatcacgt cgtctctgtt gaagtaaaga ttcggattct cgccgtcgac ttgctgcgcc   14400
acgctcgtga ctagaccttt gtgtgttagc atcactcctt tggggagacc cgtcgtgccg   14460
gatgagaaag gaagcgccac gacgtcttct ggcgaaatct tctccggtat tgagtccact   14520
cgtggttctt cggactgagt taactcgag aaacggaggc agttttcggg gatggcgtcg   14580
gagtcggtgg tgacgatcaa aacgccgtcg ttttggaggt tcttgatttt atcgacgtaa   14640
cgggattgag tgacgatgag tttcgccgcg gaggctttgg cttgtttaga aatctccgcc   14700
ggagtgaaga acgggttcgc ggaggtggtg attgcgccga tgaaggaggc ggcaaggaaa   14760
gtgaggacta cttcaggaga gttcgggagg aggatcatta caacgtcgtg ttgcttcacg   14820
ccgaggttat gaagaccggc ggcgagtttc cgagatgtta cgtggacatc ggcgtaggtg   14880
tatacttcgc cggtgggacc gttgatcaag catggcttag cggcgaactc tgagatattt   14940
tcgaagatgt agtcgtggag tgggaggtgg ttagggatgt atatatcagg caatctcgat   15000
cggaaaatga cgtcattact acactgtttc tgatcattct gatcattgac tatcacatct   15060
tgtgtcgtca ttttagcttt ttgtaattaa aacttagatt agattgctat gctttctttc   15120
taatgagcaa gaagtaaaaa aagttgtaat agaacaagaa aaatgaaact gaaacttgag   15180
aaattgaaga ccgttattta acttaaatat caatgggagg tcatcgaaag agaaaaaaat   15240
caaaaaaaaa aattttcaag aaaaagaaac gtgataaaaa tttttattgc cttttcgac    15300
gaagaaaaag aaacgaggcg gtctcttttt tcttttccaa acctttagta cgggtaatta   15360
acgacaccct agaggaagaa agaggggaaa tttagtatgc tgtgcttggg tgttttgaag   15420
tggtacggcg atgcgcggag tccgagaaaa tctggaagag taaaaaagga gtagaaacat   15480
tttgaagcta ggcgcgtcag ccggtaaaga ttccccacgc caatccggct ggttgcctcc   15540
ttcgtgaaga caaactcacg cgcctccaaa atgagctatc aaaaacgata gatcgattag   15600
```

```
gatgactttg aaatgactcc gcagtggact ggccgttaat ttcaagcgtg agtaaaatag    15660
tgcatgacaa aagatgagct aggcttttgt aaaaatatct tacgttgtaa aatttttagaa    15720 atcattattt ccttcatatc attttgtcat tgaccttcag aagaaaagag ccgaccaata    15780
atataaataa ataaataaaa ataatattcc attatttcta aacagattca atactcatta    15840
aaaaactata tcaattaatt tgaattaacc gcggttagca gattggaata ggtgcaccat    15900
tccactcttt caagcaatcc ataagtggat ctatcaactt tccctcgcac atagctgtga    15960
ataccttgtc aaattcttca cctgggctaa cgacttttc accagttagt aatttggttc    16020
ccaactcttc tctaacgaat ctgtacaaag ggtacgacct acactctttg attctatttg    16080
gtataggggc agtaccattt ccgtatgcgg ctctagcagc ttcgacttcc tttggtaaaa    16140
ctgccttcag ttcttcttca aaggcaccta tcttttggaa tattgaagta acggcatttt    16200
tctcagtttc accattggat aaagcgtgat ctacaataac ttgtctcaat ctctgcatca    16260
atggataagt agcgctacat ggatcgtcaa cgtaagtaaa tacttgttct ctatctacaa    16320
cttttaataa atcttttca cagaatcttg atgggtgcaa ttcaccattg atacctgtag    16380
ttagaacctt ttttgcaacc tgtgatacgg tattttcac tgtctgtctc aaattctctt    16440
ccaagtgtct caaatctacg gcctggcata tacccactaa aaatgttgtg gacattaatt    16500
taaggatatc aacggcctcg cttgtttttc ttgatgaaat caggcccaaa gaattaacat    16560
cctgattgtg ttgttcggct gattgtacat gagaggttac tggggttggct agatattgca    16620 gctctgaaca atagcttgcc attgctatct cagcaccttt gaaaccataa tcaagactag    16680
ggttagaaga tgcggtcaga ttcgaaggca aaccgttatt gtagaagtca ttgaccaatt    16740
cagaaaattg ggcaaacatt aatttgccaa ttgcggctat ggcaagcctg gtattatcca    16800
tactgactcc tatgggtgta ccctggaaat tgcctccatg tattgcctta ttcctcgaca    16860
catcaataag tggattatcg ttaacagagt tgatctctct ttctatagac tttgtagctt    16920
gtctaattac ttcaatttga gggccaagcc attgtgggga tgtccttaaa gcatatctat    16980
cttgtttggg tttttgcaaa gggtccattt catgaaccct ctgggctaac ttcatgtagc    17040
tagagccgtc caaaatgtgc tccatgatag ctgctgcttc aatttgtcct gggtgatgtt    17100
ttaacctgtg ggtcaagtga tcagtaaact caggttttcc actcatgact tcggcaaaaa    17160
ttgcggacaa aacttcggcc aaaactgctt gtacgttagc ttcaaacaac accatggatg    17220
ccataccgct gccgacagcg gtgccattca ccagggctaa accttccttg ggttgcaaat    17280
caaagaaacc agttgaaata ccagcttttct caaatgcttc cttagcggtt aaggattctc    17340
cgtctggacc agtggccttt gaattaggtc ttcccgttaa taagcctgcg atatatgaaa    17400
ggggaaccaa atcaccgctg gcagttattg ttcctcttaa gggcaacgaa ggagaaatgt    17460
tgtggttcaa tagtgaagtg atggcctcaa gaatttcaaa ccttattcca gagtaacctt    17520
gcaacaaagt gttcaccccta acaagcatag cagctcttgt tgccgattgg ggtaatgtat    17580
ggcaagtttc ctttgtatta ccgaaaatac cggcgttaag gaatctgatc agttctgttt    17640
gcaaagcagt gccatttta gttcttctat gagaggtagc accaaagcct gtggtaacgc    17700
cataggaatc tgtgccctg ttcatacttt ccatgaccca atctgatgaa gccttaactc    17760
cggctctact tgtttctgca agttctacct tcactgaacc gccaacggtc gaaatagcag    17820
ctacctgtcc tatcgtcaat gtctcgccgc ctagatttac gactggtctt ctgtattcct    17880
caaccatctt cttaacttca tccagatggc taccttcat ctggtcagct gccagacccc    17940
aattcaaagg atctgcaaga gttttttgtcg ttacggccac cttggtcttt tcaccaccac    18000
```

```
cgcatagcat tgcttcaatt tggtccattt taagcttttt gatagatttg actgtgttat   18060
tttgcgtgag gttatgagta gaaaataata attgagaaag gaatatgaca agaaatatga   18120
aaataaaggg aacaaaccca aatctgattg caaggagagt gaaagagcct tgtttatata   18180 ttttttttc  ctatgttcaa cgaggacagc taggtttatg caaaaatgtg ccatcaccat   18240
aagctgattc aaatgagcta aaaaaaaaat agttagaaaa taaggtggtg ttgaacgata   18300
gcaagtagat caagacaccg tctaacagaa aaggggcag  cggacaatat tatgcaatta   18360
tgaagaaaag tactcaaagg gtcggaaaaa tattcaaacg atatttgcat aaaatcctca   18420
attgattgat tattccatag taaaataccg taacaacaca aaattgttct caaattcata   18480
aattattcat tttttccacg agcctcatca cacgaaaagt cagaagagca tacataatct   18540
tttaaatgca taggttatgc attttgcaaa tgccaccagg caacaaaaat atgcgtttag   18600
cgggcggaat cgggaaggaa gccggaacca ccaaaaactg gaagctacgt ttttaaggaa   18660
ggtatgggtg cagtgtgctt atctcaagaa atattagtta tgatataagg tgttgaagtt   18720
tagagatagg taaataaacg cggggtgtgt ttattacatg aagaagaagt tagtttctgc   18780
cttgcttgtt tatcttgcac atcacatcag cggaacatat gctcacccag tcgcatggcg   18840
cgtaccacgg tgaacaatcc ccgctggctc atatttgccg ccggttcccg taaatcctcc   18900
ggtacgcgcc gggccgtata cttacatata gtagatgtca agcgtaggcg cttcccctgc   18960
cggctgtgag ggcgccataa ccaaggtatc tatagaccgc caatcagcaa actacctccg   19020
tacattcatg ttgcacccac acatttatac acccagaccg cgacaaatta cccataaggt   19080
tgtttgtgac ggcgtcgtac aagagaacgt gggaactttt taggctcacc aaaaaagaaa   19140
gaaaaaatac gagttgctga cagaagcctc aagaaaaaaa aaattcttct tcgactatgc   19200
tggaggcaga gatgatcgag ccggtagtta actatatata gctaaattgg ttccatcacc   19260
ttcttttctg gtgtcgctcc ttctagtgct atttctggct tttcctattt ttttttttcc   19320
attttctttt ctctctttct aatatataaa ttctcttgca ttttctattt ttctctctat   19380
ctattctact tgtttattcc cttcaaggtt tttttttaag gagtacttgt ttttagaata   19440
tacggtcaac gaactataat taactaaaca agcttaaaat gatggatttt gttttgttag   19500
aaaaagctct tcttggtttg ttcattgcaa ctatagtagc catcacaatc tctaagctaa   19560
ggggaaagaa acttaagttg cctccaggcc caatccctgt cccagtgttt ggtaattggt   19620
tacaagttgg cgacgactta aaccagagga atttggtaga gtatgctaaa aagttcggcg   19680
acttatttct acttaggatg ggtcaaagaa acttggtcgt ggtttcatcc cctgacttag   19740
caaaagacgt actacatacc cagggtgtcg agttcggaag tagaactaga aatgttgtgt   19800
ttgatatttt cacaggcaaa ggtcaagata tggttttac  cgtatacagc gagcactgga   19860
ggaaaatgag aagaataatg actgtcccat tctttacaaa caaagtggtt caacagtata   19920
ggttcggatg ggaggacgaa gccgctagag tagtcgagga tgttaaggca aatcctgaag   19980
ccgctaccaa cggtattgtg ttgaggaata gattacaact tttgatgtac aacaatatgt   20040
atagaataat gtttgacagg agatttgaat ctgttgatga tccattattc ctaaaactta   20100
aggcattgaa tggcgagaga tcaaggttag ctcaatcctt tgaatacaac ttcggtgact   20160
tcattcctat attgaggcca ttcttgagag gatatcttaa gttgtgtcag gaaatcaagg   20220
acaaaaggtt aaagctattc aaggactact tcgtcgacga gagaaaaaag ttggagagta   20280
tcaagagcgt aggtaataac tccttaaagt gcgccataga tcatattatc gaggcacaag   20340
```

```
aaaaaggcga gataaacgag gataacgtgt tatacatcgt cgagaatatc aacgtggctg    20400
ccattgaaac tacactttgg tctattgaat ggggtatagc agaactagtg aataaccctg    20460
aaatccagaa aaaattgaga cacgaattag acaccgtact tggagctggt gttcaaattt    20520
gtgaaccaga tgttcaaaaa ttgccttatc tacaggccgt gataaaagag actttaaggt    20580
acaggatggc aattccattg ttagtcccac atatgaatct tcacgaagcc aaattggccg    20640
gctatgatat ccctgcagag agcaaaattt tggtaaacgc ttggtggtta gccaataatc    20700
cagcacattg gaacaaacct gatgagttta gaccagaaag attttttggag gaagaatcca   20760 aggtcgaggc taatggaaac gactttaagt acatccctt cggtgttggc agaagatctt    20820
gcccaggtat aattcttgct ttaccaatcc ttggaatagt aattggtagg ttggttcaaa    20880
acttcgagtt acttccacct ccaggccaaa gcaaaataga tacagccgaa aaaggtggac    20940
agttttcatt gcaaatccta aagcattcca ctattgtgtg taaacctaga agttcttaac    21000
cgcggacaaa tcgctcttaa atatatacct aaagaacatt aaagctatat tataagcaaa   21060
gatacgtaaa ttttgcttat attattatac acatatcata tttctatatt tttaagattt    21120
ggttatataa tgtacgtaat gcaaaggaaa taaattttat acattattga acagcgtcca    21180
agtaactaca ttatgtgcac taatagttta gcgtcgtgaa gactttattg tgtcgcgaaa    21240
agtaaaaatt taaaaatta gagcaccttg aacttgcgaa aaaggttctc atcaactgtt     21300
taaaaggagg atatcaggtc ctatttctga caaacaatat acaaatttag tttcaaaggc    21360
gcgttgcaaa atggaatttc gccgcagcgg cctgaatggc tgtaccgcct gacgcggatg    21420
cgccacgcgc cgcatgccgg tagaggtgtg gtcaataaga gcgacctcat gctatacctg    21480
agaaagcaac ctgacctaca ggaaagagtt actcaagaat aagaattttc gttttaaaac    21540
ctaagagtca ctttaaaatt tgtatacact tattttttt ataacttatt taataataaa    21600
aatcataaat cataagaaat tcgcttattt agaagtgtca acaacgtatc taccaacgat    21660 ttgaccctt tccatctttt cgtaaatttc tggcaaggta gacaagccga caaccttgat    21720
tggagacttg accaaacctc tggcgaagaa gtccaaagct ctagatcaat ttaggcctgc    21780
ggccgcggtt accagacatc ttcttggtat ctacctgaag tcttgagcat cttgattagc    21840
tctgttgctt catcagtggt aatggattta ccacgggata agatgccaac caatgcggtt    21900
gacacaccct tggccatacc cttttgcatca ccacagacgt agataaatgc accgttgtta   21960
atcatttcaa atacttggtc ttcgtaatcc tttaatttat cttgaacata aacttttttg    22020
gtgtttggca acctggaatg ggccacgacc atttcgaacg aaccatccaa ttttttggcg    22080
tattctggcc attcgtcctg gtacaagaaa tcatcagtgt tacgggatcc ataaaacagt    22140
atatgcttac ctagcgaaac gttgttaccg cccttctttt gtgattcgag aacgcgaca     22200 cgctctctga taaacccacg gaatggggca acaccggtac ctggaccgat catgataact    22260
ggggtggaag ggttggaagg caatctgaag ttagaacgac gaacgtggac gggcaatttg    22320
taattggcga aaagtttacg tgggccattt aaatcgtagt gaacaggtag gttagtttcg    22380
gcaatgttaa cattgttttg agccaattga atgtttctta acaagttagt cgtaacacca    22440
acaactggag gagcatcagg caattctggg ttaggaaagt tttccacaat ggaggtgaca    22500
tggacggttt gcttttcaga cagagaagag gaagagatag agtagtaacg aggagtcatt    22560
tggggaactg attcgaccaa gaattgcatg ggtacggtgt cccatttggc gccatcagac    22620
aaatatttca gagcatctgc gatgttgaaa tatttggagg ttatctcgac ggcgaattgg    22680
tccttgtctt tcgaaagcag agtcaatttt tccttgacgt cagcgttggg ggcgaactga    22740
```

```
atcaaagatg aaaacaattg tctggagaca ggtcctgtaa tttccaaata gtgtttaata    22800
gcagcgccaa tagtagttgg cgttgggaag ggcactttga cggtgggatc caggggcttc    22860
aagtcaaaaa tggtttcagg gtccaggttg aatatggata agaactgttc gaccttttcc    22920
aatgggttgg aaggccaaac agcaagatgg tcaccagtgg agtacttgat gttagagccg    22980
gacaagtcaa attcagagtg gatgcaatta cggtcattgg aagagaacag ttcgcgagat    23040
ttcacgatgg gtgcaatata cggttgagac aaatcgaagg gacccaattg gatgccgtct    23100
gcgttgcggt tcaactgatg cgagggcaaa tagtgagcag agggttcacc aagcgacatg    23160
gagtcagtga tttcgttcaa cacagtgtac tggaattgag aggtgaactt ggcttcctgt    23220
tcgtccaaat gcagttcgtc tttcaaaacc tccaggatgg agtccttcca ggccatgtaa    23280
tcttcgtctg tagttcctgc accatcatca gcttcaccga gcttgcctag tctgatagcg    23340
cccgcagcgg agagatgctt ctcggccttc ttggcggcac cattaaagaa ttcataagta    23400
gaatttccca gaccaaacat attataccctc aggttcgata gtgcacccgc ttccgcatta    23460
caaataaagt cttcaaagtt gaccgccccg tcggggaagt ctccttcacc atatgtagag    23520
ataaaaatcg agactatgac gggcacatcg tttagcgact caaagtcgta gttctcaaca    23580
tctgcgcaca tcacgtttag gttgaacttg gccaccagct ccttggaaaa cttttttggcg    23640 taatcctcgg cagtcccagt ctgcgacgca tacaacacca agtagttctt gttgttttcg    23700
gtcaccacct gagcaatgtc tctgttgccc gagctgacag ctgtgatatc tccgtcatcg    23760
gacatcagca gttccttgat ggagtttctc tttacgtaca gtagcacggc aagcactagc    23820
cccgccagga cagtgaagtc ggtgttgtct attccaaacg gcattttact agtaagcttt    23880
gtgatgatgt tttatttgtt ttgattggtg tcttgtaaat agaaacaaga gagaataata    23940
aacaagttaa gaataaaaaa ccaaaggatg aaaagaatg aatatgaaaa agagtagaga    24000
ataactttga aaggggacca tgatataact ggaaaaaga ggttcttgga aatgaaaagt    24060
taccaaagag tatttataat tcagaaaaaa aagccaacga atatcgtttt gatggcgagc    24120 ctttttttttt tttaggaag acactaaagg tacctagcat catatgggaa ggaaaggaaa    24180
tcacttggaa gacatcacaa gcattcattt accaagagaa aaaatatgca ttttagctaa    24240
gatccattga acaaagcact cactcaactc aactgaatga acgaaagaag aaagaacagt    24300
agaaaacact ttgtgacggt gcggaacaca tttacgtagc tatcatgctg aattctacta    24360
tgaaaatctc ccaatctgtc gatggcaaaa cgacccacgt ggcagagttg ggtcaagtgc    24420
cagtttctgg attaagtaac agatacgac atcacacgcc atagaggaat cccgccgttg    24480
cgagagatgg aaaacaatag agccgaaatt gtggaagccc gatgtctggg tgtacatttt    24540 tttttttct tctttctct ttcaataatc tttcctttt ccatttagct tgccggaaaa    24600
actttcgggt agcgaaaatc tttctgccgg aaaaattagc tattttttc ttccttatta    24660 ttttttttagt tctgaagttt gaccaggcg ctaccctgac cgtatcacaa ccgacgatcc    24720
ggggtcatgg cggctatttt tttttttttt ttttttcct tgtgattgtt tatttacatt    24780
tggatcaatt ctaacaaaaa aaaaataagg ggggaaaaat aattcacctc tttttaatat    24840 tgtttgtac tgagattgat ctccaaaata gtagcattgg cgcgtgccac caacagcccc    24900
gccaatggcg ctgccgatac tcccgacaat ccccaccatt gcctg                   24945
```

<210> SEQ ID NO 11
<211> LENGTH: 3607
<212> TYPE: DNA

<213> ORGANISM: Artificial Sequence
<220> FEATURE:
<223> OTHER INFORMATION: Helper fragment

<400> SEQUENCE: 11

| | | | | | |
|---|---|---|---|---|---|
| tttcccgtct | ttcagtgcct | tgttcagttc | ttcctgacgg | gcggtatatt | tctccagctt | 60 |
| ggcctatgcg | gccctgtcag | accaagttta | cgagctcgct | tggactcctg | ttgatagatc | 120 |
| cagtaatgac | ctcagaactc | catctggatt | tgttcagaac | gctcggttgc | cgccgggcgt | 180 |
| tttttattgg | tgagaatcca | agcactaggg | acagtaagac | gggtaagcct | gttgatgata | 240 |
| ccgctgcctt | actgggtgca | ttagccagtc | tgaatgacct | gtcacgggat | aatccgaagt | 300 |
| ggtcagactg | gaaaatcaga | gggcaggaac | tgctgaacag | caaaaagtca | gatagcacca | 360 |
| catagcagac | ccgccataaa | acgccctgag | aagcccgtga | cgggcttttc | ttgtattatg | 420 |
| ggtagtttcc | ttgcatgaat | ccataaaagg | cgcctgtagt | gccatttacc | cccattcact | 480 |
| gccagagccg | tgagcgcagc | gaactgaatg | tcacgaaaaa | gacagcgact | caggtgcctg | 540 |
| atggtcggag | acaaaaggaa | tattcagcga | tttgcccgag | cttgcgaggg | tgctacttaa | 600 |
| gcctttaggg | ttttaaggtc | tgttttgtag | aggagcaaac | agcgtttgcg | acatcctttt | 660 |
| gtaatactgc | ggaactgact | aaagtagtga | gttatacaca | gggctgggat | ctattctttt | 720 |
| tatctttttt | tattctttct | ttattctata | aattataacc | acttgaatat | aaacaaaaaa | 780 |
| aacacacaaa | ggtctagcgg | aatttacaga | gggtctagca | gaatttacaa | gttttccagc | 840 |
| aaaggtctag | cagaatttac | agatacccac | aactcaaagg | aaaaggacat | gtaattatca | 900 |
| ttgactagcc | catctcaatt | ggtatagtga | ttaaaatcac | ctagaccaat | tgagatgtat | 960 |
| gtctgaatta | gttgttttca | aagcaaatga | actagcgatt | agtcgctatg | acttaacgga | 1020 |
| gcatgaaacc | aagctaattt | tatgctgtgt | ggcactactc | aacccacga | ttgaaaaccc | 1080 |
| tacaaggaaa | gaacggacgg | tatcgttcac | ttataaccaa | tacgctcaga | tgatgaacat | 1140 |
| cagtagggaa | aatgcttatg | gtgtattagc | taaagcaacc | agagagctga | tgacgagaac | 1200 |
| tgtggaaatc | aggaatcctt | tggttaaagg | ctttgagatt | ttccagtgga | caaactatgc | 1260 |
| caagttctca | agcgaaaaat | tagaattagt | ttttagtgaa | gagatattgc | cttatctttt | 1320 |
| ccagttaaaa | aaattcataa | aatataatct | ggaacatgtt | aagtcttttg | aaaacaaata | 1380 |
| ctctatgagg | atttatgagt | ggttattaaa | agaactaaca | caaagaaaa | ctcacaaggc | 1440 |
| aaatatagag | attagccttg | atgaatttaa | gttcatgtta | atgcttgaaa | ataactacca | 1500 |
| tgagtttaaa | aggcttaacc | aatgggtttt | gaaaccaata | agtaaagatt | taaacactta | 1560 |
| cagcaatatg | aaattggtgg | ttgataagcg | aggccgcccg | actgatacgt | tgatttttcca | 1620 |
| agttgaacta | gatagacaaa | tggatctcgt | aaccgaactt | gagaacaacc | agataaaaat | 1680 |
| gaatggtgac | aaaataccaa | caaccattac | atcagattcc | tacctacata | acggactaag | 1740 |
| aaaaacacta | cacgatgctt | taactgcaaa | aattcagctc | accagttttg | aggcaaaatt | 1800 |
| tttgagtgac | atgcaaagta | agtatgatct | caatggttcg | ttctcatggc | tcacgcaaaa | 1860 |
| acaacgaacc | acactagaga | acatactggc | taaatacgga | aggatctgag | gttcttatgg | 1920 |
| ctcttgtatc | tatcagtgaa | gcatcaagac | taacaaacaa | aagtagaaca | actgttcacc | 1980 |
| gttacatatc | aaagggaaaa | ctgtccatat | gcacagatga | aaacggtgta | aaaaagatag | 2040 |
| atacatcaga | gcttttacga | gttttggtg | cattcaaagc | tgttcaccat | gaacagatcg | 2100 |
| acaatgtaac | gcgccgcag | ccaatcaatt | cttgcggaga | actgtgaatg | cgcaaaccaa | 2160 |
| cccttggcag | aacatatcca | tcgcgtccgc | catctccagc | agccgcacgc | ggcgcatcgg | 2220 |

```
gggggggggg gggggtttca attcatcatt tttttttttat tctttttttt gatttcggtt    2280
tccttgaaat ttttttgatt cggtaatctc cgaacagaag gaagaacgaa ggaaggagca    2340
cagacttaga ttggtatata tacgcatatg tagtgttgaa gaaacatgaa attgcccagt    2400
attcttaacc caactgcaca gaacaaaaac ctgcaggaaa cgaagataaa tcatgtcgaa    2460
agctacatat aaggaacgtg ctgctactca tcctagtcct gttgctgcca agctatttaa    2520
tatcatgcac gaaaagcaaa caaacttgtg tgcttcattg gatgttcgta ccaccaagga    2580
attactggag ttagttgaag cattaggtcc caaaatttgt ttactaaaaa cacatgtgga    2640
tatcttgact gatttttcca tggagggcac agttaagccg ctaaaggcat tatccgccaa    2700
gtacaatttt ttactcttcg aagacagaaa atttgctgac attggtaata cagtcaaatt    2760
gcagtactct gcgggtgtat acagaatagc agaatgggca gacattacga atgcacacgg    2820
tgtggtgggc ccaggtattg ttagcggttt gaagcaggcg gcagaagaag taacaaagga    2880
acctagaggc cttttgatgt tagcagaatt gtcatgcaag ggctccctat ctactggaga    2940
atatactaag ggtactgttg acattgcgaa gagcgacaaa gattttgtta tcggctttat    3000
tgctcaaaga gacatgggtg aagagatga aggttacgat tggttgatta tgacacccgg    3060
tgtgggttta gatgacaagg gagacgcatt gggtcaacag tatagaaccg tggatgatgt    3120
ggtctctaca ggatctgaca ttattattgt tggaagagga ctatttgcaa agggaaggga    3180
tgctaaggta gagggtgaac gttacagaaa agcaggctgg gaagcatatt tgagaagatg    3240
cggccagcaa aactaaaaaa ctgtattata agtaaatgca tgtatactaa actcacaaat    3300
tagagcttca atttaattat atcagttatt acccggccgg gaatctcggt cgtaatgatt    3360
tttataatga cgaaaaaaaa aaaattggaa agaaaacccc cccccccccc ccgcagcgtt    3420
gggtcctggc cacgggtgcg catgatcgtg ctcctgtcgt tgaggacccg gctaggctgg    3480
cggggttgcc ttactggtta gcagaatgaa tcaccgatac gcgagcgaat gtggcggccg    3540
cacgcgttca tcgtccacct ccggagaaca ggccaccatc acgcatctgt gtctgaattt    3600
catcacg                                                              3607
```

<210> SEQ ID NO 12  
<211> LENGTH: 1855  
<212> TYPE: DNA  
<213> ORGANISM: Artificial Sequence  
<220> FEATURE:  
<223> OTHER INFORMATION: Helper fragment

<400> SEQUENCE: 12

```
tcatcgtcca cctccggaga acaggccacc atcacgcatc tgtgtctgaa tttcatcacg      60
acgcgcctta aggcaccaa taactgcctt aaaaaaatta cgccccgccc tgccactcat     120
cgcagtactg ttgtaattca ttaagcattc tgccgacatg gaagccatca cagacggcat     180
gatgaacctg aatcgccagc ggcatcagca ccttgtcgcc ttgcgtataa tatttgccca     240
tggtgaaaac gggggcgaag aagttgtcca tattggccac gtttaaatca aaactggtga     300
aactcaccca gggattggct gagacgaaaa acatattctc aataaaccct ttagggaaat     360
aggccaggtt ttcaccgtaa cacgccacat cttgcgaata tatgtgtaga aactgccgga     420
aatcgtcgtg gtattcactc cagagcgatg aaaacgtttc agtttgctca tggaaaacgg     480
tgtaacaagg gtgaacacta tcccatatca ccagctcacc gtctttcatt gccatacgga     540
attccggatg agcattcatc aggcgggcaa gaatgtgaat aaaggccgga taaaacttgt     600
```

```
gcttattttt ctttacggtc tttaaaaagg ccgtaatatc cagctgaacg gtctggttat      660
aggtacattg agcaactgac tgaaatgcct caaaatgttc tttacgatgc cattgggata      720
tatcaacggt ggtatatcca gtgattttt tctccatttt agcttcctta gctcctgaaa       780
atctcgataa ctcaaaaaat acgcccggta gtgatcttat ttcattatgg tgaaagttgg      840
aacctcttac gtgccgatca acgtctcatt ttcgccaaaa gttggcccag ggcttcccgg      900
tatcaacagg gacaccagga tttatttatt ctgcgaagtg atcttccgtc acaggtattg      960
gaccaccctg tgggtttata agcgcgctgc tggcgtgtaa ggcggtgacg gcgaaggaag     1020
ggtccttttc atcacgtgct ataaaaataa ttataattta aattttttaa tataaatata     1080
taaattaaaa atagaaagta aaaaagaaa ttaaagaaaa aatagttttt gttttccgaa      1140
gatgtaaaag actctagggg gatcgccaac aaatactacc ttttatccttg ctcttcctgc     1200 tctcaggtat taatgccgaa ttgtttcatc ttgtctgtgt agaagaccac acacgaaaat     1260
cctgtgattt tacattttac ttatcgttaa tcgaatgtat atctatttaa tctgcttttc     1320
ttgtctaata aatatatatg taaagtacgc ttttgttga aattttttaa acctttgttt      1380 atttttttt cttcattccg taactcttct accttcttta tttactttct aaaatccaaa      1440
tacaaaacat aaaaataaat aaacacagag taaattccca aattattcca tcattaaaag     1500
atacgaggcg cgtgtaagtt acaggcaagc gatccgtcct aagaaaccat tattatcatg     1560
acattaacct ataaaaatag gcgtatcacg aggcccttc gtctcgcgcg tttcggtgat      1620
gacggtgaaa acctctgaca catgcagctc ccggagacgg tcacagcttg tctgtaagcg     1680
gatgccggga gcagcaagc ccgtcagggc gcgtcagcgg gtgttggcgg gtgtcggggc      1740
tggcttaact atgcggcatc agagcagatt gtactgagag tgcaccacgg cgcgtggcac     1800
ccttgcgggc catgtcatac accgccttca gagcagccgg acctatctgc ccgtt          1855

<210> SEQ ID NO 13
<211> LENGTH: 732
<212> TYPE: DNA
<213> ORGANISM: Artificial Sequence
<220> FEATURE:
<223> OTHER INFORMATION: Helper fragment for multi-expression plasmid

<400> SEQUENCE: 13
gccaccaaca gccccgccaa tggcgctgcc gatactcccg acaatcccca ccattgcctg       60
acgcgtccag tatcccagca gatacgggat atcgacattt ctgcaccatt ccggcgggta      120
taggttttat tgatggcctc atccacacgc agcagcgtct gttcatcgtc gtggcggccc      180
ataataatct gccggtcaat cagccagctt tcctcacccg gccccatcc ccatacgcgc       240 atttcgtagc ggtccagctg ggagtcgata ccggcggtca ggtaagccac acggtcagga      300
acgggcgctg aataatgctc tttccgctct gccatcactt cagcatccgg acgttcgcca      360
attttcgcct cccacgtctc accgagcgtg gtgtttacga aggttttacg ttttcccgta      420 tccccttcg ttttcatcca gtctttgaca atctgcaccc aggtggtgaa cgggctgtac      480
gctgtccaga tgtgaaaggt cacactgtca ggtggctcaa tctcttcacc ggatgacgaa      540
aaccagagaa tgccatcacg ggtccagatc ccggtctttt cgcagatata acggcatca      600 gtaaagtcca gctcctgctg gcggatgacg caggcattat gctcgcagag ataaaacacg      660
ctggagacgc gttttcccgt ctttcagtgc cttgttcagt tcttcctgac gggcggtata      720
tttctccagc tt                                                          732
```

<210> SEQ ID NO 14
<211> LENGTH: 732
<212> TYPE: DNA
<213> ORGANISM: Artificial Sequence
<220> FEATURE:
<223> OTHER INFORMATION: Helper fragment for multi-expression plasmid

<400> SEQUENCE: 14

```
cttaagcaga atttctgtca tcatggacag cacggaacgg gtgaagctgc gccagttctg      60
acgcgtctcc agcgtgtttt atctctgcga gcataatgcc tgcgtcatcc gccagcagga     120
gctggacttt actgatgccc gttatatctg cgaaaagacc gggatctgga cccgtgatgg     180
cattctctgg ttttcgtcat ccggtgaaga gattgagcca cctgacagtg tgacctttca     240
catctggaca gcgtacagcc cgttccacca ctgggtgcag attgtcaaag actggatgaa     300
aacgaaaggg gatacgggaa aacgtaaaac cttcgtaaac accacgctcg gtgagacgtg     360
ggaggcgaaa attggcgaac gtccggatgc tgaagtgatg gcagagcgga aagagcatta     420
ttcagcgccc gttcctgacc gtgtggctta cctgaccgcc ggtatcgact cccagctgga     480
ccgctacgaa atgcgcgtat ggggatgggg gccgggtgag aaagctggc tgattgaccg     540
gcagattatt atgggccgcc acgacgatga acagacgctg ctgcgtgtgg atgaggccat     600
caataaaacc tatacccgcc ggaatggtgc agaaatgtcg atatcccgta tctgctggga     660
tactggacgc gttttcccgt ctttcagtgc cttgttcagt tcttcctgac gggcggtata     720
tttctccagc tt                                                         732
```

<210> SEQ ID NO 15
<211> LENGTH: 663
<212> TYPE: DNA
<213> ORGANISM: Artificial Sequence
<220> FEATURE:
<223> OTHER INFORMATION: Non-expressed stuffer

<400> SEQUENCE: 15

```
ggcctgcagg gccagcttac ccttaaattt atttgcacta ctggaaaact acctgttcca      60
tggccaacac ttgtcactac tttctcttat ggtgttcaat gcttttcccg ttatccggat     120
catatgaaac ggcatgactt tttcaagagt gccatgcccg aaggttatgt acaggaacgc     180
actatatctt tcaaagatga cgggaactac aagacgcgtg ctgaagtcaa gtttgaaggt     240
gataccccttg ttaatcgtat cgagttaaaa ggtattgatt taaagaaga tggaaacatt     300
ctcggacaca aactcgagta caactataac tcacacaatg tatacatcac ggcagacaaa     360
caaaagaatg gaatcaaagc taacttcaaa attcgccaca acattgaaga tggatccgtt     420
caactagcag accattatca acaaatactt ccaattggcg atggccctgt cctttaccaa     480
gacaaccatt acctgtcgac acaatctgcc ctttcgaaag atcccaacga aaagcgtgac     540
cacatggtcc ttcttgagtt tgtaactgct gctgggatta cacatggcat ggatgagctc     600
tacaaataat gaattcgtcg aggccgttca ggcctcgagg ccgttcaggc tcgacccggg     660
gat                                                                   663
```

<210> SEQ ID NO 16
<211> LENGTH: 717
<212> TYPE: PRT
<213> ORGANISM: Arabidopsis thaliana

<400> SEQUENCE: 16

```
Met Asp Gln Ile Glu Ala Met Leu Cys Gly Gly Gly Glu Lys Thr Lys
1               5                   10                  15
```

Val Ala Val Thr Thr Lys Thr Leu Ala Asp Pro Leu Asn Trp Gly Leu
            20                  25                  30

Ala Ala Asp Gln Met Lys Gly Ser His Leu Asp Glu Val Lys Lys Met
            35                  40                  45

Val Glu Glu Tyr Arg Arg Pro Val Val Asn Leu Gly Gly Thr Leu
50                  55                  60

Thr Ile Gly Gln Val Ala Ala Ile Ser Thr Val Gly Gly Ser Val Lys
65                  70                  75                  80

Val Glu Leu Ala Glu Thr Ser Arg Ala Gly Val Lys Ala Ser Ser Asp
            85                  90                  95

Trp Val Met Glu Ser Met Asn Lys Gly Thr Asp Ser Tyr Gly Val Thr
            100                 105                 110

Thr Gly Phe Gly Ala Thr Ser His Arg Arg Thr Lys Asn Gly Thr Ala
            115                 120                 125

Leu Gln Thr Glu Leu Ile Arg Phe Leu Asn Ala Gly Ile Phe Gly Asn
130                 135                 140

Thr Lys Glu Thr Cys His Thr Leu Pro Gln Ser Ala Thr Arg Ala Ala
145                 150                 155                 160

Met Leu Val Arg Val Asn Thr Leu Leu Gln Gly Tyr Ser Gly Ile Arg
            165                 170                 175

Phe Glu Ile Leu Glu Ala Ile Thr Ser Leu Leu Asn His Asn Ile Ser
            180                 185                 190

Pro Ser Leu Pro Leu Arg Gly Thr Ile Thr Ala Ser Gly Asp Leu Val
            195                 200                 205

Pro Leu Ser Tyr Ile Ala Gly Leu Leu Thr Gly Arg Pro Asn Ser Lys
            210                 215                 220

Ala Thr Gly Pro Asp Gly Glu Ser Leu Thr Ala Lys Glu Ala Phe Glu
225                 230                 235                 240

Lys Ala Gly Ile Ser Thr Gly Phe Phe Asp Leu Gln Pro Lys Glu Gly
            245                 250                 255

Leu Ala Leu Val Asn Gly Thr Ala Val Gly Ser Gly Met Ala Ser Met
            260                 265                 270

Val Leu Phe Glu Ala Asn Val Gln Ala Val Leu Ala Glu Val Leu Ser
            275                 280                 285

Ala Ile Phe Ala Glu Val Met Ser Gly Lys Pro Glu Phe Thr Asp His
290                 295                 300

Leu Thr His Arg Leu Lys His His Pro Gly Gln Ile Glu Ala Ala Ala
305                 310                 315                 320

Ile Met Glu His Ile Leu Asp Gly Ser Ser Tyr Met Lys Leu Ala Gln
            325                 330                 335

Lys Val His Glu Met Asp Pro Leu Gln Lys Pro Lys Gln Asp Arg Tyr
            340                 345                 350

Ala Leu Arg Thr Ser Pro Gln Trp Leu Gly Pro Gln Ile Glu Val Ile
            355                 360                 365

Arg Gln Ala Thr Lys Ser Ile Glu Arg Glu Ile Asn Ser Val Asn Asp
            370                 375                 380

Asn Pro Leu Ile Asp Val Ser Arg Asn Lys Ala Ile His Gly Gly Asn
385                 390                 395                 400

Phe Gln Gly Thr Pro Ile Gly Val Ser Met Asp Asn Thr Arg Leu Ala
            405                 410                 415

Ile Ala Ala Ile Gly Lys Leu Met Phe Ala Gln Phe Ser Glu Leu Val
            420                 425                 430

Asn Asp Phe Tyr Asn Asn Gly Leu Pro Ser Asn Leu Thr Ala Ser Ser
            435                 440                 445

Asn Pro Ser Leu Asp Tyr Gly Phe Lys Gly Ala Glu Ile Ala Met Ala
450                 455                 460

Ser Tyr Cys Ser Glu Leu Gln Tyr Leu Ala Asn Pro Val Thr Ser His
465                 470                 475                 480

Val Gln Ser Ala Glu Gln His Asn Gln Asp Val Asn Ser Leu Gly Leu
                485                 490                 495

Ile Ser Ser Arg Lys Thr Ser Glu Ala Val Asp Ile Leu Lys Leu Met
            500                 505                 510

Ser Thr Thr Phe Leu Val Gly Ile Cys Gln Ala Val Asp Leu Arg His
            515                 520                 525

Leu Glu Glu Asn Leu Arg Gln Thr Val Lys Asn Thr Val Ser Gln Val
530                 535                 540

Ala Lys Lys Val Leu Thr Thr Gly Ile Asn Gly Glu Leu His Pro Ser
545                 550                 555                 560

Arg Phe Cys Glu Lys Asp Leu Leu Lys Val Val Asp Arg Glu Gln Val
                565                 570                 575

Phe Thr Tyr Val Asp Asp Pro Cys Ser Ala Thr Tyr Pro Leu Met Gln
            580                 585                 590

Arg Leu Arg Gln Val Ile Val Asp His Ala Leu Ser Asn Gly Glu Thr
            595                 600                 605

Glu Lys Asn Ala Val Thr Ser Ile Phe Gln Lys Ile Gly Ala Phe Glu
            610                 615                 620

Glu Glu Leu Lys Ala Val Leu Pro Lys Glu Val Glu Ala Ala Arg Ala
625                 630                 635                 640

Ala Tyr Gly Asn Gly Thr Ala Pro Ile Pro Asn Arg Ile Lys Glu Cys
            645                 650                 655

Arg Ser Tyr Pro Leu Tyr Arg Phe Val Arg Glu Leu Gly Thr Lys
                660                 665                 670

Leu Leu Thr Gly Glu Lys Val Val Ser Pro Gly Glu Glu Phe Asp Lys
            675                 680                 685

Val Phe Thr Ala Met Cys Glu Gly Lys Leu Ile Asp Pro Leu Met Asp
            690                 695                 700

Cys Leu Lys Glu Trp Asn Gly Ala Pro Ile Pro Ile Cys
705                 710                 715

<210> SEQ ID NO 17
<211> LENGTH: 506
<212> TYPE: PRT
<213> ORGANISM: Ammi majus

<400> SEQUENCE: 17

Met Met Asp Phe Val Leu Leu Glu Lys Ala Leu Leu Gly Leu Phe Ile
1               5                   10                  15

Ala Thr Ile Val Ala Ile Thr Ile Ser Lys Leu Arg Gly Lys Lys Leu
            20                  25                  30

Lys Leu Pro Pro Gly Pro Ile Pro Val Pro Val Phe Gly Asn Trp Leu
            35                  40                  45

Gln Val Gly Asp Asp Leu Asn Gln Arg Asn Leu Val Glu Tyr Ala Lys
        50                  55                  60

Lys Phe Gly Asp Leu Phe Leu Leu Arg Met Gly Gln Arg Asn Leu Val
65                  70                  75                  80

Val Val Ser Ser Pro Asp Leu Ala Lys Asp Val Leu His Thr Gln Gly
                85                  90                  95

```
Val Glu Phe Gly Ser Arg Thr Arg Asn Val Val Phe Asp Ile Phe Thr
            100                 105                 110

Gly Lys Gly Gln Asp Met Val Phe Thr Val Tyr Ser Glu His Trp Arg
        115                 120                 125

Lys Met Arg Arg Ile Met Thr Val Pro Phe Phe Thr Asn Lys Val Val
    130                 135                 140

Gln Gln Tyr Arg Phe Gly Trp Glu Asp Glu Ala Ala Arg Val Val Glu
145                 150                 155                 160

Asp Val Lys Ala Asn Pro Glu Ala Ala Thr Asn Gly Ile Val Leu Arg
                165                 170                 175

Asn Arg Leu Gln Leu Leu Met Tyr Asn Asn Met Tyr Arg Ile Met Phe
            180                 185                 190

Asp Arg Arg Phe Glu Ser Val Asp Asp Pro Leu Phe Leu Lys Leu Lys
        195                 200                 205

Ala Leu Asn Gly Glu Arg Ser Arg Leu Ala Gln Ser Phe Glu Tyr Asn
    210                 215                 220

Phe Gly Asp Phe Ile Pro Ile Leu Arg Pro Phe Leu Arg Gly Tyr Leu
225                 230                 235                 240

Lys Leu Cys Gln Glu Ile Lys Asp Lys Arg Leu Lys Leu Phe Lys Asp
            245                 250                 255

Tyr Phe Val Asp Glu Arg Lys Lys Leu Glu Ser Ile Lys Ser Val Gly
        260                 265                 270

Asn Asn Ser Leu Lys Cys Ala Ile Asp His Ile Ile Glu Ala Gln Glu
    275                 280                 285

Lys Gly Glu Ile Asn Glu Asp Asn Val Leu Tyr Ile Val Glu Asn Ile
290                 295                 300

Asn Val Ala Ala Ile Glu Thr Thr Leu Trp Ser Ile Glu Trp Gly Ile
305                 310                 315                 320

Ala Glu Leu Val Asn Asn Pro Glu Ile Gln Lys Lys Leu Arg His Glu
            325                 330                 335

Leu Asp Thr Val Leu Gly Ala Gly Val Gln Ile Cys Glu Pro Asp Val
        340                 345                 350

Gln Lys Leu Pro Tyr Leu Gln Ala Val Ile Lys Glu Thr Leu Arg Tyr
    355                 360                 365

Arg Met Ala Ile Pro Leu Leu Val Pro His Met Asn Leu His Glu Ala
370                 375                 380

Lys Leu Ala Gly Tyr Asp Ile Pro Ala Glu Ser Lys Ile Leu Val Asn
385                 390                 395                 400

Ala Trp Trp Leu Ala Asn Asn Pro Ala His Trp Asn Lys Pro Asp Glu
            405                 410                 415

Phe Arg Pro Glu Arg Phe Leu Glu Glu Ser Lys Val Glu Ala Asn
        420                 425                 430

Gly Asn Asp Phe Lys Tyr Ile Pro Phe Gly Val Gly Arg Arg Ser Cys
    435                 440                 445

Pro Gly Ile Ile Leu Ala Leu Pro Ile Leu Gly Ile Val Ile Gly Arg
450                 455                 460

Leu Val Gln Asn Phe Glu Leu Leu Pro Pro Pro Gly Gln Ser Lys Ile
465                 470                 475                 480

Asp Thr Ala Glu Lys Gly Gly Gln Phe Ser Leu Gln Ile Leu Lys His
            485                 490                 495

Ser Thr Ile Val Cys Lys Pro Arg Ser Ser
        500                 505
```

<210> SEQ ID NO 18
<211> LENGTH: 556
<212> TYPE: PRT
<213> ORGANISM: Arabidopsis thaliana

<400> SEQUENCE: 18

```
Met Thr Thr Gln Asp Val Ile Val Asn Asp Gln Asn Asp Gln Lys Gln
1               5                   10                  15

Cys Ser Asn Asp Val Ile Phe Arg Ser Arg Leu Pro Asp Ile Tyr Ile
            20                  25                  30

Pro Asn His Leu Pro Leu His Asp Tyr Ile Phe Glu Asn Ile Ser Glu
        35                  40                  45

Phe Ala Ala Lys Pro Cys Leu Ile Asn Gly Pro Thr Gly Glu Val Tyr
    50                  55                  60

Thr Tyr Ala Asp Val His Val Thr Ser Arg Lys Leu Ala Ala Gly Leu
65                  70                  75                  80

His Asn Leu Gly Val Lys Gln His Asp Val Val Met Ile Leu Leu Pro
                85                  90                  95

Asn Ser Pro Glu Val Val Leu Thr Phe Leu Ala Ala Ser Phe Ile Gly
            100                 105                 110

Ala Ile Thr Thr Ser Ala Asn Pro Phe Phe Thr Pro Ala Glu Ile Ser
        115                 120                 125

Lys Gln Ala Lys Ala Ser Ala Ala Lys Leu Ile Val Thr Gln Ser Arg
    130                 135                 140

Tyr Val Asp Lys Ile Lys Asn Leu Gln Asn Asp Gly Val Leu Ile Val
145                 150                 155                 160

Thr Thr Asp Ser Asp Ala Ile Pro Glu Asn Cys Leu Arg Phe Ser Glu
                165                 170                 175

Leu Thr Gln Ser Glu Glu Pro Arg Val Asp Ser Ile Pro Glu Lys Ile
            180                 185                 190

Ser Pro Glu Asp Val Val Ala Leu Pro Phe Ser Ser Gly Thr Thr Gly
        195                 200                 205

Leu Pro Lys Gly Val Met Leu Thr His Lys Gly Leu Val Thr Ser Val
    210                 215                 220

Ala Gln Gln Val Asp Gly Glu Asn Pro Asn Leu Tyr Phe Asn Arg Asp
225                 230                 235                 240

Asp Val Ile Leu Cys Val Leu Pro Met Phe His Ile Tyr Ala Leu Asn
                245                 250                 255

Ser Ile Met Leu Cys Ser Leu Arg Val Gly Ala Thr Ile Leu Ile Met
            260                 265                 270

Pro Lys Phe Glu Ile Thr Leu Leu Leu Glu Gln Ile Gln Arg Cys Lys
        275                 280                 285

Val Thr Val Ala Met Val Val Pro Pro Ile Val Leu Ala Ile Ala Lys
    290                 295                 300

Ser Pro Glu Thr Glu Lys Tyr Asp Leu Ser Ser Val Arg Met Val Lys
305                 310                 315                 320

Ser Gly Ala Ala Pro Leu Gly Lys Glu Leu Glu Asp Ala Ile Ser Ala
                325                 330                 335

Lys Phe Pro Asn Ala Lys Leu Gly Gln Gly Tyr Gly Met Thr Glu Ala
            340                 345                 350

Gly Pro Val Leu Ala Met Ser Leu Gly Phe Ala Lys Glu Pro Phe Pro
        355                 360                 365

Val Lys Ser Gly Ala Cys Gly Thr Val Val Arg Asn Ala Glu Met Lys
    370                 375                 380
```

-continued

```
Ile Leu Asp Pro Asp Thr Gly Asp Ser Leu Pro Arg Asn Lys Pro Gly
385                 390                 395                 400

Glu Ile Cys Ile Arg Gly Asn Gln Ile Met Lys Gly Tyr Leu Asn Asp
            405                 410                 415

Pro Leu Ala Thr Ala Ser Thr Ile Asp Lys Asp Gly Trp Leu His Thr
            420                 425                 430

Gly Asp Val Gly Phe Ile Asp Asp Asp Glu Leu Phe Ile Val Asp
        435                 440                 445

Arg Leu Lys Glu Leu Ile Lys Tyr Lys Gly Phe Gln Val Ala Pro Ala
    450                 455                 460

Glu Leu Glu Ser Leu Leu Ile Gly His Pro Glu Ile Asn Asp Val Ala
465                 470                 475                 480

Val Val Ala Met Lys Glu Glu Asp Ala Gly Glu Val Pro Val Ala Phe
                485                 490                 495

Val Val Arg Ser Lys Asp Ser Asn Ile Ser Glu Asp Glu Ile Lys Gln
            500                 505                 510

Phe Val Ser Lys Gln Val Val Phe Tyr Lys Arg Ile Asn Lys Val Phe
        515                 520                 525

Phe Thr Asp Ser Ile Pro Lys Ala Pro Ser Gly Lys Ile Leu Arg Lys
    530                 535                 540

Asp Leu Arg Ala Arg Leu Ala Asn Gly Leu Met Asn
545                 550                 555

<210> SEQ ID NO 19
<211> LENGTH: 399
<212> TYPE: PRT
<213> ORGANISM: Hordeum vulgare

<400> SEQUENCE: 19

Met Ala Ala Val Arg Leu Lys Glu Val Arg Met Ala Gln Arg Ala Glu
1               5                   10                  15

Gly Leu Ala Thr Val Leu Ala Ile Gly Thr Ala Val Pro Ala Asn Cys
            20                  25                  30

Val Tyr Gln Ala Thr Tyr Pro Asp Tyr Tyr Phe Arg Val Thr Lys Ser
        35                  40                  45

Glu His Leu Ala Asp Leu Lys Glu Lys Phe Gln Arg Met Cys Asp Lys
    50                  55                  60

Ser Met Ile Arg Lys Arg His Met His Leu Thr Glu Glu Ile Leu Ile
65                  70                  75                  80

Lys Asn Pro Lys Ile Cys Ala His Met Glu Thr Ser Leu Asp Ala Arg
                85                  90                  95

His Ala Ile Ala Leu Val Glu Val Pro Lys Leu Gly Gln Gly Ala Ala
            100                 105                 110

Glu Lys Ala Ile Lys Glu Trp Gly Gln Pro Leu Ser Lys Ile Thr His
        115                 120                 125

Leu Val Phe Cys Thr Thr Ser Gly Val Asp Met Pro Gly Ala Asp Tyr
    130                 135                 140

Gln Leu Thr Lys Leu Leu Gly Leu Ser Pro Thr Val Lys Arg Leu Met
145                 150                 155                 160

Met Tyr Gln Gln Gly Cys Phe Gly Gly Ala Thr Val Leu Arg Leu Ala
                165                 170                 175

Lys Asp Ile Ala Glu Asn Asn Arg Gly Ala Arg Val Leu Val Val Cys
            180                 185                 190

Ser Glu Ile Thr Ala Met Ala Phe Arg Gly Pro Cys Lys Ser His Leu
```

```
            195                 200                 205
Asp Ser Leu Val Gly His Ala Leu Phe Gly Asp Gly Ala Ala Ala
    210                 215                 220

Ile Ile Gly Ala Asp Pro Asp Gln Leu Asp Glu Gln Pro Val Phe Gln
225                 230                 235                 240

Leu Val Ser Ala Ser Gln Thr Ile Leu Pro Glu Ser Glu Gly Ala Ile
                245                 250                 255

Asp Gly His Leu Thr Glu Ala Gly Leu Thr Ile His Leu Leu Lys Asp
            260                 265                 270

Val Pro Gly Leu Ile Ser Glu Asn Ile Glu Gln Ala Leu Glu Asp Ala
        275                 280                 285

Phe Glu Pro Leu Gly Ile His Asn Trp Asn Ser Ile Phe Trp Ile Ala
    290                 295                 300

His Pro Gly Gly Pro Ala Ile Leu Asp Arg Val Glu Asp Arg Val Gly
305                 310                 315                 320

Leu Asp Lys Lys Arg Met Arg Ala Ser Arg Glu Val Leu Ser Glu Tyr
                325                 330                 335

Gly Asn Met Ser Ser Ala Ser Val Leu Phe Val Leu Asp Val Met Arg
            340                 345                 350

Lys Ser Ala Lys Asp Gly Leu Ala Thr Thr Gly Glu Gly Lys Asp
        355                 360                 365

Trp Gly Val Leu Phe Gly Phe Gly Pro Gly Leu Thr Val Glu Thr Leu
    370                 375                 380

Val Leu His Ser Val Pro Val Pro Val Pro Thr Ala Ala Ser Ala
385                 390                 395

<210> SEQ ID NO 20
<211> LENGTH: 483
<212> TYPE: PRT
<213> ORGANISM: Malus domestica

<400> SEQUENCE: 20

Met Gly Asp Val Ile Val Leu Tyr Ala Ser Pro Gly Met Gly His Ile
1               5                   10                  15

Val Ser Met Val Glu Leu Gly Lys Phe Ile Val His Arg Tyr Gly Pro
                20                  25                  30

His Lys Phe Ser Ile Thr Ile Leu Tyr Thr Cys Gly Ser Ile Val Asp
            35                  40                  45

Thr Ala Ser Ile Pro Val Tyr Ile Arg Arg Ile Ser His Ser His Pro
        50                  55                  60

Phe Ile Ser Phe Arg Gln Phe Pro Arg Val Thr Asn Asn Ile Thr Arg
65                  70                  75                  80

Asn Ile Ser Val Pro Ala Ile Thr Phe Asp Phe Ile Arg Gln Asn Asp
                85                  90                  95

Pro His Val Arg Ser Ala Leu Gln Glu Ile Ser Lys Ser Ala Thr Val
            100                 105                 110

Arg Ala Phe Ile Ile Asp Leu Phe Cys Thr Ser Ala Leu Pro Ile Gly
        115                 120                 125

Lys Glu Phe Asn Ile Pro Thr Tyr Tyr Phe Arg Thr Ser Gly Ala Ala
    130                 135                 140

Ile Leu Ala Ala Phe Leu Tyr Leu Pro Lys Ile Asp Glu Gln Thr Lys
145                 150                 155                 160

Thr Thr Glu Ser Phe Lys Asp Leu Arg Asp Thr Val Phe Glu Phe Pro
                165                 170                 175
```

Gly Trp Lys Ser Pro Leu Lys Ala Thr His Met Val Gln Leu Val Leu
             180                 185                 190

Asp Arg Asn Asp Pro Ala Tyr Ser Asp Met Ile Tyr Phe Cys Ser His
            195                 200                 205

Leu Pro Lys Ser Asn Gly Ile Ile Val Asn Thr Phe Glu Glu Leu Glu
            210                 215                 220

Pro Pro Ser Val Leu Gln Ala Ile Ala Gly Gly Leu Cys Val Pro Asp
225                 230                 235                 240

Gly Pro Thr Pro Pro Val Tyr Tyr Val Gly Pro Leu Ile Glu Glu Glu
            245                 250                 255

Lys Glu Leu Ser Lys Asp Ala Asp Ala Ala Glu Lys Glu Asp Cys Leu
            260                 265                 270

Ser Trp Leu Asp Lys Gln Pro Ser Arg Ser Val Leu Phe Leu Cys Phe
            275                 280                 285

Gly Ser Met Gly Ser Phe Pro Ala Ala Gln Leu Lys Glu Ile Ala Asn
            290                 295                 300

Gly Leu Glu Ala Ser Gly Gln Arg Phe Leu Trp Val Val Lys Lys Pro
305                 310                 315                 320

Pro Val Glu Glu Lys Ser Lys Gln Val His Gly Val Asp Asp Phe Asp
            325                 330                 335

Leu Lys Gly Val Leu Pro Glu Gly Phe Leu Glu Arg Thr Ala Asp Arg
            340                 345                 350

Gly Met Val Val Lys Ser Trp Ala Pro Gln Val Val Leu Lys Lys
            355                 360                 365

Glu Ser Val Gly Gly Phe Val Thr His Cys Gly Trp Asn Ser Val Leu
            370                 375                 380

Glu Ala Val Val Ala Gly Val Pro Met Ile Ala Trp Pro Leu Tyr Ala
385                 390                 395                 400

Glu Gln His Met Asn Arg Asn Val Leu Val Thr Asp Met Glu Ile Ala
            405                 410                 415

Ile Gly Val Glu Gln Arg Asp Glu Glu Gly Phe Val Ser Gly Glu
            420                 425                 430

Glu Val Glu Arg Arg Val Arg Glu Leu Met Glu Ser Glu Gly Gly Arg
            435                 440                 445

Val Leu Arg Glu Arg Cys Lys Lys Leu Gly Glu Met Ala Ser Ala Ala
450                 455                 460

Leu Gly Glu Thr Gly Ser Ser Thr Arg Asn Leu Val Asn Phe Val Ser
465                 470                 475                 480

Ser Ile Thr

<210> SEQ ID NO 21
<211> LENGTH: 691
<212> TYPE: PRT
<213> ORGANISM: Saccharomyces cerevisiae

<400> SEQUENCE: 21

Met Pro Phe Gly Ile Asp Asn Thr Asp Phe Thr Val Leu Ala Gly Leu
1               5                   10                  15

Val Leu Ala Val Leu Leu Tyr Val Lys Arg Asn Ser Ile Lys Glu Leu
            20                  25                  30

Leu Met Ser Asp Asp Gly Asp Ile Thr Ala Val Ser Ser Gly Asn Arg
            35                  40                  45

Asp Ile Ala Gln Val Val Thr Glu Asn Asn Lys Asn Tyr Leu Val Leu
        50                  55                  60

```
Tyr Ala Ser Gln Thr Gly Thr Ala Glu Asp Tyr Ala Lys Lys Phe Ser
 65                  70                  75                  80

Lys Glu Leu Val Ala Lys Phe Asn Leu Asn Val Met Cys Ala Asp Val
                 85                  90                  95

Glu Asn Tyr Asp Phe Glu Ser Leu Asn Asp Val Pro Val Ile Val Ser
            100                 105                 110

Ile Phe Ile Ser Thr Tyr Gly Glu Gly Asp Phe Pro Asp Gly Ala Val
        115                 120                 125

Asn Phe Glu Asp Phe Ile Cys Asn Ala Glu Ala Gly Ala Leu Ser Asn
    130                 135                 140

Leu Arg Tyr Asn Met Phe Gly Leu Gly Asn Ser Thr Tyr Glu Phe Phe
145                 150                 155                 160

Asn Gly Ala Ala Lys Lys Ala Glu Lys His Leu Ser Ala Ala Gly Ala
                165                 170                 175

Ile Arg Leu Gly Lys Leu Gly Glu Ala Asp Gly Ala Gly Thr Thr
        180                 185                 190

Asp Glu Asp Tyr Met Ala Trp Lys Asp Ser Ile Leu Glu Val Leu Lys
        195                 200                 205

Asp Glu Leu His Leu Asp Glu Gln Ala Lys Phe Thr Ser Gln Phe
210                 215                 220

Gln Tyr Thr Val Leu Asn Glu Ile Thr Asp Ser Met Ser Leu Gly Glu
225                 230                 235                 240

Pro Ser Ala His Tyr Leu Pro Ser His Gln Leu Asn Arg Asn Ala Asp
                245                 250                 255

Gly Ile Gln Leu Gly Pro Phe Asp Leu Ser Gln Pro Tyr Ile Ala Pro
            260                 265                 270

Ile Val Lys Ser Arg Glu Leu Phe Ser Ser Asn Asp Arg Asn Cys Ile
        275                 280                 285

His Ser Glu Phe Asp Leu Ser Gly Ser Asn Ile Lys Tyr Ser Thr Gly
    290                 295                 300

Asp His Leu Ala Val Trp Pro Ser Asn Pro Leu Glu Lys Val Glu Gln
305                 310                 315                 320

Phe Leu Ser Ile Phe Asn Leu Asp Pro Glu Thr Ile Phe Asp Leu Lys
                325                 330                 335

Pro Leu Asp Pro Thr Val Lys Val Pro Phe Pro Thr Pro Thr Thr Ile
            340                 345                 350

Gly Ala Ala Ile Lys His Tyr Leu Glu Ile Thr Gly Pro Val Ser Arg
        355                 360                 365

Gln Leu Phe Ser Ser Leu Ile Gln Phe Ala Pro Asn Ala Asp Val Lys
    370                 375                 380

Glu Lys Leu Thr Leu Leu Ser Lys Asp Lys Asp Gln Phe Ala Val Glu
385                 390                 395                 400

Ile Thr Ser Lys Tyr Phe Asn Ile Ala Asp Ala Leu Lys Tyr Leu Ser
                405                 410                 415

Asp Gly Ala Lys Trp Asp Thr Val Pro Met Gln Phe Leu Val Glu Ser
            420                 425                 430

Val Pro Gln Met Thr Pro Arg Tyr Tyr Ser Ile Ser Ser Ser Ser Leu
        435                 440                 445

Ser Glu Lys Gln Thr Val His Val Thr Ser Ile Val Glu Asn Phe Pro
    450                 455                 460

Asn Pro Glu Leu Pro Asp Ala Pro Val Val Gly Val Thr Thr Asn
465                 470                 475                 480

Leu Leu Arg Asn Ile Gln Leu Ala Gln Asn Asn Val Asn Ile Ala Glu
```

```
                485                 490                 495
Thr Asn Leu Pro Val His Tyr Asp Leu Asn Gly Pro Arg Lys Leu Phe
            500                 505                 510

Ala Asn Tyr Lys Leu Pro Val His Val Arg Arg Ser Asn Phe Arg Leu
        515                 520                 525

Pro Ser Asn Pro Ser Thr Pro Val Ile Met Ile Gly Pro Gly Thr Gly
    530                 535                 540

Val Ala Pro Phe Arg Gly Phe Ile Arg Glu Arg Val Ala Phe Leu Glu
545                 550                 555                 560

Ser Gln Lys Lys Gly Gly Asn Asn Val Ser Leu Gly Lys His Ile Leu
                565                 570                 575

Phe Tyr Gly Ser Arg Asn Thr Asp Asp Phe Leu Tyr Gln Asp Glu Trp
            580                 585                 590

Pro Glu Tyr Ala Lys Lys Leu Asp Gly Ser Phe Glu Met Val Val Ala
        595                 600                 605

His Ser Arg Leu Pro Asn Thr Lys Lys Val Tyr Val Gln Asp Lys Leu
    610                 615                 620

Lys Asp Tyr Glu Asp Gln Val Phe Glu Met Ile Asn Asn Gly Ala Phe
625                 630                 635                 640

Ile Tyr Val Cys Gly Asp Ala Lys Gly Met Ala Lys Gly Val Ser Thr
                645                 650                 655

Ala Leu Val Gly Ile Leu Ser Arg Gly Lys Ser Ile Thr Thr Asp Glu
            660                 665                 670

Ala Thr Glu Leu Ile Lys Met Leu Lys Thr Ser Gly Arg Tyr Gln Glu
        675                 680                 685

Asp Val Trp
    690

<210> SEQ ID NO 22
<211> LENGTH: 310
<212> TYPE: PRT
<213> ORGANISM: Saccharomyces cerevisiae

<400> SEQUENCE: 22

Met Pro Ile Thr Ile Lys Ser Arg Ser Lys Gly Leu Arg Asp Thr Glu
1               5                   10                  15

Ile Asp Leu Ser Lys Lys Pro Thr Leu Asp Asp Val Leu Lys Lys Ile
            20                  25                  30

Ser Ala Asn Asn His Asn Ile Ser Lys Tyr Arg Ile Arg Leu Thr Tyr
        35                  40                  45

Lys Lys Glu Ser Lys Gln Val Pro Val Ile Ser Glu Ser Phe Phe Gln
    50                  55                  60

Glu Glu Ala Asp Asp Ser Met Glu Phe Phe Ile Lys Asp Leu Gly Pro
65                  70                  75                  80

Gln Ile Ser Trp Arg Leu Val Phe Phe Cys Glu Tyr Leu Gly Pro Val
                85                  90                  95

Leu Val His Ser Leu Phe Tyr Tyr Leu Ser Thr Ile Pro Thr Val Val
            100                 105                 110

Asp Arg Trp His Ser Ala Ser Ser Asp Tyr Asn Pro Phe Leu Asn Arg
        115                 120                 125

Val Ala Tyr Phe Leu Ile Leu Gly His Tyr Gly Lys Arg Leu Phe Glu
    130                 135                 140

Thr Leu Phe Val His Gln Phe Ser Leu Ala Thr Met Pro Ile Phe Asn
145                 150                 155                 160
```

| | | | | | | | | | | | |
|---|---|---|---|---|---|---|---|---|---|---|---|
| Leu | Phe | Lys | Asn | Cys | Phe | His | Tyr | Trp | Val | Leu | Ser | Gly | Leu | Ile | Ser |
| | | | | 165 | | | | 170 | | | | 175 | |
| Phe | Gly | Tyr | Phe | Gly | Tyr | Gly | Phe | Pro | Phe | Gly | Asn | Ala | Lys | Leu | Phe |
| | | | 180 | | | | | 185 | | | | | 190 | |
| Lys | Tyr | Tyr | Ser | Tyr | Leu | Lys | Leu | Asp | Asp | Leu | Ser | Thr | Leu | Ile | Gly |
| | | 195 | | | | | 200 | | | | | 205 | | |
| Leu | Phe | Val | Leu | Ser | Glu | Leu | Trp | Asn | Phe | Tyr | Cys | His | Ile | Lys | Leu |
| 210 | | | | | 215 | | | | | 220 | | | | |
| Arg | Leu | Trp | Gly | Asp | Tyr | Gln | Lys | Lys | His | Gly | Asn | Ala | Lys | Ile | Arg |
| 225 | | | | 230 | | | | | 235 | | | | | 240 |
| Val | Pro | Leu | Asn | Gln | Gly | Ile | Phe | Asn | Leu | Phe | Val | Ala | Pro | Asn | Tyr |
| | | | 245 | | | | | 250 | | | | | 255 | |
| Thr | Phe | Glu | Val | Trp | Ser | Trp | Ile | Trp | Phe | Thr | Phe | Val | Phe | Lys | Phe |
| | | 260 | | | | | 265 | | | | | 270 | | |
| Asn | Leu | Phe | Ala | Val | Leu | Phe | Leu | Thr | Val | Ser | Thr | Ala | Gln | Met | Tyr |
| | 275 | | | | | 280 | | | | | 285 | | | |
| Ala | Trp | Ala | Gln | Lys | Lys | Asn | Lys | Lys | Tyr | His | Thr | Arg | Arg | Ala | Phe |
| | 290 | | | | | 295 | | | | | 300 | | | |
| Leu | Ile | Pro | Phe | Val | Phe |
| 305 | | | | 310 | |

<210> SEQ ID NO 23
<211> LENGTH: 1182
<212> TYPE: DNA
<213> ORGANISM: Pinus densiflora

<400> SEQUENCE: 23

```
atgggtggtg ttgattttga aggtttcaga aagttgcaaa gagctgacgg ttttgcttcc      60
attttggcta ttggtactgc taatccacca acgctgttg atcaatctac ttacccagat     120
tactacttca gaatcaccgg taacgaacat aacactgaat gaaggacaa gttcaagaga     180
atctgcgaaa gatccgctat caagcaaaga tatatgtact tgaccgaaga atcttgaaa     240
aagaacccag atgtttgcgc ctttgttgaa gttccatctt tggatgctag acaagctatg     300
ttggctatgg aagttccaag attggctaaa gaagctgctg aaaaggctat ccatgaatgg     360
ggtcaatcta agtctggtat tacccatttg attttctgtt ctactaccac cccagatttg     420
ccaggtgctg atttcgaagt tgctaagttg ttgggtttac acccatctgt taagagagtt     480
ggtgttttcc aacatggttg ttttgctggt ggtactgttt tgagattagc taaggatttg     540
gccgaaaaca atagaggtgc tagagttttg gttatctgct ctgaaactac tgctgttact     600
tttagaggtc catctgaaac ccatttggat tctttggttg gtcaagcttt gtttggtgat     660
ggtgcttctg ctttgatagt tggtgctgat ccaattccac aagttgaaaa agcttgcttc     720
gaaattgtca gaacctctca aactgttgtt ccaaattcag atggtgctat tggtggtaag     780
gttagagaag ttggtttgac cttccaattg aagggtgctg ttccagattt gatttccgct     840
aacattgaaa ctgcttggt tgaagctttc tcccaattca aatttgcga ctggaacaag     900
ttgttctggg ttgttcatcc aggtggtaga gctattttgg atagagttga agctaagttg     960
aacttggacc caactaagtt gattccaacc agacatgtta tgtccgaata cggtaatatg    1020
tcctctgctt gcgttcattt catttggac gaaactagaa aggcctcttt gagaaatggt    1080
tgttctacaa ctggtgaagg tttggaaatg ggtgttttgt tcggttttgg tccaggttg    1140
actattgaaa ccgttgtttt gaagtccgtc ccattacaat ga                        1182
```

<210> SEQ ID NO 24
<211> LENGTH: 393
<212> TYPE: PRT
<213> ORGANISM: Pinus densiflora

<400> SEQUENCE: 24

```
Met Gly Gly Val Asp Phe Glu Gly Phe Arg Lys Leu Gln Arg Ala Asp
1               5                   10                  15

Gly Phe Ala Ser Ile Leu Ala Ile Gly Thr Ala Asn Pro Pro Asn Ala
            20                  25                  30

Val Asp Gln Ser Thr Tyr Pro Asp Tyr Tyr Phe Arg Ile Thr Gly Asn
        35                  40                  45

Glu His Asn Thr Glu Leu Lys Asp Lys Phe Lys Arg Ile Cys Glu Arg
    50                  55                  60

Ser Ala Ile Lys Gln Arg Tyr Met Tyr Leu Thr Glu Glu Ile Leu Lys
65                  70                  75                  80

Lys Asn Pro Asp Val Cys Ala Phe Val Glu Val Pro Ser Leu Asp Ala
                85                  90                  95

Arg Gln Ala Met Leu Ala Met Glu Val Pro Arg Leu Ala Lys Glu Ala
            100                 105                 110

Ala Glu Lys Ala Ile His Glu Trp Gly Gln Ser Lys Ser Gly Ile Thr
        115                 120                 125

His Leu Ile Phe Cys Ser Thr Thr Thr Pro Asp Leu Pro Gly Ala Asp
    130                 135                 140

Phe Glu Val Ala Lys Leu Leu Gly Leu His Pro Ser Val Lys Arg Val
145                 150                 155                 160

Gly Val Phe Gln His Gly Cys Phe Ala Gly Gly Thr Val Leu Arg Leu
                165                 170                 175

Ala Lys Asp Leu Ala Glu Asn Asn Arg Gly Ala Arg Val Leu Val Ile
            180                 185                 190

Cys Ser Glu Thr Thr Ala Val Thr Phe Arg Gly Pro Ser Glu Thr His
        195                 200                 205

Leu Asp Ser Leu Val Gly Gln Ala Leu Phe Gly Asp Gly Ala Ser Ala
    210                 215                 220

Leu Ile Val Gly Ala Asp Pro Ile Pro Gln Val Glu Lys Ala Cys Phe
225                 230                 235                 240

Glu Ile Val Arg Thr Ser Gln Thr Val Val Pro Asn Ser Asp Gly Ala
                245                 250                 255

Ile Gly Gly Lys Val Arg Glu Val Gly Leu Thr Phe Gln Leu Lys Gly
            260                 265                 270

Ala Val Pro Asp Leu Ile Ser Ala Asn Ile Glu Asn Cys Leu Val Glu
        275                 280                 285

Ala Phe Ser Gln Phe Lys Ile Cys Asp Trp Asn Lys Leu Phe Trp Val
    290                 295                 300

Val His Pro Gly Gly Arg Ala Ile Leu Asp Arg Val Glu Ala Lys Leu
305                 310                 315                 320

Asn Leu Asp Pro Thr Lys Leu Ile Pro Thr Arg His Val Met Ser Glu
                325                 330                 335

Tyr Gly Asn Met Ser Ser Ala Cys Val His Phe Ile Leu Asp Glu Thr
            340                 345                 350

Arg Lys Ala Ser Leu Arg Asn Gly Cys Ser Thr Thr Gly Glu Gly Leu
        355                 360                 365

Glu Met Gly Val Leu Phe Gly Phe Gly Pro Gly Leu Thr Ile Glu Thr
    370                 375                 380
```

Val Val Leu Lys Ser Val Pro Leu Gln
385                 390

<210> SEQ ID NO 25
<211> LENGTH: 319
<212> TYPE: PRT
<213> ORGANISM: Kluyveromyces lactis

<400> SEQUENCE: 25

Met Ser Ala Ser Ser Ile Phe Ile Lys Ser Arg Ser Lys Ser Leu
1               5                   10                  15

Lys Asp Val Lys Leu Glu Val Pro Thr Glu Asn Thr Leu Thr Tyr Gln
            20                  25                  30

Ser Val Leu Gln Gln Ile Ser Lys Ser Asn His Asn Ile Ser Val Asn
        35                  40                  45

Arg Leu Arg Leu Ser Tyr Leu Lys Glu Gly Lys Gln Val Ala Ile Gly
    50                  55                  60

Pro Ser Glu Leu Asn Asp Val Gly Lys Lys Asn Thr Phe Asp Ser Val
65                  70                  75                  80

Asn Glu Trp Tyr Val Lys Asp Leu Gly Pro Gln Ile Ser Trp Arg Leu
                85                  90                  95

Val Phe Phe Ile Glu Tyr Leu Gly Pro Ile Leu Ile His Ser Leu Val
            100                 105                 110

Tyr Leu Leu Ser Leu Asn Ala Thr Val Arg Asp Lys Phe His Ser Lys
        115                 120                 125

Asn Val Pro Tyr Asn Asp Phe Phe Asn Lys Phe Ile Tyr Arg Leu Ile
    130                 135                 140

Met Val His Tyr Leu Lys Arg Glu Phe Glu Thr Leu Phe Ile His Ser
145                 150                 155                 160

Phe Ser Leu Glu Thr Met Pro Leu Phe Asn Leu Phe Lys Asn Ser Phe
                165                 170                 175

His Tyr Trp Ile Leu Asn Gly Leu Ile Ser Leu Gly Tyr Phe Gly Tyr
            180                 185                 190

Gly Phe Pro Phe Ala Asn Lys Thr Leu Tyr Arg Val Tyr Ser Ala Leu
        195                 200                 205

Lys Ile Ser Asp Phe Arg Val Leu Thr Ala Leu Phe Gly Leu Ser Glu
    210                 215                 220

Met Phe Asn Phe Tyr Ile His Val Ala Leu Arg Arg Trp Gly Asp Glu
225                 230                 235                 240

Gln Lys Arg Asn Gly Val Thr Lys Arg Val Pro Leu Asn Ser Gly Leu
                245                 250                 255

Phe Lys Leu Leu Val Ala Pro Asn Tyr Thr Phe Glu Ser Trp Ala Trp
            260                 265                 270

Met Phe Phe Thr Leu Leu Phe Leu Asn Leu Phe Ser Val Leu Phe
        275                 280                 285

Leu Val Val Ser Val Val Gln Met Tyr Leu Trp Ala Gln Lys Lys Asn
        290                 295                 300

Lys Lys Tyr Gly Thr Lys Arg Ala Phe Leu Ile Pro Phe Leu Phe
305                 310                 315

<210> SEQ ID NO 26
<211> LENGTH: 253
<212> TYPE: PRT
<213> ORGANISM: Saccharomyces cerevisiae

<400> SEQUENCE: 26

```
Met Tyr Phe Asp Glu Glu Gln Leu Leu Lys Tyr Thr Ile Tyr Ala Tyr
1               5                   10                  15
Arg Leu Ser Phe Phe Val Gly Ile Cys Ser Leu Phe Ile Ala Lys Ser
            20                  25                  30
Cys Leu Pro Glu Phe Leu Gln Tyr Gly Lys Thr Tyr Arg Pro Lys Glu
                35                  40                  45
Asn Ser Lys Tyr Ser Ser Ile Leu Glu Arg Ile Lys Lys Phe Thr Val
        50                  55                  60
Pro Lys Ala Tyr Phe Ser His Phe Tyr Leu Ala Thr Phe Leu Ser
65              70                  75                  80
Leu Val Thr Leu Tyr Phe Tyr Pro Lys Phe Pro Ile Val Trp Ile Ile
                85                  90                  95
Phe Gly His Ser Leu Arg Arg Leu Tyr Glu Thr Leu Tyr Val Leu His
                100                 105                 110
Tyr Thr Ser Asn Ser Arg Met Asn Trp Ser His Tyr Leu Val Gly Ile
            115                 120                 125
Trp Phe Tyr Ser Val Leu Leu Leu Ile Leu Asn Ile Ser Leu Tyr Lys
    130                 135                 140
Asn Ser Ile Pro Asn Thr Leu Asn Met Asn Ala Phe Ile Ile Phe Cys
145             150                 155                 160
Ile Ala Ser Trp Asp Gln Tyr Lys Asn His Val Ile Leu Ala Asn Leu
                165                 170                 175
Val Lys Tyr Ser Leu Pro Thr Gly Arg Leu Phe Arg Leu Val Cys Cys
                180                 185                 190
Pro His Tyr Leu Asp Glu Ile Ile Ile Tyr Ser Thr Leu Leu Pro Tyr
                195                 200                 205
Glu Gln Glu Phe Tyr Leu Thr Leu Val Trp Val Ile Thr Ser Leu Thr
    210                 215                 220
Ile Ser Ala Leu Glu Thr Lys Asn Tyr Tyr Arg His Lys Phe Lys Asp
225             230                 235                 240
Asn His Val Ala Pro Tyr Ala Ile Ile Pro Phe Ile Ile
                245                 250

<210> SEQ ID NO 27
<211> LENGTH: 1173
<212> TYPE: DNA
<213> ORGANISM: Hypericum androsaemum

<400> SEQUENCE: 27
atggttactg ttgaagaagt tagaaaagct caaagggcag aaggtccagc cacagtgatg      60
gctattggaa ccgcagttcc tccaaattgt gtagatcagg ccacttatcc tgactactac    120
tttagaataa caaactctga gcataaggct gaattgaaag aaaagttcca aaggatgtgc    180
gacaaatcac agatcaagaa aagatacatg taccttaatg aggaagtcct aaaggaaaac    240
ccaaatatgt gtgcatacat ggccccttcc cttgacgcta dacaagatat tgtggttgta    300
gaggtcccaa aattgggcaa ggaagcagct gttaaagcca taaggaatg gggtcaacct    360
aagagcaaaa tcacccacct tgtgttttgc actacaagcg gagttgacat gccaggcgca    420
gattatcagc taaccaaact tttgggttta aggccttctg taaaaagatt gatgatgtac    480
caacaaggtt gtttcgctgg aggcactgtc ttaagactag ccaaggatct tgcagagaac    540
aacaaaggtg ctagggtgtt ggttgtatgc tcagaaatta cagccgtcac ctttagagga    600
ccaactgaca ctcacttaga ttccctagtt ggtcaggcat tgtttggcga cggtgctgcc    660
gcaataatca ttggaagtga tcctattcca gaggtggaaa agcctctttt tgaacttgtt    720
```

```
agcgctgccc aaactatatt gccagattct gagggtgcaa tcgacggcca cttaagggaa    780
gtaggtctaa ccttccatct tttgaaagat gtccctggtt taatttcaaa gaacgtggaa    840
aaatccctaa cagaggcttt taaaccattg ggtataagtg actggaatag cttattctgg    900
atcgctcacc caggcggccc tgccatactt gaccaggttg aagcaaaatt gagcttaaag    960
ccagaaaaac taagagctac tagacatgta ttgtcagagt atggtaacat gtccagtgcc    1020
tgtgtccttt tcattttgga tgaaatgagg agaaaaagca aggaggacgg cctaaaaacc    1080
acaggtgagg gaatcgaatg gggtgttcta ttcggctttg gtccaggcct tactgtggag    1140
acagttgtac ttcattcagt cgcaattaat tag    1173
```

<210> SEQ ID NO 28
<211> LENGTH: 1197
<212> TYPE: DNA
<213> ORGANISM: Petroselinum crispum

<400> SEQUENCE: 28

```
atggctaatc atcataatgc tgaaattgag gaaataagaa acagacaaag agcccagggt    60
ccagctaata tcttggcaat tggaactgcc acaccttcta attgtgttta tcaagctgat    120
tacccagact attacttcag aatcaccaac tcagagcaca tgacagactt aaagttgaaa    180
ttcaagagaa tgtgcgaaaa gagtatgata agaaagagat acatgcacat caccgaggag    240
tatttgaagg agaaccctaa cgtgtgcgcc tacgaggccc aagtttaga cgctagacag    300 gacttggtag tcgttgaagt gccaagatta ggaaaagaag ccgctagtaa ggccattaaa    360
gaatggggac aaccaaaatc taagatcact cacttaatat tctgtacaac ctccggtgtc    420
gacatgccag gtcagactac ccaattgaca aagttattgg gattaagacc aagtgtgaaa    480
agattcatga tgtatcagca aggatgcttc gcaggaggta ctgttttgag attggcaaag    540
gacttagccg aaaataacgc tggtgccaga gtattagtgg tgtgttctga aattacagcc    600
gtgactttca gaggaccatc cgactcccac ttggatagtt tagttggtca ggctttgttt    660
ggtgacggag ccgcagccgt gatattagga agtgaccctg atttgtcagt cgaaagacca    720
ttattccagt tgatttctgc cgcacaaact atcttaccag acagtgatgg agctatagac    780
ggtcatttga gaagtgggt ttaacatttt catttgttaa aagatgttcc tggtttaata    840
agtaagaata ttgaaaagtc attgaaggag ctttcggtc caataggaat tagtgattgg    900
aactccttat tttggatagc acacccagga ggtcctgcta tattggacca ggtagagttg    960
aagttaggtt taaaggaaga gaagatgaga gctactagac aagtcttaag tgattacggt    1020
aacatgtcat ctgcctgtgt tttgttcata ttagacgaaa tgagaaagaa atcaattgaa    1080
gagggaaaag ctaccacagg agaaggatta gactgggggtt ttttgttcgg atttggtcct    1140
ggattgactg ttgaaaccgt agtcttacat agtgtgcctg ctacattcac tcactga    1197
```

<210> SEQ ID NO 29
<211> LENGTH: 1170
<212> TYPE: DNA
<213> ORGANISM: Petunia hybrida

<400> SEQUENCE: 29

```
atggttactg ttgaagaata tagaaaagct caaagggcag agggtccagc cacagtcatg    60
gctattggaa ccgcaactcc tacaaattgt gtggatcagt ctaccctacc agactattac    120
tttagaataa ctaactcaga acataagaca gatttgaaag aaaagttcaa aaggatgtgc    180
```

```
gaaaagtcca tgatcaaaaa gagatatatg cacttaaccg aggaaattct aaaggagaac    240
cctagtatgt gtgagtacat ggccccaagc cttgacgcta gacaagatat agttgtagtc    300
gaagtgccta agctaggaaa agaagcagcc cagaaggcta tcaaagaatg gggtcaacca    360
aagagcaaaa ttacccacct tttttctgc acaacctcag gagttgacat gcctggctgt     420
gattatcaac taactaaact tttgggttta aggccatccg taaagagatt gatgatgtac    480
cagcaaggtt gctttgcagg aggcacagtc ttaagactag ctaaagatct tgccgaaaat    540
aataagggtg caagggtttt ggtggtttgt agtgagataa ctgctgtaac cttcagagga    600
cctaacgaca ctcacttaga tagcctagtc ggtcaagcct tgtttggcga cggtgcagga    660
gctatcatta ttggttctga tccaatacct ggcgtggaaa ggccattatt cgaacttgtt    720
tcagccgcac agactttgtt acctgattcc catggtgcta tcgacggaca cctaagagag    780
gtaggtctta cctttcattt gttaaaagat gtccctggtt aattagtaa gaatatagag     840 aagagcttgg aagaggcctt caagccatta ggaatcagcg actggaactc actttttggg   900
attgcacatc ctggcggccc agctatactt gaccaagttg aaatcaaatt gggcctaaag   960
cctgaaaaat tgaaggccac aagaaatgtg ttatccgatt atggaaacat gagttctgca  1020
tgtgttcttt tcattttgga tgagatgagg aaggcttcag ctaaagaagg tctaggcact  1080
acaggtgagg gcttggagtg gggtgtacta ttcggctttg gaccaggcct taccgtcgaa  1140
actgtggttt tacactctgt agccacataa                                   1170

<210> SEQ ID NO 30
<211> LENGTH: 1197
<212> TYPE: DNA
<213> ORGANISM: Hordeum vulgare

<400> SEQUENCE: 30
atggctgcta caatgaccgt tgaagaagtg agaaatgctc aaagggccga aggtcccgca     60
acagtattag ccattggcac agctactcca gcaaattgtg tttaccaggc agattatcca    120 gactatatt ttaagatcac aaaatcagat cacatggccg acttgaaaga aaagtttaaa    180
agaatgtgtg ataagagtca atcagaaag aggtatatgc atttgaccga ggaaatttta    240
gaggaaaacc caaatatgtg cgcttacatg gctccttctt tggatgctag caagacata    300 gtagttgtgg aagttcccaa gttgggaaag gcagctgcac agaaggcaat aaaagaatgg    360
ggtcagccaa gatctaagat aactcattta gtcttctgta ctacttcagg tgttgatatg    420
cccggcgctg actatcaatt gacaaagatg ttgggtttga gacatcagt taaaaggttg    480 atgatgtacc aacaaggatg tttttgccggc ggaaccgttt tgagattggc taaagacttg    540
gctgagaaca atagaggagc tagagtattg gttgttgtgca gtgaaattac agctgttact    600
tttagaggcc cacacgaatc tcacttggat tctttagtag gtcaagcatt gtttggtgat    660
ggagctgccg cagtcattat tggtgcagat ccagatttat ctgtcgaaag accattgttt    720
caattagtct ctgcctctca acaatattg ccagactcag aaggtgctat tgacggtcac    780
ttgagggagg tgggtttaac ttttcatttg ttaaaagacg taccctggatt aattagtaag    840 aatatagaaa gagcattaga agaggctttc aaacctttag cattgatca ttggaattca    900 gtgttctgga ttgcacatca gggtggtcct gctatcttag atatggttga agccaaagtt    960
aacttaaaca aagaaagaat gagagccacc aggcatgtgt taagtgaata cggcaacatg   1020
tcctccgcat gcgtattatt catcatggat gagatgagaa agagatcagc agaggatggt   1080
catgcaacaa ctggtgaagg aatggattgg ggtgtattat tcggcttcgg acctggttta   1140
```

```
actgtcgaga ccgtcgtctt acattccgtc cctatctccg ccggtgccac tgcttga        1197

<210> SEQ ID NO 31
<211> LENGTH: 1173
<212> TYPE: DNA
<213> ORGANISM: Scutellaria baicalensis

<400> SEQUENCE: 31
atggttactg tcgaagaatt ccatagggct accagggctg aaggtccagc taccgtttta       60
gccatcggta ctgccaaccc tcctaactgt gtcgagcaat ccacctacgc tgactactat      120
ttccgtattt gtaagtccga cacctaacc gacttgaaaa agaagttcga ccgtatgtgt       180
gaaaagtcct gtatcaagaa gcgttacatg cacttgaccg aagaattttt aaaagagaat      240
gataacttca ctgcttatga ggctccttct ttggacgctc gtcaagacat cgtcgttgtc      300
gaaattccta gttgggtaa ggaagctgcc caaaaagcta ttaaggaatg gggtcaacca       360
aagtctaaaa ttactcacgt tatcttctgt accacttctg tgttgacat gccaggtgcc       420
gactaccaaa tcaccaagtt attaggttta cgtccttccg tcaagagatt catgatgtac      480
caacaaggtt gcttcgctgg tggtaccgtc ttaagaatgg ccaaggattt agccgagaat      540
aatgctggtg ctagagtcct agttgtctgt tccgagatca ccgctattac cttcagaggc      600
ccatctgata cccacttaga ttctttagtt ggtcaagcct tattcggtga cggtgctgct      660
gctgttattg ttggttccga tccaatcgtc ggtgttgaaa gacctttgtt tcaattggtt      720
tctgctgctc agactatttt gccagactct gaaggtgcta ttgatggtca cgtcagagaa      780
gttggtttga cttttccattt gttgaaggat gttccaggtt tgatctctaa ggacattgaa     840
aagtctttga agaggcttt cgctccattg ggtatttccg attggaattc cttgttttgg      900
attgttcatc aggtggtcc agctatccta gatcaagtcg gtgaaaagct aggtttgaag      960
cctgaaatca tggtccctac tagacacgtt ttgtctgaat acggtaacat gtcttctgct     1020
tgcgtcttgt tcgtcatgga tgaaatgcgt aaagcctctg ctaaagatgg ttgtaccagc     1080
actggtgaag gtaaggactg gggtgtccta tttggcttcg gtccaggttt gactgttgaa     1140
accgttgttt tgcacagcgt tcctttaaac taa                                  1173

<210> SEQ ID NO 32
<211> LENGTH: 1170
<212> TYPE: DNA
<213> ORGANISM: Malus domestica

<400> SEQUENCE: 32
atggtcaccg tcgaagaagt tagaaaagct caaagagctg aaggtccagc tactgttttg       60
gctattggta ctgctactcc accaaattgt gttgatcaag ctacttaccc agactactac      120
ttcagaatta ccaactctga acacaagacc gaattgaaag aaaagttcca agaatgtgc       180
gacaagtcca tgatcaagac cagatatatg tacttgaccg aagaaatctt aaaagaaaac      240
ccaaccgtct gcgaatatat ggctccatct ttggatgcta gcaagatat ggttgttgtt      300
gaagttccaa gattgggtaa agaagctgct actaaggcta tcaaagaatg gggtcaacct      360
aagtctaaga tcacccattt ggttttctgt actacctctg tgttgatat gccaggtgct      420
gattatcaat tgactaagtt gttgggttta agaccatccg tcaagagatt gatgatgtac      480
caacaaggtt gttttgctgg tggtacagtt ttgagattgg caaagatttt ggccgaaaac      540
aacaaaggtg ctagagtttt ggttgtctgc tctgaaatta ctgctgttac ttttagaggt      600
```

| | |
|---|---|
| ccatccgata ctcatttgga ttctttggtt ggtcaagcct tgtttggtga tggtgctgct | 660 |
| gctgttatta ttggttctga tccagttcct gaagtcgaaa agccattatt cgaattggtt | 720 |
| tctgctgccc aaactatctt gccagattca gatggtgcta ttgatggtca tttgagagaa | 780 |
| gttggtttga ccttccattt gttgaaagat gtcccaggtt tgatttccaa gaacatcgaa | 840 |
| aagtctttga acgaagcctt caagccaatt ggtatttctg attggaattc cttgttctgg | 900 |
| attgctcatc caggtggtcc agcaattttg gatcaagttg aatctaagtt ggccttgaag | 960 |
| ccagaaaaat tggaagctac tagacaagtc ttgtccgatt acggtaatat gtcatctgct | 1020 |
| tgcgttttgt tcatcttgga tgaagtcaga agaaagtctg ctgaaaaggg tttgaaaact | 1080 |
| actggtgaag gtttggaatg gggtgttttg tttggttttg gtccaggttt aactgttgaa | 1140 |
| accgttgtct tgcattctgt tggtgcttaa | 1170 |

<210> SEQ ID NO 33
<211> LENGTH: 1176
<212> TYPE: DNA
<213> ORGANISM: Malus domestica

<400> SEQUENCE: 33

| | |
|---|---|
| atggttacag tcgaggaagt tcgcaaggct caacgggcgg agggtccagc cacagtcatg | 60 |
| gccatcggga cagcaactcc ttccaactgt gtggatcagg ctacctaccc cgactactac | 120 |
| tttcgtatca ccaacagcga gcacaaggtt gagctcaaag aaaaattcca gcgcatgtgc | 180 |
| gacaaatcta tgatcaagaa acgttatatg tacttgactg aagaaatttt aaaagagaac | 240 |
| ccaagtgtgt gcgagtacat ggctccttca attgatgcaa gcaggacat ggtggttgtg | 300 |
| gaagtcccaa aacttggcaa agaggctgcc accaaagcca tcaaggaatg gggacagccc | 360 |
| aagtccaaaa tcacccactt ggtcttttgc accaccagcg tgtcgacat gcctggcgcc | 420 |
| gactaccaac tcaccaagct cttgggcctc cgcccctccg tcaagcgcct catgatgtac | 480 |
| cagcaagggt gcttcgccgg tgggacggtc tccgtttgg ccaaggactt ggccgaaaac | 540 |
| aacaagggtg cacgtgttct tgttgtgtgc tctgagatca ccgcggttac cttccgtggg | 600 |
| cctagtgaca cccaccttga tagtcttgtg ggccaagctt tgtttggcga cggtgcagcg | 660 |
| gccgtaatca ttggtgcgga tccagtgccc gaagtcgaga agcccttgtt tgaattggtg | 720 |
| tcggcggcac aaaccattct ccccgacagt gatgggcta tcgacggaca tctccgtgaa | 780 |
| gtagggctta catttcacct tctcaaggat gttcccgggc ttatttcgaa gaacatcgaa | 840 |
| aagagcctta tgaggctttt caagcctatt gggatttcgg actggaactc actcttctgg | 900 |
| attgcacacc caggtggccc tgctattctg gaccaagtag aggccaagtt ggcattgaag | 960 |
| ccggagaaac tagaagcaac aaggcaagtg ttgtcggatt acggtaacat gtcgagtgct | 1020 |
| tgtgtgcttt ttattttgga cgaggtcagg aggaagtccg ccgagaaagg actcaaaacg | 1080 |
| accggggagg gactggagtg gggtgtgctt ttcggatttg gcccggcct cacggtggag | 1140 |
| accgtcgtgc ttcacagcgt gggtttaacg gcttga | 1176 |

<210> SEQ ID NO 34
<211> LENGTH: 1170
<212> TYPE: DNA
<213> ORGANISM: Malus domestica

<400> SEQUENCE: 34

| | |
|---|---|
| atggtgaccg tcgaggaagt tcgcaaggct cagagggctg agggtccggc cacagtctta | 60 |
| gctattggga ctgcaactcc ttccaattgt gtagaccagg ccacataccc tgactactac | 120 |

-continued

```
tttcgtatca ccaacagcga gcacaagact gagctcaaag aaaaatttca gcgcatgtgt    180
gacaaatcta tgatcaagaa gcgttacatg tacttgactg aagaaattct gaaagaaaac    240
ccgactgtgt gcgagtacat ggctccctca ctcgatgctc ggcaggacat ggtggttgtt    300
gaagtcccaa ggcttggcaa agaagcggcc accaaggcaa ttaaggaatg gggacagccc    360
aagtctaaaa tcacccactt ggtcttttgc accaccagcg tgtcgacat gcccggtgcc     420
gactaccagc tcaccaagct attgggcctc cgcccatccg tcaagcgcct catgatgtac    480
caacaaggct gttttgctgg aggcacggtc tccgtttgg ccaaggactt ggccgaaaac     540
aacaagggtg cacgtgttct tgttgtgtgc tctgagatca ccgcggtcac cttccgaggg    600
cctagtgaca cccaccttga tagtcttgtg ggccaagctt tgtttggcga cggtgcagcg    660
gccgtcatca ttggtgcaga tccattgccc gaagtcgaga aacccttatt tgagctagtg    720
tctgctgccc aaaccatcct ccccgacagt gatgggcta ttgacggaca tcttcgtgaa      780
gttgggctta catttcacct tctcaaggat gttcccgggc ttatttcgaa gaacatcgaa    840
aagagcctta atgaggcctt caagcctata ggcatctcgg actggaactc gcttttctgg    900
attgcacacc ctggtggccc tgctattcta gaccaagtag agtccaagtt ggcacttaag    960
ccggagaaac tagaagcaac aaggcaagtg ctgtctaatt acggcaacat gtcaagtgcg    1020
tgtgtcttgt ttattttgga cgaggtgagg aggaaatccg ctgagaaagg actcaaaaca    1080
actggagaag gactggagtg gggcgtgctc ttcggatttg ggcctggcct cactgtcgag    1140
accgttgtgc ttcacagtgt ggctgcttga                                     1170
```

<210> SEQ ID NO 35
<211> LENGTH: 1170
<212> TYPE: DNA
<213> ORGANISM: Malus domestica

<400> SEQUENCE: 35

```
atggtgaccg tcgaagaagt tcgcaaggct caacgggctg agggtccggc cactgttttg     60
gccattggga cagcaactcc tcccaactgt gtggatcaag ccacataccc cgactattac   120
tttcgtatca ccaacagtga gcacaagact gagctcaaag aaaaattcca gcgcatgtgt    180
gacaaatcta tgatcaagac gcgttacatg tacttgactg aagaaattct gaaagagaac    240
ccaactgtgt gcgagtacat ggctccctca ctcgatgctc ggcaggacat ggtggttgtt    300
gaagtcccaa ggcttggcaa agaggctgcc accaaggcca ttaaggaatg gggacagccc    360
aagtccaaaa tcacccactt ggtcttttgc accaccagcg tgtcgacat gcccggcgcc     420
gactaccaac tcaccaagct cttgggcctc cgccctccg tcaagcgcct catgatgtac     480
caacaaggtt gcttcgccgg cgggacggtc tccgtttgg ccaaggactt ggccgagaac     540
aacaagggtg cacgtgttct tgttgtgtgc tctgagatca ccgcagtcac cttccgcggg    600
cctagtgaca cccaccttga cagtcttgtg ggtcaagcct tgtttggtga cggcgcagcg    660
gccgtcatca ttggttcgga tccagtgccc gaagtcgaga agcccttgtt tgaattggtg    720
tcagcagcac aaaccattct tcccgacagt gatgggcta ttgacggcca tctccgtgaa     780
gtagggctta catttcacct tctcaaggac gttcctgggc ttatttccaa gaatatcgaa    840
aagagcctta acgaggcctt caagcctata ggcatttcag actggaactc gctcttctgg    900
attgcacacc caggtggccc tgctattctg gaccaagtag agtccaagtt ggcccttaag    960
ccggagaaac tagaagctac aaggcaagtg ctgtctgatt acggcaacat gtcgagtgcg    1020
```

```
tgtgtcttgt ttattttgga cgaagtgagg aggaagtctg ctgagaaagg actcaaaaca   1080
actggagaag gactggagtg gggcgtactc ttcggatttg gcctggcct cactgttgag   1140 accgttgtgc ttcacagtgt gggtgcttga                                    1170
```

<210> SEQ ID NO 36
<211> LENGTH: 1170
<212> TYPE: DNA
<213> ORGANISM: Malus domestica

<400> SEQUENCE: 36

```
atggtgactg tccaggaagt tcgcaaggct caacgggctg agggtccggc cacagtattc    60
gccattggga cagcaactcc tcccaattgt gtggaccaag ccacataccc cgactattac   120
tttcgtatca ccaacagtga gcacaaggct gagctcaaag aaaaattcca gcgcatgtgt   180
gacaaatcta tgatcaagaa gcgttacatg tacttgactg aggaaattct aaaggagaat   240
ccaagtgtgt gcgagtacat ggcaccatca cttgatgctc ggcaggacat ggtggttgtt   300
gaagtcccaa ggcttggcaa agaggctgcc accaaggcca tcaaggaatg ggacagccc    360 aagtccaaaa tcacccactt ggtcttttgc accaccagcg tgtcgacat gcccggcgct    420 gactaccagc tcaccaagct attgggcctc cgccctctg ttaagcgcct catgatgtac    480
caacaaggtt gtttcgctgg aggcacggtt ctccgtttgg ccaaggactt ggccgaaaac   540
aacaagggtg cacgtgttct tgttgtgtgc tctgagatca ccgcggtcac cttccgtggg   600
cctagtgaca cccaccttga cagtcttgtg ggtcaagcct gtttggcga cggtgcagcg   660 gccgtcatca ttggtgccga cccagtgccc gaagtcgaga agcccttgtt tgaattggtc   720
tcggcggcac aaaccattct cgctgacagt gatgggcta tcgacggaca tctccgtgaa   780
gtagggctta cgtttcacct tttgaaggac gttcccgggc ttatttcaaa gaacatcgaa   840
aagagcctta acgaggcctt caagcctata ggcatttcgg actggaactc actcttctgg   900
attgcacacc caggtggccc tgctattctg gaccaagtag aggccaagtt ggcgttgaag   960
ccggagaaat tagaagcgac aaggcaagtg ttgtcagatt acggcaacat gtcgagtgcg  1020
tgtgtcttgt ttatttttgga cgaggtgagg aggaagtcag ctgagaaagg actgagaca   1080 actggagaag gactggaatg gggtgtgcta tttggatttg gcctggcct cacggtggag   1140 accgtcgtgc ttcacagcgt ggctgcttga                                    1170
```

<210> SEQ ID NO 37
<211> LENGTH: 1179
<212> TYPE: DNA
<213> ORGANISM: Vitis pseudoreticulata

<400> SEQUENCE: 37

```
atggcctccg ttgaagaaat tagaaatgct caaagagcta agggtccagc tactattttg    60
gctattggta ctgctactcc agatcattgt gtttaccaat ctgattacgc cgactactac   120
ttcagagtta ctaagtctga acacatgacc gaattgaaga aaaagttcaa cagaatctgc   180
gacaagtcca tgatcaagaa gagatatatc cacttgaccg aagaaatgtt ggaagaacat   240
ccaaacattg tgcttatat ggctccatcc ttgaacatca acaagaaat tatcactgcc   300 gaagttccaa agttgggtaa agaagctgct ttgaaggctt tgaaagaatg ggtcaacct   360 aagtctaaga tcacccattt ggttttttgt actacctctg gtgttgaaat gccaggtgct   420
gattacaaat ggctaactt gttgggtttg gaaacctctg ttagaagagt tatgttgtac   480
catcaaggtt gttatgctgg tggtactgtt ttgagaactg ctaaagattt ggctgaaaac   540
```

```
aatgctggtg ctagagtttt ggttgtttgc tctgaaatta ccgttgttac tttcagaggt    600
ccatctgaag atgctttgga ttctttggtt ggtcaagctt gtttggtga tggttctgct     660 gctgttatag ttggttctga tccagatatc tccatcgaaa gacctttgtt ccaattggtt    720
tcagctgctc aaactttcat tccaaattct gctggtgcaa ttgctggtaa cttgagagaa    780
gttggtttga cttttcattt gtggccaaac gttccaactt tgatctccga aaacattgaa    840
aactgtttga ccaaggcctt tgatccaatc ggtatttctg attggaattc cttgttctgg    900
attgctcatc caggtggtcc agcaattttg gatgctgttg aagctaaggt tggtttggat    960
aagcaaaagt tgaaggccac cagacacatt ttgtctgaat acggtaatat gtcctctgcc   1020
tgcgttttgt ttattttgga cgaaatgaga aagaagtcct tgaaagaagg taagactact   1080
acaggtgaag gtttggattg gggtgttttg ttcggttttg gtccaggttt gactattgaa   1140
actgttgtct tgcattccgt tggtactgat tctaactga                          1179

<210> SEQ ID NO 38
<211> LENGTH: 1179
<212> TYPE: DNA
<213> ORGANISM: Vitis vinifera

<400> SEQUENCE: 38
atggcctctg ttgaagaatt cagaaatgct caaagagcta aggtccagc taccattttg      60 gctattggta ctgctactcc agatcattgt gtttaccaat ctgattacgc cgactactac    120
ttcagagtta ctaagtctga acacatgacc gaattgaaga aaaagttcaa cagaatctgc    180
gacaagtcca tgatcaagaa gagatatatc cacttgaccg aagaaatgtt ggaagaacat    240
ccaaacattg tgcttatat ggctccatcc ttgaacatca gacaagaaat tatcactgcc    300
gaagttccaa gattgggtag agatgctgct ttgaaggctt gaaagaatg gggtcaacct    360 aagtctaaga tcacccattt ggttttctgt actacctctg gtgttgaaat gccaggtgct    420
gattacaaat tggctaactt gttgggtttg gaaacttccg ttagaagagt tatgttgtac    480
catcaaggtt gttatgctgg tggtactgtt ttgagaactg ctaaagattt ggctgaaaac    540
aatgctggtg ctagagtttt ggttgtttgc tctgaaatta ccgttgttac tttcagaggt    600
ccatctgaag atgctttgga ttctttggtt ggtcaagctt gtttggtga tggttcttct    660 gctgttatag ttggttctga tccagatgtc tctatcgaaa gacctttgtt ccaattggtt    720
tctgctgctc aaactttcat tccaaattct gctggtgcaa ttgctggtaa cttgagagaa    780
gttggtttga cttttcattt gtggccaaac gttccaactt tgatctccga aaacattgaa    840
aagtgtttga cccaagcttt cgatccattg ggtatttctg attggaattc cttgttctgg    900
attgctcatc caggtggtcc agcaattttg gatgctgttg aagctaaatt gaacttggaa    960
aagaagaagt tggaagccac cagacatgtt ttgtctgaat acggtaatat gtcctctgct   1020
tgcgttttgt tcattttgga cgaaatgaga aaaaagtcct tgaagggtga aaaggctact   1080
actggtgaag gtttggattg gggtgttttg ttcggttttg gtccaggttt gactattgaa   1140
actgttgtct tgcattctgt tccaaccgtt accaattga                          1179

<210> SEQ ID NO 39
<211> LENGTH: 1179
<212> TYPE: DNA
<213> ORGANISM: Malus domestica

<400> SEQUENCE: 39
```

```
atggctacta ccgctgcttc ttctttacaa atggcaactg ctagaccatg catctcttca      60
tctagaagag cttttggttc ttctaccgct atgttgaatg gtaactttaa ggttgcttcc     120
tggaccaaat tatcttccgc ttgtcatatc tcctctgtcc aatcttttca aagatgcttc     180
acctcctcat ctatgaagtt ggataagttc gttactaagg ctatggctgg tgcttctgaa     240
aacaaaccag tttctggttt gccaatcaac ttgaaaggta agagagcttt cattgctggt     300
gttgctgatg ataatggtta tggttgggct attgctaaat cttTggctgc tgctggtgct     360
gaaattttgg ttggtacttg ggttccagcc ttgaatattt tcgaatcctc tttgagaaga     420
ggtaagttcg acgaatctag aattttgcca gatggttcct tgatggaaat cactaaggtt     480
tatccattgg atgccgtttt cgataaccca gaagatgttc agaagaaat caagaccaac      540
aaaagatacg ctggttcctc taattggact gttcaagaag ctgctgaatg cgttaagaat     600
gatttcggtt ccatcgatgt tttggttcac tctttggcta atggtccaga agttgttaag     660
cctttgttgg aaacttctag aaagggttac ttggctgcta tttctgcttc atcttactcc     720
tacgtcagtt tgttgaaaca cttcttgcca attatcaacc aggtggttc  ttccatttct      780
ttgacttaca ttgcctccga agaatcatt ccaggttatg gtggtggtat gtcatctgct      840
aaagctgctt tggaatctga tacaagagtt ttggcttttg aagccggtag aaagaaggg t    900
attagagtta ataccatttc cgctggtcca ttgagatcaa gagctgcaaa agctattggt     960
ttcatcgata tgatgatcga ctactcttct gctaatgccc cattggaaaa agaattgtct    1020
gctgaagaag ttggtaacac tgctgctttt ttggcttctc cattggcttc agctattact    1080
ggtggtgtta tctatgttga caatggtttg aatgctatgg gtgttggtgt tgactctcca    1140
atcttcgaaa atttgaacat tccaaaggcc caacattaa                           1179
```

<210> SEQ ID NO 40  
<211> LENGTH: 1179  
<212> TYPE: DNA  
<213> ORGANISM: Malus domestica

<400> SEQUENCE: 40

```
atggctacta ccgctgcttc ttctttacaa atggcaactg ctagaccatg catctcttca      60
tctagaagag cttttggttc ctcctccaaa atgttgaacg ataactttaa ggttgcctcc     120
tggtctaagt tatcttctac ttgtcatacc tcctccgtcc aatcttttca aagatccttt     180
acctcctcat ccatgaagat ggataagttc gttactagag ctatggctgg tgcttctgaa     240
aacaaaccag tttctggttt gccaatcgat ttgaaaggta agagagcttt cattgctggt     300
gttgctgatg ataatggtta tggttgggct attgctaaat cttTggctgc tgctggtgct     360
gaaattttgg ttggtacttg ggttccagcc ttgaatattt tcgaatcctc tttgagaaga     420
ggtaagttcg atgaatctag agttttgcca gatggttcct tgatggaaat tactaaggtt     480
tacccattgg atgccgtttt cgataatcca gaagatgttc cagaagaaat caagaccaac     540
aaaagatacg ctggttcttc taactggact gttcaagaag ctgctgaatg tgttaagaac     600
gatttcggtt ccattgatat cttggtccat tctttggcta atggtccaga agttgttaag     660
cctttgttgg aaacttctag aaagggttac ttggctgcta tttctgcttc atcttactcc     720
tacgtcagtt tgttgaaaca cttcttgcca attatcaacc aggtggttc  ttccatttct      780
ttgacttaca ttgcctccga agaatcatt ccaggttatg gtggtggtat gtcatctgct      840
aaagctgctt tggaatctga tacaagagtt ttggcttttg aagccggtag aaagaaggg t    900
attagagtta acacaatttc cgctggtcca ttgagatcaa gagctgcaaa agctattggt     960
```

```
ttcatcgata tgatgatcga ctactcttct gctaatgccc cattggaaaa agaattgtct    1020
gctgatgaag ttggtaacac tgctgctttt ttggcttctc cattggcttc agctattact    1080
ggtggtgtta tctatgttga caatggtttg aatgctatgg gtgttggtgt tgactctcca    1140
atcttcgaaa atttgaacat tccaaaggcc caacattaa                           1179

<210> SEQ ID NO 41
<211> LENGTH: 1047
<212> TYPE: DNA
<213> ORGANISM: Rubus idaeus

<400> SEQUENCE: 41
atggcttctg gtggtgaaat gcaagtctct aacaagcaag ttatcttcag agattacgtt      60
accggtttcc caaagaatc cgatatggaa ttgaccacca gatccattac tttgaaattg      120
ccacaaggtt ctaccggttt gttgttgaaa aacttgtact tgtcttgcga cccttacatg     180
agagctagaa tgactaatca tcacagattg tcctacgtcg attcttttaa accaggttcc     240
ccaattattg gttacggtgt tgctagagtt ttggaatctg gtaatccaaa gtttaaccca     300
ggtgatttgg tttgggggttt tactggttgg gaagaatact ctgttattac cgctactgaa    360
tccttgttca agatccataa taccgatgtc ccattgtctt actacactgg tttgttgggt    420
atgccaggta tgactgctta tgctggtttt tacgaaattt gctctccaaa aaagggtgaa    480
accgtttatg tttctgctgc ttcaggtgct gttggtcaat tggtcggtca atttgctaag    540
ttgactggtt gttatgttgt tggttctgcc ggttctaaag aaaaggttga tttgttgaag    600
aacaagttcg gtttcgatga agccttcaac tacaagaag aagctgattt ggacgctgct     660
ttgagaagat attttccaga tggtatcgac atctacttcg aaaatgttgg tggtaagatg    720
ttggatgctg ttttgccaaa tatgagacca aagggtagaa ttgctgtttg cggtatgatt    780
tcccaataca acttggaaca accagaaggt gttagaaact tgatggcttt gatcgttaag    840
caagtcagaa tggaaggttt catggttttc tcttactacc acttgtacgg taaattcttg    900
gaaactgtct tgcccttacat caagcaaggt aagattacct acgttgaaga tgttgttgat    960
ggtttggata atgctccagc tgctttaatt ggtttgtact ctggtagaaa cgtcggtaag    1020
caagttgttg ttgtttccag agaatga                                        1047

<210> SEQ ID NO 42
<211> LENGTH: 2037
<212> TYPE: DNA
<213> ORGANISM: Eubacterium ramulus

<400> SEQUENCE: 42
atggccgaaa agaatcaata cttcccacac ttgtttgaac cattgaaggt tggttctaag      60
accatcaaga acagaattga agctgctcca gctttgtttg ctttcgaaca ttacattgaa     120
ttgaacccag atccattcgg ttacactact ccagttccag aaagagcttt tagaatgttg    180
gaagctaaag ctaaaggtgg tgctggtata gtttgtttgg gtgaattgtc tccaaaccac    240
gaatacgata gagatttcc attcgaacca tacttggact tcacttccag atccgataag    300
caattcgaaa tcatgaaaga aaccgccgaa atgatcaaat cttacggtgc tttttccaatg    360 ggtgaattat tgtcttgtgg tgaaatcaag accaacatcg gtgatggtat taacccaaaa    420
ggtccatctg aaaaggattt gccagatggt tctcatgttg aagcctttac caagaagaa    480 atcttgtcct gctaccaaga ttacgttact gcttgtaaat ggtttcaagc tgctggttgg    540
```

```
gaaggtatta tgattcattg tggtcatggt tggttgccag ctcaattttt gtctccacaa    600
tacaacaaga gaaccgatga atacggtggt tcttttgaaa acagagctag attcaccgtc    660
gacttgttga aaactgttag agaagctatg ggtccagatt cgtcattga atcagagtc     720
tcttcctctg aacatttgcc tggtggttta gaattggaag atgctgttaa ttactgcaag    780
ttgtgcgaac cttacatcga tatgatccat gtttcttgcg gtcactactt gtcatcttct    840
agatcatggg aattcactac tgcttatgct ccacatggtc aaatattga accagctgct     900
gttatcaagc aaaacgtttc tattccagtt gctgctgttg gtggtatcaa ttctccagaa    960
caagctgaag aagctattgc ctctggtaag attgatatgg tttctatggg tagacaattc   1020
ttcgctgatc cagcatttcc taacaaagca aaagaaggtc acgctgacga aattagaaga   1080
tgtttgagat gtggtagatg ttacccaggt ccatcaggtg aacacgaaac tgaaatttgg   1140
actgttaagt tcccaccatt ggattcttgt accattaacc catatgatgt ttggccagct   1200
tctcatcata aggttttacc agatagaatg ccaaaaccag aagcctctag aaaggttttg   1260
gttgtaggtg gtggttgcgg tggtttacaa actgctatta ctgcttctga tagaggtcac   1320
caagttatct tgtgtgaaaa gtctggtgtt ttgggtggtt tgattaactt cactgatcat   1380
accgatcaca aggtcgatat cagaaacttc aaggatttgt tgatcagaga tgttgaaaaa   1440
agaccaatcg aagtcagatt gaactgtgaa gttaccccag aattgattag agaaattgct   1500
ccagaagctt tgttttggc tgttggttct gatgatttga tcttgccaat tgaaggtatc   1560
gaaaacgctg ttactgctat ggatgtttac tctaatgatt tcgccggttt gggtaaatcc   1620
actatagtat tgggtggtgg tttggttggt tgtgaagctg ctgctgatta tattgatcat   1680
ggtgttgaaa ccaccatcgt cgaaatgaag ggtgctttga tgccagaaac tactggtttg   1740
tatagaaccg ctgttcacga tttcattgat aagaatggtg gtaagtacga agttaacgcc   1800
aaggttgtta aggttggtaa ggattttgtt gttgccgaac aagacggtaa agaaattacc   1860
attaaggccg attctgttgt caatgcaatg ggtagaagag cacatgctac tgaagccttg   1920
gaaacagcta tcaaagaagc tggtattcca gtctggaaaa ttggtgattg tgttagagct   1980
agacaaatcg gtgacgctgt aagagaaggt tggactgcag ctatggaaat tatctga     2037
```

<210> SEQ ID NO 43
<211> LENGTH: 762
<212> TYPE: DNA
<213> ORGANISM: Saccharomyces cerevisiae

<400> SEQUENCE: 43

```
atgtactttg atgaagaaca attgctaaaa tatactatat atgcctatag attatccttt     60
tttgtaggca tttgctcact tttcatagca aaaagttgtc taccagaatt tcttcaatat    120
ggtaaaacct accggcccaa agagaattca agtactcaa gcattttaga acgaatcaag    180
aagttcacag ttccaaaggc gtattttcc cattttact atttggctac ctttctatcc     240
ttagtcacct tatatttcta tcctaaattc cccatcgttt ggatcatatt tggacactca    300
ttgcgccgac tttatgaaac gctttatgta ctacattata caagcaattc taggatgaat    360
tggtcccatt atctagtcgg tatatggttc tattccgtac tcttgttaat tcttaatata    420
tcactgtaca agaactccat tccaaatacg ttaaacatga atgctttcat catattctgc    480
atagcatctt gggatcagta caaaaatcat gttattctgg ccaatctggt taaatattcg    540
ctgccaacag gaaggctttt caggttggta tgctgtcctc attatctcga tgaaataatc    600
atttattcta ctctgttgcc ctatgaacaa gaattttacc taacactagt ttgggtaatc    660
```

```
acaagtttga ctatatccgc attggaaaca aaaaattatt acaggcacaa atttaaagac      720
aatcacgtag cccctacgc cataatacct tttataatct ag                         762
```

<210> SEQ ID NO 44
<211> LENGTH: 1050
<212> TYPE: DNA
<213> ORGANISM: Malus domestica

<400> SEQUENCE: 44

```
atggctgctt ctaccgaagg tgttatctct aacaagcaag ttatcttgaa ggattacgtt       60
accggtttcc caaagaatc cgatatgcaa ttgactactg ctaccactaa gttgaaattg       120
cctgaaggtt ctaaaggtgt cttggtcaaa acttgtact tgtcttgtga cccttacatg       180
agatccagaa tgacaaaaag agaaccaggt gcttcttacg ttgattcatt tgatgctggt       240
tctccaatcg ttggttatgg tgttgctaaa gttttggaat ctggtgaccc aaagtttaag       300
aagggtgatt tgatttgggg tatgactggt tgggaagaat actctgttat tacctctacc       360
gaatccttgt tcaagatcca acatatcgat gtcccattgt cttactacac tggtattttg       420
ggtatgccag gtatgacagc ttatgctggt ttttacgaaa tctgcaatcc aaaaaagggt       480
gaaaccgttt tgtttctgc tgcttctggt gctgttggtc aattggtcgg tcaatttgct       540
aagttgttgg ttgttatgt tgttggttct gccggttcca agaaaaaggt tgatttgttg       600
aagaacaagt tcggtttcga taacgccttc aactacaaag aagaaccaga tttggacgct       660
gctttgaaga gatatttcc agaaggtatc gacatctact tcgaaaatgt tggtggtaag       720
atgttggatg ctgttttgcc aaatatgaga gttcatggta gaattgctgt tgcggtttg       780 atctcccaat acaacattga tgaaccagaa ggttgcagaa acttgatgta cttgattatc       840
aagcaagtca gaatgcaagg tttcttggtt ttctcttact accacttgta cgaaaagttc       900
ttggaaatgg ttttgccagc catcaaagaa ggtaaattga cctacgttga agatgtcgtt       960
gaaggtttag aatctgctcc agctgcttta attggtttgt atgctggtag aaacgttggt       1020
aagcaagttg ttgttgtctc cagagaatga                                       1050
```

<210> SEQ ID NO 45
<211> LENGTH: 933
<212> TYPE: DNA
<213> ORGANISM: Arabidopsis thaliana

<400> SEQUENCE: 45

```
atgaaggtca ccgtcgtttc tagatcaggt agagaagttt tgaaagcccc attggatttg       60
ccagattctg ctactgttgc tgacttgcaa gaagcctttc ataagagagc taagaagttc      120
tacccatcca gacaaagatt gactttgcca gttactccag ttctaaaga taagccagtt       180 gtcttgaact ccaagaagtc cttgaaagaa tactgtgacg gtaacaacaa ctccttgact      240
gttgttttta aggatttggg tgcccaagtt tcttacagaa cttttgttctt cttcgaatac      300 ttgggtcctt tgttgatcta cccagttttt tactacttcc cagtctacaa gttttttgggt       360 tacggtgaag attgcgttat ccatccagtt caaacttacg ctatgtacta ctggtgtttc      420
cactacttca agagaatctt ggaaaccttc ttcgtccaca gatttctca tgctacttct       480 ccaattggta acgttttcag aaactgtgcc tattactggt ctttcggtgc ttatattgct      540
tactacgtta ccaccccatt atacactcca gtttcagact gcaaatgaa gattggtttt      600 ggtttcggtt tggtctgtca agttgctaac ttctactgcc atatcttgtt gaagaacttg      660
```

```
agagatccat ctggtgctgg tggttatcaa attccaagag ttttttgtt caacatcgtt    720 acctgtgcta actacactac cgaaatctat caatggttgg gtttcaacat tgccactcaa    780
actattgctg gttacgtttt tttggctgtt gccgctttga ttatgactaa ttgggctttg    840
ggtaagcact ccagattgag aaagattttc gatggtaaag acggtaagcc aaagtatcca    900
agaagatggg ttattttgcc accattcttg taa                                 933

<210> SEQ ID NO 46
<211> LENGTH: 933
<212> TYPE: DNA
<213> ORGANISM: Gossypium hirsutum

<400> SEQUENCE: 46
atgaaggtca ccttggtcag tagatcaggt agagaattca ttaagggtgg tttggaattg     60
aacgattctg ctactgttgc tgacttgcaa gaagctattc ataagagaac taagaagttc    120
tacccatcca gacaaagatt gactttgcca gttccatctg gttctagaga aagaccagtt    180
atcttgaact acaagaagtc cttgaaggat tactgtgacg gtaacgaaaa cactttgacc    240
atcgttttta aggacttggg tccacaagtt tcttacagaa ctttgttctt cttcgaatat    300
ttgggtccat tgatcttgta cccagttttc tattacttcc cagtctacaa gtacttcggt    360
tacgaagaaa agagagttat ccacccagtt caaacttatg ccttgtacta ctggtgtttc    420
cactacttca gagaattat ggaaaccttc ttcatccaca gattctctca tgctacttct    480
ccattgtcta acgttttcag aaactgtgct tactactgga ctttcggttc ttatattgcc    540
tactacgtta accacccatt atacactcca gtttcagact tgcaaatgaa gattggtttt    600
ggtttcggta tcgtttgtca attggctaac ttctactgcc acatcatctt gaagaatttg    660
agatcaccag atggttctgg tggttaccaa attccaagag ttttttgtt caacatcgtt    720 acctgtgcta actacactac cgaaatctat caatggttgg gtttcaacat tgctactcaa    780
acagttgctg gttacgtttt cttggttgtt gctacctcta ttatgactaa ttgggccttg    840
gctaaacaca gaagattgaa gaaattattc gacggtaagg acggtagacc aaagtatcca    900
agaagatggg ttattttgcc accattcttg taa                                 933

<210> SEQ ID NO 47
<211> LENGTH: 933
<212> TYPE: DNA
<213> ORGANISM: Malus domestica

<400> SEQUENCE: 47
atgaaggtca ccgtcgtttc tagatcaggt agagaagttg ttaagggtgg tttggaattg     60
tctgattctg ctactgttgc tgacttgcaa gatgctattc ataagagaac taagaagttc    120
tacccagcca gacaaagatt gactttgcca gttcaaccag ttctaaaga aagaccagtt    180 gtcttgtctt acaagaagtc attgcaagac tacatctccg gtaactctga aacttgact     240 gttgttttca aggacttggg tccacaagtt tcttacagaa ctttgttctt cttcgaatat    300
ttgggtccat tgatcttgta cccaatcttc tactacttcc cagtttacga ttacttgggt    360
ttcaagggtg atagagttat ccatccagtt caaacttatg ccttgtacta ctggtgtttc    420
cactacttca gagaattat ggaaaccttc ttcgtccaca gattctctca tgctacttct    480
ccattgtcta acgttttcag aaactgtgct tactattggt ctttcggtgc ttttattgct    540
tactacttga accacccatt atacactcca gtttcagact tgcaaatgaa gattggtttc    600
ggtattggta tcatctgcca aatctctaac ttctactgcc acatcttgtt gagaaacttg    660
```

```
agatcaccag atggtaatgg tggttaccaa attccaagag gtttcttgtt caacatcgtt      720
acctgtgcta actacactac cgaaatctat caatggttgg gttttaacat tgccactcaa      780
acagttgccg gttacatttt tttgatcgtt gctgcttcta tcatgaccaa ttgggctttg      840
gctaaacaca gaagattgaa gaaaatcttc gatggtaagg acggtagacc aaagtatcca      900
agaagatggg ttattttgcc accattcttg taa                                   933
```

<210> SEQ ID NO 48
<211> LENGTH: 960
<212> TYPE: DNA
<213> ORGANISM: Kluyveromyces lactis

<400> SEQUENCE: 48

```
atgtccgcct cctcctccat tttcatcaaa tctagatcca agtccttgaa ggacgttaag       60
ttagaagttc aactgaaaaa caccttgacc taccaatccg ttttacaaca aatctccaag      120
tccaaccaca acatctccgt taatagattg agattgtcct acttgaaaga aggtaagcaa      180
gttgctattg gtccatccga attgaatgat gttggtaaga gaacaccttt cgactctgtt      240
aatgaatggt atgtcaaaga cttgggtcca caaattagtt ggagattggt tttcttcatc      300
gaatatttgg gtccaatctt gatccactcc ttggtttatt tgttgtcttt gaacgctacc      360
gtcagagata agtccattc taagaatgtt ccatacaacg atttcttcaa caagttcatc      420
tacagattga tcatggtcca ctacttgaag agagaattcg aaaccttgtt catccattcc      480
ttctcattgg aaactatgcc tttgttcaac ttgttcaaaa actccttcca ctactggatc      540
ttgaacggtt tgatttcttt gggttacttc ggttacggtt ttccatttgc taacaagacc      600
ttgtacagag tttactccgc tttgaagatt tccgatttca gagttttgac tgccttgttc      660
ggtttgtctg aaatgtttaa cttctacatc cacgtcgctt tgagaagatg gggtgatgaa      720
caaaaaagaa acggtgttac taagagagtc ccattgaatt ctggttttgtt taagttgttg      780 gttgccccaa actacacttt tgaatcttgg gcttggatgt tcttcacctt gttgttcaag      840
ttgaatttgt tctccgtctt gttcttggtt gtttccgttg ttcaaatgta cttgtgggcc      900
caaaagaaaa acaagaagta cggtacaaag agagccttct tgattccatt cttgttctaa      960
```

<210> SEQ ID NO 49
<211> LENGTH: 390
<212> TYPE: PRT
<213> ORGANISM: Hypericum androsaemum

<400> SEQUENCE: 49

```
Met Val Thr Val Glu Glu Val Arg Lys Ala Gln Arg Ala Glu Gly Pro
1               5                   10                  15

Ala Thr Val Met Ala Ile Gly Thr Ala Val Pro Pro Asn Cys Val Asp
                20                  25                  30

Gln Ala Thr Tyr Pro Asp Tyr Tyr Phe Arg Ile Thr Asn Ser Glu His
            35                  40                  45

Lys Ala Glu Leu Lys Glu Lys Phe Gln Arg Met Cys Asp Lys Ser Gln
        50                  55                  60

Ile Lys Lys Arg Tyr Met Tyr Leu Asn Glu Glu Val Leu Lys Glu Asn
65                  70                  75                  80

Pro Asn Met Cys Ala Tyr Met Ala Pro Ser Leu Asp Ala Arg Gln Asp
                85                  90                  95

Ile Val Val Val Glu Val Pro Lys Leu Gly Lys Glu Ala Ala Val Lys
                100                 105                 110
```

```
Ala Ile Lys Glu Trp Gly Gln Pro Lys Ser Lys Ile Thr His Leu Val
        115                 120                 125

Phe Cys Thr Thr Ser Gly Val Asp Met Pro Gly Ala Asp Tyr Gln Leu
    130                 135                 140

Thr Lys Leu Leu Gly Leu Arg Pro Ser Val Lys Arg Leu Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Lys Gly Ala Arg Val Leu Val Val Cys Ser Glu
            180                 185                 190

Ile Thr Ala Val Thr Phe Arg Gly Pro Thr Asp Thr His Leu Asp Ser
        195                 200                 205

Leu Val Gly Gln Ala Leu Phe Gly Asp Gly Ala Ala Ala Ile Ile Ile
    210                 215                 220

Gly Ser Asp Pro Ile Pro Glu Val Glu Lys Pro Leu Phe Glu Leu Val
225                 230                 235                 240

Ser Ala Ala Gln Thr Ile Leu Pro Asp Ser Glu Gly Ala Ile Asp Gly
                245                 250                 255

His Leu Arg Glu Val Gly Leu Thr Phe His Leu Leu Lys Asp Val Pro
            260                 265                 270

Gly Leu Ile Ser Lys Asn Val Glu Lys Ser Leu Thr Glu Ala Phe Lys
        275                 280                 285

Pro Leu Gly Ile Ser Asp Trp Asn Ser Leu Phe Trp Ile Ala His Pro
    290                 295                 300

Gly Gly Pro Ala Ile Leu Asp Gln Val Glu Ala Lys Leu Ser Leu Lys
305                 310                 315                 320

Pro Glu Lys Leu Arg Ala Thr Arg His Val Leu Ser Glu Tyr Gly Asn
                325                 330                 335

Met Ser Ser Ala Cys Val Leu Phe Ile Leu Asp Glu Met Arg Arg Lys
            340                 345                 350

Ser Lys Glu Asp Gly Leu Lys Thr Thr Gly Glu Gly Ile Glu Trp Gly
        355                 360                 365

Val Leu Phe Gly Phe Gly Pro Gly Leu Thr Val Glu Thr Val Val Leu
    370                 375                 380

His Ser Val Ala Ile Asn
385                 390

<210> SEQ ID NO 50
<211> LENGTH: 398
<212> TYPE: PRT
<213> ORGANISM: Petroselinum crispum

<400> SEQUENCE: 50

Met Ala Asn His His Asn Ala Glu Ile Glu Glu Ile Arg Asn Arg Gln
1               5                   10                  15

Arg Ala Gln Gly Pro Ala Asn Ile Leu Ala Ile Gly Thr Ala Thr Pro
                20                  25                  30

Ser Asn Cys Val Tyr Gln Ala Asp Tyr Pro Asp Tyr Tyr Phe Arg Ile
            35                  40                  45

Thr Asn Ser Glu His Met Thr Asp Leu Lys Leu Lys Phe Lys Arg Met
        50                  55                  60

Cys Glu Lys Ser Met Ile Arg Lys Arg Tyr Met His Ile Thr Glu Glu
65                  70                  75                  80

Tyr Leu Lys Glu Asn Pro Asn Val Cys Ala Tyr Glu Ala Pro Ser Leu
```

```
                  85                  90                  95

Asp Ala Arg Gln Asp Leu Val Val Glu Val Pro Arg Leu Gly Lys
            100                 105                 110

Glu Ala Ala Ser Lys Ala Ile Lys Glu Trp Gly Gln Pro Lys Ser Lys
        115                 120                 125

Ile Thr His Leu Ile Phe Cys Thr Thr Ser Gly Val Asp Met Pro Gly
    130                 135                 140

Ala Asp Tyr Gln Leu Thr Lys Leu Leu Gly Leu Arg Pro Ser Val Lys
145                 150                 155                 160

Arg Phe Met Met Tyr Gln Gln Gly Cys Phe Ala Gly Gly Thr Val Leu
                165                 170                 175

Arg Leu Ala Lys Asp Leu Ala Glu Asn Asn Ala Gly Ala Arg Val Leu
            180                 185                 190

Val Val Cys Ser Glu Ile Thr Ala Val Thr Phe Arg Gly Pro Ser Asp
        195                 200                 205

Ser His Leu Asp Ser Leu Val Gly Gln Ala Leu Phe Gly Asp Gly Ala
    210                 215                 220

Ala Ala Val Ile Leu Gly Ser Asp Pro Asp Leu Ser Val Glu Arg Pro
225                 230                 235                 240

Leu Phe Gln Leu Ile Ser Ala Ala Gln Thr Ile Leu Pro Asp Ser Asp
                245                 250                 255

Gly Ala Ile Asp Gly His Leu Arg Glu Val Gly Leu Thr Phe His Leu
            260                 265                 270

Leu Lys Asp Val Pro Gly Leu Ile Ser Lys Asn Ile Glu Lys Ser Leu
        275                 280                 285

Lys Glu Ala Phe Gly Pro Ile Gly Ile Ser Asp Trp Asn Ser Leu Phe
    290                 295                 300

Trp Ile Ala His Pro Gly Gly Pro Ala Ile Leu Asp Gln Val Glu Leu
305                 310                 315                 320

Lys Leu Gly Leu Lys Glu Glu Lys Met Arg Ala Thr Arg Gln Val Leu
                325                 330                 335

Ser Asp Tyr Gly Asn Met Ser Ser Ala Cys Val Leu Phe Ile Leu Asp
            340                 345                 350

Glu Met Arg Lys Lys Ser Ile Glu Gly Lys Ala Thr Thr Gly Glu
        355                 360                 365

Gly Leu Asp Trp Gly Val Leu Phe Gly Phe Gly Pro Gly Leu Thr Val
    370                 375                 380

Glu Thr Val Val Leu His Ser Val Pro Ala Thr Phe Thr His
385                 390                 395

<210> SEQ ID NO 51
<211> LENGTH: 389
<212> TYPE: PRT
<213> ORGANISM: Petunia hybrida

<400> SEQUENCE: 51

Met Val Thr Val Glu Glu Tyr Arg Lys Ala Gln Arg Ala Glu Gly Pro
1               5                   10                  15

Ala Thr Val Met Ala Ile Gly Thr Ala Thr Pro Thr Asn Cys Val Asp
            20                  25                  30

Gln Ser Thr Tyr Pro Asp Tyr Tyr Phe Arg Ile Thr Asn Ser Glu His
        35                  40                  45

Lys Thr Asp Leu Lys Glu Lys Phe Lys Arg Met Cys Glu Lys Ser Met
    50                  55                  60
```

```
Ile Lys Lys Arg Tyr Met His Leu Thr Glu Glu Ile Leu Lys Glu Asn
 65                  70                  75                  80

Pro Ser Met Cys Glu Tyr Met Ala Pro Ser Leu Asp Ala Arg Gln Asp
                 85                  90                  95

Ile Val Val Glu Val Pro Lys Leu Gly Lys Glu Ala Ala Gln Lys
                100                 105                 110

Ala Ile Lys Glu Trp Gly Gln Pro Lys Ser Lys Ile Thr His Leu Phe
            115                 120                 125

Phe Cys Thr Thr Ser Gly Val Asp Met Pro Gly Cys Asp Tyr Gln Leu
        130                 135                 140

Thr Lys Leu Leu Gly Leu Arg Pro Ser Val Lys Arg Leu Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Lys Gly Ala Arg Val Leu Val Val Cys Ser Glu
                180                 185                 190

Ile Thr Ala Val Thr Phe Arg Gly Pro Asn Asp Thr His Leu Asp Ser
            195                 200                 205

Leu Val Gly Gln Ala Leu Phe Gly Asp Gly Ala Gly Ala Ile Ile Ile
210                 215                 220

Gly Ser Asp Pro Ile Pro Gly Val Glu Arg Pro Leu Phe Glu Leu Val
225                 230                 235                 240

Ser Ala Ala Gln Thr Leu Leu Pro Asp Ser His Gly Ala Ile Asp Gly
                245                 250                 255

His Leu Arg Glu Val Gly Leu Thr Phe His Leu Leu Lys Asp Val Pro
            260                 265                 270

Gly Leu Ile Ser Lys Asn Ile Glu Lys Ser Leu Glu Glu Ala Phe Lys
            275                 280                 285

Pro Leu Gly Ile Ser Asp Trp Asn Ser Leu Phe Trp Ile Ala His Pro
            290                 295                 300

Gly Gly Pro Ala Ile Leu Asp Gln Val Glu Ile Lys Leu Gly Leu Lys
305                 310                 315                 320

Pro Glu Lys Leu Lys Ala Thr Arg Asn Val Leu Ser Asp Tyr Gly Asn
                325                 330                 335

Met Ser Ser Ala Cys Val Leu Phe Ile Leu Asp Glu Met Arg Lys Ala
                340                 345                 350

Ser Ala Lys Glu Gly Leu Gly Thr Thr Gly Glu Gly Leu Glu Trp Gly
            355                 360                 365

Val Leu Phe Gly Phe Gly Pro Gly Leu Thr Val Glu Thr Val Val Leu
            370                 375                 380

His Ser Val Ala Thr
385

<210> SEQ ID NO 52
<211> LENGTH: 398
<212> TYPE: PRT
<213> ORGANISM: Hordeum vulgare

<400> SEQUENCE: 52

Met Ala Ala Thr Met Thr Val Glu Glu Val Arg Asn Ala Gln Arg Ala
1               5                   10                  15

Glu Gly Pro Ala Thr Val Leu Ala Ile Gly Thr Ala Thr Pro Ala Asn
                20                  25                  30

Cys Val Tyr Gln Ala Asp Tyr Pro Asp Tyr Tyr Phe Lys Ile Thr Lys
            35                  40                  45
```

```
Ser Asp His Met Ala Asp Leu Lys Glu Lys Phe Lys Arg Met Cys Asp
 50                  55                  60
Lys Ser Gln Ile Arg Lys Arg Tyr Met His Leu Thr Glu Glu Ile Leu
 65                  70                  75                  80
Glu Glu Asn Pro Asn Met Cys Ala Tyr Met Ala Pro Ser Leu Asp Ala
                 85                  90                  95
Arg Gln Asp Ile Val Val Glu Val Pro Lys Leu Gly Lys Ala Ala
            100                 105                 110
Ala Gln Lys Ala Ile Lys Glu Trp Gly Gln Pro Arg Ser Lys Ile Thr
        115                 120                 125
His Leu Val Phe Cys Thr Thr Ser Gly Val Asp Met Pro Gly Ala Asp
    130                 135                 140
Tyr Gln Leu Thr Lys Met Leu Gly Leu Arg Pro Ser Val Lys Arg Leu
145                 150                 155                 160
Met Met Tyr Gln Gln Gly Cys Phe Ala Gly Gly Thr Val Leu Arg Leu
                165                 170                 175
Ala Lys Asp Leu Ala Glu Asn Asn Arg Gly Ala Arg Val Leu Val Val
            180                 185                 190
Cys Ser Glu Ile Thr Ala Val Thr Phe Arg Gly Pro His Glu Ser His
        195                 200                 205
Leu Asp Ser Leu Val Gly Gln Ala Leu Phe Gly Asp Gly Ala Ala Ala
    210                 215                 220
Val Ile Ile Gly Ala Asp Pro Asp Leu Ser Val Glu Arg Pro Leu Phe
225                 230                 235                 240
Gln Leu Val Ser Ala Ser Gln Thr Ile Leu Pro Asp Ser Glu Gly Ala
                245                 250                 255
Ile Asp Gly His Leu Arg Glu Val Gly Leu Thr Phe His Leu Leu Lys
            260                 265                 270
Asp Val Pro Gly Leu Ile Ser Lys Asn Ile Glu Arg Ala Leu Glu Glu
        275                 280                 285
Ala Phe Lys Pro Leu Gly Ile Asp His Trp Asn Ser Val Phe Trp Ile
    290                 295                 300
Ala His Gln Gly Gly Pro Ala Ile Leu Asp Met Val Glu Ala Lys Val
305                 310                 315                 320
Asn Leu Asn Lys Glu Arg Met Arg Ala Thr Arg His Val Leu Ser Glu
                325                 330                 335
Tyr Gly Asn Met Ser Ser Ala Cys Val Leu Phe Ile Met Asp Glu Met
            340                 345                 350
Arg Lys Arg Ser Ala Glu Asp Gly His Ala Thr Thr Gly Glu Gly Met
        355                 360                 365
Asp Trp Gly Val Leu Phe Gly Phe Gly Pro Gly Leu Thr Val Glu Thr
    370                 375                 380
Val Val Leu His Ser Val Pro Ile Ser Ala Gly Ala Thr Ala
385                 390                 395

<210> SEQ ID NO 53
<211> LENGTH: 390
<212> TYPE: PRT
<213> ORGANISM: Scutellaria baicalensis

<400> SEQUENCE: 53

Met Val Thr Val Glu Glu Phe His Arg Ala Thr Arg Ala Glu Gly Pro
1               5                  10                  15

Ala Thr Val Leu Ala Ile Gly Thr Ala Asn Pro Pro Asn Cys Val Glu
```

```
                  20                  25                  30
Gln Ser Thr Tyr Ala Asp Tyr Tyr Phe Arg Ile Cys Lys Ser Glu His
            35                  40                  45
Leu Thr Asp Leu Lys Lys Lys Phe Asp Arg Met Cys Glu Lys Ser Cys
 50                  55                  60
Ile Lys Lys Arg Tyr Met His Leu Thr Glu Glu Phe Leu Lys Glu Asn
 65                  70                  75                  80
Asp Asn Phe Thr Ala Tyr Glu Ala Pro Ser Leu Asp Ala Arg Gln Asp
                85                  90                  95
Ile Val Val Val Glu Ile Pro Lys Leu Gly Lys Glu Ala Ala Gln Lys
                100                 105                 110
Ala Ile Lys Glu Trp Gly Gln Pro Lys Ser Lys Ile Thr His Val Ile
            115                 120                 125
Phe Cys Thr Thr Ser Gly Val Asp Met Pro Gly Ala Asp Tyr Gln Ile
            130                 135                 140
Thr Lys Leu Leu Gly Leu Arg Pro Ser Val Lys Arg Phe Met Met Tyr
145                 150                 155                 160
Gln Gln Gly Cys Phe Ala Gly Gly Thr Val Leu Arg Met Ala Lys Asp
                165                 170                 175
Leu Ala Glu Asn Asn Ala Gly Ala Arg Val Leu Val Val Cys Ser Glu
                180                 185                 190
Ile Thr Ala Ile Thr Phe Arg Gly Pro Ser Asp Thr His Leu Asp Ser
                195                 200                 205
Leu Val Gly Gln Ala Leu Phe Gly Asp Gly Ala Ala Ala Val Ile Val
            210                 215                 220
Gly Ser Asp Pro Ile Val Gly Val Glu Arg Pro Leu Phe Gln Leu Val
225                 230                 235                 240
Ser Ala Ala Gln Thr Ile Leu Pro Asp Ser Glu Gly Ala Ile Asp Gly
                245                 250                 255
His Val Arg Glu Val Gly Leu Thr Phe His Leu Leu Lys Asp Val Pro
                260                 265                 270
Gly Leu Ile Ser Lys Asp Ile Glu Lys Ser Leu Lys Glu Ala Phe Ala
            275                 280                 285
Pro Leu Gly Ile Ser Asp Trp Asn Ser Leu Phe Trp Ile Val His Pro
            290                 295                 300
Gly Gly Pro Ala Ile Leu Asp Gln Val Gly Glu Lys Leu Gly Leu Lys
305                 310                 315                 320
Pro Glu Ile Met Val Pro Thr Arg His Val Leu Ser Glu Tyr Gly Asn
                325                 330                 335
Met Ser Ser Ala Cys Val Leu Phe Val Met Asp Glu Met Arg Lys Ala
                340                 345                 350
Ser Ala Lys Asp Gly Cys Thr Ser Thr Gly Glu Gly Lys Asp Trp Gly
            355                 360                 365
Val Leu Phe Gly Phe Gly Pro Gly Leu Thr Val Glu Thr Val Val Leu
            370                 375                 380
His Ser Val Pro Leu Asn
385                 390

<210> SEQ ID NO 54
<211> LENGTH: 391
<212> TYPE: PRT
<213> ORGANISM: Malus domestica

<400> SEQUENCE: 54
```

```
Met Val Thr Val Glu Val Arg Lys Ala Gln Arg Ala Glu Gly Pro
1               5                   10                  15

Ala Thr Val Met Ala Ile Gly Thr Ala Thr Pro Ser Asn Cys Val Asp
            20                  25                  30

Gln Ala Thr Tyr Pro Asp Tyr Tyr Phe Arg Ile Thr Asn Ser Glu His
            35                  40                  45

Lys Val Glu Leu Lys Glu Lys Phe Gln Arg Met Cys Asp Lys Ser Met
50                  55                  60

Ile Lys Lys Arg Tyr Met Tyr Leu Thr Glu Ile Leu Lys Glu Asn
65                  70                  75                  80

Pro Ser Val Cys Glu Tyr Met Ala Pro Ser Ile Asp Ala Arg Gln Asp
                85                  90                  95

Met Val Val Val Glu Val Pro Lys Leu Gly Lys Glu Ala Ala Thr Lys
            100                 105                 110

Ala Ile Lys Glu Trp Gly Gln Pro Lys Ser Lys Ile Thr His Leu Val
            115                 120                 125

Phe Cys Thr Thr Ser Gly Val Asp Met Pro Gly Ala Asp Tyr Gln Leu
        130                 135                 140

Thr Lys Leu Leu Gly Leu Arg Pro Ser Val Lys Arg Leu Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Lys Gly Ala Arg Val Leu Val Val Cys Ser Glu
            180                 185                 190

Ile Thr Ala Val Thr Phe Arg Gly Pro Ser Asp Thr His Leu Asp Ser
            195                 200                 205

Leu Val Gly Gln Ala Leu Phe Gly Asp Gly Ala Ala Ala Val Ile Ile
        210                 215                 220

Gly Ala Asp Pro Val Pro Glu Val Glu Lys Pro Leu Phe Glu Leu Val
225                 230                 235                 240

Ser Ala Ala Gln Thr Ile Leu Pro Asp Ser Gly Ala Ile Asp Gly
                245                 250                 255

His Leu Arg Glu Val Gly Leu Thr Phe His Leu Leu Lys Asp Val Pro
            260                 265                 270

Gly Leu Ile Ser Lys Asn Ile Glu Lys Ser Leu Asn Glu Ala Phe Lys
        275                 280                 285

Pro Ile Gly Ile Ser Asp Trp Asn Ser Leu Phe Trp Ile Ala His Pro
            290                 295                 300

Gly Gly Pro Ala Ile Leu Asp Gln Val Glu Ala Lys Leu Ala Leu Lys
305                 310                 315                 320

Pro Glu Lys Leu Glu Ala Thr Arg Gln Val Leu Ser Asp Tyr Gly Asn
                325                 330                 335

Met Ser Ser Ala Cys Val Leu Phe Ile Leu Asp Glu Val Arg Arg Lys
            340                 345                 350

Ser Ala Glu Lys Gly Leu Lys Thr Thr Gly Glu Gly Leu Glu Trp Gly
        355                 360                 365

Val Leu Phe Gly Phe Gly Pro Gly Leu Thr Val Glu Thr Val Val Leu
370                 375                 380

His Ser Val Gly Leu Thr Ala
385                 390

<210> SEQ ID NO 55
<211> LENGTH: 389
<212> TYPE: PRT
```

<213> ORGANISM: Malus domestica

<400> SEQUENCE: 55

Met Val Thr Val Glu Val Arg Lys Ala Gln Arg Ala Glu Gly Pro
1               5                   10                  15

Ala Thr Val Leu Ala Ile Gly Thr Ala Thr Pro Ser Asn Cys Val Asp
            20                  25                  30

Gln Ala Thr Tyr Pro Asp Tyr Tyr Phe Arg Ile Thr Asn Ser Glu His
            35                  40                  45

Lys Thr Glu Leu Lys Glu Lys Phe Gln Arg Met Cys Asp Lys Ser Met
50                  55                  60

Ile Lys Lys Arg Tyr Met Tyr Leu Thr Glu Glu Ile Leu Lys Glu Asn
65                  70                  75                  80

Pro Thr Val Cys Glu Tyr Met Ala Pro Ser Leu Asp Ala Arg Gln Asp
                85                  90                  95

Met Val Val Glu Val Pro Arg Leu Gly Lys Glu Ala Ala Thr Lys
            100                 105                 110

Ala Ile Lys Glu Trp Gly Gln Pro Lys Ser Lys Ile Thr His Leu Val
            115                 120                 125

Phe Cys Thr Thr Ser Gly Val Asp Met Pro Gly Ala Asp Tyr Gln Leu
130                 135                 140

Thr Lys Leu Leu Gly Leu Arg Pro Ser Val Lys Arg Leu Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Lys Gly Ala Arg Val Leu Val Val Cys Ser Glu
            180                 185                 190

Ile Thr Ala Val Thr Phe Arg Gly Pro Ser Asp Thr His Leu Asp Ser
            195                 200                 205

Leu Val Gly Gln Ala Leu Phe Gly Asp Gly Ala Ala Ala Val Ile Ile
210                 215                 220

Gly Ala Asp Pro Leu Pro Glu Val Glu Lys Pro Leu Phe Glu Leu Val
225                 230                 235                 240

Ser Ala Ala Gln Thr Ile Leu Pro Asp Ser Asp Gly Ala Ile Asp Gly
                245                 250                 255

His Leu Arg Glu Val Gly Leu Thr Phe His Leu Leu Lys Asp Val Pro
            260                 265                 270

Gly Leu Ile Ser Lys Asn Ile Glu Lys Ser Leu Asn Glu Ala Phe Lys
            275                 280                 285

Pro Ile Gly Ile Ser Asp Trp Asn Ser Leu Phe Trp Ile Ala His Pro
290                 295                 300

Gly Gly Pro Ala Ile Leu Asp Gln Val Glu Ser Lys Leu Ala Leu Lys
305                 310                 315                 320

Pro Glu Lys Leu Glu Ala Thr Arg Gln Val Leu Ser Asn Tyr Gly Asn
                325                 330                 335

Met Ser Ser Ala Cys Val Leu Phe Ile Leu Asp Glu Val Arg Arg Lys
            340                 345                 350

Ser Ala Glu Lys Gly Leu Lys Thr Thr Gly Glu Gly Leu Glu Trp Gly
            355                 360                 365

Val Leu Phe Gly Phe Gly Pro Gly Leu Thr Val Glu Thr Val Val Leu
370                 375                 380

His Ser Val Ala Ala
385

<210> SEQ ID NO 56
<211> LENGTH: 389
<212> TYPE: PRT
<213> ORGANISM: Malus domestica

<400> SEQUENCE: 56

Met Val Thr Val Glu Val Arg Lys Ala Gln Arg Ala Glu Gly Pro
1               5                   10                  15

Ala Thr Val Leu Ala Ile Gly Thr Ala Thr Pro Pro Asn Cys Val Asp
                20                  25                  30

Gln Ala Thr Tyr Pro Asp Tyr Tyr Phe Arg Ile Thr Asn Ser Glu His
                35                  40                  45

Lys Thr Glu Leu Lys Glu Lys Phe Gln Arg Met Cys Asp Lys Ser Met
50                  55                  60

Ile Lys Thr Arg Tyr Met Tyr Leu Thr Glu Ile Leu Lys Glu Asn
65                  70                  75                  80

Pro Thr Val Cys Glu Tyr Met Ala Pro Ser Leu Asp Ala Arg Gln Asp
                85                  90                  95

Met Val Val Glu Val Pro Arg Leu Gly Lys Glu Ala Ala Thr Lys
                100                 105                 110

Ala Ile Lys Glu Trp Gly Gln Pro Lys Ser Lys Ile Thr His Leu Val
                115                 120                 125

Phe Cys Thr Thr Ser Gly Val Asp Met Pro Gly Ala Asp Tyr Gln Leu
130                 135                 140

Thr Lys Leu Leu Gly Leu Arg Pro Ser Val Lys Arg Leu Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Lys Gly Ala Arg Val Leu Val Val Cys Ser Glu
                180                 185                 190

Ile Thr Ala Val Thr Phe Arg Gly Pro Ser Asp Thr His Leu Asp Ser
                195                 200                 205

Leu Val Gly Gln Ala Leu Phe Gly Asp Gly Ala Ala Ala Val Ile Ile
                210                 215                 220

Gly Ser Asp Pro Val Pro Glu Val Glu Lys Pro Leu Phe Glu Leu Val
225                 230                 235                 240

Ser Ala Ala Gln Thr Ile Leu Pro Asp Ser Asp Gly Ala Ile Asp Gly
                245                 250                 255

His Leu Arg Glu Val Gly Leu Thr Phe His Leu Leu Lys Asp Val Pro
                260                 265                 270

Gly Leu Ile Ser Lys Asn Ile Glu Lys Ser Leu Asn Glu Ala Phe Lys
                275                 280                 285

Pro Ile Gly Ile Ser Asp Trp Asn Ser Leu Phe Trp Ile Ala His Pro
                290                 295                 300

Gly Gly Pro Ala Ile Leu Asp Gln Val Glu Ser Lys Leu Ala Leu Lys
305                 310                 315                 320

Pro Glu Lys Leu Glu Ala Thr Arg Gln Val Leu Ser Asp Tyr Gly Asn
                325                 330                 335

Met Ser Ser Ala Cys Val Leu Phe Ile Leu Asp Glu Val Arg Arg Lys
                340                 345                 350

Ser Ala Glu Lys Gly Leu Lys Thr Thr Gly Glu Gly Leu Glu Trp Gly
                355                 360                 365

Val Leu Phe Gly Phe Gly Pro Gly Leu Thr Val Glu Thr Val Val Leu
370                 375                 380

His Ser Val Gly Ala
385

<210> SEQ ID NO 57
<211> LENGTH: 389
<212> TYPE: PRT
<213> ORGANISM: Malus domestica

<400> SEQUENCE: 57

Met Val Thr Val Gln Glu Val Arg Lys Ala Gln Arg Ala Glu Gly Pro
1               5                   10                  15

Ala Thr Val Phe Ala Ile Gly Thr Ala Thr Pro Pro Asn Cys Val Asp
            20                  25                  30

Gln Ala Thr Tyr Pro Asp Tyr Tyr Phe Arg Ile Thr Asn Ser Glu His
        35                  40                  45

Lys Ala Glu Leu Lys Glu Lys Phe Gln Arg Met Cys Asp Lys Ser Met
    50                  55                  60

Ile Lys Lys Arg Tyr Met Tyr Leu Thr Glu Glu Ile Leu Lys Glu Asn
65                  70                  75                  80

Pro Ser Val Cys Glu Tyr Met Ala Pro Ser Leu Asp Ala Arg Gln Asp
                85                  90                  95

Met Val Val Glu Val Pro Arg Leu Gly Lys Glu Ala Ala Thr Lys
            100                 105                 110

Ala Ile Lys Glu Trp Gly Gln Pro Lys Ser Lys Ile Thr His Leu Val
        115                 120                 125

Phe Cys Thr Thr Ser Gly Val Asp Met Pro Gly Ala Asp Tyr Gln Leu
130                 135                 140

Thr Lys Leu Leu Gly Leu Arg Pro Ser Val Lys Arg Leu Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Lys Gly Ala Arg Val Leu Val Val Cys Ser Glu
            180                 185                 190

Ile Thr Ala Val Thr Phe Arg Gly Pro Ser Asp Thr His Leu Asp Ser
        195                 200                 205

Leu Val Gly Gln Ala Leu Phe Gly Asp Gly Ala Ala Ala Val Ile Ile
    210                 215                 220

Gly Ala Asp Pro Val Pro Glu Val Glu Lys Pro Leu Phe Glu Leu Val
225                 230                 235                 240

Ser Ala Ala Gln Thr Ile Leu Ala Asp Ser Asp Gly Ala Ile Asp Gly
                245                 250                 255

His Leu Arg Glu Val Gly Leu Thr Phe His Leu Leu Lys Asp Val Pro
            260                 265                 270

Gly Leu Ile Ser Lys Asn Ile Glu Lys Ser Leu Asn Glu Ala Phe Lys
        275                 280                 285

Pro Ile Gly Ile Ser Asp Trp Asn Ser Leu Phe Trp Ile Ala His Pro
    290                 295                 300

Gly Gly Pro Ala Ile Leu Asp Gln Val Glu Ala Lys Leu Ala Leu Lys
305                 310                 315                 320

Pro Glu Lys Leu Glu Ala Thr Arg Gln Val Leu Ser Asp Tyr Gly Asn
                325                 330                 335

Met Ser Ser Ala Cys Val Leu Phe Ile Leu Asp Glu Val Arg Arg Lys
            340                 345                 350

Ser Ala Glu Lys Gly Leu Glu Thr Thr Gly Glu Gly Leu Glu Trp Gly

```
                355                 360                 365
Val Leu Phe Gly Phe Gly Pro Gly Leu Thr Val Glu Thr Val Val Leu
    370                 375                 380

His Ser Val Ala Ala
385

<210> SEQ ID NO 58
<211> LENGTH: 392
<212> TYPE: PRT
<213> ORGANISM: Vitis pseudoreticulata

<400> SEQUENCE: 58

Met Ala Ser Val Glu Glu Ile Arg Asn Ala Gln Arg Ala Lys Gly Pro
1               5                   10                  15

Ala Thr Ile Leu Ala Ile Gly Thr Ala Thr Pro Asp His Cys Val Tyr
                20                  25                  30

Gln Ser Asp Tyr Ala Asp Tyr Tyr Phe Arg Val Thr Lys Ser Glu His
            35                  40                  45

Met Thr Glu Leu Lys Lys Lys Phe Asn Arg Ile Cys Asp Lys Ser Met
        50                  55                  60

Ile Lys Lys Arg Tyr Ile His Leu Thr Glu Glu Met Leu Glu Glu His
65                  70                  75                  80

Pro Asn Ile Gly Ala Tyr Met Ala Pro Ser Leu Asn Ile Arg Gln Glu
                85                  90                  95

Ile Ile Thr Ala Glu Val Pro Lys Leu Gly Lys Glu Ala Ala Leu Lys
            100                 105                 110

Ala Leu Lys Glu Trp Gly Gln Pro Lys Ser Lys Ile Thr His Leu Val
        115                 120                 125

Phe Cys Thr Thr Ser Gly Val Glu Met Pro Gly Ala Asp Tyr Lys Leu
    130                 135                 140

Ala Asn Leu Leu Gly Leu Glu Thr Ser Val Arg Arg Val Met Leu Tyr
145                 150                 155                 160

His Gln Gly Cys Tyr Ala Gly Gly Thr Val Leu Arg Thr Ala Lys Asp
                165                 170                 175

Leu Ala Glu Asn Asn Ala Gly Ala Arg Val Leu Val Val Cys Ser Glu
            180                 185                 190

Ile Thr Val Val Thr Phe Arg Gly Pro Ser Glu Asp Ala Leu Asp Ser
        195                 200                 205

Leu Val Gly Gln Ala Leu Phe Gly Asp Gly Ser Ala Ala Val Ile Val
    210                 215                 220

Gly Ser Asp Pro Asp Ile Ser Ile Glu Arg Pro Leu Phe Gln Leu Val
225                 230                 235                 240

Ser Ala Ala Gln Thr Phe Ile Pro Asn Ser Ala Gly Ala Ile Ala Gly
                245                 250                 255

Asn Leu Arg Glu Val Gly Leu Thr Phe His Leu Trp Pro Asn Val Pro
            260                 265                 270

Thr Leu Ile Ser Glu Asn Ile Glu Asn Cys Leu Thr Lys Ala Phe Asp
        275                 280                 285

Pro Ile Gly Ile Ser Asp Trp Asn Ser Leu Phe Trp Ile Ala His Pro
    290                 295                 300

Gly Gly Pro Ala Ile Leu Asp Ala Val Glu Ala Lys Val Gly Leu Asp
305                 310                 315                 320

Lys Gln Lys Leu Lys Ala Thr Arg His Ile Leu Ser Glu Tyr Gly Asn
                325                 330                 335
```

```
Met Ser Ser Ala Cys Val Leu Phe Ile Leu Asp Glu Met Arg Lys Lys
                340                 345                 350

Ser Leu Lys Glu Gly Lys Thr Thr Thr Gly Glu Gly Leu Asp Trp Gly
            355                 360                 365

Val Leu Phe Gly Phe Gly Pro Gly Leu Thr Ile Glu Thr Val Val Leu
    370                 375                 380

His Ser Val Gly Thr Asp Ser Asn
385                 390

<210> SEQ ID NO 59
<211> LENGTH: 392
<212> TYPE: PRT
<213> ORGANISM: Vitis vinifera

<400> SEQUENCE: 59

Met Ala Ser Val Glu Glu Phe Arg Asn Ala Gln Arg Ala Lys Gly Pro
1               5                   10                  15

Ala Thr Ile Leu Ala Ile Gly Thr Ala Thr Pro Asp His Cys Val Tyr
            20                  25                  30

Gln Ser Asp Tyr Ala Asp Tyr Tyr Phe Arg Val Thr Lys Ser Glu His
        35                  40                  45

Met Thr Glu Leu Lys Lys Lys Phe Asn Arg Ile Cys Asp Lys Ser Met
    50                  55                  60

Ile Lys Lys Arg Tyr Ile His Leu Thr Glu Glu Met Leu Glu Glu His
65                  70                  75                  80

Pro Asn Ile Gly Ala Tyr Met Ala Pro Ser Leu Asn Ile Arg Gln Glu
                85                  90                  95

Ile Ile Thr Ala Glu Val Pro Arg Leu Gly Arg Asp Ala Ala Leu Lys
            100                 105                 110

Ala Leu Lys Glu Trp Gly Gln Pro Lys Ser Lys Ile Thr His Leu Val
        115                 120                 125

Phe Cys Thr Thr Ser Gly Val Glu Met Pro Gly Ala Asp Tyr Lys Leu
    130                 135                 140

Ala Asn Leu Leu Gly Leu Glu Thr Ser Val Arg Arg Val Met Leu Tyr
145                 150                 155                 160

His Gln Gly Cys Tyr Ala Gly Gly Thr Val Leu Arg Thr Ala Lys Asp
                165                 170                 175

Leu Ala Glu Asn Asn Ala Gly Ala Arg Val Leu Val Val Cys Ser Glu
            180                 185                 190

Ile Thr Val Val Thr Phe Arg Gly Pro Ser Glu Asp Ala Leu Asp Ser
        195                 200                 205

Leu Val Gly Gln Ala Leu Phe Gly Asp Gly Ser Ser Ala Val Ile Val
    210                 215                 220

Gly Ser Asp Pro Asp Val Ser Ile Glu Arg Pro Leu Phe Gln Leu Val
225                 230                 235                 240

Ser Ala Ala Gln Thr Phe Ile Pro Asn Ser Ala Gly Ala Ile Ala Gly
                245                 250                 255

Asn Leu Arg Glu Val Gly Leu Thr Phe His Leu Trp Pro Asn Val Pro
            260                 265                 270

Thr Leu Ile Ser Glu Asn Ile Glu Lys Cys Leu Thr Gln Ala Phe Asp
        275                 280                 285

Pro Leu Gly Ile Ser Asp Trp Asn Ser Leu Phe Trp Ile Ala His Pro
    290                 295                 300

Gly Gly Pro Ala Ile Leu Asp Ala Val Glu Ala Lys Leu Asn Leu Glu
305                 310                 315                 320
```

-continued

```
Lys Lys Lys Leu Glu Ala Thr Arg His Val Leu Ser Glu Tyr Gly Asn
            325                 330                 335

Met Ser Ser Ala Cys Val Leu Phe Ile Leu Asp Glu Met Arg Lys Lys
            340                 345                 350

Ser Leu Lys Gly Glu Lys Ala Thr Thr Gly Glu Gly Leu Asp Trp Gly
            355                 360                 365

Val Leu Phe Gly Phe Gly Pro Gly Leu Thr Ile Glu Thr Val Val Leu
370                 375                 380

His Ser Val Pro Thr Val Thr Asn
385                 390

<210> SEQ ID NO 60
<211> LENGTH: 392
<212> TYPE: PRT
<213> ORGANISM: Malus domestica

<400> SEQUENCE: 60

Met Ala Thr Thr Ala Ala Ser Ser Leu Gln Met Ala Thr Ala Arg Pro
1               5                   10                  15

Cys Ile Ser Ser Ser Arg Arg Ala Phe Gly Ser Ser Thr Ala Met Leu
            20                  25                  30

Asn Gly Asn Phe Lys Val Ala Ser Trp Thr Lys Leu Ser Ser Ala Cys
        35                  40                  45

His Ile Ser Ser Val Gln Ser Phe Gln Arg Cys Phe Thr Ser Ser Ser
    50                  55                  60

Met Lys Leu Asp Lys Phe Val Thr Lys Ala Met Ala Gly Ala Ser Glu
65                  70                  75                  80

Asn Lys Pro Val Ser Gly Leu Pro Ile Asn Leu Lys Gly Lys Arg Ala
                85                  90                  95

Phe Ile Ala Gly Val Ala Asp Asp Asn Gly Tyr Gly Trp Ala Ile Ala
            100                 105                 110

Lys Ser Leu Ala Ala Ala Gly Ala Glu Ile Leu Val Gly Thr Trp Val
            115                 120                 125

Pro Ala Leu Asn Ile Phe Glu Ser Ser Leu Arg Arg Gly Lys Phe Asp
130                 135                 140

Glu Ser Arg Ile Leu Pro Asp Gly Ser Leu Met Glu Ile Thr Lys Val
145                 150                 155                 160

Tyr Pro Leu Asp Ala Val Phe Asp Asn Pro Glu Asp Val Pro Glu Glu
                165                 170                 175

Ile Lys Thr Asn Lys Arg Tyr Ala Gly Ser Ser Asn Trp Thr Val Gln
            180                 185                 190

Glu Ala Ala Glu Cys Val Lys Asn Asp Phe Gly Ser Ile Asp Val Leu
            195                 200                 205

Val His Ser Leu Ala Asn Gly Pro Glu Val Val Lys Pro Leu Leu Glu
210                 215                 220

Thr Ser Arg Lys Gly Tyr Leu Ala Ala Ile Ser Ala Ser Ser Tyr Ser
225                 230                 235                 240

Tyr Val Ser Leu Leu Lys His Phe Leu Pro Ile Ile Asn Pro Gly Gly
                245                 250                 255

Ser Ser Ile Ser Leu Thr Tyr Ile Ala Ser Glu Arg Ile Ile Pro Gly
            260                 265                 270

Tyr Gly Gly Gly Met Ser Ser Ala Lys Ala Ala Leu Glu Ser Asp Thr
        275                 280                 285

Arg Val Leu Ala Phe Glu Ala Gly Arg Lys Lys Gly Ile Arg Val Asn
```

```
              290                 295                 300
Thr Ile Ser Ala Gly Pro Leu Arg Ser Arg Ala Ala Lys Ala Ile Gly
305                 310                 315                 320

Phe Ile Asp Met Met Ile Asp Tyr Ser Ser Ala Asn Ala Pro Leu Glu
                325                 330                 335

Lys Glu Leu Ser Ala Glu Glu Val Gly Asn Thr Ala Ala Phe Leu Ala
            340                 345                 350

Ser Pro Leu Ala Ser Ala Ile Thr Gly Gly Val Ile Tyr Val Asp Asn
        355                 360                 365

Gly Leu Asn Ala Met Gly Val Gly Val Asp Ser Pro Ile Phe Glu Asn
    370                 375                 380

Leu Asn Ile Pro Lys Ala Gln His
385                 390

<210> SEQ ID NO 61
<211> LENGTH: 392
<212> TYPE: PRT
<213> ORGANISM: Malus domestica

<400> SEQUENCE: 61

Met Ala Thr Thr Ala Ala Ser Ser Leu Gln Met Ala Thr Ala Arg Pro
1               5                   10                  15

Cys Ile Ser Ser Ser Arg Arg Ala Phe Gly Ser Ser Ser Lys Met Leu
            20                  25                  30

Asn Asp Asn Phe Lys Val Ala Ser Trp Ser Lys Leu Ser Ser Thr Cys
        35                  40                  45

His Thr Ser Ser Val Gln Ser Phe Gln Arg Ser Phe Thr Ser Ser Ser
    50                  55                  60

Met Lys Met Asp Lys Phe Val Thr Arg Ala Met Ala Gly Ala Ser Glu
65                  70                  75                  80

Asn Lys Pro Val Ser Gly Leu Pro Ile Asp Leu Lys Gly Lys Arg Ala
                85                  90                  95

Phe Ile Ala Gly Val Ala Asp Asp Asn Gly Tyr Gly Trp Ala Ile Ala
            100                 105                 110

Lys Ser Leu Ala Ala Ala Gly Ala Glu Ile Leu Val Gly Thr Trp Val
        115                 120                 125

Pro Ala Leu Asn Ile Phe Glu Ser Ser Leu Arg Arg Gly Lys Phe Asp
    130                 135                 140

Glu Ser Arg Val Leu Pro Asp Gly Ser Leu Met Glu Ile Thr Lys Val
145                 150                 155                 160

Tyr Pro Leu Asp Ala Val Phe Asp Asn Pro Glu Asp Val Pro Glu Glu
                165                 170                 175

Ile Lys Thr Asn Lys Arg Tyr Ala Gly Ser Ser Asn Trp Thr Val Gln
            180                 185                 190

Glu Ala Ala Glu Cys Val Lys Asn Asp Phe Gly Ser Ile Asp Ile Leu
        195                 200                 205

Val His Ser Leu Ala Asn Gly Pro Glu Val Val Lys Pro Leu Leu Glu
    210                 215                 220

Thr Ser Arg Lys Gly Tyr Leu Ala Ala Ile Ser Ala Ser Ser Tyr Ser
225                 230                 235                 240

Tyr Val Ser Leu Leu Lys His Phe Leu Pro Ile Ile Asn Pro Gly Gly
                245                 250                 255

Ser Ser Ile Ser Leu Thr Tyr Ile Ala Ser Glu Arg Ile Ile Pro Gly
            260                 265                 270
```

```
Tyr Gly Gly Gly Met Ser Ser Lys Ala Ala Leu Glu Ser Asp Thr
            275                 280                 285

Arg Val Leu Ala Phe Glu Ala Gly Arg Lys Gly Ile Arg Val Asn
290                 295                 300

Thr Ile Ser Ala Gly Pro Leu Arg Ser Arg Ala Ala Lys Ala Ile Gly
305                 310                 315                 320

Phe Ile Asp Met Met Ile Asp Tyr Ser Ser Ala Asn Ala Pro Leu Glu
                325                 330                 335

Lys Glu Leu Ser Ala Asp Glu Val Gly Asn Thr Ala Ala Phe Leu Ala
            340                 345                 350

Ser Pro Leu Ala Ser Ala Ile Thr Gly Val Ile Tyr Val Asp Asn
            355                 360                 365

Gly Leu Asn Ala Met Gly Val Gly Val Asp Ser Pro Ile Phe Glu Asn
370                 375                 380

Leu Asn Ile Pro Lys Ala Gln His
385                 390
```

<210> SEQ ID NO 62
<211> LENGTH: 348
<212> TYPE: PRT
<213> ORGANISM: Rubus idaeus

<400> SEQUENCE: 62

```
Met Ala Ser Gly Gly Glu Met Gln Val Ser Asn Lys Gln Val Ile Phe
1               5                   10                  15

Arg Asp Tyr Val Thr Gly Phe Pro Lys Glu Ser Asp Met Glu Leu Thr
                20                  25                  30

Thr Arg Ser Ile Thr Leu Lys Leu Pro Gln Gly Ser Thr Gly Leu Leu
            35                  40                  45

Leu Lys Asn Leu Tyr Leu Ser Cys Asp Pro Tyr Met Arg Ala Arg Met
50                  55                  60

Thr Asn His His Arg Leu Ser Tyr Val Asp Ser Phe Lys Pro Gly Ser
65                  70                  75                  80

Pro Ile Ile Gly Tyr Gly Val Ala Arg Val Leu Glu Ser Gly Asn Pro
                85                  90                  95

Lys Phe Asn Pro Gly Asp Leu Val Trp Gly Phe Thr Gly Trp Glu Glu
            100                 105                 110

Tyr Ser Val Ile Thr Ala Thr Glu Ser Leu Phe Lys Ile His Asn Thr
        115                 120                 125

Asp Val Pro Leu Ser Tyr Tyr Thr Gly Leu Leu Gly Met Pro Gly Met
130                 135                 140

Thr Ala Tyr Ala Gly Phe Tyr Glu Ile Cys Ser Pro Lys Lys Gly Glu
145                 150                 155                 160

Thr Val Tyr Val Ser Ala Ala Ser Gly Ala Val Gly Gln Leu Val Gly
                165                 170                 175

Gln Phe Ala Lys Leu Thr Gly Cys Tyr Val Val Gly Ser Ala Gly Ser
            180                 185                 190

Lys Glu Lys Val Asp Leu Leu Lys Asn Lys Phe Gly Phe Asp Glu Ala
        195                 200                 205

Phe Asn Tyr Lys Glu Glu Ala Asp Leu Asp Ala Ala Leu Arg Arg Tyr
210                 215                 220

Phe Pro Asp Gly Ile Asp Ile Tyr Phe Glu Asn Val Gly Gly Lys Met
225                 230                 235                 240

Leu Asp Ala Val Leu Pro Asn Met Arg Pro Lys Gly Arg Ile Ala Val
                245                 250                 255
```

```
Cys Gly Met Ile Ser Gln Tyr Asn Leu Glu Gln Pro Glu Gly Val Arg
            260                 265                 270

Asn Leu Met Ala Leu Ile Val Lys Gln Val Arg Met Glu Gly Phe Met
            275                 280                 285

Val Phe Ser Tyr Tyr His Leu Tyr Gly Lys Phe Leu Glu Thr Val Leu
            290                 295                 300

Pro Tyr Ile Lys Gln Gly Lys Ile Thr Tyr Val Glu Asp Val Val Asp
305                 310                 315                 320

Gly Leu Asp Asn Ala Pro Ala Leu Ile Gly Leu Tyr Ser Gly Arg
                325                 330                 335

Asn Val Gly Lys Gln Val Val Val Ser Arg Glu
            340                 345

<210> SEQ ID NO 63
<211> LENGTH: 678
<212> TYPE: PRT
<213> ORGANISM: Eubacterium ramulus

<400> SEQUENCE: 63

Met Ala Glu Lys Asn Gln Tyr Phe Pro His Leu Phe Glu Pro Leu Lys
1               5                   10                  15

Val Gly Ser Lys Thr Ile Lys Asn Arg Ile Glu Ala Ala Pro Ala Leu
            20                  25                  30

Phe Ala Phe Glu His Tyr Ile Glu Leu Asn Pro Asp Pro Phe Gly Tyr
        35                  40                  45

Thr Thr Pro Val Pro Glu Arg Ala Phe Arg Met Leu Glu Ala Lys Ala
    50                  55                  60

Lys Gly Gly Ala Gly Ile Val Cys Leu Gly Glu Leu Ser Pro Asn His
65                  70                  75                  80

Glu Tyr Asp Lys Arg Phe Pro Phe Glu Pro Tyr Leu Asp Phe Thr Ser
                85                  90                  95

Arg Ser Asp Lys Gln Phe Glu Ile Met Lys Glu Thr Ala Glu Met Ile
            100                 105                 110

Lys Ser Tyr Gly Ala Phe Pro Met Gly Glu Leu Leu Ser Cys Gly Glu
        115                 120                 125

Ile Lys Thr Asn Ile Gly Asp Gly Ile Asn Pro Lys Gly Pro Ser Glu
    130                 135                 140

Lys Asp Leu Pro Asp Gly Ser His Val Glu Ala Phe Thr Lys Glu Glu
145                 150                 155                 160

Ile Leu Ser Cys Tyr Gln Asp Tyr Val Thr Ala Cys Lys Trp Phe Gln
                165                 170                 175

Ala Ala Gly Trp Glu Gly Ile Met Ile His Cys Gly His Gly Trp Leu
            180                 185                 190

Pro Ala Gln Phe Leu Ser Pro Gln Tyr Asn Lys Arg Thr Asp Glu Tyr
        195                 200                 205

Gly Gly Ser Phe Glu Asn Arg Ala Arg Phe Thr Val Asp Leu Leu Lys
    210                 215                 220

Thr Val Arg Glu Ala Met Gly Pro Asp Phe Val Ile Glu Ile Arg Val
225                 230                 235                 240

Ser Ser Ser Glu His Leu Pro Gly Gly Leu Glu Leu Glu Asp Ala Val
                245                 250                 255

Asn Tyr Cys Lys Leu Cys Glu Pro Tyr Ile Asp Met Ile His Val Ser
            260                 265                 270

Cys Gly His Tyr Leu Ser Ser Ser Arg Ser Trp Glu Phe Thr Thr Ala
```

```
            275                 280                 285
Tyr Ala Pro His Gly Pro Asn Ile Glu Pro Ala Ala Val Ile Lys Gln
290                 295                 300
Asn Val Ser Ile Pro Val Ala Ala Val Gly Gly Ile Asn Ser Pro Glu
305                 310                 315                 320
Gln Ala Glu Glu Ala Ile Ala Ser Gly Lys Ile Asp Met Val Ser Met
                325                 330                 335
Gly Arg Gln Phe Phe Ala Asp Pro Ala Phe Pro Asn Lys Ala Lys Glu
            340                 345                 350
Gly His Ala Asp Glu Ile Arg Arg Cys Leu Arg Cys Gly Arg Cys Tyr
        355                 360                 365
Pro Gly Pro Ser Gly Glu His Glu Thr Glu Ile Trp Thr Val Lys Phe
370                 375                 380
Pro Pro Leu Asp Ser Cys Thr Ile Asn Pro Tyr Asp Val Trp Pro Ala
385                 390                 395                 400
Ser His His Lys Val Leu Pro Asp Arg Met Pro Lys Pro Glu Ala Ser
                405                 410                 415
Arg Lys Val Leu Val Val Gly Gly Cys Gly Gly Leu Gln Thr Ala
            420                 425                 430
Ile Thr Ala Ser Asp Arg Gly His Gln Val Ile Leu Cys Glu Lys Ser
        435                 440                 445
Gly Val Leu Gly Gly Leu Ile Asn Phe Thr Asp His Thr Asp His Lys
450                 455                 460
Val Asp Ile Arg Asn Phe Lys Asp Leu Leu Ile Arg Asp Val Glu Lys
465                 470                 475                 480
Arg Pro Ile Glu Val Arg Leu Asn Cys Glu Val Thr Pro Glu Leu Ile
                485                 490                 495
Arg Glu Ile Ala Pro Glu Ala Val Val Leu Ala Val Gly Ser Asp Asp
            500                 505                 510
Leu Ile Leu Pro Ile Glu Gly Ile Glu Asn Ala Val Thr Ala Met Asp
        515                 520                 525
Val Tyr Ser Asn Asp Phe Ala Gly Leu Gly Lys Ser Thr Ile Val Leu
530                 535                 540
Gly Gly Gly Leu Val Gly Cys Glu Ala Ala Ala Asp Tyr Ile Asp His
545                 550                 555                 560
Gly Val Glu Thr Thr Ile Val Glu Met Lys Gly Ala Leu Met Pro Glu
                565                 570                 575
Thr Thr Gly Leu Tyr Arg Thr Ala Val His Asp Phe Ile Asp Lys Asn
            580                 585                 590
Gly Gly Lys Tyr Glu Val Asn Ala Lys Val Val Lys Val Gly Lys Asp
        595                 600                 605
Phe Val Ala Glu Gln Asp Gly Lys Glu Ile Thr Ile Lys Ala Asp
610                 615                 620
Ser Val Val Asn Ala Met Gly Arg Arg Ala His Ala Thr Glu Ala Leu
625                 630                 635                 640
Glu Thr Ala Ile Lys Glu Ala Gly Ile Pro Val Trp Lys Ile Gly Asp
                645                 650                 655
Cys Val Arg Ala Arg Gln Ile Gly Asp Ala Val Arg Glu Gly Trp Thr
            660                 665                 670
Ala Ala Met Glu Ile Ile
            675

<210> SEQ ID NO 64
```

<211> LENGTH: 349
<212> TYPE: PRT
<213> ORGANISM: Malus domestica

<400> SEQUENCE: 64

Met Ala Ala Ser Thr Glu Gly Val Ile Ser Asn Lys Gln Val Ile Leu
1               5                   10                  15

Lys Asp Tyr Val Thr Gly Phe Pro Lys Glu Ser Asp Met Gln Leu Thr
            20                  25                  30

Thr Ala Thr Thr Lys Leu Lys Leu Pro Glu Gly Ser Lys Gly Val Leu
        35                  40                  45

Val Lys Asn Leu Tyr Leu Ser Cys Asp Pro Tyr Met Arg Ser Arg Met
50                  55                  60

Thr Lys Arg Glu Pro Gly Ala Ser Tyr Val Asp Ser Phe Asp Ala Gly
65                  70                  75                  80

Ser Pro Ile Val Gly Tyr Gly Val Ala Lys Val Leu Glu Ser Gly Asp
                85                  90                  95

Pro Lys Phe Lys Lys Gly Asp Leu Ile Trp Gly Met Thr Gly Trp Glu
            100                 105                 110

Glu Tyr Ser Val Ile Thr Ser Thr Glu Ser Leu Phe Lys Ile Gln His
        115                 120                 125

Ile Asp Val Pro Leu Ser Tyr Tyr Thr Gly Ile Leu Gly Met Pro Gly
130                 135                 140

Met Thr Ala Tyr Ala Gly Phe Tyr Glu Ile Cys Asn Pro Lys Lys Gly
145                 150                 155                 160

Glu Thr Val Phe Val Ser Ala Ala Ser Gly Ala Val Gly Gln Leu Val
                165                 170                 175

Gly Gln Phe Ala Lys Leu Leu Gly Cys Tyr Val Val Gly Ser Ala Gly
            180                 185                 190

Ser Lys Glu Lys Val Asp Leu Leu Lys Asn Lys Phe Gly Phe Asp Asn
        195                 200                 205

Ala Phe Asn Tyr Lys Glu Glu Pro Asp Leu Asp Ala Ala Leu Lys Arg
210                 215                 220

Tyr Phe Pro Glu Gly Ile Asp Ile Tyr Phe Glu Asn Val Gly Gly Lys
225                 230                 235                 240

Met Leu Asp Ala Val Leu Pro Asn Met Arg Val His Gly Arg Ile Ala
                245                 250                 255

Val Cys Gly Leu Ile Ser Gln Tyr Asn Ile Asp Glu Pro Glu Gly Cys
            260                 265                 270

Arg Asn Leu Met Tyr Leu Ile Ile Lys Gln Val Arg Met Gln Gly Phe
        275                 280                 285

Leu Val Phe Ser Tyr Tyr His Leu Tyr Glu Lys Phe Leu Glu Met Val
290                 295                 300

Leu Pro Ala Ile Lys Glu Gly Lys Leu Thr Tyr Val Glu Asp Val Val
305                 310                 315                 320

Glu Gly Leu Glu Ser Ala Pro Ala Leu Ile Gly Leu Tyr Ala Gly
                325                 330                 335

Arg Asn Val Gly Lys Gln Val Val Val Ser Arg Glu
            340                 345

<210> SEQ ID NO 65
<211> LENGTH: 310
<212> TYPE: PRT
<213> ORGANISM: Arabidopsis thaliana

<400> SEQUENCE: 65

Met Lys Val Thr Val Ser Arg Ser Gly Arg Glu Val Leu Lys Ala
1               5                   10                  15

Pro Leu Asp Leu Pro Asp Ser Ala Thr Val Ala Asp Leu Gln Glu Ala
            20                  25                  30

Phe His Lys Arg Ala Lys Lys Phe Tyr Pro Ser Arg Gln Arg Leu Thr
            35                  40                  45

Leu Pro Val Thr Pro Gly Ser Lys Asp Lys Pro Val Val Leu Asn Ser
50                  55                  60

Lys Lys Ser Leu Lys Glu Tyr Cys Asp Gly Asn Asn Ser Leu Thr
65                  70                  75                  80

Val Val Phe Lys Asp Leu Gly Ala Gln Val Ser Tyr Arg Thr Leu Phe
            85                  90                  95

Phe Phe Glu Tyr Leu Gly Pro Leu Leu Ile Tyr Pro Val Phe Tyr Tyr
            100                 105                 110

Phe Pro Val Tyr Lys Phe Leu Gly Tyr Gly Glu Asp Cys Val Ile His
            115                 120                 125

Pro Val Gln Thr Tyr Ala Met Tyr Tyr Trp Cys Phe His Tyr Phe Lys
130                 135                 140

Arg Ile Leu Glu Thr Phe Phe Val His Arg Phe Ser His Ala Thr Ser
145                 150                 155                 160

Pro Ile Gly Asn Val Phe Arg Asn Cys Ala Tyr Tyr Trp Ser Phe Gly
            165                 170                 175

Ala Tyr Ile Ala Tyr Val Asn His Pro Leu Tyr Thr Pro Val Ser
            180                 185                 190

Asp Leu Gln Met Lys Ile Gly Phe Gly Phe Gly Leu Val Cys Gln Val
            195                 200                 205

Ala Asn Phe Tyr Cys His Ile Leu Leu Lys Asn Leu Arg Asp Pro Ser
210                 215                 220

Gly Ala Gly Gly Tyr Gln Ile Pro Arg Gly Phe Leu Phe Asn Ile Val
225                 230                 235                 240

Thr Cys Ala Asn Tyr Thr Thr Glu Ile Tyr Gln Trp Leu Gly Phe Asn
                245                 250                 255

Ile Ala Thr Gln Thr Ile Ala Gly Tyr Val Phe Leu Ala Val Ala Ala
            260                 265                 270

Leu Ile Met Thr Asn Trp Ala Leu Gly Lys His Ser Arg Leu Arg Lys
            275                 280                 285

Ile Phe Asp Gly Lys Asp Gly Lys Pro Lys Tyr Pro Arg Arg Trp Val
            290                 295                 300

Ile Leu Pro Pro Phe Leu
305                 310

<210> SEQ ID NO 66
<211> LENGTH: 310
<212> TYPE: PRT
<213> ORGANISM: Gossypium hirsutum

<400> SEQUENCE: 66

Met Lys Val Thr Leu Val Ser Arg Ser Gly Arg Glu Phe Ile Lys Gly
1               5                   10                  15

Gly Leu Glu Leu Asn Asp Ser Ala Thr Val Ala Asp Leu Gln Glu Ala
            20                  25                  30

Ile His Lys Arg Thr Lys Lys Phe Tyr Pro Ser Arg Gln Arg Leu Thr
            35                  40                  45

Leu Pro Val Pro Ser Gly Ser Arg Glu Arg Pro Val Ile Leu Asn Tyr

Lys Lys Ser Leu Lys Asp Tyr Cys Asp Gly Asn Glu Asn Thr Leu Thr
65                  70                  75                  80

Ile Val Phe Lys Asp Leu Gly Pro Gln Val Ser Tyr Arg Thr Leu Phe
                85                  90                  95

Phe Phe Glu Tyr Leu Gly Pro Leu Ile Leu Tyr Pro Val Phe Tyr Tyr
            100                 105                 110

Phe Pro Val Tyr Lys Tyr Phe Gly Tyr Glu Glu Lys Arg Val Ile His
            115                 120                 125

Pro Val Gln Thr Tyr Ala Leu Tyr Tyr Trp Cys Phe His Tyr Phe Lys
            130                 135                 140

Arg Ile Met Glu Thr Phe Phe Ile His Arg Phe Ser His Ala Thr Ser
145                 150                 155                 160

Pro Leu Ser Asn Val Phe Arg Asn Cys Ala Tyr Tyr Trp Thr Phe Gly
                165                 170                 175

Ser Tyr Ile Ala Tyr Tyr Val Asn His Pro Leu Tyr Thr Pro Val Ser
            180                 185                 190

Asp Leu Gln Met Lys Ile Gly Phe Gly Phe Gly Ile Val Cys Gln Leu
            195                 200                 205

Ala Asn Phe Tyr Cys His Ile Ile Leu Lys Asn Leu Arg Ser Pro Asp
210                 215                 220

Gly Ser Gly Tyr Gln Ile Pro Arg Gly Phe Leu Phe Asn Ile Val
225                 230                 235                 240

Thr Cys Ala Asn Tyr Thr Thr Glu Ile Tyr Gln Trp Leu Gly Phe Asn
                245                 250                 255

Ile Ala Thr Gln Thr Val Ala Gly Tyr Val Phe Leu Val Val Ala Thr
            260                 265                 270

Ser Ile Met Thr Asn Trp Ala Leu Ala Lys His Arg Arg Leu Lys Lys
            275                 280                 285

Leu Phe Asp Gly Lys Asp Gly Arg Pro Lys Tyr Pro Arg Arg Trp Val
            290                 295                 300

Ile Leu Pro Pro Phe Leu
305                 310

<210> SEQ ID NO 67
<211> LENGTH: 310
<212> TYPE: PRT
<213> ORGANISM: Malus domestica

<400> SEQUENCE: 67

Met Lys Val Thr Val Ser Arg Ser Gly Arg Glu Val Val Lys Gly
1               5                   10                  15

Gly Leu Glu Leu Ser Asp Ser Ala Thr Val Ala Asp Leu Gln Asp Ala
                20                  25                  30

Ile His Lys Arg Thr Lys Lys Phe Tyr Pro Ala Arg Gln Arg Leu Thr
            35                  40                  45

Leu Pro Val Gln Pro Gly Ser Lys Glu Arg Pro Val Val Leu Ser Tyr
            50                  55                  60

Lys Lys Ser Leu Gln Asp Tyr Ile Ser Gly Asn Ser Asp Asn Leu Thr
65                  70                  75                  80

Val Val Phe Lys Asp Leu Gly Pro Gln Val Ser Tyr Arg Thr Leu Phe
                85                  90                  95

Phe Phe Glu Tyr Leu Gly Pro Leu Ile Leu Tyr Pro Ile Phe Tyr Tyr
            100                 105                 110

```
Phe Pro Val Tyr Asp Tyr Leu Gly Phe Lys Gly Asp Arg Val Ile His
            115                 120                 125

Pro Val Gln Thr Tyr Ala Leu Tyr Tyr Trp Cys Phe His Tyr Phe Lys
    130                 135                 140

Arg Ile Met Glu Thr Phe Phe Val His Arg Phe Ser His Ala Thr Ser
145                 150                 155                 160

Pro Leu Ser Asn Val Phe Arg Asn Cys Ala Tyr Tyr Trp Ser Phe Gly
                165                 170                 175

Ala Phe Ile Ala Tyr Tyr Leu Asn His Pro Leu Tyr Thr Pro Val Ser
            180                 185                 190

Asp Leu Gln Met Lys Ile Gly Phe Gly Ile Gly Ile Ile Cys Gln Ile
        195                 200                 205

Ser Asn Phe Tyr Cys His Ile Leu Leu Arg Asn Leu Arg Ser Pro Asp
    210                 215                 220

Gly Asn Gly Gly Tyr Gln Ile Pro Arg Gly Phe Leu Phe Asn Ile Val
225                 230                 235                 240

Thr Cys Ala Asn Tyr Thr Thr Glu Ile Tyr Gln Trp Leu Gly Phe Asn
                245                 250                 255

Ile Ala Thr Gln Thr Val Ala Gly Tyr Ile Phe Leu Ile Val Ala Ala
            260                 265                 270

Ser Ile Met Thr Asn Trp Ala Leu Ala Lys His Arg Arg Leu Lys Lys
        275                 280                 285

Ile Phe Asp Gly Lys Asp Gly Arg Pro Lys Tyr Pro Arg Arg Trp Val
    290                 295                 300

Ile Leu Pro Pro Phe Leu
305                 310

<210> SEQ ID NO 68
<211> LENGTH: 1200
<212> TYPE: DNA
<213> ORGANISM: Hordeum vulgare

<400> SEQUENCE: 68
atggctgcag taagattgaa agaagttaga atggcacaga gggctgaagg tttagctaca      60
gttttagcaa tcggtactgc cgttccagct aattgtgttt atcaagctac ctatccagat     120
tattatttta gggttactaa aagtgagcac ttggcagatt taaaggagaa gtttcaaaga     180
atgtgtgaca atcaatgat tagaaagaga cacatgcact tgaccgagga atattgatc       240 aagaacccaa agatctgtgc acacatggag acctcattgg atgctagaca cgccatcgca     300
ttagttgaag ttcccaaatt gggccaaggt gcagctgaga aggccattaa ggagtggggc     360
caacccttgt ctaagattac tcatttggta ttttgcacaa catccggcgt tgacatgccc     420
ggtgctgatt accaattaac aaagttgtta ggtttgtccc ctacagtcaa aggttaatg     480 atgtaccaac aaggttgctt tggtggtgca actgttttga gattggcaaa agatatcgct     540
gaaaataata gaggtgccag agtgttagtc gtttgttccg agataactgc tatgaccttc     600
agaggtccat gcaagagtca tttagattcc ttggtaggtc atgccttgtt cggtgatggt     660
gccgctgctg caattatagg cgctgaccca gaccaattag acgaacaacc agttttccag     720
ttggtatcag cttctcagac tatattacca gaatcagaag gtgccataga tggccattta     780
acagaagctg gtttaactat acatttatta aaagatgttc ctggtttaat ttcagagaac     840
attgaacagg ctttggagga tgcctttgaa cctttaggta ttcataactg gaattcaatt     900
ttctggattg cacatcctgg tggccctgcc attttagaca gagttgaaga tagagtagga     960
```

```
ttggataaga agagaatgag ggcttctagg gaagtgttat ctgaatacgg aaatatgtct   1020
agtgcctctg tgttgtttgt gttagatgtc atgaggaaaa gttctgctaa agacggattg   1080
gcaaccacag gagaaggaaa agattgggga gtgttgtttg gattcggacc aggcttgact   1140
gtagaaacct tagtgttgca tagtgtccca gtccctgtcc ctactgcagc ttctgcatga   1200
```

<210> SEQ ID NO 69
<211> LENGTH: 1200
<212> TYPE: DNA
<213> ORGANISM: Hordeum vulgare

<400> SEQUENCE: 69

```
atggctgcag taagattgaa agaagttaga atggcacaga gggctgaagg tttagctaca     60
gttttagcaa tcggtactgc cgttccagct aattgtgttt atcaagctac ctatccagat    120
tattatttta gggttactaa aagtgagcac ttggcagatt taaggagaa gtttcaaaga     180 atgtgtgaca aatcaatgat tagaaagaga cacatgcact tgaccgagga aatattgatc    240
aagaacccaa agatctgtgc acacatggag acctcattgg atgctagaca cgccatcgca    300
ttagttgaag ttcccaaatt gggccaaggt gcagctgaga aggccattaa ggagtggggc    360
caacccttgt ctaagattac tcatttggta ttttgcacaa catccggcgt tgacatgccc    420
ggtgctgatt accaattaac aaagttgtta ggtttgtccc ctacagtcaa aaggttaatg    480
atgtaccaac aaggttgctt tggtggtgca actgttttga gattggcaaa agatatcgct    540
gaaaataata gaggtgccag agtgttagtc gtttgttccg agataactgc tatgaccttc    600
agaggtccat gcaagagtca tttagattcc ttggtaggtc atgccttgtt cggtgatggt    660
gccgctgctg caattatagg cgctgacccc agaccaattag acgaacaacc agttttccag    720
ttggtatcag cttctcagac tatattacca gaatcagaag gtgccataga tggccattta    780
acagaagctg gtttaacttt tcatttatta aaagatgttc ctggtttaat ttcagagaac    840
attgaacagg ctttggagga tgccttgaa cctttaggta ttcataactg gaattcaatt    900
ttctggattg cacatcctgg tggccctgcc attttagaca gagttgaaga tagagtagga    960
ttggataaga agagaatgag ggcttctagg gaagtgttat ctgaatacgg aaatatgtct   1020
agtgcctctg tgttgtttgt gttagatgtc atgaggaaaa gttctgctaa agacggattg   1080
gcaaccacag gagaaggaaa agattgggga gtgttgtttg gattcggacc aggcttgact   1140
gtagaaacct tagtgttgca tagtgtccca gtccctgtcc ctactgcagc ttctgcatga   1200
```

<210> SEQ ID NO 70
<211> LENGTH: 1200
<212> TYPE: DNA
<213> ORGANISM: Hordeum vulgare

<400> SEQUENCE: 70

```
atggctgcag taagattgaa agaagttaga atggcacaga gggctgaagg tttagctaca     60
gttttagcaa tcggtactgc cgttccagct aattgtgttt atcaagctac ctatccagat    120
tattatttta gggttactaa aagtgagcac ttggcagatt taaggagaa gtttcaaaga     180 atgtgtgaca aatcaatgat tagaaagaga cacatgcact tgaccgagga aatattgatc    240
aagaacccaa agatctgtgc acacatggag acctcattgg atgctagaca cgccatcgca    300
ttagttgaag ttcccaaatt gggccaaggt gcagctgaga aggccattaa ggagtggggc    360
caacccttgt ctaagattac tcatttggta ttttgcacaa catccggcgt tgacatgccc    420
ggtgctgatt accaattaac aaagttgtta ggtttgtccc ctacagtcaa aaggttaatg    480
```

```
atgtaccaac aaggttgctt tggtggtgca actgttttga gattggcaaa agatatcgct    540
gaaaataata gaggtgccag agtgttagtc gtttgttccg agataactgc tatggccttc    600
agaggtccat gcaagagtca tttagattcc ttggtaggtc atgccttgtt cggtgatggt    660
gccgctgctg caattatagg cgctgaccca gaccaattag acgaacaacc agttttccag    720
ttggtatcag cttctcagac tatattacca gaatcagaag gtgccataga tggccattta    780
acagaagctg gtttaacttt tcatttatta aaagatgttc ctggtttaat ttcagagaac    840
attgaacagg cttttggagga tgcctttgaa cctttaggta ttcataactg gaattcaatt    900
ttctggattg cacatcctgg tggccctgcc attttagaca gagttgaaga tagagtagga    960
ttggataaga agagaatgag ggcttctagg gaagtgttat ctgaatacgg aaatatgtct   1020
agtgcctctg tgttgtttgt gttagatgtc atgaggaaaa gttctgctaa agacggattg   1080
gcaaccacag gagaaggaaa agattgggga gtgttgtttg gattcggacc aggcttgact   1140
gtagaaacct tagtgttgca tagtgtccca gtccctgtcc ctactgcagc ttctgcatga   1200
```

<210> SEQ ID NO 71
<211> LENGTH: 399
<212> TYPE: PRT
<213> ORGANISM: Hordeum vulgare

<400> SEQUENCE: 71

```
Met Ala Ala Val Arg Leu Lys Glu Val Arg Met Ala Gln Arg Ala Glu
1               5                   10                  15

Gly Leu Ala Thr Val Leu Ala Ile Gly Thr Ala Val Pro Ala Asn Cys
            20                  25                  30

Val Tyr Gln Ala Thr Tyr Pro Asp Tyr Tyr Phe Arg Val Thr Lys Ser
        35                  40                  45

Glu His Leu Ala Asp Leu Lys Glu Lys Phe Gln Arg Met Cys Asp Lys
    50                  55                  60

Ser Met Ile Arg Lys Arg His Met His Leu Thr Glu Glu Ile Leu Ile
65                  70                  75                  80

Lys Asn Pro Lys Ile Cys Ala His Met Glu Thr Ser Leu Asp Ala Arg
                85                  90                  95

His Ala Ile Ala Leu Val Glu Val Pro Lys Leu Gly Gln Gly Ala Ala
            100                 105                 110

Glu Lys Ala Ile Lys Glu Trp Gly Gln Pro Leu Ser Lys Ile Thr His
        115                 120                 125

Leu Val Phe Cys Thr Thr Ser Gly Val Asp Met Pro Gly Ala Asp Tyr
    130                 135                 140

Gln Leu Thr Lys Leu Leu Gly Leu Ser Pro Thr Val Lys Arg Leu Met
145                 150                 155                 160

Met Tyr Gln Gln Gly Cys Phe Gly Gly Ala Thr Val Leu Arg Leu Ala
                165                 170                 175

Lys Asp Ile Ala Glu Asn Asn Arg Gly Ala Arg Val Leu Val Val Cys
            180                 185                 190

Ser Glu Ile Thr Ala Met Thr Phe Arg Gly Pro Cys Lys Ser His Leu
        195                 200                 205

Asp Ser Leu Val Gly His Ala Leu Phe Gly Asp Gly Ala Ala Ala Ala
    210                 215                 220

Ile Ile Gly Ala Asp Pro Asp Gln Leu Asp Glu Gln Pro Val Phe Gln
225                 230                 235                 240

Leu Val Ser Ala Ser Gln Thr Ile Leu Pro Glu Ser Glu Gly Ala Ile
```

```
                    245                 250                 255
Asp Gly His Leu Thr Glu Ala Gly Leu Thr Ile His Leu Leu Lys Asp
            260                 265                 270

Val Pro Gly Leu Ile Ser Glu Asn Ile Glu Gln Ala Leu Glu Asp Ala
            275                 280                 285

Phe Glu Pro Leu Gly Ile His Asn Trp Asn Ser Ile Phe Trp Ile Ala
            290                 295                 300

His Pro Gly Gly Pro Ala Ile Leu Asp Arg Val Glu Asp Arg Val Gly
305                 310                 315                 320

Leu Asp Lys Lys Arg Met Arg Ala Ser Arg Glu Val Leu Ser Glu Tyr
            325                 330                 335

Gly Asn Met Ser Ser Ala Ser Val Leu Phe Val Leu Asp Val Met Arg
            340                 345                 350

Lys Ser Ser Ala Lys Asp Gly Leu Ala Thr Thr Gly Glu Gly Lys Asp
            355                 360                 365

Trp Gly Val Leu Phe Gly Phe Gly Pro Gly Leu Thr Val Glu Thr Leu
            370                 375                 380

Val Leu His Ser Val Pro Val Pro Val Pro Thr Ala Ala Ser Ala
385                 390                 395

<210> SEQ ID NO 72
<211> LENGTH: 399
<212> TYPE: PRT
<213> ORGANISM: Hordeum vulgare

<400> SEQUENCE: 72

Met Ala Ala Val Arg Leu Lys Glu Val Arg Met Ala Gln Arg Ala Glu
1               5                   10                  15

Gly Leu Ala Thr Val Leu Ala Ile Gly Thr Ala Val Pro Ala Asn Cys
            20                  25                  30

Val Tyr Gln Ala Thr Tyr Pro Asp Tyr Tyr Phe Arg Val Thr Lys Ser
            35                  40                  45

Glu His Leu Ala Asp Leu Lys Glu Lys Phe Gln Arg Met Cys Asp Lys
        50                  55                  60

Ser Met Ile Arg Lys Arg His Met His Leu Thr Glu Glu Ile Leu Ile
65                  70                  75                  80

Lys Asn Pro Lys Ile Cys Ala His Met Glu Thr Ser Leu Asp Ala Arg
            85                  90                  95

His Ala Ile Ala Leu Val Glu Val Pro Lys Leu Gly Gln Gly Ala Ala
            100                 105                 110

Glu Lys Ala Ile Lys Glu Trp Gly Gln Pro Leu Ser Lys Ile Thr His
        115                 120                 125

Leu Val Phe Cys Thr Thr Ser Gly Val Asp Met Pro Gly Ala Asp Tyr
130                 135                 140

Gln Leu Thr Lys Leu Leu Gly Leu Ser Pro Thr Val Lys Arg Leu Met
145                 150                 155                 160

Met Tyr Gln Gln Gly Cys Phe Gly Gly Ala Thr Val Leu Arg Leu Ala
            165                 170                 175

Lys Asp Ile Ala Glu Asn Asn Arg Gly Ala Arg Val Leu Val Val Cys
            180                 185                 190

Ser Glu Ile Thr Ala Met Ala Phe Arg Gly Pro Cys Lys Ser His Leu
        195                 200                 205

Asp Ser Leu Val Gly His Ala Leu Phe Gly Asp Gly Ala Ala Ala Ala
    210                 215                 220
```

```
Ile Ile Gly Ala Asp Pro Asp Gln Leu Asp Glu Gln Pro Val Phe Gln
225                 230                 235                 240

Leu Val Ser Ala Ser Gln Thr Ile Leu Pro Glu Ser Glu Gly Ala Ile
            245                 250                 255

Asp Gly His Leu Thr Glu Ala Gly Leu Thr Phe His Leu Leu Lys Asp
            260                 265                 270

Val Pro Gly Leu Ile Ser Glu Asn Ile Glu Gln Ala Leu Glu Asp Ala
            275                 280                 285

Phe Glu Pro Leu Gly Ile His Asn Trp Asn Ser Ile Phe Trp Ile Ala
            290                 295                 300

His Pro Gly Gly Pro Ala Ile Leu Asp Arg Val Glu Asp Arg Val Gly
305                 310                 315                 320

Leu Asp Lys Lys Arg Met Arg Ala Ser Arg Glu Val Leu Ser Glu Tyr
                325                 330                 335

Gly Asn Met Ser Ser Ala Ser Val Leu Phe Val Leu Asp Val Met Arg
                340                 345                 350

Lys Ser Ser Ala Lys Asp Gly Leu Ala Thr Thr Gly Glu Gly Lys Asp
                355                 360                 365

Trp Gly Val Leu Phe Gly Phe Gly Pro Gly Leu Thr Val Glu Thr Leu
            370                 375                 380

Val Leu His Ser Val Pro Val Pro Val Pro Thr Ala Ala Ser Ala
385                 390                 395

<210> SEQ ID NO 73
<211> LENGTH: 399
<212> TYPE: PRT
<213> ORGANISM: Hordeum vulgare

<400> SEQUENCE: 73

Met Ala Ala Val Arg Leu Lys Glu Val Arg Met Ala Gln Arg Ala Glu
1               5                   10                  15

Gly Leu Ala Thr Val Leu Ala Ile Gly Thr Ala Val Pro Ala Asn Cys
            20                  25                  30

Val Tyr Gln Ala Thr Tyr Pro Asp Tyr Tyr Phe Arg Val Thr Lys Ser
            35                  40                  45

Glu His Leu Ala Asp Leu Lys Glu Lys Phe Gln Arg Met Cys Asp Lys
        50                  55                  60

Ser Met Ile Arg Lys Arg His Met His Leu Thr Glu Glu Ile Leu Ile
65                  70                  75                  80

Lys Asn Pro Lys Ile Cys Ala His Met Glu Thr Ser Leu Asp Ala Arg
                85                  90                  95

His Ala Ile Ala Leu Val Glu Val Pro Lys Leu Gly Gln Gly Ala Ala
            100                 105                 110

Glu Lys Ala Ile Lys Glu Trp Gly Gln Pro Leu Ser Lys Ile Thr His
            115                 120                 125

Leu Val Phe Cys Thr Thr Ser Gly Val Asp Met Pro Gly Ala Asp Tyr
130                 135                 140

Gln Leu Thr Lys Leu Leu Gly Leu Ser Pro Thr Val Lys Arg Leu Met
145                 150                 155                 160

Met Tyr Gln Gln Gly Cys Phe Gly Gly Ala Thr Val Leu Arg Leu Ala
                165                 170                 175

Lys Asp Ile Ala Glu Asn Asn Arg Gly Ala Arg Val Leu Val Val Cys
            180                 185                 190

Ser Glu Ile Thr Ala Met Thr Phe Arg Gly Pro Cys Lys Ser His Leu
            195                 200                 205
```

```
Asp Ser Leu Val Gly His Ala Leu Phe Gly Asp Gly Ala Ala Ala Ala
        210                 215                 220

Ile Ile Gly Ala Asp Pro Asp Gln Leu Asp Glu Gln Pro Val Phe Gln
225                 230                 235                 240

Leu Val Ser Ala Ser Gln Thr Ile Leu Pro Glu Ser Glu Gly Ala Ile
            245                 250                 255

Asp Gly His Leu Thr Glu Ala Gly Leu Thr Phe His Leu Leu Lys Asp
        260                 265                 270

Val Pro Gly Leu Ile Ser Glu Asn Ile Glu Gln Ala Leu Glu Asp Ala
    275                 280                 285

Phe Glu Pro Leu Gly Ile His Asn Trp Asn Ser Ile Phe Trp Ile Ala
290                 295                 300

His Pro Gly Gly Pro Ala Ile Leu Asp Arg Val Glu Asp Arg Val Gly
305                 310                 315                 320

Leu Asp Lys Lys Arg Met Arg Ala Ser Arg Glu Val Leu Ser Glu Tyr
                325                 330                 335

Gly Asn Met Ser Ser Ala Ser Val Leu Phe Val Leu Asp Val Met Arg
            340                 345                 350

Lys Ser Ser Ala Lys Asp Gly Leu Ala Thr Thr Gly Glu Gly Lys Asp
        355                 360                 365

Trp Gly Val Leu Phe Gly Phe Gly Pro Gly Leu Thr Val Glu Thr Leu
370                 375                 380

Val Leu His Ser Val Pro Val Pro Val Pro Thr Ala Ala Ser Ala
385                 390                 395
```

<210> SEQ ID NO 74
<211> LENGTH: 28
<212> TYPE: DNA
<213> ORGANISM: Artificial Sequence
<220> FEATURE:
<223> OTHER INFORMATION: Forward Primer for restriction enyzme-based cloning

<400> SEQUENCE: 74
acaaaaagct taaaatggct gcagtaag    28

<210> SEQ ID NO 75
<211> LENGTH: 16
<212> TYPE: DNA
<213> ORGANISM: Artificial Sequence
<220> FEATURE:
<223> OTHER INFORMATION: Reverse Primer for restriction enyzme-based cloning

<400> SEQUENCE: 75
acgtgccgcg gtcatg    16

<210> SEQ ID NO 76
<211> LENGTH: 31
<212> TYPE: DNA
<213> ORGANISM: Artificial Sequence
<220> FEATURE:
<223> OTHER INFORMATION: Reverse Primer

<400> SEQUENCE: 76
atggacctct gaaggtcata gcagttatct c    31

<210> SEQ ID NO 77
<211> LENGTH: 31
<212> TYPE: DNA

```
<213> ORGANISM: Artificial Sequence
<220> FEATURE:
<223> OTHER INFORMATION: Forward primer

<400> SEQUENCE: 77
gagataactg ctatgacctt cagaggtcca t                                     31

<210> SEQ ID NO 78
<211> LENGTH: 38
<212> TYPE: DNA
<213> ORGANISM: Artificial Sequence
<220> FEATURE:
<223> OTHER INFORMATION: Reverse primer

<400> SEQUENCE: 78
acatctttta ataaatgaaa agttaaacca gcttctgt                              38

<210> SEQ ID NO 79
<211> LENGTH: 38
<212> TYPE: DNA
<213> ORGANISM: Artificial Sequence
<220> FEATURE:
<223> OTHER INFORMATION: Forward primer

<400> SEQUENCE: 79
acagaagctg gtttaacttt tcatttatta aaagatgt                              38

<210> SEQ ID NO 80
<211> LENGTH: 669
<212> TYPE: DNA
<213> ORGANISM: Citrus sinensis

<400> SEQUENCE: 80
atgaatccat ctccatctgt tactgaattg caagtagaga acgtcacctt taccccaagt      60
gttcagcctc caggtagtac taaaagccat ttcttaggag gcgctggtga aagaggacta     120
gagattgaag gcaagtttgt gaaattcaca gcaataggtg tatatcttga agatgacgcc     180
gtccctttgt tagctggtaa gtggaaagga agaccgcag aggaactaac tgaatctgtg      240 gagttttca gggatgttgt aacaggccca tttgaaaaat tcatgaaggt caccatgatc      300
cttcctttga ctggtgccca atactcagaa aaagttgctg agaattgtat tgcaatatgg     360
aagtttttcg gaatctatac agacgccgaa gctaaagcaa ttgagaagtt taccgaagtg     420
ttcaaagatg aaatatttcc acctggttcc agtatccttt ttactcagag cccaggctct     480
ttgacaattt cattctccaa ggacggtagt attcctaaag atggagttgc tgtaatagag     540
tctaacttac taagcgaagc cgtccttgaa tcaatgatcg gtaaaaatgg cgtgtcccca     600
gcagctaaga aaagtttggc cgagagatta tctgcactat tgaacgttac ttcagataag     660
atgaaatga                                                            669

<210> SEQ ID NO 81
<211> LENGTH: 726
<212> TYPE: DNA
<213> ORGANISM: Petunia hybrida

<400> SEQUENCE: 81
atgtctccac cagtttctgt tacaaaaatg caagtcgaaa attatgcttt tgcaccaaca      60
gtgaaccctg ccggttccac caatactttg ttcttagctg gagcaggcca tagaggtcta     120
gagattgaag gaaagtttgt gaaattcaca gccataggcg tataccttga ggaaagtgct     180
atcccatttt tggcagaaaa gtggaaaggt aagacccctc aggagttaac tgatagcgtc     240
```

```
gagttcttta gggacgtggt tacaggtcca ttcgaaaagt ttaccagagt aactatgatt    300
ctacctctta caggaaagca atattctgag aaagtcgccg aaaactgtgt tgctcactgg    360
aagggcatag gtacctacac tgatgacgaa ggaagggcaa tcgagaaatt cttggatgtg    420
tttagatcag aaacattccc acctggtgct tccattatgt ttactcagag tccattaggc    480
ttgttaacca tcagctttgc caaggacgat tcagttaccg gtactgcaaa tgctgtaatc    540
gagaacaaac aactatcaga agccgtcctt gaatccatta ttggaaagca tggtgtgagt    600
cctgcagcca aatgctctgt tgccgagaga gtagcagaat tgttaaaaaa gagctatgct    660
gaagaggcct cagtgttcgg caaaccagaa accgaaaagt ccacaatacc tgttatcggt    720
gtgtag                                                               726
```

<210> SEQ ID NO 82
<211> LENGTH: 663
<212> TYPE: DNA
<213> ORGANISM: Petunia hybrida

<400> SEQUENCE: 82

```
atgtctccat ctgtttctgt tactaaagtc caagtggaaa attatgtctt tcctccaaca     60
gtgaagcctc cagctagtac caaaactttg ttcttaggtg agcaggcca tagaggtcta    120 gatgttgagg gaaagtttgt gaaattcaca gttattggcg tataccttga agagagcgcc    180
gtccagtttt tggctcctaa gtggaaaggt aagtctgcag aagaattaat acactcagtt    240
gacttcttta gggatatcgt gaccggtcca ttcgagaagt ttactagagt taggttcatt    300
ctacctctta caggaaagca attttccgaa aaagtagccg aaaactgtgt cgctcattgg    360
aaggcaaccg gcacttatag tgacgccggt agcagagcta tagagaaatt cttgaatgtg    420
gttaagtctg aaacattttt accaggagca tcaatcttgt ttacccagtc cccttttaggt    480 agtctaacta tttctttcac aaaagatgac agcatatccg aagctggcaa cgccgtaatc    540
gagaacaaac agtttagtga ggccgtcctt gagactatta ttggtgaaca cggagttagt    600
ccagctgcca agtgctctat agcagctaga atgtcagaat tgttcaaaaa cagcttattt    660
tga                                                                  663
```

<210> SEQ ID NO 83
<211> LENGTH: 672
<212> TYPE: DNA
<213> ORGANISM: Pisum sativum

<400> SEQUENCE: 83

```
atgtgttgtt ctattttgca tcacagaaat ccaaggaggg aacatgagtt tcctgctgtt     60
gtaacttcac cagtcacaga aaaccacata ttcttaggtg agcaggcga gagaggtcta    120 accatcaatg aacttttat caaattcaca tgtataggcg tgtatcttga agataaggcc    180
gacaaatcct tggctaccaa gtgggaaggc aaattagagg aactactaga aacattggat    240
ttttacagag acatcattag tggcccttc gagaagttaa taagaaggag caaaatcaag    300
gaattgtccg gtccagaata ttcaagaaaa gtcatggaga actgcgttgc acacttaaag    360
tccgtaggca catacggtga tgccgaagtg gaggctattc aaaatctaca gaaacttagt    420
agaatgttga ttttcactt agttctattg aagaagaaca ggcaaagccc tgatggaata    480
ttaggtcttt cttcatccaa agatatcagt attccagaaa aggaggatgc aataatcgag    540
aataaggccg cttctagcgc agtattggag actatgattg gcgaacatgc tgtctctcca    600
```

```
gacttaaaaa gatgtctagc cgcaaggctt ccagctttgt taaacgaagg tactttcaaa      660
ataggaaatt ga                                                          672

<210> SEQ ID NO 84
<211> LENGTH: 675
<212> TYPE: DNA
<213> ORGANISM: Pueraria Montana var. lobata

<400> SEQUENCE: 84
atggctgctg ctgctgctgt tgctactatt tctgccgtac aagtcgaatt tttggagttc       60
ccagcagtgg ttacaagccc tgcctccggt agaacctatt ttttaggagg cgctggtgaa      120
aggggactaa ctatagaggg caaattcatc aagtttacag gtattggtgt ataccttgaa      180
gataaagcag tcagtagttt ggctgccaag tggaaaggaa agccatctga agagttagtg      240
gaaaccctag acttctatag agatataatc tcaggccctt ttgaaaaact tattagggt       300 tccaagatat tgccattaag tggagttgag tacagcaaaa aggtaatgga aaattgtgtc      360
gcacatatga atctgttggt tacttatggc gacgctgaag ccgcagctat cgagaagttc      420
gccgaagcct ttaaaaacgt gaatttccag cctggtgcta cagttttta cagacaatca      480 ccagatggag tattgggttt atccttcagt gaggacgtca ccattcctga taacgaagcc      540
gcagtgattg aaaataaggc tgtttctgcc gcagtactag agactatgat aggcgaacac      600
gctgtcagcc cagatcttaa aagatcacta gcatccaggc ttcctgccgt tctaagtcat      660
ggtatcattg tgtga                                                       675

<210> SEQ ID NO 85
<211> LENGTH: 702
<212> TYPE: DNA
<213> ORGANISM: Oryza sativa subsp. japonica

<400> SEQUENCE: 85
atggctgctg tctctgaagt tgaagttgac ggtgtcgttt ccctccagt tgctagacca        60 ccaggctctg gtcatgctca cttcttggct ggtgctggtg tccgtggtgt tgaaatcgct      120
ggtaatttca tcaagttcac cgctattggc gtctacctag aagaaggtgc cgccgttcca      180
gctttggcta agaagtgggc cggtaagtct gctgatgagt tggctgctga tgctgccttt      240
ttccgtgacg ttgttaccgg tgacttcgaa aaattcacca gagtcaccat gatcttgcca      300
ctaaccggtg agcagtattc cgacaaggtc accgaaaact gtgttgctgc ttggaaggcc      360
gctggcgttt atactgacgc cgaaggtgct gctgctgata aattcaagga agcctttaaa      420
ccacattcct tcccaccagg tgcttctatc ttgttcactc attctccacc aggtgtctta      480
accgttgcct ttagcaaaga ctcctccgtc ccagaaggcg ctgttgctgc tgctgctatc      540
gaaaacaggg ctttgtgcga agctgtccta gactccatta tcggtgagca tggtgtttct      600
ccagctgcca aaagatccat cgctgctcgt gtctctcaat tgttgaaagc tgaatccacc      660
ggcgacgtcg ctgctgctga accagctcct gtctctgctt aa                         702

<210> SEQ ID NO 86
<211> LENGTH: 669
<212> TYPE: DNA
<213> ORGANISM: Medicago sativa

<400> SEQUENCE: 86
atggctgctt ccattaccgc tattaccgtt gaaaatttgg aatacccagc tgttgttact       60
tctccagtta ctggtaagtc ttactttttg ggtggtgctg gtgaaagagg tttgactatt      120
```

-continued

```
gaaggtaact tcattaagtt caccgccatc ggtgtttact tggaagatat tgctgttgct      180
tctttggctg ctaaatggaa gggtaaatcc tccgaagaat tattggaaac cttggacttc      240
tacagagaca ttatttctgg tccattcgaa aagttgatca gaggttccaa gatcagagaa      300
ttgtctggtc cagaatactc cagaaaggtt atggaaaatt gcgttgccca tttgaagtct      360
gttggtactt atggtgatgc tgaagctgaa gctatgcaaa aatttgctga agcctttaag      420
ccagttaatt ttccaccagg tgcttccgtt ttttacagac aatctccaga tggtatcttg      480
ggtttgtctt tttcaccaga tacctccatc ccagaaaaag aagctgcttt gattgaaaac      540
aaggctgttt cttctgctgt cttggaaact atgattggtg aacatgctgt tcccccagat      600
ttgaaaagat gtttagctgc tagattgcct gccttgttga atgaaggtgc ttttaagatt      660
ggtaactaa                                                              669
```

```
<210> SEQ ID NO 87
<211> LENGTH: 222
<212> TYPE: PRT
<213> ORGANISM: Citrus sinensis

<400> SEQUENCE: 87

Met Asn Pro Ser Pro Ser Val Thr Glu Leu Gln Val Glu Asn Val Thr
1               5                   10                  15

Phe Thr Pro Ser Val Gln Pro Pro Gly Ser Thr Lys Ser His Phe Leu
            20                  25                  30

Gly Gly Ala Gly Glu Arg Gly Leu Glu Ile Glu Gly Lys Phe Val Lys
        35                  40                  45

Phe Thr Ala Ile Gly Val Tyr Leu Glu Asp Asp Ala Val Pro Leu Leu
    50                  55                  60

Ala Gly Lys Trp Lys Gly Lys Thr Ala Glu Glu Leu Thr Glu Ser Val
65                  70                  75                  80

Glu Phe Phe Arg Asp Val Val Thr Gly Pro Phe Glu Lys Phe Met Lys
                85                  90                  95

Val Thr Met Ile Leu Pro Leu Thr Gly Ala Gln Tyr Ser Glu Lys Val
            100                 105                 110

Ala Glu Asn Cys Ile Ala Ile Trp Lys Phe Phe Gly Ile Tyr Thr Asp
        115                 120                 125

Ala Glu Ala Lys Ala Ile Glu Lys Phe Thr Glu Val Phe Lys Asp Glu
    130                 135                 140

Ile Phe Pro Pro Gly Ser Ser Ile Leu Phe Thr Gln Ser Pro Gly Ser
145                 150                 155                 160

Leu Thr Ile Ser Phe Ser Lys Asp Gly Ser Ile Pro Lys Asp Gly Val
                165                 170                 175

Ala Val Ile Glu Ser Asn Leu Leu Ser Glu Ala Val Leu Glu Ser Met
            180                 185                 190

Ile Gly Lys Asn Gly Val Ser Pro Ala Ala Lys Lys Ser Leu Ala Glu
        195                 200                 205

Arg Leu Ser Ala Leu Leu Asn Val Thr Ser Asp Lys Met Lys
    210                 215                 220

<210> SEQ ID NO 88
<211> LENGTH: 241
<212> TYPE: PRT
<213> ORGANISM: Petunia hybrida

<400> SEQUENCE: 88
```

```
Met Ser Pro Pro Val Ser Val Thr Lys Met Gln Val Glu Asn Tyr Ala
1               5                   10                  15
Phe Ala Pro Thr Val Asn Pro Ala Gly Ser Thr Asn Thr Leu Phe Leu
            20                  25                  30
Ala Gly Ala Gly His Arg Gly Leu Glu Ile Glu Gly Lys Phe Val Lys
        35                  40                  45
Phe Thr Ala Ile Gly Val Tyr Leu Glu Glu Ser Ala Ile Pro Phe Leu
    50                  55                  60
Ala Glu Lys Trp Lys Gly Lys Thr Pro Gln Glu Leu Thr Asp Ser Val
65                  70                  75                  80
Glu Phe Phe Arg Asp Val Val Thr Gly Pro Phe Glu Lys Phe Thr Arg
                85                  90                  95
Val Thr Met Ile Leu Pro Leu Thr Gly Lys Gln Tyr Ser Glu Lys Val
                100                 105                 110
Ala Glu Asn Cys Val Ala His Trp Lys Gly Ile Gly Thr Tyr Thr Asp
            115                 120                 125
Asp Glu Gly Arg Ala Ile Glu Lys Phe Leu Asp Val Phe Arg Ser Glu
        130                 135                 140
Thr Phe Pro Pro Gly Ala Ser Ile Met Phe Thr Gln Ser Pro Leu Gly
145                 150                 155                 160
Leu Leu Thr Ile Ser Phe Ala Lys Asp Asp Ser Val Thr Gly Thr Ala
                165                 170                 175
Asn Ala Val Ile Glu Asn Lys Gln Leu Ser Glu Ala Val Leu Glu Ser
            180                 185                 190
Ile Ile Gly Lys His Gly Val Ser Pro Ala Ala Lys Cys Ser Val Ala
        195                 200                 205
Glu Arg Val Ala Glu Leu Leu Lys Lys Ser Tyr Ala Glu Glu Ala Ser
    210                 215                 220
Val Phe Gly Lys Pro Glu Thr Glu Lys Ser Thr Ile Pro Val Ile Gly
225                 230                 235                 240
Val
```

<210> SEQ ID NO 89
<211> LENGTH: 220
<212> TYPE: PRT
<213> ORGANISM: Petunia hybrida

<400> SEQUENCE: 89

```
Met Ser Pro Ser Val Ser Val Thr Lys Val Gln Val Glu Asn Tyr Val
1               5                   10                  15
Phe Pro Pro Thr Val Lys Pro Ala Ser Thr Lys Thr Leu Phe Leu
            20                  25                  30
Gly Gly Ala Gly His Arg Gly Leu Asp Val Glu Gly Lys Phe Val Lys
        35                  40                  45
Phe Thr Val Ile Gly Val Tyr Leu Glu Glu Ser Ala Val Gln Phe Leu
    50                  55                  60
Ala Pro Lys Trp Lys Gly Lys Ser Ala Glu Glu Leu Ile His Ser Val
65                  70                  75                  80
Asp Phe Phe Arg Asp Ile Val Thr Gly Pro Phe Glu Lys Phe Thr Arg
                85                  90                  95
Val Arg Phe Ile Leu Pro Leu Thr Gly Lys Gln Phe Ser Glu Lys Val
                100                 105                 110
Ala Glu Asn Cys Val Ala His Trp Lys Ala Thr Gly Thr Tyr Ser Asp
            115                 120                 125
```

Ala Gly Ser Arg Ala Ile Glu Lys Phe Leu Asn Val Lys Ser Glu
        130                 135                 140

Thr Phe Leu Pro Gly Ala Ser Ile Leu Phe Thr Gln Ser Pro Leu Gly
145                 150                 155                 160

Ser Leu Thr Ile Ser Phe Thr Lys Asp Asp Ser Ile Ser Glu Ala Gly
                165                 170                 175

Asn Ala Val Ile Glu Asn Lys Gln Phe Ser Glu Ala Val Leu Glu Thr
            180                 185                 190

Ile Ile Gly Glu His Gly Val Ser Pro Ala Ala Lys Cys Ser Ile Ala
        195                 200                 205

Ala Arg Met Ser Glu Leu Phe Lys Asn Ser Leu Phe
210                 215                 220

<210> SEQ ID NO 90
<211> LENGTH: 223
<212> TYPE: PRT
<213> ORGANISM: Pisum sativum

<400> SEQUENCE: 90

Met Cys Cys Ser Ile Leu His His Arg Asn Pro Arg Arg Glu His Glu
1               5                   10                  15

Phe Pro Ala Val Val Thr Ser Pro Val Thr Glu Asn His Ile Phe Leu
            20                  25                  30

Gly Gly Ala Gly Glu Arg Gly Leu Thr Ile Asn Gly Thr Phe Ile Lys
        35                  40                  45

Phe Thr Cys Ile Gly Val Tyr Leu Glu Asp Lys Ala Asp Lys Ser Leu
    50                  55                  60

Ala Thr Lys Trp Glu Gly Lys Leu Glu Glu Leu Leu Glu Thr Leu Asp
65                  70                  75                  80

Phe Tyr Arg Asp Ile Ile Ser Gly Pro Phe Glu Lys Leu Ile Arg Arg
                85                  90                  95

Ser Lys Ile Lys Glu Leu Ser Gly Pro Glu Tyr Ser Arg Lys Val Met
            100                 105                 110

Glu Asn Cys Val Ala His Leu Lys Ser Val Gly Thr Tyr Gly Asp Ala
        115                 120                 125

Glu Val Glu Ala Ile Gln Asn Leu Gln Lys Leu Ser Arg Met Leu Ile
    130                 135                 140

Phe His Leu Val Leu Leu Lys Lys Asn Arg Gln Ser Pro Asp Gly Ile
145                 150                 155                 160

Leu Gly Leu Ser Ser Ser Lys Asp Ile Ser Ile Pro Glu Lys Glu Asp
                165                 170                 175

Ala Ile Ile Glu Asn Lys Ala Ala Ser Ser Ala Val Leu Glu Thr Met
            180                 185                 190

Ile Gly Glu His Ala Val Ser Pro Asp Leu Lys Arg Cys Leu Ala Ala
        195                 200                 205

Arg Leu Pro Ala Leu Leu Asn Glu Gly Thr Phe Lys Ile Gly Asn
    210                 215                 220

<210> SEQ ID NO 91
<211> LENGTH: 224
<212> TYPE: PRT
<213> ORGANISM: Pueraria montana

<400> SEQUENCE: 91

Met Ala Ala Ala Ala Val Thr Ile Ser Ala Val Gln Val Glu
1               5                   10                  15

```
Phe Leu Glu Phe Pro Ala Val Val Thr Ser Pro Ala Ser Gly Arg Thr
            20                  25                  30

Tyr Phe Leu Gly Gly Ala Gly Glu Arg Gly Leu Thr Ile Glu Gly Lys
        35                  40                  45

Phe Ile Lys Phe Thr Gly Ile Gly Val Tyr Leu Glu Asp Lys Ala Val
    50                  55                  60

Ser Ser Leu Ala Ala Lys Trp Lys Gly Lys Pro Ser Glu Glu Leu Val
65                  70                  75                  80

Glu Thr Leu Asp Phe Tyr Arg Asp Ile Ile Ser Gly Pro Phe Glu Lys
                85                  90                  95

Leu Ile Arg Gly Ser Lys Ile Leu Pro Leu Ser Gly Val Glu Tyr Ser
            100                 105                 110

Lys Lys Val Met Glu Asn Cys Val Ala His Met Lys Ser Val Gly Thr
        115                 120                 125

Tyr Gly Asp Ala Glu Ala Ala Ile Glu Lys Phe Ala Glu Ala Phe
    130                 135                 140

Lys Asn Val Asn Phe Gln Pro Gly Ala Thr Val Phe Tyr Arg Gln Ser
145                 150                 155                 160

Pro Asp Gly Val Leu Gly Leu Ser Phe Ser Glu Asp Val Thr Ile Pro
                165                 170                 175

Asp Asn Glu Ala Ala Val Ile Glu Asn Lys Ala Val Ser Ala Ala Val
            180                 185                 190

Leu Glu Thr Met Ile Gly Glu His Ala Val Ser Pro Asp Leu Lys Arg
        195                 200                 205

Ser Leu Ala Ser Arg Leu Pro Ala Val Leu Ser His Gly Ile Ile Val
210                 215                 220

<210> SEQ ID NO 92
<211> LENGTH: 233
<212> TYPE: PRT
<213> ORGANISM: Oryza sativa subsp. japonica

<400> SEQUENCE: 92

Met Ala Ala Val Ser Glu Val Glu Val Asp Gly Val Val Phe Pro Pro
1               5                   10                  15

Val Ala Arg Pro Pro Gly Ser Gly His Ala His Phe Leu Ala Gly Ala
            20                  25                  30

Gly Val Arg Gly Val Glu Ile Ala Gly Asn Phe Ile Lys Phe Thr Ala
        35                  40                  45

Ile Gly Val Tyr Leu Glu Glu Gly Ala Ala Val Pro Ala Leu Ala Lys
    50                  55                  60

Lys Trp Ala Gly Lys Ser Ala Asp Glu Leu Ala Ala Asp Ala Ala Phe
65                  70                  75                  80

Phe Arg Asp Val Val Thr Gly Asp Phe Glu Lys Phe Thr Arg Val Thr
                85                  90                  95

Met Ile Leu Pro Leu Thr Gly Glu Gln Tyr Ser Asp Lys Val Thr Glu
            100                 105                 110

Asn Cys Val Ala Ala Trp Lys Ala Ala Gly Val Tyr Thr Asp Ala Glu
        115                 120                 125

Gly Ala Ala Ala Asp Lys Phe Lys Glu Ala Phe Lys Pro His Ser Phe
    130                 135                 140

Pro Pro Gly Ala Ser Ile Leu Phe Thr His Ser Pro Pro Gly Val Leu
145                 150                 155                 160

Thr Val Ala Phe Ser Lys Asp Ser Ser Val Pro Glu Gly Ala Val Ala
                165                 170                 175
```

Ala Ala Ala Ile Glu Asn Arg Ala Leu Cys Glu Ala Val Leu Asp Ser
            180                 185                 190

Ile Ile Gly Glu His Gly Val Ser Pro Ala Ala Lys Arg Ser Ile Ala
        195                 200                 205

Ala Arg Val Ser Gln Leu Leu Lys Ala Glu Ser Thr Gly Asp Val Ala
210                 215                 220

Ala Ala Glu Pro Ala Pro Val Ser Ala
225                 230

<210> SEQ ID NO 93
<211> LENGTH: 222
<212> TYPE: PRT
<213> ORGANISM: Medicago sativa

<400> SEQUENCE: 93

Met Ala Ala Ser Ile Thr Ala Ile Thr Val Glu Asn Leu Glu Tyr Pro
1               5                   10                  15

Ala Val Val Thr Ser Pro Val Thr Gly Lys Ser Tyr Phe Leu Gly Gly
            20                  25                  30

Ala Gly Glu Arg Gly Leu Thr Ile Glu Gly Asn Phe Ile Lys Phe Thr
        35                  40                  45

Ala Ile Gly Val Tyr Leu Glu Asp Ile Ala Val Ala Ser Leu Ala Ala
    50                  55                  60

Lys Trp Lys Gly Lys Ser Ser Glu Glu Leu Leu Glu Thr Leu Asp Phe
65                  70                  75                  80

Tyr Arg Asp Ile Ile Ser Gly Pro Phe Glu Lys Leu Ile Arg Gly Ser
                85                  90                  95

Lys Ile Arg Glu Leu Ser Gly Pro Glu Tyr Ser Arg Lys Val Met Glu
            100                 105                 110

Asn Cys Val Ala His Leu Lys Ser Val Gly Thr Tyr Gly Asp Ala Glu
        115                 120                 125

Ala Glu Ala Met Gln Lys Phe Ala Glu Ala Phe Lys Pro Val Asn Phe
    130                 135                 140

Pro Pro Gly Ala Ser Val Phe Tyr Arg Gln Ser Pro Asp Gly Ile Leu
145                 150                 155                 160

Gly Leu Ser Phe Ser Pro Asp Thr Ser Ile Pro Glu Lys Glu Ala Ala
                165                 170                 175

Leu Ile Glu Asn Lys Ala Val Ser Ser Ala Val Leu Glu Thr Met Ile
            180                 185                 190

Gly Glu His Ala Val Ser Pro Asp Leu Lys Arg Cys Leu Ala Ala Arg
        195                 200                 205

Leu Pro Ala Leu Leu Asn Glu Gly Ala Phe Lys Ile Gly Asn
    210                 215                 220

<210> SEQ ID NO 94
<211> LENGTH: 948
<212> TYPE: DNA
<213> ORGANISM: Arabidopsis thaliana

<400> SEQUENCE: 94
aagcttaaaa tgaaggtcac cgtcgtttct agatcaggta gagaagtttt gaaagcccca      60
ttggatttgc cagattctgc tactgttgct gacttgcaag aagcctttca taagagagct     120
aagaagttct acccatccag acaaagattg actttgccag ttactccagg ttctaaagat     180
aagccagttg tcttgaactc caagaagtcc ttgaaagaat actgtgacgg taacaacaac     240

```
tccttgactg ttgtttttaa ggatttgggt gcccaagttt cttacagaac tttgttcttc    300
ttcgaatact tgggtccttt gttgatctac ccagttttt actacttccc agtctacaag    360
tttttgggtt acggtgaaga ttgcgttatc catccagttc aaacttacgc tatgtactac    420
tggtgtttcc actacttcaa gagaatcttg gaaaccttct tcgtccacag attttctcat    480
gctacttctc caattggtaa cgttttcaga aactgtgcct attactggtc tttcggtgct    540
tatattgctt actacgttaa ccacccatta tacactccag tttcagactt gcaaatgaag    600
attggttttg gtttcggttt ggtctgtcaa gttgctaact tctactgcca tatcttgttg    660
aagaacttga gagatccatc tggtgctggt ggttatcaaa ttccaagagg tttttttgttc   720 aacatcgtta cctgtgctaa ctacactacc gaaatctatc aatggttggg tttcaacatt    780
gccactcaaa ctattgctgg ttacgttttt ttggctgttg ccgctttgat tatgactaat    840
tgggctttgg gtaagcactc cagattgaga aagattttcg atggtaaaga cggtaagcca    900
aagtatccaa gaagatgggt tattttgcca ccattcttgt aaccgcgg                 948
```

<210> SEQ ID NO 95
<211> LENGTH: 948
<212> TYPE: DNA
<213> ORGANISM: Gossypium hirsutum

<400> SEQUENCE: 95

```
aagcttaaaa tgaaggtcac cttggtcagt agatcaggta gagaattcat taagggtggt    60
ttggaattga acgattctgc tactgttgct gacttgcaag aagctattca taagagaact    120
aagaagttct acccatccag acaaagattg actttgccag ttccatctgg ttctagagaa    180
agaccagtta tcttgaacta caagaagtcc ttgaaggatt actgtgacgg taacgaaaac    240
actttgacca tcgtttttaa ggacttgggt ccacaagttt cttacagaac tttgttcttc    300
ttcgaatatt tgggtccatt gatcttgtac ccagttttct attacttccc agtctacaag    360
tacttcggtt acgaagaaaa gagagttatc cacccagttc aaacttatgc cttgtactac    420
tggtgtttcc actacttcaa gagaattatg gaaaccttct tcatccacag attctctcat    480
gctacttctc cattgtctaa cgttttcaga aactgtgctt actactggac tttcggttct    540
tatattgcct actacgttaa ccacccatta tacactccag tttcagactt gcaaatgaag    600
attggttttg gtttcggtat cgtttgtcaa ttggctaact tctactgcca catcatcttg    660
aagaatttga gatcaccaga tggttctggt ggttaccaaa ttccaagagg tttttttgttc   720 aacatcgtta cctgtgctaa ctacactacc gaaatctatc aatggttggg tttcaacatt    780
gctactcaaa cagttgctgg ttacgttttc ttggttgttg ctacctctat tatgactaat    840
tgggccttgg ctaaacacag aagattgaag aaattattcg acggtaagga cggtagacca    900
aagtatccaa gaagatgggt tattttgcca ccattcttgt aaccgcgg                 948
```

<210> SEQ ID NO 96
<211> LENGTH: 933
<212> TYPE: DNA
<213> ORGANISM: Malus domestica

<400> SEQUENCE: 96

```
atgaaggtca ccgtcgtttc tagatcaggt agagaagttg ttaagggtgg tttggaattg     60
tctgattctg ctactgttgc tgacttgcaa gatgctattc ataagagaac taagaagttc    120
tacccagcca gacaaagatt gactttgcca gttcaaccag ttctaaaga aagaccagtt     180 gtcttgtctt acaagaagtc attgcaagac tacatctccg gtaactctga taacttgact    240
```

```
gttgttttca aggacttggg tccacaagtt tcttacagaa cttttgttctt cttcgaatat    300 ttgggtccat tgatcttgta cccaatcttc tactacttcc cagtttacga ttacttgggt    360
ttcaagggtg atagagttat ccatccagtt caaacttatg ccttgtacta ctggtgtttc    420
cactacttca agagaattat ggaaaccttc ttcgtccaca gattctctca tgctacttct    480
ccattgtcta acgttttcag aaactgtgcc tactattggt ctttcggtgc ttttattgct    540
tactacttga accacccatt atacactcca gtttcagact tgcaaatgaa gattggtttc    600
ggtattggta tcatctgcca aatctctaac ttctactgcc acatcttgtt gagaaacttg    660
agatcaccag atggtaatgg tggttaccaa attccaagag gtttcttgtt caacatcgtt    720
acctgtgcta actacactac cgaaatctat caatggttgg gttttaacat tgccactcaa    780
acagttgccg gttacatttt tttgatcgtt gctgcttcta tcatgaccaa ttgggctttg    840
gctaaacaca gaagattgaa gaaaatcttc gatggtaagg acggtagacc aaagtatcca    900
agaagatggg ttattttgcc accattcttg taa                                 933

<210> SEQ ID NO 97
<211> LENGTH: 3702
<212> TYPE: DNA
<213> ORGANISM: Arabidopsis thaliana

<400> SEQUENCE: 97
atggatttgt tattgctgga aaagtcactt attgctgtat ttgtggcagt tattctagcc     60
acggttattt ctaaattaag aggtaagaaa ctaaaactac ctcctggtcc catccccata    120 ccaattttg gtaattggtt gcaagtgggc gatgatttga atcacagaaa tttggtagac    180
tatgctaaga agttcggtga cctttttcttg cttagaatgg gtcaaaggaa tttggtagtg    240
gttagctcac ctgatttgac taaggaggtc ttattaacgc aaggcgttga gtttggctcc    300
agaactagaa atgttgtgtt tgatattttc actggtaaag gtcaagatat ggttttttaca    360 gtttacggtg agcactggag aaaaatgaga agaatcatga ccgtaccatt ctttactaac    420
aaggttgttc aacaaaatag agaaggttgg gagtttgagg cagcttccgt agtggaagac    480
gtaaagaaaa atccagattc ggccacaaag ggtatagtac taagaaaaag actacaattg    540
atgatgtaca acaatatgtt cagaattatg tttgacagaa gatttgaaag tgaagatgac    600
cctttgttcc tgagacttaa ggctttgaat ggtgaaagat cgagattggc tcaaagtttc    660
gaatataatt acggtgactt tattccaatc ttaagaccat ttttgagagg ctatttgaaa    720
atttgccaag acgtcaagga taggaggatc gctcttttca agaagtactt tgtggacgag    780
agaaagcaaa tagcttcttc caagcccaca ggttcggaag gtttaaaatg tgcaattgat    840 catatttag aagctgaaca aaaaggtgaa attaacgaag ataatgtttt gtacattgta    900
gaaaatatca atgtggctgc aatagaaaca accttatggt caatagaatg gggtattgct    960
gaattggtga atcacccaga aatacaatct aaactgagaa acgagctaga taccgttttta   1020 ggtccaggtg tccaagttac agaacctgat ttgcataagt taccctactt gcaagctgtg   1080
gttaaagaaa ccttgagatt gagaatggct attcctcttc tagttcctca tatgaacta   1140 catgatgcta aactggccgg ttatgatatt ccagcagaaa gtaagatttt agtaaatgca   1200
tggtggttgg ccaacaatcc aaacagttgg aaaaagcctg aagaattcag acctgaaaga   1260
ttcttcgaag aggaatctca tgttgaagcc aacggaaatg acttcagata tgtacctttt   1320
ggcgttggca agatcgtg tccaggaata atactagcct taccaatatt gggtatcaca   1380
```

```
attggtagga tggttcaaaa ttttgagttg ctaccaccac ccggacaatc gaaagtcgat      1440
acttcagaga aaggaggaca attctcattg catattttga atcattccat tatagtcatg      1500
aaacccagaa attgtagcgc tgaagctgca gcaaaagaag ctgcagcuaa agaagctgca      1560
gcaaaagctt ccagtagctc ttcctcctca acctcgatga tcgacttaat ggctgctatt      1620
ataaaaggag aaccagttat agttagtgac cctgctaacg caagcgctta cgaatccgtt      1680
gcagccgagt tgtcaagtat gcttatagaa aatagacagt ttgctatgat tgtaacgacc      1740
agcatcgccg ttttaattgg ttgcatcgtg atgttggtgt ggaggaggag cggttcgggc      1800
aattcaaaga gggttgaacc actaaagcca ttagttatca aacctagaga agaggaaatt      1860
gacgatggaa ggaagaaagt cactatattc ttcggcaccc aaacaggtac agctgaaggt      1920
tttgctaagg ctctaggaga agaagcaaaa gctagatatg aaaagacgag attcaaaatt      1980
gtcgatctgg atgactatgc cgccgatgat gacgaatacg aagaaaaatt gaagaaagaa      2040
gatgtcgcat ttttcttcct tgccacctac ggcgacggtg aaccaacaga taatgccgca      2100
aggttttaca gtggtttac tgaaggtaat gacagaggag aatggctgaa gaatttgaaa      2160
tatggtgtgt tcggccttgg taacagacag tacgagcatt ttaataaggt cgctaaggtt      2220
gtagatgata tacttgttga acaaggtgct caaaggttag tgcaggtggg cttgggtgac      2280
gatgatcaat gtattgaaga tgactttact gcttggagag aagccttgtg gcctgaatta      2340
gatactatcc ttagaagaa aggtgacact gctgttgcta ccccctacac tgcagcagtc      2400
ctagaatata gagtctcaat ccatgattca gaagacgcca aattcaatga tattaacatg      2460
gccaacggta acggttacac cgtttttgac gcacaacatc catacaaagc taatgttgct      2520
gttaaaaggg aacttcacac cccagaaagt gacaggtcat gtatacattt ggaatttgat      2580
atcgctggta gtggttttgac ttacgaaaca ggtgaccatg tcggagtact ttgcgataat      2640
ttgtcagaaa ctgttgatga agctttgagg ttattggata tgtcaccaga tacttacttc      2700
tcattgcatg cagaaaaaga agacggaact ccaatatcaa gctcgcttcc ccctccattc      2760
cctccctgta acttaagaac agccctaact agatatgctt gtttactgtc ttctccaaag      2820
aaaagtgctt tggttgcatt ggcagcccac gcatccgatc ctaccgaagc tgagagatta      2880
aagcatttgg cttcaccagc cggtaaagat gaatacagta agtgggtagt ggagagccaa      2940
agatcgcttt tagaagtgat ggctgagttt ccaagtgcta aacctcctct gggtgtattt      3000
ttcgctggtg tggccccaag attgcagcct agattttatt ccatatcctc atctccaaaa      3060
attgccgaaa ccagaattca cgtgacatgt gctctggtct acgaaaagat gccaacaggt      3120
aggattcaca agggtgtctg ttctacctgg atgaaaaatg ctgtacccta tgaaaaatcc      3180
gaaaattgtt ctagtgcacc aatttttcgta agacaatcta atttcaagtt accaagcgat      3240
tctaaagtac ccattattat gatcggtcca ggtactggtt tggcccccatt cagaggcttc      3300
ttgcaagaaa gattggcttt agtggagagt ggagttgaat tgggtccttc agttttattc      3360
tttggttgta gaaacagaag aatggacttt atctacgaag aagaattgca gagatttgtt      3420
gaaagtggtg cattggccga attgagtgtt gcattcagca gggaaggtcc aaccaaagaa      3480
tacgttcaac acaagatgat ggacaaggct tctgatatct ggaatatgat ttcccaaggt      3540
gcttatttgt atgtttgtgg tgacgctaaa ggaatggcta gagatgttca tagatcactg      3600
catacaatcg cacaagaaca aggtagcatg gattcaacaa aagcagaggg ctttgtaaag      3660
aatcttcaga caagcggtag atatctgaga gatgtatggt aa                        3702
```

<210> SEQ ID NO 98
<211> LENGTH: 2178
<212> TYPE: DNA
<213> ORGANISM: Arabidopsis thaliana

<400> SEQUENCE: 98

| | | | | | |
|---|---|---|---|---|---|
| atggagatta | acggggcaca | caagagcaac | ggaggaggag | tggacgctat | gttatgcggc | 60 |
| ggagacatca | agacaaagaa | catggtgatc | aacgcggagg | atcctctcaa | ctggggagct | 120 |
| gcagcggagc | aaatgaaagg | tagccatttg | gatgaagtga | agagaatggt | tgctgagttt | 180 |
| aggaagccag | ttgtgaatct | tggtggtgag | actctgacca | ttggacaagt | ggctgcgatc | 240 |
| tcaactattg | gtaacagtgt | gaaggtggag | ctatcggaga | cagctagagc | cggtgtgaat | 300 |
| gctagtagtg | attgggttat | ggagagtatg | aacaaaggca | ctgatagtta | tggtgttact | 360 |
| actggttttg | gtgctacttc | tcatcggaga | accaaaaacg | tgtcgcact | tcagaaggaa | 420 |
| cttattagat | tccttaacgc | cggaatattc | ggaagcacga | agaaacaag | ccacacattg | 480 |
| ccacactccg | ccacaagagc | cgccatgctt | gtacgaatca | acactctcct | ccaaggattt | 540 |
| tccggtatcc | gatttgagat | tctcgaagca | attaccagtt | tcctcaacaa | caacatcact | 600 |
| ccatctctcc | ccctccgtgg | tacaatcacc | gcctccggag | atctcgttcc | tctctcctac | 660 |
| atcgccggac | ttctcaccgg | tcgtcccaat | tccaaagcta | ctggtcccaa | cggtgaagct | 720 |
| ttaacagcag | aggaagcttt | caaattagca | ggaatcagct | ccggattctt | tgatctccag | 780 |
| cctaaggaag | gtctcgcgct | agtcaatggc | acggcggttg | gatctggaat | ggcgtcaatg | 840 |
| gtgttattcg | aaacgaatgt | tctctctgtt | ttggctgaga | ttttgtcggc | ggttttcgca | 900 |
| gaggtgatga | gtggtaagcc | tgagttcacc | gatcatctca | ctcacagact | aaacatcat | 960 |
| cccggtcaaa | tcgaagcggc | ggcgataatg | gagcatatcc | tcgacggaag | ctcgtacatg | 1020 |
| aaattagctc | agaagcttca | cgagatggat | ccgttacaga | aacctaaaca | agatcgttac | 1080 |
| gctcttcgta | cttctcctca | atggttaggt | cctcaaatcg | aagtgatccg | ttacgcaacg | 1140 |
| aaatcgatcg | agcgtgagat | taactccgtc | aacgataatc | cgttgatcga | tgtttcgagg | 1200 |
| aacaaggcga | ttcacggtgg | taacttccaa | ggaacaccaa | tcggagtttc | aatggataac | 1260 |
| acgagattgg | cgatagcagc | gattggtaaa | ctcatgtttg | ctcaattctc | agagcttgtg | 1320 |
| aatgatttct | acaacaatgg | tttaccctcg | aatctaaccg | cttcgaggaa | tccaagtttg | 1380 |
| gattatggat | tcaagggagc | tgagattgca | atggcttctt | attgttcaga | gcttcaatac | 1440 |
| ttagctaatc | ctgtgactag | ccatgttcaa | tcagcagagc | aacataacca | agatgtcaac | 1500 |
| tctttgggac | taatctcgtc | tcgcaaaact | tctgaagctg | ttgatattct | caagcttatg | 1560 |
| tcaacaacgt | tcctcgttgc | gatttgtcaa | gctgtggatt | tgagacattt | ggaggagaat | 1620 |
| ttgagacaga | ctgtgaagaa | cactgtctct | caagtggcga | agaaagttct | tactactgga | 1680 |
| gtcaatggtg | agcttcatcc | ttctcgcttc | tgcgaaaagg | atttactcaa | agttgtagac | 1740 |
| cgtgaacaag | tctacacata | cgcggatgat | ccttgtagcg | caacgtaccc | gttgattcag | 1800 |
| aagctgagac | aagttattgt | tgaccatgct | ttgatcaatg | gtgagagtga | aagaatgca | 1860 |
| gtgacttcaa | tcttccataa | gattggagct | ttcgaggagg | agcttaaggc | agtgctaccg | 1920 |
| aaagaagtgg | aagcagcaag | agcagcctac | gataacggaa | catcggctat | cccgaacagg | 1980 |
| atcaaggaat | gtaggtcgta | tccattgtat | agattcgtga | gggaagagct | tggaacagag | 2040 |
| cttttgaccg | gagagaaagt | gacgtcgcct | ggagaagagt | tcgacaaggt | tttcacggcg | 2100 |
| atttgtgaag | gtaaaatcat | tgatccgatg | atggaatgtc | tcaacgagtg | gaacggagct | 2160 |

```
cccattccaa tatgttaa                                                 2178
```

<210> SEQ ID NO 99
<211> LENGTH: 2154
<212> TYPE: DNA
<213> ORGANISM: Arabidopsis thaliana

<400> SEQUENCE: 99

```
atggatcaaa tcgaagctat gttgtgtggt ggtggtgaaa aaacaaaagt tgctgttact     60
actaagacct tggctgatcc attgaattgg ggtttggctg ctgatcaaat gaagggttct    120
catttggatg aagtcaagaa gatggtcgaa gaatacagaa gaccagttgt taatttgggt    180
ggtgaaactt tgactattgg tcaagttgct gctatttcta ctgttggtgg ttctgttaag    240
gttgaattgg ctgaaacttc aagagctggt gttaaggctt cttctgattg gttatggaa    300
tctatgaaca agggtactga ttcttacggt gttactacag gttttggtgc tacttctcat    360
agaagaacta agaatggtac tgccttgcaa accgaattga tcagattttt gaacgccggt    420
attttcggta acaccaaaga aacttgtcat accttgccac aatctgctac tagagctgct    480
atgttggtta gagttaacac tttgttgcaa ggttactccg gtatcagatt cgaaattttg    540
gaagctatca cctccttgtt gaaccataac atttctccat ctttgccatt gagaggtact    600
attactgctt ctggtgattt ggttccattg tcttatattg ctggtttgtt gactggtaga    660
ccaaactcta agctactgg tccagatggt gaatcattga ctgctaaaga agcctttgaa    720
aaggctggta tctctactgg tttttttcgac ttgcaaccta agaaggtttt ggctttggtt    780
aatggtacag ctgttggttc tggtatggct tctatggttt tgtttgaagc taacgttcaa    840
gctgttttgg ccgaagtttt gtctgctatt tttgctgaag ttatgtccgg taagccagaa    900
ttcactgatc atttgaccca tagattgaaa catcacccag tcaaattga agctgctgca    960
attatggaac atatcttgga tggttcctct tacatgaagt tggctcaaaa agttcacgaa   1020
atggacccat tgcaaaagcc aaaacaagat agatacgctt tgagaacttc tccacaatgg   1080
ttgggtccac aaatagaagt tattagacaa gccaccaagt ccatcgaaag agaaatcaat   1140
tctgttaacg acaacccatt gatcgacgtc agtagaaaca aagctattca tggtggtaac   1200
ttccaaggta ctccaattgg tgtttctatg gacaacacta gattggctat tgctgccatt   1260
ggtaaattga tgttcgctca attctccgaa ttggtcaacg atttttacaa caacggtttg   1320
ccttctaact tgaccgcttc ttctaatcca tcattggatt acggttttaa gggtgctgaa   1380
attgctatgg cttcatactg ttctgaattg caatacttgg ctaacccagt tacctctcat   1440
gttcaatctg ctgaacaaca caatcaagac gttaactcct tgggtttgat ctcttccaga   1500
aaaacttctg aagccgttga catttttgaag ttgatgtcta ctaccttctt ggtcggtatt   1560
tgtcaagcag ttgatttgag acacttggaa gaaaacttga caaaccgt taagaacacc   1620
gtttcccaag ttgctaaaaa ggttttgact accggtatta acggtgaatt gcatccatcc   1680
agattctgcg aaaaagattt gttgaaggtc gttgacagag aacaagtttt cacctatgtt   1740
gatgatccat gttctgctac ctatccattg atgcaaagat tgagacaagt catcgttgat   1800
catgcttttgt ctaatggtga aaccgaaaag aacgctgtta cctccattt ccaaaagatt   1860
ggtgctttcg aagaagaatt gaaggccgtt ttgccaaaag aagttgaagc agctagagca   1920
gcttacggta acggtactgc tccaattcca aatagaatca agaatgcag atcctaccca   1980
ttatacagat tcgttagaga agaattaggt actaagttg tgaccggtga aaaggttgtt   2040
tctccaggtg aagaattcga taaggttttc actgctatgt gcgaaggtaa attgatcgat   2100
```
ccattgatgg actgcttgaa agaatggaat ggtgctccta ttcctatctg ctaa         2154

<210> SEQ ID NO 100
<211> LENGTH: 2112
<212> TYPE: DNA
<213> ORGANISM: Aspergillus niger

<400> SEQUENCE: 100
atgttggaca agcacatccc agacggtcac ttagaaacca ctagcgccca ctggagggat    60
ttaaaccaag ttgttcaaaa cggtgaatta tctattgacg ttactccttg tccttggcc    120 gatgttgttg ctgtcgctaa gtatggttgc aaccaagat tgactgacaa gccagagact    180
attgatgcta ttaacggttc tgtcatcgcc ttggctgaat gtttaaggga tggtcatcac    240
atttacggtg ttaacactgg ttttggtggt tctgccgatt ccagaaccaa ccagaccact    300
actttgcaaa gctccttgtt gcaattgttg caatccggta tcttaactgc ttctgacact    360
accaatgaag gtttgcagtt gaacttgcaa ggtcaaagca gccattctat gccatctgag    420
tgggttaaag ctaccatgtt ggttcgttct aactctgtcg ctagaggcca ttctgctgtc    480
agcttgccag ctatttccgc cattttgaga ttgatcagag aagatatcgt cccagttatt    540
ccattgagag gtactatctc cgcttccggt gacttgatgc cattggctta cgttgtcggt    600
gccattgaag gttctccagg tatttacgtt agagtcaagg atggttctga acatcaagtc    660
gttaccgctc aaaaggccct acaaactatc ggtgctaagg gtgttacttt gggccctaaa    720
gagggtttag gtttggtcaa tggtactgct gcttctggtg ccttagctgg tttggttttg    780
tatgaggctc atcaattggc cgtcttggct caagctgtca ccgccttaac tgtcgaagct    840
attcaaggtt ctaccgaatc ctttcaccct tttatcgctc aagtccgtcc acatgaaggt    900
cagatcgagg ctgctgaaaa catcctatct ctattaaaag gtagcttgtt ggccagaggt    960
agctctacta cccaaaccag aaccggtcta gtccaagaca gatactcctt gagaactgct   1020
tctcaatgga tcggtcctca attggaagat ttattgttgg ccgacagaca ggtccaagtc   1080
gaactaaatt ctaccagcga caacccatta atcgatactg ttctaaaac tttctacact   1140 ggtggtaact tccaagctac cagcattacc tccgctatga aaaagactag gttggctttg   1200
caaatgttcg gtaagatgtt attcgtccaa tgtaatgaaa tgatcgaccc aaacttgaac   1260
aacggtctac ctaccaactt ggttgctgat gacccatcct tgtccttcac catgaaaggc   1320
gtcgatatca acatggctgc ttatatgtct gaattggctt acttggctaa tccagtctcc   1380
tcccacgttc aaactgctga atgcaaaac caagccttga actccttggc tttcgttagc   1440
gctaggtata ctatgaaagc tgttgatatc gtctctatga tgggtgcttg tgctttgtat   1500
gtcgcttgtc aagccttaga cttgagggtc ttgcaattgc gtttcttcca aagagtccaa   1560
ggtgtcgcta agaaatcgc tcacggtgcc tttggtaagg ccttggaacc tttcgaaatc   1620
gaccaggttg ctgatcactt gtctgaagct attcaaaact cctggccatc tacctctagg   1680
ttggacttga gagacagatg caaaagggtt gctgaaatgt ttatcccagt cttgttcggt   1740
gctttgttgc aaattatccc acagaacaga caaacctctg atttattcac cgccatctct   1800
gcttgtaaga tgatttccgt ttttaagttg gaaggcgttt acagagaagt tttcgctgaa   1860
ttttgcactt cccaacctac cgctgacttt ttgggtaccg gtactaagga aatctacacc   1920 tcatcagac acgacttgag agtcccattc caccagggtt cgtcgaaca tccatccgcc   1980 tctcaaaccg acttaccaga aactatcaac ggtagagtta aaaagaccgt cggtggttgg   2040

```
atttctgtcg tttacgaagc cttgagaaat ggtaccttaa gcggtactat tttgaactcc    2100
ttccaacaat aa                                                        2112

<210> SEQ ID NO 101
<211> LENGTH: 2151
<212> TYPE: DNA
<213> ORGANISM: Rhodosporidium toruloides

<400> SEQUENCE: 101
atggctccat cattggattc tatttctcat tcttttgcaa acggtgttgc atctgcaaaa      60
caagctgtta atggtgcatc tactaatttg gcagttgctg ttctcatttt accaactacc     120
caagttacac aagttgatat tgttgaaaag atgttagcag cacctactga ttctaccttg     180
gaattggatg ttactctttt aaatttaggt gatgttgttt ctgcagctag aaagggtaga     240
ccagttagag ttaaagattc tgatgaaatt agatctaaaa ttgataaatc tgttgaattt     300
ttgagatctc aattatcaat gtcagtttat ggtgttacaa ctggtttcgg tggttcagct     360
gatactagaa ctgaagatgc aatttcttta caaaaggcat tgttggaaca tcaattatgt     420
ggtgttttgc cttcatcatt cgattctttt agattaggta gaggtttaga aaactctttg     480
ccattagaag ttgttagagg tgcaatgaca attagagtta attctttaac aagaggtcat     540
tctgctgtta gattggttgt tttagaagct ttgactaact ttttgaacca tggtattact     600
ccaattgttc cattaagagg tacaatttct gcatctggtg atttgtctcc tttgtcttat     660
attgcagctg ctatttcagg tcatccagat tcaaaggttc atgttgttca tgaaggtaag     720
gaaaagattt tatatgcaag agaagctatg gctttattta atttagaacc agttgtttta     780
ggtcctaagg aaggtttagg tttagttaac ggtacagctg tttcagcatc tatggctacc     840
ttagctttgc atgatgctca tatgttatct ttgttatctc aatcattaac agctatgact     900
gttgaagcta tggttggtca tgctggttct tttcatccat tcttgcatga tgttaccaga     960
cctcatccaa cacaaattga agttgctggt aatattagaa agttgttaga aggttctaga    1020
ttcgcagttc atcatgaaga agaagttaaa gttaaggatg atgaaggtat tttgagacaa    1080
gatagatacc cattgagaac ttcaccacaa tggttgggtc cattggtttc tgatttgatt    1140
catgctcatg cagttttgac cattgaagca ggtcaatcta acagataa tccattgatt     1200 gatgttgaaa acaaaacatc acatcatggt ggtaattttc aagcagctgc tgttgctaat    1260
acaatggaaa agacaagatt aggtttggca caaattggta agttaaattt cacacaatta    1320
actgaaatgt tgaatgcagg tatgaataga ggttttgccat cttgtttggc agctgaagat    1380
ccttcattat cttatcattg taaaggtttg gatattgcag cagcagctta tcttcagaa     1440 ttaggtcatt tagcaaatcc agttactaca catgttcaac cagctgaaat ggctaatcaa    1500
gctgttaatt ctttagcatt gatttcagct agaagaacca ctgaatcaaa cgatgttttg    1560
tcattattat tagctactca tttatattgt gttttacaag ctattgattt gagagcaatt    1620
gaatttgaat ttaaaaagca atttggtcca gctattgttt cattaattga tcaacatttt    1680
ggttctgcaa tgactggttc aaatttgaga gatgaattag ttgaaaaggt taacaagacc    1740
ttggctaaaa gattagaaca aactaactct tacgatttgg ttccaagatg gcatgatgct    1800
ttttcttttg ctgcaggtac agttgttgaa gttttgtcat ctacctcatt gtctttggca    1860
gctgttaacg cttggaaagt tgctgctgct gaatcagcta tttcattaac tagacaagtt    1920
agagaaactt tttggtctgc tgcttcaact tcttcacctg ctttgtctta cttgtctcca    1980
agaactcaaa ttttgtacgc tttcgttaga gaagaattgg gtgttaaagc tagaagaggt    2040
```
gatgttttct taggtaagca agaagttact attggttcta atgtttctaa aatttacgaa    2100
gctattaaat caggtagaat taataacgtt ttgttgaaga tgttagcata a             2151

<210> SEQ ID NO 102
<211> LENGTH: 1173
<212> TYPE: DNA
<213> ORGANISM: Hypericum androsaemum

<400> SEQUENCE: 102
atggttacag tcgaagaagt gagaaaggct caaagagccg agggaccagc tactgtcatg    60
gcaattggta ccgctgtacc tcctaactgt gtcgatcaag ctacataccc tgactattac    120
tttagaatta caaattcaga acacaaagcc gaactgaagg aaaaatttca agaatgtgc    180 gacaaatctc agatcaaaaa gagatacatg tatttaaacg aggaggttct aaaagagaat    240
ccaaatatgt gcgcgtacat ggcacccctca ctggatgcaa gacaagacat agtcgttgtt    300
gaagtaccaa agcttggtaa ggaggccgcc gttaaggcta ttaaggaatg gggccaacct    360
aaatctaaaa ttacacattt ggtcttctgt acaaccagtg gcgtggatat gcccggtgct    420
gactaccaac taaccaagtt gcttggttta aggccctccg ttaaaagatt aatgatgtat    480
caacagggtt gtttcgctgg aggaacagtt ctaagattag ctaaagattt agcagaaaac    540
aacaaaggcg ctagggtact gtagtatgt tcagaaatca ctgctgtaac ttttcgtggt    600
ccaaccgaca ctcatttaga ttccttagtt ggacaggctc tatttggaga tggggccgcc    660
gccatcatta tcggttctga tccgatccca gaggtagaga accattgtt cgaattggtt    720 tccgctgctc aaacaattct gcctgactcc gaaggtgcca tagacggtca cttgagagag    780
gtcggattga cctttcattt attaaaggat gtgcccggtt tgataagtaa aaacgtcgag    840
aaatccttaa ctgaagcatt caaaccatta gggatatccg attggaacag tttattctgg    900
atcgctcatc caggcggtcc agccatccta gatcaagtag aagctaaatt atcattaaaa    960
cctgaaaagt taagagcaac gagacatgtc ttgtcagaat atggtaatat gtctagcgcg    1020
tgtgttcttt tcatcttgga tgaaatgcgt agaaaatcta agaagacgg tttgaagacg    1080 actggtgaag gtattgaatg gggtgttttg ttcggctttg gtccgggtct aaccgtcgaa    1140
actgtggtat gcactccgt tgccataaat taa                                 1173

<210> SEQ ID NO 103
<211> LENGTH: 1170
<212> TYPE: DNA
<213> ORGANISM: Hypericum androsaemum

<400> SEQUENCE: 103
gttaccgtag aagaggtacg taaagctcag agagcagagg ggcccgctac cgttatggcc    60
attggtaccg ccgtgccgcc aaactgcgtt gatcaagcta cttatcctga ttactatttc    120
agaattacta attctgaaca taaggccgaa ttgaaagaga gtttcaaag gatgtgcgac    180 aaatcacaga taaagaagcg ttatatgtac ttgaacgaag aagtgttgaa ggaaaatcca    240
aatatgtgtg cctatatggc tccttcatta gatgccagac aagatattgt tgtggttgaa    300
gttcccaagt tgggcaagga agcggcagtc aaagctatta ggaatggggg acaaccaaaa    360
tcaaaaatta cgcatttagt gttttgtacc acttctggcg tagatatgcc tggtgccgac    420
tatcaattaa cgaaattgct tggtttacgt ccatcagtaa aaagattgat gatgtatcaa    480
caaggttgct ttgccggtgg tacagttctt cgtcttgcca aggaccttgc agaaaacaat    540

| aaagggggcaa gggtgttggt tgtatgttct gaaataacgg ccgtgacgtt tagaggtccc | 600 |
| actgataccc atttggattc attagtaggc caagctttat ttggtgacgg tgcagcagca | 660 |
| atcataatcg gttccgatcc gataccagaa gtggaaaagc ctttgtttga attggttagc | 720 |
| gcagcccaaa ccatacttcc agactctgaa ggtgcaattg atggtcattt gagggaggtg | 780 |
| ggtctaacat tccatctttt gaaggacgtg ccgggactta tttctaagaa tgtagaaaag | 840 |
| tctttgactg aagcattcaa accactggga atttctgact ggaattcttt gttctggatc | 900 |
| gctcacccag gtggccctgc gattctagat caggtcgagg caaaactttc actaaagcct | 960 |
| gaaaaattga gggcgacgag acatgttttg tcagaatacg gcaatatgtc atcagcttgc | 1020 |
| gtattgttca tattggatga aatgagaaga aaatctaaag aggatggcct gaaaacgact | 1080 |
| ggtgaaggta ttgaatgggg tgtcttgttt ggtttcggtc ctggcttgac tgtcgagact | 1140 |
| gttgtgttgc atagtgttgc tattaattga | 1170 |

<210> SEQ ID NO 104
<211> LENGTH: 1173
<212> TYPE: DNA
<213> ORGANISM: Hypericum androsaemum

<400> SEQUENCE: 104

| atggtgactg ttgaagaagt aagaaaggct caaagagctg aaggtcctgc tactgttatg | 60 |
| gccataggga cagcggtccc accaaactgt gttgatcagg cgacttatcc tgattattat | 120 |
| ttcagaatca cgaattccga gcacaaagcc gagctaaaag agaaatttca aggatgtgc | 180 |
| gataaaagcc agataaaaaa gagatatatg tatctaaatg aagaagtctt aaaagagaac | 240 |
| ccgaacatgt gcgcttacat ggcaccatcc ctagatgcta gacaagatat cgtagtggtt | 300 |
| gaagttccaa agctgggtaa ggaggcagcg gtaaaagcaa ttaaggaatg ggccaacca | 360 |
| aagtcaaaga ttactcactt agtattttgc actacttccg gtgtagatat gcccggtgcc | 420 |
| gactatcaac ttaccaaact acttggtttg cgtccaagcg ttaaacgtct aatgatgtac | 480 |
| caacaaggat gctttgctgg tggcaccgtg ttaagattag caaaagatct ggccgagaat | 540 |
| aacaagggcg ctagagtttt agttgtatgt tcagaaatta cggctgtgac tttcagaggc | 600 |
| cctacagaca ctcatcttga ttcattagtg ggccaagctt tgttcggaga cggagcagca | 660 |
| gcaatcatta tcggttcaga tccaattcca gaagtcgaaa aaccactgtt cgaactagtt | 720 |
| tctgcagccc aaacaatttt accggattct gaaggcgcta ttgacggtca tttaagggaa | 780 |
| gtgggtttga ctttccattt gttgaaagac gttccaggtc tgatatccaa aaatgtggag | 840 |
| aaatcattga ccgaagcatt taaccattgg gtatctctg attggaattc actattttgg | 900 |
| attgctcacc ccggtggacc agcaatactg gatcaagttg aagcgaaatt gtcactgaag | 960 |
| cctgaaaaat tgagggctac gaggcatgtg ttatccgaat acggaatat gtctagcgca | 1020 |
| tgtgtgttgt ttatacttga tgaaatgcgt aggaaatcta aggaagatgg cttgaagact | 1080 |
| accggtgaag gtattgaatg gggtgtctta tttggatttg gccctggttt gacagtggaa | 1140 |
| actgttgttc ttcactcagt agctattaat taa | 1173 |

<210> SEQ ID NO 105
<211> LENGTH: 1233
<212> TYPE: PRT
<213> ORGANISM: Arabidopsis thaliana

<400> SEQUENCE: 105

Met Asp Leu Leu Leu Leu Glu Lys Ser Leu Ile Ala Val Phe Val Ala

-continued

```
1               5                   10                  15
Val Ile Leu Ala Thr Val Ile Ser Lys Leu Arg Gly Lys Lys Leu Lys
                20                  25                  30

Leu Pro Pro Gly Pro Ile Pro Ile Pro Ile Phe Gly Asn Trp Leu Gln
            35                  40                  45

Val Gly Asp Asp Leu Asn His Arg Asn Leu Val Asp Tyr Ala Lys Lys
        50                  55                  60

Phe Gly Asp Leu Phe Leu Leu Arg Met Gly Gln Arg Asn Leu Val Val
65                  70                  75                  80

Val Ser Ser Pro Asp Leu Thr Lys Glu Val Leu Leu Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
    130                 135                 140

Gln Asn Arg Glu Gly Trp Glu Phe Glu Ala Ala Ser Val Val Glu Asp
145                 150                 155                 160

Val Lys Lys Asn Pro Asp Ser Ala Thr Lys Gly Ile Val Leu Arg Lys
                165                 170                 175

Arg Leu Gln Leu Met Met Tyr Asn Asn Met Phe Arg Ile Met Phe Asp
            180                 185                 190

Arg Arg Phe Glu Ser Glu Asp Asp Pro Leu Phe Leu Arg Leu Lys Ala
        195                 200                 205

Leu Asn Gly Glu Arg Ser Arg Leu Ala Gln Ser Phe Glu Tyr Asn Tyr
    210                 215                 220

Gly Asp Phe Ile Pro Ile Leu Arg Pro Phe Leu Arg Gly Tyr Leu Lys
225                 230                 235                 240

Ile Cys Gln Asp Val Lys Asp Arg Arg Ile Ala Leu Phe Lys Lys Tyr
            245                 250                 255

Phe Val Asp Glu Arg Lys Gln Ile Ala Ser Ser Lys Pro Thr Gly Ser
        260                 265                 270

Glu Gly Leu Lys Cys Ala Ile Asp His Ile Leu Glu Ala Glu Gln Lys
    275                 280                 285

Gly Glu Ile Asn Glu Asp Asn Val Leu Tyr Ile Val Glu Asn Ile Asn
290                 295                 300

Val Ala Ala Ile Glu Thr Thr Leu Trp Ser Ile Glu Trp Gly Ile Ala
305                 310                 315                 320

Glu Leu Val Asn His Pro Glu Ile Gln Ser Lys Leu Arg Asn Glu Leu
            325                 330                 335

Asp Thr Val Leu Gly Pro Gly Val Gln Val Thr Glu Pro Asp Leu His
        340                 345                 350

Lys Leu Pro Tyr Leu Gln Ala Val Val Lys Glu Thr Leu Arg Leu Arg
    355                 360                 365

Met Ala Ile Pro Leu Leu Val Pro His Met Asn Leu His Asp Ala Lys
370                 375                 380

Leu Ala Gly Tyr Asp Ile Pro Ala Glu Ser Lys Ile Leu Val Asn Ala
385                 390                 395                 400

Trp Trp Leu Ala Asn Asn Pro Asn Ser Trp Lys Lys Pro Glu Glu Phe
            405                 410                 415

Arg Pro Glu Arg Phe Phe Glu Glu Glu Ser His Val Glu Ala Asn Gly
        420                 425                 430
```

```
Asn Asp Phe Arg Tyr Val Pro Phe Gly Val Gly Arg Ser Cys Pro
        435                 440                 445

Gly Ile Ile Leu Ala Leu Pro Ile Leu Gly Ile Thr Ile Gly Arg Met
    450                 455                 460

Val Gln Asn Phe Glu Leu Leu Pro Pro Gly Gln Ser Lys Val Asp
465                 470                 475                 480

Thr Ser Glu Lys Gly Gly Gln Phe Ser Leu His Ile Leu Asn His Ser
                485                 490                 495

Ile Ile Val Met Lys Pro Arg Asn Cys Ser Ala Glu Ala Ala Ala Lys
                500                 505                 510

Glu Ala Ala Ala Lys Glu Ala Ala Lys Ala Ser Ser Ser Ser
            515                 520                 525

Ser Ser Thr Ser Met Ile Asp Leu Met Ala Ala Ile Ile Lys Gly Glu
    530                 535                 540

Pro Val Ile Val Ser Asp Pro Ala Asn Ala Ser Ala Tyr Glu Ser Val
545                 550                 555                 560

Ala Ala Glu Leu Ser Ser Met Leu Ile Glu Asn Arg Gln Phe Ala Met
                565                 570                 575

Ile Val Thr Thr Ser Ile Ala Val Leu Ile Gly Cys Ile Val Met Leu
            580                 585                 590

Val Trp Arg Arg Ser Gly Ser Gly Asn Ser Lys Arg Val Glu Pro Leu
        595                 600                 605

Lys Pro Leu Val Ile Lys Pro Arg Glu Glu Ile Asp Asp Gly Arg
    610                 615                 620

Lys Lys Val Thr Ile Phe Phe Gly Thr Gln Thr Gly Thr Ala Glu Gly
625                 630                 635                 640

Phe Ala Lys Ala Leu Gly Glu Glu Ala Lys Ala Arg Tyr Glu Lys Thr
                645                 650                 655

Arg Phe Lys Ile Val Asp Leu Asp Asp Tyr Ala Ala Asp Asp Glu
            660                 665                 670

Tyr Glu Glu Lys Leu Lys Lys Glu Asp Val Ala Phe Phe Phe Leu Ala
        675                 680                 685

Thr Tyr Gly Asp Gly Glu Pro Thr Asp Asn Ala Ala Arg Phe Tyr Lys
    690                 695                 700

Trp Phe Thr Glu Gly Asn Asp Arg Gly Glu Trp Leu Lys Asn Leu Lys
705                 710                 715                 720

Tyr Gly Val Phe Gly Leu Gly Asn Arg Gln Tyr Glu His Phe Asn Lys
                725                 730                 735

Val Ala Lys Val Val Asp Asp Ile Leu Val Glu Gln Gly Ala Gln Arg
            740                 745                 750

Leu Val Gln Val Gly Leu Gly Asp Asp Asp Gln Cys Ile Glu Asp Asp
        755                 760                 765

Phe Thr Ala Trp Arg Glu Ala Leu Trp Pro Glu Leu Asp Thr Ile Leu
    770                 775                 780

Arg Glu Glu Gly Asp Thr Ala Val Ala Thr Pro Tyr Thr Ala Ala Val
785                 790                 795                 800

Leu Glu Tyr Arg Val Ser Ile His Asp Ser Glu Asp Ala Lys Phe Asn
                805                 810                 815

Asp Ile Asn Met Ala Asn Gly Asn Gly Tyr Thr Val Phe Asp Ala Gln
            820                 825                 830

His Pro Tyr Lys Ala Asn Val Ala Val Lys Arg Glu Leu His Thr Pro
        835                 840                 845
```

-continued

Glu Ser Asp Arg Ser Cys Ile His Leu Glu Phe Asp Ile Ala Gly Ser
850                 855                 860

Gly Leu Thr Tyr Glu Thr Gly Asp His Val Gly Val Leu Cys Asp Asn
865                 870                 875                 880

Leu Ser Glu Thr Val Asp Glu Ala Leu Arg Leu Leu Asp Met Ser Pro
            885                 890                 895

Asp Thr Tyr Phe Ser Leu His Ala Glu Lys Glu Asp Gly Thr Pro Ile
        900                 905                 910

Ser Ser Ser Leu Pro Pro Pro Phe Pro Pro Cys Asn Leu Arg Thr Ala
    915                 920                 925

Leu Thr Arg Tyr Ala Cys Leu Leu Ser Ser Pro Lys Lys Ser Ala Leu
930                 935                 940

Val Ala Leu Ala Ala His Ala Ser Asp Pro Thr Glu Ala Glu Arg Leu
945                 950                 955                 960

Lys His Leu Ala Ser Pro Ala Gly Lys Asp Glu Tyr Ser Lys Trp Val
            965                 970                 975

Val Glu Ser Gln Arg Ser Leu Leu Glu Val Met Ala Glu Phe Pro Ser
        980                 985                 990

Ala Lys Pro Pro Leu Gly Val Phe Phe Ala Gly Val Ala Pro Arg Leu
    995                 1000                1005

Gln Pro Arg Phe Tyr Ser Ile Ser Ser Ser Pro Lys Ile Ala Glu
    1010                1015                1020

Thr Arg Ile His Val Thr Cys Ala Leu Val Tyr Glu Lys Met Pro
    1025                1030                1035

Thr Gly Arg Ile His Lys Gly Val Cys Ser Thr Trp Met Lys Asn
    1040                1045                1050

Ala Val Pro Tyr Glu Lys Ser Glu Asn Cys Ser Ser Ala Pro Ile
    1055                1060                1065

Phe Val Arg Gln Ser Asn Phe Lys Leu Pro Ser Asp Ser Lys Val
    1070                1075                1080

Pro Ile Ile Met Ile Gly Pro Gly Thr Gly Leu Ala Pro Phe Arg
    1085                1090                1095

Gly Phe Leu Gln Glu Arg Leu Ala Leu Val Glu Ser Gly Val Glu
    1100                1105                1110

Leu Gly Pro Ser Val Leu Phe Phe Gly Cys Arg Asn Arg Arg Met
    1115                1120                1125

Asp Phe Ile Tyr Glu Glu Glu Leu Gln Arg Phe Val Glu Ser Gly
    1130                1135                1140

Ala Leu Ala Glu Leu Ser Val Ala Phe Ser Arg Glu Gly Pro Thr
    1145                1150                1155

Lys Glu Tyr Val Gln His Lys Met Met Asp Lys Ala Ser Asp Ile
    1160                1165                1170

Trp Asn Met Ile Ser Gln Gly Ala Tyr Leu Tyr Val Cys Gly Asp
    1175                1180                1185

Ala Lys Gly Met Ala Arg Asp Val His Arg Ser Leu His Thr Ile
    1190                1195                1200

Ala Gln Glu Gln Gly Ser Met Asp Ser Thr Lys Ala Glu Gly Phe
    1205                1210                1215

Val Lys Asn Leu Gln Thr Ser Gly Arg Tyr Leu Arg Asp Val Trp
    1220                1225                1230

<210> SEQ ID NO 106
<211> LENGTH: 725
<212> TYPE: PRT

<213> ORGANISM: Arabidopsis thaliana

<400> SEQUENCE: 106

```
Met Glu Ile Asn Gly Ala His Lys Ser Asn Gly Gly Val Asp Ala
1               5                   10                  15

Met Leu Cys Gly Gly Asp Ile Lys Thr Lys Asn Met Val Ile Asn Ala
                20                  25                  30

Glu Asp Pro Leu Asn Trp Gly Ala Ala Glu Gln Met Lys Gly Ser
            35                  40                  45

His Leu Asp Glu Val Lys Arg Met Val Ala Glu Phe Arg Lys Pro Val
        50                  55                  60

Val Asn Leu Gly Gly Glu Thr Leu Thr Ile Gly Gln Val Ala Ala Ile
65                  70                  75                  80

Ser Thr Ile Gly Asn Ser Val Lys Val Glu Leu Ser Glu Thr Ala Arg
                85                  90                  95

Ala Gly Val Asn Ala Ser Ser Asp Trp Val Met Glu Ser Met Asn Lys
                100                 105                 110

Gly Thr Asp Ser Tyr Gly Val Thr Thr Gly Phe Gly Ala Thr Ser His
            115                 120                 125

Arg Arg Thr Lys Asn Gly Val Ala Leu Gln Lys Glu Leu Ile Arg Phe
130                 135                 140

Leu Asn Ala Gly Ile Phe Gly Ser Thr Lys Glu Thr Ser His Thr Leu
145                 150                 155                 160

Pro His Ser Ala Thr Arg Ala Ala Met Leu Val Arg Ile Asn Thr Leu
                165                 170                 175

Leu Gln Gly Phe Ser Gly Ile Arg Phe Glu Ile Leu Glu Ala Ile Thr
            180                 185                 190

Ser Phe Leu Asn Asn Asn Ile Thr Pro Ser Leu Pro Leu Arg Gly Thr
        195                 200                 205

Ile Thr Ala Ser Gly Asp Leu Val Pro Leu Ser Tyr Ile Ala Gly Leu
210                 215                 220

Leu Thr Gly Arg Pro Asn Ser Lys Ala Thr Gly Pro Asn Gly Glu Ala
225                 230                 235                 240

Leu Thr Ala Glu Glu Ala Phe Lys Leu Ala Gly Ile Ser Ser Gly Phe
                245                 250                 255

Phe Asp Leu Gln Pro Lys Glu Gly Leu Ala Leu Val Asn Gly Thr Ala
            260                 265                 270

Val Gly Ser Gly Met Ala Ser Met Val Leu Phe Glu Thr Asn Val Leu
        275                 280                 285

Ser Val Leu Ala Glu Ile Leu Ser Ala Val Phe Ala Glu Val Met Ser
    290                 295                 300

Gly Lys Pro Glu Phe Thr Asp His Leu Thr His Arg Leu Lys His His
305                 310                 315                 320

Pro Gly Gln Ile Glu Ala Ala Ile Met Glu His Ile Leu Asp Gly
                325                 330                 335

Ser Ser Tyr Met Lys Leu Ala Gln Lys Leu His Glu Met Asp Pro Leu
            340                 345                 350

Gln Lys Pro Lys Gln Asp Arg Tyr Ala Leu Arg Thr Ser Pro Gln Trp
        355                 360                 365

Leu Gly Pro Gln Ile Glu Val Ile Arg Tyr Ala Thr Lys Ser Ile Glu
    370                 375                 380

Arg Glu Ile Asn Ser Val Asn Asp Asn Pro Leu Ile Asp Val Ser Arg
385                 390                 395                 400
```

Asn Lys Ala Ile His Gly Gly Asn Phe Gln Gly Thr Pro Ile Gly Val
            405                 410                 415

Ser Met Asp Asn Thr Arg Leu Ala Ile Ala Ile Gly Lys Leu Met
            420                 425                 430

Phe Ala Gln Phe Ser Glu Leu Val Asn Asp Phe Tyr Asn Asn Gly Leu
            435                 440                 445

Pro Ser Asn Leu Thr Ala Ser Arg Asn Pro Ser Leu Asp Tyr Gly Phe
        450                 455                 460

Lys Gly Ala Glu Ile Ala Met Ala Ser Tyr Cys Ser Glu Leu Gln Tyr
465                 470                 475                 480

Leu Ala Asn Pro Val Thr Ser His Val Gln Ser Ala Glu Gln His Asn
                485                 490                 495

Gln Asp Val Asn Ser Leu Gly Leu Ile Ser Ser Arg Lys Thr Ser Glu
            500                 505                 510

Ala Val Asp Ile Leu Lys Leu Met Ser Thr Thr Phe Leu Val Ala Ile
            515                 520                 525

Cys Gln Ala Val Asp Leu Arg His Leu Glu Glu Asn Leu Arg Gln Thr
        530                 535                 540

Val Lys Asn Thr Val Ser Gln Val Ala Lys Lys Val Leu Thr Thr Gly
545                 550                 555                 560

Val Asn Gly Glu Leu His Pro Ser Arg Phe Cys Glu Lys Asp Leu Leu
                565                 570                 575

Lys Val Val Asp Arg Glu Gln Val Tyr Thr Tyr Ala Asp Pro Cys
            580                 585                 590

Ser Ala Thr Tyr Pro Leu Ile Gln Lys Leu Arg Gln Val Ile Val Asp
            595                 600                 605

His Ala Leu Ile Asn Gly Glu Ser Glu Lys Asn Ala Val Thr Ser Ile
        610                 615                 620

Phe His Lys Ile Gly Ala Phe Glu Glu Glu Leu Lys Ala Val Leu Pro
625                 630                 635                 640

Lys Glu Val Glu Ala Ala Arg Ala Ala Tyr Asp Asn Gly Thr Ser Ala
                645                 650                 655

Ile Pro Asn Arg Ile Lys Glu Cys Arg Ser Tyr Pro Leu Tyr Arg Phe
            660                 665                 670

Val Arg Glu Glu Leu Gly Thr Glu Leu Leu Thr Gly Glu Lys Val Thr
            675                 680                 685

Ser Pro Gly Glu Glu Phe Asp Lys Val Phe Thr Ala Ile Cys Glu Gly
        690                 695                 700

Lys Ile Ile Asp Pro Met Met Glu Cys Leu Asn Glu Trp Asn Gly Ala
705                 710                 715                 720

Pro Ile Pro Ile Cys
            725

<210> SEQ ID NO 107
<211> LENGTH: 703
<212> TYPE: PRT
<213> ORGANISM: Aspergillus niger

<400> SEQUENCE: 107

Met Leu Asp Lys His Ile Pro Asp Gly His Leu Glu Thr Ser Ala
1               5                   10                  15

His Trp Arg Asp Leu Asn Gln Val Val Gln Asn Gly Glu Leu Ser Ile
            20                  25                  30

Asp Gly Tyr Ser Leu Ser Leu Ala Asp Val Val Ala Val Ala Lys Tyr
        35                  40                  45

-continued

Gly Cys Gln Pro Arg Leu Thr Asp Lys Pro Glu Thr Ile Asp Ala Ile
50                   55                  60

Asn Gly Ser Val Ile Ala Leu Ala Glu Cys Leu Arg Asp Gly His His
65                  70                  75                  80

Ile Tyr Gly Val Asn Thr Gly Phe Gly Gly Ser Ala Asp Ser Arg Thr
                    85                  90                  95

Asn Gln Thr Thr Thr Leu Gln Ser Ser Leu Leu Gln Leu Leu Gln Ser
            100                 105                 110

Gly Ile Leu Thr Ala Ser Asp Thr Thr Asn Glu Gly Leu Gln Leu Asn
            115                 120                 125

Leu Gln Gly Gln Ser Ser His Ser Met Pro Ser Glu Trp Val Lys Ala
            130                 135                 140

Thr Met Leu Val Arg Ser Asn Ser Val Ala Arg Gly His Ser Ala Val
145                 150                 155                 160

Ser Leu Pro Ala Ile Ser Ala Ile Leu Arg Leu Ile Arg Glu Asp Ile
                165                 170                 175

Val Pro Val Ile Pro Leu Arg Gly Thr Ile Ser Ala Ser Gly Asp Leu
                180                 185                 190

Met Pro Leu Ala Tyr Val Gly Ala Ile Glu Gly Ser Pro Gly Ile
            195                 200                 205

Tyr Val Arg Val Lys Asp Gly Ser Glu His Gln Val Val Thr Ala Gln
            210                 215                 220

Lys Ala Leu Gln Thr Ile Gly Ala Lys Gly Val Thr Leu Gly Pro Lys
225                 230                 235                 240

Glu Gly Leu Gly Leu Val Asn Gly Thr Ala Ala Ser Gly Ala Leu Ala
                245                 250                 255

Gly Leu Val Leu Tyr Glu Ala His Gln Leu Ala Val Leu Ala Gln Ala
            260                 265                 270

Val Thr Ala Leu Thr Val Glu Ala Ile Gln Gly Ser Thr Glu Ser Phe
            275                 280                 285

His Pro Phe Ile Ala Gln Val Arg Pro His Glu Gly Gln Ile Glu Ala
            290                 295                 300

Ala Glu Asn Ile Leu Ser Leu Leu Lys Gly Ser Leu Leu Ala Arg Gly
305                 310                 315                 320

Ser Ser Thr Thr Gln Thr Arg Thr Gly Leu Val Gln Asp Arg Tyr Ser
                325                 330                 335

Leu Arg Thr Ala Ser Gln Trp Ile Gly Pro Gln Leu Glu Asp Leu Leu
            340                 345                 350

Leu Ala Asp Arg Gln Val Gln Val Glu Leu Asn Ser Thr Ser Asp Asn
            355                 360                 365

Pro Leu Ile Asp Thr Gly Ser Lys Thr Phe Tyr Thr Gly Gly Asn Phe
370                 375                 380

Gln Ala Thr Ser Ile Thr Ser Ala Met Glu Lys Thr Arg Leu Ala Leu
385                 390                 395                 400

Gln Met Phe Gly Lys Met Leu Phe Val Gln Cys Asn Glu Met Ile Asp
                405                 410                 415

Pro Asn Leu Asn Asn Gly Leu Pro Thr Asn Leu Val Ala Asp Asp Pro
            420                 425                 430

Ser Leu Ser Phe Thr Met Lys Gly Val Asp Ile Asn Met Ala Ala Tyr
            435                 440                 445

Met Ser Glu Leu Ala Tyr Leu Ala Asn Pro Val Ser Ser His Val Gln
450                 455                 460

-continued

```
Thr Ala Glu Met Gln Asn Gln Ala Leu Asn Ser Leu Ala Phe Val Ser
465                 470                 475                 480

Ala Arg Tyr Thr Met Lys Ala Val Asp Ile Val Ser Met Met Gly Ala
                485                 490                 495

Cys Ala Leu Tyr Val Ala Cys Gln Ala Leu Asp Leu Arg Val Leu Gln
            500                 505                 510

Leu Arg Phe Phe Gln Arg Val Gln Gly Val Ala Lys Glu Ile Ala His
        515                 520                 525

Gly Ala Phe Gly Lys Ala Leu Glu Pro Phe Glu Ile Asp Gln Val Ala
530                 535                 540

Asp His Leu Ser Glu Ala Ile Gln Asn Ser Trp Pro Ser Thr Ser Arg
545                 550                 555                 560

Leu Asp Leu Arg Asp Arg Cys Lys Arg Val Ala Glu Met Phe Ile Pro
                565                 570                 575

Val Leu Phe Gly Ala Leu Leu Gln Ile Ile Pro Gln Asn Arg Gln Thr
            580                 585                 590

Ser Asp Leu Phe Thr Ala Ile Ser Ala Cys Lys Met Ile Ser Val Phe
        595                 600                 605

Lys Leu Glu Gly Val Tyr Arg Glu Val Phe Ala Glu Phe Cys Thr Ser
610                 615                 620

Gln Pro Thr Ala Asp Phe Leu Gly Thr Gly Thr Lys Glu Ile Tyr Thr
625                 630                 635                 640

Phe Ile Arg His Asp Leu Arg Val Pro Phe His Gln Gly Phe Val Glu
                645                 650                 655

His Pro Ser Ala Ser Gln Thr Asp Leu Pro Glu Thr Ile Asn Gly Arg
            660                 665                 670

Val Lys Lys Thr Val Gly Gly Trp Ile Ser Val Val Tyr Glu Ala Leu
        675                 680                 685

Arg Asn Gly Thr Leu Ser Gly Thr Ile Leu Asn Ser Phe Gln Gln
690                 695                 700

<210> SEQ ID NO 108
<211> LENGTH: 716
<212> TYPE: PRT
<213> ORGANISM: Rhodosporidium toruloides

<400> SEQUENCE: 108

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
                20                  25                  30

Ala Gly Ser His Leu Pro Thr Thr Gln Val Thr Gln Val Asp Ile Val
            35                  40                  45

Glu Lys Met Leu Ala Ala Pro Thr Asp Ser Thr Leu Glu Leu Asp Gly
        50                  55                  60

Tyr Ser Leu Asn Leu Gly Asp Val Val Ser Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Asp Ala Ile
        115                 120                 125

Ser Leu Gln Lys Ala Leu Leu Glu His Gln Leu Cys Gly Val Leu Pro
130                 135                 140
```

```
Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
            165                 170                 175

Thr Arg Gly His Ser Ala Val Arg Leu Val Val Leu Glu Ala Leu Thr
            180                 185                 190

Asn Phe Leu Asn His Gly Ile Thr Pro Ile Val Pro Leu Arg Gly Thr
        195                 200                 205

Ile Ser Ala Ser Gly Asp Leu Ser Pro Leu Ser Tyr Ile Ala Ala Ala
        210                 215                 220

Ile Ser Gly His Pro Asp Ser Lys Val His Val His Glu Gly Lys
225                 230                 235                 240

Glu Lys Ile Leu Tyr Ala Arg Glu Ala Met Ala Leu Phe Asn Leu Glu
            245                 250                 255

Pro Val Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
        275                 280                 285

Leu Ser Leu Leu Ser Gln Ser Leu Thr Ala Met Thr Val Glu Ala Met
290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
            325                 330                 335

Glu Gly Ser Arg Phe Ala Val His His Glu Glu Glu Val Lys Val Lys
            340                 345                 350

Asp Asp Glu Gly Ile Leu Arg Gln Asp Arg Tyr Pro Leu Arg Thr Ser
        355                 360                 365

Pro Gln Trp Leu Gly Pro Leu Val Ser Asp Leu Ile His Ala His Ala
370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
            405                 410                 415

Ala Val Ala Asn Thr Met Glu Lys Thr Arg Leu Gly Leu Ala Gln Ile
            420                 425                 430

Gly Lys Leu Asn Phe Thr Gln Leu Thr Glu Met Leu Asn Ala Gly Met
        435                 440                 445

Asn Arg Gly Leu Pro Ser Cys Leu Ala Ala Glu Asp Pro Ser Leu Ser
450                 455                 460

Tyr His Cys Lys Gly Leu Asp Ile Ala Ala Ala Tyr Thr Ser Glu
465                 470                 475                 480

Leu Gly His Leu Ala Asn Pro Val Thr Thr His Val Gln Pro Ala Glu
            485                 490                 495

Met Ala Asn Gln Ala Val Asn Ser Leu Ala Leu Ile Ser Ala Arg Arg
        500                 505                 510

Thr Thr Glu Ser Asn Asp Val Leu Ser Leu Leu Leu Ala Thr His Leu
        515                 520                 525

Tyr Cys Val Leu Gln Ala Ile Asp Leu Arg Ala Ile Glu Phe Glu Phe
        530                 535                 540

Lys Lys Gln Phe Gly Pro Ala Ile Val Ser Leu Ile Asp Gln His Phe
545                 550                 555                 560
```

```
Gly Ser Ala Met Thr Gly Ser Asn Leu Arg Asp Glu Leu Val Glu Lys
            565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
            595                 600                 605

Val Glu Val Leu Ser Ser Thr Ser Leu Ser Leu Ala Ala Val Asn Ala
            610                 615                 620

Trp Lys Val Ala Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
            645                 650                 655

Tyr Leu Ser Pro Arg Thr Gln Ile Leu Tyr Ala Phe Val Arg Glu Glu
            660                 665                 670

Leu Gly Val Lys Ala Arg Arg Gly Asp Val Phe Leu Gly Lys Gln Glu
            675                 680                 685

Val Thr Ile Gly Ser Asn Val Ser Lys Ile Tyr Glu Ala Ile Lys Ser
            690                 695                 700

Gly Arg Ile Asn Asn Val Leu Leu Lys Met Leu Ala
705                 710                 715

<210> SEQ ID NO 109
<211> LENGTH: 390
<212> TYPE: PRT
<213> ORGANISM: Hypericum androsaemum

<400> SEQUENCE: 109

Met Val Thr Val Glu Glu Val Arg Lys Ala Gln Arg Ala Glu Gly Pro
1               5                   10                  15

Ala Thr Val Met Ala Ile Gly Thr Ala Val Pro Pro Asn Cys Val Asp
            20                  25                  30

Gln Ala Thr Tyr Pro Asp Tyr Tyr Phe Arg Ile Thr Asn Ser Glu His
            35                  40                  45

Lys Ala Glu Leu Lys Glu Lys Phe Gln Arg Met Cys Asp Lys Ser Gln
50                  55                  60

Ile Lys Lys Arg Tyr Met Tyr Leu Asn Glu Glu Val Leu Lys Glu Asn
65                  70                  75                  80

Pro Asn Met Cys Ala Tyr Met Ala Pro Ser Leu Asp Ala Arg Gln Asp
            85                  90                  95

Ile Val Val Val Glu Val Pro Lys Leu Gly Lys Glu Ala Ala Val Lys
            100                 105                 110

Ala Ile Lys Glu Trp Gly Gln Pro Lys Ser Lys Ile Thr His Leu Val
            115                 120                 125

Phe Cys Thr Thr Ser Gly Val Asp Met Pro Gly Ala Asp Tyr Gln Leu
            130                 135                 140

Thr Lys Leu Leu Gly Leu Arg Pro Ser Val Lys Arg Leu Met Met Tyr
145                 150                 155                 160

Gln Gln Gly Cys Phe Ala Gly Gly Thr Val Leu Arg Leu Ala Lys Asp
            165                 170                 175

Leu Ala Glu Asn Asn Lys Gly Ala Arg Val Leu Val Val Cys Ser Glu
            180                 185                 190

Ile Thr Ala Val Thr Phe Arg Gly Pro Thr Asp Thr His Leu Asp Ser
            195                 200                 205

Leu Val Gly Gln Ala Leu Phe Gly Asp Gly Ala Ala Ala Ile Ile Ile
            210                 215                 220
```

```
Gly Ser Asp Pro Ile Pro Glu Val Glu Lys Pro Leu Phe Glu Leu Val
225                 230                 235                 240

Ser Ala Ala Gln Thr Ile Leu Pro Asp Ser Glu Gly Ala Ile Asp Gly
                245                 250                 255

His Leu Arg Glu Val Gly Leu Thr Phe His Leu Leu Lys Asp Val Pro
            260                 265                 270

Gly Leu Ile Ser Lys Asn Val Glu Lys Ser Leu Thr Glu Ala Phe Lys
            275                 280                 285

Pro Leu Gly Ile Ser Asp Trp Asn Ser Leu Phe Trp Ile Ala His Pro
        290                 295                 300

Gly Gly Pro Ala Ile Leu Asp Gln Val Glu Ala Lys Leu Ser Leu Lys
305                 310                 315                 320

Pro Glu Lys Leu Arg Ala Thr Arg His Val Leu Ser Glu Tyr Gly Asn
                325                 330                 335

Met Ser Ser Ala Cys Val Leu Phe Ile Leu Asp Glu Met Arg Arg Lys
                340                 345                 350

Ser Lys Glu Asp Gly Leu Lys Thr Thr Gly Glu Gly Ile Glu Trp Gly
            355                 360                 365

Val Leu Phe Gly Phe Gly Pro Gly Leu Thr Val Glu Thr Val Val Leu
    370                 375                 380

His Ser Val Ala Ile Asn
385                 390
```